(12) United States Patent
Greenwood et al.

(10) Patent No.: US 10,793,574 B2
(45) Date of Patent: Oct. 6, 2020

(54) TYK2 INHIBITORS AND USES THEREOF

(71) Applicant: Nimbus Lakshmi, Inc., Cambridge, MA (US)

(72) Inventors: Jeremy Robert Greenwood, Brooklyn, NY (US); Geraldine C. Harriman, Charlestown, RI (US); Silvana Marcel Leit de Moradei, Burlington, MA (US); Craig E. Masse, Cambridge, MA (US); Thomas H. McLean, Cambridge, MA (US); Sayan Mondal, New York, NY (US)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

(21) Appl. No.: 16/399,296

(22) Filed: Apr. 30, 2019

(65) Prior Publication Data

US 2019/0284194 A1 Sep. 19, 2019

Related U.S. Application Data

(62) Division of application No. 15/783,250, filed on Oct. 13, 2017, now Pat. No. 10,323,036.

(60) Provisional application No. 62/410,327, filed on Oct. 19, 2016, provisional application No. 62/468,749, filed on Mar. 8, 2017, provisional application No. 62/546,278, filed on Aug. 16, 2017, provisional application No. 62/410,334, filed on Oct. 19, 2016, provisional application No. 62/468,767, filed on Mar. 8, 2017, provisional application No. 62/413,829, filed on Oct. 27, 2016, provisional application No. 62/415,920, filed on Nov. 1, 2016, provisional application No. 62/468,807, filed on Mar. 8, 2017, provisional application No. 62/408,464, filed on Oct. 14, 2016.

(51) Int. Cl.

| C07D 487/04 | (2006.01) |
|---|---|
| C07D 471/04 | (2006.01) |
| C07D 401/14 | (2006.01) |
| C07D 417/14 | (2006.01) |
| A61P 5/00 | (2006.01) |
| A61P 37/02 | (2006.01) |
| A61P 35/02 | (2006.01) |
| A61P 25/28 | (2006.01) |
| A61P 29/00 | (2006.01) |
| C07D 413/14 | (2006.01) |
| C07D 519/00 | (2006.01) |

(52) U.S. Cl.
CPC ............ *C07D 487/04* (2013.01); *A61P 5/00* (2018.01); *A61P 25/28* (2018.01); *A61P 29/00* (2018.01); *A61P 35/02* (2018.01); *A61P 37/02* (2018.01); *C07D 401/14* (2013.01); *C07D 413/14* (2013.01); *C07D 417/14* (2013.01); *C07D 471/04* (2013.01); *C07D 519/00* (2013.01)

(58) Field of Classification Search
None
See application file for complete search history.

(56) References Cited

U.S. PATENT DOCUMENTS

| 4,650,750 | A | 3/1987 | Giese |
|---|---|---|---|
| 4,709,016 | A | 11/1987 | Giese |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,552,065 | B2 | 4/2003 | Remiszewski et al. |
| 7,390,799 | B2 | 6/2008 | Bruncko et al. |
| 8,138,347 | B2 | 3/2012 | Knight et al. |
| 2009/0163545 | A1 | 6/2009 | Goldfarb |
| 2016/0251376 | A1 | 9/2016 | Dahlgren et al. |

FOREIGN PATENT DOCUMENTS

| WO | 2001042246 | 6/2001 |
|---|---|---|
| WO | 2002088112 | 11/2002 |
| WO | 2003063794 | 8/2003 |
| WO | 2004019973 | 3/2004 |
| WO | 2004089925 | 10/2004 |
| WO | 2004106328 | 12/2004 |
| WO | 2005007623 | 1/2005 |
| WO | 2005113554 | 12/2005 |
| WO | 2006078846 | 7/2006 |
| WO | 2006122806 | 11/2006 |
| WO | 2007016176 | 2/2007 |
| WO | 2007044729 | 4/2007 |
| WO | 2007053452 | 5/2007 |
| WO | 2007070514 | 6/2007 |
| WO | 2007084786 | 7/2007 |

(Continued)

OTHER PUBLICATIONS

Bacon et al., "Interleukin 12 (IL-12) induces tyrosine phosphorylation of Jak2 and Tyk2: differential use of Janus family kinases by IL-2 and IL-12," The Journal of Experimental Medicine, vol. 181, Jan. 1995 (pp. 399-404).

(Continued)

*Primary Examiner* — Zinna Northington-Davis
(74) *Attorney, Agent, or Firm* — Andrea L. C. Reid; Paul R. Fleming; Dechert LLP

(57) ABSTRACT

The present invention provides compounds, compositions thereof, and methods of using the same for the inhibition of TYK2, and the treatment of TYK2-mediated disorders.

12 Claims, No Drawings
Specification includes a Sequence Listing.

(56) References Cited

FOREIGN PATENT DOCUMENTS

| WO | 2007129161 | | 11/2007 |
| --- | --- | --- | --- |
| WO | 2008039218 | | 4/2008 |
| WO | 2008109943 | | 9/2008 |
| WO | 2008118802 | | 10/2008 |
| WO | 2009114512 | | 9/2009 |
| WO | 2009155156 | A1 | 12/2009 |
| WO | 2011090760 | A1 | 7/2011 |
| WO | 2012/066061 | A1 | 5/2012 |
| WO | WO 2013/106641 | A1 * | 7/2013 |
| WO | 2014074660 | A1 | 5/2014 |
| WO | 2014074661 | A1 | 5/2014 |
| WO | 2015089143 | A1 | 6/2015 |
| WO | 2015131080 | A1 | 9/2015 |
| WO | 2016/027195 | A1 | 2/2016 |

OTHER PUBLICATIONS

Ban et al., "Replication analysis identifies TYK2 as a multiple sclerosis susceptibility factor," European Journal of Human Genetics, vol. 17, Mar. 2009 (pp. 1309-1313).

Berge et al., "Pharmaceutical Salts," Journal of Pharmaceutical Sciences, vol. 66, No. 1, Jan. 1977 (pp. 1-19).

Chemical Abstracts 93: 114436, Balicki et al, Abstract of Polish Journal of Chemistry (1979), 53 (12), pp. 2491-2499 (Year: 1980).

Chemical Abstract 52:25500, Papini et al., Abstract of Gazzetta Chimica Italiana (1957), 87, pp. 931-948 (Year: 1958).

Cho et al., "Genomics and the multifactorial nature of human auto-immune disease," The New England Journal of Medicine, vol. 365, No. 17, Oct. 2011 (pp. 1612-1623).

Cortes et al., "Identification of multiple risk variants for ankylosing spondylitis through high-density genotyping of immune-related loci," Nature Genetics, vol. 45, No. 7, Jul. 2013 (pp. 730-738).

Duerr et al., "A Genome-Wide Association Study Identifies IL23R as an Inflammatory Bowel Disease Gene," Science, vol. 314, Dec. 2006 (pp. 1461-1463).

Finbloom et al., "IL-10 induces the tyrosine phosphorylation of Tyk2 and Jak1 and the differential assembly of Stat1 and Stat3 complexes in human T cells and monocytes," The Journal of Immunology, vol. 155, No. 3, Aug. 1995 (pp. 1079-1090).

Fontan et al. "Discovering What Makes STAT Signaling TYK in T-ALL," Cancer Discovery, vol. 3, May 2013 (pp. 494-496).

Graham et al., "Association of NCF2, IKZF1, IRF8, IFIH1, and TYK2 with Systemic Lupus Erythematosus," PLoS Genetics, vol. 7, No. 10, Oct. 2011 (9 pages).

Harel et al., "Pharmacologic inhibition of JAK-STAT signaling promotes hair growth," Science Advances, vol. 1, No. 9, Oct. 2015 (12 pages).

International Search Report and Written Opinion issued by the United States Patent and Trademark Office as International Searching Authority for International Application No. PCT/US2017/056555, dated Feb. 13, 2018 (12 pages).

Ishizaki et al., "Tyk2 deficiency protects joints against destruction in anti-type II collagen antibody-induced arthritis in mice," International Immunology, vol. 23, No. 9, Jul. 2011 (pp. 575-582).

Ishizaki et al., "Tyk2 is a therapeutic target for psoriasis-like skin inflammation," International Immunology, Dec. 2013 (11 pages).

Kantlehner et al., Journal fuer Praktische Chemie/Chemiker-Zeitung, 340(5), 408-423 (Year: 1998).

Levenberg, "A method of solution of certain non-linear problems in least squares," Quarterly of Applied Mathematics, vol. 2, No Month Listed 1944 (pp. 164-168).

Oyamada et al., "Tyrosine Kinase 2 Plays Critical Roles in the Pathogenic CD4 T Cell Responses for the Development of Experimental Autoimmune Encephalomyelitis," The Journal of Immunology, vol. 183, No Month Listed 2009 (pp. 7539-7546).

Parham et al., "A receptor for the heterodimeric cytokine IL-23 is composed of IL-12Rβ1 and a novel cytokine receptor subunit, IL-23R," The Journal of Immunology, vol. 168, No Month Listed 2002 (pp. 5699-5708).

PubChem, Compound Summary for CID 303955, 3-phenylimidazo[1,5-a]pyrazine, Mar. 26, 2005 (14 pages).

PubChem, Compound Summary for CID 824807, AC1LGOCP, Aug. 9, 2005 (13 pages).

PubChem, Compound Summary for CID 57799363, 2-chloro-4-4(4-chlorophenyl)-3,4'-bipyridine-, Aug. 19, 2012 (13 pages).

Ramirez et al., "Defining causative factors contributing in the activation of hedgehog signaling in diffuse large B-cell lymphoma," Leukemia Research, vol. 36, No. 10, Oct. 2012 (pp. 1267-1273).

Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).

Rostovtsev et al., A Stepwise Huisgen Cycloaddition Process: Copper(I)-Catalyzed Regioselective "Ligation" of Azides and Terminal Alkynes, Angewandte Chemie International Edition, vol. 114, No. 14, Jul. 2002 (pp. 2708-2711).

Sanda et al. "TYK2-STAT1-BCL2 Pathway Dependence in T-Cell Acute Lymphoblastic Leukemia," Cancer Discovery, vol. 3, No. 5, May 2013 (pp. 564-577).

Sigurdsson et al., "Polymorphisms in the Tyrosine Kinase 2 and Interferon Regulatory Factor 5 Genes Are Associated with Systemic Lupus Erythematosus," The American Journal of Human Genetics, vol. 76, Jan. 2005 (pp. 528-537).

Simma et al. "Identification of an Indispensable Role for Tyrosine Kinase 2 in CTL-Mediated Tumor Surveillance," Cancer Research, vol. 69, No. 1, Jan. 2009 (pp. 203-211).

Stahl et al., "Association and activation of Jak-Tyk kinases by CNTF-LIF-OSM-IL-6β receptor components," Science, vol. 263, Jan. 1994 (pp. 92-95).

Strange et al., "A genome-wide association study identifies new psoriasis susceptibility loci and an interaction between HLA-C and ERAP1," Nature Genetics, vol. 42, No. 11, Nov. 2010 (pp. 985-992).

Sun et al., "Carbohydrate and Protein Immobilization onto Solid Surfaces by Sequential Diels-Alder and Azide-Alkyne Cycloadditions," Bioconjugate Chemistry, vol. 17, No Month Listed 2006 (pp. 52-57).

Velasquez et al., "A protein kinase in the interferon α/β signaling pathway," Cell, vol. 70, Jul. 1992 (pp. 313-322).

Wan et al. "Tyk/STAT3 Signaling Mediates β-Amyloid-Induced Neuronal Cell Death: Implications in Alzheimer's Disease," The Journal of Neuroscience, vol. 30, No. 20, May 2010 (pp. 6873-6881).

Welham et al., "Interleukin-13 signal transduction in lymphohemopoietic cells: similarities and differences in signal transduction with interleukin-4 and insulin," The Journal of Biological Chemistry, vol. 270, No. 20, May 1995 (pp. 12286-12296).

Xing et al., "Alopecia areata is driven by cytotoxic T lymphocytes and is reversed by JAK inhibition," Nature Medicine, vol. 20, No. 9, Sep. 2014 (pp. 1043-1049).

Zhang et al., "Docking protein Gab2 regulates mucin expression and goblet cell hyperplasia through TYK2/STAT6 pathway," The FASEB Journal, vol. 26, No Month Listed 2012 (pp. 1-11).

Eldin et al., "Reactions with Pyridine-2-Thiones: A New Route for the Synthesis of Several New Pyridines and Fused Azolo- and Azinopyridines," Phosphorus Sulfur and Silicon and the Related Elements 2001, 176(1): 49-59.

Kidwai et al., "A facile synthesis of substituted pyridines and pyrazolo[3,4-b]pyridines," Journal of Heterocyclic Chemistry 2009, 42(6): 1181-1183.

Supplementary Partial European Search Report in EP 17860009.4 dated Apr. 20, 2020 (14 pages).

Xu et al., "A facile and efficient reaction of α,β-unsaturated ketones and 3-amino-1-phenyl-1H-pyrazol-5(4H)-one in aqueous and acetonitrile medium," Tetrahedron 2016, 72(38): 5754-5761.

* cited by examiner

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1
gggaattccc                                                            10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Ser Arg Gly Asp Tyr Met Thr Met Gln Ile Gly
1               5                   10
```

TYK2 INHIBITORS AND USES THEREOF

CROSS-REFERENCE TO RELATED APPLICATIONS

The present application is a division of U.S. patent application Ser. No. 15/783,250, filed Oct. 13, 2017, which claims the benefit of U.S. Provisional Application No. 62/546,278, filed Aug. 16, 2017, U.S. Provisional Application No. 62/468,807, filed Mar. 8, 2017, U.S. Provisional Application No. 62/468,767, filed Mar. 8, 2017, U.S. Provisional Application No. 62/468,749, filed Mar. 8, 2017, U.S. Provisional Application No. 62/415,920, filed Nov. 1, 2016, U.S. Provisional Application No. 62/413,829, filed Oct. 27, 2016, U.S. Provisional Application No. 62/410,334, filed Oct. 19, 2016, U.S. Provisional Application No. 62/410,327, filed Oct. 19, 2016, and U.S. Provisional Application No. 62/408,464, filed Oct. 14, 2016, the entirety of each of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

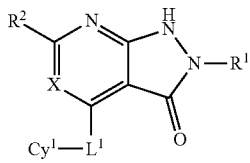

I or a pharmaceutically acceptable salt thereof, wherein each of X, $L^1$, $R^1$, $R^2$, and $Cy^1$ is as defined below and described in embodiments herein, both singly and in combination.

In some embodiments, the present invention provides a pharmaceutical composition comprising a compound of formula I, and a pharmaceutically acceptable carrier, adjuvant, or diluent.

In some embodiments, the present invention provides a method of treating a TYK2-mediated disease, disorder, or condition comprising administering to a patient in need thereof, a compound of formula I or a pharmaceutically acceptable salt thereof.

In certain embodiments, the present invention provides a compound of formula VIII:

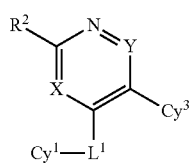

VIII or a pharmaceutically acceptable salt thereof, wherein each of X, $L^1$, $R^1$, $R^2$, and $Cy^1$ is as defined below and described in embodiments herein, both singly and in combination.

In some embodiments, the present invention provides a pharmaceutical composition comprising a compound of formula VIII, and a pharmaceutically acceptable carrier, adjuvant, or diluent.

In some embodiments, the present invention provides a method of treating a TYK2-mediated disease, disorder, or condition comprising administering to a patient in need thereof, a a compound of formula VIII or a pharmaceutically acceptable salt thereof.

In certain embodiments, the present invention provides a compound of formula XVI':

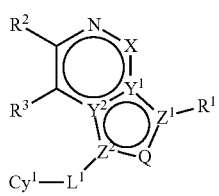

XVI' or a pharmaceutically acceptable salt thereof, wherein each of Q, X, $Y^1$, $Y^2$, $Z^1$, $Z^2$, $L^1$, $R^1$, $R^2$, and $Cy^1$ is as defined below and described in embodiments herein, both singly and in combination.

In some embodiments, the present invention provides a pharmaceutical composition comprising a compound of formula XVI', and a pharmaceutically acceptable carrier, adjuvant, or diluent.

In some embodiments, the present invention provides a method of treating a TYK2-mediated disease, disorder, or condition comprising administering to a patient in need thereof, a a compound of formula XVI' or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

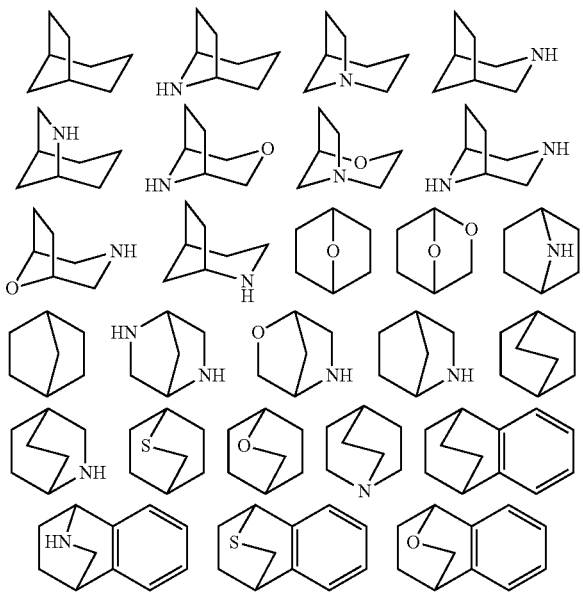

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(RO)C(O)RO; —N(R°)C(S)R°; —(CH$_2$)$_{0-4}$N(R)C(O)NR°$_2$; —N(R°)C(S)NR°$_2$; —(CH$_2$)$_{0-4}$N(R)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SRO; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an IC$_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

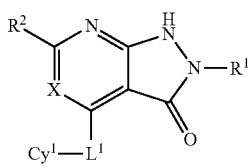

or a pharmaceutically acceptable salt thereof, wherein:
X is N or C($R^3$);
$R^1$ is R, $R^D$, or —OR;
$R^2$ is H, $R^C$, —N(R)C(O)$Cy^2$, —N(R)S(O)$_2Cy^2$, —N(R)$Cy^2$, —O$Cy^2$, —S$Cy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$;
each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;

$L^1$ is a covalent bond or a $C_{1-4}$ bivalent saturated or unsaturated, straight or branched hydrocarbon chain wherein one or two methylene units of the chain are optionally and independently replaced by —C($R^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each instance of $R^4$, $R^5$, $R^6$, and $R^7$ is independently $R^A$ or $R^B$, and is substituted by q instances of $R^C$;

each instance of $R^A$ is independently oxo, halogen, —CN, —NO$_2$, —OR, —OR$^D$, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^D$ is a $C_{1-4}$ aliphatic group wherein one or more hydrogens are replaced by deuterium;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

As defined generally above, X is N or C(R³). In some embodiments, X is N. In some embodiments, X is C(R³). In some embodiments, X is C(H). In some embodiments, X is C(R³), where R³ is halogen. In some embodiments, X is C(R³), where R³ is fluoro.

As defined generally above, R¹ is R, $R^D$, or —OR. In some embodiments, R¹ is R. In some embodiments, R¹ is $R^D$. In some embodiments, R¹ is —OR. In some embodiments, R¹ is an optionally substituted $C_{1-6}$ aliphatic group. In some embodiments, R¹ is an optionally substituted ethyl group. In some embodiments, R¹ is hydrogen, methyl or —CD₃. In some embodiments, R¹ is hydrogen. In some embodiments, R¹ is methyl or —CD₃. In some embodiments, R¹ is methyl. In some embodiments, R¹ is —CD₃. In some embodiments, R¹ is —OH.

As defined generally above, R² is H, $R^C$, —N(R)C(O)Cy², —N(R)Cy², —OCy², —SCy², or Cy². In some embodiments, R² is H. In some embodiments, R² is $R^C$, —N(R)C(O)Cy², —N(R)Cy², —OCy², —SCy², or Cy². In some embodiments, R² is $R^C$. In some embodiments, R² is —N(R)C(O)R. In some embodiments, R² is —N(R)C(O)Cy², —N(R)Cy², or Cy². In some embodiments, R² is —N(R)C(O)R, —N(R)C(O)Cy², —N(R)Cy², or Cy². In some embodiments, R² is —N(H)C(O)R, —N(H)C(O)Cy², —N(H)Cy², or Cy². In some embodiments, R² is —N(H)C(O)R, —N(H)C(O)Cy², or —N(H)Cy². In some embodiments, R² is —N(H)C(O)R. In some embodiments, R² is —N(H)C(O)R wherein R in this instance is optionally substituted $C_{1-6}$ aliphatic. In some embodiments, R² is —N(H)C(O)Cy². In some embodiments, R² is —N(H)Cy². In some embodiments, R² is —N(H)C(O)Cy² where Cy² is cyclopropyl. In some embodiments, R² is

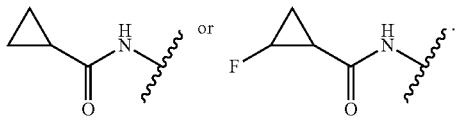 [SMILES: *NC(=O)C1CC1 ; "or" ; *NC(=O)C1CC1F ; "."]

As defined generally above, R³ is H, halogen, or $C_{1-6}$ aliphatic. In some embodiments, R³ is H. In some embodiments, R³ is halogen, or $C_{1-6}$ aliphatic. In some embodiments, R³ is halogen. In some embodiments, R³ is fluoro. In some embodiments, R³ is $C_{1-6}$ aliphatic.

In some embodiments, R² and R³ are taken together with their intervening atoms to form a 4-7 membered partially unsaturated or aromatic ring having 0-3 heteroatoms independently selected from nitrogen, oxygen, and sulfur; wherein said ring is substituted with m instances of R⁴. In some embodiments, R² and R³ are taken together with their intervening atoms to form a 5-membered partially unsaturated or aromatic ring having 1-3 heteroatoms independently selected from nitrogen, oxygen, and sulfur; wherein said ring is substituted with m instances of R⁴.

As defined generally above, Cy¹ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy¹ is substituted with n instances of R⁵.

In some embodiments, Cy¹ is phenyl. In some embodiments, Cy¹ is a 5-6 membered heteroaryl having 1-4 heteroatoms independently selected from nitrogen, oxygen, and sulfur. In some embodiments, Cy¹ is a 5-membered heteroaryl having 1-4 heteroatoms independently selected from nitrogen, oxygen, and sulfur. In some embodiments, Cy¹ is a 6-membered heteroaryl having 1-4 nitrogens. In some embodiments, Cy¹ is pyridyl. In some embodiments, Cy¹ is pyrazinyl. In some embodiments, Cy¹ is pyrimidinyl. In some embodiments, Cy¹ is triazinyl. In some embodiments, Cy¹ is pyrrolyl, pyrazolyl, imidazolyl, triazolyl, or tetrazolyl. In some embodiments, Cy¹ is furanyl, oxazolyl, isoxazolyl, or oxadiazolyl. In some embodiments, Cy¹ is thiophenyl, thiazolyl, isothiazolyl, or thiadiazolyl. In some embodiments, Cy¹ is an 8-10 membered bicyclic heteroaryl ring having 1-4 heteroatoms independently selected from nitrogen, oxygen, and sulfur. In some embodiments, Cy¹ is a 3-7 membered saturated or partially unsaturated heterocyclic ring having 1-2 heteroatoms independently selected from nitrogen, oxygen, and sulfur. In some embodiments, Cy¹ is a 3-7 membered saturated or partially unsaturated monocyclic carbocyclic ring. In some embodiments, Cy¹ is a 7-12 membered saturated or partially unsaturated bicyclic heterocyclic ring having 1-4 heteroatoms independently selected from nitrogen, oxygen, and sulfur.

In some embodiments, $Cy^1(R^5)_n$ taken together is selected from the following:

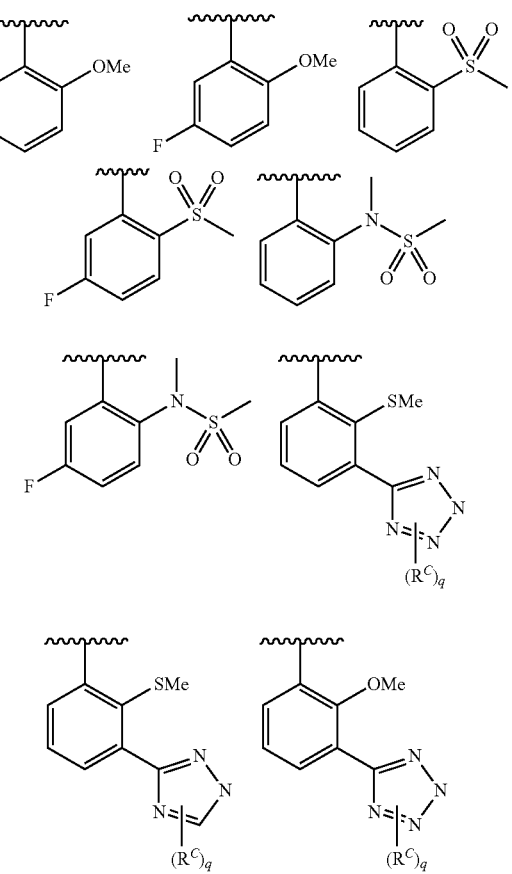

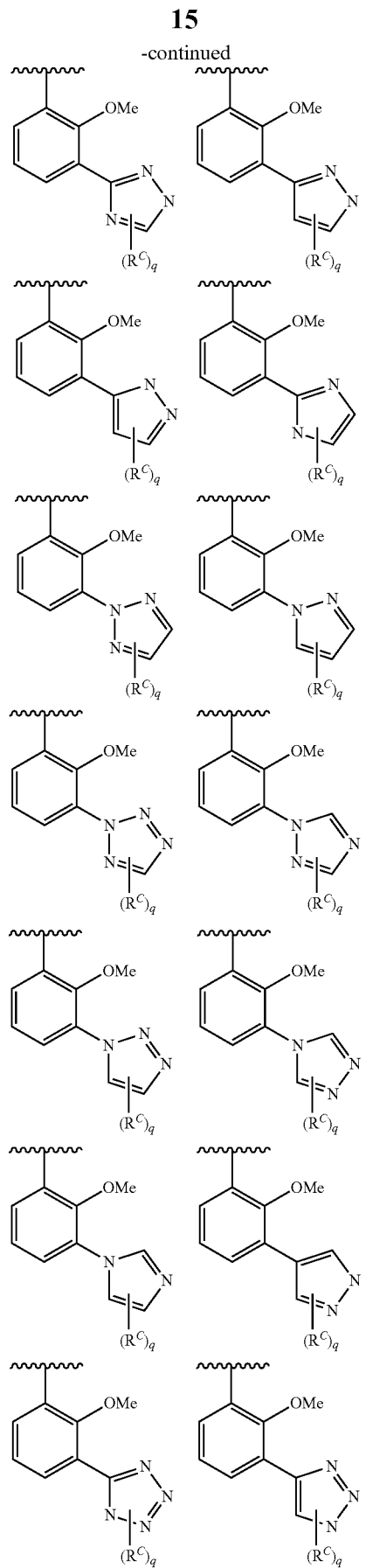
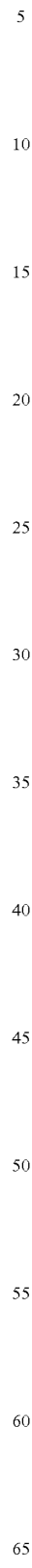
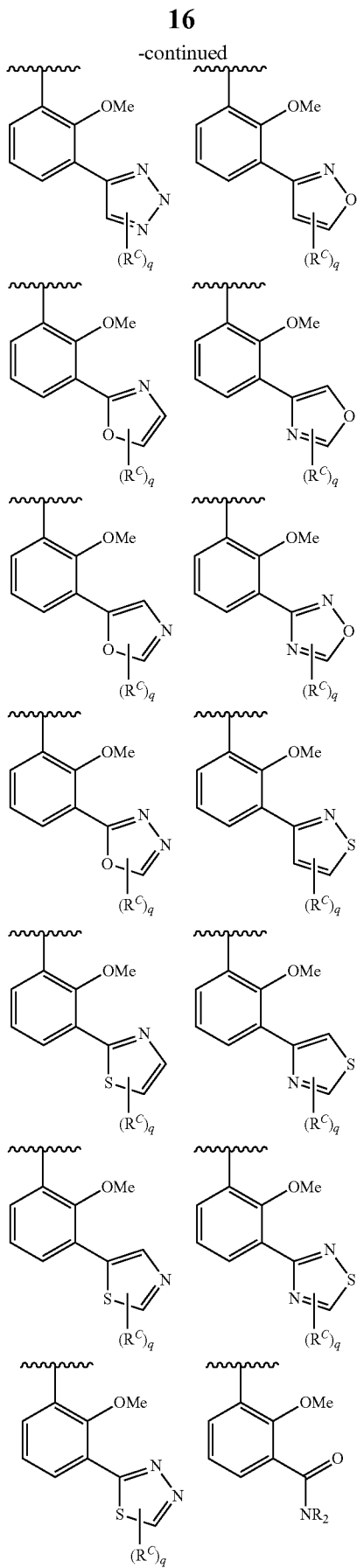

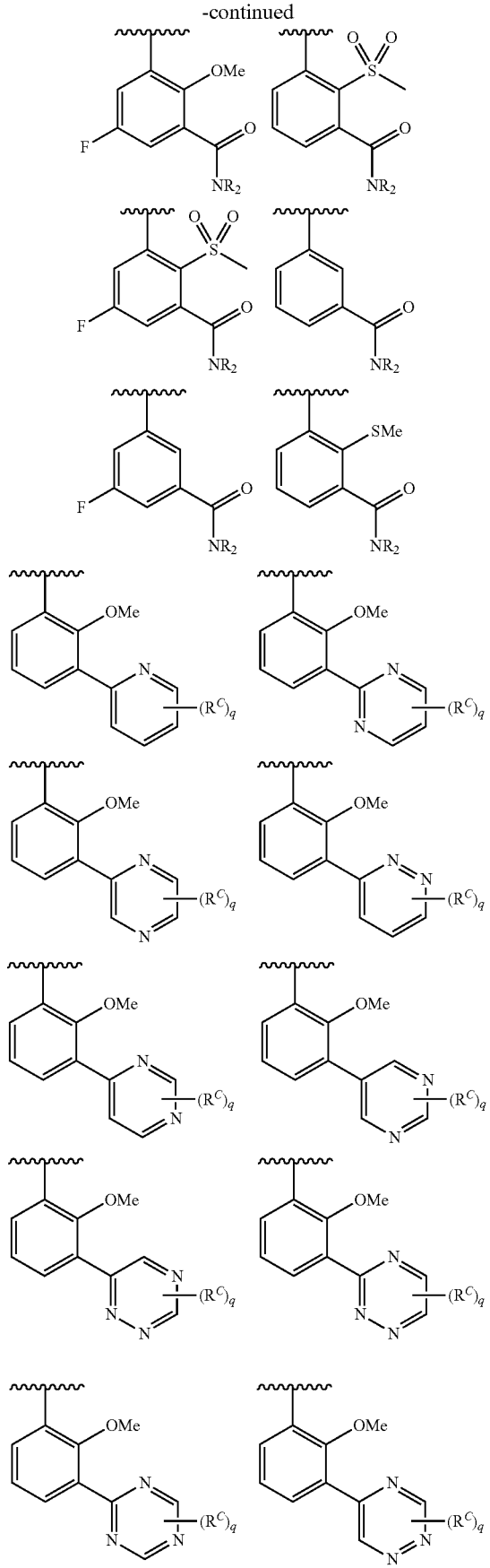
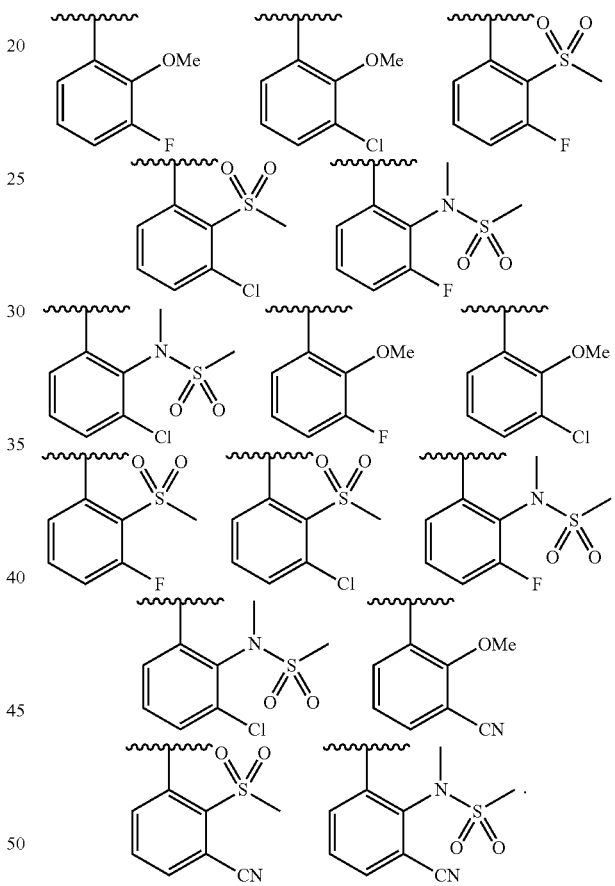
wherein each of R, $R^C$, and q is as defined above and described in embodiments herein, both singly and in combination.
In some embodiments, $Cy^1(R^5)_n$ taken together is selected from the groups in the preceding paragraph or the following:
In some embodiments, $Cy^1(R^5)_n$ taken together is selected from the groups in the preceding two paragraph or the following:
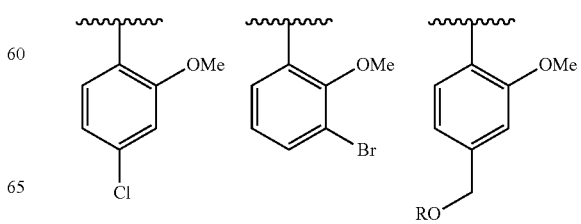

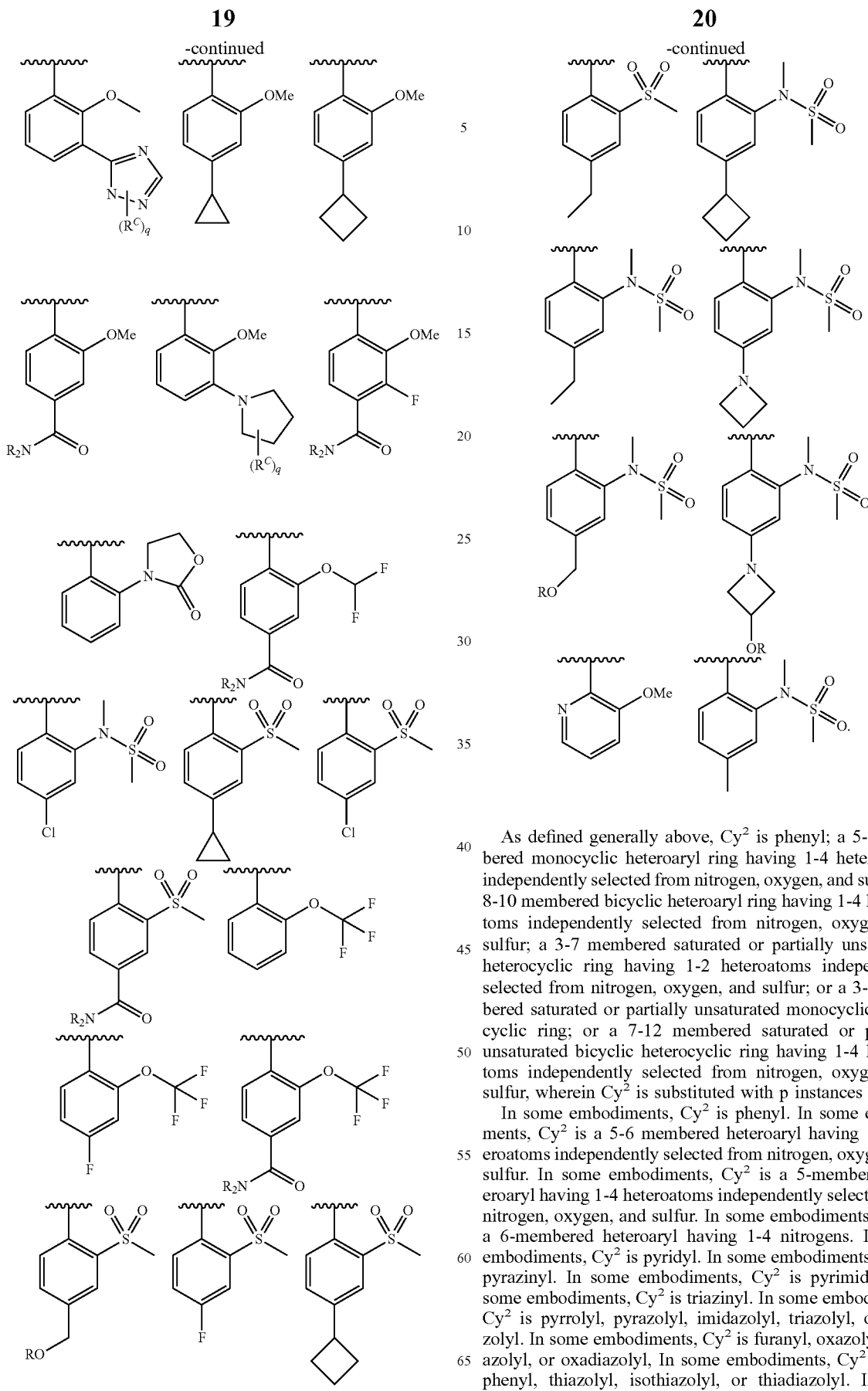

As defined generally above, $Cy^2$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^2$ is substituted with p instances of $R^6$.

In some embodiments, $Cy^2$ is phenyl. In some embodiments, $Cy^2$ is a 5-6 membered heteroaryl having 1-4 heteroatoms independently selected from nitrogen, oxygen, and sulfur. In some embodiments, $Cy^2$ is a 5-membered heteroaryl having 1-4 heteroatoms independently selected from nitrogen, oxygen, and sulfur. In some embodiments, $Cy^2$ is a 6-membered heteroaryl having 1-4 nitrogens. In some embodiments, $Cy^2$ is pyridyl. In some embodiments, $Cy^2$ is pyrazinyl. In some embodiments, $Cy^2$ is pyrimidinyl. In some embodiments, $Cy^2$ is triazinyl. In some embodiments, $Cy^2$ is pyrrolyl, pyrazolyl, imidazolyl, triazolyl, or tetrazolyl. In some embodiments, $Cy^2$ is furanyl, oxazolyl, isoxazolyl, or oxadiazolyl, In some embodiments, $Cy^2$ is thiophenyl, thiazolyl, isothiazolyl, or thiadiazolyl. In some embodiments, $Cy^2$ is an 8-10 membered bicyclic heteroaryl ring having 1-4 heteroatoms independently selected from nitrogen, oxygen, and sulfur. In some embodiments, $Cy^2$ is a 3-7 membered saturated or partially unsaturated heterocyclic ring having 1-2 heteroatoms independently selected from nitrogen, oxygen, and sulfur. In some embodiments, $Cy^2$ is a 3-7 membered saturated or partially unsaturated monocyclic carbocyclic ring. In some embodiments, $Cy^2$ is $C_{3-7}$ cycloalkyl. In some embodiments, $Cy^2$ is cyclopropyl. In some embodiments, $Cy^2$ is a 7-12 membered saturated or partially unsaturated bicyclic heterocyclic ring having 1-4 heteroatoms independently selected from nitrogen, oxygen, and sulfur.

In some embodiments, $Cy^2$ is selected from the following, each of which is substituted by p instances of $R^6$:

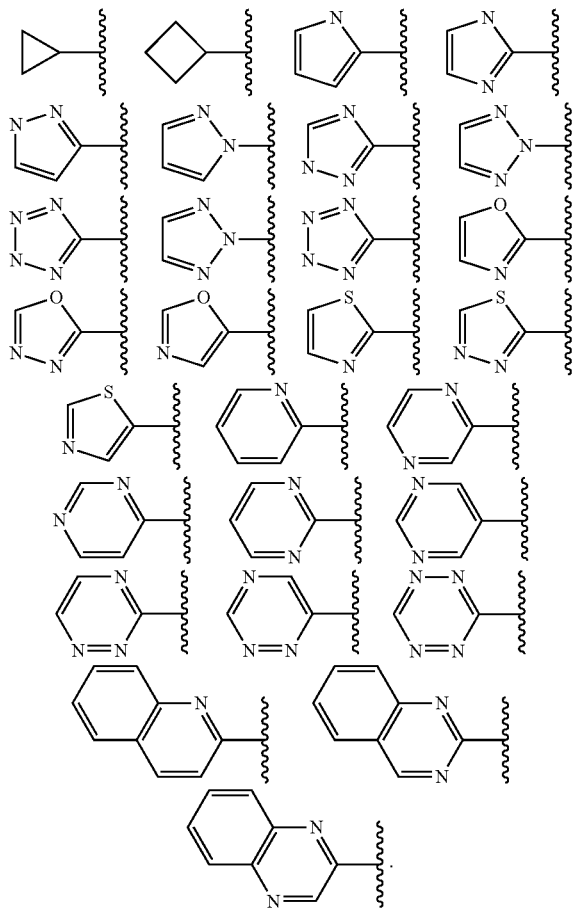

In some embodiments, $Cy^2$ is selected from the groups in the preceding paragraph, or the following, each of which is substituted by p instances of $R^6$:

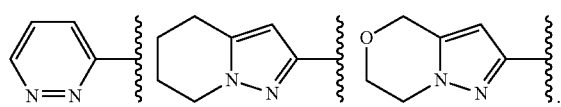

In some embodiments, p is 1 or 2 and at least one instance of $R^6$ is —CN, —$CH_3$, —$CHF_2$, or —$CF_3$.

As defined generally above, $L^1$ is a covalent bond or a $C_{1-4}$ bivalent saturated or unsaturated, straight or branched hydrocarbon chain wherein one or two methylene units of the chain are optionally and independently replaced by —C($R^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C($R^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is —N(R)—. In some embodiments, $L^1$ is —N(H)—.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, the present invention provides a compound of formula I, wherein $L^1$ is —N(H)—, thereby forming a compound of formula I-a:

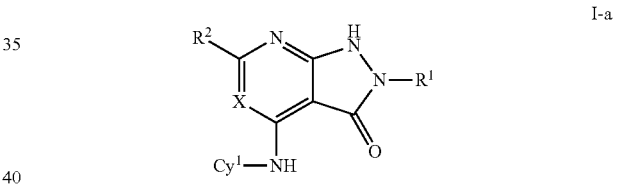

or a pharmaceutically acceptable salt thereof, wherein each of X, $Cy^1$, $R^1$, and $R^2$ is as defined above and described in embodiments herein, both singly and in combination.

In some embodiments, the present invention provides a compound of formula I, wherein X is N or C($R^3$), thereby forming a compound of formulas I-b or I-c respectively:

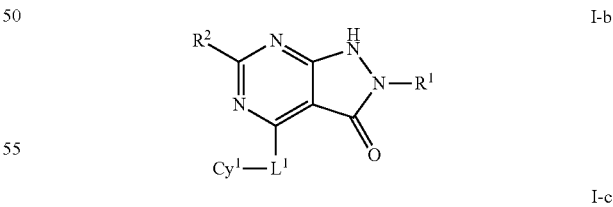

or a pharmaceutically acceptable salt thereof, wherein each of $Cy^1$, $L^1$, $R^1$, $R^2$, and $R^3$ is as defined above and described in embodiments herein, both singly and in combination.

In some embodiments, the present invention provides a compound of formula I-a, wherein $L^1$ is N or $C(R^3)$, thereby forming a compound of formulas II-a or II-b respectively:

II-a
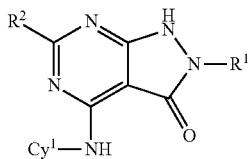

II-b

or a pharmaceutically acceptable salt thereof, wherein each of $Cy^1$, $R^1$, $R^2$, and $R^3$ is as defined above and described in embodiments herein, both singly and in combination.

In some embodiments, the present invention provides a compound of formula II-a or II-b wherein $Cy^1$ is phenyl, thereby forming a compound of formulas III-a or III-b respectively:

III-a
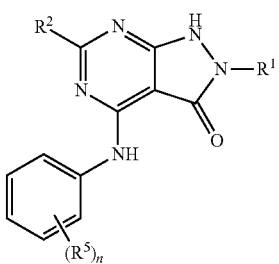

III-b
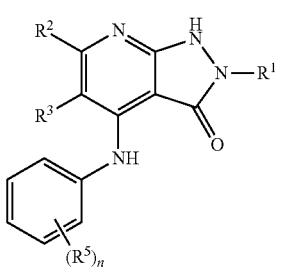

or a pharmaceutically acceptable salt thereof, wherein each of $R^1$, $R^2$, $R^3$, $R^5$, and n is as defined above and described in embodiments herein, both singly and in combination.

In some embodiments, the present invention provides a compound of formula III-a or III-b, wherein n is 1, 2 or 3, and at least one instance of $R^5$ is ortho to the NH point of attachment, thereby forming a compound of formulas IV-a or IV-b respectively:

IV-a
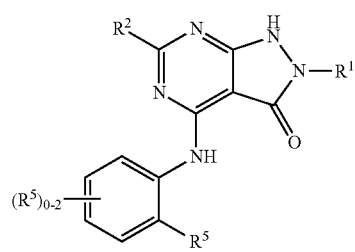

IV-b
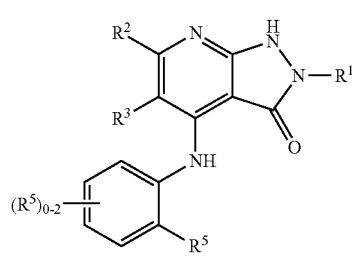

or a pharmaceutically acceptable salt thereof, wherein each of $R^1$, $R^2$, $R^3$, and $R^5$ is as defined above and described in embodiments herein, both singly and in combination.

In some embodiments, the present invention provides a compound of formula IV-a or IV-b, wherein the ortho $R^5$ group is —OR, —S(O)$_2$R, —C(O)NR$_2$, or —N(R)S(O)$_2$R, thereby forming a compound of formulas V-a, V-b, V-c, V-d, V-e, V-f, V-g, or V-h respectively:

V-a
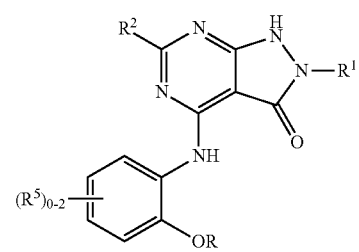

V-b
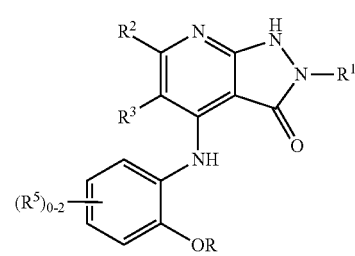

V-c
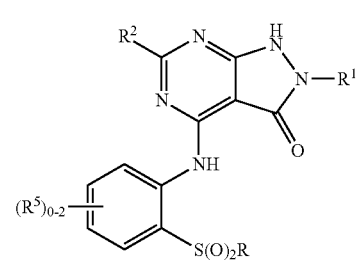

-continued

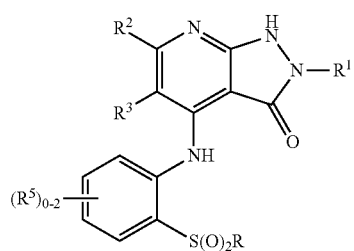

V-d

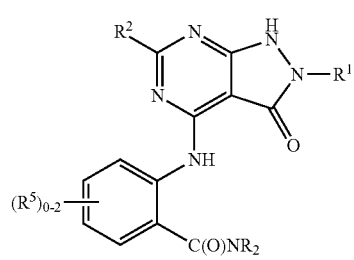

V-e

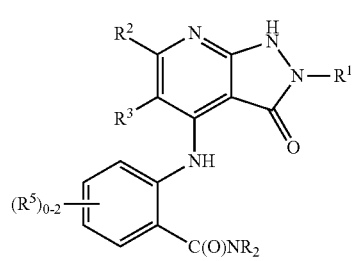

V-f

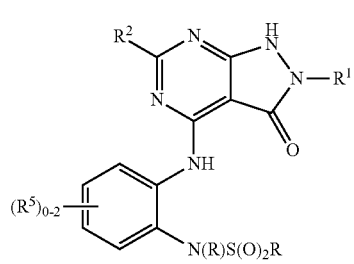

V-g

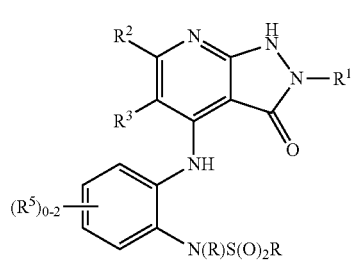

V-h or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula V-a or V-b, wherein a second $R^5$ group ($R^{5b}$) is meta to the NH point of attachment, thereby forming a compound of formulas VI-a, or VI-b respectively:

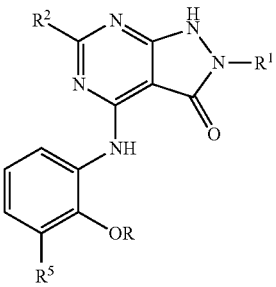

VI-a

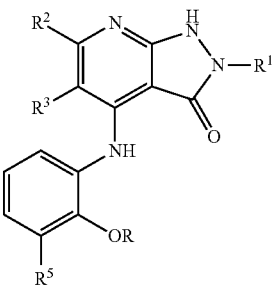

VI-b or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula VI-a or VI-b, wherein $R^5$ is $R^B$. In some embodiments, the present invention provides a compound of formula VI-a or VI-b, wherein $R^5$ is —C(O)NR$_2$ or a 5-6 membered monocyclic heteroaryl ring having 1-4 heteroatoms independently selected from nitrogen, oxygen, and sulfur, said ring being substituted by q instances of $R^C$.

In some embodiments, the present invention provides a compound of formula VI-a or VI-b, wherein —OR is methoxy, fluoromethoxy, or difluoromethoxy.

In some embodiments, the present invention provides a compound of formula II-a or II-b wherein $Cy^1$ is pyridyl, n is 2, and one instance of $R^5$ is oxo, thereby forming a pyridone compound of formulas VII-a or VII-b respectively:

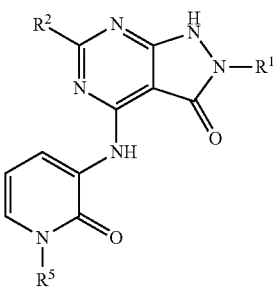

VII-a

-continued

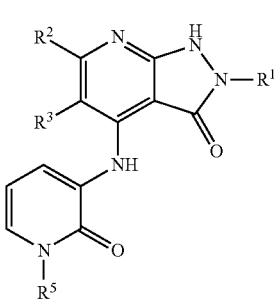
VII-b or a pharmaceutically acceptable salt thereof, wherein each of $R^1$, $R^2$, $R^3$, and $R^5$, is as defined above and described in embodiments herein, both singly and in combination.

As described above, in certain embodiments, the present invention provides a compound of formula VIII:

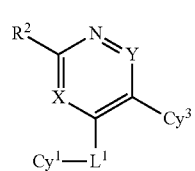
VIII or a pharmaceutically acceptable salt thereof, wherein:
X is N or $C(R^3)$;
Y is N or $C(R^1)$;
$R^1$ is H, D, or halogen;
R, $R^D$, or —OR;
$R^2$ is H, $R^C$, —N(R)C(O)$Cy^2$, —N(R)S(O)$_2Cy^2$, —N(R)$Cy^2$, —O$Cy^2$, —S$Cy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$; each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur; wherein $Cy^1$ is substituted with n instances of $R^5$; and; wherein $Cy^2$ is substituted with p instances of $R^6$;
$Cy^3$ is a 5-6 membered monocyclic partially unsaturated or heteroaromatic ring having 1-4 heteroatoms independently selected from nitrogen, oxygen, and sulfur; wherein $Cy^3$ is substituted with r instances of $R^8$;
$L^1$ is a covalent bond or a $C_{1-4}$ bivalent saturated or unsaturated, straight or branched hydrocarbon chain wherein one or two methylene units of the chain are optionally and independently replaced by —C($R^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —OC(O)N(R)—, —N(R)C(O)O—, —S—, —S(O)— or —S(O)$_2$—;
each instance of $R^4$, $R^5$, $R^6$, $R^7$ and $R^8$ is independently $R^A$ or $R^B$, and is substituted by q instances of $R^C$;
each instance of $R^A$ is independently oxo, halogen, —CN, —NO$_2$, —OR, —OR$^D$, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;
each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^D$ is a $C_{1-4}$ aliphatic group wherein one or more hydrogens are replaced by deuterium;
each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and
each of m, n, p, q, and r is independently 0, 1, 2, 3, or 4.

As defined generally above, X is N or $C(R^3)$. In some embodiments, X is N. In some embodiments, X is $C(R^3)$. In some embodiments, X is C(H). In some embodiments, X is $C(R^3)$, where $R^3$ is halogen. In some embodiments, X is $C(R^3)$, where $R^3$ is fluoro.

As defined generally above, Y is N or $C(R^1)$. In some embodiments, Y is N. In some embodiments, Y is $C(R^1)$. In some embodiments, Y is C(H). In some embodiments, Y is C(D). In some embodiments, Y is $C(R^1)$, where $R^1$ is halogen. In some embodiments, X is $C(R^1)$, where $R^3$ is fluoro.

As defined generally above, $R^1$ is H, D, or halogen. In some embodiments, $R^1$ is H. In some embodiments, $R^1$ is D. In some embodiments, $R^1$ is halogen. In some embodiments, $R^1$ is fluoro.

As defined generally above, R² is H, R^C, —N(R)C(O)Cy², —N(R)C(O)Cy², —N(R)Cy², —OCy², —SCy², or Cy². In some embodiments, R² is H. In some embodiments, R² is R^C, —N(R)C(O)Cy², —N(R)Cy², —OCy², —SCy², or Cy². In some embodiments, R² is R^C. In some embodiments, R² is —N(R)C(O)R. In some embodiments, R² is —N(R)C(O)Cy², —N(R)Cy², or Cy². In some embodiments, R² is —N(R)C(O)R, —N(R)C(O)Cy², —N(R)Cy², or Cy². In some embodiments, R² is —N(H)C(O)R, —N(H)C(O)Cy², —N(H)Cy², or Cy². In some embodiments, R² is —N(H)C(O)R, —N(H)C(O)Cy², or —N(H)Cy². In some embodiments, R² is —N(H)C(O)R. In some embodiments, R² is —N(H)C(O)R wherein R in this instance is optionally substituted $C_{1-6}$ aliphatic. In some embodiments, R² is —N(H)C(O)Cy². In some embodiments, R² is —N(H)Cy². In some embodiments, R² is —N(H)C(O)Cy² where Cy² is cyclopropyl. In some embodiments, R² is

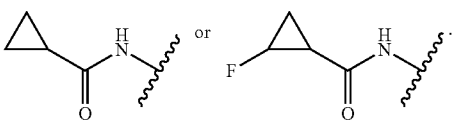 [SMILES: *NC(=O)C1CC1 ; "or" ; *NC(=O)C1CC1F ; "."]

In some embodiments, R² and R³ are taken together with their intervening atoms to form a 4-7 membered partially unsaturated or aromatic ring having 0-3 heteroatoms independently selected from nitrogen, oxygen, and sulfur; wherein said ring is substituted with m instances of R⁴. In some embodiments, R² and R³ are taken together with their intervening atoms to form a 5-membered partially unsaturated or aromatic ring having 1-3 heteroatoms independently selected from nitrogen, oxygen, and sulfur; wherein said ring is substituted with m instances of R⁴.

As defined generally above, Cy¹ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy¹ is substituted with n instances of R⁵.

In some embodiments, Cy¹ is phenyl. In some embodiments, Cy¹ is a 5-6 membered heteroaryl having 1-4 heteroatoms independently selected from nitrogen, oxygen, and sulfur. In some embodiments, Cy¹ is a 5-membered heteroaryl having 1-4 heteroatoms independently selected from nitrogen, oxygen, and sulfur. In some embodiments, Cy¹ is a 6-membered heteroaryl having 1-4 nitrogens. In some embodiments, Cy¹ is pyridyl. In some embodiments, Cy¹ is pyrazinyl. In some embodiments, Cy¹ is pyrimidinyl. In some embodiments, Cy¹ is triazinyl. In some embodiments, Cy¹ is pyrrolyl, pyrazolyl, imidazolyl, triazolyl, or tetrazolyl. In some embodiments, Cy¹ is furanyl, oxazolyl, isoxazolyl, or oxadiazolyl. In some embodiments, Cy¹ is thiophenyl, thiazolyl, isothiazolyl, or thiadiazolyl. In some embodiments, Cy¹ is an 8-10 membered bicyclic heteroaryl ring having 1-4 heteroatoms independently selected from nitrogen, oxygen, and sulfur. In some embodiments, Cy¹ is a 3-7 membered saturated or partially unsaturated heterocyclic ring having 1-2 heteroatoms independently selected from nitrogen, oxygen, and sulfur. In some embodiments, Cy¹ is a 3-7 membered saturated or partially unsaturated monocyclic carbocyclic ring. In some embodiments, Cy¹ is a 7-12 membered saturated or partially unsaturated bicyclic heterocyclic ring having 1-4 heteroatoms independently selected from nitrogen, oxygen, and sulfur.

In some embodiments, $Cy^1(R^5)_n$ taken together is selected from the following:

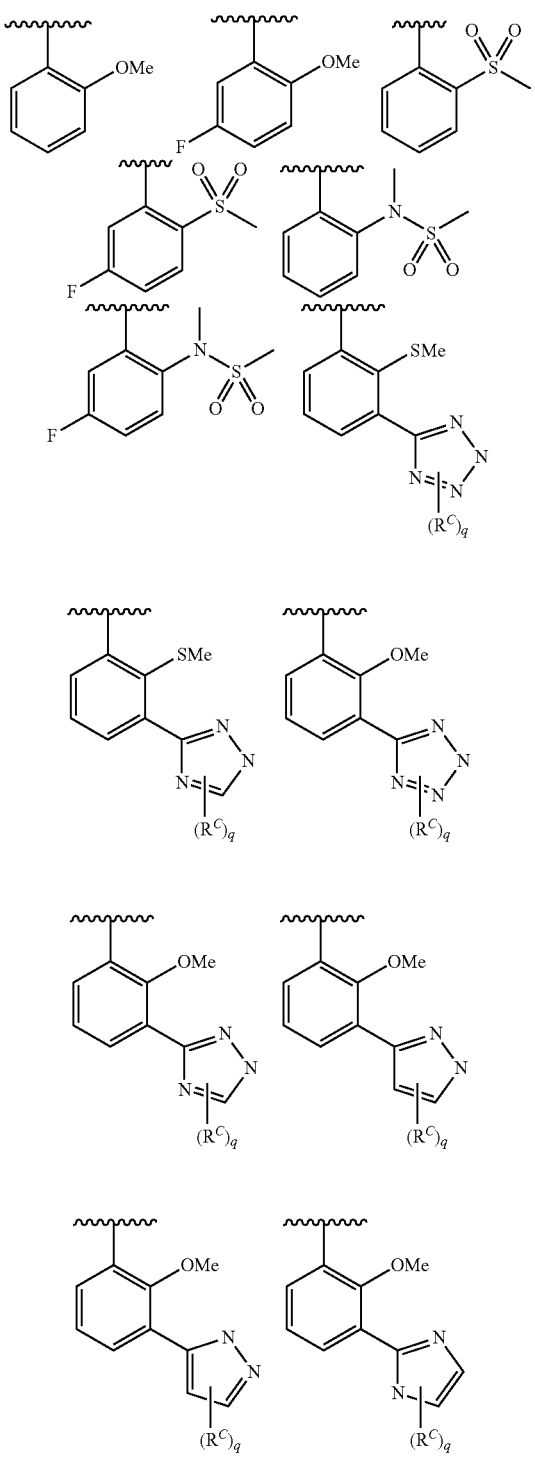

-continued
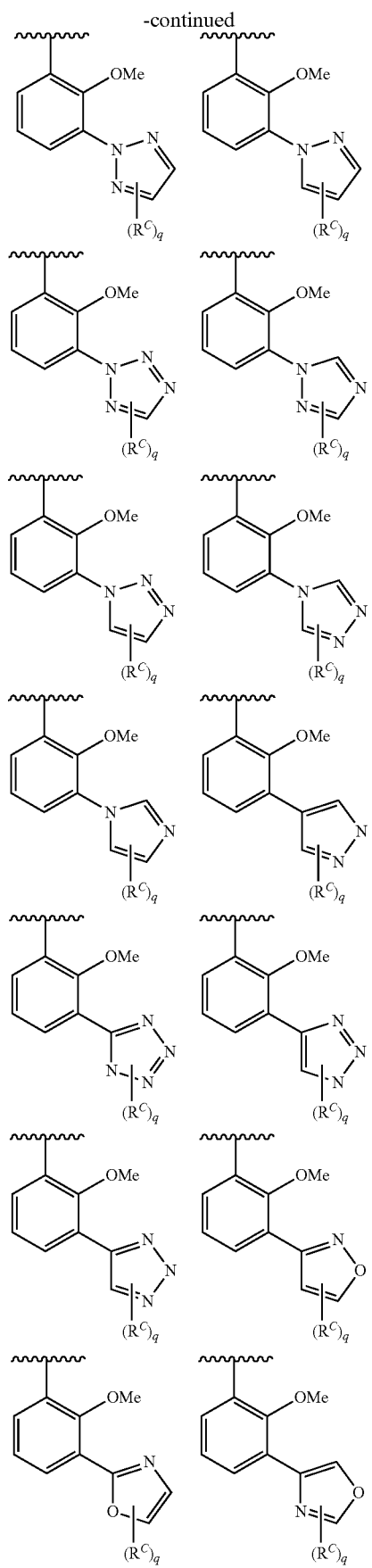
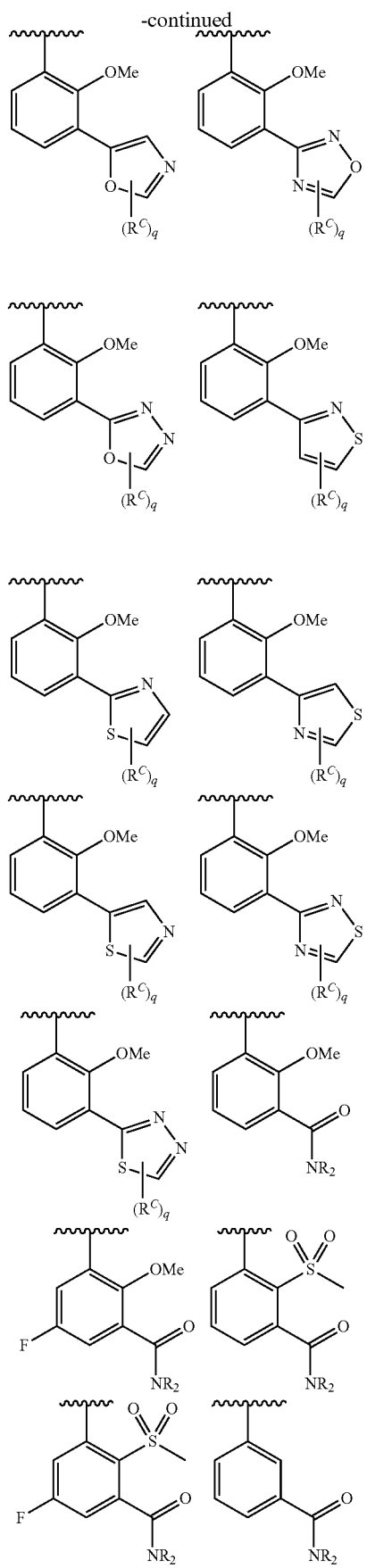

-continued

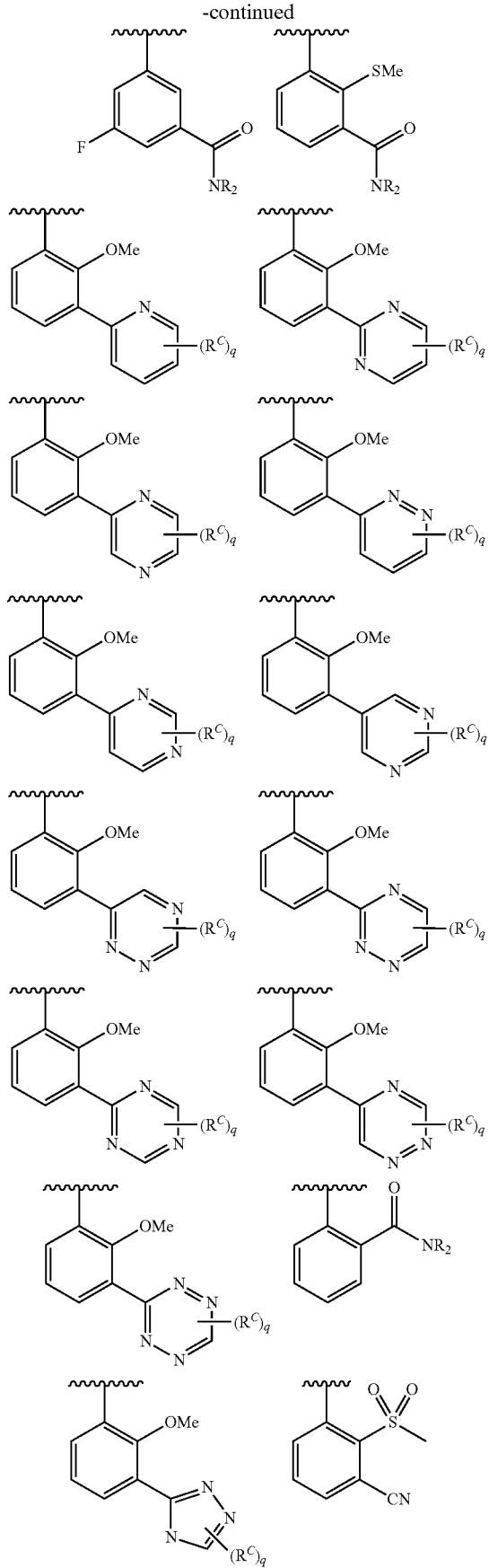

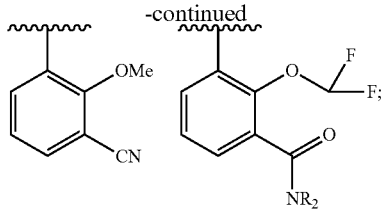

-continued wherein each of R, $R^C$, and q is as defined above and described in embodiments herein, both singly and in combination.

As defined generally above, $Cy^2$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^2$ is substituted with p instances of $R^6$.

In some embodiments, $Cy^2$ is phenyl. In some embodiments, $Cy^2$ is a 5-6 membered heteroaryl having 1-4 heteroatoms independently selected from nitrogen, oxygen, and sulfur. In some embodiments, $Cy^2$ is a 5-membered heteroaryl having 1-4 heteroatoms independently selected from nitrogen, oxygen, and sulfur. In some embodiments, $Cy^2$ is a 6-membered heteroaryl having 1-4 nitrogens. In some embodiments, $Cy^2$ is pyridyl. In some embodiments, $Cy^2$ is pyrazinyl. In some embodiments, $Cy^2$ is pyrimidinyl. In some embodiments, $Cy^2$ is triazinyl. In some embodiments, $Cy^2$ is pyrrolyl, pyrazolyl, imidazolyl, triazolyl, or tetrazolyl. In some embodiments, $Cy^2$ is furanyl, oxazolyl, isoxazolyl, or oxadiazolyl, In some embodiments, $Cy^2$ is thiophenyl, thiazolyl, isothiazolyl, or thiadiazolyl. In some embodiments, $Cy^2$ is an 8-10 membered bicyclic heteroaryl ring having 1-4 heteroatoms independently selected from nitrogen, oxygen, and sulfur. In some embodiments, $Cy^2$ is a 3-7 membered saturated or partially unsaturated heterocyclic ring having 1-2 heteroatoms independently selected from nitrogen, oxygen, and sulfur. In some embodiments, $Cy^2$ is a 3-7 membered saturated or partially unsaturated monocyclic carbocyclic ring. In some embodiments, $Cy^2$ is $C_{3-7}$ cycloalkyl. In some embodiments, $Cy^2$ is cyclopropyl. In some embodiments, $Cy^2$ is a 7-12 membered saturated or partially unsaturated bicyclic heterocyclic ring having 1-4 heteroatoms independently selected from nitrogen, oxygen, and sulfur.

In some embodiments, $Cy^2$ is selected from the following, each of which is substituted by p instances of $R^6$:

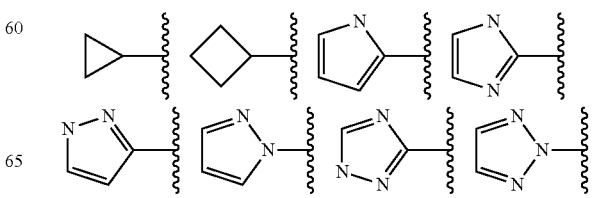

-continued

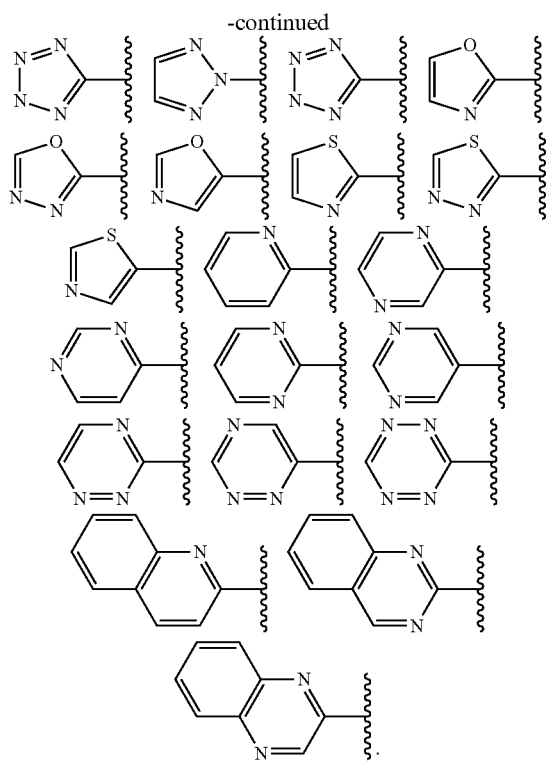

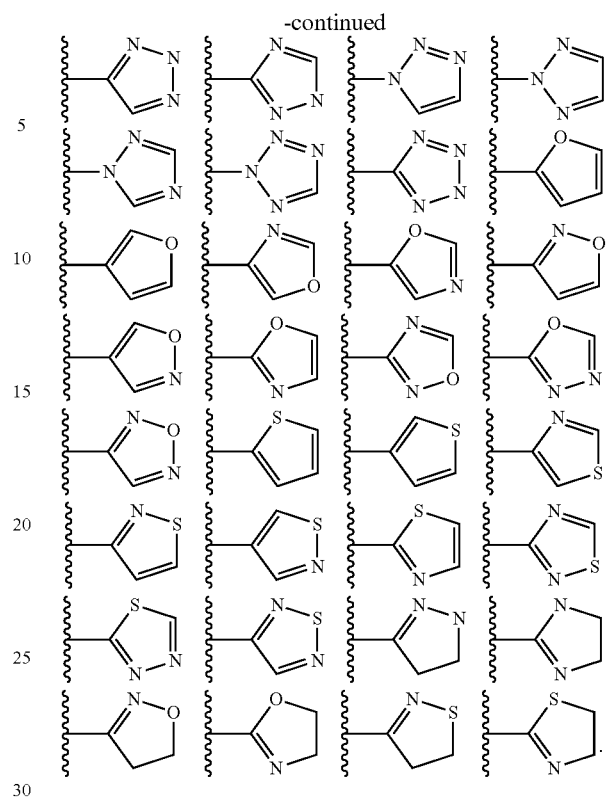

In some embodiments, Cy² is selected from the groups in the preceding paragraph, or the following, which is substituted by p instances of $R^6$:

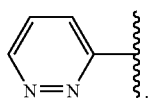

As defined generally above, $Cy^3$ is a 5-6 membered monocyclic partially unsaturated or heteroaromatic ring having 1-4 heteroatoms independently selected from nitrogen, oxygen, and sulfur; wherein $Cy^3$ is substituted with r instances of $R^8$. In some embodiments, $Cy^3$ is a 5-membered monocyclic partially unsaturated or heteroaromatic ring ring having 1-4 heteroatoms independently selected from nitrogen, oxygen, and sulfur. In some embodiments, $Cy^3$ is a 5-membered monocyclic partially unsaturated ring having 1-3 heteroatoms independently selected from nitrogen, oxygen, and sulfur. In some embodiments, $Cy^3$ is a 5-membered monocyclic heteroaromatic ring having 1-3 heteroatoms independently selected from nitrogen, oxygen, and sulfur.

In some embodiments, $Cy^3$ is selected from the following, each of which is substituted by r instances of $R^8$:

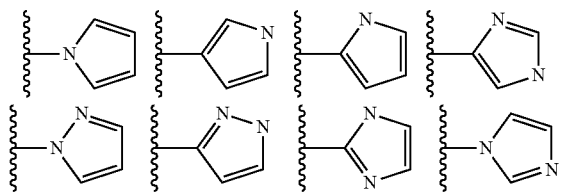

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—. In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—. In some embodiments, $L^1$ is —N(R)—. In some embodiments, $L^1$ is —N(H)—.

As defined generally above, $R^8$ is independently $R^A$ or $R^B$, and is substituted by q instances of $R^C$. In some embodiments, $R^8$ is halogen or $C_{1-6}$ aliphatic substituted by 1-2 $R^C$. In some embodiments, $R^8$ is halogen. In some embodiments, $R^8$ is $C_{1-6}$ aliphatic substituted by 0-2 $R^C$. In some embodiments, $R^8$ is chloro or fluoro. In some embodiments, $R^8$ is hydroxymethyl. In some embodiments, $R^8$ is chloro, fluoro, methyl, cyclopropyl, or hydroxymethyl. In some embodiments, $R^8$ is chloro, fluoro, or hydroxymethyl.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, the present invention provides a compound of formula VIII, wherein $L^1$ is —N(H)—, thereby forming a compound of formula VIII-a:

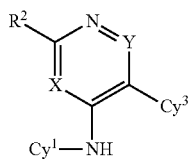

VIII-a or a pharmaceutically acceptable salt thereof, wherein each of X, $Cy^1$, $R^1$, and $R^2$ is as defined above and described in embodiments herein, both singly and in combination.

In some embodiments, the present invention provides a compound of formula VIII, wherein X is $C(R^3)$ and Y is $C(R^1)$, or X is $C(R^3)$ and Y is N, or X is N and Y is $C(R^1)$, or both X and Y are N; thereby forming a compound of formulas IX-a, IX-b, IX-c, or IX-d respectively:

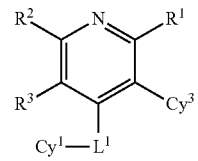

IX-a

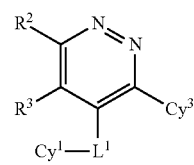

IX-b

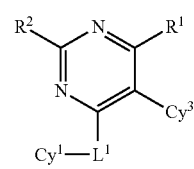

IX-d

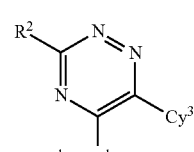

IX-b or a pharmaceutically acceptable salt thereof, wherein each of $Cy^1$, $Cy^3$, $L^1$, $R^1$, $R^2$, and $R^3$ is as defined above and described in embodiments herein, both singly and in combination.

In some embodiments, the present invention provides a compound of formulas IX-a, IX-b, IX-c, or IX-d, wherein $L^1$ is —N(H)—, thereby forming a compound of formulas X-a or X-b, X-c, or X-d respectively:

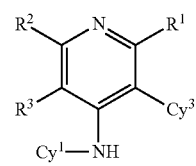

X-a

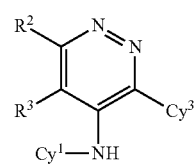

X-b

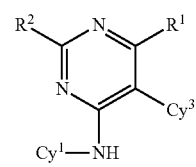

X-c

X-d or a pharmaceutically acceptable salt thereof, wherein each of $Cy^1$, $Cy^3$, $R^1$, $R^2$, and $R^3$ is as defined above and described in embodiments herein, both singly and in combination.

In some embodiments, the present invention provides a compound of formula VIII-a, wherein $Cy^1$ is phenyl, thereby forming a compound of formula XI-a:

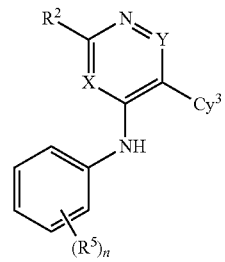

XI-a or a pharmaceutically acceptable salt thereof, wherein each of X, Y, $R^2$, $R^5$, and n is as defined above and described in embodiments herein, both singly and in combination.

In some embodiments, the present invention provides a compound of formula X-a, X-b, X-c, or X-d wherein $Cy^1$ is phenyl, thereby forming a compound of formulas XI-b, XI-c, XI-d, or XI-e respectively:

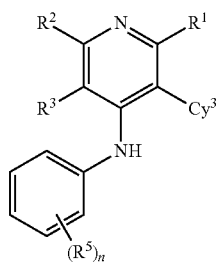

XI-b

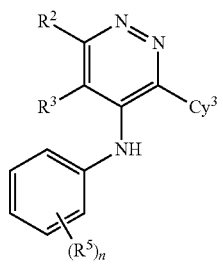

XI-c

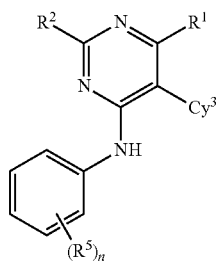

XI-d

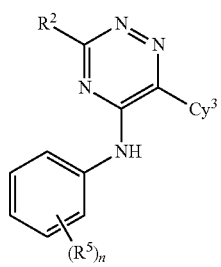

XI-e or a pharmaceutically acceptable salt thereof, wherein each of $R^1$, $R^2$, $R^3$, $R^5$, and n is as defined above and described in embodiments herein, both singly and in combination.

In some embodiments, the present invention provides a compound of formula XI-a, wherein n is 1, 2 or 3, and at least one instance of $R^5$ is ortho to the NH point of attachment, thereby forming a compound of formula XII-a:

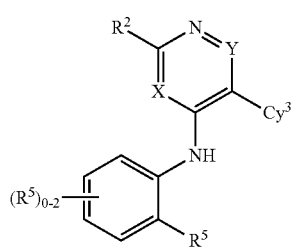

XII-a or a pharmaceutically acceptable salt thereof, wherein each of X, Y, $Cy^3$, $R^2$, and $R^5$ is as defined above and described in embodiments herein, both singly and in combination.

In some embodiments, the present invention provides a compound of formula XI-b, XI-c, XI-d, or XI-e wherein n is 1, 2 or 3, and at least one instance of $R^5$ is ortho to the NH point of attachment, thereby forming a compound of formula XII-b, XII-c, XII-d, or XII-e respectively:

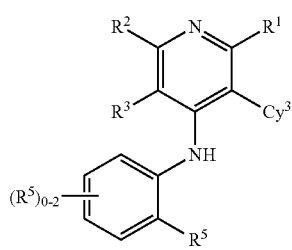

XII-b

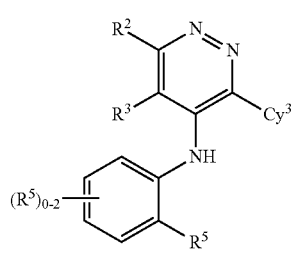

XII-c

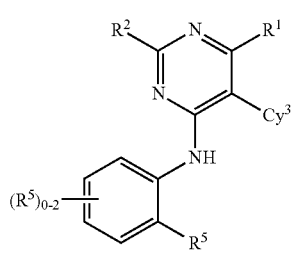

XII-d

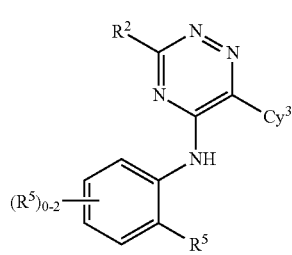

XII-e or a pharmaceutically acceptable salt thereof, wherein each of $Cy^3$, $R^1$, $R^2$, $R^3$, and $R^5$ is as defined above and described in embodiments herein, both singly and in combination.

In some embodiments, the present invention provides a compound of formula XII-a, wherein the ortho $R^5$ group is —OR, —S(O)$_2$R, —C(O)NR$_2$, or —N(R)S(O)$_2$R, thereby forming a compound of formulas XII-a-i, XII-a-ii, XII-a-iii, or XII-a-iv respectively:

XII-a-i

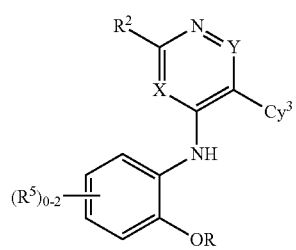

XII-a-ii

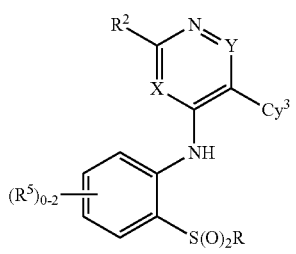

XII-a-iii

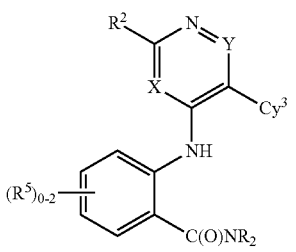

XII-a-iv

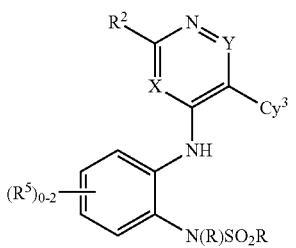

or a pharmaceutically acceptable salt thereof, wherein each of X, Y, Cy³, R, R¹, R², R³, and R⁵ is as defined above and described in embodiments herein, both singly and in combination.

In some embodiments, the present invention provides a compound of formula XII-b, wherein the ortho R⁵ group is —OR, —S(O)₂R, —C(O)NR₂, or —N(R)S(O)₂R, thereby forming a compound of formulas XII-b-i, XII-b-ii, XII-b-iii, or XII-b-iv respectively:

XII-b-i

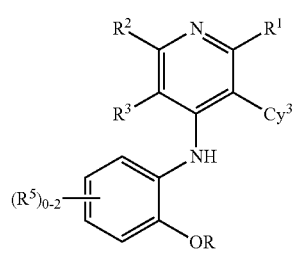

XII-b-ii

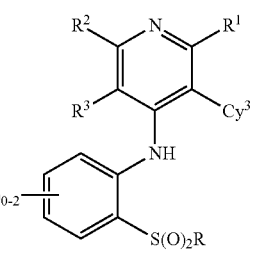

XII-b-iii

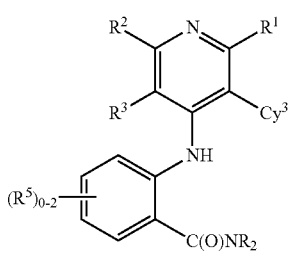

XII-b-iv

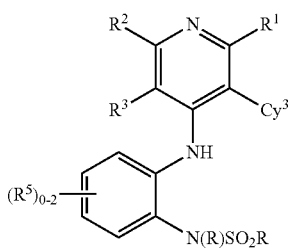

or a pharmaceutically acceptable salt thereof, wherein each of Cy³, R, R¹, R², R³, and R⁵ is as defined above and described in embodiments herein, both singly and in combination.

In some embodiments, the present invention provides a compound of formula XII-c, wherein the ortho R⁵ group is —OR, —S(O)₂R, —C(O)NR₂, or —N(R)S(O)₂R, thereby forming a compound of formulas XII-c-i, XII-c-ii, XII-c-iii, or XII-c-iv respectively:

XII-c-i

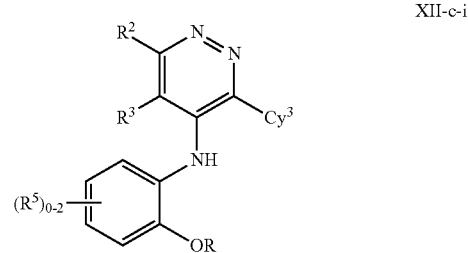

XII-c-ii

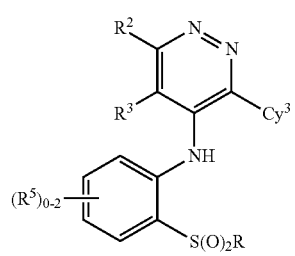

-continued

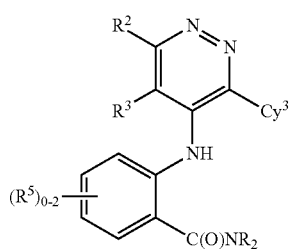
XII-c-iii

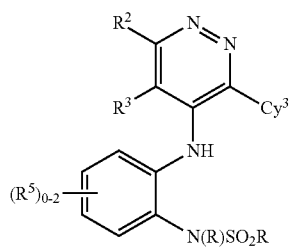
XII-c-iv or a pharmaceutically acceptable salt thereof, wherein each of $Cy^3$, R, $R^2$, $R^3$, and $R^5$ is as defined above and described in embodiments herein, both singly and in combination.

In some embodiments, the present invention provides a compound of formula XII-d, wherein the ortho $R^5$ group is —OR, —S(O)$_2$R, —C(O)NR$_2$, or —N(R)S(O)$_2$R, thereby forming a compound of formulas XII-d-i, XII-d-ii, XII-d-iii, or XII-d-iv respectively:

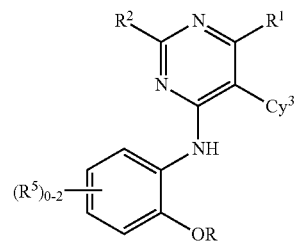
XII-d-i

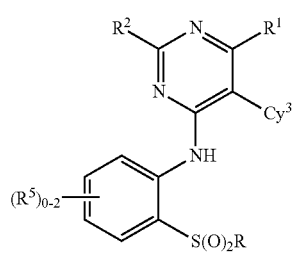
XII-d-ii

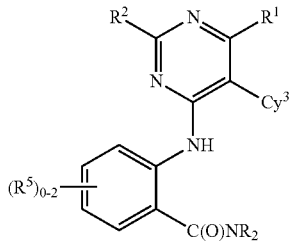
XII-d-iii

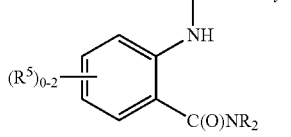
XII-d-iv or a pharmaceutically acceptable salt thereof, wherein each of $Cy^3$, R, $R^1$, $R^2$, and $R^5$ is as defined above and described in embodiments herein, both singly and in combination.

In some embodiments, the present invention provides a compound of formula XII-e, wherein the ortho $R^5$ group is —OR, —S(O)$_2$R, —C(O)NR$_2$, or —N(R)S(O)$_2$R, thereby forming a compound of formulas XII-e-i, XII-e-ii, XII-e-iii, or XII-e-iv respectively:

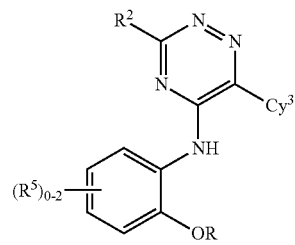
XII-e-i

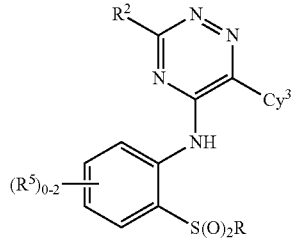
XII-e-ii

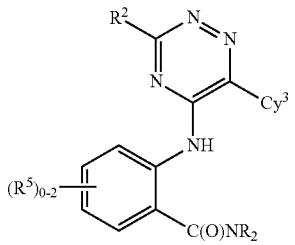
XII-e-iii

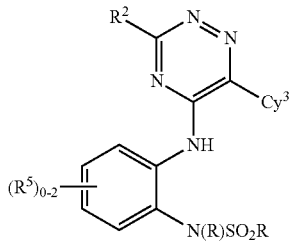
XII-e-iv or a pharmaceutically acceptable salt thereof, wherein each of $Cy^3$, R, $R^2$, and $R^5$ is as defined above and described in embodiments herein, both singly and in combination.

In some embodiments, the present invention provides a compound of formula XII-a-i, wherein a second R⁵ group is meta to the NH point of attachment, thereby forming a compound of formula XIII-a:

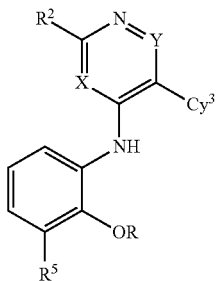

XIII-a or a pharmaceutically acceptable salt thereof, wherein each of X, Y, Cy³, R, R², and R⁵ is as defined above and described in embodiments herein, both singly and in combination.

In some embodiments, the present invention provides a compound of formula XII-b-i, XII-c-i, XII-d-i, or XII-e-i, wherein a second R⁵ group is meta to the NH point of attachment, thereby forming a compound of formula XIII-b, XIII-c, XIII-d, or XIII-e, respectively:

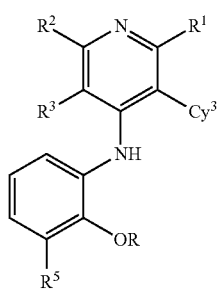

XIII-b

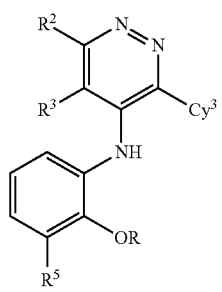

XIII-c

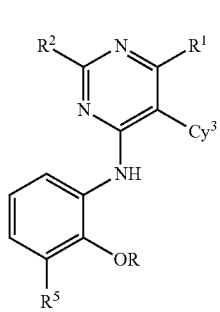

XIII-d

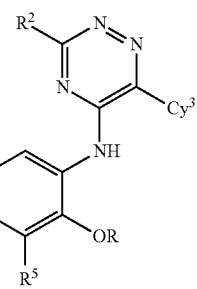

XIII-e or a pharmaceutically acceptable salt thereof, wherein each of Cy³, R, R¹, R², R³, and R⁵ is as defined above and described in embodiments herein, both singly and in combination.

In some embodiments, the present invention provides a compound of formula XIII-a, XIII-b, XIII-c, XIII-d, or XIII-e wherein R⁵ is R^B. In some embodiments, the present invention provides a compound of formula XIII-a, XIII-b, XIII-c, XIII-d, or XIII-e wherein R⁵ is —C(O)NR₂ or a 5-6 membered monocyclic heteroaryl ring having 1-4 heteroatoms independently selected from nitrogen, oxygen, and sulfur, said ring being substituted by q instances of R^C.

In some embodiments, the present invention provides a compound of formula XIII-a, XIII-b, XIII-c, XIII-d, or XIII-e wherein —OR is methoxy, fluoromethoxy, or difluoromethoxy.

In some embodiments, the present invention provides a compound of formula I-a, wherein Cy¹ is pyridyl, n is 2, and one instance of R⁵ is oxo, thereby forming a pyridone compound of formula XIV-a:

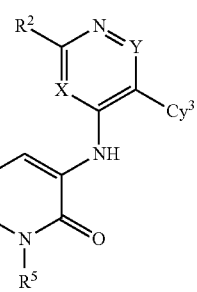

XIV-a or a pharmaceutically acceptable salt thereof, wherein each of X, Y, Cy³, R², and R⁵ is as defined above and described in embodiments herein, both singly and in combination.

In some embodiments, the present invention provides a compound of formula X-a or X-b, X-c, or X-d, wherein Cy¹ is pyridyl, n is 2, and one instance of R⁵ is oxo, thereby forming a pyridone compound of formula XV-a, XV-b, XV-c, or XV-d:

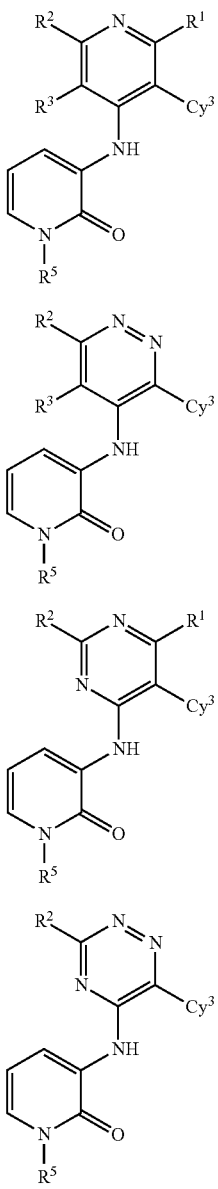

or a pharmaceutically acceptable salt thereof, wherein each of $Cy^3$, $R^1$, $R^2$, $R^3$, and $R^5$ is as defined above and described in embodiments herein, both singly and in combination.

As described above, in certain embodiments, the present invention provides a compound of formula XVI':

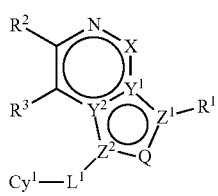

XVI' or a pharmaceutically acceptable salt thereof, wherein:
Q is CH or N;
X is N or $C(R^X)$;
one of $Y^1$, $Y^2$, $Z^1$, and $Z^2$ is N, and the other three are C;
$R^1$ is D, R, $R^D$, $-NR_2$, $-NRR^D$, $-N(R^D)_2$, $-N(R)C(O)NR_2$, $-N(R)C(NR)NR_2$, $-N(R)C(O)NRR^D$, $-N(R)C(NR)NRR^D$, $-OR$, or $-OR^D$;
$R^2$ is H, $R^C$, $-N(R)C(O)Cy^2$, $-N(R)S(O)_2Cy^2$, $-N(R)Cy^2$, $-OCy^2$, $-SCy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$; each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;
$L^1$ is a covalent bond or a $C_{1-4}$ bivalent saturated or unsaturated, straight or branched hydrocarbon chain wherein one or two methylene units of the chain are optionally and independently replaced by $-C(R^7)_2-$, $-N(R)-$, $-N(R)C(O)-$, $-C(O)N(R)-$, $-N(R)S(O)_2-$, $-S(O)_2N(R)-$, $-O-$, $-C(O)-$, $-OC(O)-$, $-C(O)O-$, $-S-$, $-S(O)-$ or $-S(O)_2-$;
each instance of $R^4$, $R^5$, $R^6$, and $R^7$ is independently $R^A$ or $R^B$, and is substituted by q instances of $R^C$;
each instance of $R^A$ is independently oxo, halogen, $-CN$, $-NO_2$, $-OR$, $-OR^D$, $-SR$, $-NR_2$, $-S(O)_2R$, $-S(O)_2NR_2$, $-S(O)R$, $-S(O)NR_2$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)C(NR)NR_2$, $-N(R)S(O)_2NR_2$, or $-N(R)S(O)_2R$;
each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, $-CN$, $-NO_2$, $-OR$, $-SR$, $-NR_2$, $-S(O)_2R$, $-S(O)_2NR_2$, $-S(O)R$, $-S(O)NR_2$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)C(NR)NR_2$, $-N(R)S(O)_2NR_2$, or $-N(R)S(O)_2R$ or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^D$ is a $C_{1-4}$ aliphatic group wherein one or more hydrogens are replaced by deuterium;

$R^X$ is H, halogen, or $C_{1-6}$ aliphatic each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

As defined generally above, Q is CH or N. In some embodiments, Q is CH. In some embodiments, Q is N.

As defined generally above, X is N or $C(R^X)$. In some embodiments, X is N. In some embodiments, X is $C(R^X)$. In some embodiments, X is C(H). In some embodiments, X is $C(R^X)$, where $R^X$ is halogen. In some embodiments, X is $C(R^X)$, where $R^X$ is fluoro.

As defined generally above, $R^1$ is D, R, $R^D$, —$NR_2$, —$NRR^D$, —$N(R^D)_2$, —$N(R)C(O)NR_2$, —$N(R)C(NR)NR_2$, —$N(R)C(O)NRR^D$, —$N(R)C(NR)NRR^D$, —OR, or —$OR^D$. In some embodiments, $R^1$ is D. In some embodiments, $R^1$ is R. In some embodiments, $R^1$ is $R^D$. In some embodiments, $R^1$ is —$NR_2$. In some embodiments, $R^1$ is —$NRR^D$. In some embodiments, $R^1$ is —$N(R^D)_2$. In some embodiments, $R^1$ is —OR. In some embodiments, $R^1$ is —$OR^D$. In some embodiments, $R^1$ is an optionally substituted $C_{1-6}$ aliphatic group. In some embodiments, $R^1$ is an optionally substituted ethyl group. In some embodiments, $R^1$ is hydrogen, methyl or —$CD_3$. In some embodiments, $R^1$ is hydrogen. In some embodiments, $R^1$ is methyl or —$CD_3$. In some embodiments, $R^1$ is methyl. In some embodiments, $R^1$ is —$CD_3$. In some embodiments, $R^1$ is —$OCH_3$. In some embodiments, $R^1$ is D, R, $R^D$, —$NR_2$, —$NRR^D$, —$N(R^D)_2$, —$N(R)C(O)NR_2$, —$N(R)C(NR)NR_2$, —$N(R)C(O)NRR^D$, —$N(R)C(NR)NRR^D$, —OR, or —$OR^D$, wherein $R^1$ is not hydrogen. In some embodiments, $R^1$ is —$NR_2$, —$NRR^D$, —$N(R^D)_2$, —$N(R)C(O)NR_2$, —$N(R)C(NR)NR_2$, —$N(R)C(O)NRR^D$, —$N(R)C(NR)NRR^D$, —OR, or —$OR^D$. In some embodiments, $R^1$ is —$NR_2$, —$NRR^D$, —$N(R^D)_2$, —$N(R)C(O)NR_2$, —$N(R)C(NR)NR_2$, —$N(R)C(O)NRR^D$, —$N(R)C(NR)NR R^D$. In some embodiments, $R^1$ is —$NR_2$, or —$NRR^D$. In some embodiments, $R^1$ is optionally substituted $C_{1-6}$ aliphatic, —$NR_2$, or —$NRR^D$. In some embodiments, $R^1$ is —NHR or $NHR^D$. In some embodiments, $R^1$ is —$NHCH_3$ or $NHCD_3$.

As defined generally above, $R^2$ is H, $R^C$, —N(R)C(O)$Cy^2$, —N(R)$Cy^2$, —O$Cy^2$, —S$Cy^2$, or $Cy^2$. In some embodiments, $R^2$ is H. In some embodiments, $R^2$ is $R^C$, —N(R)C(O)$Cy^2$, —N(R)$Cy^2$, —O$Cy^2$, —S$Cy^2$, or $Cy^2$. In some embodiments, $R^2$ is $R^C$. In some embodiments, $R^2$ is —N(R)C(O)R. In some embodiments, $R^2$ is —N(R)C(O)$Cy^2$, —N(R)$Cy^2$, or $Cy^2$. In some embodiments, $R^2$ is —N(R)C(O)R, —N(R)C(O)$Cy^2$, —N(R)$Cy^2$, or $Cy^2$. In some embodiments, $R^2$ is —N(H)C(O)R, —N(H)C(O)$Cy^2$, —N(H)$Cy^2$, or $Cy^2$. In some embodiments, $R^2$ is —N(H)C(O)R, —N(H)C(O)$Cy^2$, or —N(H)$Cy^2$. In some embodiments, $R^2$ is —N(H)C(O)R. In some embodiments, $R^2$ is —N(H)C(O)R wherein R in this instance is optionally substituted $C_{1-6}$ aliphatic. In some embodiments, $R^2$ is —N(H)C(O)$Cy^2$. In some embodiments, $R^2$ is —N(H)$Cy^2$. In some embodiments, $R^2$ is —N(H)C(O)$Cy^2$ where $Cy^2$ is cyclopropyl. In some embodiments, $R^2$ is

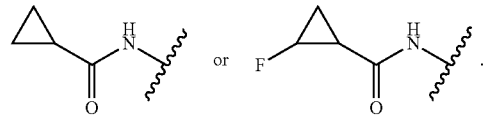 [SMILES: *NC(=O)C1CC1 ; *NC(=O)C1CC1F]

As defined generally above, $R^3$ is H, halogen, or $C_{1-6}$ aliphatic. In some embodiments, $R^3$ is H. In some embodiments, $R^3$ is halogen, or $C_{1-6}$ aliphatic. In some embodiments, $R^3$ is halogen. In some embodiments, $R^3$ is fluoro. In some embodiments, $R^3$ is $C_{1-6}$ aliphatic.

In some embodiments, $R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$. In some embodiments, $R^2$ and $R^3$ are taken together with their intervening atoms to form a 5-membered partially unsaturated or aromatic ring having 1-3 heteroatoms independently selected from nitrogen, oxygen, and sulfur; wherein said ring is substituted with m instances of $R^4$.

As defined generally above, $Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$.

In some embodiments, $Cy^1$ is phenyl. In some embodiments, $Cy^1$ is a 5-6 membered heteroaryl having 1-4 heteroatoms independently selected from nitrogen, oxygen, and sulfur. In some embodiments, $Cy^1$ is a 5-membered heteroaryl having 1-4 heteroatoms independently selected from nitrogen, oxygen, and sulfur. In some embodiments, $Cy^1$ is a 6-membered heteroaryl having 1-4 nitrogens. In some embodiments, $Cy^1$ is pyridyl. In some embodiments, $Cy^1$ is pyrazinyl. In some embodiments, $Cy^1$ is pyrimidinyl. In some embodiments, $Cy^1$ is triazinyl. In some embodiments, $Cy^1$ is pyrrolyl, pyrazolyl, imidazolyl, triazolyl, or tetrazolyl. In some embodiments, $Cy^1$ is furanyl, oxazolyl, isoxazolyl, or oxadiazolyl, In some embodiments, $Cy^1$ is thiophenyl, thiazolyl, isothiazolyl, or thiadiazolyl. In some embodiments, $Cy^1$ is an 8-10 membered bicyclic heteroaryl ring having 1-4 heteroatoms independently selected from nitrogen, oxygen, and sulfur. In some embodiments, $Cy^1$ is a 3-7 membered saturated or partially unsaturated heterocyclic ring having 1-2 heteroatoms independently selected from nitrogen, oxygen, and sulfur. In some embodiments, $Cy^1$ is a 3-7 membered saturated or partially unsaturated monocyclic carbocyclic ring. In some embodiments, $Cy^1$ is a 7-12 membered saturated or partially unsaturated bicyclic heterocyclic ring having 1-4 heteroatoms independently selected from nitrogen, oxygen, and sulfur.

In some embodiments, $Cy^1(R^5)_n$ taken together is selected from the following:

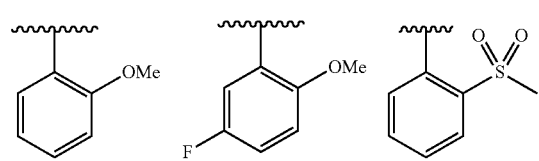
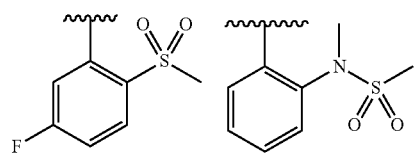
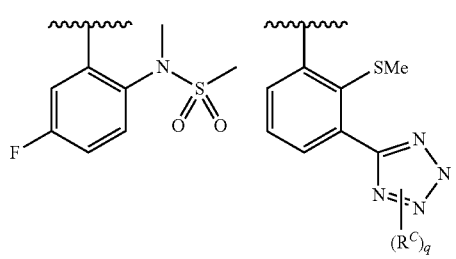
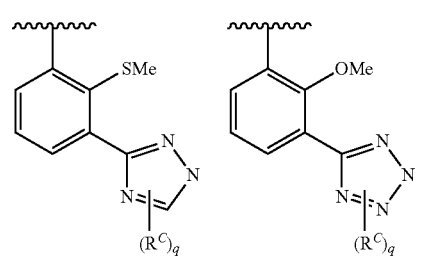
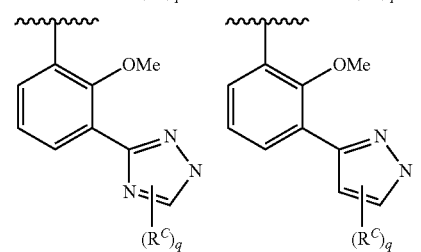
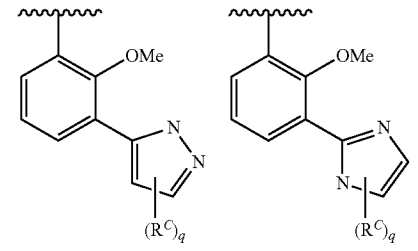
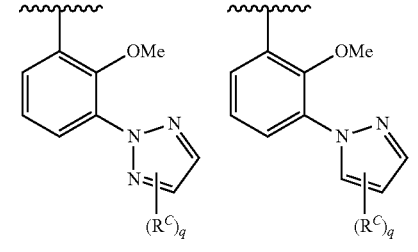
-continued
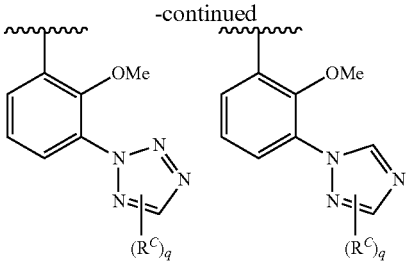
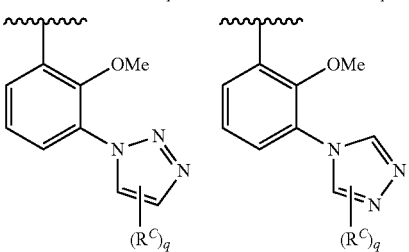
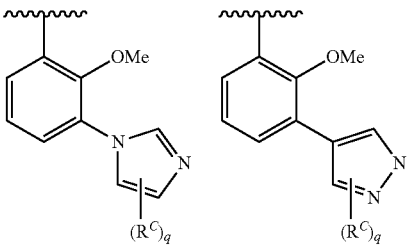
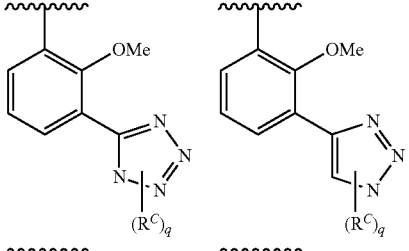
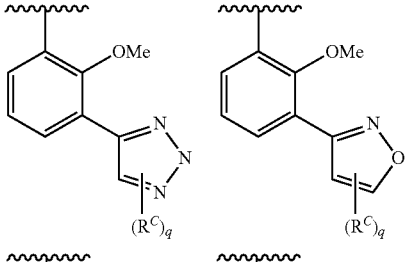
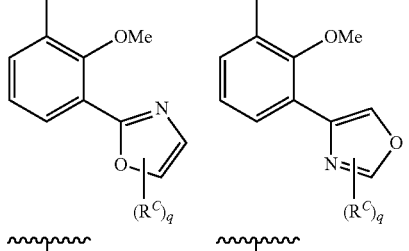
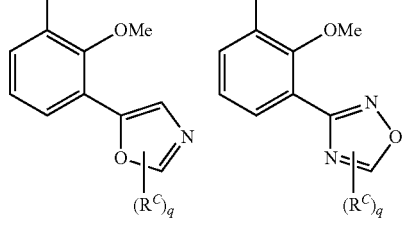

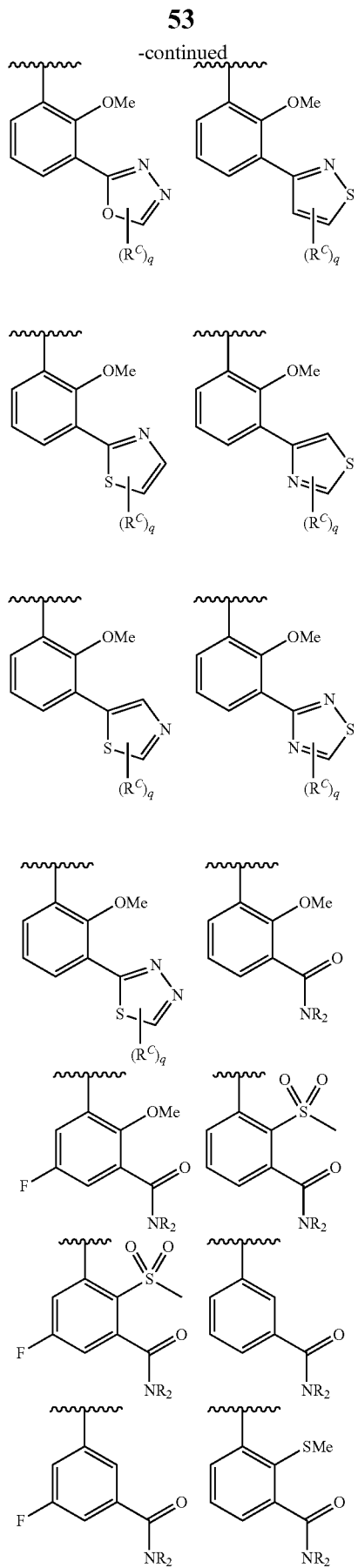
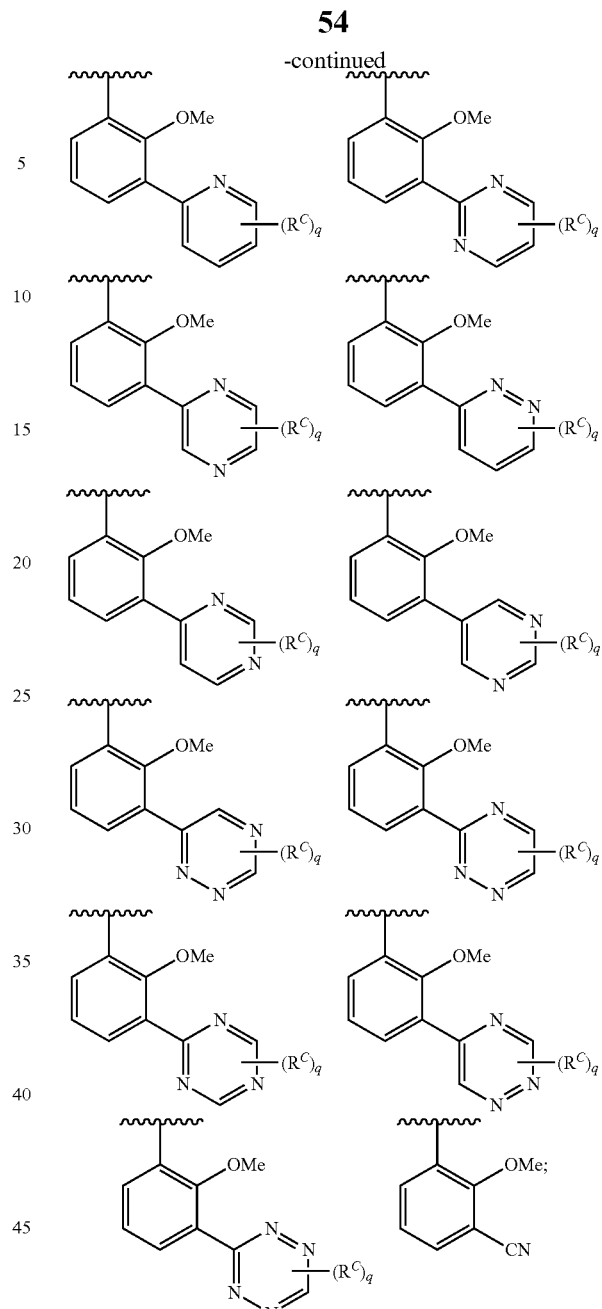

wherein each of R, $R^C$, and q is as defined above and described in embodiments herein, both singly and in combination.

As defined generally above, $Cy^2$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^2$ is substituted with p instances of $R^6$.

In some embodiments, $Cy^2$ is phenyl. In some embodiments, $Cy^2$ is a 5-6 membered heteroaryl having 1-4 heteroatoms independently selected from nitrogen, oxygen, and sulfur. In some embodiments, Cy² is a 5-membered heteroaryl having 1-4 heteroatoms independently selected from nitrogen, oxygen, and sulfur. In some embodiments, Cy² is a 6-membered heteroaryl having 1-4 nitrogens. In some embodiments, Cy² is pyridyl. In some embodiments, Cy² is pyrazinyl. In some embodiments, Cy² is pyrimidinyl. In some embodiments, Cy² is triazinyl. In some embodiments, Cy² is pyrrolyl, pyrazolyl, imidazolyl, triazolyl, or tetrazolyl. In some embodiments, Cy² is furanyl, oxazolyl, isoxazolyl, or oxadiazolyl, In some embodiments, Cy² is thiophenyl, thiazolyl, isothiazolyl, or thiadiazolyl. In some embodiments, Cy² is an 8-10 membered bicyclic heteroaryl ring having 1-4 heteroatoms independently selected from nitrogen, oxygen, and sulfur. In some embodiments, Cy² is a 3-7 membered saturated or partially unsaturated heterocyclic ring having 1-2 heteroatoms independently selected from nitrogen, oxygen, and sulfur. In some embodiments, Cy² is a 3-7 membered saturated or partially unsaturated monocyclic carbocyclic ring. In some embodiments, Cy² is $C_{3-7}$ cycloalkyl. In some embodiments, Cy² is cyclopropyl. In some embodiments, Cy² is a 7-12 membered saturated or partially unsaturated bicyclic heterocyclic ring having 1-4 heteroatoms independently selected from nitrogen, oxygen, and sulfur.

In some embodiments, Cy² is selected from the following, each of which is substituted by p instances of $R^6$:

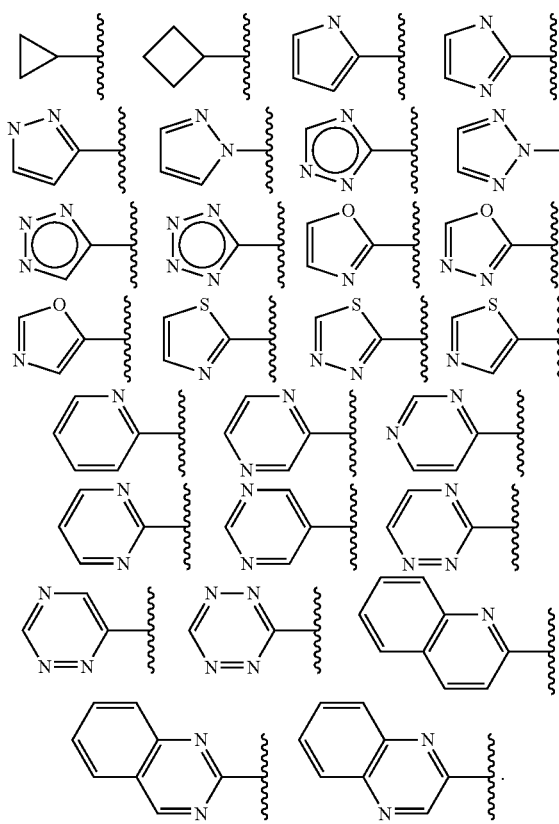

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—. In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, the present invention provides a compound of formula XVI' wherein Q is N, thereby forming a compound of formula XVI:

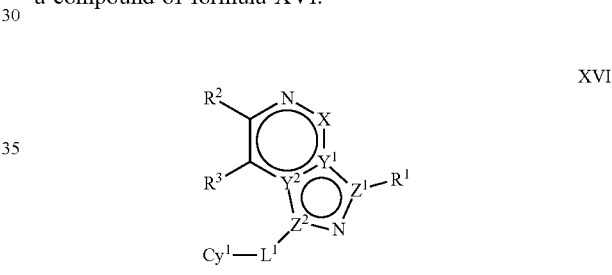

XVI or a pharmaceutically acceptable salt thereof, wherein:
X is N or C(R^X);
one of Y¹, Y², Z¹, and Z² is N, and the other three are C;
R¹ is D, R, R^D, —NR₂, —NRR^D, —N(R^D)₂, —N(R)C(O)NR₂, —N(R)C(NR)NR₂, —N(R)C(O)NRR^D, —N(R)C(NR)NRR^D, —OR, or —OR^D;
R² is H, R^C, —N(R)C(O)Cy², —N(R)S(O)₂Cy², —N(R)Cy², —OCy², —SCy², or Cy²;
R³ is H, halogen, or $C_{1-6}$ aliphatic; or
R² and R³ are taken together with their intervening atoms to form a 4-7 membered partially unsaturated or aromatic ring having 0-3 heteroatoms independently selected from nitrogen, oxygen, and sulfur; wherein said ring is substituted with m instances of R⁴;
each of Cy¹ and Cy² is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;

$L^1$ is a covalent bond or a $C_{1-4}$ bivalent saturated or unsaturated, straight or branched hydrocarbon chain wherein one or two methylene units of the chain are optionally and independently replaced by —$C(R^7)_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each instance of $R^4$, $R^5$, $R^6$, and $R^7$ is independently $R^A$ or $R^B$, and is substituted by q instances of $R^C$;

each instance of $R^A$ is independently oxo, halogen, —CN, —NO$_2$, —OR, —OR$^D$, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^D$ is a $C_{1-4}$ aliphatic group wherein one or more hydrogens are replaced by deuterium;

$R^X$ is H, halogen, or $C_{1-6}$ aliphatic each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

In some embodiments, the present invention provides a compound of formula XVI, wherein $L^1$ is a covalent bond, thereby forming a compound of formula XVI-a:

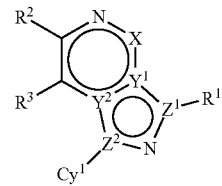

XVI-a or a pharmaceutically acceptable salt thereof, wherein each of X, $Y^1$, $Y^2$, $Z^1$, $Z^2$, $Cy^1$, $R^1$, $R^2$, and $R^3$ is as defined above and described in embodiments herein, both singly and in combination.

In some embodiments, the present invention provides a compound of formula XVI, wherein X is N or $C(R^X)$, thereby forming a compound of formula XVI-b or XVI-c respectively:

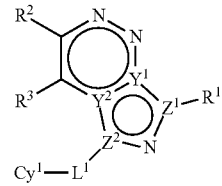

XVI-b

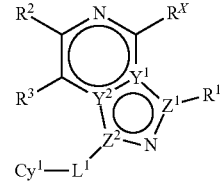

XVI-c or a pharmaceutically acceptable salt thereof, wherein each of $L^1$, $Y^1$, $Y^2$, $Z^1$, $Z^2$, $Cy^1$, $R^X$, $R^1$, $R^2$, and $R^3$ is as defined above and described in embodiments herein, both singly and in combination.

In some embodiments, the present invention provides a compound of formula XVI-b or XVI-c, wherein $R^X$ and $R^3$ are both H, thereby forming a compound of formula XVII-a or XVII-b respectively:

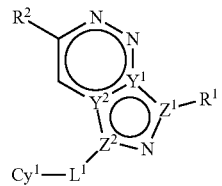

XVII-a

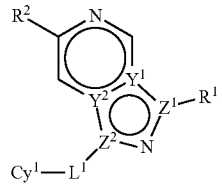

XVII-b or a pharmaceutically acceptable salt thereof, wherein each of $Y^1$, $Y^2$, $Z^1$, $Z^2$, $Cy^1$, $R^1$, $R^2$, and $R^3$ is as defined above and described in embodiments herein, both singly and in combination.

In some embodiments, the present invention provides a compound of formula XVII-a or XVII-b, wherein $L^1$ is a covalent bond, thereby forming a compound of formula XVIII-a or XVIII-b respectively:

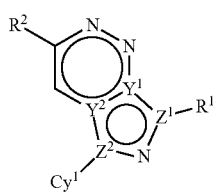

XVIII-a

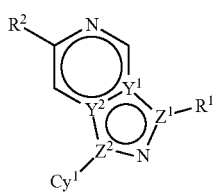

XVIII-b or a pharmaceutically acceptable salt thereof, wherein each of $Y^1$, $Y^2$, $Z^1$, $Z^2$, $Cy^1$, $R^1$, and $R^2$ is as defined above and described in embodiments herein, both singly and in combination.

In some embodiments, the present invention provides a compound of formula XVIII-a or XVIII-b wherein $Cy^1$ is phenyl, thereby forming a compound of formula XIX-a or XIX-b respectively:

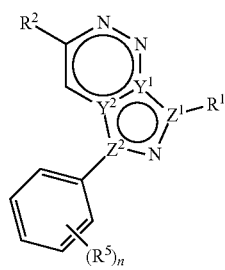

XIX-a

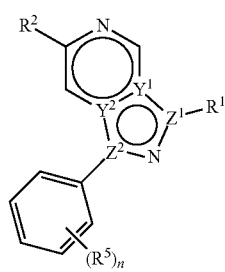

XIX-b or a pharmaceutically acceptable salt thereof, wherein each of $Y^1$, $Y^2$, $Z^1$, $Z^2$, $R^1$, $R^2$, and n is as defined above and described in embodiments herein, both singly and in combination.

In some embodiments, the present invention provides a compound of formula XIX-a or XIX-b, wherein n is 1, 2 or 3, and at least one instance of $R^5$ is ortho to the NH point of attachment, thereby forming a compound of formula XX-a or XX-b respectively:

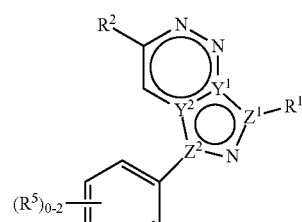

XX-a

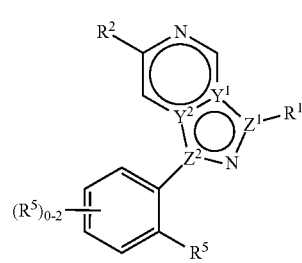

XX-b or a pharmaceutically acceptable salt thereof, wherein each of $Y^1$, $Y^2$, $Z^1$, $Z^2$, $R^1$, and $R^2$ is as defined above and described in embodiments herein, both singly and in combination.

In some embodiments, the present invention provides a compound of formula XX-a or XX-b, wherein the ortho $R^5$ group is —OR, —S(O)$_2$R, —C(O)NR$_2$, or —N(R)S(O)$_2$R, thereby forming a compound of formula XXI-a, XXI-b, XXI-c, XXI-d, XXI-e, XXI-f, XXI-g, or XXI-h respectively:

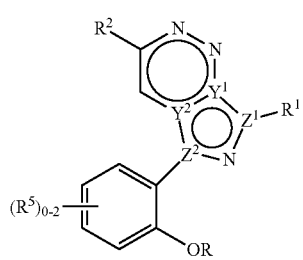

XXI-a

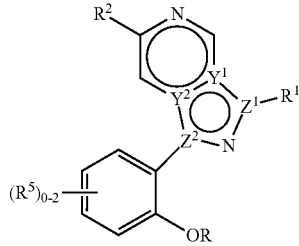

XXI-b

-continued

XXI-c
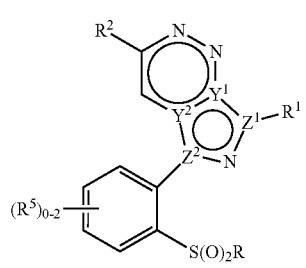

XXI-d
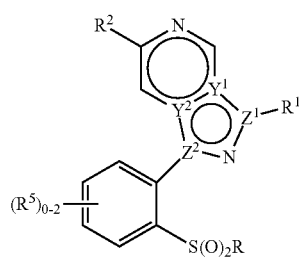

XXI-e
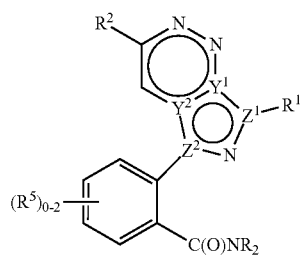

XXI-f
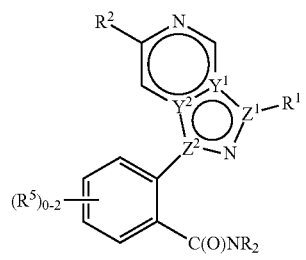

XXI-g
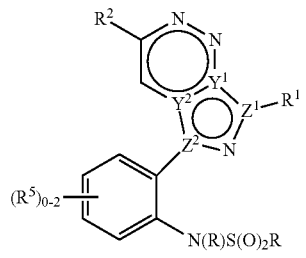

XXI-h
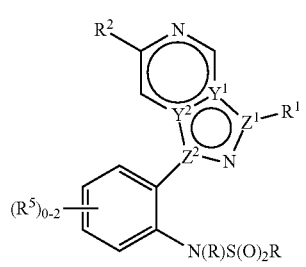

or a pharmaceutically acceptable salt thereof, wherein each of $Y^1$, $Y^2$, $Z^1$, $Z^2$, R, $R^1$, $R^2$, and $R^5$ is as defined above and described in embodiments herein, both singly and in combination.

In some embodiments, the present invention provides a compound of formula XXI-a or XXI-b, wherein a second $R^5$ group is meta to the NH point of attachment, thereby forming a compound of formula XXII-a, or XXII-b respectively:

XXII-a
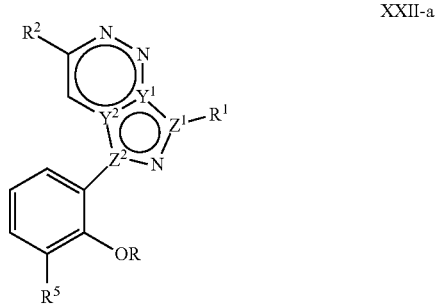

XXII-b
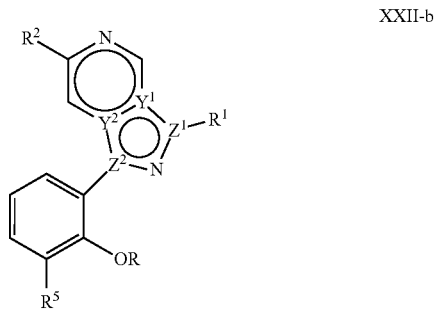

or a pharmaceutically acceptable salt thereof, wherein each of $Y^1$, $Y^2$, $Z^1$, $Z^2$, R, $R^1$, $R^2$, and $R^5$ is as defined above and described in embodiments herein, both singly and in combination.

In some embodiments, the present invention provides a compound of formula XXII-a or XXII-b, wherein $R^5$ is $R^B$. In some embodiments, the present invention provides a compound of formula XXII-a or XXII-b, wherein $R^5$ is —CN, —C(O)NR$_2$ or a 5-6 membered monocyclic heteroaryl ring having 1-4 heteroatoms independently selected from nitrogen, oxygen, and sulfur, said ring being substituted by q instances of $R^C$.

In some embodiments, the present invention provides a compound of formula XXII-a or XXII-b, wherein —OR is methoxy, fluoromethoxy, or difluoromethoxy.

In some embodiments, the present invention provides a compound of formula XVIII-a or XVIII-b wherein $Cy^1$ is pyridyl, n is 2, and one instance of $R^5$ is oxo, thereby forming a pyridone compound of formula XXIII-a or XXIII-b respectively:

XXIII-a

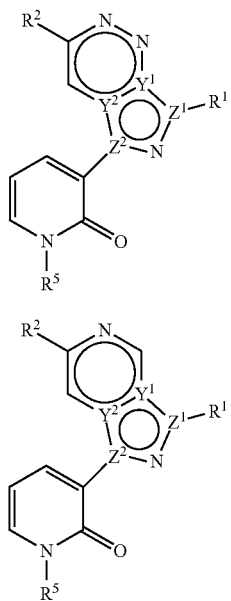

XXIII-b

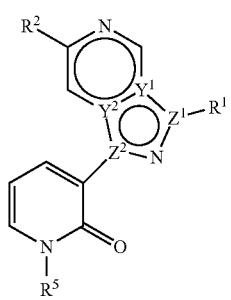

or a pharmaceutically acceptable salt thereof, wherein each of $Y^1$, $Y^2$, $Z^1$, $Z^2$, $R^1$, $R^2$, and $R^5$, is as defined above and described in embodiments herein, both singly and in combination.

In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, or XXIII-b wherein $Z^2$ is N, and $Y^1$, $Y^2$, and $Z^1$ are C. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, or XXIII-b wherein $Y^2$ is N, and $Y^1$, $Z^1$, and $Z^2$ are C.

In some embodiments, the present invention provides a compound of formula I wherein $Z^2$ is N, and $Y^1$, $Y^2$, and $Z^1$ are C; or wherein $Y^2$ is N, and $Y^1$, $Z^1$, and $Z^2$ are C, thereby forming a compound of formula XXIV-a or XXIV-b respectively:

XXIV-a

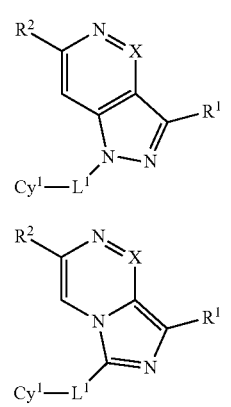

XXIV-b or a pharmaceutically acceptable salt thereof, wherein each of X, $L^1$, $Cy^1$, $R^1$, and $R^2$, is as defined above and described in embodiments herein, both singly and in combination.

In some embodiments, the present invention provides a compound of formula XXIV-a or XXIV-b wherein $L^1$ is a covalent bond, thereby forming a compound of formula XXV-a or XXV-b respectively:

XXV-a

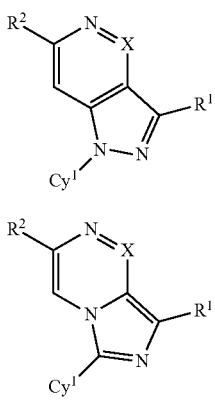

XXV-b or a pharmaceutically acceptable salt thereof, wherein each of X, $Cy^1$, $R^1$, and $R^2$ is as defined above and described in embodiments herein, both singly and in combination.

In some embodiments, the present invention provides a compound of formula XXV-a or XXV-b wherein X is C, and $R^x$ is H, thereby forming a compound of formula XXVI-a or XXVI-b respectively:

XXVI-a

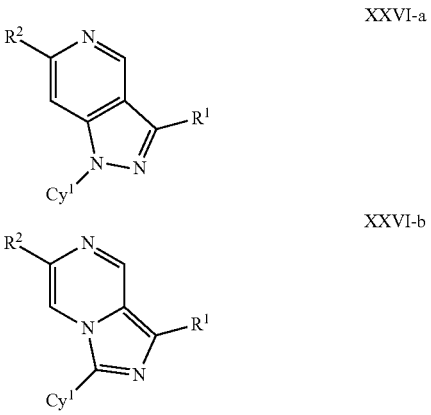

XXVI-b or a pharmaceutically acceptable salt thereof, wherein each of $Cy^1$, $R^1$, and $R^2$ is as defined above and described in embodiments herein, both singly and in combination.

In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is —N(R)C(O)R, —N(R)C(O)$Cy^2$, —N(R)$Cy^2$, or $Cy^2$. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is —N(H)C(O)R, —N(H)C(O)$Cy^2$, —N(H)$Cy^2$, or $Cy^2$. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is —N(H)C(O)R, —N(H)C(O)$Cy^2$, or —N(H)$Cy^2$. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is —N(H)C(O)R. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is

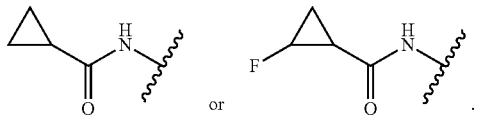 [SMILES: *NC(=O)C1CC1 ; *NC(=O)C1CC1F]

In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, or XXVI-b wherein $R^2$ is —N(H)$Cy^2$, wherein $Cy^2$ is selected from the following, each of which is substituted by p instances of $R^6$:

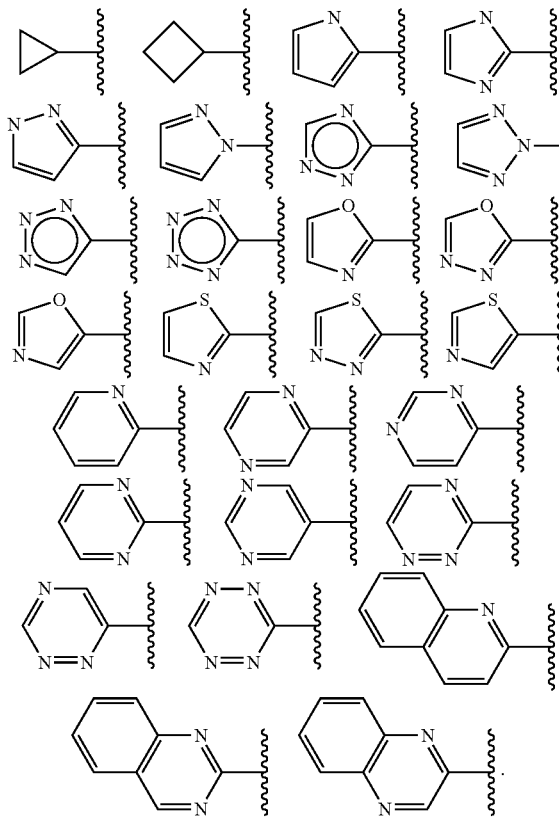

In some embodiments, the present invention provides a compound of formula XVI' wherein Q is CH, thereby forming a compound of formula XVI":

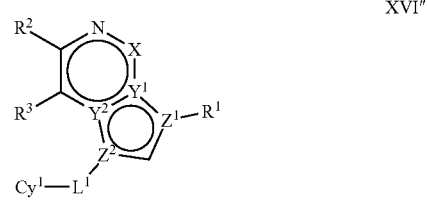

or a pharmaceutically acceptable salt thereof, wherein each of X, $Y^1$, $Y^2$, $Z^1$, $Z^2$, $Cy^1$, $R^1$, $R^2$, and $R^3$ is as defined above and described in embodiments herein, both singly and in combination.

In some embodiments, the present invention provides a compound of formula XVI", wherein $L^1$ is a covalent bond, thereby forming a compound of formula XVI-a':

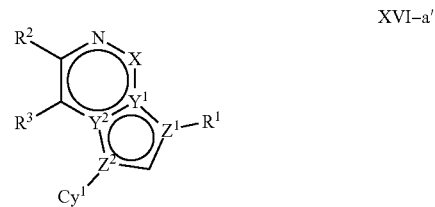

or a pharmaceutically acceptable salt thereof, wherein each of X, $Y^1$, $Y^2$, $Z^1$, $Z^2$, $Cy^1$, $R^1$, $R^2$, and $R^3$ is as defined above and described in embodiments herein, both singly and in combination.

In some embodiments, the present invention provides a compound of formula XVI", wherein X is N or C($R^X$), thereby forming a compound of formula XVI-b' or XVI-c' respectively:

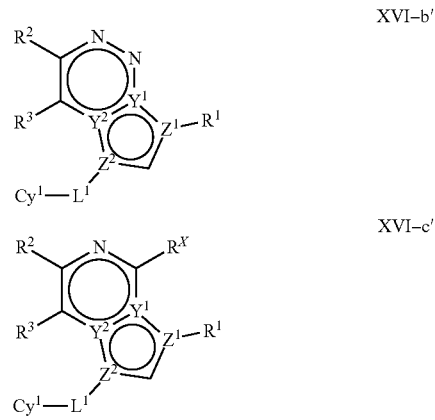

or a pharmaceutically acceptable salt thereof, wherein each of $L^1$, $Y^1$, $Y^2$, $Z^1$, $Z^2$, $Cy^1$, $R^X$, $R^1$, $R^2$, and $R^3$ is as defined above and described in embodiments herein, both singly and in combination.

In some embodiments, the present invention provides a compound of formula XVI-b' or XVI-c', wherein $R^X$ and $R^3$ are both H, thereby forming a compound of formula XVII-a' or XVII-b' respectively:

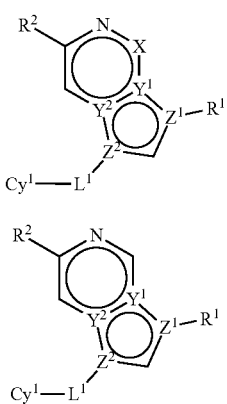

XVII-a'

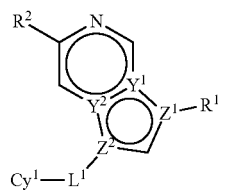

XVII-b' or a pharmaceutically acceptable salt thereof, wherein each of $Y^1$, $Y^2$, $Z^1$, $Z^2$, $Cy^1$, $R^1$, $R^2$, and $R^3$ is as defined above and described in embodiments herein, both singly and in combination.

In some embodiments, the present invention provides a compound of formula XVII-a' or XVII-b', wherein $L^1$ is a covalent bond, thereby forming a compound of formula XVIII-a' or XVIII-b' respectively:

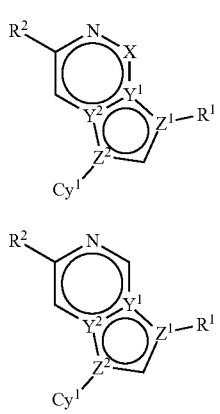

XVIII-a'

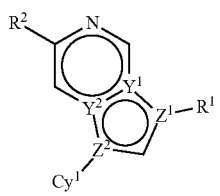

XVIII-b' or a pharmaceutically acceptable salt thereof, wherein each of $Y^1$, $Y^2$, $Z^1$, $Z^2$, $Cy^1$, $R^1$, and $R^2$ is as defined above and described in embodiments herein, both singly and in combination.

In some embodiments, the present invention provides a compound of formula XVIII-a' or XVIII-b' wherein $Cy^1$ is phenyl, thereby forming a compound of formula XIX-a' or XIX-b' respectively:

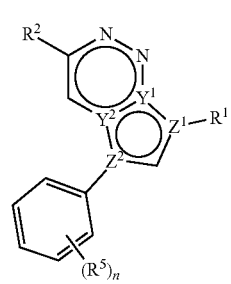

XIX-a'

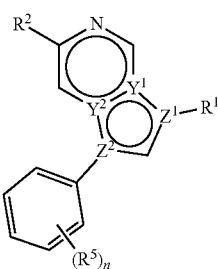

XIX-b' or a pharmaceutically acceptable salt thereof, wherein each of $Y^1$, $Y^2$, $Z^1$, $Z^2$, $R^1$, $R^2$, and n is as defined above and described in embodiments herein, both singly and in combination.

In some embodiments, the present invention provides a compound of formula XIX-a' or XIX-b', wherein n is 1, 2 or 3, and at least one instance of $R^5$ is ortho to the NH point of attachment, thereby forming a compound of formula XX-a' or XX-b' respectively:

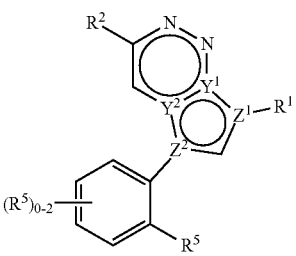

XX-a'

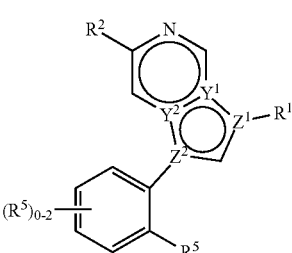

XX-b' or a pharmaceutically acceptable salt thereof, wherein each of $Y^1$, $Y^2$, $Z^1$, $Z^2$, $R^1$, and $R^2$ is as defined above and described in embodiments herein, both singly and in combination.

In some embodiments, the present invention provides a compound of formula XX-a' or XX-b', wherein the ortho $R^5$ group is —OR, —S(O)$_2$R, —C(O)NR$_2$, or —N(R)S(O)$_2$R, thereby forming a compound of formula XXI-a', XXI-b', XXI-c', XXI-d', XXI-e', XXI-f', XXI-g', or XXI-h' respectively:

XXI-a'
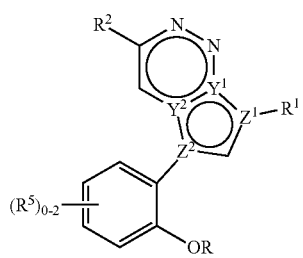

XXI-b'
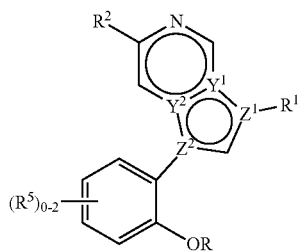

XXI-c'
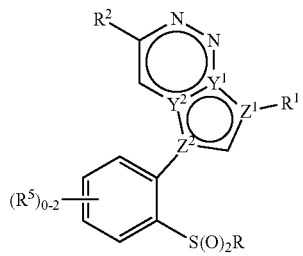

XXI-d'
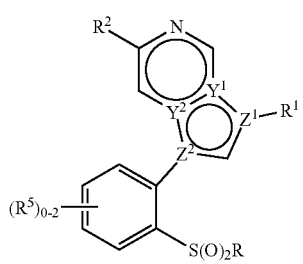

XXI-e'
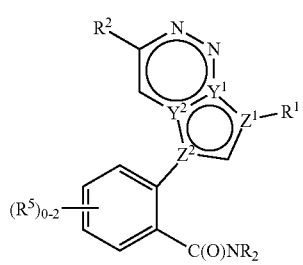

XXI-f'
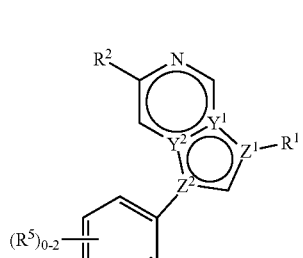

-continued

XXI-g'
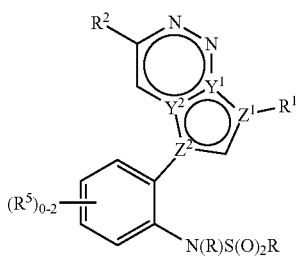

XXI-h'
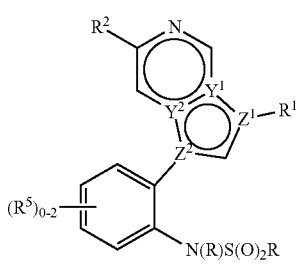

or a pharmaceutically acceptable salt thereof, wherein each of $Y^1$, $Y^2$, $Z^1$, $Z^2$, R, $R^1$, $R^2$, and $R^5$ is as defined above and described in embodiments herein, both singly and in combination.

In some embodiments, the present invention provides a compound of formula XXI-a' or XXI-b', wherein a second $R^5$ group is meta to the NH point of attachment, thereby forming a compound of formula XXII-a', or XXII-b' respectively:

XXII-a'
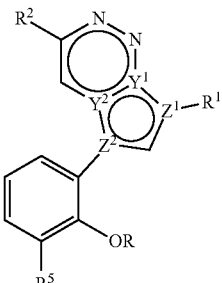

XXII-b'
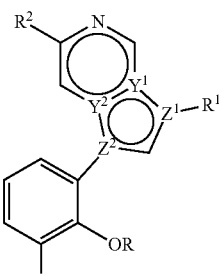

or a pharmaceutically acceptable salt thereof, wherein each of $Y^1$, $Y^2$, $Z^1$, $Z^2$, R, $R^1$, $R^2$, and $R^5$ is as defined above and described in embodiments herein, both singly and in combination.

In some embodiments, the present invention provides a compound of formula XXII-a' or XXII-b', wherein $R^5$ is $R^B$. In some embodiments, the present invention provides a compound of formula XXII-a' or XXII-b', wherein $R^5$ is —CN, —C(O)NR₂ or a 5-6 membered monocyclic heteroaryl ring having 1-4 heteroatoms independently selected from nitrogen, oxygen, and sulfur, said ring being substituted by q instances of $R^C$.

In some embodiments, the present invention provides a compound of formula XXII-a' or XXII-b', wherein —OR is methoxy, fluoromethoxy, or difluoromethoxy.

In some embodiments, the present invention provides a compound of formula XVIII-a' or XVIII-b' wherein $Cy^1$ is pyridyl, n is 2, and one instance of $R^5$ is oxo, thereby forming a pyridone compound of formula XXIII-a' or XXIII-b' respectively:

XXIII-a

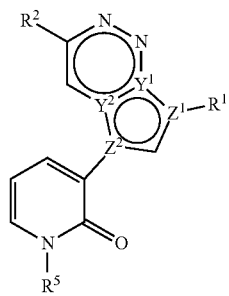

XXIII-b

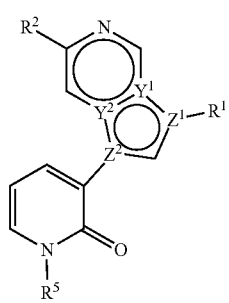

or a pharmaceutically acceptable salt thereof, wherein each of $Y^1$, $Y^2$, $Z^1$, $Z^2$, $R^1$, $R^2$, and $R^5$, is as defined above and described in embodiments herein, both singly and in combination.

In some embodiments, the present invention provides a compound of one of formulas XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', or XXIII-b' wherein $Z^2$ is N, and $Y^1$, $Y^2$, and $Z^1$ are C. In some embodiments, the present invention provides a compound of one of formulas XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', or XXIII-b' wherein $Y^2$ is N, and $Y^1$, $Z^1$, and $Z^2$ are C.

In some embodiments, the present invention provides a compound of formula I' wherein $Z^2$ is N, and $Y^1$, $Y^2$, and $Z^1$ are C; or wherein $Y^2$ is N, and $Y^1$, $Z^1$, and $Z^2$ are C, thereby forming a compound of formula XXIV-a' or XXIV-b' respectively:

XXIV-a'

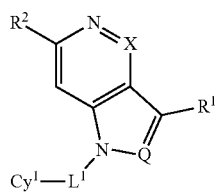

XXIV-b'

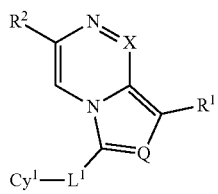

or a pharmaceutically acceptable salt thereof, wherein each of Q, X, $L^1$, $Cy^1$, $R^1$, and $R^2$, is as defined above and described in embodiments herein, both singly and in combination.

In some embodiments, the present invention provides a compound of formula XXIV-a' or XXIV-b' wherein $L^1$ is a covalent bond, thereby forming a compound of formula XXV-a' or XXV-b' respectively:

XXV-a'

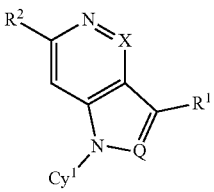

XXV-b'

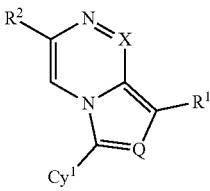

or a pharmaceutically acceptable salt thereof, wherein each of Q, X, $Cy^1$, $R^1$, and $R^2$ is as defined above and described in embodiments herein, both singly and in combination.

In some embodiments, the present invention provides a compound of formula XXV-a' or XXV-b' wherein X is C, and $R^X$ is H, thereby forming a compound of formula XXVI-a' or XXVI-b' respectively:

XXVI-a'

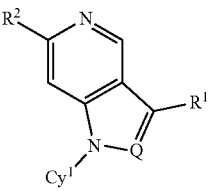

-continued

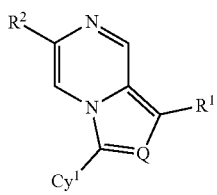
XXVI-b' or a pharmaceutically acceptable salt thereof, wherein each of Q, Cy¹, R¹, and R² is as defined above and described in embodiments herein, both singly and in combination.

In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is —N(R)C(O)R, —N(R)C(O)Cy², —N(R)Cy², or Cy². In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is —N(H)C(O)R, —N(H)C(O)Cy², —N(H)Cy², or Cy². In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is —N(H)C(O)R, —N(H)C(O)Cy², or —N(H)Cy². In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is —N(H)C(O)R. In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is

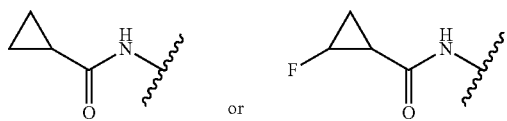

In some embodiments, the present invention provides a compound of one of formulas XVI-a, XVI-b, XVI-c, XVII-a, XVII-b, XVIII-a, XVIII-b, XIX-a, XIX-b, XX-a, XX-b, XXI-a, XXI-b, XXI-c, XXI-d, XXI-e, XXI-f, XXI-g, XXI-h, XXII-a, XXII-b, XXIII-a, XXIII-b, XXIV-a, XXIV-b, XXV-a, XXV-b, XXVI-a, XXVI-b, XVI', XVI'', XVI-a', XVI-b', XVI-c', XVII-a', XVII-b', XVIII-a', XVIII-b', XIX-a', XIX-b', XX-a', XX-b', XXI-a', XXI-b', XXI-c', XXI-d', XXI-e', XXI-f', XXI-g', XXI-h', XXII-a', XXII-b', XXIII-a', XXIII-b', XXIV-a', XXIV-b', XXV-a', XXV-b', XXVI-a', or XXVI-b' wherein R² is —N(H)Cy², wherein Cy² is selected from the following, each of which is substituted by p instances of R⁶:

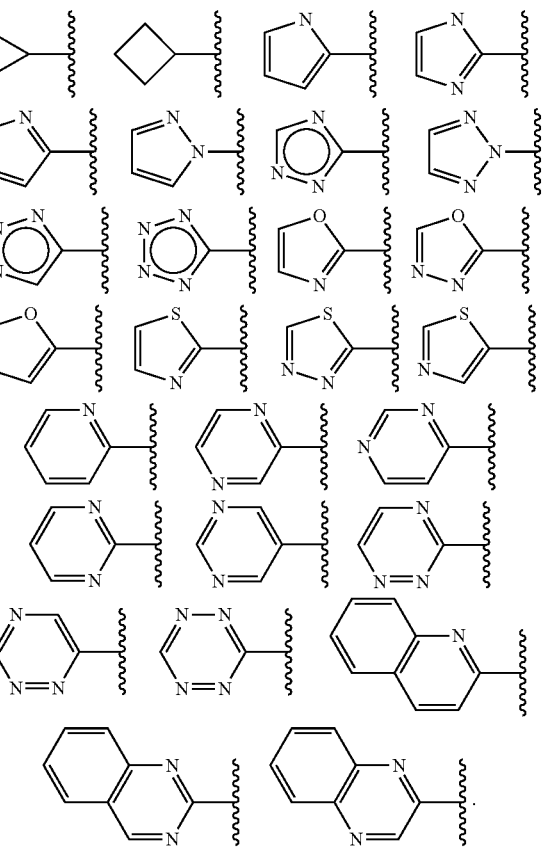

TABLE 1
Exemplary Compounds
| Compound | Structure |
|---|---|
| I-1 | 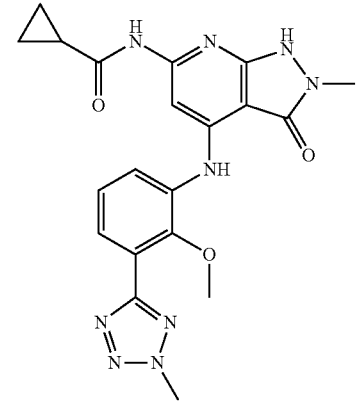 [SMILES: COc1c(Nc2cc(NC(=O)C3CC3)nc3[nH]n(C)c(=O)c23)cccc1-c1nnn(C)n1] |
| I-2 | 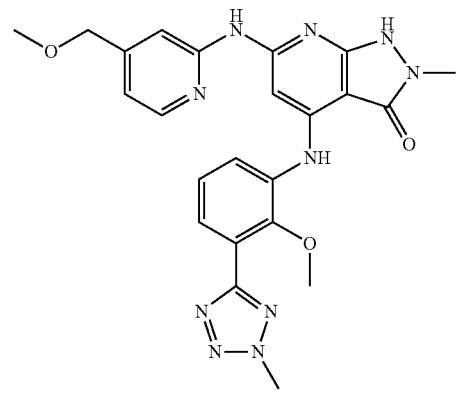 |
| I-3 | 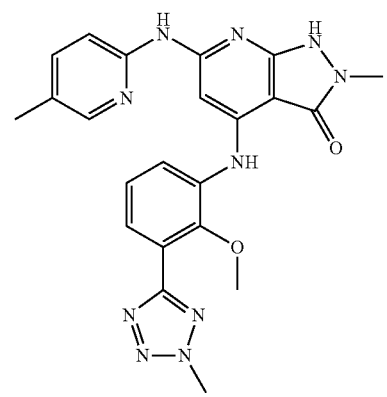 |
TABLE 1-continued
Exemplary Compounds
| Compound | Structure |
|---|---|
| I-4 | 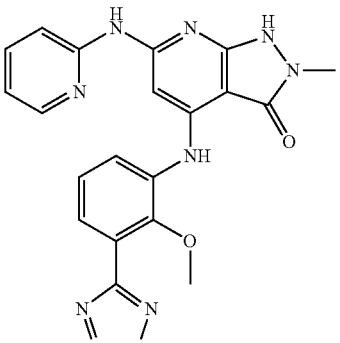 |
| I-5 | 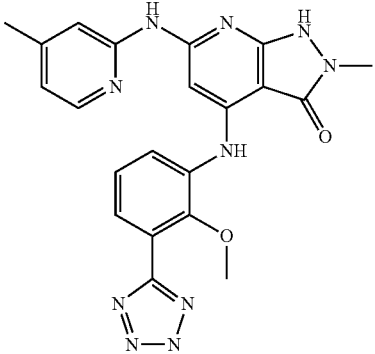 |
| I-6 | 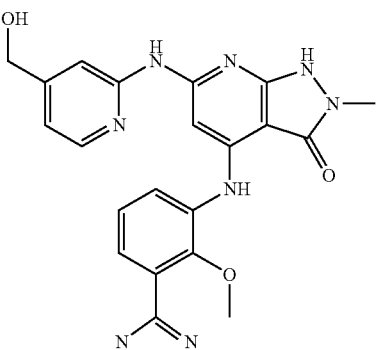 |

TABLE 1-continued
Exemplary Compounds
| Compound | Structure |
|---|---|
| I-7 | 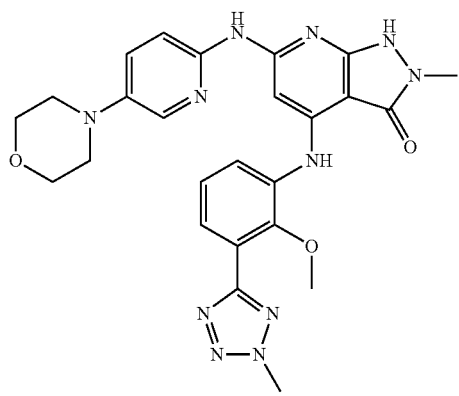 |
| I-8 | 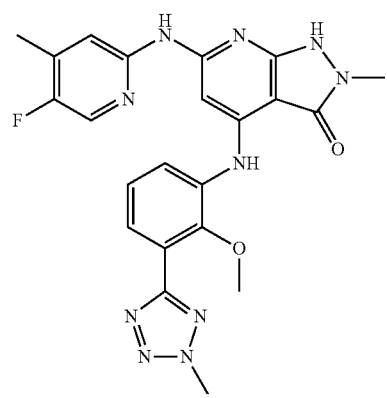 [SMILES: COc1c(Nc2cc(Nc3cc(C)c(F)cn3)nc3[nH]n(C)c(=O)c23)cccc1-c1nnn(C)n1] |
| I-9 | 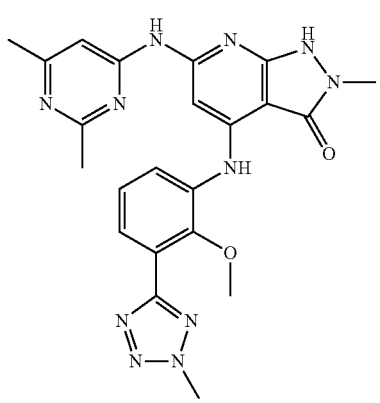 |
| I-10 | 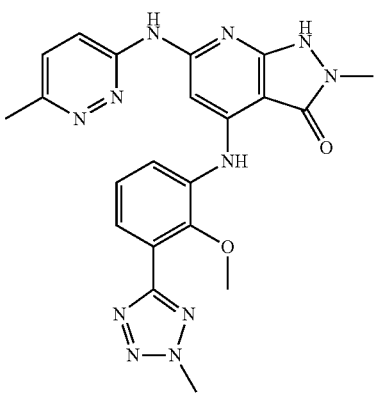 |
| I-11 | 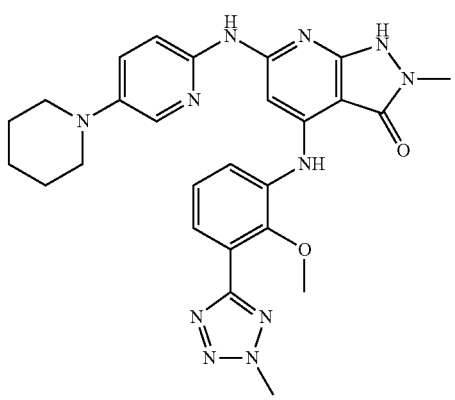 [SMILES: COc1c(Nc2cc(Nc3ccc(N4CCCCC4)cn3)nc3[nH]n(C)c(=O)c23)cccc1-c1nnn(C)n1] |
| I-12 | 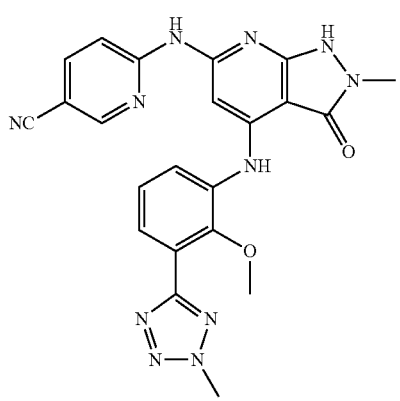 [SMILES: COc1c(Nc2cc(Nc3ccc(C#N)cn3)nc3[nH]n(C)c(=O)c23)cccc1-c1nnn(C)n1] |

TABLE 1-continued
Exemplary Compounds
| Compound | Structure |
|---|---|
| I-13 | 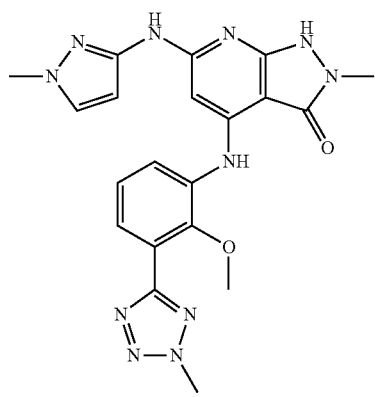 |
| I-14 | 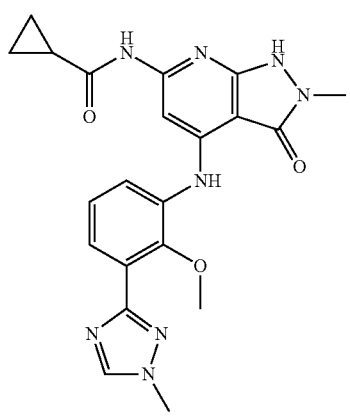 [SMILES: COc1c(Nc2cc(NC(=O)C3CC3)nc3[nH]n(C)c(=O)c23)cccc1-c1ncn(C)n1] |
| I-15 | 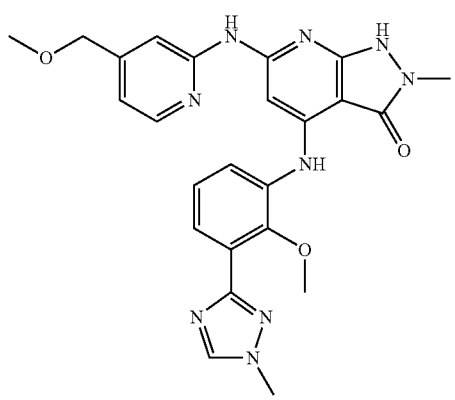 |
| I-16 | 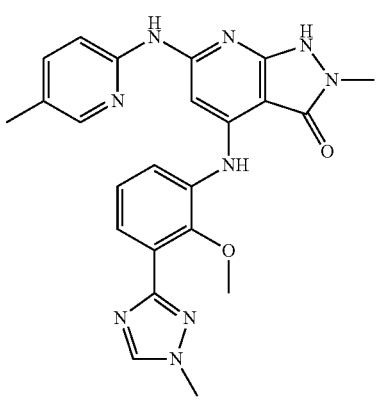 |
| I-17 | 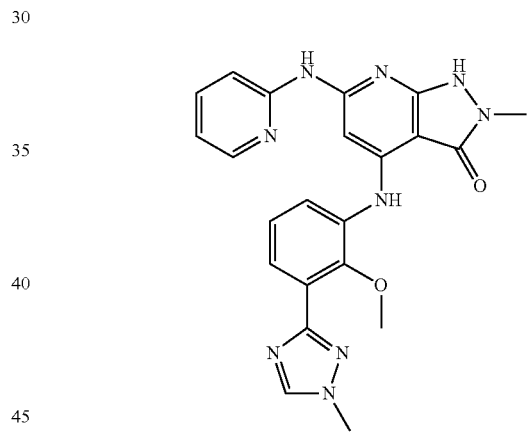 |
| I-18 | 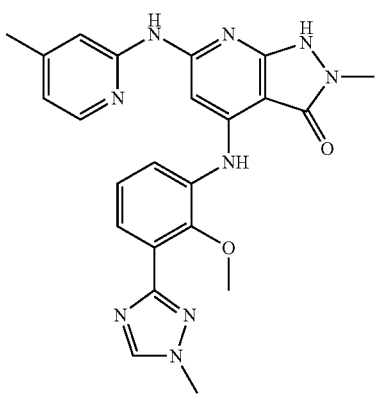 |

TABLE 1-continued
Exemplary Compounds
| Compound | Structure |
|---|---|
| I-19 | 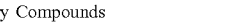 |
| I-20 | 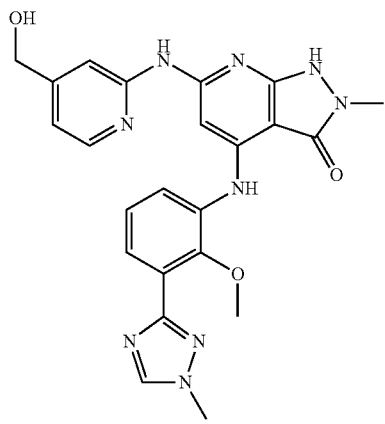 [SMILES: COc1c(Nc2cc(Nc3cc(CO)ccn3)nc3[nH]n(C)c(=O)c23)cccc1-c1ncn(C)n1] |
| I-21 | 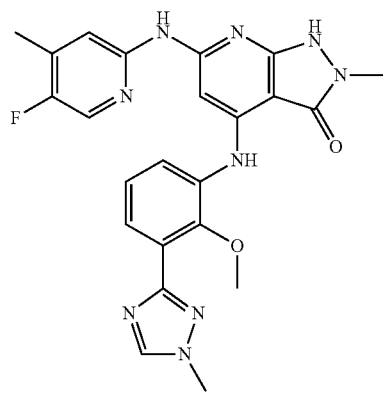 |
| I-22 | 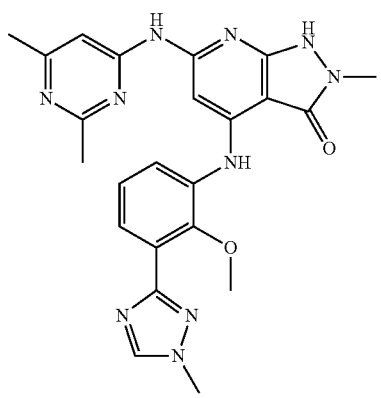 |
| I-23 | 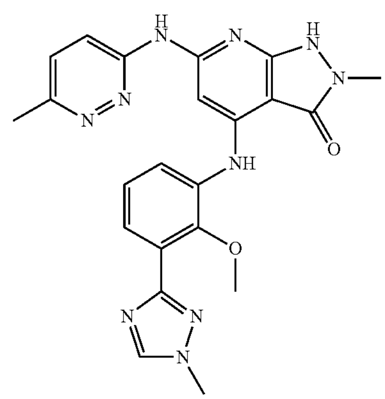 |
| I-24 | 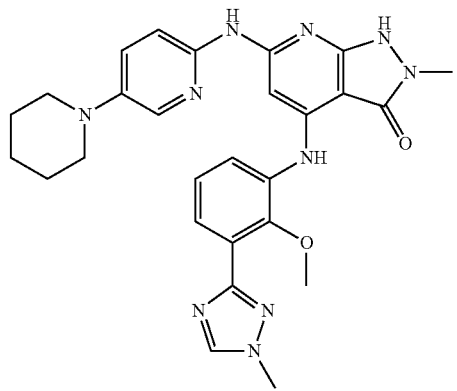 [SMILES: COc1c(Nc2cc(Nc3ccc(N4CCCCC4)cn3)nc3[nH]n(C)c(=O)c23)cccc1-c1ncn(C)n1] |

TABLE 1-continued
Exemplary Compounds
| Compound | Structure |
|---|---|
| I-25 | 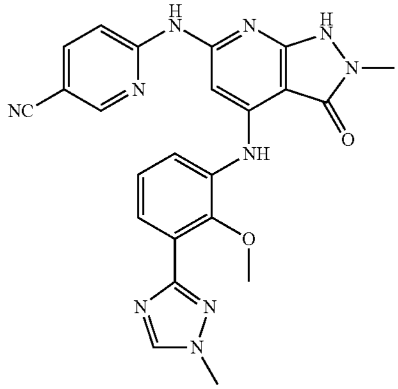 [SMILES: COc1c(Nc2cc(Nc3ccc(C#N)cn3)nc3[nH]n(C)c(=O)c23)cccc1-c1ncn(C)n1] |
| I-26 | 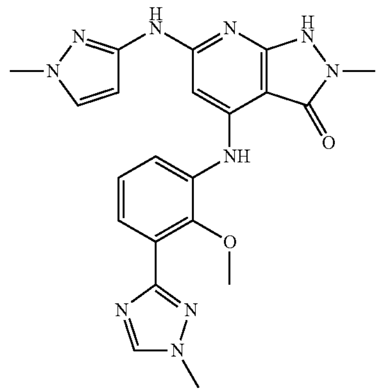 |
| I-27 | 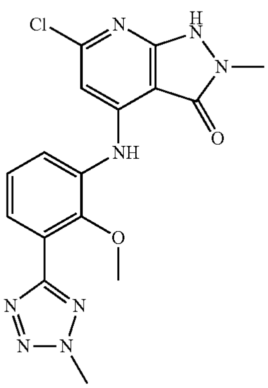 [SMILES: COc1c(Nc2cc(Cl)nc3[nH]n(C)c(=O)c23)cccc1-c1nnn(C)n1] |
| I-28 | 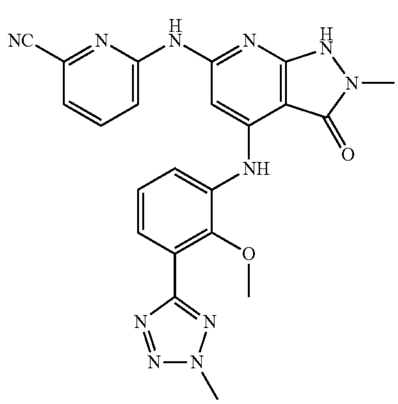 |
| I-29 | |
| I-30 | |
| I-31 | |
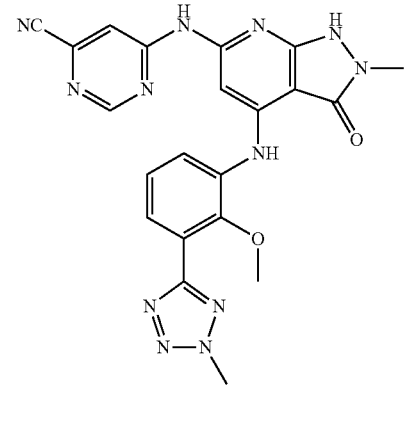 [SMILES: COc1c(Nc2cc(Nc3cc(C#N)ncn3)nc3[nH]n(C)c(=O)c23)cccc1-c1nnn(C)n1]

TABLE 1-continued

Exemplary Compounds

| Compound | Structure |
|---|---|
| I-32 | |
| I-33 | |
| I-34 | |
| I-35 | |
| I-36 | 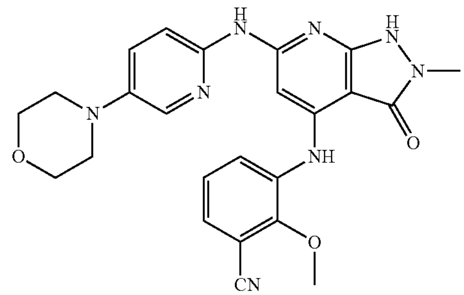 [SMILES: COc1c(C#N)cccc1Nc1cc(Nc2ccc(N3CCOCC3)cn2)nc2[nH]n(C)c(=O)c12] |
| I-37 | 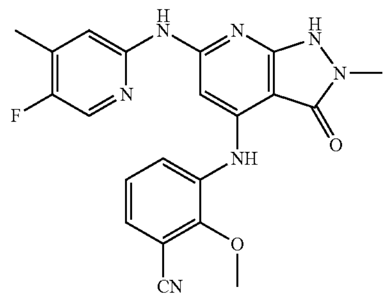 [SMILES: COc1c(C#N)cccc1Nc1cc(Nc2cc(C)c(F)cn2)nc2[nH]n(C)c(=O)c12] |
| I-38 | 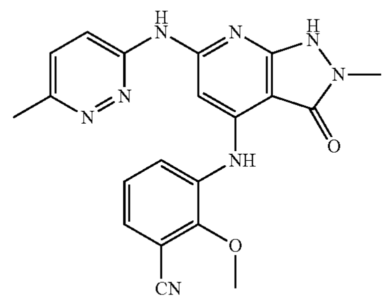 |
| I-39 | 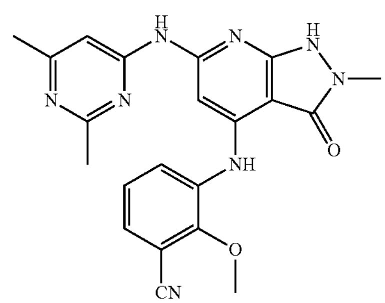 |
| I-40 | 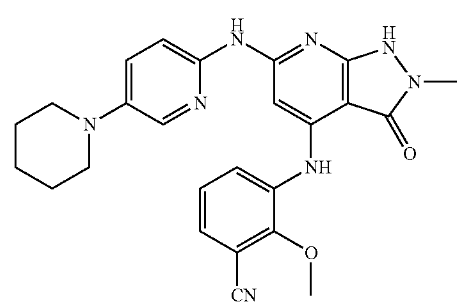 [SMILES: COc1c(C#N)cccc1Nc1cc(Nc2ccc(N3CCCCC3)cn2)nc2[nH]n(C)c(=O)c12] |

TABLE 1-continued
Exemplary Compounds
| Compound | Structure |
|---|---|
| I-41 | 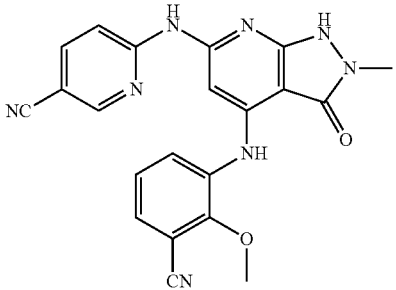 [SMILES: COc1c(C#N)cccc1Nc1cc(Nc2ccc(C#N)cn2)nc2[nH]n(C)c(=O)c12] |
| I-42 | 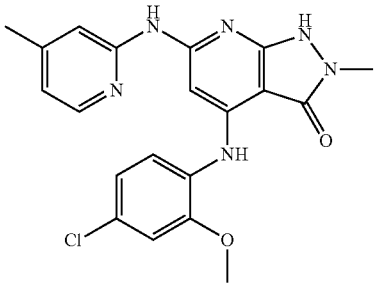 |
| I-43 | 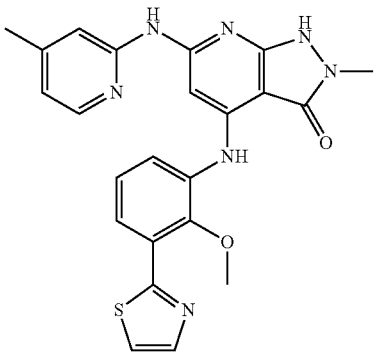 |
| I-44 | 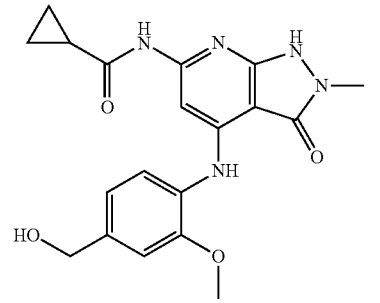 [SMILES: COc1cc(CO)ccc1Nc1cc(NC(=O)C2CC2)nc2[nH]n(C)c(=O)c12] |
| I-45 | 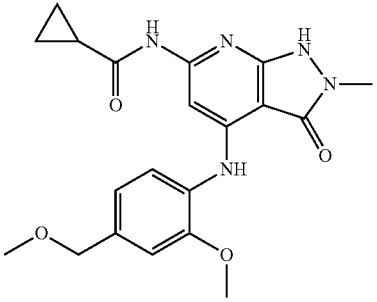 |
| I-46 | 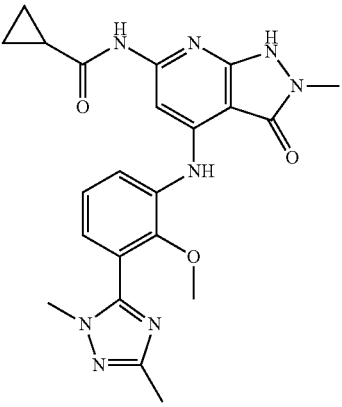 [SMILES: COc1c(Nc2cc(NC(=O)C3CC3)nc3[nH]n(C)c(=O)c23)cccc1-c1nc(C)nn1C] |
| I-47 | 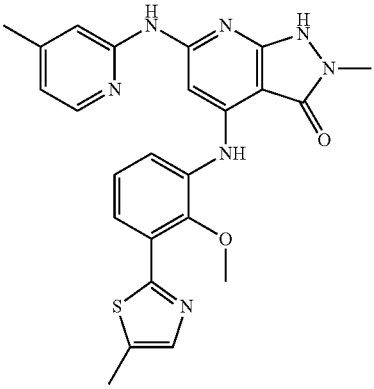 |
| I-48 | 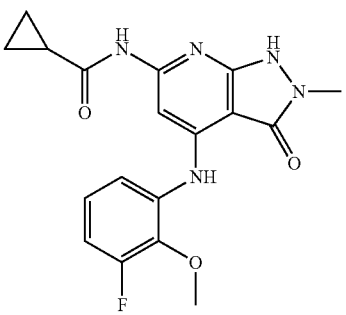 [SMILES: COc1c(F)cccc1Nc1cc(NC(=O)C2CC2)nc2[nH]n(C)c(=O)c12] |

TABLE 1-continued

Exemplary Compounds

| Compound | Structure |
|---|---|
| I-49 | (cyclopropanecarboxamide-pyrazolopyridinone with 3-chloro-2-methoxyphenylamino substituent) |
| I-50 | (cyclopropanecarboxamide-pyrazolopyridinone with 4-cyclopropyl-2-methoxyphenylamino substituent) |
| I-51 | (cyclopropanecarboxamide-pyrazolopyridinone with 4-cyclobutyl-2-methoxyphenylamino substituent) |
| I-52 | (cyclopropanecarboxamide-pyrazolopyridinone with 2-methoxy-3-(1-methyl-1H-tetrazol-5-yl)phenylamino substituent) |
| I-53 | (cyclopropanecarboxamide-pyrazolopyridinone with 3-(1,5-dimethyl-1H-1,2,4-triazol-3-yl)-2-methoxyphenylamino substituent) |
| I-54 | (cyclopropanecarboxamide-pyrazolopyridinone with 2-methoxy-3-(1-methyl-1H-1,2,4-triazol-5-yl)phenylamino substituent) |
| I-55 | (cyclopropanecarboxamide-pyrazolopyridinone with 2-methoxy-3-(1-methyl-1H-pyrazol-4-yl)phenylamino substituent) |

TABLE 1-continued

Exemplary Compounds

| Compound | Structure |
|---|---|
| I-56 | (structure) |
| I-57 | (structure) |
| I-58 | (structure) |
| I-59 | (structure) |
| I-60 | (structure) |
| I-61 | (structure) |
| I-62 | (structure) |

TABLE 1-continued
Exemplary Compounds
| Compound | Structure |
|---|---|
| I-63 | 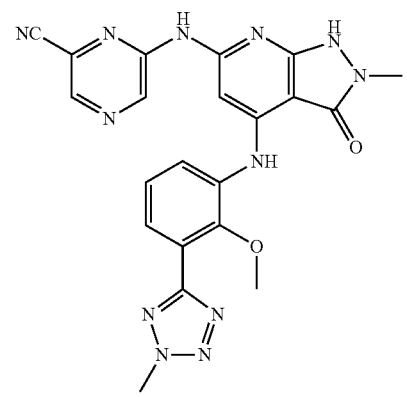 |
| I-64 | 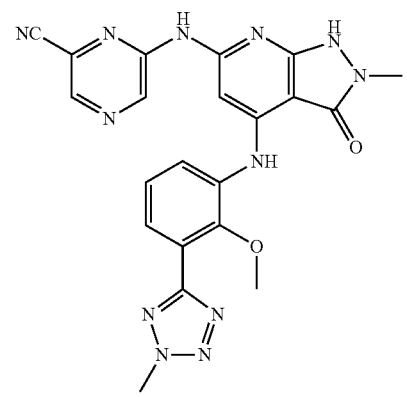 |
| I-65 | 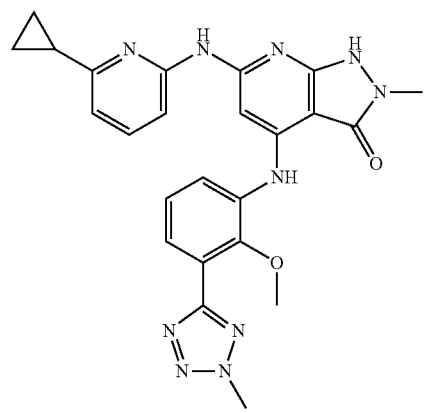 [SMILES: COc1c(Nc2cc(Nc3cccc(C4CC4)n3)nc3[nH]n(C)c(=O)c23)cccc1-c1nnn(C)n1] |
TABLE 1-continued
Exemplary Compounds
| Compound | Structure |
|---|---|
| I-66 | 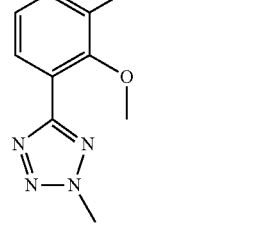 |
| I-67 | 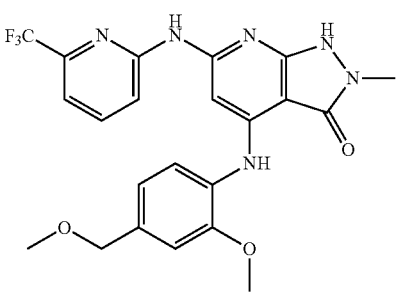 |
| I-68 | 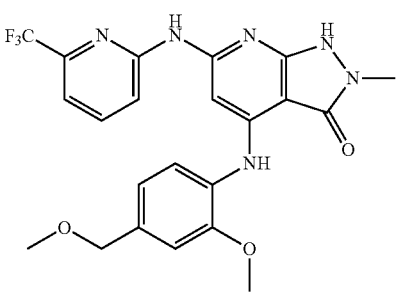 |
| I-69 | 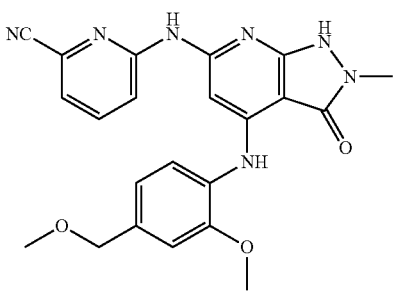 |

TABLE 1-continued

Exemplary Compounds

| Compound | Structure |
|---|---|
| I-70 | 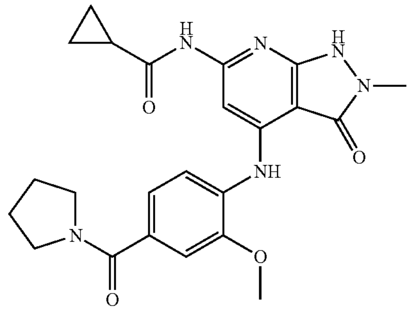 [SMILES: COc1cc(C(=O)N2CCCC2)ccc1Nc1cc(NC(=O)C2CC2)nc2[nH]n(C)c(=O)c12] |
| I-71 | 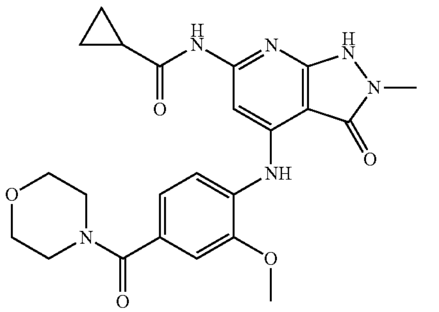 [SMILES: COc1cc(C(=O)N2CCOCC2)ccc1Nc1cc(NC(=O)C2CC2)nc2[nH]n(C)c(=O)c12] |
| I-72 | 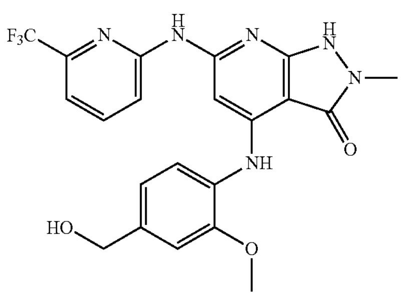 [SMILES: COc1cc(CO)ccc1Nc1cc(Nc2cccc(C(F)(F)F)n2)nc2[nH]n(C)c(=O)c12] |
| I-73 | 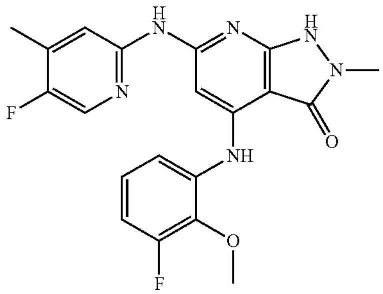 |
| I-74 | 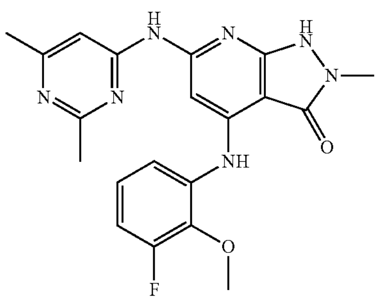 |
| I-75 | |
| I-76 | |
| I-77 | |
| I-78 | |
| I-79 | |

TABLE 1-continued

Exemplary Compounds

| Compound | Structure |
|---|---|
| I-80 | 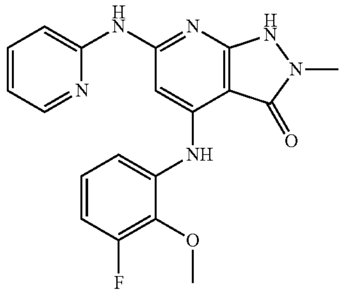 [SMILES: COc1c(F)cccc1Nc1cc(Nc2ccccn2)nc2[nH]n(C)c(=O)c12] |
| I-81 | 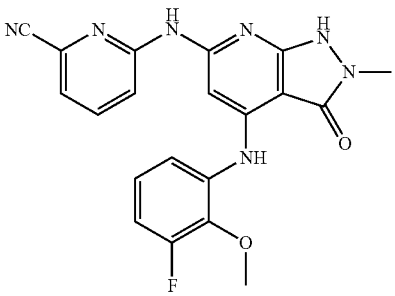 [SMILES: COc1c(F)cccc1Nc1cc(Nc2cccc(C#N)n2)nc2[nH]n(C)c(=O)c12] |
| I-82 | 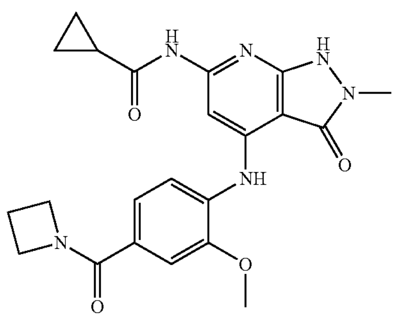 [SMILES: COc1cc(C(=O)N2CCC2)ccc1Nc1cc(NC(=O)C2CC2)nc2[nH]n(C)c(=O)c12] |
| I-83 | 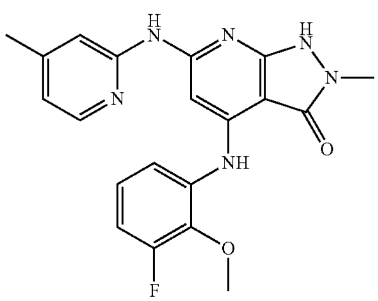 |
| I-84 | 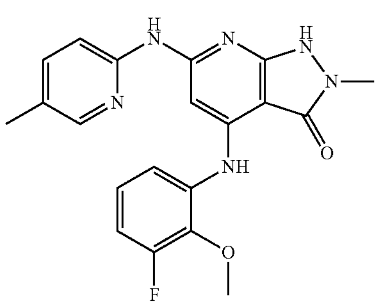 |
| I-85 | 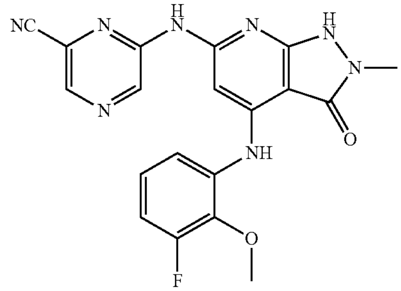 [SMILES: COc1c(F)cccc1Nc1cc(Nc2cncc(C#N)n2)nc2[nH]n(C)c(=O)c12] |
| I-86 | 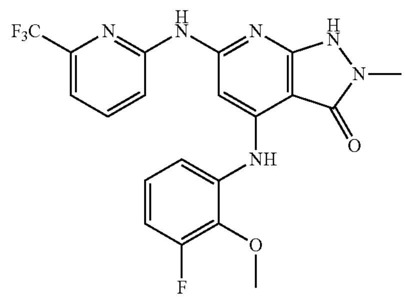 [SMILES: COc1c(F)cccc1Nc1cc(Nc2cccc(C(F)(F)F)n2)nc2[nH]n(C)c(=O)c12] |
| I-87 | 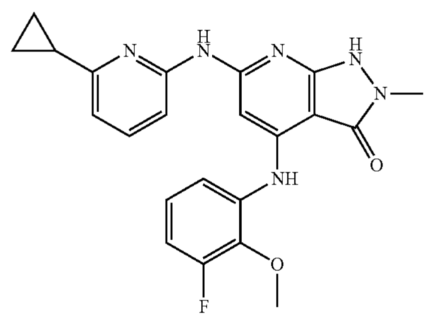 [SMILES: COc1c(F)cccc1Nc1cc(Nc2cccc(C3CC3)n2)nc2[nH]n(C)c(=O)c12] |
| I-88 | 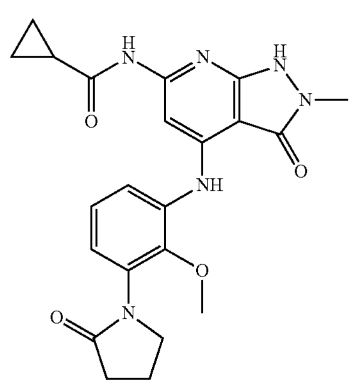 [SMILES: COc1c(Nc2cc(NC(=O)C3CC3)nc3[nH]n(C)c(=O)c23)cccc1N1CCCC1=O] |

TABLE 1-continued

Exemplary Compounds

| Compound | Structure |
|---|---|
| I-89 | (structure) |
| I-90 | (structure) |
| I-91 | (structure) |
| I-92 | (structure) |
| I-93 | (structure) |
| I-94 | (structure) |
| I-95 | (structure) |
| I-96 | (structure) |
| I-97 | (structure) |
| I-98 | (structure) |

TABLE 1-continued

Exemplary Compounds

| Compound | Structure |
|---|---|
| I-99 | 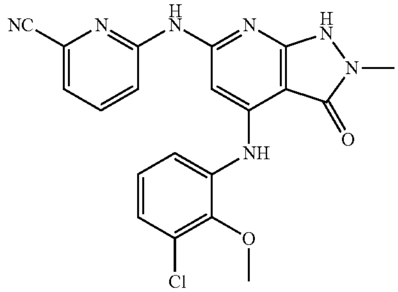 [SMILES: COc1c(Cl)cccc1Nc1cc(Nc2cccc(C#N)n2)nc2[nH]n(C)c(=O)c12] |
| I-100 | 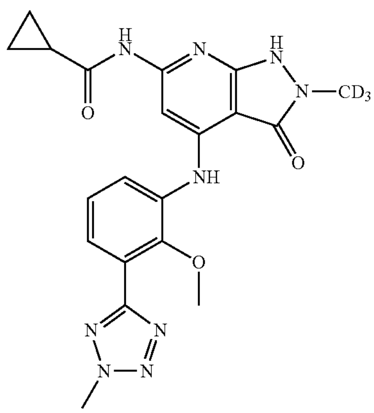 [SMILES: [2H]C([2H])([2H])n1[nH]c2nc(NC(=O)C3CC3)cc(Nc3cccc(-c4nnn(C)n4)c3OC)c2c1=O] |
| I-101 | 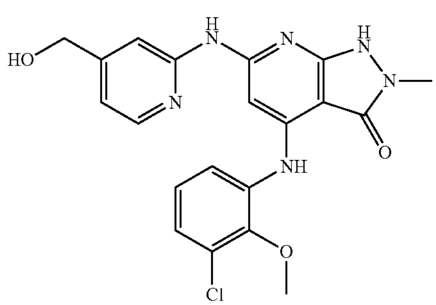 [SMILES: COc1c(Cl)cccc1Nc1cc(Nc2cc(CO)ccn2)nc2[nH]n(C)c(=O)c12] |
| I-102 | 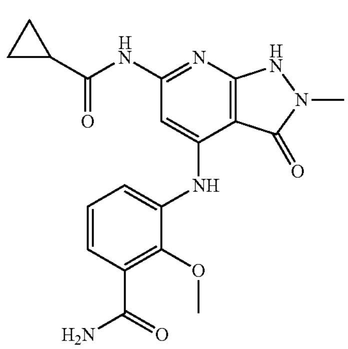 [SMILES: COc1c(Nc2cc(NC(=O)C3CC3)nc3[nH]n(C)c(=O)c23)cccc1C(N)=O] |
| I-103 | 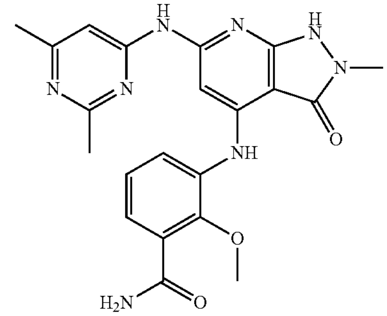 |
| I-104 | 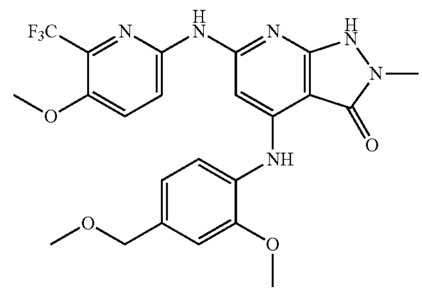 |
| I-105 | 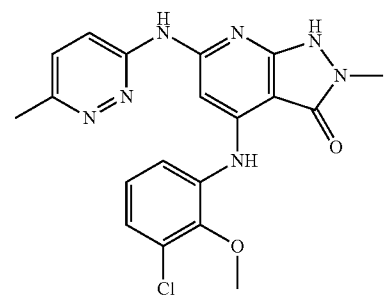 |
| I-106 | 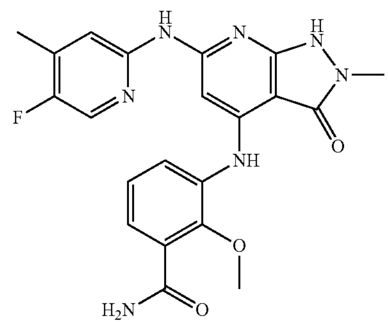 [SMILES: COc1c(Nc2cc(Nc3cc(C)c(F)cn3)nc3[nH]n(C)c(=O)c23)cccc1C(N)=O] |
| I-107 | 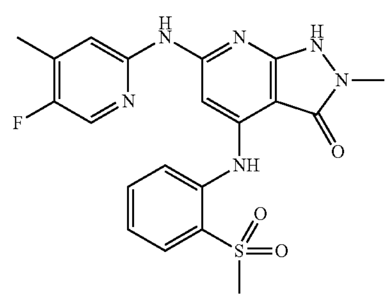 [SMILES: Cc1cc(Nc2cc(Nc3ccccc3S(C)(=O)=O)c3c(=O)n(C)[nH]c3n2)ncc1F] |

TABLE 1-continued
Exemplary Compounds
| Compound | Structure |
|---|---|
| I-108 | 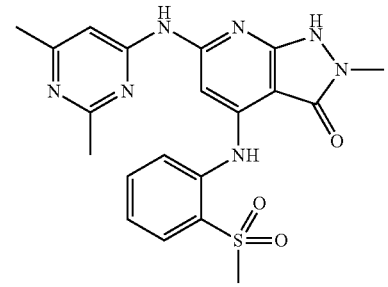 |
| I-109 | 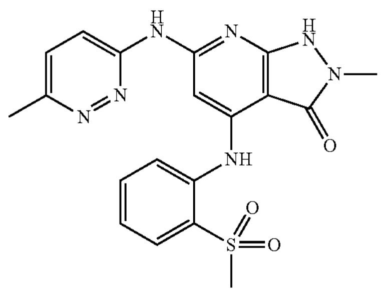 |
| I-110 | 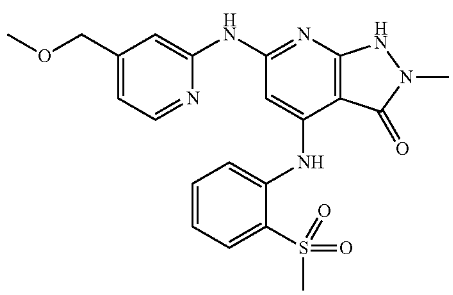 |
| I-111 | 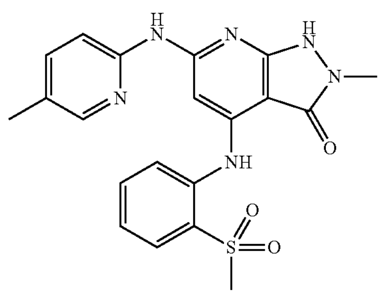 |
| I-112 | 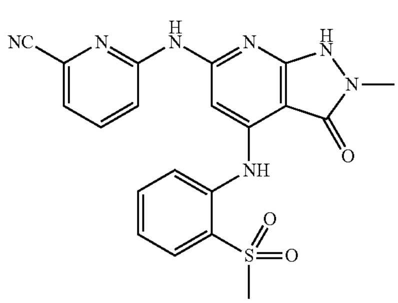 [SMILES: Cn1[nH]c2nc(Nc3cccc(C#N)n3)cc(Nc3ccccc3S(C)(=O)=O)c2c1=O] |
| I-113 | 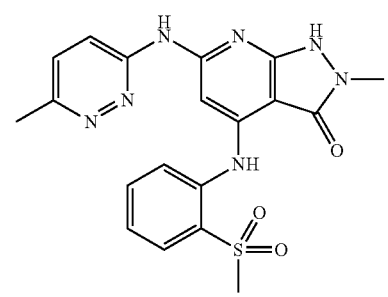 |
| I-114 | |
| I-115 | 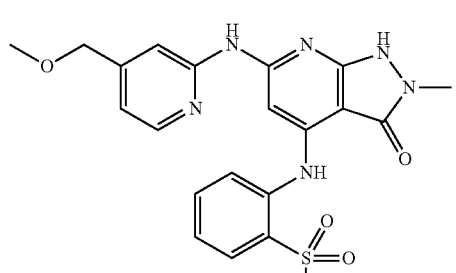 |
| I-116 | 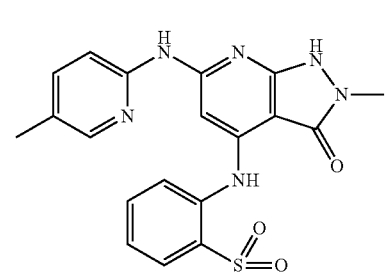 |
| I-117 | 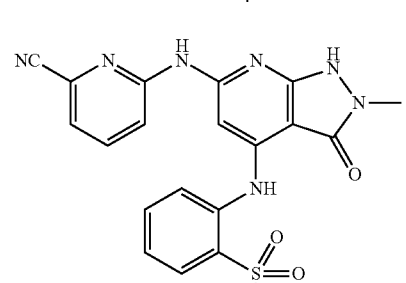 |

TABLE 1-continued
Exemplary Compounds
| Compound | Structure |
|---|---|
| I-118 | 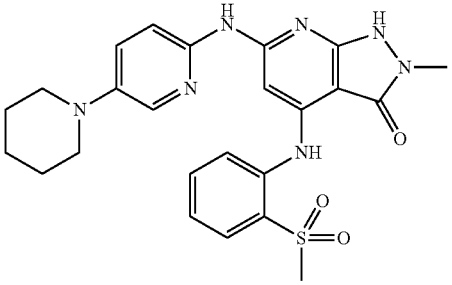 [SMILES: Cn1[nH]c2nc(Nc3ccc(N4CCCCC4)cn3)cc(Nc3ccccc3S(C)(=O)=O)c2c1=O] |
| I-119 | 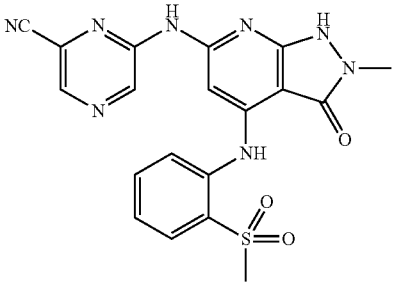 [SMILES: Cn1[nH]c2nc(Nc3cncc(C#N)n3)cc(Nc3ccccc3S(C)(=O)=O)c2c1=O] |
| I-120 | 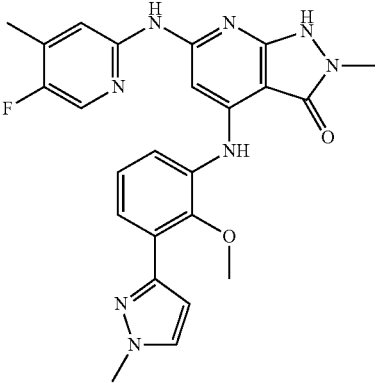 |
| I-121 | 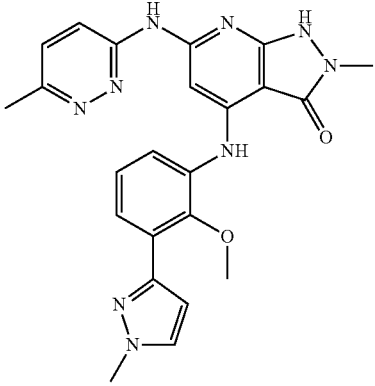 |
| I-122 | 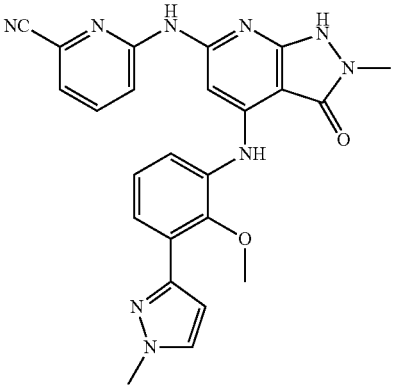 [SMILES: COc1c(Nc2cc(Nc3cccc(C#N)n3)nc3[nH]n(C)c(=O)c23)cccc1-c1ccn(C)n1] |
| I-123 | 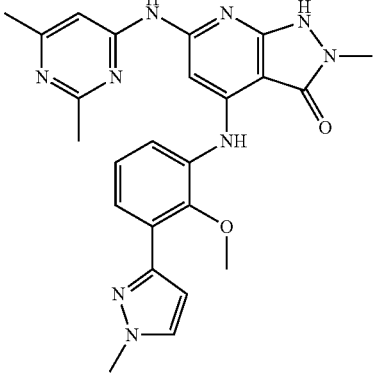 |
| I-124 | 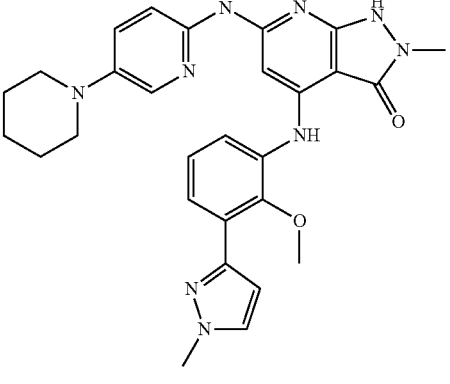 |
| I-125 | 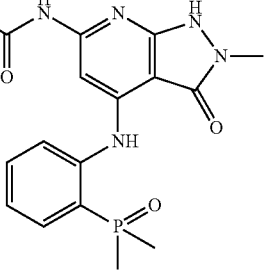 |

TABLE 1-continued
Exemplary Compounds
| Compound | Structure |
|---|---|
| I-126 | 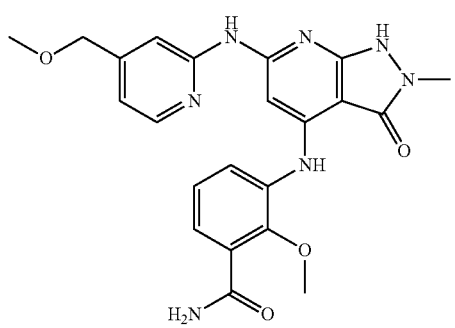 |
| I-127 | 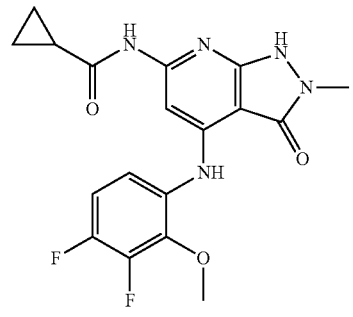 [SMILES: COc1c(Nc2cc(NC(=O)C3CC3)nc3[nH]n(C)c(=O)c23)ccc(F)c1F] |
| I-128 | 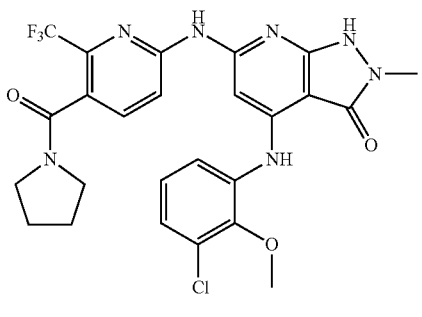 [SMILES: COc1c(Cl)cccc1Nc1cc(Nc2ccc(C(=O)N3CCCC3)c(C(F)(F)F)n2)nc2[nH]n(C)c(=O)c12] |
| I-129 | 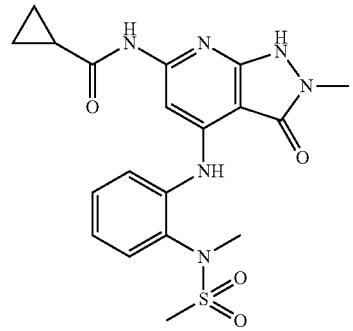 [SMILES: CN(c1ccccc1Nc1cc(NC(=O)C2CC2)nc2[nH]n(C)c(=O)c12)S(C)(=O)=O] |
| I-130 | 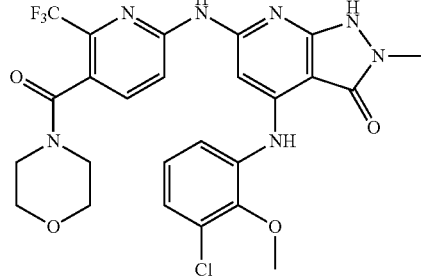 |
| I-131 | 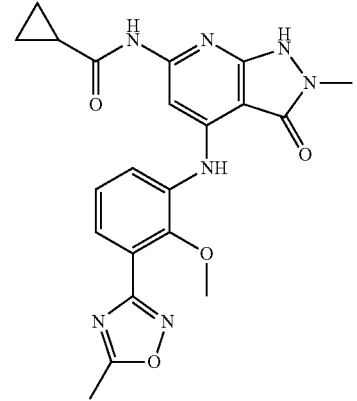 [SMILES: COc1c(Nc2cc(NC(=O)C3CC3)nc3[nH]n(C)c(=O)c23)cccc1-c1noc(C)n1] |
| I-132 | 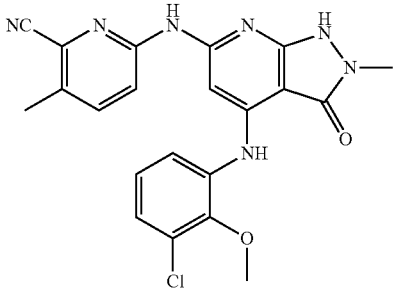 |
| I-133 | 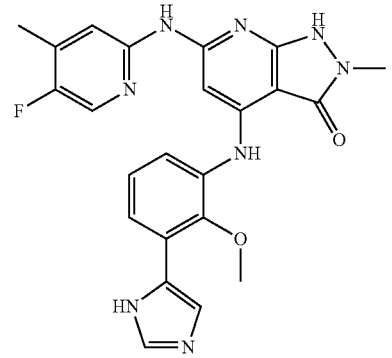 |

TABLE 1-continued
Exemplary Compounds
| Compound | Structure |
|---|---|
| I-134 | 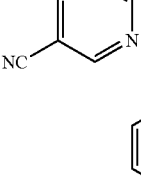 |
| I-135 | 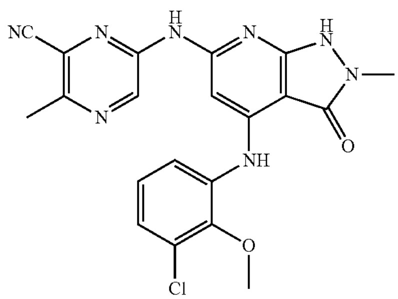 |
| I-136 | 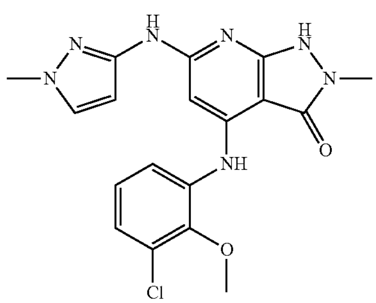 |
| I-137 | 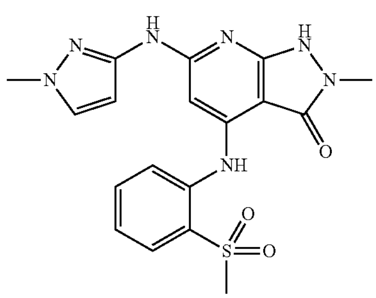 |
| I-138 | 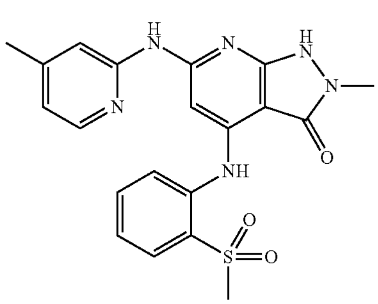 |
| I-139 | 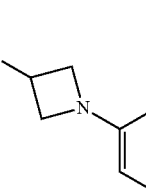 |
| I-140 | |
| I-141 | |
| I-142 | |
| I-143 | |

TABLE 1-continued
Exemplary Compounds
| Compound | Structure |
|---|---|
| I-144 | 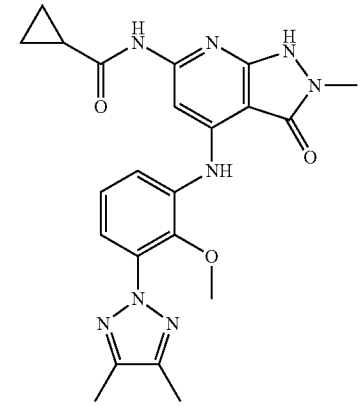 |
| I-145 | 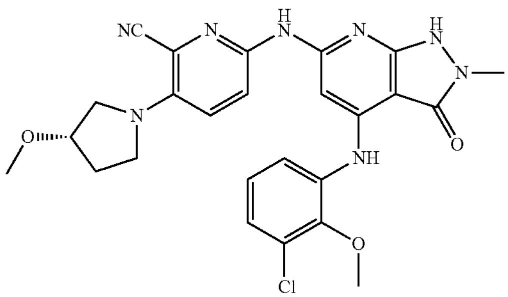 |
| I-146 | 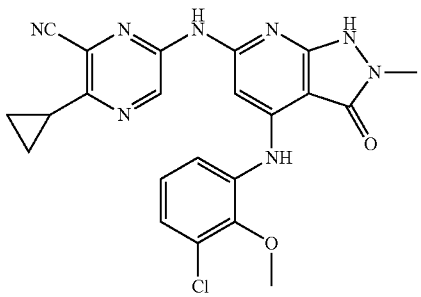 [SMILES: COc1c(Cl)cccc1Nc1cc(Nc2cnc(C3CC3)c(C#N)n2)nc2[nH]n(C)c(=O)c12] |
| I-147 | 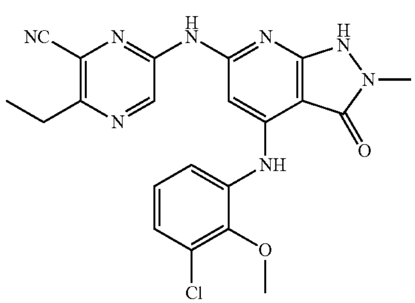 [SMILES: CCc1ncc(Nc2cc(Nc3cccc(Cl)c3OC)c3c(=O)n(C)[nH]c3n2)nc1C#N] |
| I-148 | 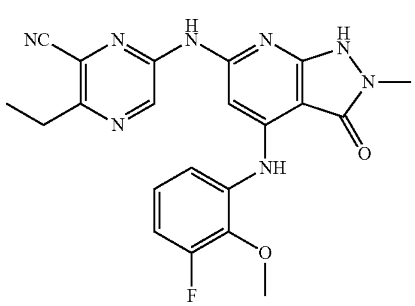 [SMILES: CCc1ncc(Nc2cc(Nc3cccc(F)c3OC)c3c(=O)n(C)[nH]c3n2)nc1C#N] |
| I-149 | 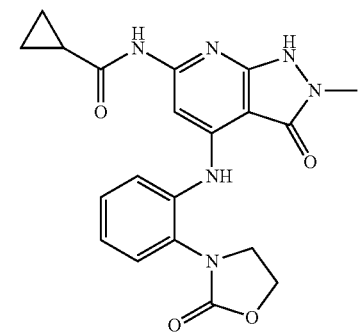 [SMILES: Cn1[nH]c2nc(NC(=O)C3CC3)cc(Nc3ccccc3N3CCOC3=O)c2c1=O] |
| I-150 | |
| I-151 | |
| I-152 | |

TABLE 1-continued

Exemplary Compounds

| Compound | Structure |
|---|---|
| I-153 | (structure) |
| I-154 | (structure) |
| I-155 | (structure) |
| I-156 | (structure) |
| I-157 | (structure) |
| I-158 | (structure) |
| I-159 | (structure) |
| I-160 | (structure) |
| I-161 | (structure) |

TABLE 1-continued

Exemplary Compounds

| Compound | Structure |
|---|---|
| I-162 | |
| I-163 | |
| I-164 | |
| I-165 | |
| I-166 | 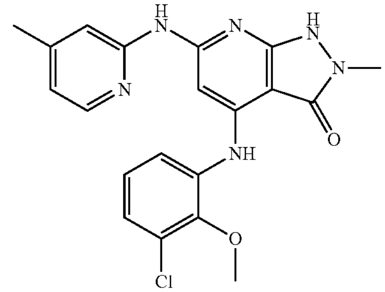 |
| I-167 | 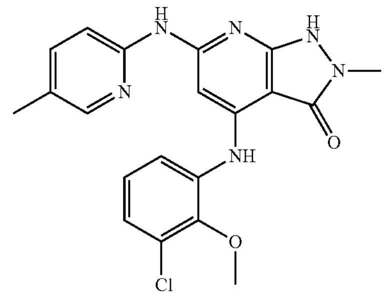 |
| I-168 | 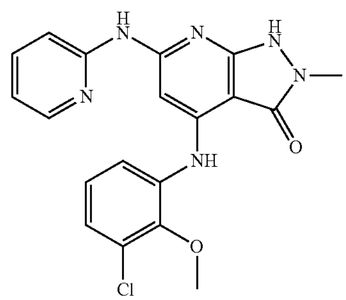 |
| I-169 | 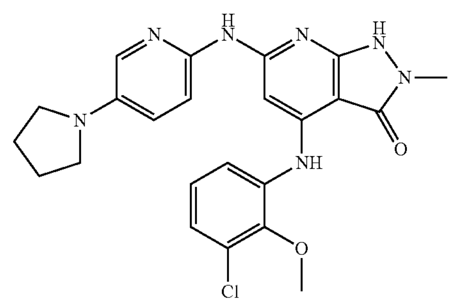 [SMILES: COc1c(Cl)cccc1Nc1cc(Nc2ccc(N3CCCC3)cn2)nc2[nH]n(C)c(=O)c12] |
| I-170 | 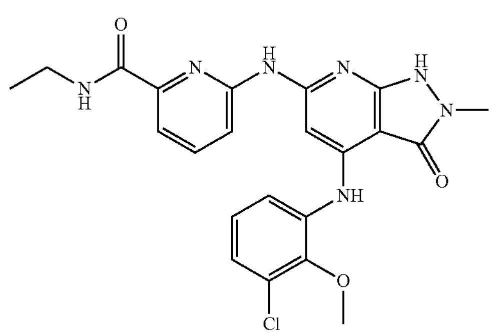 [SMILES: CCNC(=O)c1cccc(Nc2cc(Nc3cccc(Cl)c3OC)c3c(=O)n(C)[nH]c3n2)n1] |

TABLE 1-continued

Exemplary Compounds

| Compound | Structure |
|---|---|
| I-171 | (structure) |
| I-172 | (structure) |
| I-173 | (structure) |
| I-174 | (structure) |
| I-175 | (structure) |
| I-176 | (structure) |
| I-177 | (structure) |
| I-178 | (structure) |
| I-179 | (structure) |

TABLE 1-continued
Exemplary Compounds
| Compound | Structure |
|---|---|
| I-180 | 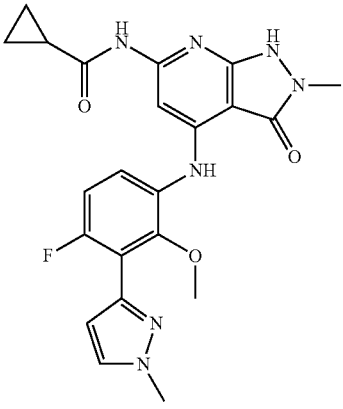 [SMILES: COc1c(Nc2cc(NC(=O)C3CC3)nc3[nH]n(C)c(=O)c23)ccc(F)c1-c1ccn(C)n1] |
| I-181 | 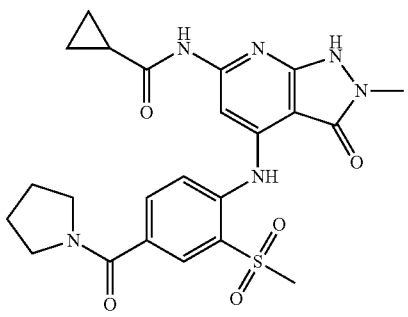 [SMILES: Cn1[nH]c2nc(NC(=O)C3CC3)cc(Nc3ccc(C(=O)N4CCCC4)cc3S(C)(=O)=O)c2c1=O] |
| I-182 | 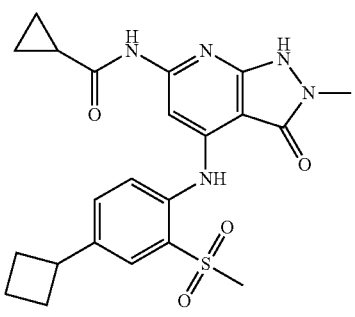 [SMILES: Cn1[nH]c2nc(NC(=O)C3CC3)cc(Nc3ccc(C4CCC4)cc3S(C)(=O)=O)c2c1=O] |
| I-183 | 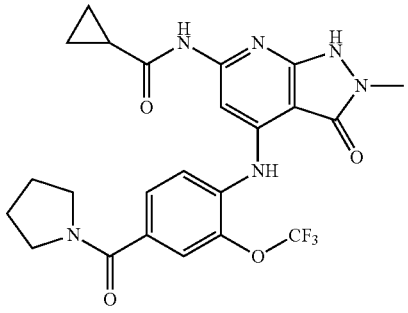 [SMILES: Cn1[nH]c2nc(NC(=O)C3CC3)cc(Nc3ccc(C(=O)N4CCCC4)cc3OC(F)(F)F)c2c1=O] |
| I-184 | 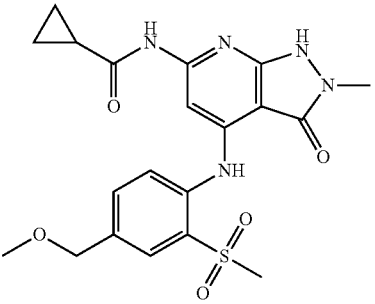 |
| I-185 | 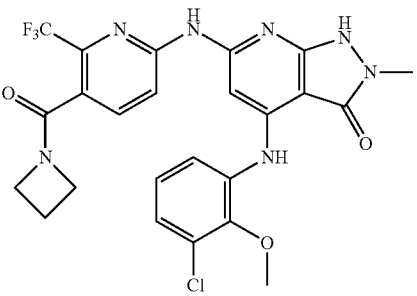 [SMILES: COc1c(Cl)cccc1Nc1cc(Nc2ccc(C(=O)N3CCC3)c(C(F)(F)F)n2)nc2[nH]n(C)c(=O)c12] |
| I-186 | 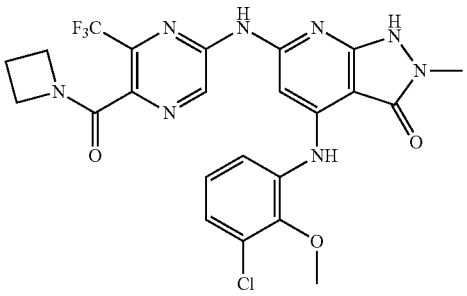 [SMILES: COc1c(Cl)cccc1Nc1cc(Nc2cnc(C(=O)N3CCC3)c(C(F)(F)F)n2)nc2[nH]n(C)c(=O)c12] |
| I-187 | 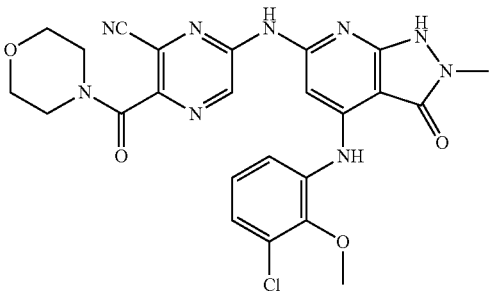 [SMILES: COc1c(Cl)cccc1Nc1cc(Nc2cnc(C(=O)N3CCOCC3)c(C#N)n2)nc2[nH]n(C)c(=O)c12] |
| I-188 | 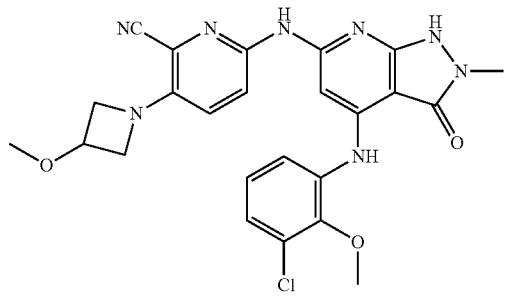 |

TABLE 1-continued
Exemplary Compounds
| Compound | Structure |
|---|---|
| I-189 | 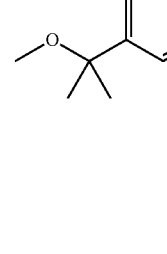 |
| I-190 | 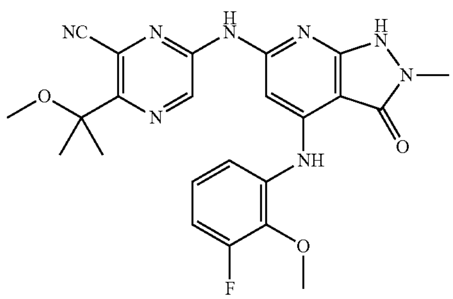 |
| I-191 | 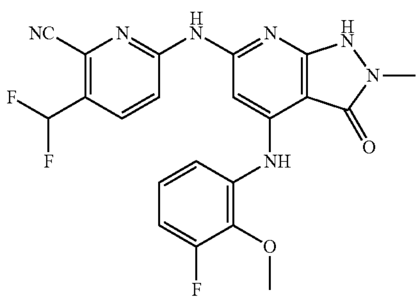 [SMILES: COc1c(F)cccc1Nc1cc(Nc2ccc(C(F)F)c(C#N)n2)nc2[nH]n(C)c(=O)c12] |
| I-192 | 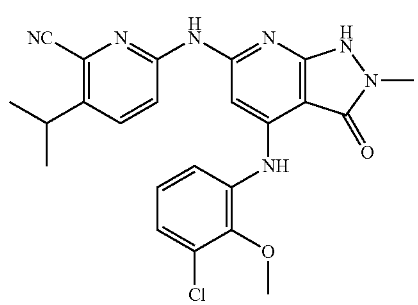 [SMILES: COc1c(Cl)cccc1Nc1cc(Nc2ccc(C(C)C)c(C#N)n2)nc2[nH]n(C)c(=O)c12] |
| I-193 | 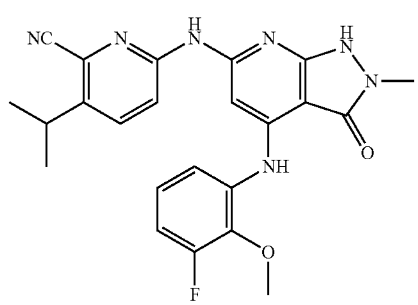 [SMILES: COc1c(F)cccc1Nc1cc(Nc2ccc(C(C)C)c(C#N)n2)nc2[nH]n(C)c(=O)c12] |
| I-194 | 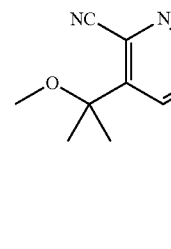 |
| I-195 | |
| I-196 | |
| I-197 | |
| I-198 | |

TABLE 1-continued

Exemplary Compounds

| Compound | Structure |
|---|---|
| I-199 | (structure) |
| I-200 | (structure) |
| I-201 | (structure) |
| I-202 | (structure) |
| I-203 | (structure) |
| I-204 | (structure) |
| I-205 | (structure) |
| I-206 | (structure) |
| I-207 | (structure) |
| I-208 | (structure) |

TABLE 1-continued
Exemplary Compounds
| Compound | Structure |
|---|---|
| I-209 | 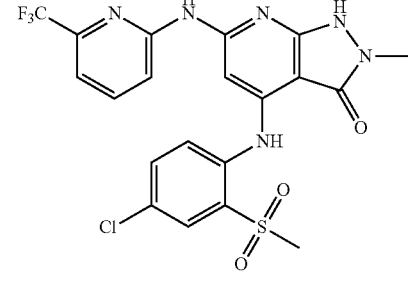 |
| I-210 | 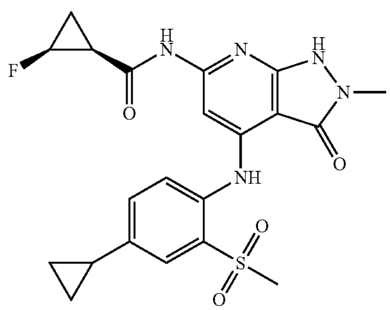 [SMILES: Cn1[nH]c2nc(NC(=O)[C@@H]3C[C@@H]3F)cc(Nc3ccc(C4CC4)cc3S(C)(=O)=O)c2c1=O] |
| I-211 | 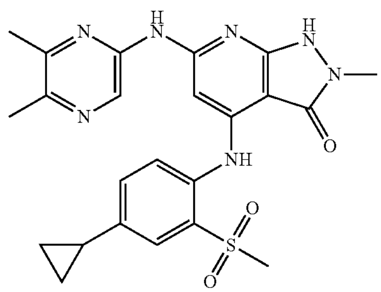 |
| I-212 | 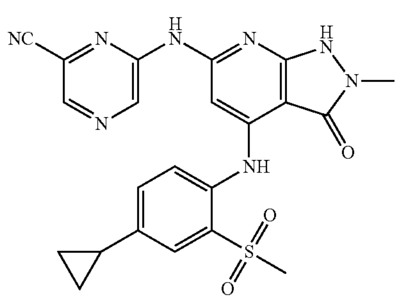 [SMILES: Cn1[nH]c2nc(Nc3cncc(C#N)n3)cc(Nc3ccc(C4CC4)cc3S(C)(=O)=O)c2c1=O] |
| I-213 | 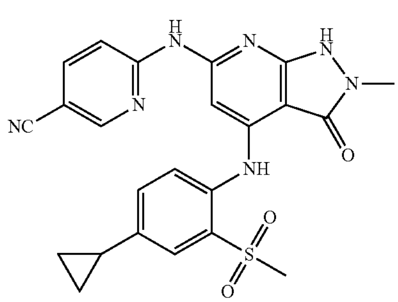 [SMILES: Cn1[nH]c2nc(Nc3ccc(C#N)cn3)cc(Nc3ccc(C4CC4)cc3S(C)(=O)=O)c2c1=O] |
| I-214 | 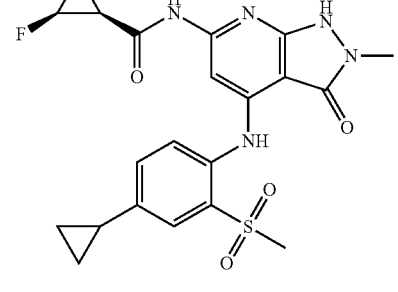 |
| I-215 | |
| I-216 | |
| I-217 | |
| I-218 | |

TABLE 1-continued
Exemplary Compounds
| Compound | Structure |
|---|---|
| I-219 | 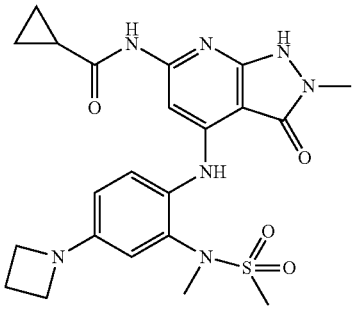 [SMILES: CN(c1cc(N2CCC2)ccc1Nc1cc(NC(=O)C2CC2)nc2[nH]n(C)c(=O)c12)S(C)(=O)=O] |
| I-220 | 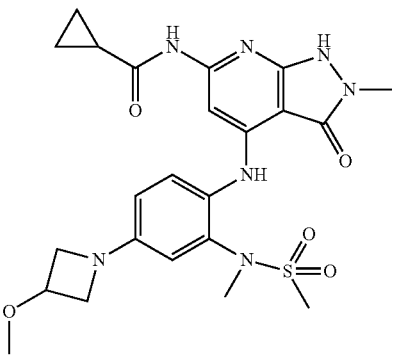 [SMILES: COC1CN(c2ccc(Nc3cc(NC(=O)C4CC4)nc4[nH]n(C)c(=O)c34)c(N(C)S(C)(=O)=O)c2)C1] |
| I-221 | 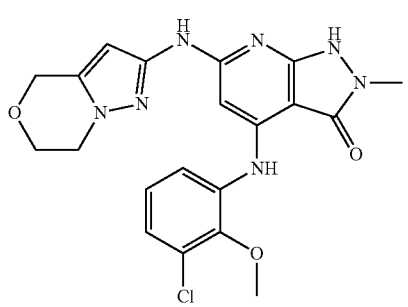 [SMILES: COc1c(Cl)cccc1Nc1cc(Nc2cc3n(n2)CCOC3)nc2[nH]n(C)c(=O)c12] |
| I-222 | 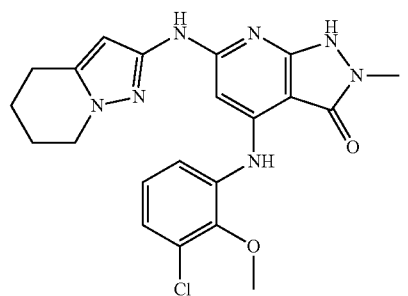 [SMILES: COc1c(Cl)cccc1Nc1cc(Nc2cc3n(n2)CCCC3)nc2[nH]n(C)c(=O)c12] |
| I-223 | 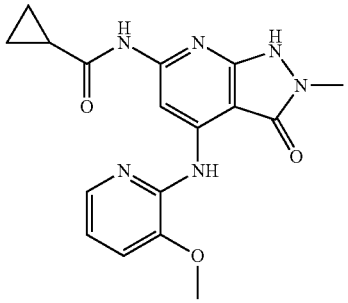 |
| I-224 | 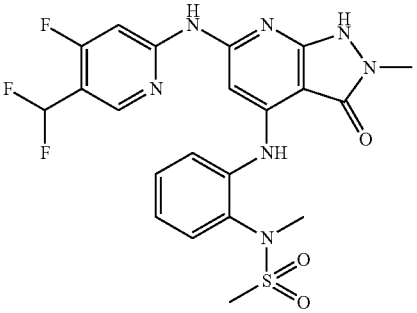 [SMILES: CN(c1ccccc1Nc1cc(Nc2cc(F)c(C(F)F)cn2)nc2[nH]n(C)c(=O)c12)S(C)(=O)=O] |
| I-225 | 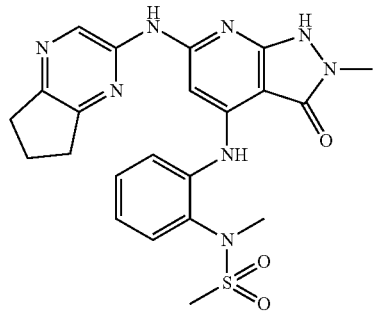 [SMILES: CN(c1ccccc1Nc1cc(Nc2cnc3c(n2)CCC3)nc2[nH]n(C)c(=O)c12)S(C)(=O)=O] |
| I-226 | 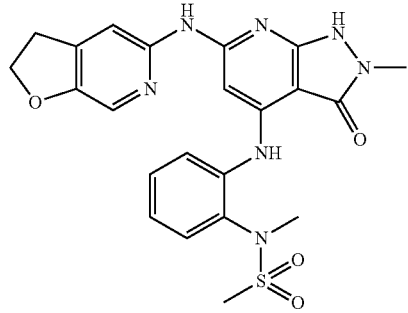 [SMILES: CN(c1ccccc1Nc1cc(Nc2cc3c(cn2)OCC3)nc2[nH]n(C)c(=O)c12)S(C)(=O)=O] |

TABLE 1-continued

Exemplary Compounds

| Compound | Structure |
|---|---|
| I-227 | (structure) |
| I-228 | (structure) |
| I-229 | (structure) |
| I-230 | (structure) |
| I-231 | (structure) |
| I-232 | (structure) |
| I-234 | (structure) |
| I-235 | (structure) |

TABLE 1-continued

Exemplary Compounds

| Compound | Structure |
|---|---|
| I-236 | 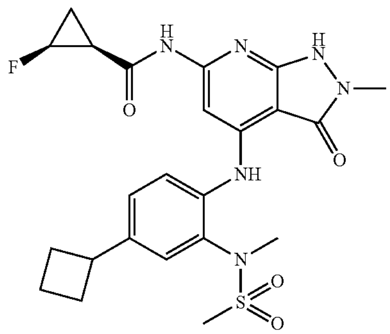 [SMILES: CN(c1cc(C2CCC2)ccc1Nc1cc(NC(=O)[C@@H]2C[C@@H]2F)nc2[nH]n(C)c(=O)c12)S(C)(=O)=O] |
| I-237 | 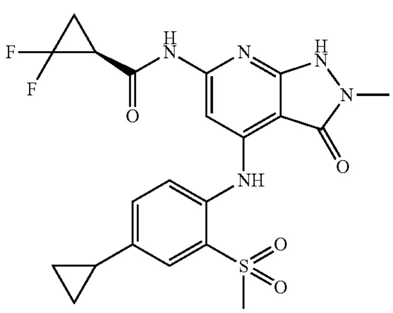 [SMILES: Cn1[nH]c2nc(NC(=O)[C@@H]3CC3(F)F)cc(Nc3ccc(C4CC4)cc3S(C)(=O)=O)c2c1=O] |
| I-238 | 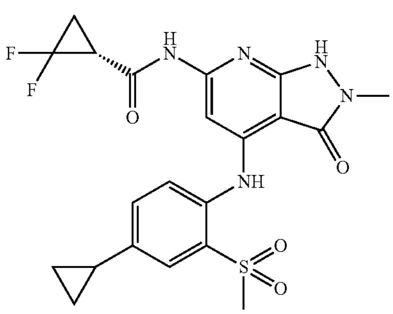 [SMILES: Cn1[nH]c2nc(NC(=O)[C@H]3CC3(F)F)cc(Nc3ccc(C4CC4)cc3S(C)(=O)=O)c2c1=O] |
| I-239 | 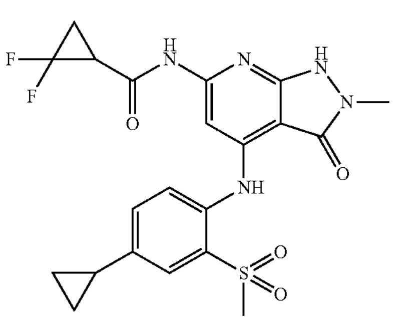 [SMILES: Cn1[nH]c2nc(NC(=O)C3CC3(F)F)cc(Nc3ccc(C4CC4)cc3S(C)(=O)=O)c2c1=O] |

TABLE 1-continued

Exemplary Compounds

| Compound | Structure |
|---|---|
| I-240 | 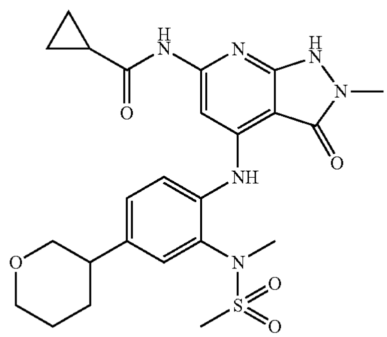 [SMILES: CN(c1cc(C2CCCOC2)ccc1Nc1cc(NC(=O)C2CC2)nc2[nH]n(C)c(=O)c12)S(C)(=O)=O] |
| I-241 | 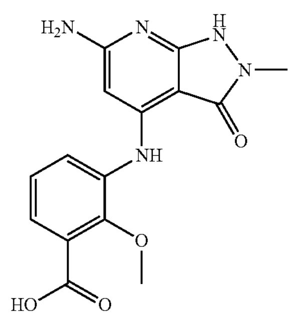 [SMILES: COc1c(Nc2cc(N)nc3[nH]n(C)c(=O)c23)cccc1C(=O)O] |

Exemplary compounds of the invention are set forth in Table 2, below.

TABLE 2

Exemplary Compounds

| Compound | Structure |
|---|---|
| VIII-1 | |

TABLE 2-continued
Exemplary Compounds
| Compound | Stucture |
|---|---|
| VIII-2 | 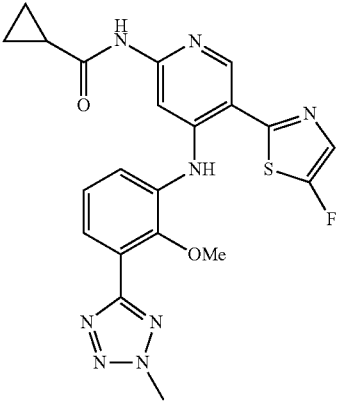 [SMILES: COc1c(Nc2cc(NC(=O)C3CC3)ncc2-c2ncc(F)s2)cccc1-c1nnn(C)n1] |
| VIII-3 | 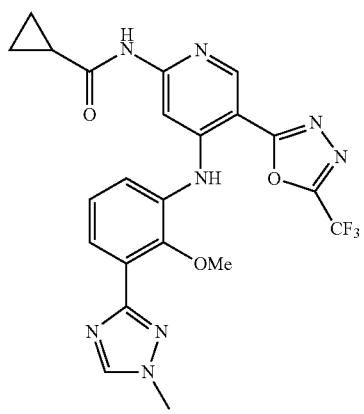 [SMILES: COc1c(Nc2cc(NC(=O)C3CC3)ncc2-c2nnc(C(F)(F)F)o2)cccc1-c1ncn(C)n1] |
| VIII-4 | 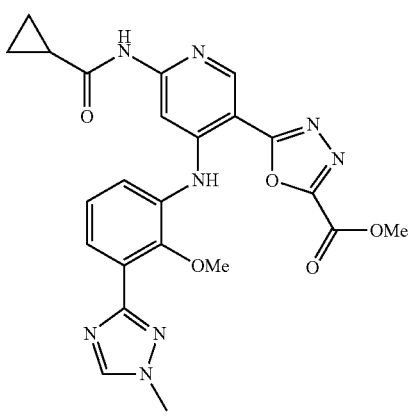 [SMILES: COC(=O)c1nnc(-c2cnc(NC(=O)C3CC3)cc2Nc2cccc(-c3ncn(C)n3)c2OC)o1] |
| VIII-5 | 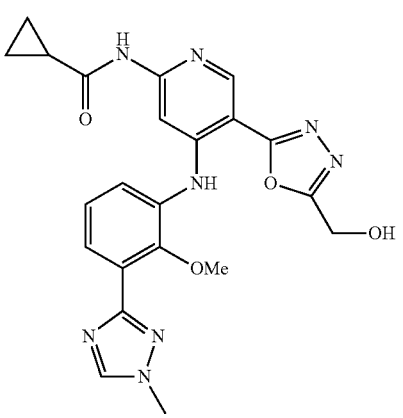 [SMILES: COc1c(Nc2cc(NC(=O)C3CC3)ncc2-c2nnc(CO)o2)cccc1-c1ncn(C)n1] |
| VIII-6 | 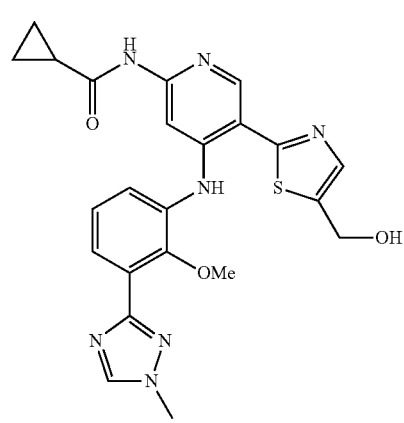 [SMILES: COc1c(Nc2cc(NC(=O)C3CC3)ncc2-c2ncc(CO)s2)cccc1-c1ncn(C)n1] |
| VIII-7 | 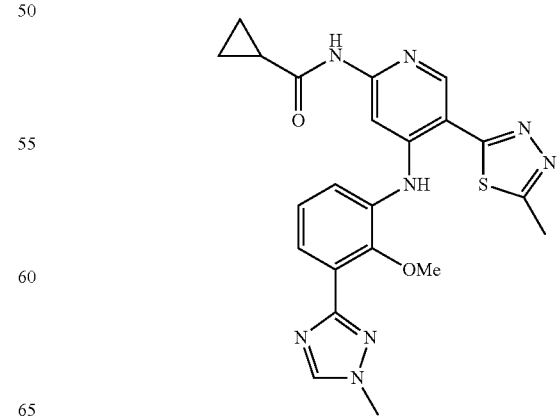 |

TABLE 2-continued
Exemplary Compounds
| Compound | Structure |
|---|---|
| VIII-8 | 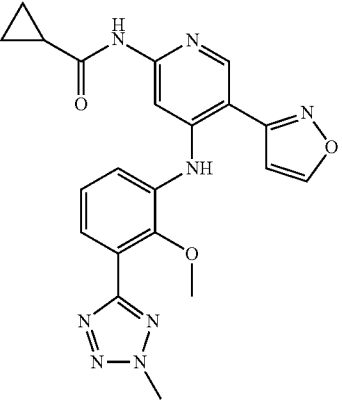 [SMILES: COc1c(Nc2cc(NC(=O)C3CC3)ncc2-c2ccon2)cccc1-c1nnn(C)n1] |
| VIII-9 | 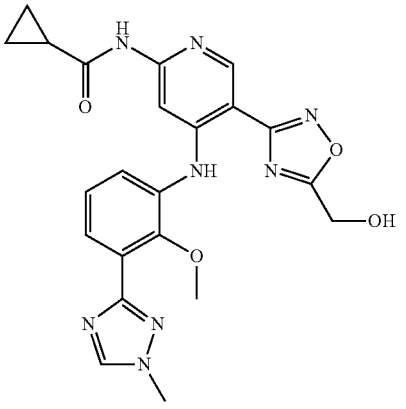 [SMILES: COc1c(Nc2cc(NC(=O)C3CC3)ncc2-c2noc(CO)n2)cccc1-c1ncn(C)n1] |
| VIII-10 | 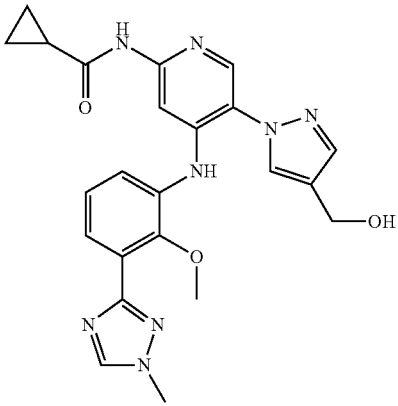 [SMILES: COc1c(Nc2cc(NC(=O)C3CC3)ncc2-n2cc(CO)cn2)cccc1-c1ncn(C)n1] |
| VIII-11 | 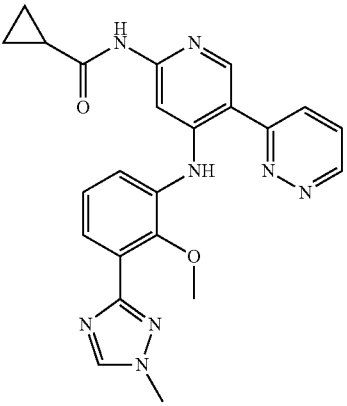 [SMILES: COc1c(Nc2cc(NC(=O)C3CC3)ncc2-c2cccnn2)cccc1-c1ncn(C)n1] |
| VIII-12 | 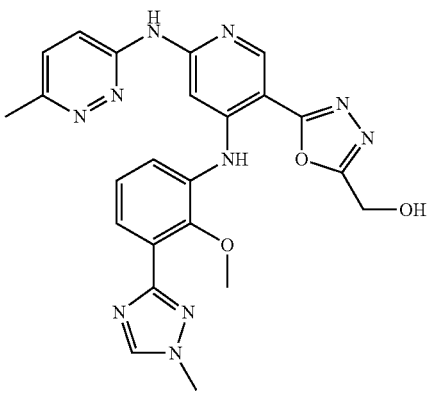 [SMILES: COc1c(Nc2cc(Nc3ccc(C)nn3)ncc2-c2nnc(CO)o2)cccc1-c1ncn(C)n1] |
| VIII-13 | 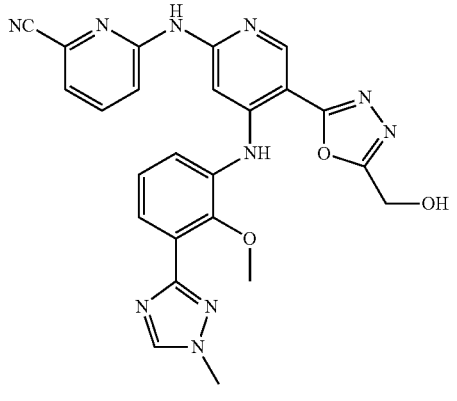 [SMILES: COc1c(Nc2cc(Nc3cccc(C#N)n3)ncc2-c2nnc(CO)o2)cccc1-c1ncn(C)n1] |

TABLE 2-continued
Exemplary Compounds
| Compound | Stucture |
|---|---|
| VIII-14 | 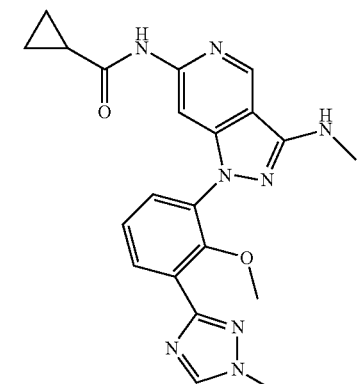 |
| VIII-15 | |
| VIII-16 | |
| VIII-17 | |
Exemplary compounds of the invention are set forth in Table 3, below.
TABLE 3
Exemplary Compounds
| Compound | Stucture |
|---|---|
| XVI-1 | 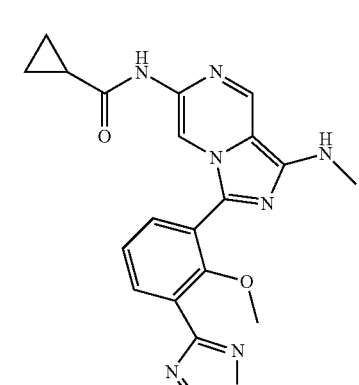 |
| XVI-2 | |
| XVI-3 | |

TABLE 3-continued

Exemplary Compounds

| Compound | Structure |
|---|---|
| XVI-4 | |
| XVI-5 | |
| XVI-6 | |

In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the method employs a compound set forth in Table 2, above, or a pharmaceutically acceptable salt thereof. In some embodiments, the present invention provides a compound set forth in Table 2, above, or a pharmaceutically acceptable salt thereof. In some embodiments, the present invention provides a pharmaceutical composition comprising a compound set forth in Table 2 above, or a pharmaceutically acceptable salt thereof, together with a pharmaceutically acceptable carrier, excipient, or diluent.

In some embodiments, the method employs a compound set forth in Table 3, above, or a pharmaceutically acceptable salt thereof. In some embodiments, the present invention provides a compound set forth in Table 3, above, or a pharmaceutically acceptable salt thereof. In some embodiments, the present invention provides a pharmaceutical composition comprising a compound set forth in Table 3 above, or a pharmaceutically acceptable salt thereof, together with a pharmaceutically acceptable carrier, excipient, or diluent.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In some embodiments, compounds of formula I are prepared according to the following general procedure, depicted in Scheme 1.

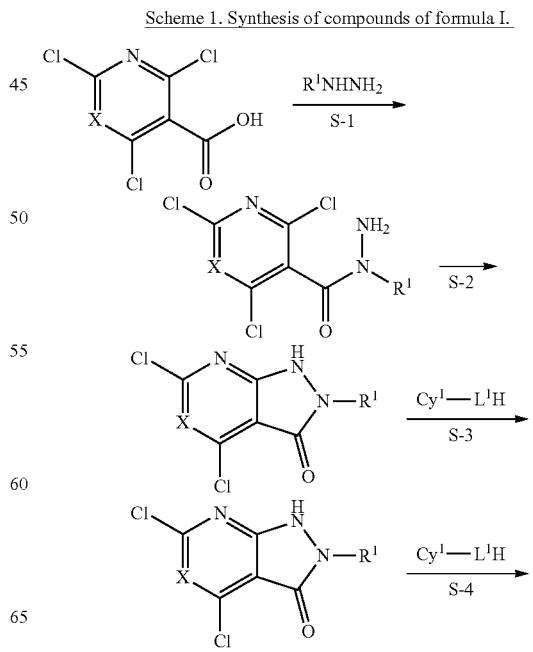

Scheme 1. Synthesis of compounds of formula I.

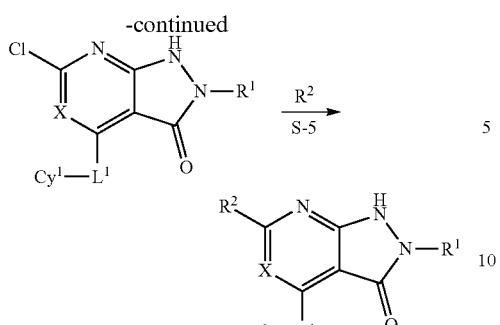

In some embodiments, where $L^1$ is NH, intermediates of formula $Cy^1$-$NH_2$ are prepared according to the methods described in WO2014074660A1, WO2014074661A1, and WO2015089143A1, the entirety of each of which is incorporated herein by reference.

In some embodiments, compounds of formula VIIII are prepared according to the following general procedure, depicted in Scheme 2.

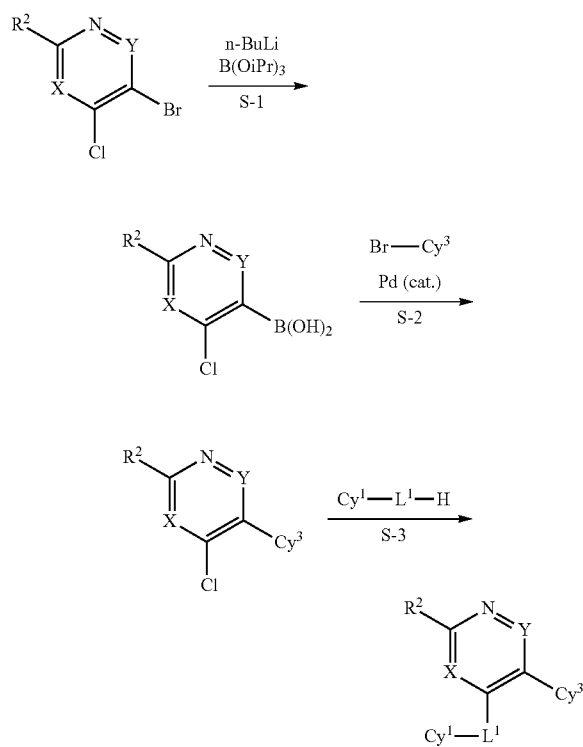

In some embodiments, where $L^1$ is NH, intermediates of formula Cy-$NH_2$ are prepared according to the methods described in WO2014074660A1, WO2014074661A1, and WO2015089143A1, the entirety of each of which is incorporated herein by reference.

In some embodiments, compounds of formula XXIV-b are prepared according to the following general procedure, depicted in Scheme 3.

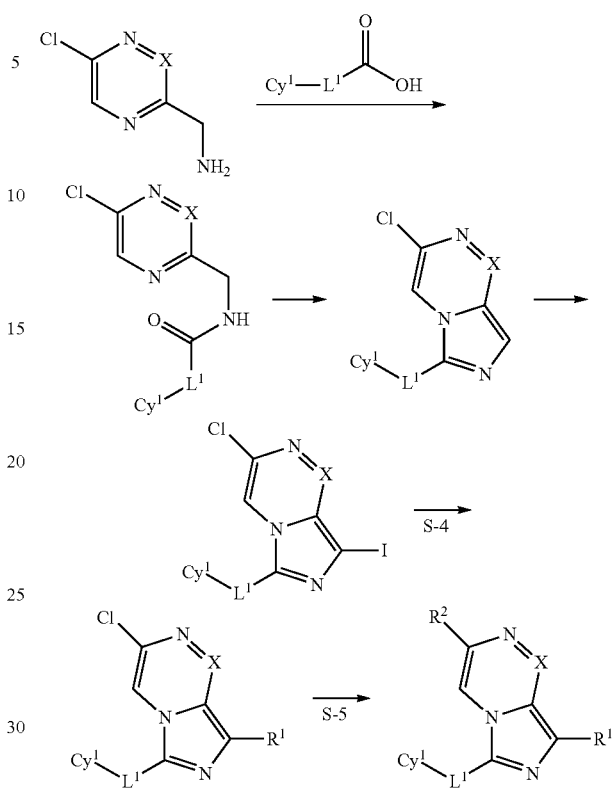

wherein each of X, $L^1$, and $Cy^1$ is as defined above and in embodiments herein, singly and in combination.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12R31 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupus Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I1), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I, VIII, or XVI', and one or more additional therapeutic agents. The therapeutic agent may be administered together with a compound of formula I, VIII, or XVI', or may be administered prior to or following administration of a compound of formula I, VIII, or XVI'. Suitable therapeutic agents are described in further detail below. In certain embodiments, a compound of formula I, VIII, or XVI' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I, VIII, or XVI' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I, VIII, or XVI' and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmicort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I, VIII, or XVI' and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I, VIII, or XVI' and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I, VIII, or XVI' and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I, VIII, or XVI' and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I, VIII, or XVI' and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I, VIII, or XVI' and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, In another embodiment, the present invention provides a method of treating a hematological malignancy comprising administering to a patient in need thereof a compound of formula I, VIII, or XVI' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I, VIII, or XVI' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I, VIII, or XVI' and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I, VIII, or XVI' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I, VIII, or XVI' and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I, VIII, or XVI' and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I, VIII, or XVI' and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I, VIII, or XVI' and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Duclos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I, VIII, or XVI' and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I, VIII, or XVI'. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD 180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclomethasone dipropionate, fluticasone propionate, ciclesonide or mometasone furoate; non-steroidal glucocorticoid receptor agonists; LTB4 antagonists such LY293111, CGS025019C, CP-195543, SC-53228, BITL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and terfenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these.

Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of N-(4-((2-methoxy-3-(2-methyl-2H-tetrazol-5-yl)phenyl)amino)-2-methyl-3-oxo-2,3-dihydro-1H-pyrazolo[3,4-b]pyridin-6-yl)cyclopropanecarboxamide, I-1

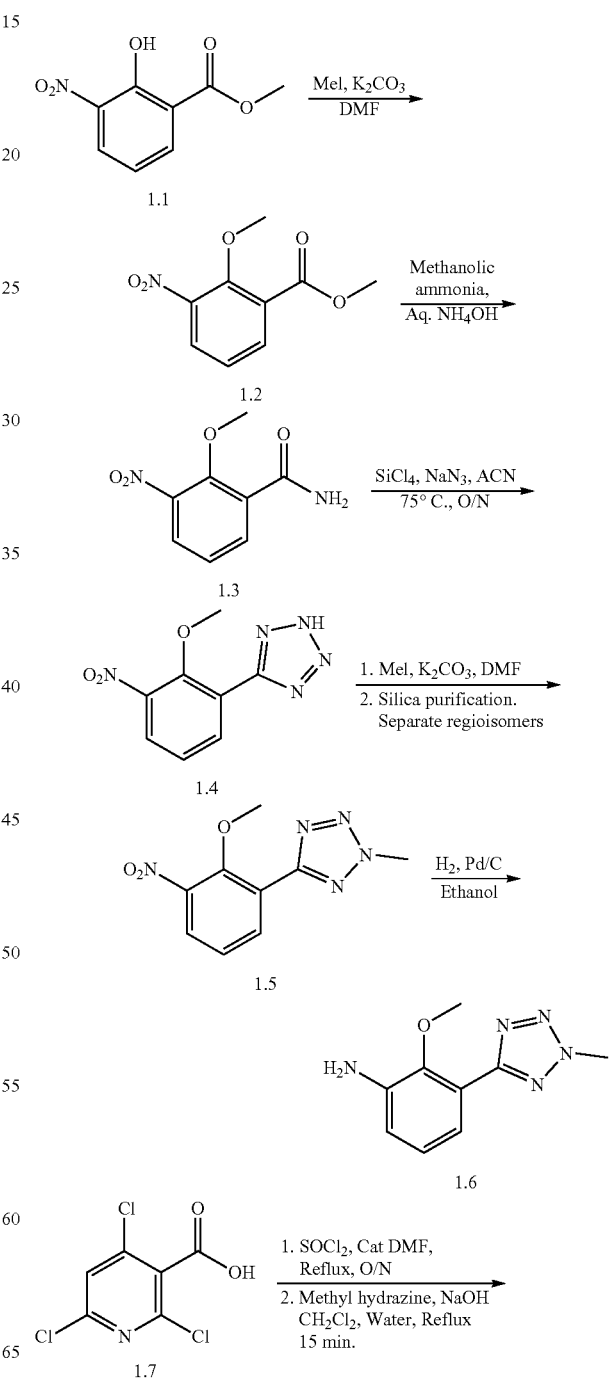

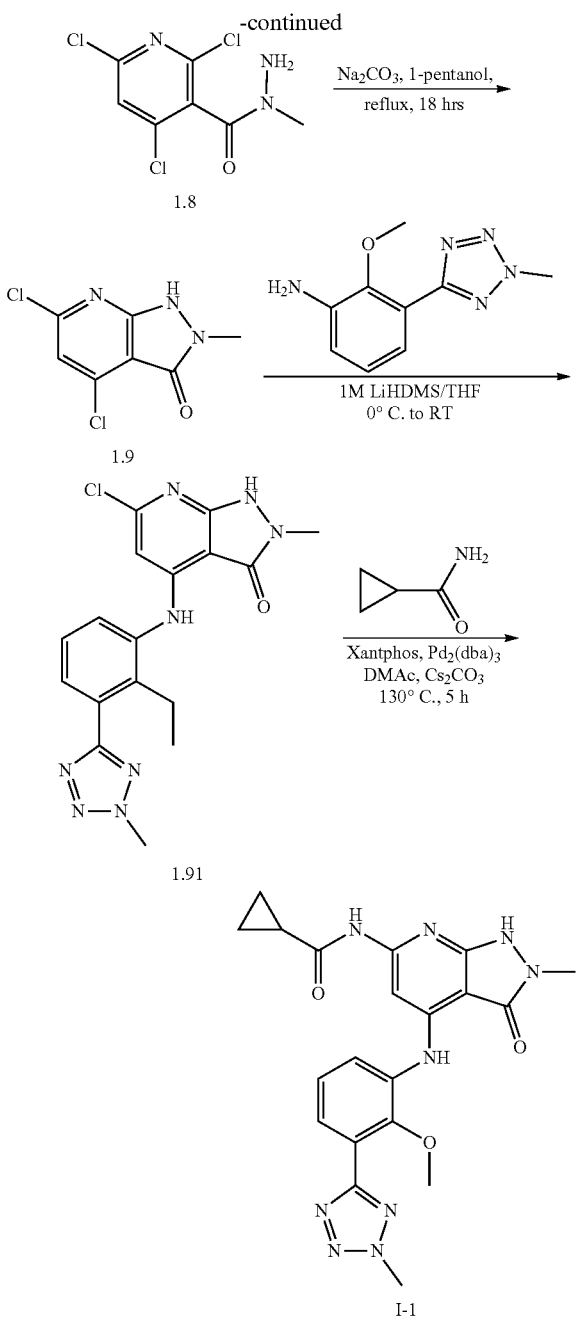

Synthesis of Compound 1.2.

To a solution of 1.1 (50 g, 253.6 mmol, 1.0 eq) in DMF (500 mL), was added K₂CO₃ (70 g, 507.6 mmol, 2.0 eq) at 0° C. and stirred for 15 min. To the suspension was added MeI (72 g, 507.6 mmol, 2.0 eq) dropwise and reaction mixture was stirred at 60° C. for 2 h. After completion of the reaction, reaction mixture was transferred into ice-water. Precipitated product was filtered, dried to provide 1.2 (50.0 g, 93.0%). MS(ES): m/z 212.2 [M+H]⁺.

Synthesis of Compound 1.3.

To 1.2 (50 g, 236.7 mmol, 1.0 eq) was added aq. NH₄OH (300 mL) followed by methanolic NH₃ (1600 mL). Reaction mixture was stirred at room temperature for 16 h. After completion of the reaction, reaction mixture was concentrated under reduced pressure and residue was washed with ice cold water. Precipitate was dried to furnish 1.3 (45.0 g, 96.0%). MS(ES): m/z 197.2 [M+H]⁺.

Synthesis of Compound 1.4

To a suspension of NaN₃ (21.8 g, 336 mmol, 3.0 eq) in acetonitrile (220 mL) was added SiCl₄ (28.6 g, 168 mmol, 1.5 eq). To the stirred suspension was added compound 1.3 (22.0 g, 112 mmol, 1.0 eq) and the reaction mixture was stirred at 75° C. for 16 h. Reaction mixture was cooled to room temperature and water was added. Solid precipitated out was filtered to provide 1.4 (18.0 g, 72.5%). MS(ES): m/z 222.2 [M+H]⁺.

Synthesis of Compound 1.5

To a stirred solution of 1.4 (15.0 g, 67.8 mmol, 1.0 eq) in DMF (150 mL) was added K₂CO₃ (23.4 g, 169.7 mmol, 2.5 eq) at 0° C. To this added MeI (19.1 g, 135.7 mmol, 2.0 eq) dropwise. Reaction mixture was stirred at room temperature for 24 h. After completion of the reaction, mixture was transferred into water and extracted with EtOAc. Organic layers were combined, washed with brine, dried over Na₂SO₄ and concentrated under reduced pressure to pressure to obtain crude material. The crude was purified by column chromatography to provide desired regioisomer 1.5 (10.0 g, 62.7%). MS(ES): m/z 236.2 [M+H]⁺.

Synthesis of Compound 1.6

To a solution of 1.5 (10.0 g, 42.5 mmol, 1.0 eq) in MeOH (100 mL), 10% Pd/C (2.0 g) was added. Hydrogen was purged through reaction mixture for 4 h. After completion of the reaction, mixture was filtered through Celite-bed and washed with MeOH. Filtrate was concentrated under reduced pressure to obtain 1.6. (5.3 g, 60.7%). MS(ES): m/z 206.3 [M+H]⁺.

Synthesis of Compound 1.8

To 1.7 (1.0 g, 4.42 mmol, 1.0 eq) was added SOCl₂ (5.0 mL) followed by DMF (catalytic) and refluxed for 16 h. Reaction mixture was concentrated under reduced pressure to obtain acyl chloride. Methyl hydrazine (0.20 g, 42.5 mmol, 1.0 eq) was dissolved in CH₂Cl₂ (20.0 mL) followed by addition of solution of NaOH (0.72 g, 177 mmol, 4.0 eq) in water (5.0 mL). To the solution was added previously made acyl chloride solution in CH₂Cl₂ (20.0 mL) dropwise. Reaction mixture was refluxed for 15 min. After completion of reaction, reaction mixture was transferred into water and extracted with CH₂Cl₂. Organic layers were combined, washed with brine, dried over Na₂SO₄ and concentrated under reduced pressure to pressure to obtain crude which was purified by column chromatography to provide 1.8. (1.1 g, 97.0%). MS(ES): m/z 255.5 [M+H]⁺.

Synthesis of Compound 1.9

To a suspension of 1.8 (1.0 g, 3.93 mmol, 1.0 eq) in 1-pentanol (15.0 mL) was added Na₂CO₃ (0.49 g, 3.93 mmol, 1.0 eq) and reaction mixture was stirred at 120° C. for 16 h. After completion of the reaction, reaction mixture was cooled to room temperature and pH=6.0 was adjusted using 1 N HCl. Reaction mixture was concentrated under reduced pressure to obtain crude which was purified by preparative HPLC to furnish 1.9. (0.15 g, 17.5%). MS(ES): m/z 219.2 [M+H]⁺.

Synthesis of Compound 1.9

To a solution of 1.9 (0.1 g, 0.45 mmol, 1.0 eq) and 1.6 (0.188 g, 0.917 mmol, 2.0 eq) in THF (2.0 mL) was added 1.0 M solution of LHMDS (1.6 mL, 1.57 mmol, 3.5 eq) in tetrahydrofuran at −78° C. Reaction mixture was stirred at room temperature for 18 h. After completion of the reaction, reaction mixture was transferred into water and extracted with EtOAc. Aqueous layer was acidified with 1.0 N HCl and extracted with EtOAc. Organic layers were combined, washed with brine, dried over Na₂SO₄ and concentrated under reduced pressure to pressure to get pure 1.91. (0.1 g, 56.37%). MS(ES): m/z 387.9 [M+H]+.

Synthesis of Compound I-1

To 1.91 (0.020 g, 0.051 mmol, 1.0 eq) in DMA (0.5 mL) was added cyclopropanecarboxamide (0.005 g, 0.062 mmol, 1.2 eq), $Cs_2CO_3$ (0.033 g, 0.102 mmol, 2.0 eq). The reaction mixture was degassed for 10 min. under argon atmosphere, then $Pd_2(dba)_3$ (0.005 g, 0.005 mmol, 0.1 eq) and Xantphos (0.006 g, 0.01 mmol, 0.2 eq) were added. Suspension was degassed for additional 5 minutes. The reaction was then heated at 130° C. for 5 hours. After completion of the reaction, reaction mixture was diluted with $CH_2Cl_2$ (1 mL) and pass through silica plug column using 10% methanol in $CH_2Cl_2$ as eluent. Obtained fractions were combined and concentrated under reduced pressure to obtain crude material. This was further purified by reverse phase HPLC to obtain I-1 (0.005 g, 22.2%). MS(ES): m/z 436.6 [M+H]+; $^1$H NMR (CDCl$_3$, 400 MHz): 8.92 (s, 1H), 7.79-7.77 (d, 1H), 7.67-7.66 (d, 1H), 7.45-7.40 (m, 1H), 4.45 (s, 3H), 3.88 (s, 3H), 3.47 (s, 3H), 1.69-1.59 (m, 1H), 1.13-1.12 (m, 2H), 0.91-0.90 (m, 2H).

Example 2. Synthesis of 4-((2-methoxy-3-(2-methyl-2H-tetrazol-5-yl)phenyl)amino)-6-((4-(methoxymethyl)pyridin-2-yl)amino)-2-methyl-1,2-dihydro-3H-pyrazolo[3,4-b]pyridin-3-one 1-2

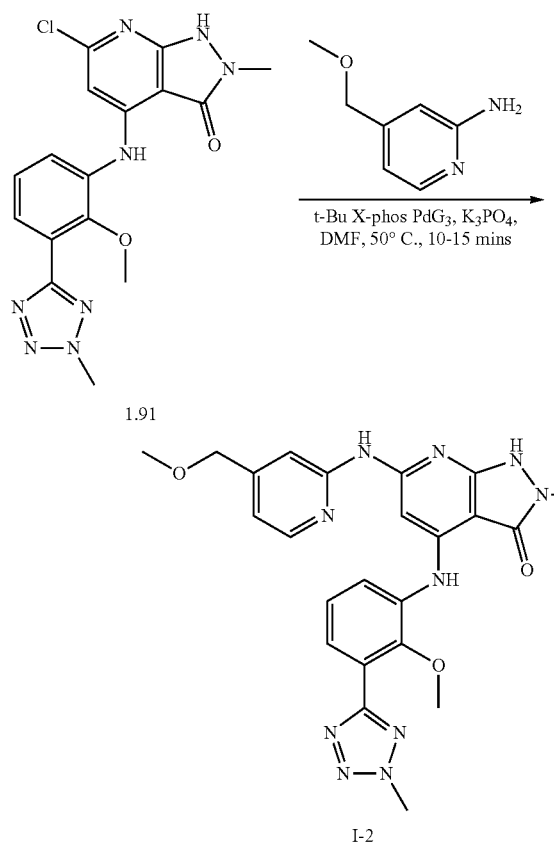

To compound 1.91 (0.040 g, 0.103 mmol, 1.0 eq) in DMF (1.0 ml) was added 4-(methoxymethyl)pyridin-2-amine (0.021 g, 0.155 mmol, 1.5 eq), and $K_3PO_4$ (0.043 g, 0.206 mmol, 2.0 eq). The reaction mixture was degassed for 10 minutes using argon, then [(2-di-tert-butylphosphino-2',4', 6'-triisopropyl-1,1'-biphenyl)-2-(2'-amino-1,1'-biphenyl)] palladium(II)methanesulfonate (0.008 g, 0.01 mmol, 0.1 eq) was added. Suspension was degassed for additional five minutes. The reaction was stirred at 50° C. for 15 min. After completion of the reaction, mixture was diluted with $CH_2Cl_2$ (1.0 mL) and pass through silica plug column using 8% methanol in $CH_2Cl_2$ as eluent. Obtained fractions were combined and concentrated under reduced pressure to obtain crude which was purified by reverse phase HPLC to obtain I-2 (0.008 g, 15.84%). MS(ES): m/z 489.75 [M+H]+; $^1$H NMR (CDCl$_3$, 400 MHz): 9.27 (s, 1H), 8.95 (s, 1H), 8.14-8.12 (d, 1H), 7.70-7.68 (d, 1H), 7.41-7.39 (d, 1H), 7.11-7.08 (t, 1H), 7.00 (s, 1H), 6.89-6.88 (d, 1H), 4.43 (s, 3H), 3.78 (s, 3H), 3.65 (s, 2H), 3.57 (s, 3H), 3.43 (s, 3H).

Example 3. Synthesis of 4-((2-methoxy-3-(2-methyl-2H-tetrazol-5-yl)phenyl)amino)-2-methyl-6-((5-methylpyridin-2-yl)amino)-1,2-dihydro-3H-pyrazolo[3,4-b]pyridin-3-one, I-3

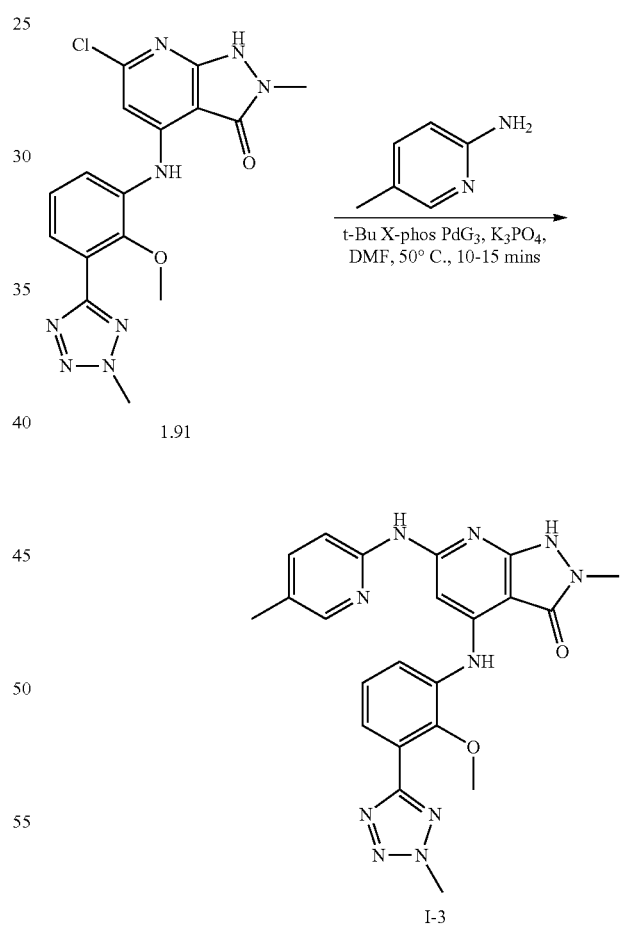

Compound I-3 was prepared from compound 1.91 and 5-methylpyridin-2-amine using procedure described in Example 2. MS(ES): m/z 459.64 [M+H]+; $^1$H NMR (DMSO-d$_6$, 400 MHz): 10.68 (s, 2H), 9.76 (s, 1H), 8.93 (s, 1H), 8.11 (s, 1H), 7.79-7.77 (d, 1H), 7.65-7.57 (m, 2H), 7.42-7.38 (m, 1H), 7.2 (s, 1H), 4.47 (s, 3H), 3.79 (s, 3H), 3.29 (s, 3H), 2.24 (s, 3H).

Example 4. Synthesis of 4-((2-methoxy-3-(2-methyl-2H-tetrazol-5-yl)phenyl)amino)-2-methyl-6-(pyridin-2-ylamino)-1,2-dihydro-3H-pyrazolo[3,4-b]pyridin-3-one, I-4

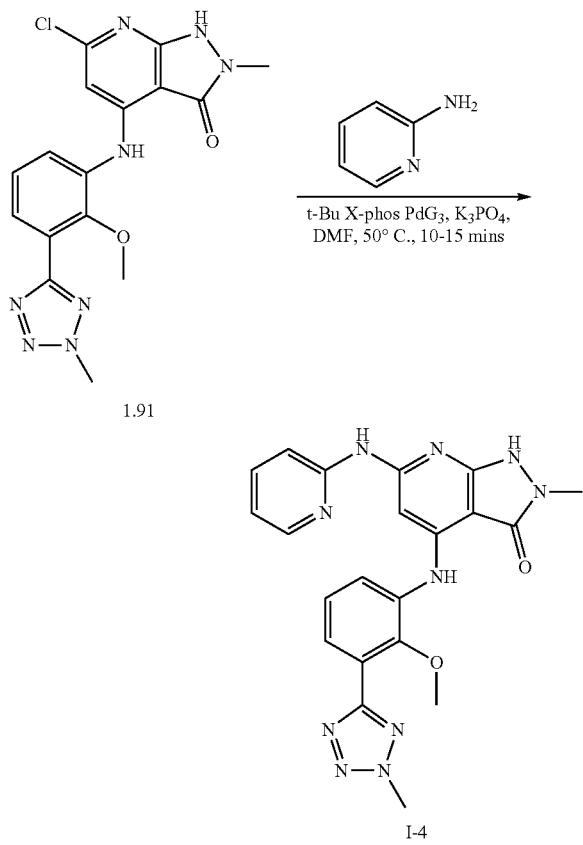

I-4

Compound I-4 was prepared from compound 1.91 and pyridin-2-amine using procedure described in Example 2. MS(ES): m/z 445.68 [M+H]$^+$ $^1$H NMR (DMSO-d$_6$, 400 MHz): 9.97 (s, 1H), 8.95 (s, 1H), 8.27-8.26 (d, 1H), 8.16 (s, 1H), 7.89 (s, 1H), 7.80-7.78 (d, 1H), 7.74-7.71 (m, 1H), 7.65-7.63 (d, 1H), 7.42-7.38 (t, 1H), 6.97-6.94 (t, 1H), 4.47 (s, 3H), 3.79 (s, 3H), 3.29 (s, 3H).

Example 5. Synthesis of 4-((2-methoxy-3-(2-methyl-2H-tetrazol-5-yl)phenyl)amino)-2-methyl-6-((4-methylpyridin-2-yl)amino)-1,2-dihydro-3H-pyrazolo[3,4-b]pyridin-3-one, I-5

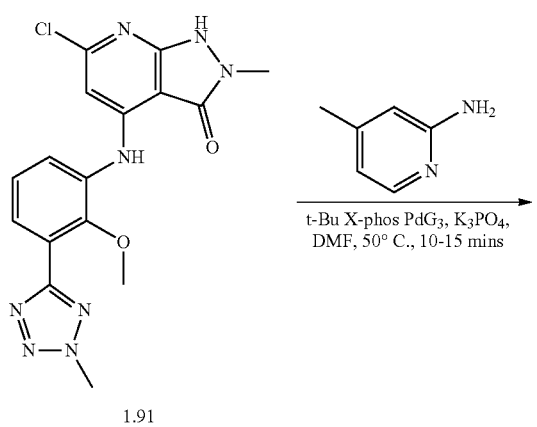

1.91

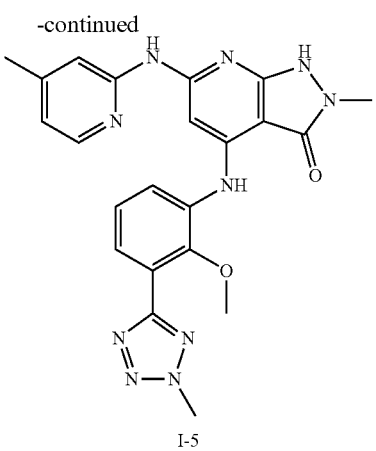

I-5

Compound I-5 was prepared from compound 1.91 and 4-methylpyridin-2-amine using procedure described in Example 2. MS(ES): m/z 459.7 [M+H]$^+$; $^1$H NMR (DMSO-d$_6$, 400 MHz): 9.98 (s, 1H), 8.96 (s, 1H), 8.17 (s, 1H), 8.14-8.13 (d, 1H), 7.79-7.77 (d, 1H), 7.65-7.63 (d, 1H), 7.42-7.38 (t, 1H), 6.82-6.81 (d, 1H), 4.47 (s, 3H), 3.79 (s, 3H), 3.30 (s, 3H), 2.30 (s, 3H).

Example 6. Synthesis of 6-((4-(hydroxymethyl)pyridin-2-yl)amino)-4-((2-methoxy-3-(2-methyl-2H-tetrazol-5-yl)phenyl)amino)-2-methyl-1,2-dihydro-3H-pyrazolo[3,4-b]pyridin-3-one, I-6

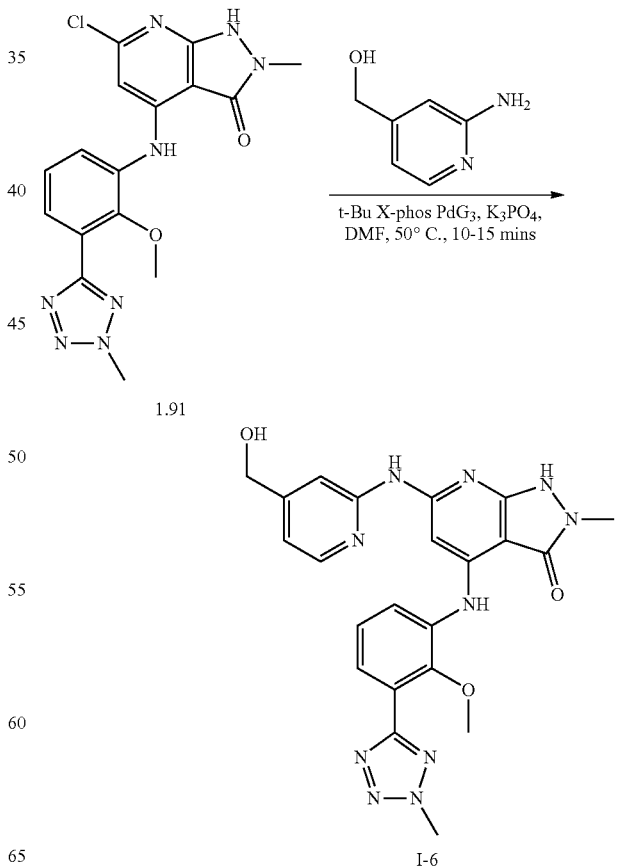

I-6

Compound I-6 was prepared from compound 1.91 and (2-aminopyridin-4-yl)methanol using procedure described in Example 2. MS(ES): m/z 475.58 [M+H]+; ¹H NMR (DMSO-d₆, 400 MHz): 10.01 (s, 1H), 8.97 (s, 1H), 8.20-8.19 (d, 1H), 8.17 (s, 1H), 7.79-7.77 (d, 1H), 7.66-7.64 (d, 1H), 7.42-7.38 (t, 1H), 6.92-6.90 (d, 1H), 5.42 (s, 1H), 4.52 (s, 2H), 4.47 (s, 3H), 3.79 (s, 3H), 3.30 (s, 3H).

Example 7. Synthesis of N-(4-((2-methoxy-3-(2-methyl-2H-tetrazol-5-yl)phenyl)amino)-2-methyl-3-oxo-2,3-dihydro-1H-pyrazolo[3,4-b]pyridin-6-yl)cyclopropanecarboxamide, I-14

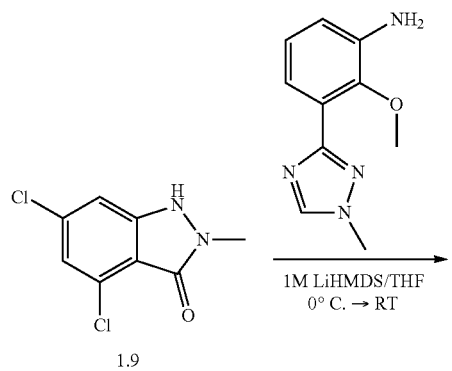

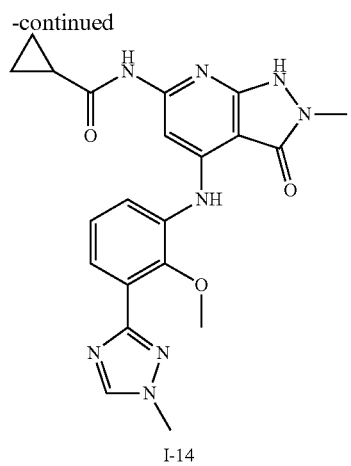

I-14

Compound 1.92 was prepared according to the procedure used for 1.91. Compound I-14 was prepared from compound 1.91 and cyclopropanecarboxamide using procedure described in Example 2. (Yield: 22.2%). MS(ES): m/z 436.6 [M+H]+, LCMS purity: 96%, HPLC purity: 91%, ¹H NMR (CDCl₃, 400 MHZ): 8.92 (s, 1H), 7.79-7.77 (d, J=8 Hz, 1H), 7.67-7.66 (d, J=7.2 Hz, 1H), 7.45-7.40 (m, 1H), 4.45 (s, 3H), 3.88 (s, 3H), 3.47 (s, 3H), 1.69-1.59 (m, 1H), 1.13-1.12 (m, 2H), 0.91-0.90 (m, 2H).

Example 13. Synthesis of 4-((2-methoxy-3-(2-methyl-2H-tetrazol-5-yl)phenyl)amino)-2-methyl-6-((5-morpholinopyridin-2-yl)amino)-1,2-dihydro-3H-pyrazolo[3,4-b]pyridin-3-one, I-7

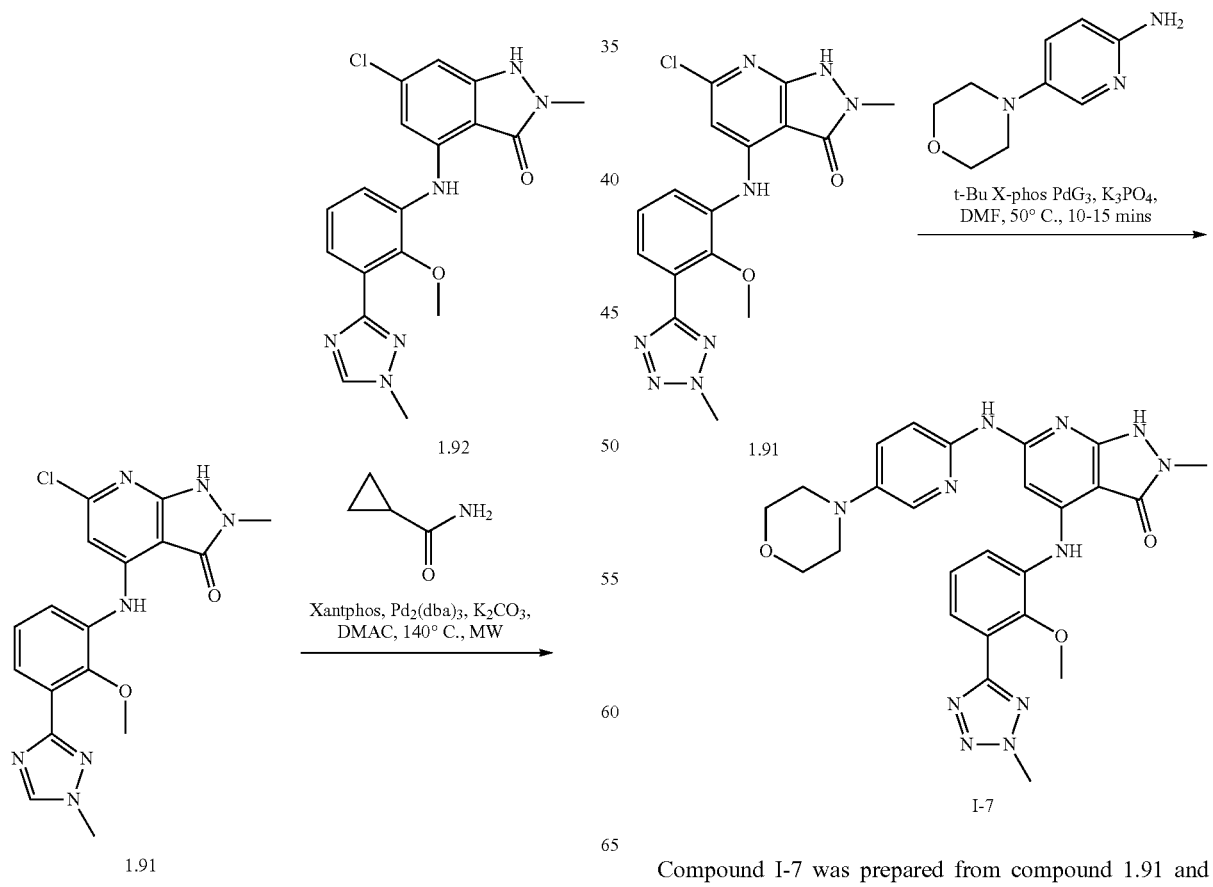

I-7

Compound I-7 was prepared from compound 1.91 and 5-morpholinopyridin-2-amine using procedure described in Example 2 (Yield: 8.76%). MS(ES): m/z 530.81 [M+H]+, LCMS purity: 100%, HPLC purity: 98.59%, 1H NMR (DMSO-d6, 400 MHZ): 9.79-9.75 (bs, 2H), 8.94 (s, 1H), 8.14 (s, 1H), 7.98 (s, 1H), 7.78-7.76 (d, J=8 Hz, 1H), 7.64-7.63 (d, J=7.6 Hz, 1H), 7.46-7.38 (m, 3H), 4.47 (s, 3H), 3.79 (s, 3H), 3.77-3.74 (t, 4H), 3.29 (s, 3H), 3.10-3.08 (t, 4H).

Example 14. Synthesis of 6-((5-fluoro-4-methyl-pyridin-2-yl)amino)-4-((2-methoxy-3-(2-methyl-2H-tetrazol-5-yl)phenyl)amino)-2-methyl-1,2-dihydro-3H-pyrazolo[3,4-b]pyridin-3-one, I-8

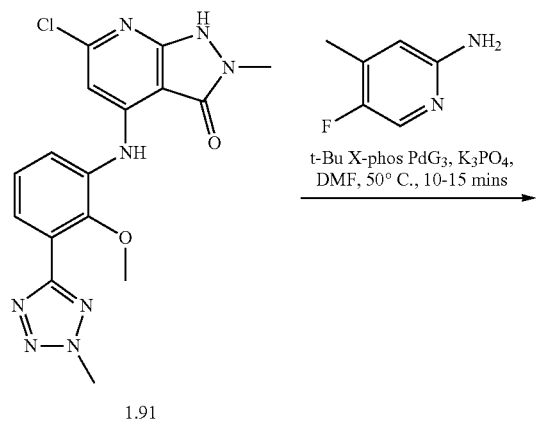

1.91

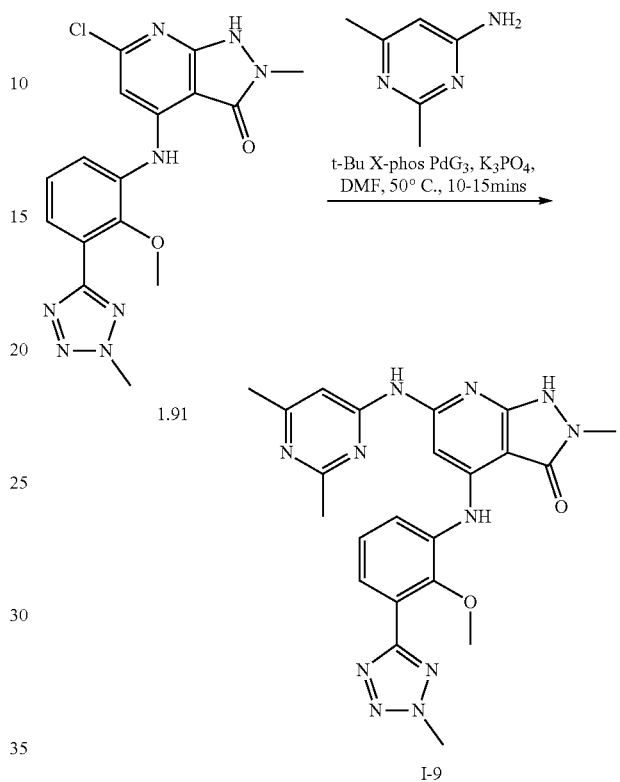

I-8

Compound I-8 was prepared from compound 1.91 and 5-fluoro-4-methylpyridin-2-amine using procedure described in Example 2 (Yield: 16.24%). MS(ES): m/z 477.43 [M+H]+, LCMS purity: 99.71%, HPLC purity: 99.14%, 1H NMR (DMSO-d6, 400 MHZ): 9.87 (s, 1H), 8.92 (s, 1H), 8.22 (s, 1H), 8.15 (s, 1H), 7.94 (s, 1H), 7.78-7.76 (d, J=8 Hz, 1H), 7.64-7.62 (d, J=7.2 Hz, 1H), 7.42-7.38 (t, 1H), 6.96 (s, 1H), 4.47 (s, 3H), 3.79 (s, 3H), 3.30 (s, 3H), 2.28 (s, 3H).

Example 15. Synthesis of 6-((2,6-dimethylpyrimidin-4-yl)amino)-4-((2-methoxy-3-(2-methyl-2H-tetrazol-5-yl)phenyl)amino)-2-methyl 1,2-dihydro-3H-pyrazolo[3,4-b]pyridin-3-one, I-9

Compound I-9 was prepared from compound 1.91 and 2,6-dimethylpyrimidin-4-amine using procedure described in Example 2 (Yield: 11.98%). MS(ES): m/z 474.58 [M+H]+, LCMS purity: 99.76%, HPLC purity: 96.42%, 1H NMR (MeOD, 400 MHZ): 8.34-8.29 (bs, 2H), 7.86-7.84 (d, J=7.6 Hz, 1H), 7.73-7.71 (d, J=8 Hz, 1H), 7.41-7.37 (t, 1H), 6.89 (s, 1H), 6.25 (s, 1H), 4.48 (s, 3H), 3.85 (s, 3H), 3.53 (s, 3H), 2.64 (s, 3H), 2.42 (s, 3H).

Example 16. Synthesis of 4-((2-methoxy-3-(2-methyl-2H-tetrazol-5-yl)phenyl)amino)-2-methyl-6-((6-methylpyridazin-3-yl)amino)-1,2-dihydro-3H-pyrazolo[3,4-b]pyridin-3-one, I-10

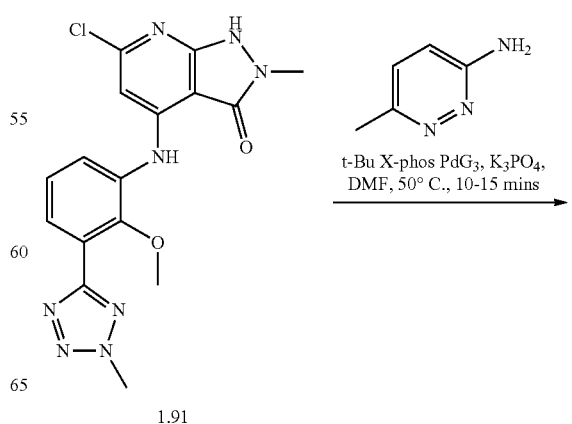

1.91

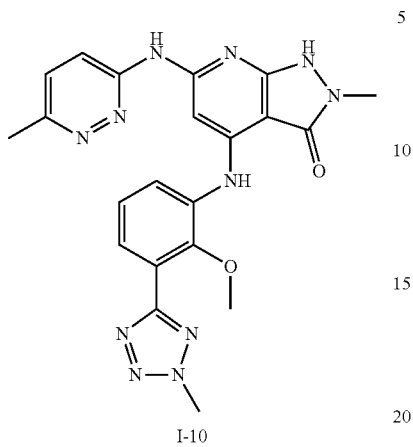

I-10

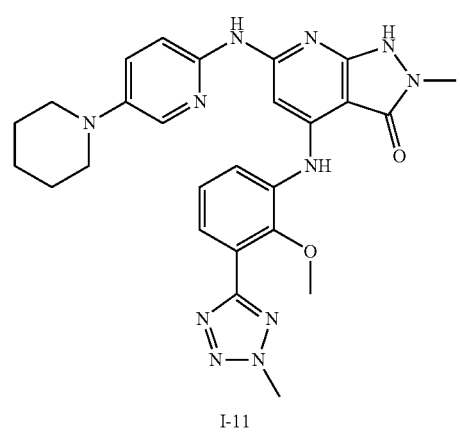

I-11

Compound I-10 was prepared from compound 1.91 and 6-methylpyridazin-3-amine using procedure described in Example 2 (Yield: 14.03%). m/z 460.43 [M+H]+, LCMS purity: 98.69%, HPLC purity: 98.00%, 1H NMR (DMSO-d6, 400 MHZ): 10.23 (bs, 1H), 8.93 (s, 1H), 8.29-8.27 (d, J=8.8 Hz, 1H), 8.16 (s, 1H), 7.79-7.77 (d, J=8 Hz, 1H), 7.65-7.64 (d, J=7.2 Hz, 1H), 7.50-7.48 (d, J=9.2 Hz, 1H), 7.40-7.36 (t, J=8 Hz, 1H), 6.99 (bs, 1H), 4.47 (s, 3H), 3.80 (s, 3H), 3.30 (s, 3H), 2.53 (s, 3H).

Compound I-11 was prepared from compound 1.91 and 5-(piperidin-1-yl)pyridin-2-amine using procedure described in Example 2 (Yield: 9.78%). MS(ES): m/z 528.68 [M+H]+, LCMS purity: 96.10%, HPLC purity: 98.65%, 1H NMR (CDCl3, 400 MHZ): 9.76 (bs, 1H), 8.89 (s, 1H), 7.71 (s, 1H), 7.66-7.64 (d, J=7.2 Hz, 1H), 7.28 (s, 1H), 7.03-7.00 (m, 2H), 5.72 (s, 1H), 4.40 (s, 3H), 3.77 (s, 3H), 3.54 (s, 3H), 3.17-3.03 (m, 4H), 2.63 (s, 1H), 1.72 (s, 4H), 1.60-1.59 (d, 2H).

Example 17. Synthesis of 4-((2-methoxy-3-(2-methyl-2H-tetrazol-5-yl)phenyl)amino)-2-methyl-6-((5-(piperidin-1-yl)pyridin-2-yl)amino)-1,2-dihydro-3H-pyrazolo[3,4-b]pyridin-3-one, I-11

Example 18. Synthesis of 4-((2-methoxy-3-(2-methyl-2H-tetrazol-5-yl)phenyl)amino)-2-methyl-6-((5-(pyrrolidin-1-yl)pyridin-2-yl)amino)-1,2-dihydro-3H-pyrazolo[3,4-b]pyridin-3-one, I-58

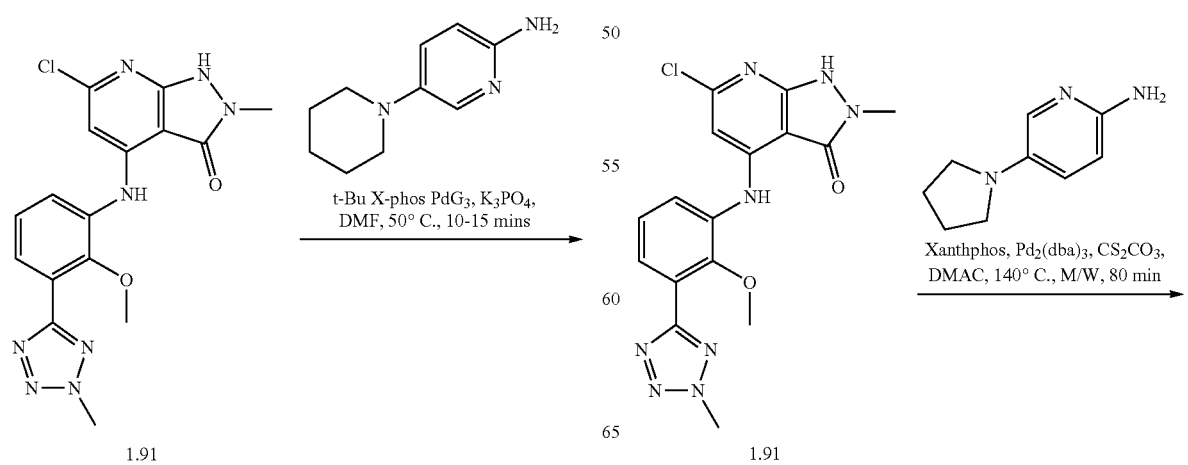

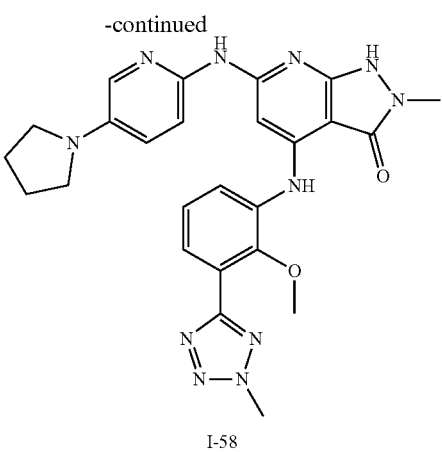

I-58

Compound I-58 was prepared from compound 1.91 and 5-(pyrrolidin-1-yl)pyridin-2-amine using procedure described in Example 2 (Yield: 11.08%), MS(ES): m/z 514.46 [M+H]+, LCMS purity: 96.44%, HPLC purity: 97.39%, 1H NMR (DMSO-d6, 400 MHz): 9.96 (s, 1H), 8.68 (s, 1H), 7.72-7.621 (m, 3H), 7.51 (s, 2H), 7.24-6.98 (m, 2H), 6.40 (s, 1H), 4.50 (s, 3H), 3.68 (s, 4H), 3.45 (s, 3H), 3.25 (s, 3H), 1.98 (s, 4H).

Example 19. Synthesis of 6-((5-cyclopropylpyridin-2-yl)amino)-4-((2-methoxy-3-(2-methyl-2H-tetrazol-5-yl)phenyl)amino)-2-methyl-1,2-dihydro-3H-pyrazolo[3,4-b]pyridin-3-one, I-59

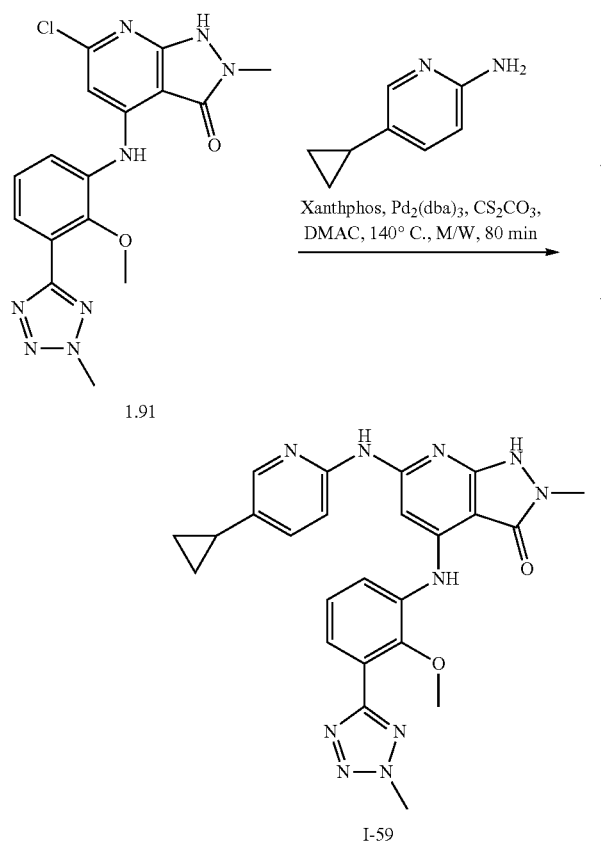

I-59

Compound I-59 was prepared from compound 1.91 and 5-cyclopropylpyridin-2-amine using procedure described in Example 2 (Yield: 23.28%), MS(ES): m/z 485.53 [M+H]+, LCMS purity: 98.26%, HPLC purity: 97.44%, 1H NMR (DMSO-d6, 400 MHz): 10.72 (s, 1H), 9.74 (s, 1H), 8.90 (s, 1H), 8.09 (s, 1H), 7.95-7.93 (d, J=6.8 Hz, 1H), 7.81-7.79 (d, J=7.6 Hz, 1H), 7.63-7.61 (d, J=7.2 Hz, 1H), 7.43-7.36 (m, 2H), 7.18 (s, 1H), 4.48 (s, 3H), 3.79 (s, 3H), 3.16 (s, 3H), 1.89 (s, 1H), 0.94-0.93 (d, J=6.8 Hz, 2H), 0.69-0.68 (d, J=6.8 Hz, 2H).

Example 20. Synthesis of 4-((2-methoxy-3-(2-methyl-2H-tetrazol-5-yl)phenyl)amino)-2-methyl-6-((6-(trifluoromethyl)pyridin-2-yl)amino)-1,2-dihydro-3H-pyrazolo[3,4-b]pyridin-3-one, I-60

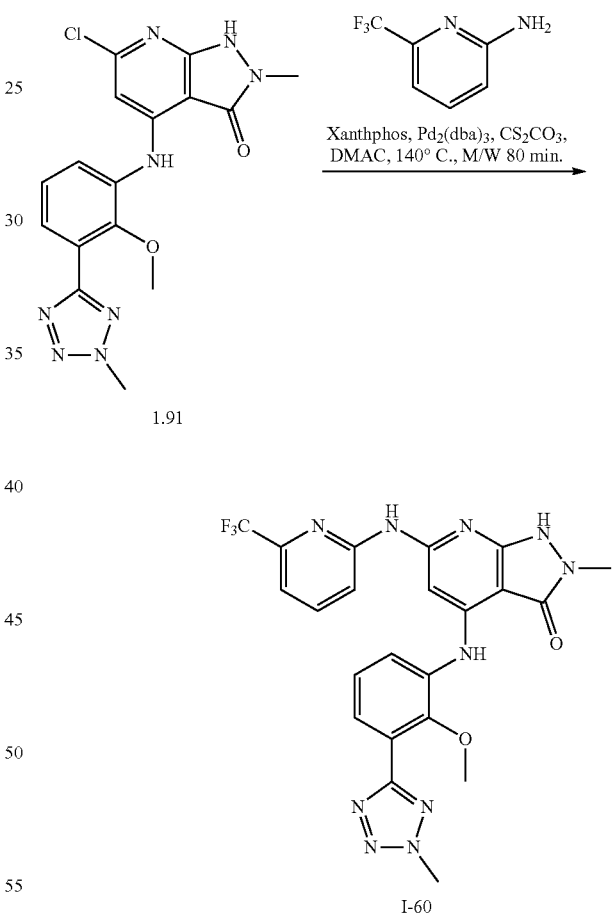

I-60

Compound I-60 was prepared from compound 1.91 and 6-(trifluoromethyl)pyridin-2-amine using procedure described in Example 2 (Yield: 39.25%), MS(ES): m/z 513.43 [M+H]+, LCMS purity: 99.01%, HPLC purity: 98.84%, 1H NMR (DMSO-d6, 400 MHz): 10.85 (s, 1H), 10.29 (s, 1H), 9.06 (s, 1H), 8.13-8.11 (d, J=8.8 Hz, 1H), 7.98-7.94 (t, J=8.0 Hz, 1H), 7.82-7.79 (d, J=8.0 Hz, 1H), 7.65-7.64 (d, J=6.8 Hz, 1H), 7.48 (s, 1H), 7.40-7.33 (m, 2H), 4.48 (s, 3H), 3.80 (s, 3H), 3.32 (s, 3H).

Example 21. Synthesis of 4-((2-methoxy-3-(2-methyl-2H-tetrazol-5-yl)phenyl)amino)-6-((6-(3-methoxyazetidin-1-yl)pyridin-2-yl)amino)-2-methyl-1,2-dihydro-3H-pyrazolo[3,4-b]pyridin-3-one, I-63

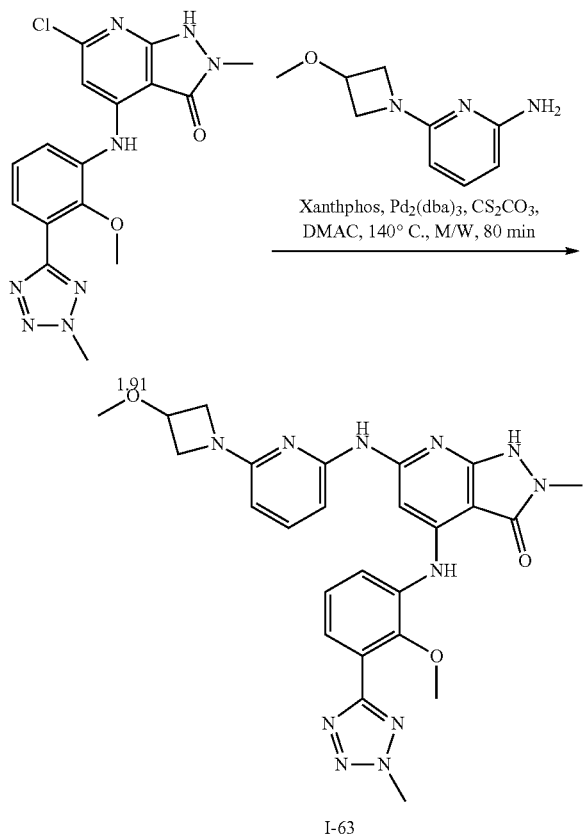

I-63

Compound I-63 was prepared from compound 1.91 and 6-(3-methoxyazetidin-1-yl)pyridin-2-amine using procedure described in Example 2 (Yield: 19.48%), MS(ES): m/z 530.40 [M+H]+, LCMS purity: 100.00%, HPLC purity: 98.25%, 1H NMR (CDCl3, 400 MHz): 9.49 (bs, 1H), 8.98 (s, 1H), 7.68-7.66 (d, J=6.8 Hz, 1H), 7.38-7.34 (t, J=8.0 Hz, 2H), 7.05-7.01 (t, J=8.0 Hz, 1H), 6.26-6.24 (d, J=7.2 Hz, 1H), 5.88-5.86 (d, J=8.0 Hz, 1H), 5.73 (bs, 1H), 4.40 (s, 3H), 4.37-4.32 (m, 1H), 4.29-4.25 (m, 2H), 3.96-3.93 (m, 2H), 3.78 (s, 3H), 3.51 (s, 3H), 3.36 (s, 3H).

Example 22. Synthesis of 6-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)pyrazine-2-carbonitrile, I-64

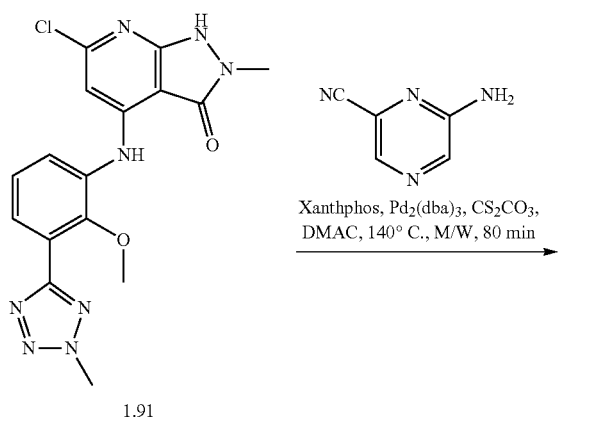

1.91

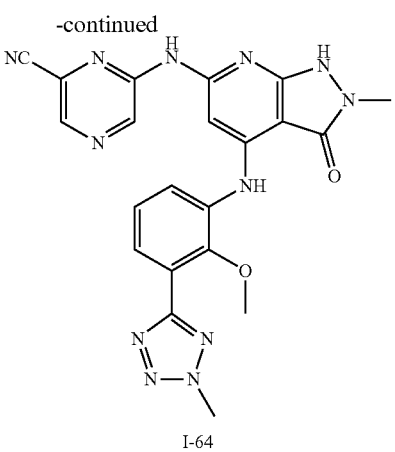

I-64

Compound I-64 was prepared from compound 1.91 and 6-aminopyrazine-2-carbonitrile using procedure described in Example 2 (Yield: 20.55%), MS(ES): m/z 471.48 [M+H]+, LCMS purity: 100.00%, HPLC purity: 98.79%, 1H NMR (DMSO-d6, 400 MHz): 10.96 (s, 1H), 10.66 (s, 1H), 9.36 (s, 1H), 9.01 (s, 1H), 8.66 (s, 1H), 7.83-7.81 (d, J=8.0 Hz, 1H), 7.68-7.66 (dd, J=1.2 Hz, 8.0 Hz, 1H), 7.44-7.42 (d, J=8.0 Hz, 1H), 7.40-7.38 (d, J=8.0 Hz, 1H), 4.47 (s, 3H), 3.80 (s, 3H), 3.43 (s, 3H).

Example 23. Synthesis of 6-((6-cyclopropylpyridin-2-yl)amino)-4-((2-methoxy-3-(2-methyl-2H-tetrazol-5-yl)phenyl)amino)-2-methyl-1,2-dihydro-3H-pyrazolo[3,4-b]pyridin-3-one, I-65

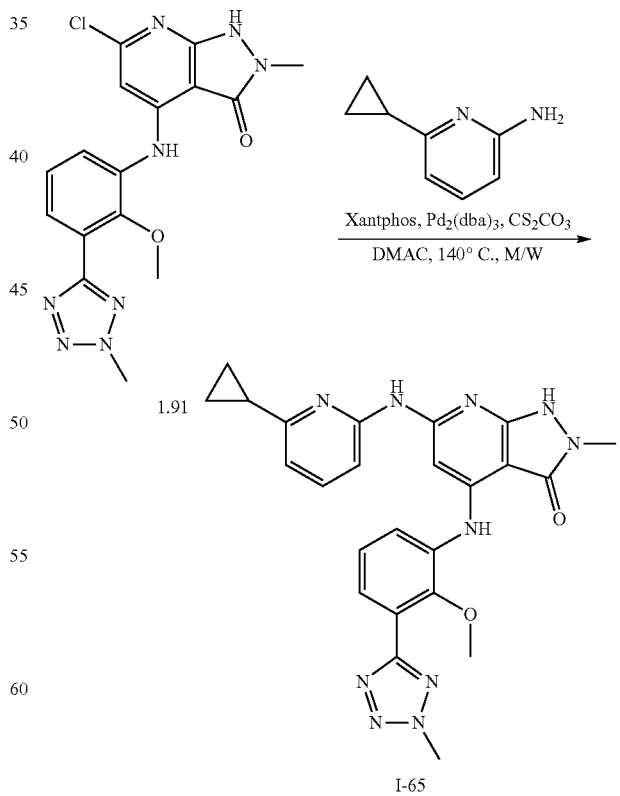

I-65

Compound I-65 was prepared from compound 1.91 and 6-cyclopropylpyridin-2-amine using procedure described in Example 2 (Yield: 7.98%), MS(ES): m/z 485.53 [M+H]+, LCMS purity: 96.64%, HPLC purity: 96.85%, 1H NMR (DMSO-d6, 400 MHz): 11.42 (s, 1H), 9.09 (s, 1H), 7.93 (s, 1H), 7.81-7.79 (d, J=6.4 Hz, 1H), 7.66-7.64 (d, J=6.4 Hz, 1H), 7.41 (s, 1H), 7.09-7.07 (d, J=7.2 Hz, 1H), 6.98-6.96 (d, J=7.2 Hz, 1H), 6.02 (s, 1H), 4.44 (s, 3H), 3.74 (s, 3H), 3.48 (s, 3H), 2.28 (s, 1H), 1.26 (s, 2H), 1.09 (s, 2H).

Example 24. Synthesis of N-ethyl-6-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)picolinamide, I-66

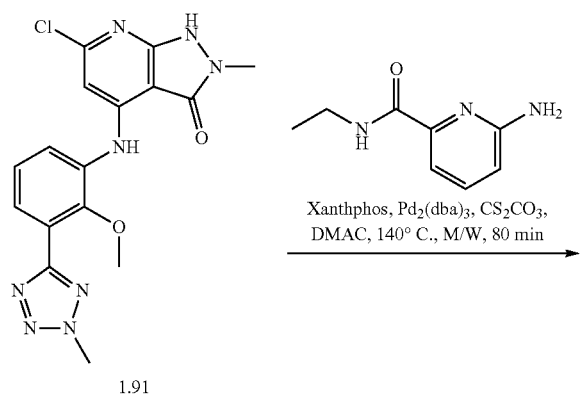

1.91

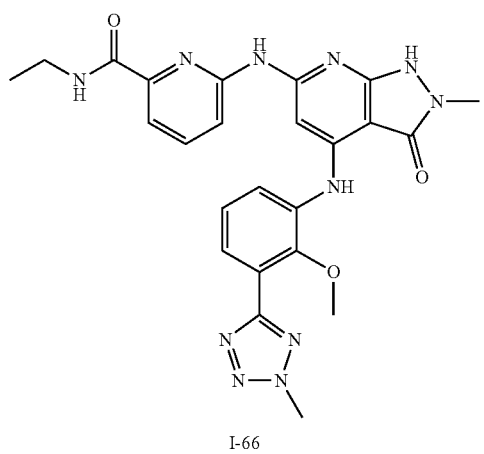

I-66

Compound I-66 was prepared from compound 1.91 and 6-amino-N-methylpicolinamide using procedure described in Example 2 (Yield: 12.50%), MS(ES): m/z 516.41 [M+H]+, LCMS purity: 96.85%, HPLC purity: 95.48%, 1H NMR (MeOD, 400 MHz): 8.18 (s, 1H), 7.91-7.86 (t, 1H), 7.82-7.80 (d, J=8.0 Hz, 1H), 7.74-7.72 (m, 1H), 7.68-7.67 (d, 1H), 7.39-7.35 (t, J=8.0 Hz, 1H), 6.19 (s, 1H), 4.48 (s, 3H), 3.84 (s, 3H), 3.53 (s, 3H), 3.52-3.46 (q, J=7.2 Hz, 2H), 1.28-1.25 (t, J=7.2 Hz, 3H).

Example 26. Synthesis of 4-((2-methoxy-3-(1-methyl-1H-1,2,4-triazol-3-yl)phenyl)amino)-2-methyl-6-((5-methylpyridin-2-yl)amino)-1H-pyrazolo[3,4-b]pyridin-3(2H)-one, I-16

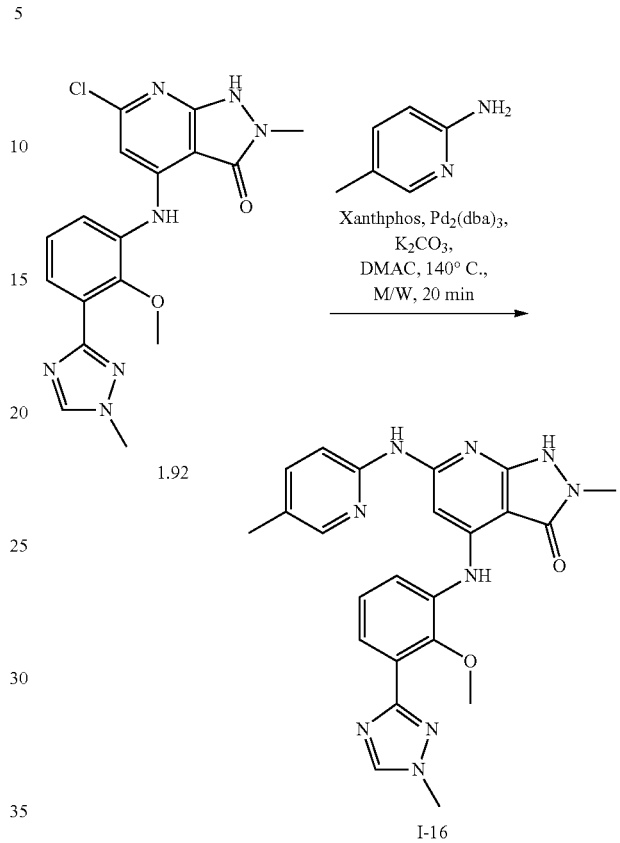

Compound I-16 was prepared from compound 1.92 and 5-methylpyridin-2-amine using procedure described in Example 2 (Yield: 19.68%). MS (ES): m/z 458.2 [M+H]+, LCMS purity: 99.65%, HPLC purity: 99.81%, 1H NMR (DMSO-d6, 400 MHZ): 10.67 (s, 1H), 9.76 (s, 1H), 8.93 (s, 1H), 8.57 (s, 1H), 8.11 (s, 1H), 7.84 (s, 1H), 7.68-7.66 (d, J=8 Hz, 1H), 7.59-7.57 (m, 2H), 7.32-7.18 (m, 1H), 3.96 (s, 3H), 3.78 (s, 3H), 3.29 (s, 3H), 2.23 (s, 3H).

Example 27. Synthesis of 6-((4-((2-methoxy-3-(1-methyl-1H-1,2,4-triazol-3-yl)phenyl)amino)-2-methyl-3-oxo-2,3-dihydro-1H-pyrazolo[3,4-b]pyridin-6-yl)amino)nicotinonitrile, I-25

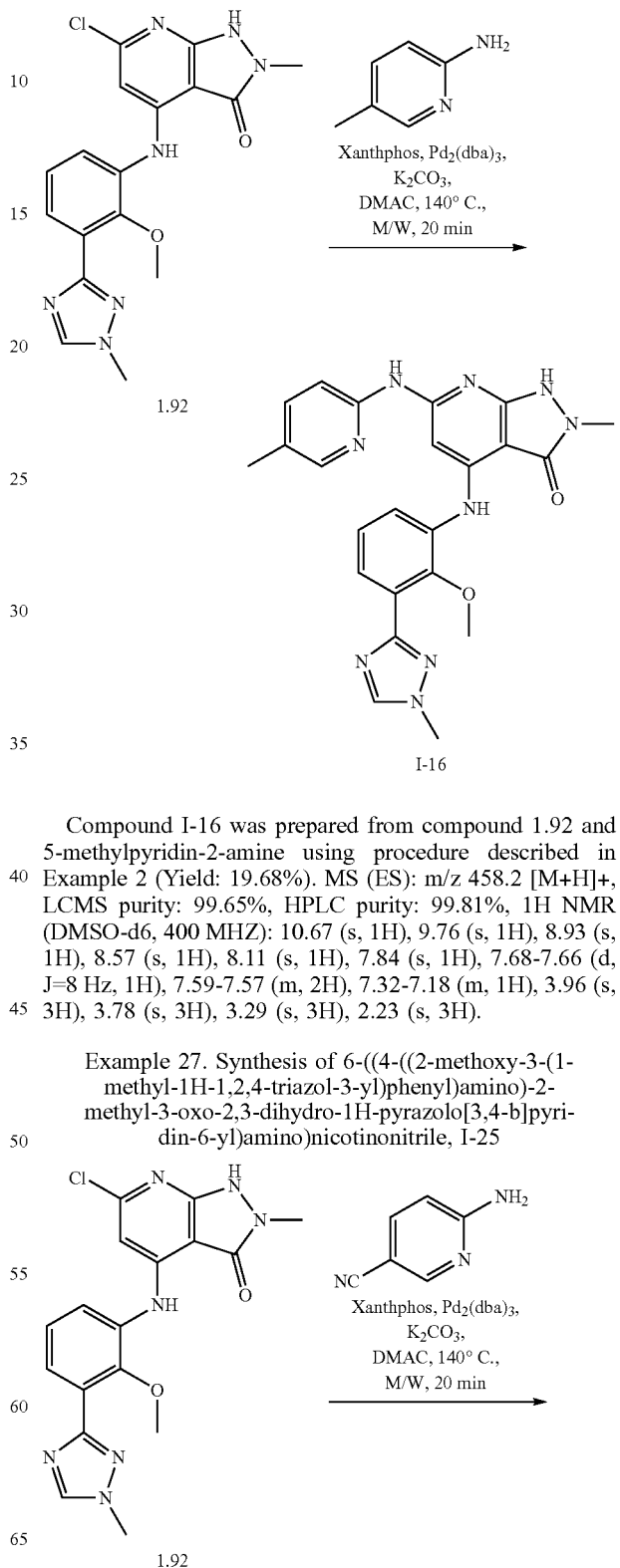

1.92

-continued

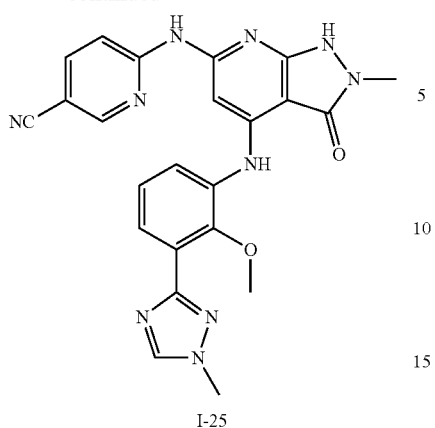

I-25

Compound I-25 was prepared from compound 1.92 and 6-aminonicotinonitrile using procedure described in Example 2 (Yield: 12.08%). MS (ES): m/z 469.7 [M+H]+, LCMS purity: 99.49%, HPLC purity: 99.22%, 1H NMR (DMSO-d6, 400 MHZ): 10.39 (s, 1H), 8.95 (s, 1H), 8.69 (s, 1H), 8.57 (s, 1H), 8.25-8.23 (m, 1H), 8.14-8.11 (m, 1H), 7.68-7.66 (d, J=7.2 Hz, 1H), 7.60-7.58 (d, J=8 Hz, 1H), 7.33-7.29 (m, 1H), 7.10 (s, 1H), 3.96 (s, 3H), 3.78 (s, 3H), 3.31 (s, 3H).

Example 28. Synthesis of 4-((4-chloro-2-methoxyphenyl)amino)-2-methyl-6-((4-methylpyridin-2-yl)amino)-1,2-dihydro-3H-pyrazolo[3,4-b]pyridin-3-one, I-42

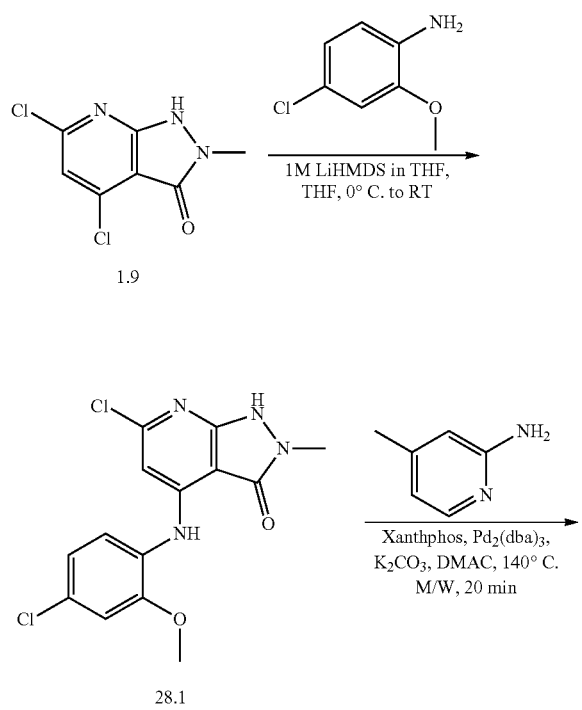

-continued

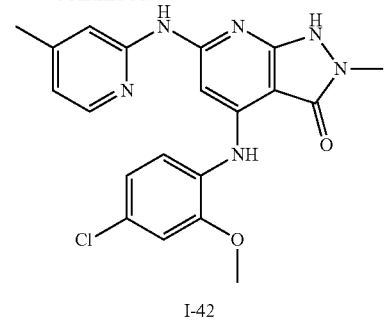

I-42

Synthesis of compound 28.1.
Following the procedure used to prepare 1.91, 28.1 was obtained (Yield: 24%). MS (ES): m/z 340.2 [M+H]+.
Compound I-42 was prepared from compound 28.1 and 4-methylpyridin-2-amine using procedure described in Example 2 (Yield: 12.53%), MS(ES): m/z 411.52 [M+H]+, LCMS purity: 100.00%, HPLC purity: 98.32%, 1H NMR (MeOD, 400 MHZ): 8.18-8.17 (d, J=5.2 Hz, 1H), 7.47-7.45 (d, J=8.4 Hz, 1H), 7.19 (s, 1H), 7.08-7.06 (d, J=8.0 Hz, 1H), 6.96-6.94 (d, J=4.8 Hz, 1H), 6.79 (s, 1H), 5.69 (s, 1H), 3.98 (s, 3H), 3.53 (s, 3H), 2.37 (s, 3H).

Example 29. Synthesis of N-(4-((4-(hydroxymethyl)-2-methoxyphenyl)amino)-2-methyl-3-oxo-2,3-dihydro-1H-pyrazolo[3,4-b]pyridin-6-yl)cyclopropanecarboxamide, I-42

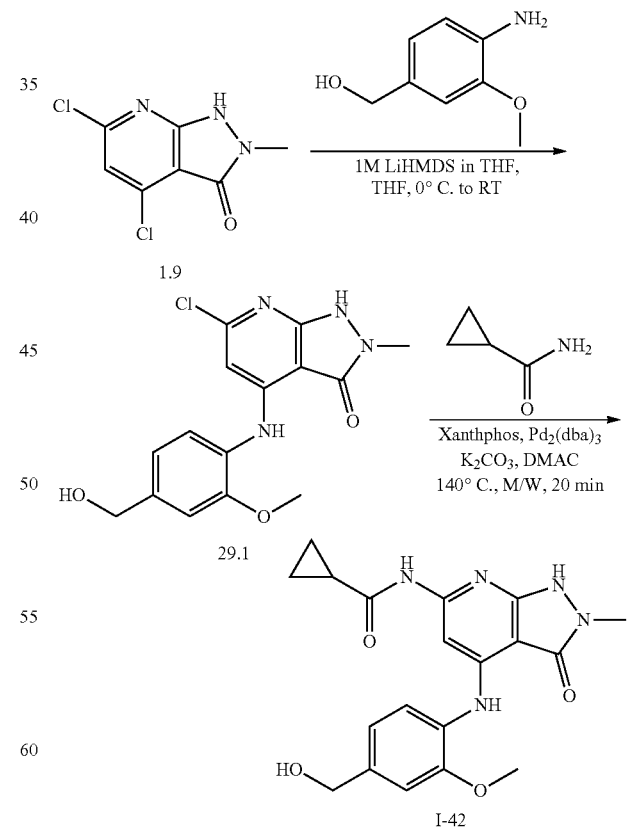

Synthesis of compound 29.1.
Following the procedure used to prepare 1.91, 29.1 was obtained (Yield: 57.32%). MS (ES): m/z 335.8 [M+H]+.

Compound I-42 was prepared from compound 29.1 and cyclopropanecarboxamide using procedure described in Example 2 (Yield: 17.46%), MS(ES): m/z 384.51 [M+H]+, LCMS purity: 95.04%, HPLC purity: 93.08%, 1H NMR (DMSO-d6, 400 MHZ): 10.67-10.64 (d, J=1.2 Hz, 2H), 8.41 (s, 1H), 7.64 (s, 1H), 7.38-7.36 (d, J=8.0 Hz, 1H), 7.09 (s, 1H), 6.96-6.94 (d, J=8.0 Hz, 1H), 5.24 (t, J=8.0 Hz, 1H), 4.51-4.49 (d, J=8.0 Hz, 2H), 3.85 (s, 3H), 3.19 (s, 3H), 1.99 (s, 1H), 0.79 (s, 4H).

Example 30. Synthesis of N-(4-((2-methoxy-4-(methoxymethyl)phenyl)amino)-2-methyl-3-oxo-2,3-dihydro-1H-pyrazolo[3,4-b]pyridin-6-yl)cyclopropanecarboxamide, I-45

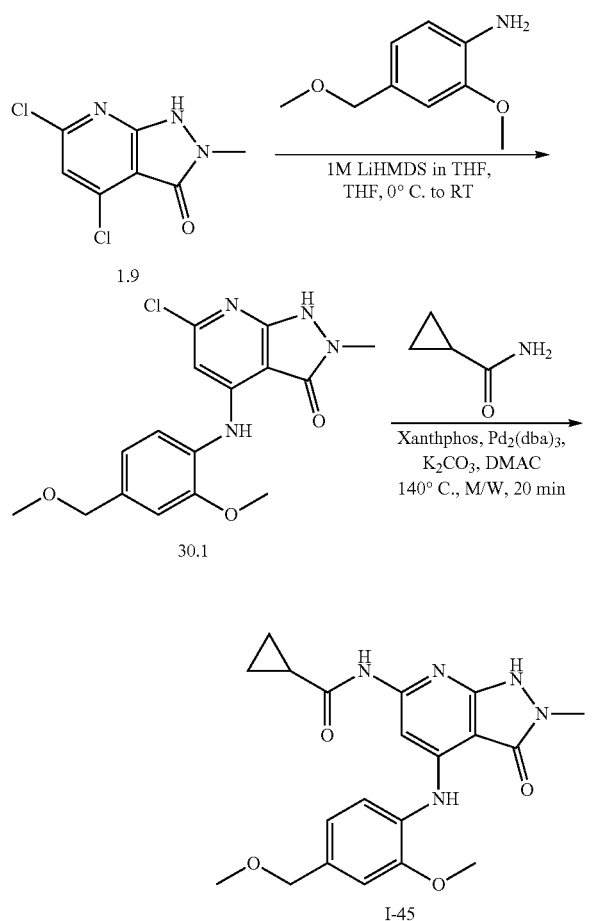

Synthesis of compound 30.1.

Following the procedure used to prepare 1.91, 30.1 was obtained (Yield: 57.51%). MS (ES): m/z 349.8 [M+H]+.

Compound I-45 was prepared from compound 30.1 and cyclopropanecarboxamide using procedure described in Example 2 (Yield: 23.4%), MS(ES): m/z 398.38 [M+H]+, LCMS purity: 96.46%, HPLC purity: 95.23%, 1H NMR (DMSO-d6, 400 MHZ): 10.70-10.67 (d, J=12.4 Hz, 2H), 8.49 (s, 1H), 7.68 (s, 1H), 7.41-7.39 (d, J=8.0 Hz, 1H), 7.07 (s, 1H), 6.96-6.94 (d, J=8.4 Hz, 1H), 4.40 (s, 2H), 3.85 (s, 3H), 3.35 (s, 3H), 3.29 (s, 3H), 1.99 (s, 1H), 0.79-0.78 (d, J=3.6 Hz, 4H).

Example 31. Synthesis of N-(4-((3-(1,3-dimethyl-1H-1,2,4-triazol-5-yl)-2-methoxyphenyl)amino)-2-methyl-3-oxo-2,3-dihydro-1H-pyrazolo[3,4-b]pyridin-6-yl)cyclopropanecarboxamide, I-46

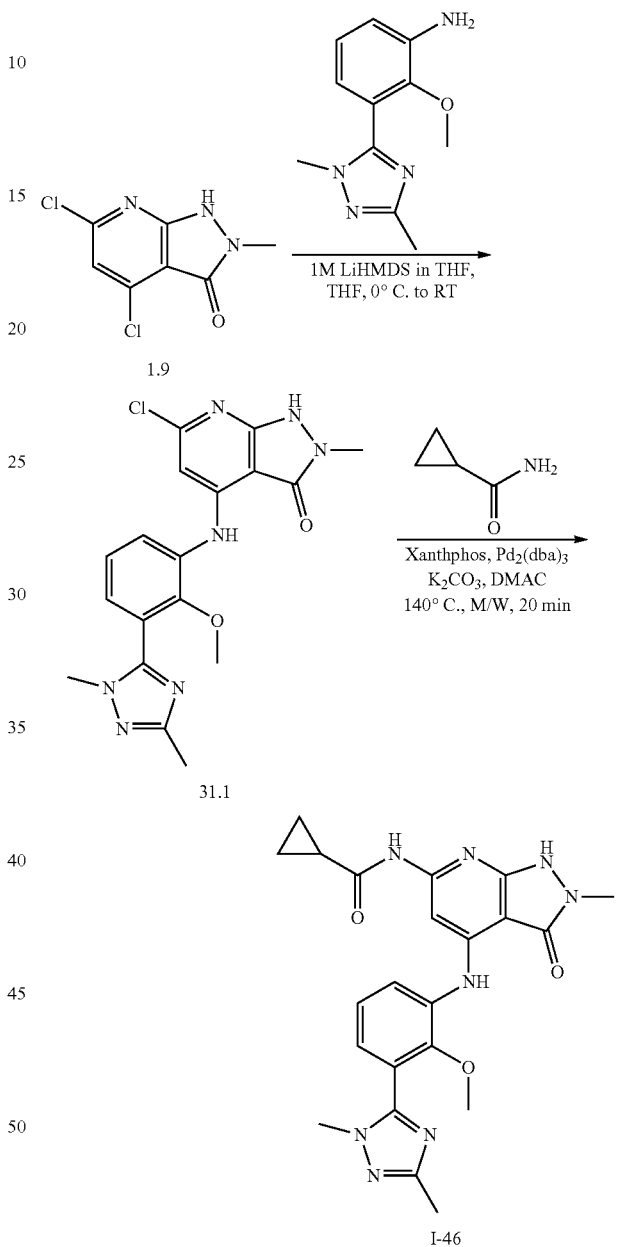

Synthesis of compound 31.1.

Following the procedure used to prepare 1.91, 31.1 was obtained (Yield: 49.08%). MS (ES): m/z 400.7 [M+H]+.

Compound I-46 was prepared from compound 31.1 and cyclopropanecarboxamide using procedure described in Example 2 (Yield: 5.45%), MS(ES): m/z 449.37 [M+H]+, LCMS purity: 95.95%, HPLC purity: 97.22%, 1H NMR (MeOD, 400 MHZ): 7.79-7.77 (d, J=8.0 Hz, 1H), 7.43-7.34 (m, 3H), 3.77 (s, 3H), 3.56 (s, 3H), 3.49 (s, 3H), 2.41 (s, 3H), 1.84 (s, 1H), 1.02-0.90 (m, 4H).

Example 32. Synthesis of 4-((2-methoxy-3-(5-methylthiazol-2-yl)phenyl)amino)-2-methyl-6-((4-methylpyridin-2-yl)amino)-1,2-dihydro-3H-pyrazolo[3,4-b]pyridin-3-one, I-47

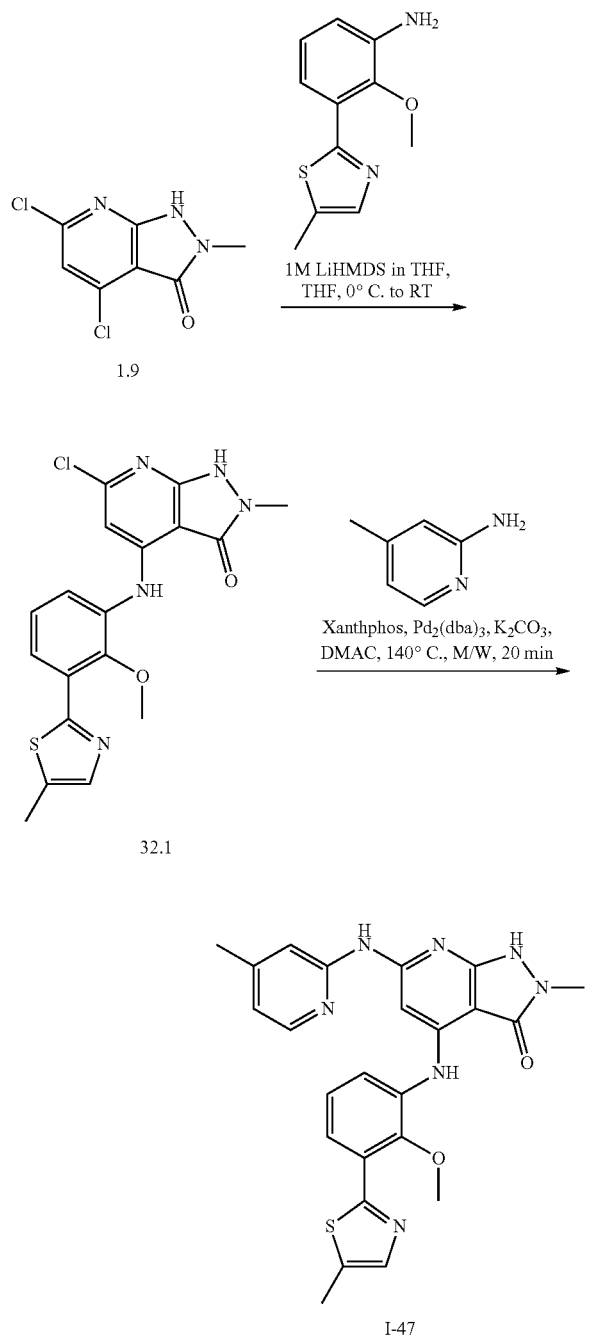

Synthesis of compound 32.1

Following the procedure used to prepare 1.91, 32.1 was obtained (Yield: 21.10%). MS (ES): m/z 402.7 [M+H]+.

Compound I-47 was prepared from compound 32.1 and 4-methylpyridin-2-amine using procedure described in Example 2 (Yield: 27.88%), MS(ES): m/z 474.48 [M+H]+, LCMS purity: 97.47%, HPLC purity: 95.33%, 1H NMR (CDCl3, 400 MHZ): 8.71 (s, 1H), 8.10-8.09 (d, J=4.8 Hz, 1H), 7.76 (s, 1H), 7.55-7.53 (d, J=8.0 Hz, 1H), 7.46 (s, 1H), 7.35-7.33 (d, J=8.0 Hz, 1H), 6.96-6.92 (d, J=8.0 Hz, 1H), 6.75 (s, 2H), 3.39 (s, 6H), 2.55 (s, 3H), 2.37 (s, 3H).

Example 33. Synthesis of N-(4-((3-fluoro-2-methoxyphenyl)amino)-2-methyl-3-oxo-2,3-dihydro-1H-pyrazolo[3,4-b]pyridin-6-yl)cyclopropanecarboxamide, I-48

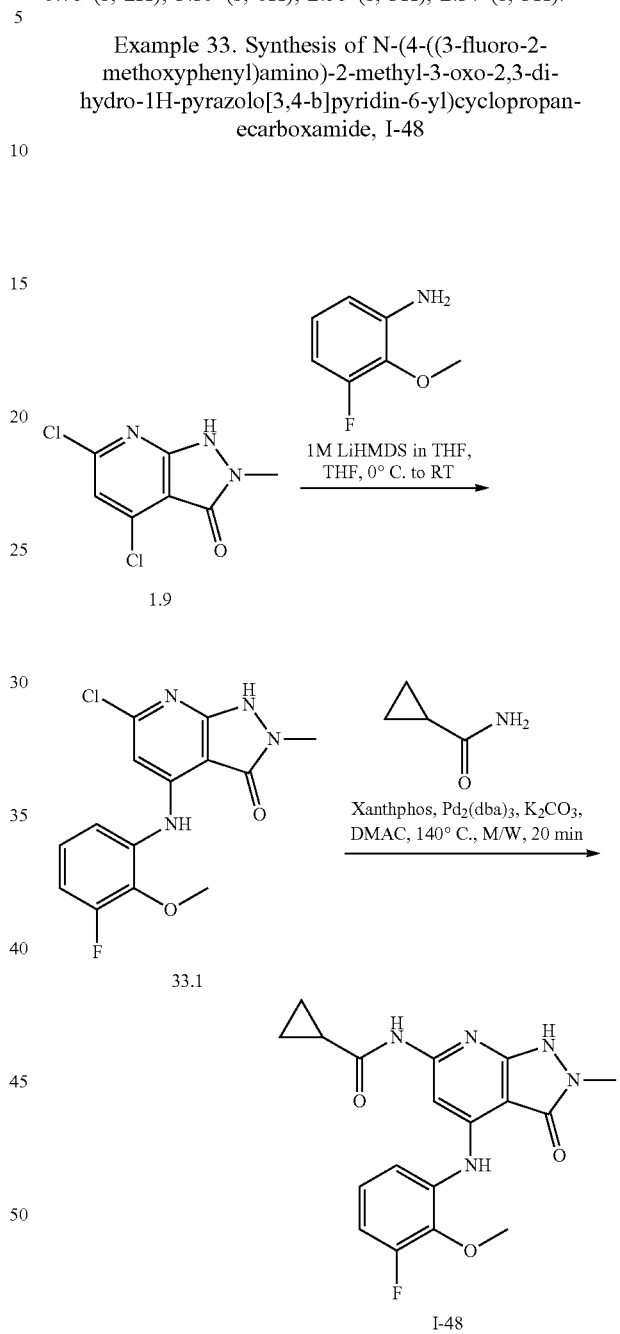

Synthesis of compound 33.1.

Following the procedure used to prepare 1.91, 33.1 was obtained (Yield: 54.05%). MS (ES): m/z 323.7 [M+H]+.

Compound I-48 was prepared from compound 33.1 and cyclopropanecarboxamide using procedure described in Example 2 (Yield: 18.47%), MS(ES): m/z 372.33 [M+H]+, LCMS purity: 98.91%, HPLC purity: 95.67%, 1H NMR (DMSO-d6, 400 MHZ): 10.79 (s, 1H), 8.83 (s, 1H), 8.17 (s, 1H), 7.75 (s, 1H), 7.32-7.30 (d, J=8.0 Hz, 1H), 7.21-7.15 (m, 1H), 7.06-7.03 (d, J=10.0 Hz, 1H), 3.88 (s, 3H), 3.31 (s, 3H), 2.03-2.01 (t, J=5.6 Hz, 1H), 0.81-0.81 (d, J=5.6 Hz, 4H).

Example 34. Synthesis of N-(4-((3-chloro-2-methoxyphenyl)amino)-2-methyl-3-oxo-2,3-dihydro-1H-pyrazolo[3,4-b]pyridin-6-yl)cyclopropanecarboxamide, I-49

Example 35: Synthesis of N-(4-((4-cyclopropyl-2-methoxyphenyl)amino)-2-methyl-3-oxo-2,3-dihydro-1H-pyrazolo[3,4-b]pyridin-6-yl)cyclopropanecarboxamide, I-50

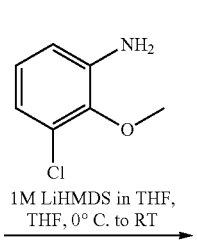
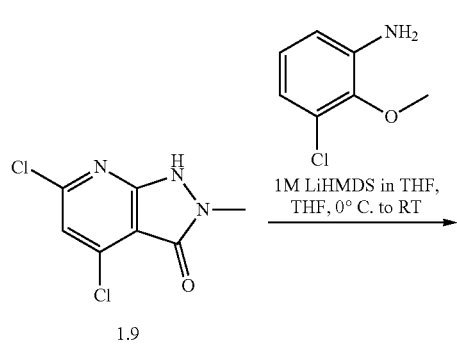
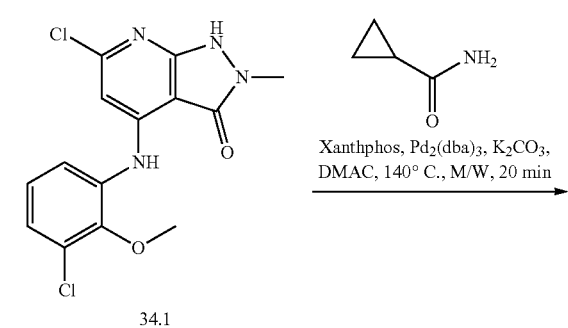
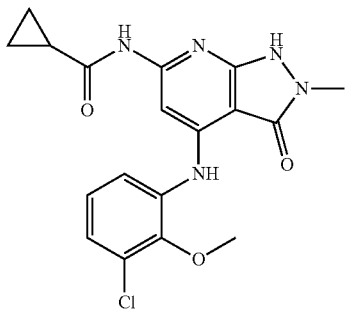
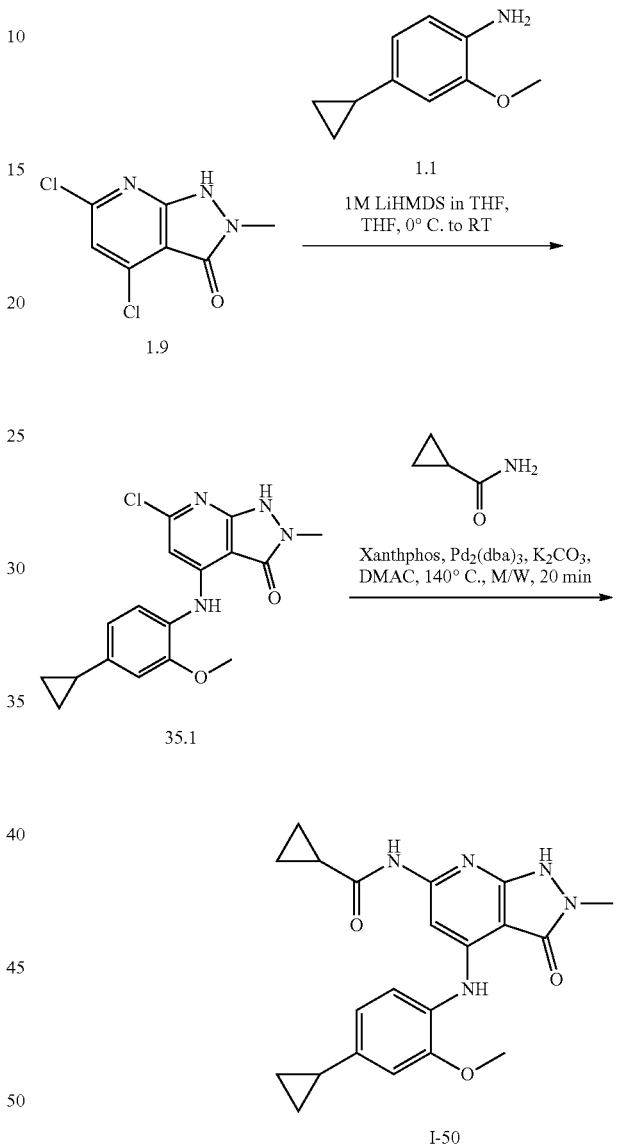

Following the procedure used to prepare 1.91, 34.1 was obtained (Yield: 47.14%). MS (ES): m/z 340.2 [M+H]+.

Compound I-49 was prepared from compound 34.1 and cyclopropanecarboxamide using procedure described in Example 2. (Yield: 39.36%), MS(ES): m/z 388.13 [M+H]+, LCMS purity: 99.46%, HPLC purity: 98.93%, 1H NMR (DMSO-d6, 400 MHz): 10.78 (s, 2H), 8.84 (s, 1H), 7.74 (bs, 1H), 7.46-7.43 (t, J=4.8 Hz, 1H), 7.22-7.20 (d, J=4.8 Hz, 2H), 3.77 (s, 3H), 3.29 (s, 3H), 1.98 (s, 1H), 0.77 (s, 4H).

Following the procedure used to prepare 1.91, 35.1 was obtained (Yield: 54.80%). MS (ES): m/z 345.7 [M+H]+.

Compound I-50 was prepared from compound 35.1 and cyclopropanecarboxamide using procedure described in Example 2 (Yield: 16.18%), MS(ES): m/z 394.61 [M+H]+, LCMS purity: 94.66%, HPLC purity: 99.76%, 1H NMR (DMSO-d6, 400 MHz): 10.67-10.62 (d, J=17.6 Hz, 2H), 8.36 (s, 1H), 7.58 (bs, 1H), 7.29-7.268 (d, J=8.0 Hz, 1H), 6.83-6.83 (d, J=1.6 Hz, 1H), 6.72-6.69 (dd, J=1.6 Hz, 8.0 Hz, 1H), 3.83 (s, 3H), 3.28 (s, 3H), 2.01-1.90 (m, 2H), 0.96-0.90 (m, 2H), 0.79-0.77 (d, J=5.2 Hz, 4H), 0.74-0.72 (dd, J=3.2 Hz, 4.8 Hz, 2H).

Example 36: Synthesis of N-(4-((4-cyclobutyl-2-methoxyphenyl)amino)-2-methyl-3-oxo-2,3-dihydro-1H-pyrazolo[3,4-b]pyridin-6-yl)cyclopropanecarboxamide, I-51

Example 37: Synthesis of N-(4-((2-methoxy-3-(1-methyl-1H-tetrazol-5-yl)phenyl)amino)-2-methyl-3-oxo-2,3-dihydro-1H-pyrazolo[3,4-b]pyridin-6-yl)cyclopropanecarboxamide, I-52

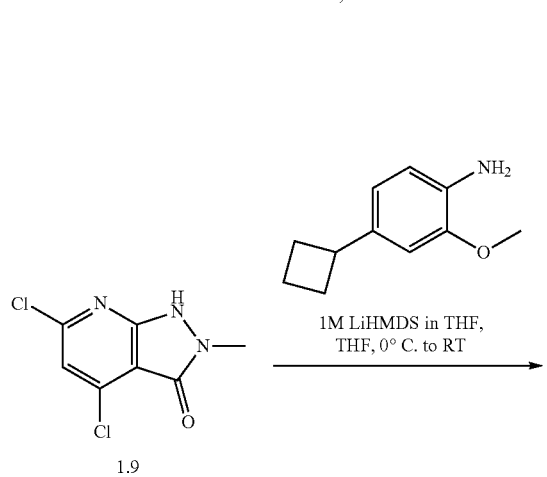

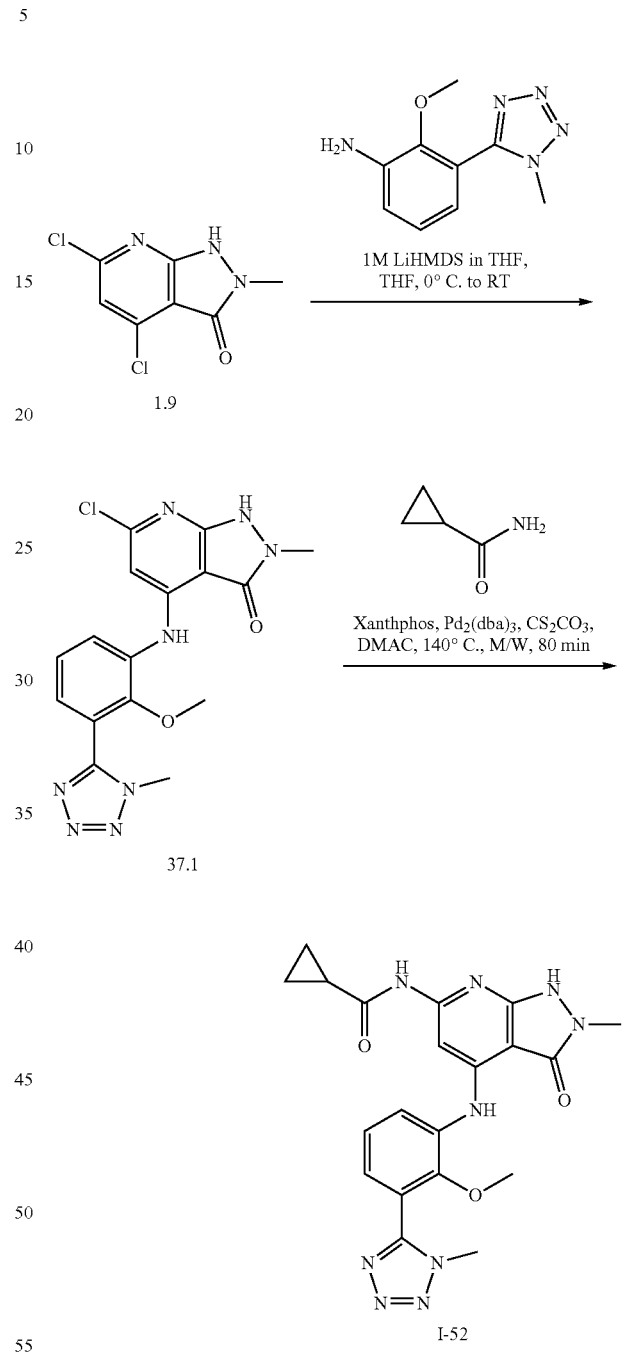

Following the procedure used to prepare 1.91, 36.1 was obtained (Yield: 50.64%). MS (ES): m/z 359.8 [M+H]+.

Compound I-51 was prepared from compound 36.1 and cyclopropanecarboxamide using procedure described in Example 2 (Yield: 42.27%), MS(ES): m/z 408.37 [M+H]+, LCMS purity: 96.20%, HPLC purity: 96.45%, 1H NMR (DMSO-d6, 400 MHz): 10.67-10.63 (d, J=17.2 Hz, 2H), 8.41 (s, 1H), 7.64 (s, 1H), 7.35-7.33 (d, J=8.0 Hz, 1H), 6.97 (s, 1H), 6.88-6.87 (d, J=8.0 Hz, 1H), 3.85 (s, 3H), 3.54-3.48 (q, J=8.8 Hz, 1H), 3.28 (s, 3H), 2.33-2.25 (m, 2H), 2.19-2.09 (m, 2H), 2.02-1.93 (m, 2H), 1.85-1.80 (m, 1H), 0.79-0.78 (d, J=5.2 Hz, 4H).

Following the procedure used to prepare 1.91, 37.1 was obtained (Yield: 68.77%). MS (ES): m/z 387.7 [M+H]+.

Compound I-52 was prepared from compound 37.1 and cyclopropanecarboxamide using procedure described in Example 2 (Yield: 22.21%), MS(ES): m/z 436.37 [M+H]+, LCMS purity: 97.49%, HPLC purity: 94.04%, 1H NMR (DMSO-d6, 400 MHz): 10.78 (s, 1H), 8.82 (s, 1H), 8.19 (s, 1H), 7.75-7.73 (d, J=7.6 Hz, 1H), 7.65 (s, 1H), 7.4467.40 (t, J=7.6 Hz, 1H), 7.36-7.34 (d, J=6.4 Hz, 1H), 3.99 (s, 3H), 3.47 (s, 3H), 2.61 (s, 3H), 2.03-2.00 (t, J=6.0 Hz, 1H), 0.81-0.79 (d, J=6.0 Hz, 4H).

Example 38: Synthesis of N-(4-((3-(1,5-dimethyl-1H-1,2,4-triazol-3-yl)-2-methoxyphenyl)amino)-2-methyl-3-oxo-2,3-dihydro-1H-pyrazolo[3,4-b]pyridin-6-yl)cyclopropanecarboxamide, I-53

Example 39: Synthesis of N-(4-((2-methoxy-3-(1-methyl-1H-1,2,4-triazol-5-yl)phenyl)amino)-2-methyl-3-oxo-2,3-dihydro-1H-pyrazolo[3,4-b]pyridin-6-yl)cyclopropanecarboxamide, I-54

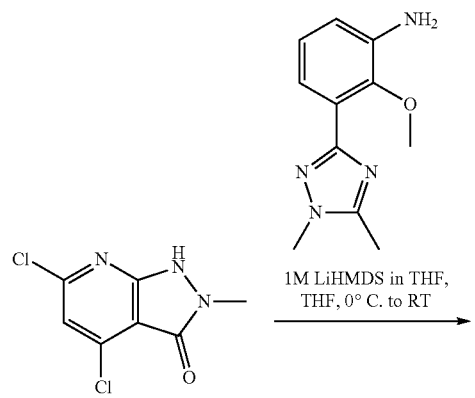

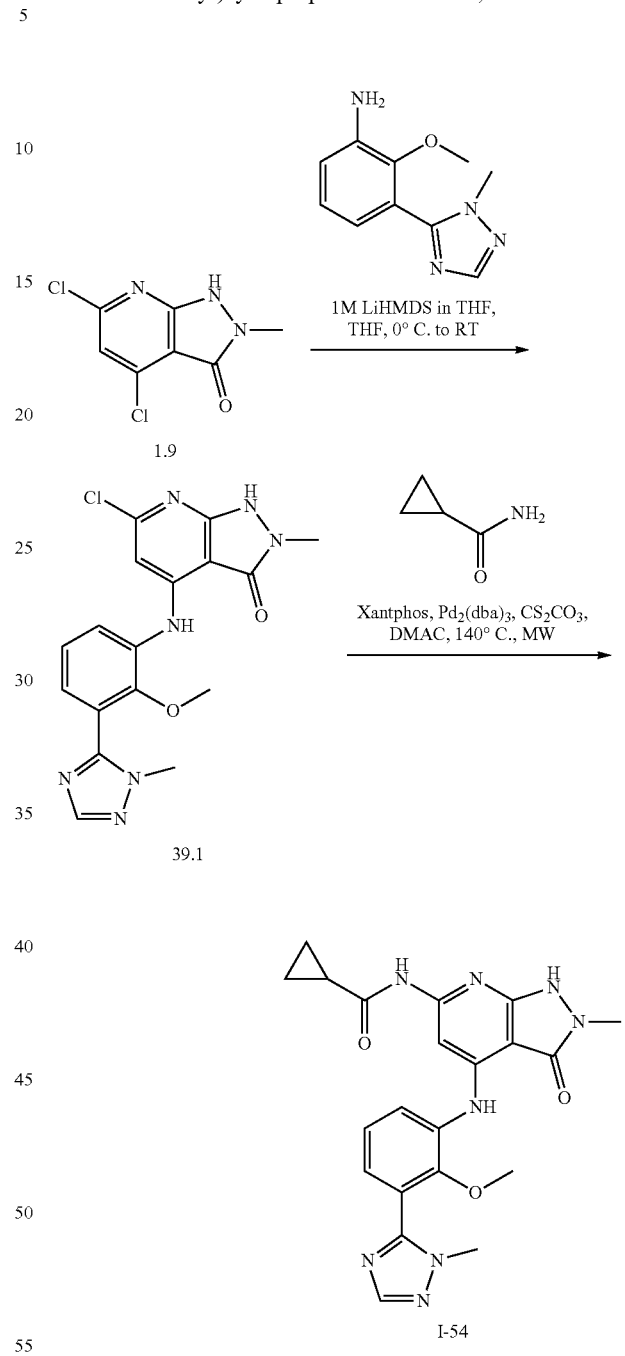

Following the procedure used to prepare 1.91, 38.1 was obtained (Yield: 68.16%). MS (ES): m/z 400.8 [M+H]+.

Compound I-53 was prepared from compound 38.1 and cyclopropanecarboxamide using procedure described in Example 2 (Yield: 30.67%), MS(ES): m/z 449.37 [M+H]+, LCMS purity: 98.48%, HPLC purity: 95.33%, 1H NMR (CDCl3, 400 MHz): 9.59 (bs, 1H), 8.89 (s, 1H), 7.59-7.57 (d, J=7.6 Hz, 1H), 7.49-7.47 (d, J=8.0 Hz, 1H), 7.13-7.02 (m, 2H), 3.89 (s, 3H), 3.71 (s, 3H), 3.47 (s, 3H), 2.52 (s, 3H), 1.65 (s, 1H), 1.11 (s, 2H), 0.90 (s, 2H).

Following the procedure used to prepare 1.91, 39.1 was obtained (Yield: 62.17%). MS (ES): m/z 386.6 [M+H]+.

Compound I-54 was prepared from compound 39.1 and cyclopropanecarboxamide using procedure described in Example 2 (Yield: 17.76%), MS(ES): m/z 435.32 [M+H]+, LCMS purity: 99.53%, HPLC purity: 99.60%, 1H NMR (DMSO-d6, 400 MHz): 10.78 (bs, 1H), 8.84 (s, 1H), 8.08 (s, 1H), 7.71 (s, 1H), 7.68-7.66 (d, J=8.0 Hz, 1H), 7.38-7.34 (m, 1H), 7.25-7.23 (d, J=8.0 Hz, 1H), 3.74 (s, 3H), 3.49 (s, 3H), 3.22 (s, 3H), 2.03-2.00 (m, 1H), 0.81-0.79 (d, J=5.2 Hz, 4H).

Example 40: Synthesis of N-(4-((2-methoxy-3-(1-methyl-1H-pyrazol-4-yl)phenyl)amino)-2-methyl-3-oxo-2,3-dihydro-1H-pyrazolo[3,4-b]pyridin-6-yl)cyclopropanecarboxamide, I-55

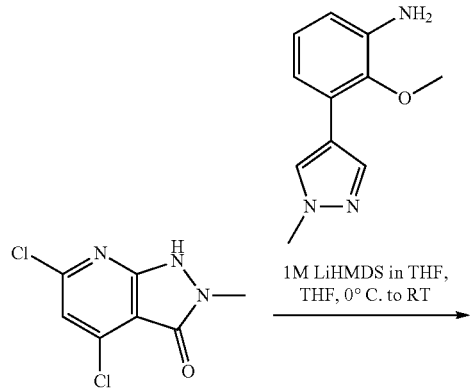

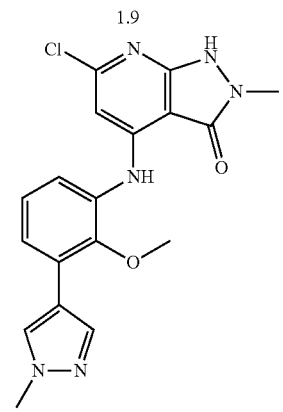

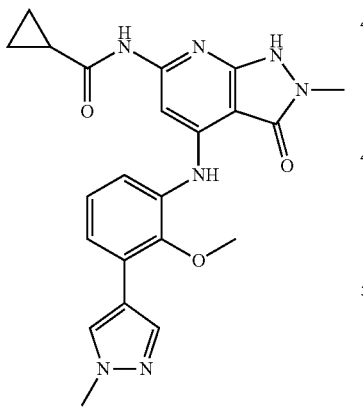

Example 41: Synthesis of N-(4-((2-methoxy-3-(1H-pyrazol-1-yl)phenyl)amino)-2-methyl-3-oxo-2,3-dihydro-1H-pyrazolo[3,4-b]pyridin-6-yl)cyclopropanecarboxamide, I-56

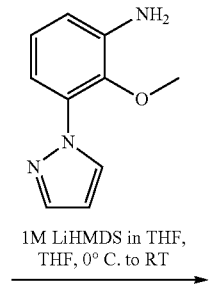

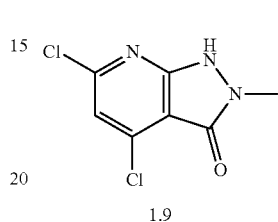

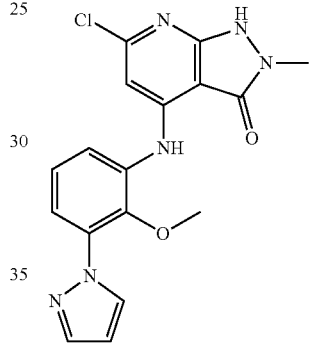

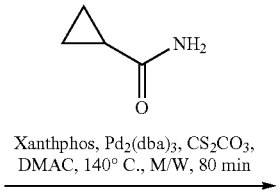

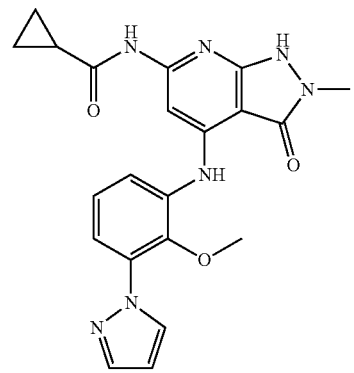

Following the procedure used to prepare 1.91, 40.1 was obtained (Yield: 48.16%). MS (ES): m/z 385.7 [M+H]+.

Compound I-55 was prepared from compound 40.1 and cyclopropanecarboxamide using procedure described in Example 2 (Yield: 20.89%), MS(ES): m/z 434.48 [M+H]+, LCMS purity: 100.00%, HPLC purity: 100.00%, 1H NMR (DMSO-d6, 400 MHz): 10.76 (bs, 1H), 8.81 (s, 1H), 8.19 (s, 1H), 7.92 (s, 1H), 7.77 (s, 1H), 7.38-7.33 (t, J=10.0 Hz, 2H), 7.21-7.19 (d, J=8.0 Hz, 1H), 3.90 (s, 3H), 3.61 (s, 3H), 3.32 (s, 3H), 2.02 (s, 1H), 0.80 (s, 4H).

Following the procedure used to prepare 1.91, 41.1 was obtained (Yield: 58.80%). MS (ES): m/z 371.8 [M+H]+.

Compound I-56 was prepared from compound 41.1 and cyclopropanecarboxamide using procedure described in Example 2 (Yield: 22.10%), MS(ES): m/z 420.48 [M+H]+, LCMS purity: 99.87%, HPLC purity: 99.66%, 1H NMR (DMSO-d6, 400 MHz): 10.80 (bs, 1H), 8.88 (s, 1H), 8.23-8.22 (d, J=2.0 Hz, 1H), 7.79 (s, 2H), 7.52-7.50 (d, J=7.6 Hz, 1H), 7.39-7.31 (m, 2H), 6.57 (s, 1H), 3.45 (s, 3H), 3.32 (s, 3H), 2.02 (s, 1H), 0.81 (s, 4H).

Example 42: Synthesis of N-(4-((2-methoxy-3-(1-methyl-1H-pyrazol-3-yl)phenyl)amino)-2-methyl-3-oxo-2,3-dihydro-1H-pyrazolo[3,4-b]pyridin-6-yl)cyclopropanecarboxamide, I-57

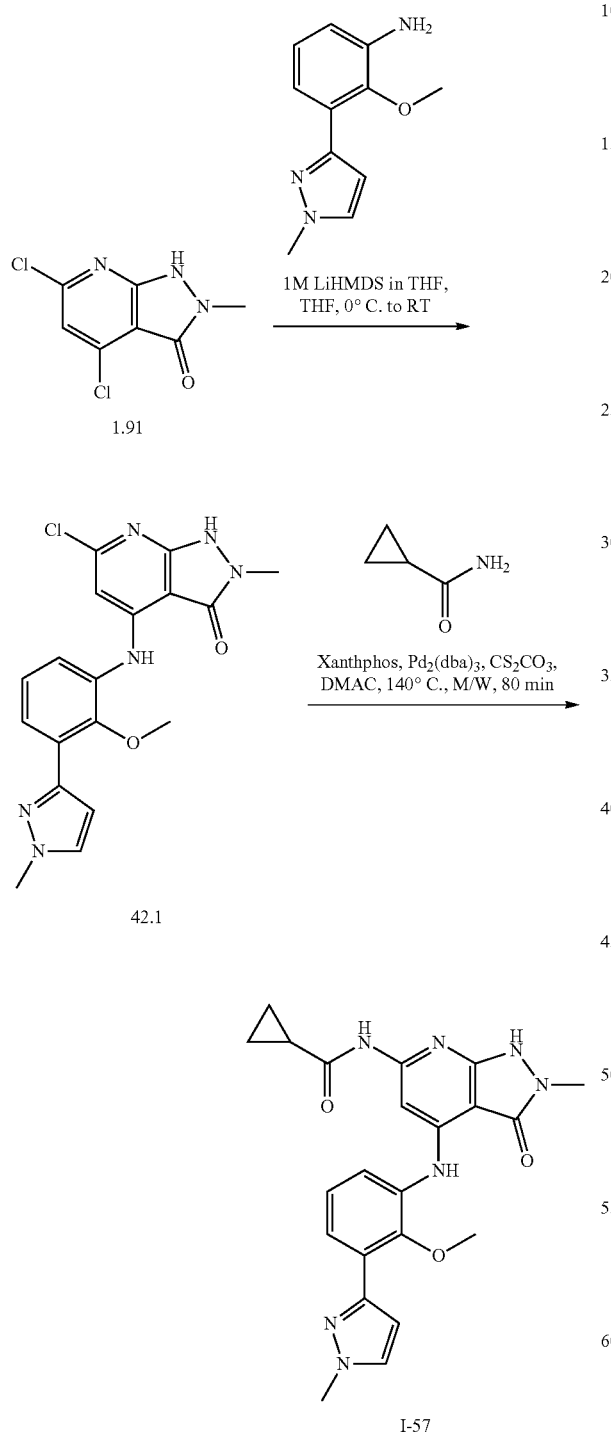

Following the procedure used to prepare 1.91, 42.1 was obtained (Yield: 37.77%). MS (ES): m/z 385.5 [M+H]+.

Compound I-57 was prepared from compound 42.1 and cyclopropanecarboxamide using procedure described in Example 2 (Yield: 31.07%), MS(ES): m/z 434.63 [M+H]+, LCMS purity: 100.00%, HPLC purity: 96.16%, 1H NMR (DMSO-d6, 400 MHz): 10.76 (bs, 2H), 8.83 (s, 1H), 7.79 (s, 2H), 7.62-7.60 (d, J=7.6 Hz, 1H), 7.44-7.42 (d, J=7.6 Hz, 1H), 7.24-7.22 (m, 1H), 6.74-6.73 (d, J=2.4 Hz, 1H), 3.91 (s, 3H), 3.61 (s, 3H), 3.31 (s, 3H), 2.02 (s, 1H), 0.81 (s, 4H).

Example 46: Synthesis of N-(4-((2-methoxyphenyl)amino)-2-methyl-3-oxo-2,3-dihydro-1H-pyrazolo[3,4-b]pyridin-6-yl)cyclopropanecarboxamide, I-61

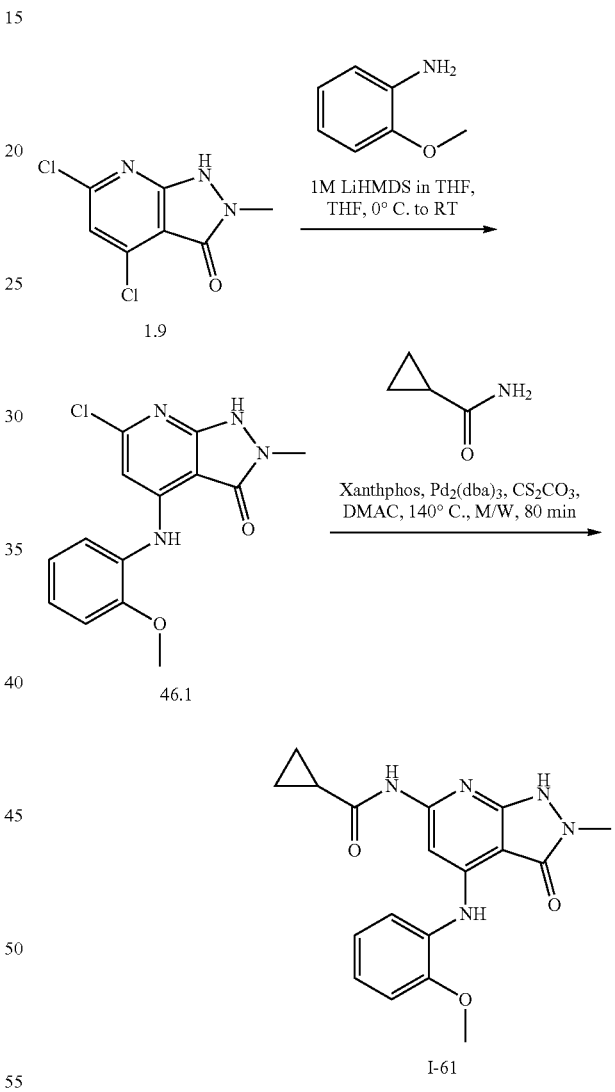

Following the procedure used to prepare 1.91, 46.1 was obtained (Yield: 75.13%). MS (ES): m/z 305.7 [M+H]+.

Compound I-61 was prepared from compound 46.1 and cyclopropanecarboxamide using procedure described in Example 2 (Yield: 19.83%), MS(ES): m/z 354.38 [M+H]+, LCMS purity: 100.00%, HPLC purity: 98.86%, 1H NMR (DMSO-d6, 400 MHz): 10.69-10.67 (d, J=10.8 Hz, 2H), 8.53 (s, 1H), 7.69 (s, 1H), 7.45-7.43 (d, J=8.0 Hz, 1H), 7.13-7.12 (d, J=4.0 Hz, 2H), 7.03-6.99 (m, 1H), 3.85 (s, 3H), 3.29 (s, 3H), 1.99 (s, 1H), 0.78 (s, 4H).

Example 51: Synthesis of 4-((2-methoxy-4-(methoxymethyl)phenyl)amino)-2-methyl-6-((6-(trifluoromethyl)pyridin-2-yl)amino)-1,2-dihydro-3H-pyrazolo[3,4-b]pyridin-3-one, I-67

Example 52: Synthesis of 6-((4-((2-methoxy-4-(methoxymethyl)phenyl)amino)-2-methyl-3-oxo-2,3-dihydro-1H-pyrazolo[3,4-b]pyridin-6-yl)amino)picolinonitrile, I-68

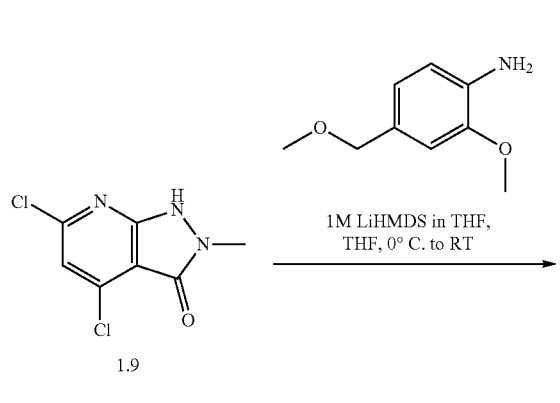

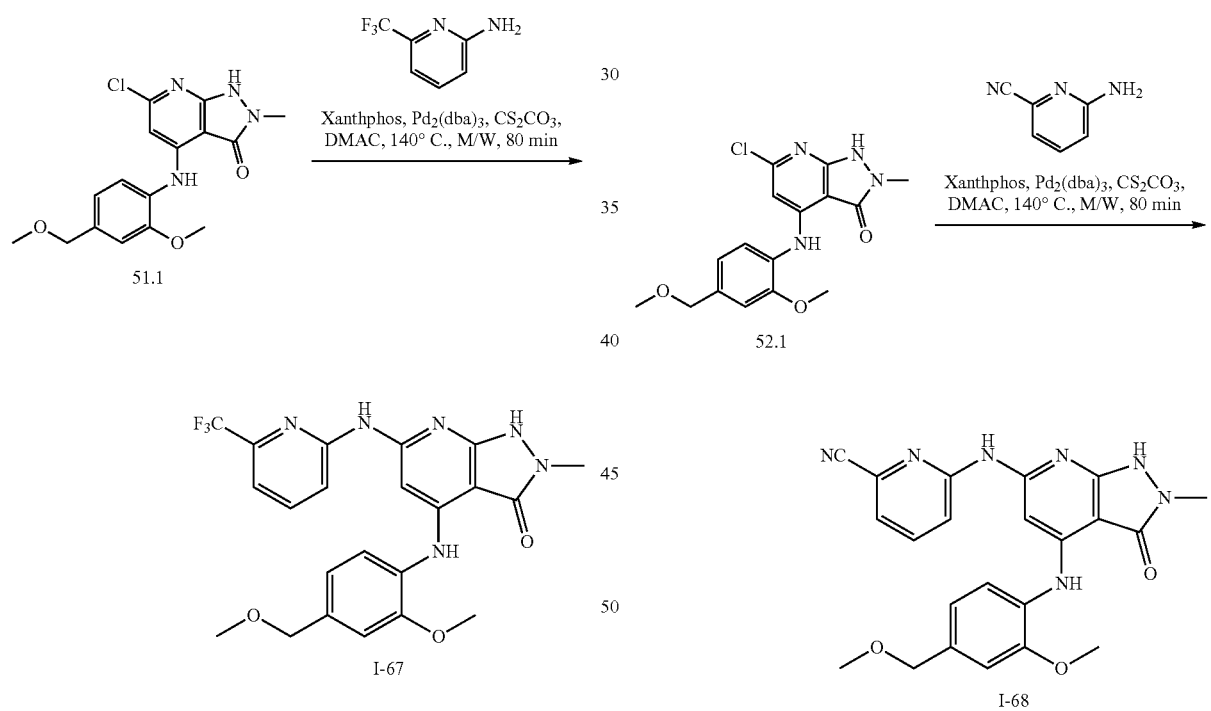

Following the procedure used to prepare 1.91, 51.1 was obtained (Yield: 78.14%). MS (ES): m/z 349.7 [M+H]⁺.

Compound I-67 was prepared from compound 51.1 and 6-(trifluoromethyl)pyridin-2-amine using procedure described in Example 2 (Yield: 14.70%), MS(ES): m/z 475.35 [M+H]⁺, LCMS purity: 100.00%, HPLC purity: 95.73%, 1H NMR (DMSO-d6, 400 MHz): 10.72 (s, 1H), 10.21 (s, 1H), 8.69 (s, 1H), 8.13-8.10 (d, J=8.4 Hz, 1H), 7.96-7.92 (t, J=8.4 Hz, 1H), 7.54-7.52 (d, J=8.0 Hz, 1H), 7.38-7.36 (d, J=7.2 Hz, 1H), 7.32 (s, 1H), 7.06 (s, 1H), 6.95-6.93 (d, J=7.6 Hz, 1H), 4.42 (s, 2H), 3.88 (s, 3H), 3.31 (s, 3H), 3.28 (s, 3H).

Following the procedure used to prepare 1.91, 52.1 was obtained (Yield: 78.14%). MS (ES): m/z 349.7 [M+H]⁺.

Compound I-68 was prepared from compound 52.1 and 6-aminopicolinonitrile using procedure described in Example 2 (Yield: 32.34%), MS(ES): m/z 432.34 [M+H]⁺, LCMS purity: 97.69%, HPLC purity: 96.47%, 1H NMR (DMSO-d6, 400 MHz): 10.72 (s, 1H), 10.24 (s, 1H), 8.64 (s, 1H), 8.08 (s, 1H), 7.89 (s, 1H), 7.56-7.53 (d, J=10.0 Hz, 2H), 7.32 (s, 1H), 7.08-7.05 (d, J=10.4 Hz, 2H), 4.41 (s, 2H), 3.88 (s, 3H), 3.33 (s, 3H), 3.28 (s, 3H).

Example 53: Synthesis of N-(4-((3-bromo-2-methoxyphenyl)amino)-2-methyl-3-oxo-2,3-dihydro-1H-pyrazolo[3,4-b]pyridin-6-yl)cyclopropanecarboxamide, I-69

Example 54: Synthesis of 4-((4-(hydroxymethyl)-2-methoxyphenyl)amino)-2-methyl-6-((6-(trifluoromethyl)pyridin-2-yl)amino)-1,2-dihydro-3H-pyrazolo[3,4-b]pyridin-3-one, I-72

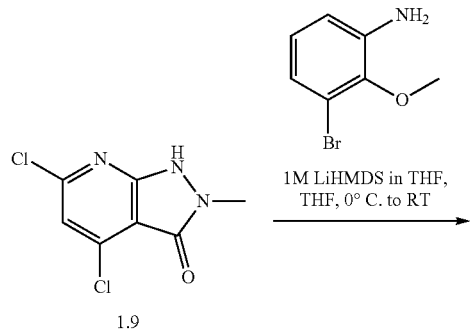

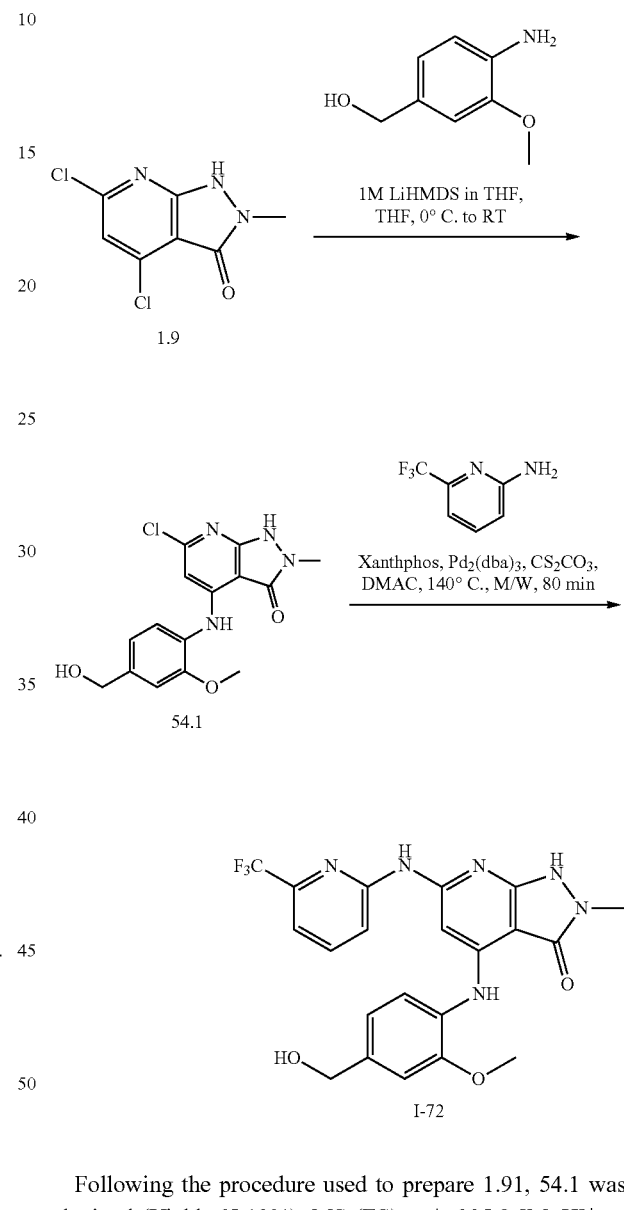

Following the procedure used to prepare 1.91, 53.1 was obtained (Yield: 56.84%). MS (ES): m/z 384.6 [M+H]+.

Compound I-69 was prepared from compound 53.1 and cyclopropanecarboxamide using procedure described in Example 2 (Yield: 15.53%), MS(ES): m/z 434.27 [M+H]+, LCMS purity: 98.62%, HPLC purity: 98.29%, 1H NMR (DMSO-d6, 400 MHz): 10.79-10.78 (d, J=7.6 Hz, 2H), 8.83 (s, 1H), 7.75 (s, 1H), 7.46-7.44 (t, J=9.6 Hz, 1H), 7.22 (s, 1H), 7.21 (s, 1H), 3.78 (s, 3H), 3.32 (s, 3H), 1.98 (s, 1H), 0.79 (s, 4H).

Following the procedure used to prepare 1.91, 54.1 was obtained (Yield: 65.13%). MS (ES): m/z 335.8 [M+H]+.

Compound I-72 was prepared from compound 54.1 and 6-(trifluoromethyl)pyridin-2-amine using procedure described in Example 2 (Yield: 14.54%), MS(ES): m/z 461.38 [M+H]+, LCMS purity: 98.86%, HPLC purity: 95.52%, 1H NMR (DMSO-d6, 400 MHz): 10.71 (s, 1H), 10.20 (s, 1H), 8.66 (s, 1H), 8.15-8.13 (d, J=9.2 Hz, 1H), 7.96-7.92 (t, J=7.6 Hz, 1H), 7.52-7.49 (d, J=8.0 Hz, 1H), 7.38-7.36 (d, J=7.2 Hz, 1H), 7.27 (s, 1H), 7.08 (s, 1H), 6.95-6.94 (d, J=7.6 Hz, 1H), 5.24-5.22 (t, J=5.6 Hz, 1H), 4.51-4.50 (d, J=5.6 Hz, 2H), 3.87 (s, 3H), 3.28 (s, 3H).

Example 55: Synthesis of 4-((3-fluoro-2-methoxyphenyl)amino)-2-methyl-6-((5-(piperidin-1-yl)pyridin-2-yl)amino)-1,2-dihydro-3H-pyrazolo[3,4-b]pyridin-3-one, I-77

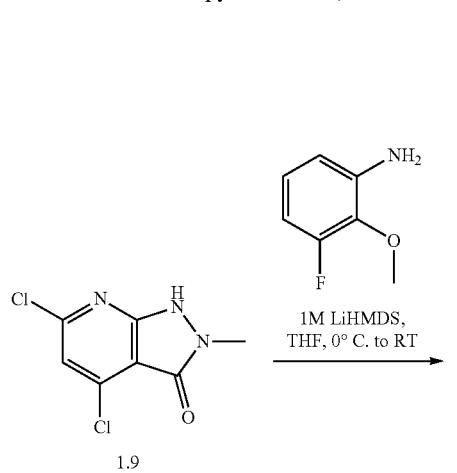

Following the procedure used to prepare 1.91, 55.1 was obtained (Yield: 81.07%). MS (ES): m/z 323.7 [M+H]⁺.

Compound I-77 was prepared from compound 55.1 and 5-(piperidin-1-yl)pyridin-2-amine using procedure described in Example 2 (Yield: 20.89%), MS(ES): m/z 464.53 [M+H]⁺, LCMS purity: 100.00%, HPLC purity: 98.80%, 1H NMR (DMSO-d6, 400 MHz): 10.67 (s, 1H), 9.58 (s, 1H), 8.90 (s, 1H), 8.02 (s, 2H), 7.40 (s, 2H), 7.22-7.17 (q, J=8.4 Hz, 1H), 7.01 (s, 2H), 3.89 (s, 3H), 3.27 (s, 3H), 3.08 (s, 4H), 1.64 (s, 4H), 1.23 (s, 2H).

Example 56: Synthesis of 4-((3-fluoro-2-methoxyphenyl)amino)-2-methyl-6-((1-methyl-1H-pyrazol-3-yl)amino)-1,2-dihydro-3H-pyrazolo[3,4-b]pyridin-3-one, I-78

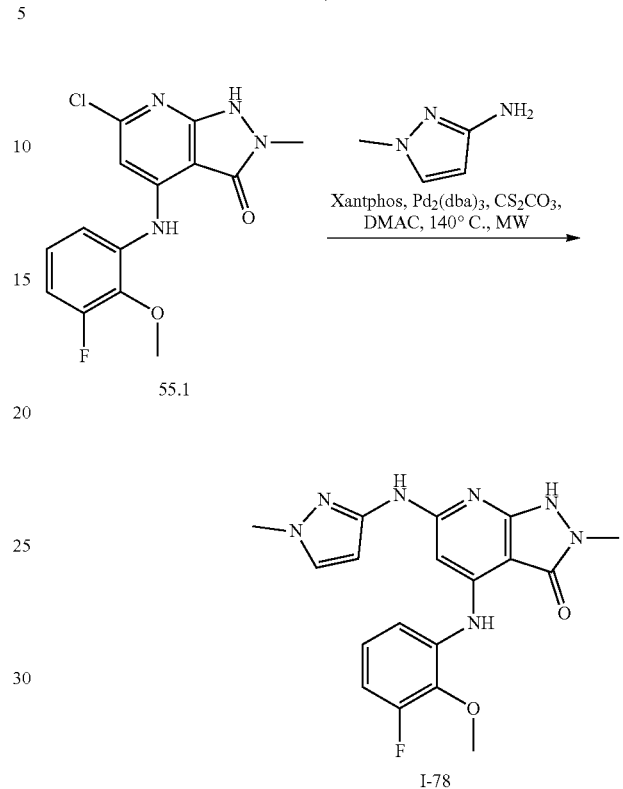

Compound I-78 was prepared from compound 55.1 and 1-methyl-1H-pyrazol-3-amine using procedure described in Example 2 (Yield: 37.88%), MS(ES): m/z 384.43 [M+H]⁺, LCMS purity: 97.80%, HPLC purity: 93.71%, 1H NMR (DMSO-d6, 400 MHz): 10.52 (bs, 1H), 9.52 (bs, 1H), 8.78 (s, 1H), 7.54 (s, 1H), 7.42-7.39 (d, J=8.4 Hz, 1H), 7.21-7.15 (q, J=8.4 Hz, 1H), 7.01-6.97 (d, J=9.6 Hz, 1H), 6.88 (s, 1H), 6.35 (s, 1H), 3.89 (s, 3H), 3.72 (s, 3H), 3.25 (s, 3H).

Example 57: Synthesis of 6-((4-((3-fluoro-2-methoxyphenyl)amino)-2-methyl-3-oxo-2,3-dihydro-1H-pyrazolo[3,4-b]pyridin-6-yl)amino)nicotinonitrile, I-79

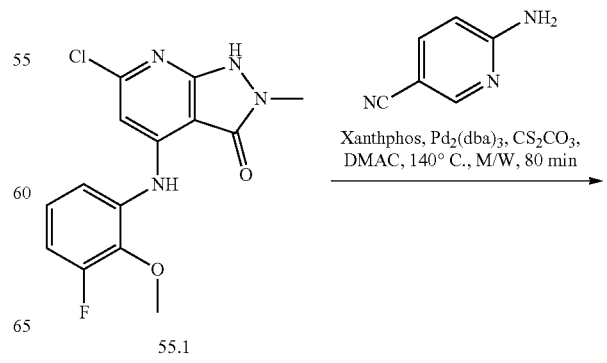

-continued

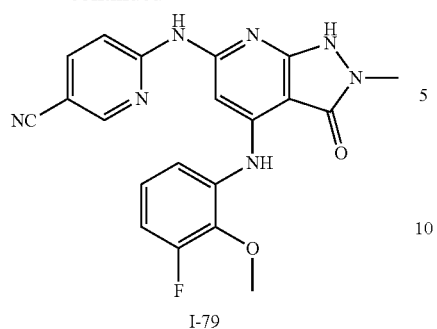

I-79

Compound I-79 was prepared from compound 55.1 and 6-aminonicotinonitrile using procedure described in Example 2 (Yield: 39.80%), MS(ES): m/z 406.29 [M+H]$^+$, LCMS purity: 98.61%, HPLC purity: 99.01%, 1H NMR (DMSO-d6, 400 MHz): 10.99 (s, 1H), 10.44 (s, 1H), 8.88 (s, 1H), 8.69 (s, 1H), 8.23-8.21 (d, J=8.8 Hz, 1H), 8.15-8.13 (dd, J=1.6 Hz, 8.8 Hz, 1H), 7.43-7.41 (d, J=8.4 Hz, 1H), 7.25-7.19 (q, J=8.4 Hz, 1H), 7.15 (s, 1H), 7.06-7.01 (d, J=8.8 Hz, 1H), 3.89 (s, 3H), 3.35 (s, 3H).

Example 58: Synthesis of 4-((3-fluoro-2-methoxyphenyl)amino)-2-methyl-6-(pyridin-2-ylamino)-1,2-dihydro-3H-pyrazolo[3,4-b]pyridin-3-one, I-80

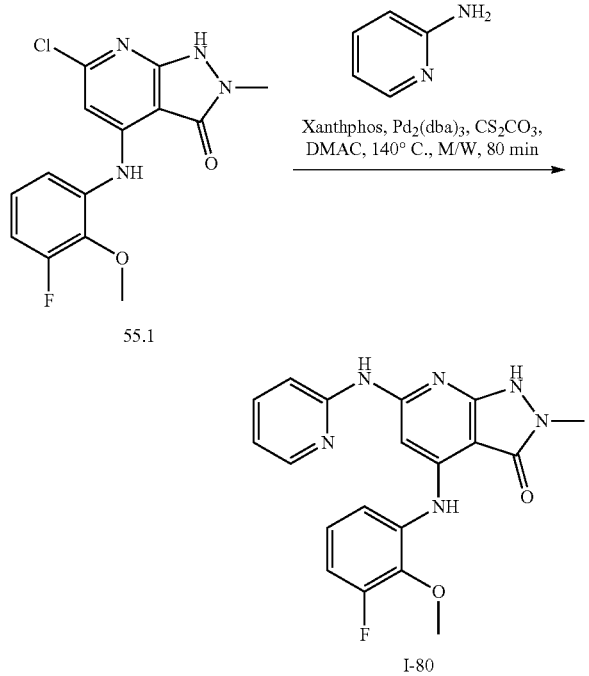

Compound I-80 was prepared from compound 55.1 and pyridin-2-amine using procedure described in Example 2 (Yield: 21.21%), MS(ES): m/z 381.28 [M+H]$^+$, LCMS purity: 97.64%, HPLC purity: 97.36%, 1H NMR (DMSO-d6, 400 MHz): 10.78 (s, 1H), 9.85 (s, 1H), 8.85 (s, 1H), 8.26 (s, 1H), 8.03 (s, 1H), 7.71 (s, 1H), 7.44 (s, 1H), 7.21 (s, 2H), 7.06-6.83 (m, 2H), 3.96 (s, 3H), 3.29 (s, 3H).

Example 59: Synthesis of 6-((4-((3-fluoro-2-methoxyphenyl)amino)-2-methyl-3-oxo-2,3-dihydro-1H-pyrazolo[3,4-b]pyridin-6-yl)amino)picolinonitrile, I-81

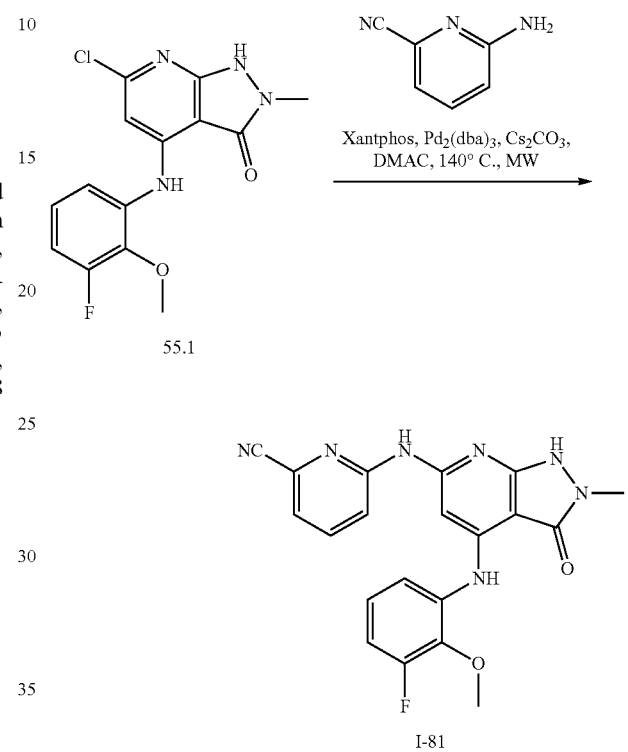

I-81

Compound I-81 was prepared from compound 55.1 and 6-aminopicolinonitrile using procedure described in Example 2 (Yield: 43.78%), MS(ES): m/z 406.43 [M+H]$^+$, LCMS purity: 100.00%, HPLC purity: 100.00%, 1H NMR (DMSO-d6, 400 MHz): 10.84 (s, 1H), 10.32 (s, 1H), 8.95 (s, 1H), 8.05-8.03 (d, J=8.4 Hz, 1H), 7.93-7.89 (t, J=8.4 Hz, 1H), 7.56-7.49 (m, 3H), 7.26-7.20 (q, J=8.0 Hz, 1H), 7.06-7.01 (t, J=9.2 Hz, 1H), 3.91 (s, 3H), 3.30 (s, 3H).

Example 60: Synthesis of N-(4-((4-(azetidine-1-carbonyl)-2-methoxyphenyl)amino)-2-methyl-3-oxo-2,3-dihydro-1H-pyrazolo[3,4-b]pyridin-6-yl)cyclopropanecarboxamide, I-82

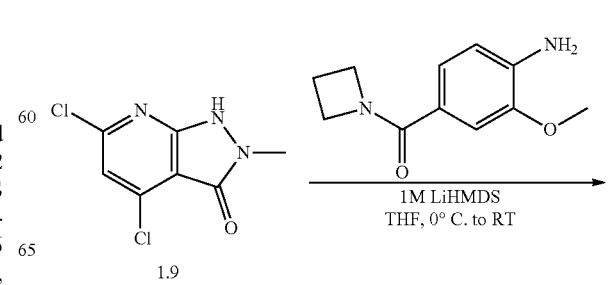

215

-continued

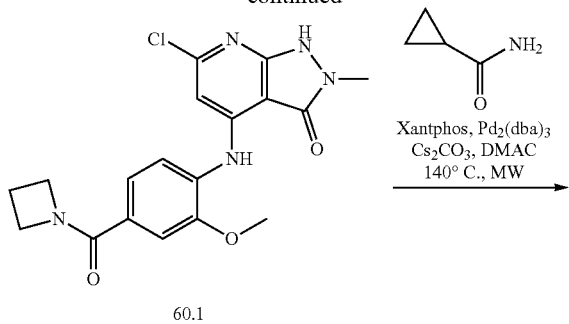

60.1

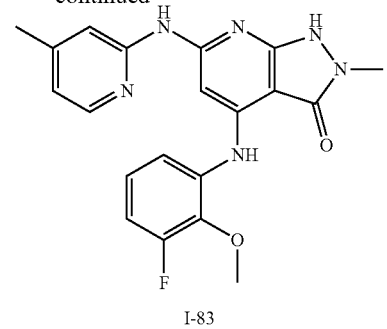

I-83

Compound I-83 was prepared from compound 55.1 and 4-methylpyridin-2-amine using procedure described in Example 2 (Yield: 30.68%), MS(ES): m/z 395.28 [M+H]⁺, LCMS purity: 98.12%, HPLC purity: 97.83%, 1H NMR (DMSO-d6, 400 MHz): 10.72 (s, 1H), 9.72 (s, 1H), 8.82 (s, 1H), 8.09 (s, 1H), 7.83 (s, 1H), 7.43-7.42 (d, J=7.2 Hz, 1H), 7.20-7.14 (m, 2H), 6.98 (s, 1H), 6.76 (s, 1H), 3.87 (s, 3H), 3.26 (s, 3H), 2.28 (s, 3H).

I-82

Following the procedure used to prepare 1.91, 60.1 was obtained (Yield: 24.74%). MS (ES): m/z 388.8 [M+H]⁺.

Compound I-82 was prepared from compound 60.1 and cyclopropanecarboxamide using procedure described in Example 2 (Yield: 21%), MS(ES): m/z 437.37 [M+H]⁺, LCMS purity: 100.00%, HPLC purity: 98.68%, 1H NMR (MeOD, 400 MHz): 7.61-7.59 (d, J=8.0 Hz, 2H), 7.39 (s, 1H), 7.34-7.32 (d, J=8.4 Hz, 1H), 4.51-4.47 (t, J=6.4 Hz, 2H), 4.25-4.21 (t, J=6.4 Hz, 2H), 3.99 (s, 3H), 3.49 (s, 3H), 2.45-2.38 (qui, J=6.4 Hz, 2H), 1.84 (s, 1H), 1.04-0.96 (m, 4H).

Example 62: Synthesis of 4-((3-fluoro-2-methoxyphenyl)amino)-2-methyl-6-((5-methylpyridin-2-yl)amino)-1,2-dihydro-3H-pyrazolo[3,4-b]pyridin-3-one, I-84

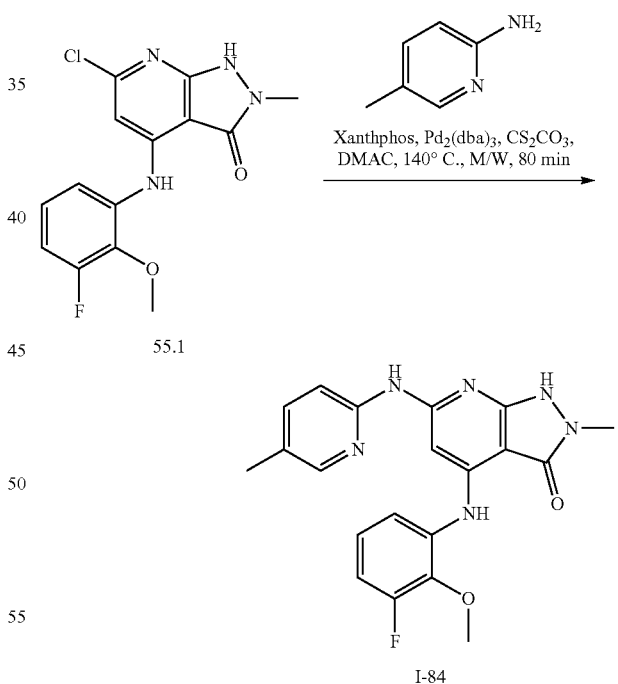

Example 61: Synthesis of 4-((3-fluoro-2-methoxyphenyl)amino)-2-methyl-6-((4-methylpyridin-2-yl)amino)-1,2-dihydro-3H-pyrazolo[3,4-b]pyridin-3-one, I-83

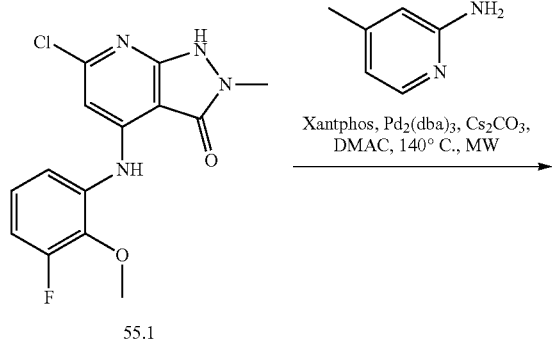

55.1

Compound I-84 was prepared from compound 55.1 and 5-methylpyridin-2-amine using procedure described in Example 2 (Yield: 20.46%), MS(ES): m/z 395.32 [M+H]⁺, LCMS purity: 97.72%, HPLC purity: 97.18%, 1H NMR (MeOD, 400 MHz): 8.15 (s, 1H), 7.65-7.62 (dd, J=2.0 Hz, 8.4 Hz, 1H), 7.33-7.31 (d, J=8.0 Hz, 1H), 7.18-7.13 (m, 2H), 7.08-7.03 (t, J=8.8 Hz, 1H), 6.89-6.87 (d, J=7.6 Hz, 1H), 3.97 (s, 3H), 3.54 (s, 3H), 2.31 (s, 3H).

Example 63: Synthesis of 6-((4-((3-fluoro-2-methoxyphenyl)amino)-2-methyl-3-oxo-2,3-dihydro-1H-pyrazolo[3,4-b]pyridin-6-yl)amino)pyrazine-2-carbonitrile, I-85

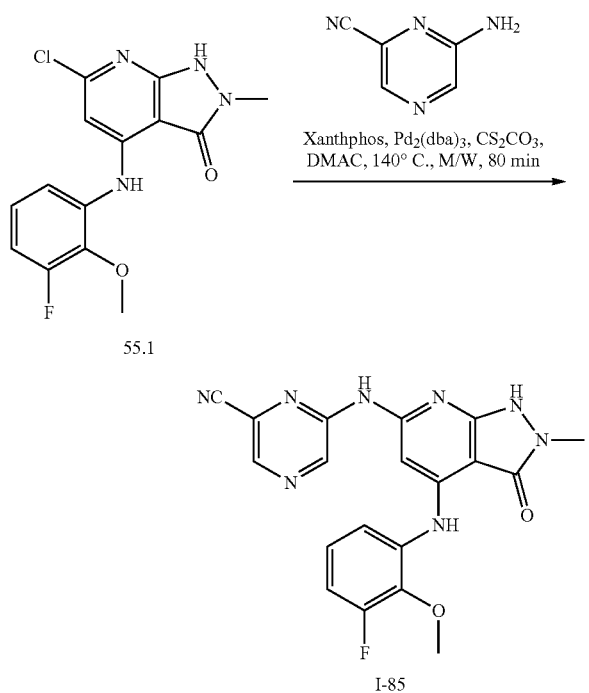

Compound I-85 was prepared from compound 55.1 and 6-aminopyrazine-2-carbonitrile using procedure described in Example 2 (Yield: 17.87%), MS(ES): m/z 407.27 [M+H]$^+$, LCMS purity: 99.70%, HPLC purity: 99.67%, 1H NMR (DMSO-d6, 400 MHz): 10.96 (bs, 1H), 10.67 (bs, 1H), 9.31 (s, 1H), 8.92 (s, 1H), 8.65 (s, 1H), 7.47-7.45 (d, J=8.0 Hz, 1H), 7.38 (s, 1H), 7.24-7.18 (q, J=8.0 Hz, 1H), 7.08-7.03 (t, J=6.0 Hz, 1H), 3.91 (s, 3H), 3.35 (s, 3H).

Example 64: Synthesis of 4-((3-fluoro-2-methoxyphenyl)amino)-2-methyl-6-((6-(trifluoromethyl)pyridin-2-yl)amino)-1,2-dihydro-3H-pyrazolo[3,4-b]pyridin-3-one, I-86

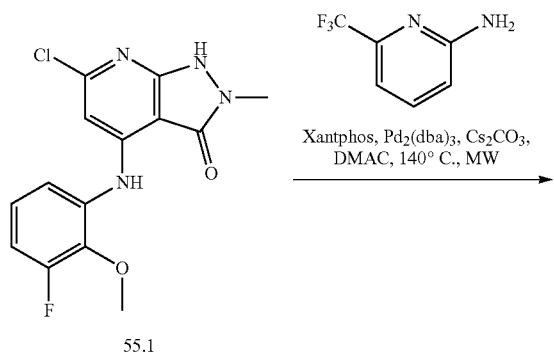

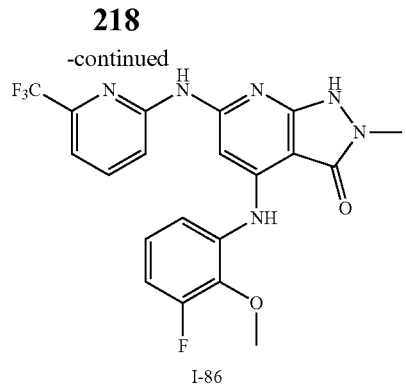

Compound I-86 was prepared from compound 55.1 and 6-(trifluoromethyl)pyridin-2-amine using procedure described in Example 2 (Yield: 14.99%), MS(ES): m/z 449.32 [M+H]$^+$, LCMS purity: 99.81%, HPLC purity: 99.80%, 1H NMR (DMSO-d6, 400 MHz): 10.80 (bs, 1H), 10.24 (bs, 1H), 8.95 (s, 1H), 8.08-8.06 (d, J=8.0 Hz, 1H), 7.95-7.91 (t, J=8.0 Hz, 1H), 7.43-7.35 (m, 3H), 7.14-7.09 (q, J=8.0 Hz, 1H), 7.03-6.98 (t, J=8.0 Hz, 1H), 3.88 (s, 3H), 3.28 (s, 3H).

Example 65: Synthesis of 6-((6-cyclopropylpyridin-2-yl)amino)-4-((3-fluoro-2-methoxyphenyl)amino)-2-methyl-1,2-dihydro-3H-pyrazolo[3,4-b]pyridin-3-one, I-87

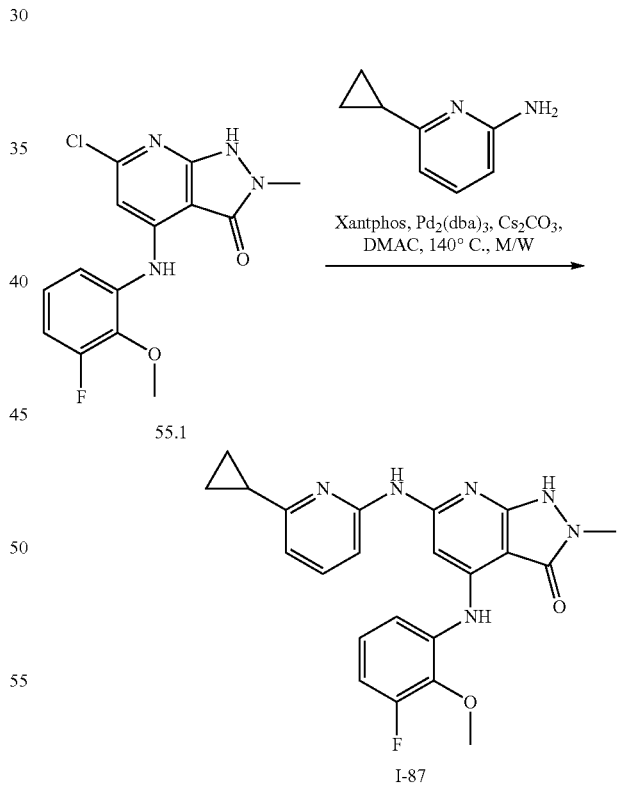

Compound I-87 was prepared from compound 55.1 and 6-cyclopropylpyridin-2-amine using procedure described in Example 2 (Yield: 19.19%), MS(ES): m/z 421.32 [M+H]$^+$, LCMS purity: 98.94%, HPLC purity: 94.15%, 1H NMR (DMSO-d6, 400 MHz): 11.46 (s, 1H), 8.99 (s, 1H), 7.95-7.91 (t, J=8.0 Hz, 1H), 7.29-7.27 (d, J=7.2 Hz, 1H), 7.18-7.16 (d, J=8.4 Hz, 2H), 7.08-7.06 (d, J=7.2 Hz, 1H), 6.99-

6.97 (d, J=8.4 Hz, 1H), 6.04 (s, 1H), 3.85 (s, 3H), 3.45 (s, 3H), 2.31-2.24 (m, 1H), 1.28-1.23 (m, 2H), 1.11-1.06 (m, 2H).

Example 66: Synthesis of N-(4-((2-methoxy-3-(2-oxopyrrolidin-1-yl)phenyl)amino)-2-methyl-3-oxo-2,3-dihydro-1H-pyrazolo[3,4-b]pyridin-6-yl)cyclopropanecarboxamide, I-88

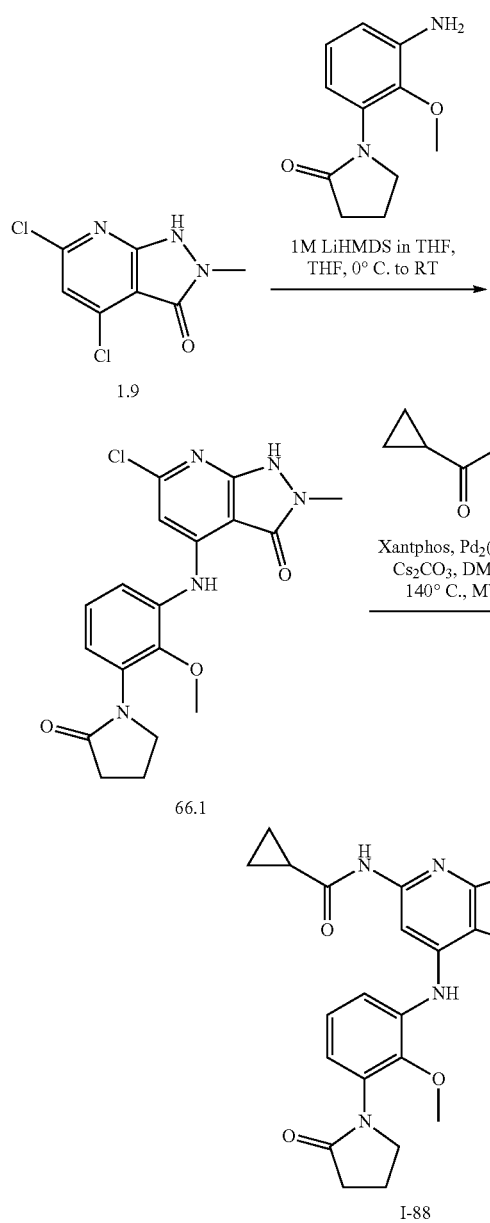

Following the procedure used to prepare 1.91, 66.1 was obtained (Yield: 56.22%). MS (ES): m/z 388.7 [M+H]⁺.

Compound I-88 was prepared from compound 66.1 and cyclopropanecarboxamide using procedure described in Example 2 (Yield: 17.06%), MS(ES): m/z 437.37 [M+H]⁺, LCMS purity: 96.29%, HPLC purity: 95.84%, 1H NMR (DMSO-d6, 400 MHz): 10.77 (s, 1H), 8.77 (s, 1H), 7.79 (s, 1H), 7.44-7.42 (d, J=7.6 Hz, 1H), 7.23-7.19 (t, J=8.0 Hz, 1H), 7.06-7.04 (d, J=7.6 Hz, 1H), 3.74-3.71 (t, J=6.8 Hz, 2H), 3.669 (s, 3H), 3.311 (s, 3H), 2.46-2.42 (d, J=8.0 Hz, 2H), 2.17-2.10 (qui, J=6.8 Hz, 2H), 2.017 (s, 1H), 0.78 (s, 4H).

Example 67: 4-((3-fluoro-2-methoxyphenyl)amino)-2-methyl-6-((5-morpholinopyridin-2-yl)amino)-1,2-dihydro-3H-pyrazolo[3,4-b]pyridin-3-one, I-89

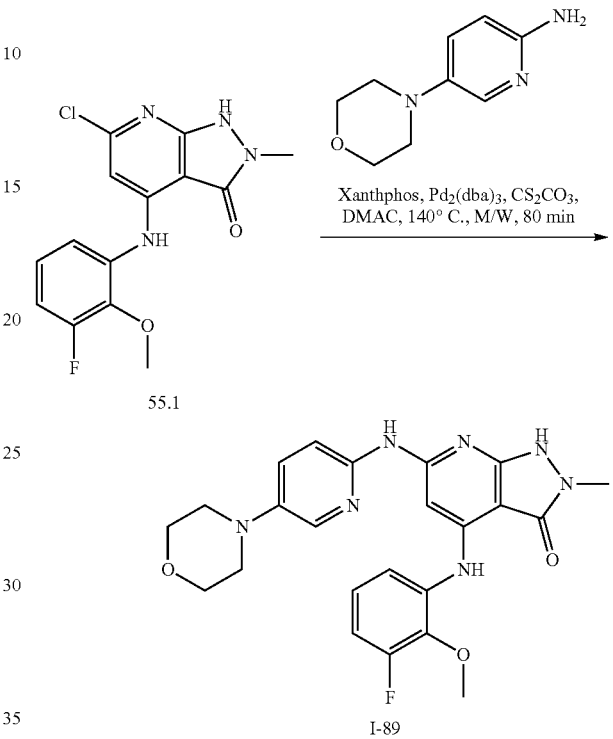

Compound I-89 was prepared from compound 55.1 and 5-morpholinopyridin-2-amine using procedure described in Example 2 (Yield: 13.87%), MS(ES): m/z 466.52 [M+H]⁺, LCMS purity: 95.70%, HPLC purity: 95.05%, 1H NMR (DMSO-d6, 400 MHz): 11.33 (s, 1H), 8.91 (s, 1H), 8.05-8.02 (dd, J=2.4 Hz, 9.2 Hz, 1H), 7.83-7.82 (d, J=2.4 Hz, 1H), 7.32-7.11 (m, 5H), 6.09 (s, 1H), 3.86 (s, 3H), 3.75 (s, 4H), 3.38 (s, 3H), 3.12 (s, 4H).

Example 68: Synthesis of 4-((3-fluoro-2-methoxyphenyl)amino)-2-methyl-6-((5-(pyrrolidin-1-yl)pyridin-2-yl)amino)-1,2-dihydro-3-pyrazolo[3,4-b]pyridin-3-one, I-90

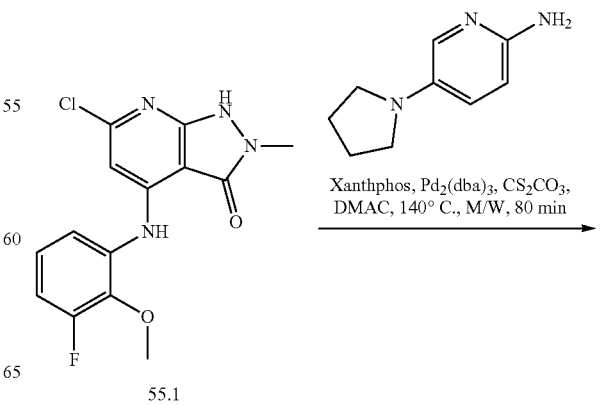

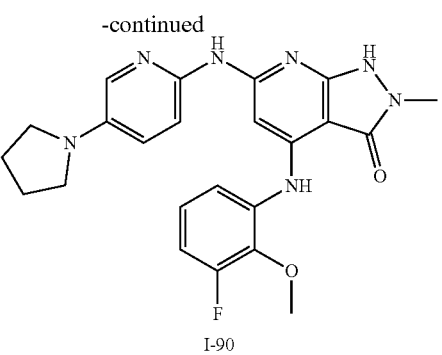

I-90

Compound I-90 was prepared from compound 55.1 and 5-(pyrrolidin-1-yl)pyridin-2-amine using procedure described in Example 2 (Yield: 17.95%), MS(ES): m/z 450.42 [M+H]$^+$, LCMS purity: 97.66%, HPLC purity: 96.95%, 1H NMR (DMSO-d6, 400 MHz): 7.61-7.58 (dd, J=2.4 Hz, 9.6 Hz, 1H), 7.47-7.47 (d, J=2.4 Hz, 1H), 7.30-7.28 (d, J=8.4 Hz, 1H), 7.22-7.19 (d, J=9.6 Hz, 1H), 7.16-7.11 (m, 1H), 7.05-7.00 (d, J=9.6 Hz, 1H), 6.15 (s, 1H), 3.85 (s, 3H), 3.34 (s, 3H), 3.21 (s, 4H), 1.95 (s, 4H).

Example 69: Synthesis of 6-((5-cyclopropylpyridin-2-yl)amino)-4-((3-fluoro-2-methoxyphenyl)amino)-2-methyl-1,2-dihydro-3H-pyrazolo[3,4-b]pyridin-3-one, I-91

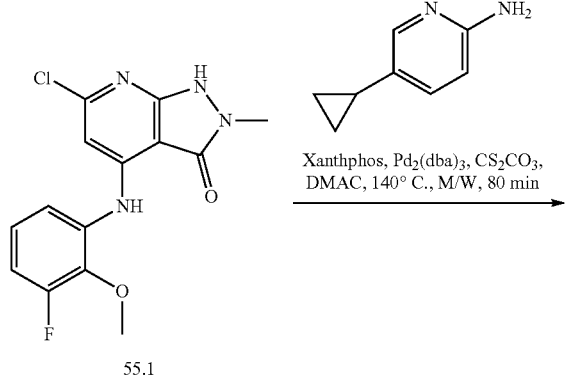

I-91

Compound I-91 was prepared from compound 55.1 and 5-cyclopropylpyridin-2-amine using procedure described in Example 2 (Yield: 15.99%), MS(ES): m/z 421.29 [M+H]$^+$, LCMS purity: 95.97%, HPLC purity: 95.65%, 1H NMR (DMSO-d6, 400 MHz): 11.50 (s, 1H), 8.93 (s, 1H), 8.17 (s, 1H), 7.85-7.83 (d, J=8.4 Hz, 1H), 7.31-7.29 (d, J=7.2 Hz, 1H), 7.23-7.12 (m, 3H), 6.14 (s, 1H), 3.85 (s, 3H), 3.38 (s, 3H), 2.04 (s, 1H), 1.02 (s, 2H), 0.72 (s, 2H).

Example 70: Synthesis of 4-((2-methoxy-4-(methoxymethyl)phenyl)amino)-2-methyl-6-((5-(pyrrolidine-1-carbonyl)-6-(trifluoromethyl)pyridin-2-yl)amino)-1,2-dihydro-3H-pyrazolo[3,4-b]pyridin-3-one, I-92

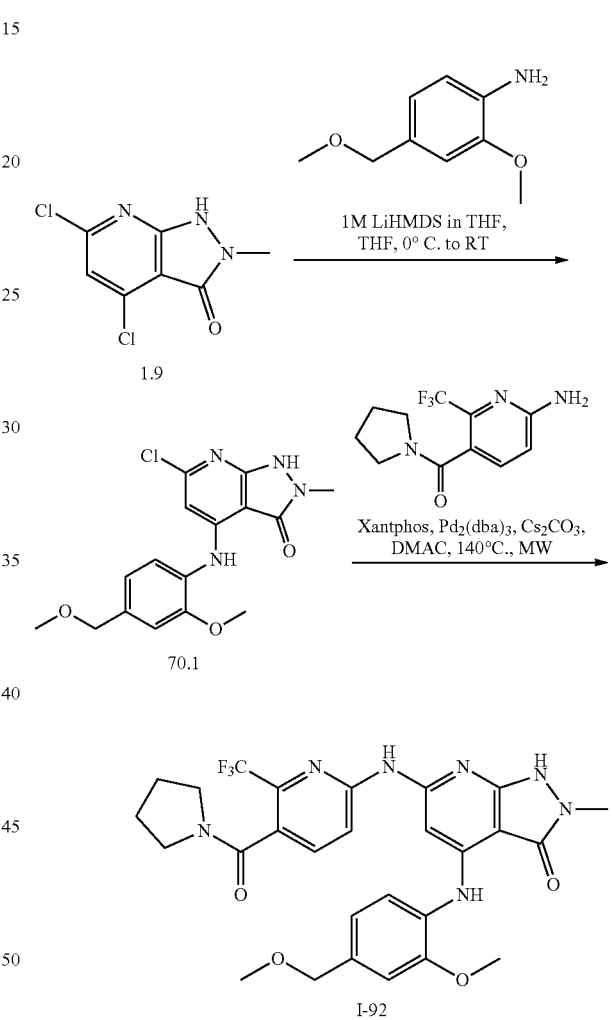

I-92

Following the procedure used to prepare 1.91, 70.1 was obtained (Yield: 78.14%). MS (ES): m/z 349.7 [M+H]$^+$.

Compound I-92 was prepared from compound 70.1 and (6-amino-2-(trifluoromethyl)pyridin-3-yl)(pyrrolidin-1-yl)methanone using procedure described in Example 2 (Yield: 17.09%), MS(ES): m/z 572.37 [M+H]$^+$, LCMS purity: 94.64%, HPLC purity: 95.10%, 1H NMR (DMSO-d6, 400 MHz): 10.78 (s, 1H), 10.32 (s, 1H), 8.67 (s, 1H), 8.22-8.20 (d, J=8.8 Hz, 1H), 7.89-7.87 (d, J=8.8 Hz, 1H), 7.53-7.51 (d, J=8.0 Hz, 1H), 7.21 (s, 1H), 7.07 (s, 1H), 6.95-6.93 (d, J=8.0 Hz, 1H), 4.42 (s, 2H), 3.88 (s, 3H), 3.47-3.43 (t, J=6.0 Hz, 2H), 3.31 (s, 3H), 3.28 (s, 3H), 3.13-3.10 (t, J=6.0 Hz, 2H), 1.89-1.81 (m, 4H).

Example 71: Synthesis of 4-((2-methoxy-4-(methoxymethyl)phenyl)amino)-2-methyl-6-((5-methyl-6-(trifluoromethyl)pyridin-2-yl)amino)-1,2-dihydro-3H-pyrazolo[3,4-b]pyridin-3-one, I-93

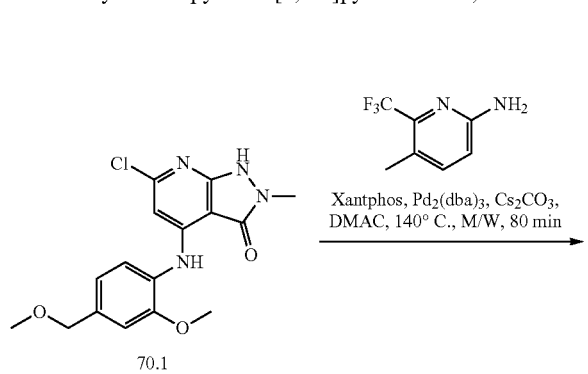

Compound I-93 was prepared from compound 70.1 and 5-methyl-6-(trifluoromethyl)pyridin-2-amine using procedure described in Example 2 (Yield: 26.18%), MS(ES): m/z 489.43 [M+H]$^+$, LCMS purity: 94.92%, HPLC purity: 99.24%, 1H NMR (DMSO-d6, 400 MHz): 10.68 (s, 1H), 10.01 (s, 1H), 8.63 (s, 1H), 8.10-8.08 (d, J=8.4 Hz, 1H), 7.79-7.77 (d, J=8.4 Hz, 1H), 7.52-7.50 (d, J=7.6 Hz, 1H), 7.17 (s, 1H), 7.06 (s, 1H), 6.95-6.93 (d, J=7.6 Hz, 1H), 4.41 (s, 2H), 3.88 (s, 3H), 3.34 (s, 3H), 3.27 (s, 3H), 2.29 (s, 3H).

Example 72: Synthesis of 4-((3-fluoro-2-methoxyphenyl)amino)-6-((6-(3-methoxyazetidin-1-yl)pyridin-2-yl)amino)-2-methyl-1,2-dihydro-3H-pyrazolo[3,4-b]pyridin-3-one, I-94

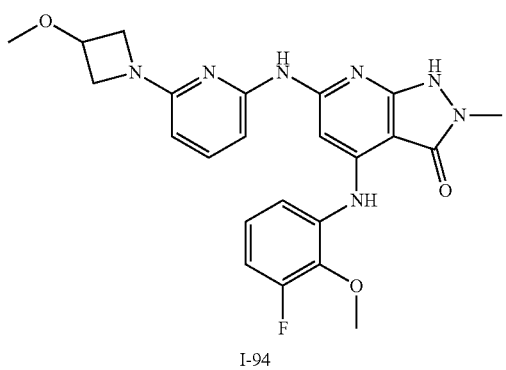

Compound I-94 was prepared from compound 55.1 and 6-(3-methoxyazetidin-1-yl)pyridin-2-amine using procedure described in Example 2 (Yield: 11.56%), MS(ES): m/z 466.30 [M+H]$^+$, LCMS purity: 99.23%, HPLC purity: 99.29%, 1H NMR (DMSO-d6, 400 MHz): 10.66 (s, 1H), 9.51 (s, 1H), 8.82 (s, 1H), 7.45-7.36 (m, 1H), 7.17-7.00 (m, 2H), 5.94-5.92 (d, J=7.2 Hz, 1H), 4.28 (s, 1H), 4.04 (s, 2H), 3.87 (s, 3H), 3.67 (s, 2H), 3.26 (s, 3H), 3.22 (s, 3H).

Example 73: 4-((3-chloro-2-methoxyphenyl)amino)-6-((5-fluoro-4-methylpyridin-2-yl)amino)-2-methyl-1,2-dihydro-3H-pyrazolo[3,4-b]pyridin-3-one, I-95

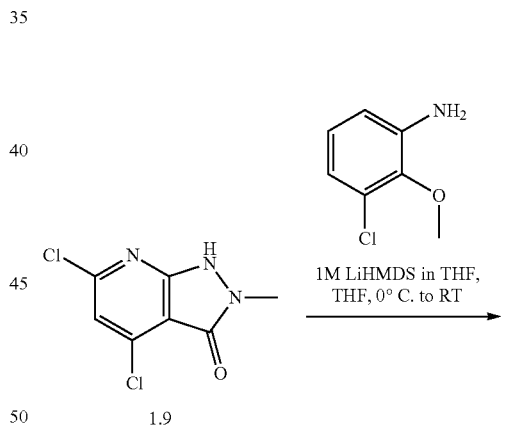

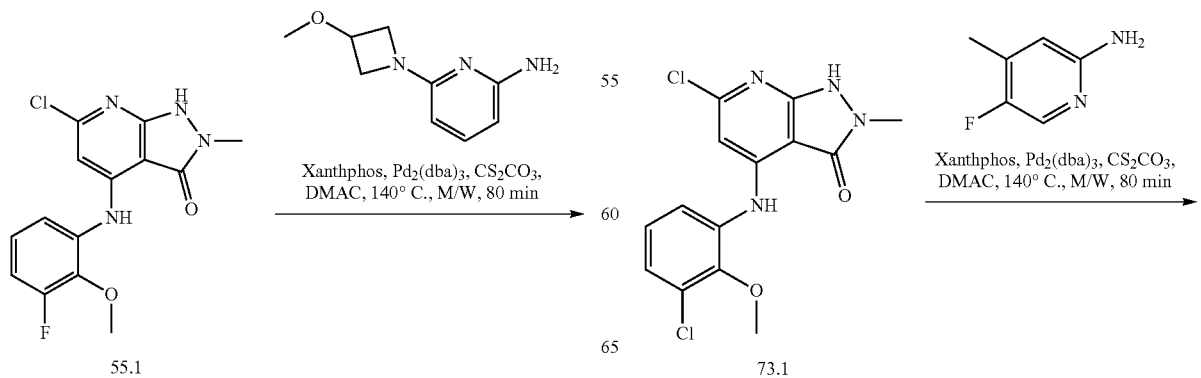

(s, 1H), 7.24-7.23 (d, J=4.8 Hz, 2H), 3.82 (s, 3H), 3.31 (s, 3H), 2.44 (s, 3H), 2.32 (s, 3H).

Example 75: Synthesis of 4-((3-chloro-2-methoxyphenyl)amino)-6-((4-(methoxymethyl)pyridin-2-yl)amino)-2-methyl-1,2-dihydro-3H-pyrazolo[3,4-b]pyridin-3-one, I-97

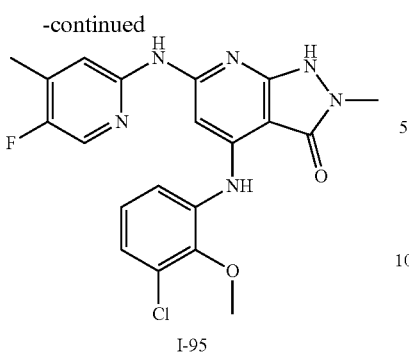

I-95

Following the procedure used to prepare 1.91, 73.1 was obtained (Yield: 70.71%). MS (ES): m/z 340.2 [M+H]⁺.

Compound I-95 was prepared from compound 73.1 and 5-fluoro-4-methylpyridin-2-amine using procedure described in Example 2 (Yield: 15.82%), MS(ES): m/z 429.27 [M+H]⁺, LCMS purity: 95.01%, HPLC purity: 95.80%, 1H NMR (DMSO-d6, 400 MHz): 9.84 (s, 1H), 8.86 (s, 1H), 8.17-8.13 (m, 1H), 7.95 (s, 1H), 7.56-7.54 (d, J=8.0 Hz, 1H), 7.25-7.17 (m, 2H), 6.95 (s, 1H), 3.79 (s, 3H), 3.27 (s, 3H), 2.26 (s, 3H).

Example 74: Synthesis of 4-((3-chloro-2-methoxyphenyl)amino)-6-((2,6-dimethylpyrimidin-4-yl)amino)-2-methyl-1,2-dihydro-3H-pyrazolo[3,4-b]pyridin-3-on, I-96

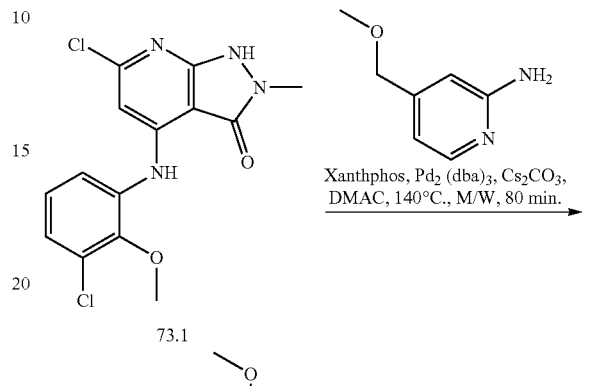

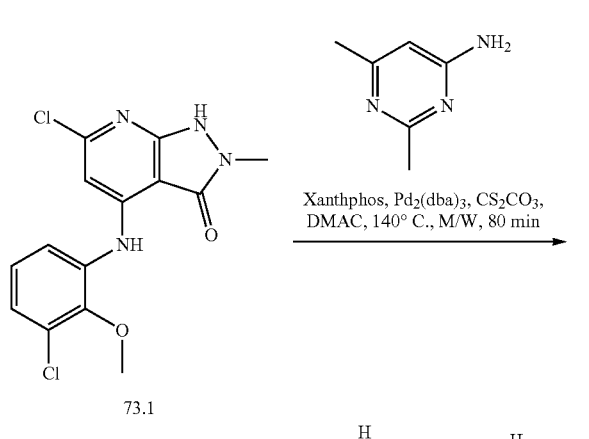

I-96

Compound I-96 was prepared from compound 73.1 and 2,6-dimethylpyrimidin-4-amine using procedure described in Example 2 (Yield: 14.34%), MS(ES): m/z 426.40 [M+H]⁺, LCMS purity: 96.62%, HPLC purity: 96.51%, 1H NMR (DMSO-d6, 400 MHz): 10.13 (s, 1H), 8.91 (s, 1H), 8.18 (s, 1H), 7.63-7.60 (d, J=4.8 Hz, 1H), 7.49 (s, 1H), 7.45

I-97

Compound I-97 was prepared from compound 73.1 and 4-(methoxymethyl)pyridin-2-amine using procedure described in Example 2 (Yield: 12.82%), MS(ES): m/z 441.29 [M+H]⁺, LCMS purity: 98.70%, HPLC purity: 98.80%, 1H NMR (DMSO-d6, 400 MHz): 10.78 (s, 1H), 9.83 (s, 1H), 8.88 (s, 1H), 8.21 (s, 1H), 7.97 (s, 1H), 7.59 (s, 1H), 7.25-7.23 (d, J=7.6 Hz, 3H), 6.87 (s, 1H), 4.44 (s, 2H), 3.83 (s, 3H), 3.36 (s, 3H), 3.29 (s, 3H).

Example 76: Synthesis of 6-((4-((3-chloro-2-methoxyphenyl)amino)-2-methyl-3-oxo-2,3-dihydro-1H-pyrazolo[3,4-b]pyridin-6-yl)amino)nicotinonitrile, I-98

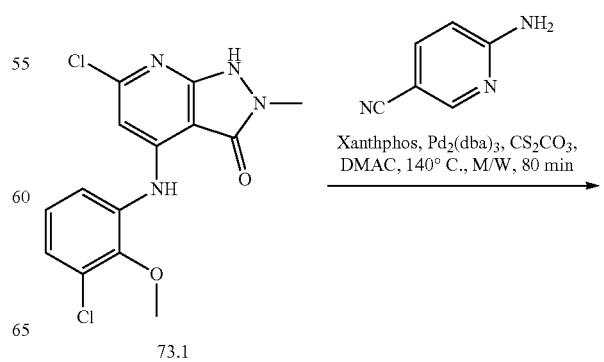

-continued

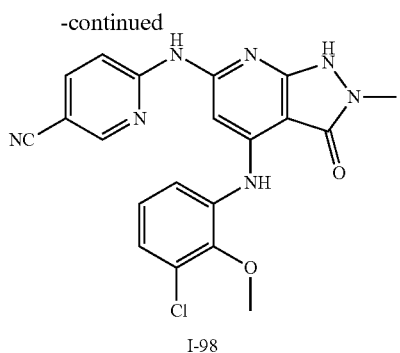

I-98

Compound I-98 was prepared from compound 73.1 and 6-aminonicotinonitrile using procedure described in Example 2 (Yield: 13.40%), m/z 422.32 [M+H]$^+$, LCMS purity: 98.00%, HPLC purity: 97.94%, 1H NMR (DMSO-d6, 400 MHz): 11.01 (s, 1H), 10.44 (s, 1H), 8.91 (s, 1H), 8.70 (s, 1H), 8.23-8.16 (m, 2H), 7.59-7.57 (d, J=8.0 Hz, 1H), 7.27-7.24 (m, 2H), 7.14 (s, 1H), 3.82 (s, 3H), 3.31 (s, 3H).

Example 77: Synthesis of 6-((4-((3-chloro-2-methoxyphenyl)amino)-2-methyl-3-oxo-2,3-dihydro-1H-pyrazolo[3,4-b]pyridin-6-yl)amino)picolinonitrile, I-99

I-99

Compound I-99 was prepared from compound 73.1 and 6-aminopicolinonitrile using procedure described in Example 2 (Yield: 13.14%), m/z 422.35 [M+H]$^+$, LCMS purity: 95.93%, HPLC purity: 95.55%, 1H NMR (DMSO-d6, 400 MHz): 10.87 (s, 1H), 10.33 (s, 1H), 8.98 (s, 1H), 8.04 (s, 1H), 7.91 (s, 1H), 7.67 (s, 1H), 7.56 (s, 1H), 7.50 (s, 1H), 7.27-7.24 (m, 2H), 3.83 (s, 3H), 3.31 (s, 3H).

Example 78: Synthesis of 4-((2-methoxy-4-(methoxymethyl)phenyl)amino)-6-((5-methoxy-6-(trifluoromethyl)pyridin-2-yl)amino)-2-methyl-1,2-dihydro-3H-pyrazolo[3,4-b]pyridin-3-one, I-104

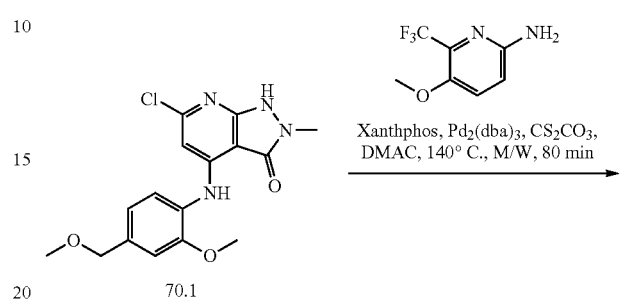

70.1

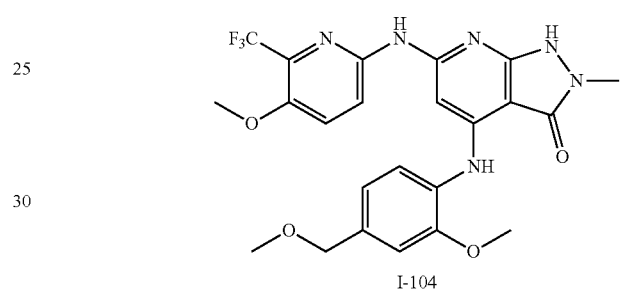

I-104

Compound I-104 was prepared from compound 70.1 and 5-methoxy-6-(trifluoromethyl)pyridin-2-amine using procedure described in Example 2 (Yield: 11.52%), MS(ES): m/z 505.36 [M+H]$^+$, LCMS purity: 97.99%, HPLC purity: 96.46%, 1H NMR (DMSO-d6, 400 MHz): 7.82-7.80 (d, J=9.2 Hz, 1H), 7.32-7.23 (m, 3H), 7.10 (s, 1H), 6.98-6.96 (d, J=8.0 Hz, 1H), 4.39 (s, 2H), 3.85 (s, 3H), 3.79 (s, 3H), 3.57 (s, 3H), 3.29 (s, 3H).

Example 79: Synthesis of 4-((3-chloro-2-methoxyphenyl)amino)-2-methyl-6-((6-methylpyridazin-3-yl)amino)-1,2-dihydro-3H-pyrazolo[3,4-b]pyridin-3-one, II-105

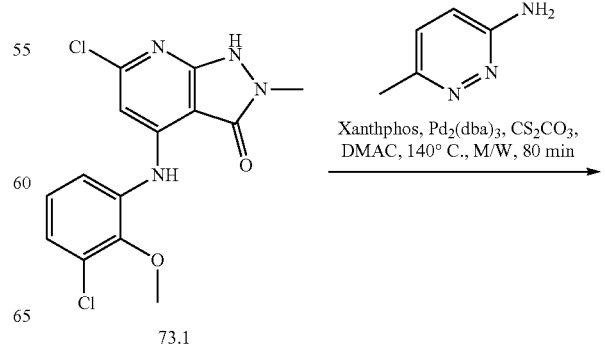

73.1

-continued

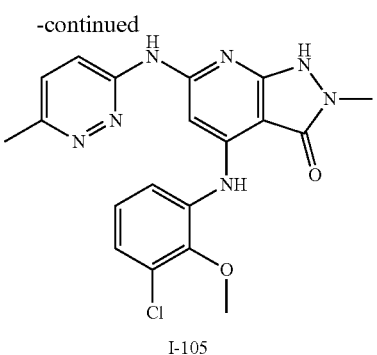

I-105

Compound I-105 was prepared from compound 73.1 and 6-methylpyridazin-3-amine using procedure described in Example 2 (Yield: 5.49%), m/z 412.29 [M+H]⁺, LCMS purity: 97.66%, HPLC purity: 95.98%, 1H NMR (DMSO-d6, 400 MHz): 10.21 (s, 1H), 8.87 (s, 1H), 8.29 (s, 1H), 7.56 (s, 1H), 7.48-7.46 (d, J=9.2 Hz, 1H), 7.21-7.20 (d, J=4.0 Hz, 1H), 7.11-7.09 (d, J=8.8 Hz, 1H), 6.69-6.67 (d, J=9.2 Hz, 1H), 6.10 (s, 1H), 3.81 (s, 3H), 3.27 (s, 3H), 2.34 (s, 3H).

Example 80: Synthesis of 6-((4-((3-chloro-2-methoxyphenyl)amino)-2-methyl-3-oxo-2,3-di-hydro-1H-pyrazolo[3,4-b]pyridin-6-yl)amino)pyrazine-2-carbonitrile, I-117

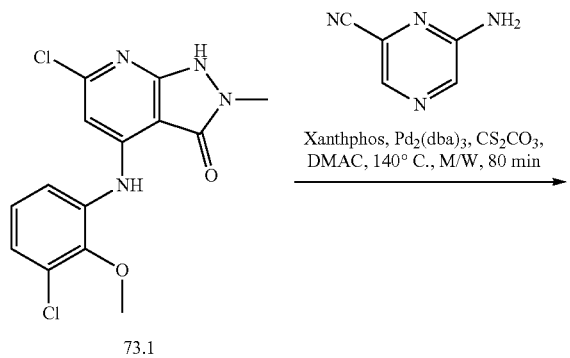

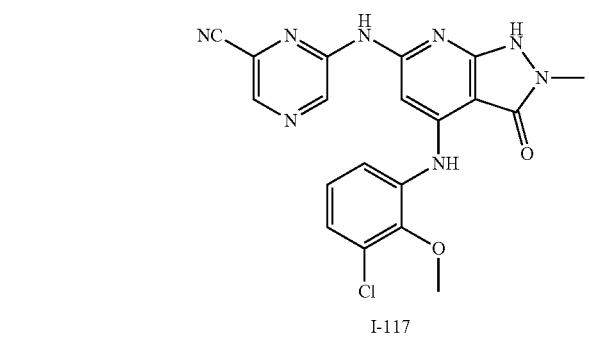

I-117

Compound I-117 was prepared from compound 73.1 and 6-methylpyridazin-3-amine using procedure described in Example 2 (Yield: 21.39%), m/z 423.27 [M+H]⁺, LCMS purity: 96.80%, HPLC purity: 95.08%, 1H NMR (DMSO-d6, 400 MHz): 10.96 (s, 1H), 10.65 (s, 1H), 9.31 (s, 1H), 8.93 (s, 1H), 8.64 (s, 1H), 7.61-7.59 (d, J=4.0 Hz, 1H), 7.35 (s, 1H), 7.27-7.23 (m, 2H), 3.86 (s, 3H), 3.30 (s, 3H).

Example 81: Synthesis of N-(4-((3,4-difluoro-2-methoxyphenyl)amino)-2-methyl-3-oxo-2,3-di-hydro-1H-pyrazolo[3,4-b]pyridin-6-yl)cyclopropan-ecarboxamide, I-127

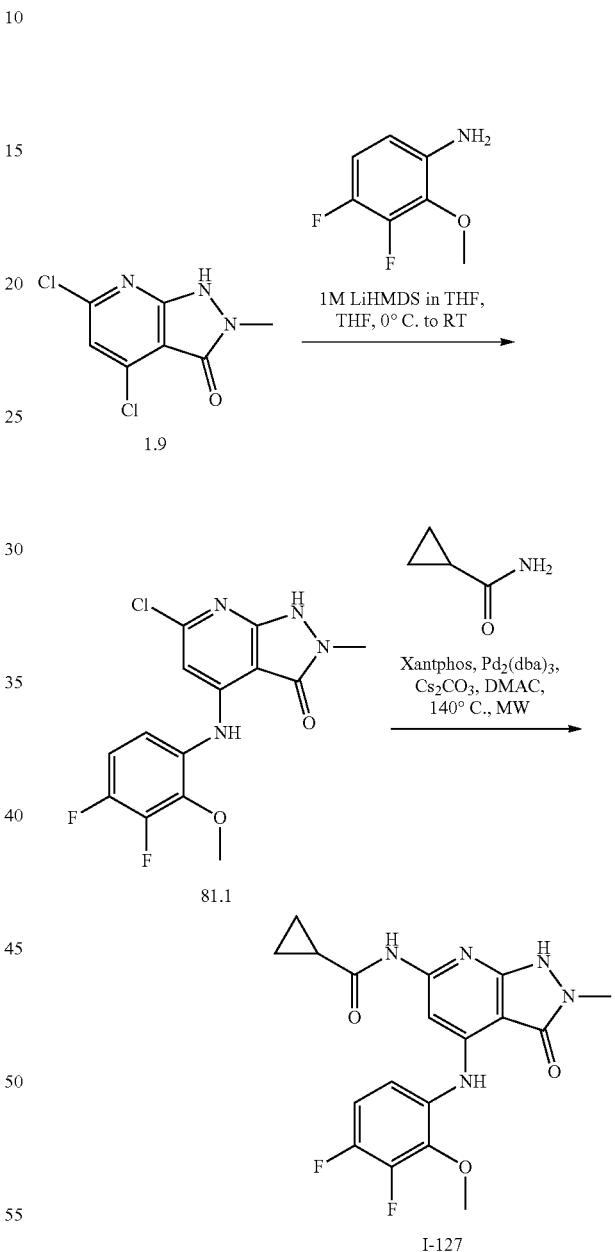

Following the procedure used to prepare 1.91, 81.1 was obtained (Yield: 63.99%). MS (ES): m/z 341.7 [M+H]⁺.

Compound I-127 was prepared from compound 81.1 and cyclopropanecarboxamide using procedure described in Example 2 (Yield: 17.5%), m/z 390.27 [M+H]⁺, LCMS purity: 99.27%, HPLC purity: 99.63%, 1H NMR (DMSO-d6, 400 MHz): 10.72 (s, 2H), 8.55 (s, 1H), 7.49 (s, 1H), 7.29-7.20 (m, 2H), 3.89 (s, 3H), 3.28 (s, 3H), 1.99-1.95 (m, 1H), 0.77-0.75 (d, J=6.4 Hz, 4H).

Example 82: N-(4-((2-methoxy-3-(2-methyl-2H-tetrazol-5-yl)phenyl)amino)-2-(methyl-d3)-3-oxo-2,3-dihydro-1H-pyrazolo[3,4-b]pyridin-6-yl)cyclopropanecarboxamide, I-100

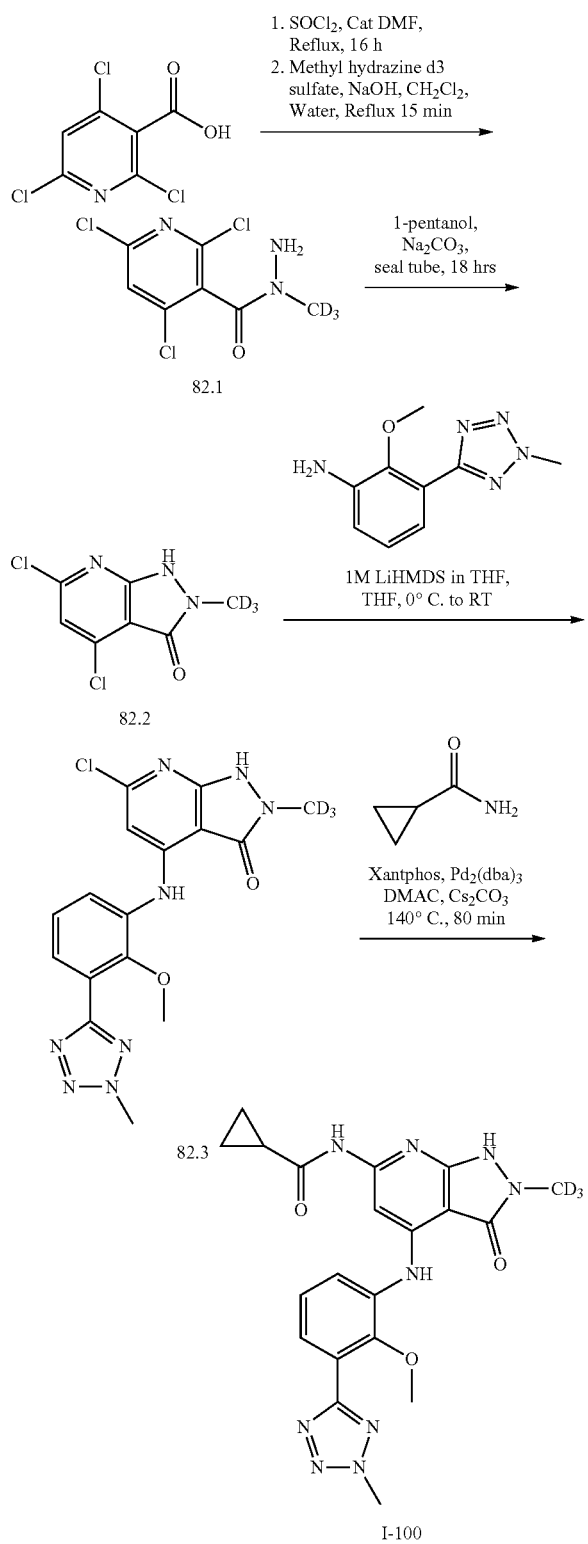

Synthesis of Compound 82.1.

To 2,4,6-trichloronicotinic acid (0.25 g, 1.10 mmol, 1.0 eq) was added thionyl chloride (1.2 mL) followed by N,N-dimethylformamide(catalytic) and refluxed for 16 h. Reaction mixture was concentrated under reduced pressure to obtain acid chloride. Methyl hydrazine d3 sulfate (0.16 g, 1.10 mmol, 1.0 eq) was dissolved in dichloromethane (5 mL) followed by addition of solution of sodium hydroxide (0.18 g, 4.40 mmol, 4.0 eq) in water (1.2 mL). To this added solution of previously made acid chloride in dichloromethane (5 mL) dropwise and reaction mixture was refluxed for 15 min. After completion of reaction, reaction mixture was transferred into water and extracted with dichloromethane. Organic layer was combined, washed with brine solution, dried over sodium sulphate and concentrated under reduced pressure to pressure to obtain crude material. This was further purified by column chromatography and the product was eluted in 30% ethyl acetate in hexane to get pure 1.1. (0.2 g, 70.35%). MS(ES): m/z 258.5 [M+H]⁺.

Synthesis of compound 82.2. To a suspension of 83.1 (0.2 g, 0.776 mmol, 1.0 eq) in 1-pentanol (5 mL) was added sodium carbonate (0.083 g, 0.776 mmol, 1.0 eq) and reaction mixture was stirred at 120° C. for 18 h. After completion of reaction, reaction mixture was cooled to room temperature and pH=6 was adjusted using 1N hydrochloric acid. Reaction mixture was concentrated under reduced pressure to obtain crude material. This was further purified by Preparative HPLC using 0.1% Formic acid in water/Acetonitrile in gradient method to obtain pure 1.2. (0.085 g, 49.51%). MS(ES): m/z 222.06 [M+H]⁺.

Synthesis of Compound 82.3

Following the procedure used to prepare 1.91, 82.3 was obtained (Yield: 30.78%). MS (ES): m/z 390.82 [M+H]⁺.

Compound I-100 was prepared from compound 82.3 and cyclopropanecarboxamide using procedure described in Example 2 (0.025 g, Yield: 23.40%). MS(ES): m/z 439.42 [M+H]⁺, LCMS purity: 99.10%, HPLC purity: 97.85%, 1H NMR (DMSO-d6, 400 MHz): 10.79 (s, 2H), 8.89 (s, 1H), 7.81 (s, 1H), 7.68-7.64 (t, J=8.0 Hz, 2H), 7.40-7.36 (t, J=8.0 Hz, 1H), 4.47 (s, 3H), 3.77 (s, 3H), 2.02 (s, 1H), 0.81 (s, 4H).

Example 83: Synthesis of 3-((6-(cyclopropanecarboxamido)-2-methyl-3-oxo-2,3-dihydro-1H-pyrazolo[3,4-b]pyridin-4-yl)amino)-2-methoxybenzamide, I-102

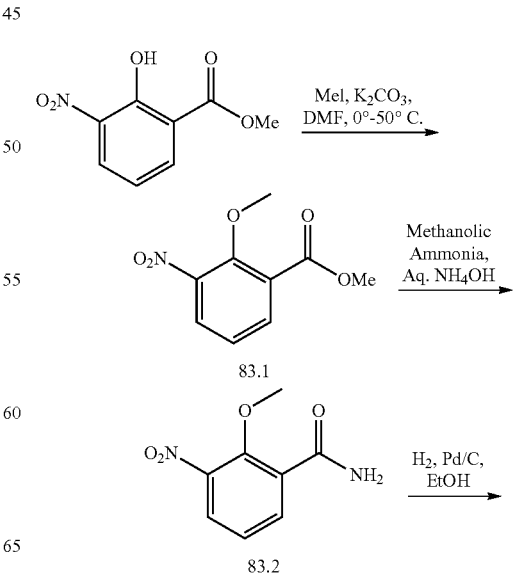

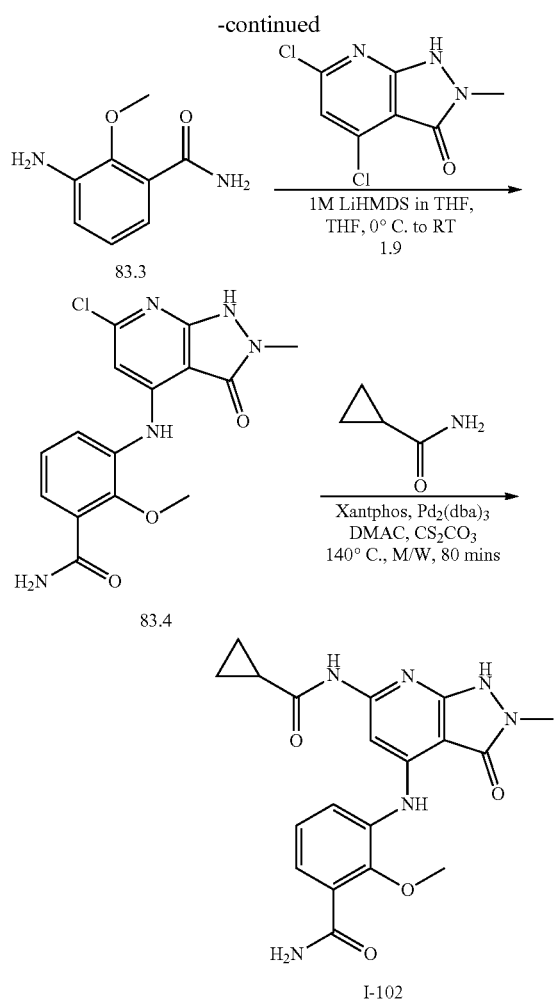

Synthesis of Compound 83.4

Following the procedure used to prepare 1.91, 84.4 was obtained (Yield: 62.70%). MS (ES): m/z 348.76 [M+H]$^+$.

Compound I-102 was prepared from compound 83.4 and cyclopropanecarboxamide using procedure described in Example 2 (Yield: 2.63%). MS(ES): m/z 397.41 [M+H]$^+$, LCMS purity: 98.76%, HPLC purity: 98.65%, 1H NMR (DMSO-d6, 400 MHz): 10.81 (s, 1H), 8.56 (s, 1H), 8.12 (s, 1H), 7.69-7.68 (d, J=6.4 Hz, 1H), 7.65-7.63 (d, J=8.0 Hz, 1H), 7.57-7.55 (d, J=8.0 Hz, 1H), 6.95-6.91 (t, J=8.0 Hz, 1H), 3.29 (s, 3H), 3.27 (s, 3H), 1.49-1.46 (m, 1H), 0.78-0.77 (m, 4H).

Example 84: Synthesis of 3-((6-((2,6-dimethylpyrimidin-4-yl)amino)-2-methyl-3-oxo-2,3-dihydro-1H-pyrazolo[3,4-b]pyridin-4-yl)amino)-2-methoxybenzamide, I-103

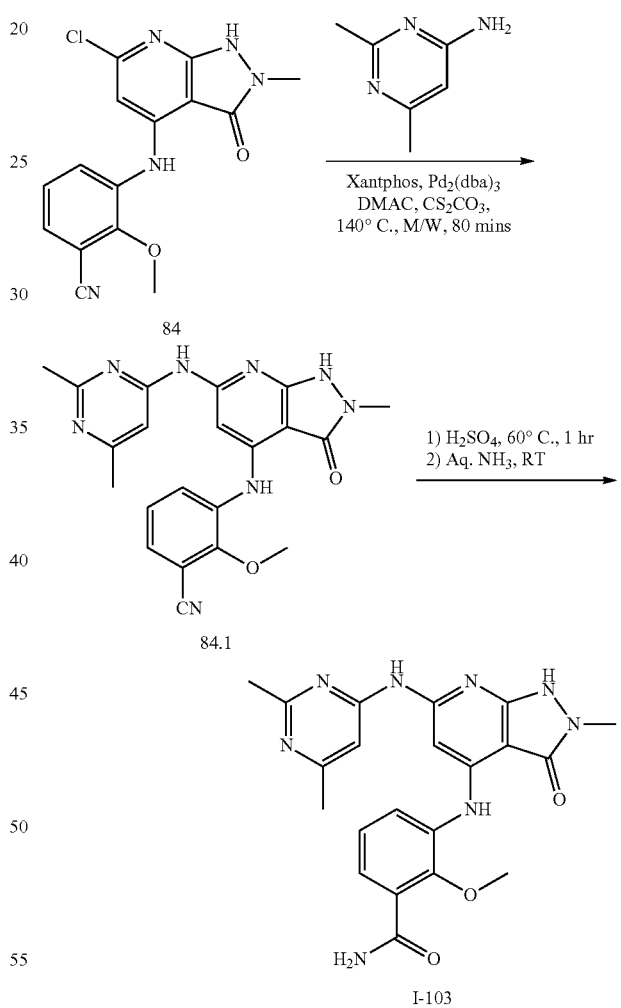

Compound 84.1 was prepared from compound 84 and 2,6-dimethylpyrimidin-4-amine using procedure described in Example 2 (Yield: 19.00%). MS (ES): m/z 417.45 [M+H]$^+$.

Synthesis of compound I-103

To 84.1 (0.120 g, 0.363 mmol, 1 eq) was added sulfuric acid (2 mL) and stirred at 60° C. for 1 h. After completion of reaction, water and aqueous ammonia was added to reaction mixture and stirred at room temperature for 10 min.

Synthesis of Compound 83.1

To a solution of methyl 2-hydroxy-3-nitrobenzoate (5.0 g, 25.36 mmol, 1.0 eq) in N,N-dimethylformamide (50 mL), was added potassium carbonate (7.0 g, 50.76 mmol, 2.0 eq) at 0° C. and stirred for 15 min. To this added methyl iodide (7.2 g, 50.76 mmol, 2 eq) dropwise and reaction mixture was stirred at 60° C. for 2 h. After completion of reaction, reaction mixture was transferred in ice-water and precipitated product was filtered, dried well to obtain 83.1 (5.0 g, 93%). MS(ES): m/z 212.2 [M+H]$^+$.

Synthesis of Compound 83.2

To 83.1 (5 g, 23.67 mmol, 1.0 eq) was added aqueous ammonia (30 mL) followed by methanolic ammonia (160 mL). Reaction mixture was stirred at room temperature for 16 h. After completion of reaction, reaction mixture was concentrated under reduced pressure and residue was washed with ice cold water. Solid was dried well to obtain 83.2 (4.5 g, 96%). MS(ES): m/z 197.2 [M+H]$^+$.

Synthesis of Compound 83.3

To a solution of 83.2 (4.5 g, 22.94 mmol, 1.0 eq) in methanol (45 mL), 10% palladium on charcoal (1.0 g) was added. Hydrogen was purged through reaction mixture for 4 h. After completion of reaction, reaction mixture was filtered through celite-bed and washed with methanol. Filtrate was concentrated under reduced pressure to obtain 83.3. (3.0 g, 78.69%). MS(ES): m/z 167.18 [M+H]$^+$.

Reaction mixture was concentrated under reduced pressure to obtain crude material. This was further purified by Preparative HPLC using 0.1% Formic acid in water/Acetonitrile in gradient method to obtain pure I-84 (0.02 g, Yield: 15.98%). MS(ES): m/z 435.46 [M+H]+, LCMS purity: 100.00%, HPLC purity: 95.03%, 1H NMR (DMSO-d6, 400 MHz): 14.19 (s, 1H), 10.15 (s, 1H), 8.61 (s, 2H), 8.15 (s, 1H), 7.73-7.65 (d, J=7.6 Hz, 2H), 7.48 (s, 2H), 6.97-6.93 (t, J=8.0 Hz, 1H), 3.34 (s, 3H), 3.29 (s, 3H), 2.43 (s, 3H), 2.34 (s, 3H).

Example 85: Synthesis of 4-((2-methoxy-4-(methoxymethyl)phenyl)amino)-6-((5-methoxy-6-(trifluoromethyl)pyridin-2-yl)amino)-2-methyl-1,2-dihydro-3H-pyrazolo[3,4-b]pyridin-3-one, I-106 to obtain crude material. This was further purified by Preparative HPLC using 0.1% Formic acid in water/Acetonitrile in gradient method to obtain pure I-106 (0.022 g, Yield: 16.88%). MS(ES): m/z 438.44 [M+H]+, LCMS purity: 98.97%, HPLC purity: 96.36%, 1H NMR (DMSO-d6, 400 MHz): 14.21 (bs, 1H), 9.84 (s, 1H), 8.64 (s, 1H), 8.56 (s, 1H), 8.15-8.11 (m, 2H), 8.02-8.01 (d, J=5.6 Hz, 1H), 7.66-7.61 (d, J=8.0 Hz, 2H), 7.00-6.92 (m, 2H), 3.32 (s, 3H), 3.24 (s, 3H), 2.28 (s, 3H).

Example 86: Synthesis of 6-((5-fluoro-4-methylpyridin-2-yl)amino)-2-methyl-4-((2-(methylsulfonyl)phenyl)amino)-1,2-dihydro-3H-pyrazolo[3,4-b]pyridin-3-one, I-107

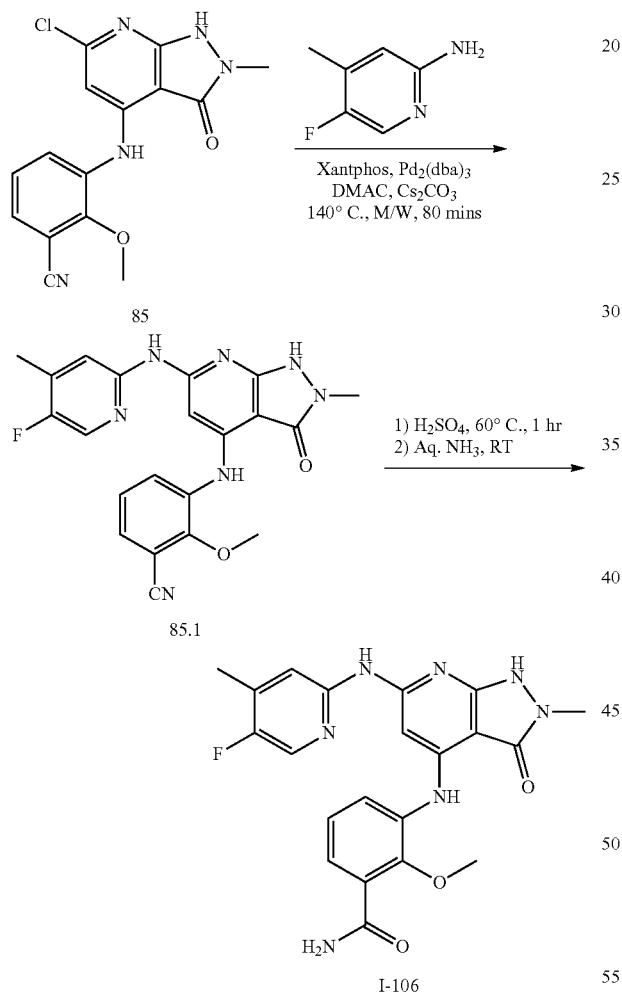

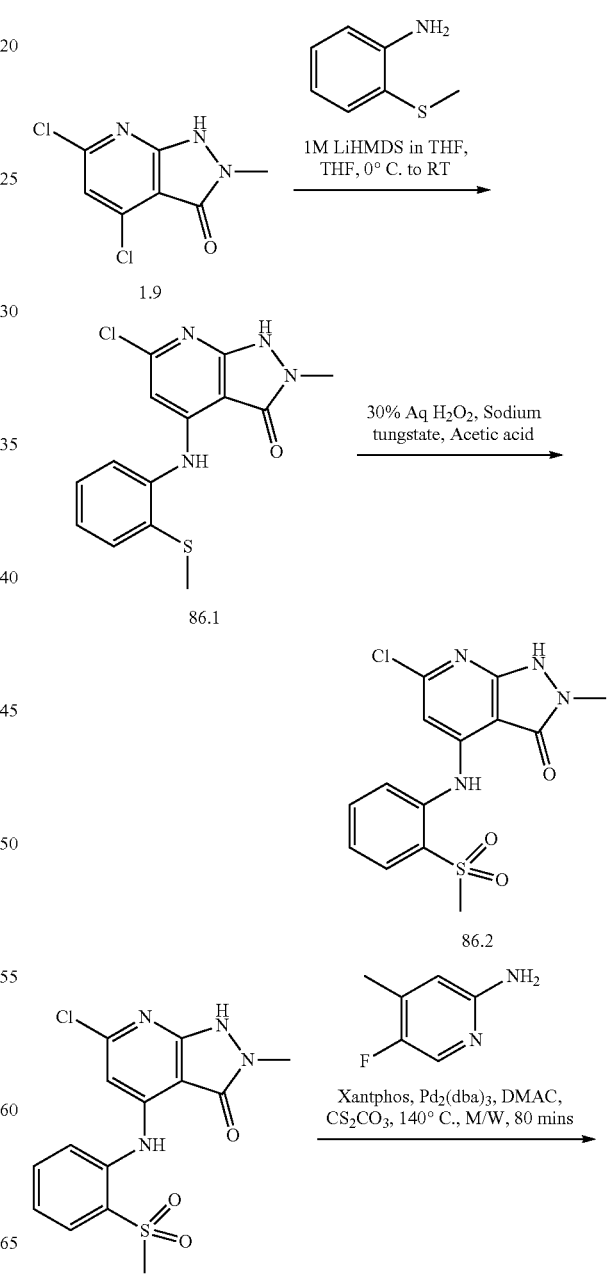

Compound 85.1 was prepared from compound 85 and 5-fluoro-4-methylpyridin-2-amine using procedure described in Example 2 (Yield: 19.65%). MS (ES): m/z 420.42 [M+H]+.

Synthesis of compound I-106.

To 85.1 (0.125 g, 0.298 mmol, 1 eq) was added sulfuric acid (2 mL) and stirred at 60° C. for 1 h. After completion of reaction, water and aqueous ammonia was added to reaction mixture and stirred at room temperature for 10 min. Reaction mixture was concentrated under reduced pressure

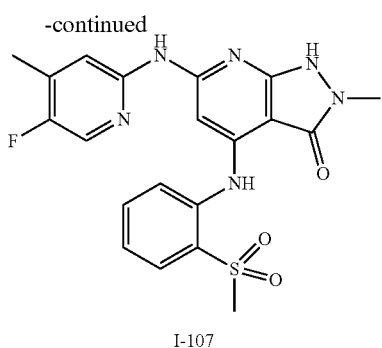

I-107

Following the procedure used to prepare 1.91, 86.1 was obtained (Yield: 76.89%). MS (ES): m/z 321.80 [M+H]⁺.

Synthesis of Compound 86.2.

To a solution of 86.1 (1.81 g, 5.64 mmol, 1 eq) in acetic acid (2.5 mL) was added 30% hydrogen peroxide (3.83 g, 112.8 mmol, 20 eq) and sodium tungstate dihydrate (1.85 g, 5.64 mmol, 1 eq). Reaction mixture was stirred at room temperature for 2 h. After completion of reaction, reaction mixture was transferred in ice-water and precipitated product was filtered, washed with 50% ethyl acetate in hexane and dried well to obtain 86.2 (1.25 g, Yield: 62.80%). MS(ES): m/z 353.79 [M+H]⁺.

Compound I-107 was prepared from compound 86.2 and 5-fluoro-4-methylpyridin-2-amine using procedure described in Example 2 (0.060 g, Yield: 31.89%). MS(ES): m/z 443.47 [M+H]⁺, LCMS purity: 99.63%, HPLC purity: 99.37%, 1H NMR (DMSO-d6, 400 MHz): 10.72 (s, 1H), 9.76 (s, 1H), 9.06 (s, 1H), 8.07 (s, 1H), 7.93-7.91 (d, J=7.2 Hz, 2H), 7.84-7.77 (m, 2H), 7.39-7.36 (t, J=7.2 Hz, 1H), 6.94 (s, 1H), 3.25 (s, 3H), 3.16 (s, 3H), 2.25 (s, 3H).

Example I-87: Synthesis of 6-((2,6-dimethylpyrimidin-4-yl)amino)-2-methyl-4-((2-(methylsulfonyl)phenyl)amino)-1,2-dihydro-3H-pyrazolo[3,4-b]pyridin-3-one, I-109

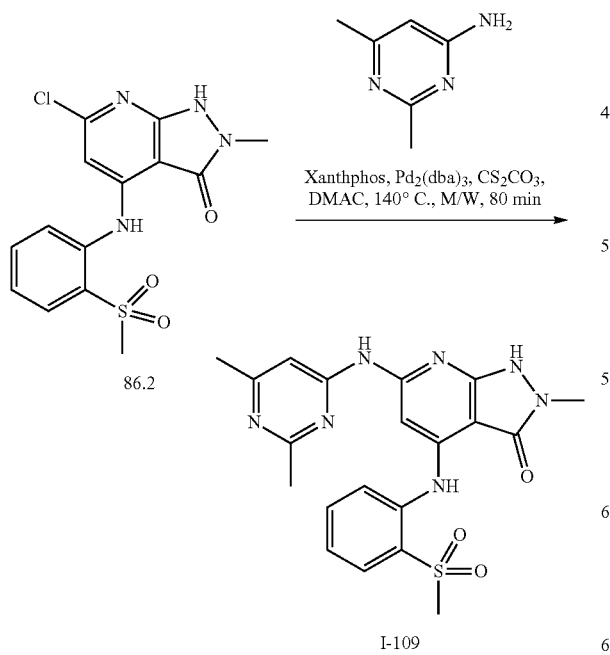

Compound I-109 was prepared from compound 86.2 and 2,6-dimethylpyrimidin-4-amine using procedure described in Example 2 (Yield: 27.52%), MS(ES): m/z 440.40 [M+H]⁺, LCMS purity: 98.42%, HPLC purity: 95.04%, 1H NMR (DMSO-d6, 400 MHz): 10.84 (bs, 1H), 10.09 (s, 1H), 9.15 (s, 1H), 7.94-7.92 (dd, J=1.2 Hz, 8.0 Hz, 1H), 7.87-7.85 (d, J=8.0 Hz, 1H), 7.81-7.77 (t, J=8.0 Hz, 1H), 7.44-7.34 (m, 3H), 3.27 (s, 3H), 3.16 (s, 3H), 2.37 (s, 3H), 2.29 (s, 3H).

Example 88: Synthesis of 2-methyl-6-((6-methylpyridazin-3-yl)amino)-4-((2-(methylsulfonyl)phenyl)amino)-1,2-dihydro-3H-pyrazolo[3,4-b]pyridin-3-one, I-109

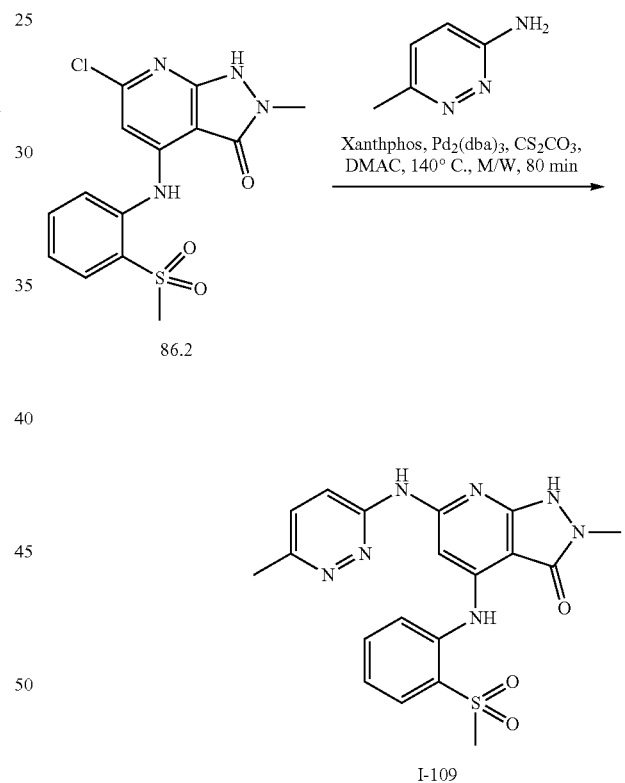

Compound I-109 was prepared from compound 86.2 and 6-methylpyridazin-3-amine using procedure described in Example 2 (Yield: 32.58%), MS(ES): m/z 426.19 [M+H]⁺, LCMS purity: 97.90%, HPLC purity: 96.09%, 1H NMR (DMSO-d6, 400 MHz): 10.59 (bs, 1H), 10.17 (s, 1H), 9.09 (s, 1H), 8.19 (s, 1H), 7.94-7.92 (d, J=8.0 Hz, 1H), 7.84-7.75 (m, 2H), 7.47-7.38 (m, 2H), 6.95 (s, 1H), 3.171 (s, 3H), 3.059 (s, 3H), 2.314 (s, 3H).

Example 89: Synthesis of 6-((4-(methoxymethyl)pyridin-2-yl)amino)-2-methyl-4-((2-(methylsulfonyl)phenyl)amino)-1,2-dihydro-3H-pyrazolo[3,4-b]pyridin-3-one, I-110

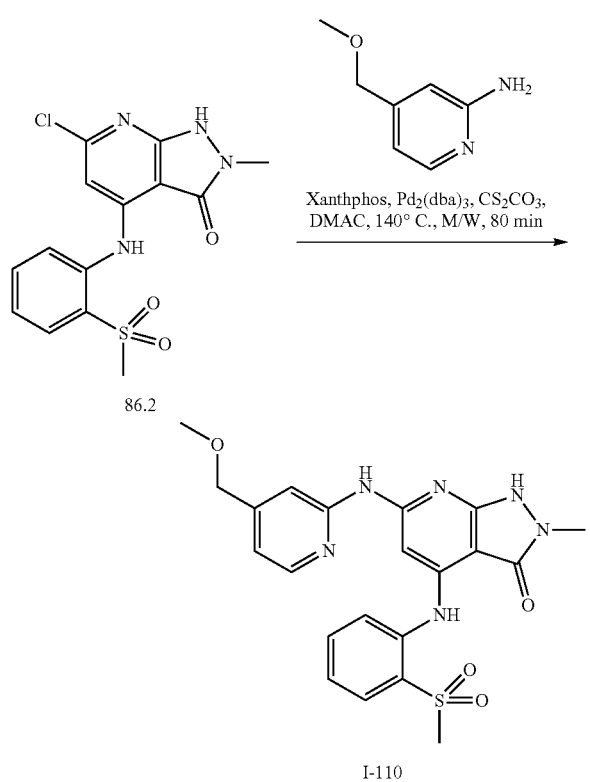

I-110

Compound I-110 was prepared from compound 86.2 and 4-(methoxymethyl)pyridin-2-amine using procedure described in Example 2 (Yield: 14.42%), MS(ES): m/z 455.20 [M+H]$^+$ LCMS purity: 94.46%, HPLC purity: 95.28%, 1H NMR (DMSO-d6, 400 MHz): 11.62 (s, 1H), 9.24 (s, 1H), 8.32-8.30 (d, J=6.4 Hz, 1H), 8.00-7.98 (d, J=7.2 Hz, 1H), 7.84-7.80 (m, 2H), 7.51 (t, 1H), 7.24-7.19 (m, 2H), 6.21 (s, 1H), 4.59 (s, 2H), 3.39 (s, 3H), 3.36 (s, 3H), 3.19 (s, 3H).

Example 90: Synthesis of 2-methyl-6-((5-methylpyridin-2-yl)amino)-4-((2-(methylsulfonyl)phenyl)amino)-1,2-dihydro-3H-pyrazolo[3,4-b]pyridin-3-one, I-111

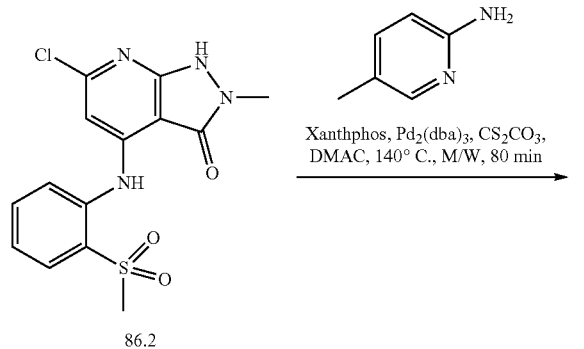

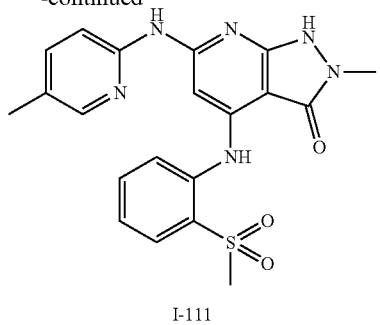

I-111

Compound I-111 was prepared from compound 86.2 and 5-methylpyridin-2-amine using procedure described in Example 2 (Yield: 20.78%), MS(ES): m/z 425.19 [M+H]$^+$, LCMS purity: 97.76%, HPLC purity: 96.61%, 1H NMR (MeOD, 400 MHz): 8.14 (s, 1H), 8.06-8.04 (d, J=8.0 Hz, 1H), 7.82-7.76 (m, 2H), 7.63-7.61 (d, J=8.0 Hz, 1H), 7.49-7.46 (t, J=6.8 Hz, 1H), 6.90 (s, 1H), 5.81 (s, 1H), 3.56 (s, 3H), 3.34 (s, 1H), 3.11 (s, 3H), 2.30 (s, 3H).

Example 91: Synthesis of 6-((2-methyl-4-((2-(methylsulfonyl)phenyl)amino)-3-oxo-2,3-dihydro-1H-pyrazolo[3,4-b]pyridin-6-yl)amino)picolinonitrile, I-112

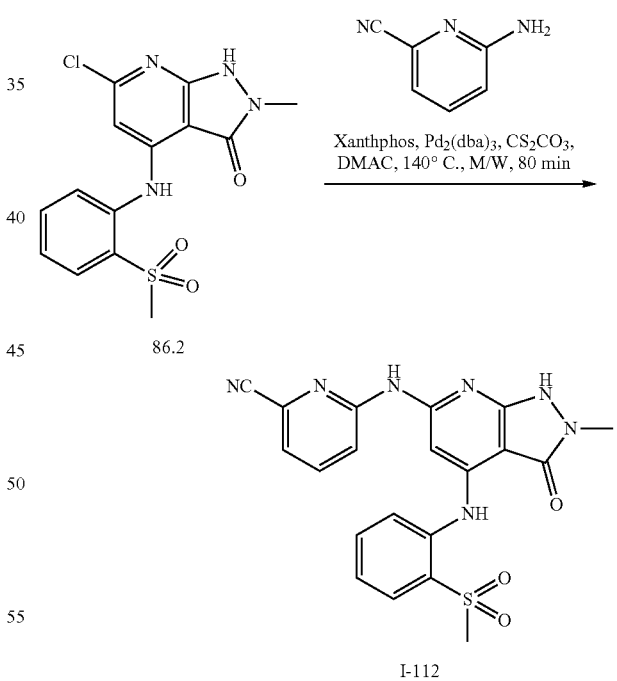

I-112

Compound I-112 was prepared from compound 86.2 and 6-aminopicolinonitrile using procedure described in Example 2 (Yield: 23.15%), MS(ES): m/z 436.35 [M+H]$^+$, LCMS purity: 100.00%, HPLC purity: 100.00%, 1H NMR (DMSO-d6, 400 MHz): 10.81 (s, 1H), 10.28 (s, 1H), 9.18 (s, 1H), 8.05-8.03 (d, J=8.8 Hz, 1H), 7.94-7.80 (m, 4H), 7.52-7.50 (d, J=7.2 Hz, 1H), 7.41-7.38 (t, J=7.2 Hz, 1H), 7.24 (s, 1H), 3.27 (s, 3H), 3.16 (s, 3H).

241

Example 92: Synthesis of 4-((3-chloro-2-methoxy-phenyl)amino)-2-methyl-6-((5-(pyrrolidine-1-carbo-nyl)-6-(trifluoromethyl)pyridin-2-yl)amino)-1,2-dihydro-3H-pyrazolo[3,4-b]pyridin-3-one, I-128

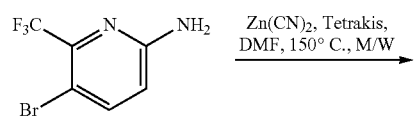

Zn(CN)₂, Tetrakis, DMF, 150° C., M/W

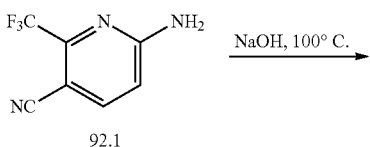

92.1

NaOH, 100° C.

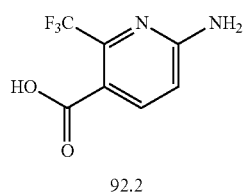

92.2

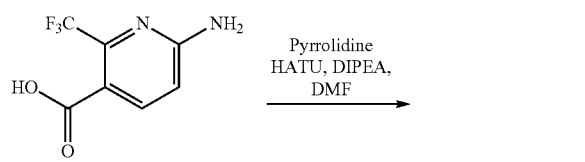

Pyrrolidine
HATU, DIPEA, DMF

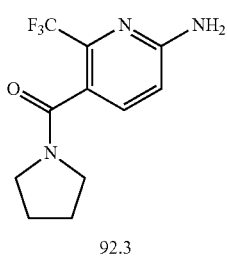

92.3

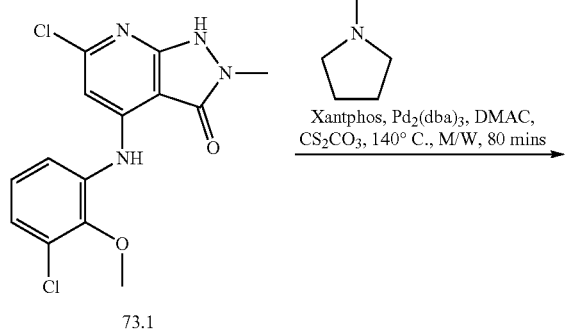

73.1

Xantphos, Pd₂(dba)₃, DMAC, Cs₂CO₃, 140° C., M/W, 80 mins

242

-continued

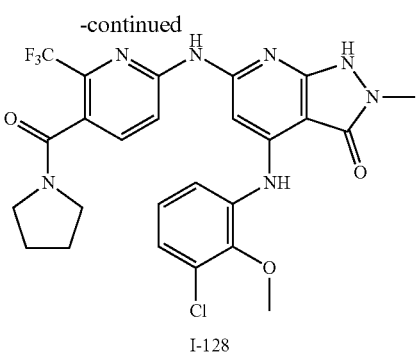

I-128

Synthesis of Compound 92.1.

To 5-bromo-6-(trifluoromethyl)pyridin-2-amine (3.0 g, 12.45 mmol, 1.0 eq) in dimethylformamide (1 ml) was added zinc cyanide (1.456 g, 12.45 mmol, 1.0 eq). The reaction mixture was then heated in microwave at 150° C. for 15 min. After completion of reaction, water was added to reaction mixture and extracted with ethyl acetate. Organic layer was combined, dried over sodium sulphate and concentrated under reduced pressure to obtain crude material. This was further purified by column chromatography and compound was eluted in 20% ethyl acetate in hexane to obtain 92.1. (Yield: 68.69%). MS (ES): m/z 188.13 [M+H]⁺.

Synthesis of Compound 92.2.

To compound 92.1 (1.6 g, 8.55 mmol, 1.0 eq) and sodium hydroxide (1.0 g, 25.65 mmol, 3.0 eq) was added in water (30 mL) The reaction mixture was stirred at 100° C. for 16 h. After completion of reaction, reaction mixture was extracted with ethyl acetate. Aqueous layer was acidified with hydrochloric acid and extracted with ethyl acetate. Organic layer was combined, dried over sodium sulphate and concentrated under reduced pressure to obtain crude material. This was further purified by column chromatography and compound was eluted in 5% methanol in dichloromethane to obtain 93.2. (Yield: 62.41%). MS (ES): m/z 207.12 [M+H]⁺.

Synthesis of Compound 92.3.

To a cooled solution of 92.2 (0.5 g, 2.43 mmol, 1.0 eq) and pyrrolidine (0.19 g, 2.67 mmol, 1.1 eq) in N,N-dimethylformamide (5 mL) at 0° C. was added ((1-[Bis(dimethylamino)methylene]-1H-1,2,3-triazolo[4,5-b]pyridinium3-oxid hexafluoro-phosphate)) (1.846 g, 4.86 mmol, 2.0 eq) followed by N,N-Diisopropylethylamine (0.94 g, 7.29 mmol, 3.0 eq) and the reaction mixture was stirred at room temperature for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 3% methanol in dichloromethane to obtain pure 92.3 (0.39 g, 62.34%). MS(ES): m/z 260.23 [M+H]⁺.

Compound I-128 was prepared from compound 73.1 and compound 93.3 using procedure described in Example 2 (Yield: 10.06%). MS(ES): m/z 563.35 [M+H]⁺, LCMS purity: 90.57%, HPLC purity: 94.43%, 1H NMR (DMSO-d6, 400 MHz): 10.91 (bs, 1H), 10.36 (s, 1H), 8.97 (s, 1H), 8.18-8.16 (d, J=8.4 Hz, 1H), 7.89-7.87 (d, J=8.4 Hz, 1H), 7.58-7.55 (dd, J=1.6 Hz, 7.6 Hz, 1H), 7.30 (s, 1H), 7.21-7.14 (m, 2H), 3.81 (s, 3H), 3.45-3.42 (m, 2H), 3.29 (s, 3H), 3.12-3.08 (m, 2H), 1.88-1.79 (m, 4H).

Example 93: Synthesis of 4-((3-chloro-2-methoxyphenyl)amino)-2-methyl-6-((5-(morpholine-4-carbonyl)-6-(trifluoromethyl)pyridin-2-yl)amino)-1,2-dihydro-3H-pyrazolo[3,4-b]pyridin-3-one, I-130

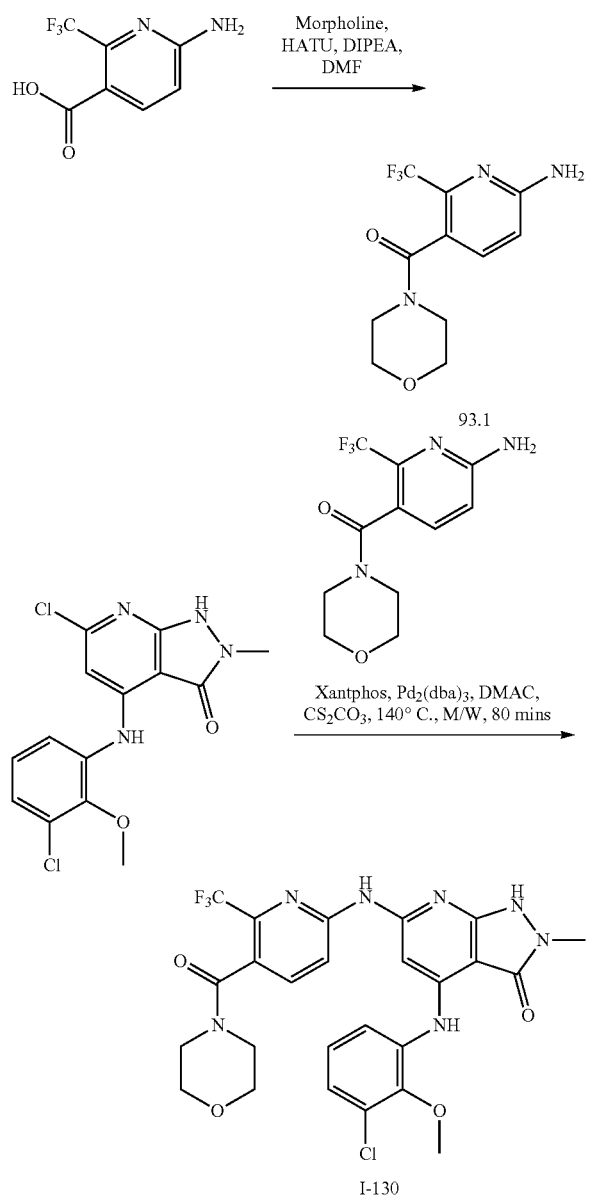

Synthesis of compound 93.1. To a cooled solution of 6-amino-2-(trifluoromethyl)nicotinic acid (0.5 g, 2.43 mmol, 1.0 eq) and morpholine (0.23 g, 2.67 mmol, 1.1 eq) in N, N-dimethylformamide (5 mL) at 0° C. was added ((1-[Bis(dimethylamino)methylene]-1H-1,2,3-triazolo[4,5-b]pyridinium 3-oxid hexafluoro-phosphate)) (1.846 g, 4.86 mmol, 2.0 eq) followed by N,N-Diisopropylethylamine (0.94 g, 7.29 mmol, 3.0 eq) and the reaction mixture was stirred at room temperature for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 3% methanol in dichloromethane to obtain pure 93.1 (0.4 g, 59.91%). MS(ES): m/z 276.23 [M+H]$^+$.

Compound I-130 was prepared from compound 73.1 and compound 93.1 using procedure described in Example 2 (Yield: 30.52%), MS(ES): m/z 578.41 [M+H]$^+$, LCMS purity: 97.65%, HPLC purity: 97.61%, 1H NMR (DMSO-d6, 400 MHz): 10.89 (s, 1H), 10.38 (s, 1H), 8.97 (s, 1H), 8.17-8.15 (d, J=8.4 Hz, 1H), 7.87-7.84 (d, J=8.8 Hz, 1H), 7.57-7.56 (d, J=7.6 Hz, 1H), 7.32 (s, 1H), 7.22-7.14 (m, 2H), 3.81 (s, 3H), 3.66-3.42 (m, 6H), 3.29 (s, 3H), 3.19-3.15 (m, 2H).

Example 94: Synthesis of 6-((4-((3-chloro-2-methoxyphenyl)amino)-2-methyl-3-oxo-2,3-dihydro-1H-pyrazolo[3,4-b]pyridin-6-yl)amino)-3-methylpicolinonitrile, I-132

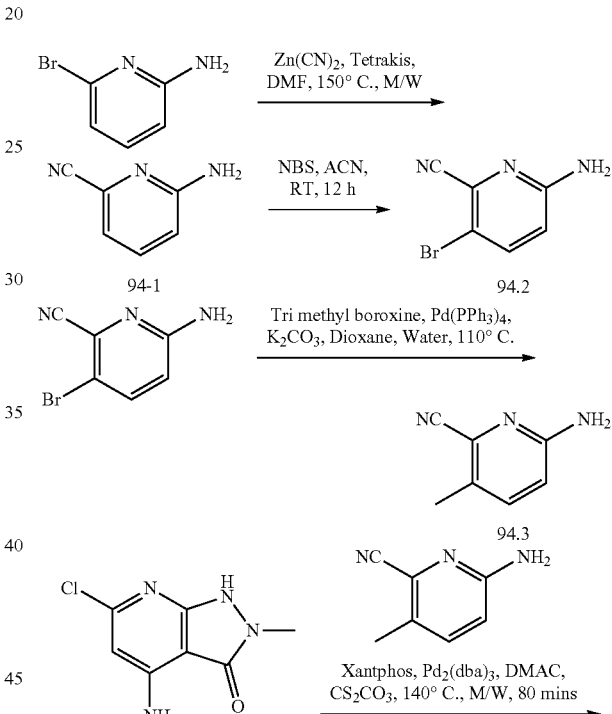

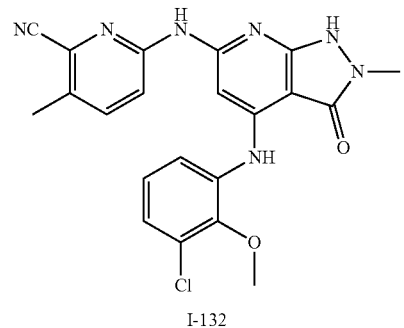

Synthesis of Compound 94.1.

To 6-bromopyridin-2-amine (2.0 g, 11.56 mmol, 1.0 eq) in dimethylformamide (1 ml) was added zinc cyanide (1.35 g, 11.56 mmol, 1.0 eq). The reaction mixture was then heated in microwave at 150° C. for 15 min. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane to obtain 94.1. (1.0 g, Yield: 72.62%). MS (ES): m/z 120.13 [M+H]$^+$.

Synthesis of Compound 94.2.

To compound 94.1 (1.0 g, 8.39 mmol, 1.0 eq) in acetonitrile was added N-Bromosuccinimide (2.24 g, 12.58 mmol, 1.5 eq). The reaction mixture was stirred at room temperature for 12 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 25% ethyl acetate in hexane to obtain 94.2. (0.42 g, Yield: 25.27%). MS (ES): m/z 199.02 [M+H]$^+$.

Synthesis of Compound 94.3.

To a solution of 94.2 (0.42 g, 2.12 mmol, 1.0 eq) in mixture of water (5 mL) and 1,4-dioxane (15 mL) was added trimethylboroxine (0.4 g, 3.18 mmol, 1.5 eq), tetrakis (0.073 g, 0.064 mmol, 0.03 eq) and potassium carbonate (0.878 g, 6.36 mmol, 3.0 eq). The reaction mixture was degassed by argon for 30 min. Further reaction mixture was stirred at 110° C. for 4 h. After completion of reaction, reaction mixture was cooled to room temperature transferred into water and extracted with ethyl acetate. Organic layer was combined, dried over sodium sulphate and concentrated under reduced pressure to obtain crude material. This was further purified in 20% ethyl acetate in hexane to get pure 95.3 (0.1 g, 35.41%). MS(ES): m/z 134.15 [M+H]$^+$.

Compound I-132 was prepared from compound 73.1 and compound 94.3 using procedure described in Example 2 (Yield: 17.51%). MS(ES): m/z 436.40 [M+H]$^+$, LCMS purity: 95.36%, HPLC purity: 95.07%, 1H NMR (DMSO-d6, 400 MHz): 10.80 (s, 1H), 10.19 (s, 1H), 8.96 (s, 1H), 7.96-7.94 (d, J=8.0 Hz, 1H), 7.80-7.78 (d, J=8.8 Hz, 1H), 7.64-7.62 (d, J=8.0 Hz, 1H), 7.45 (s, 1H), 7.27-7.18 (m, 2H), 3.81 (s, 3H), 3.28 (s, 3H), 2.39 (s, 3H).

Example 95: Synthesis of 2-methyl-6-((1-methyl-1H-pyrazol-3-yl)amino)-4-((2-(methylsulfonyl)phenyl)amino)-1,2-dihydro-3H-pyrazolo[3,4-b]pyridin-3-one, I-137

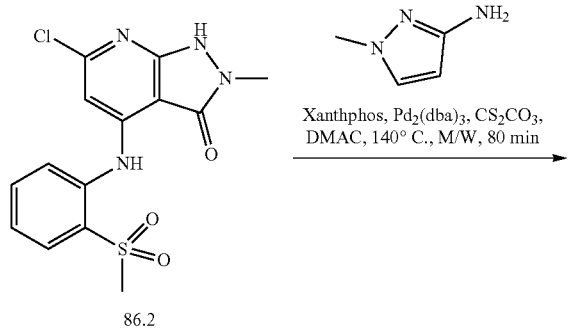

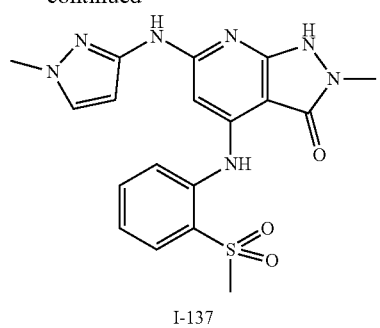

Compound I-137 was prepared from compound 86.2 and 1-methyl-1H-pyrazol-3-amine using procedure described in Example 2 (Yield: 31.03%), MS(ES): m/z 414.19 [M+H]$^+$, LCMS purity: 100.00%, HPLC purity: 95.12%, 1H NMR (DMSO-d6, 400 MHz): 10.49 (s, 1H), 9.47 (s, 1H), 9.02 (s, 1H), 7.94-7.92 (d, J=8.0 Hz, 1H), 7.86-7.78 (m, 2H), 7.52 (s, 1H), 7.40-7.37 (m, 1H), 6.76 (bs, 1H), 6.34 (bs, 1H), 3.71 (s, 3H), 3.24 (s, 3H), 3.17 (s, 3H).

Example 96: Synthesis of 2-methyl-6-((4-methylpyridin-2-yl)amino)-4-((2-(methylsulfonyl)phenyl)amino)-1,2-dihydro-3H-pyrazolo[3,4-b]pyridin-3-one, I-138

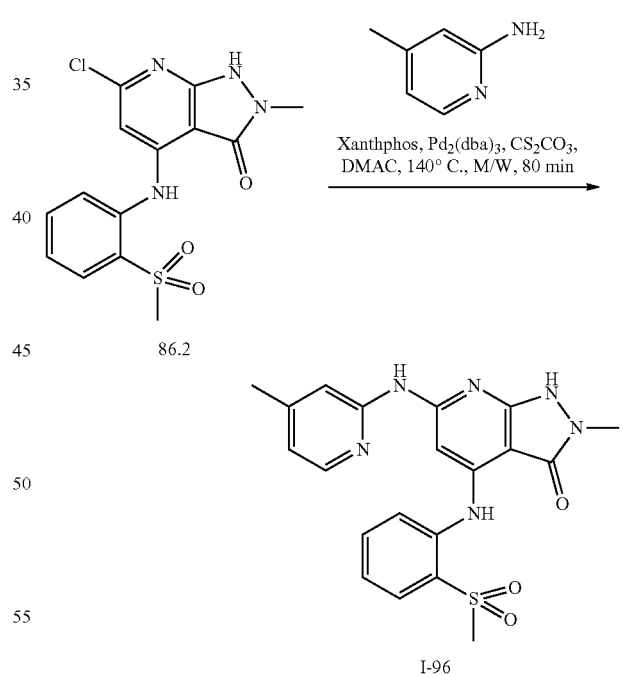

Compound I-138 was prepared from compound 86.2 and 4-methylpyridin-2-amine using procedure described in Example 2 (Yield: 22.67%), MS(ES): m/z 425.07 [M+H]$^+$, LCMS purity: 100.00%, HPLC purity: 99.85%, 1H NMR (DMSO-d6, 400 MHz): 10.69 (s, 1H), 9.70 (s, 1H), 9.08 (s, 1H), 8.05 (s, 1H), 7.93-7.91 (d, J=8.0 Hz, 1H), 7.85-7.73 (m, 3H), 7.39 (s, 1H), 7.14 (s, 1H), 6.75 (s, 1H), 3.26 (s, 3H), 3.16 (s, 3H), 2.27 (s, 3H).

Example 97: Synthesis of 6-((2-methyl-4-((2-(methylsulfonyl)phenyl)amino)-3-oxo-2,3-dihydro-1H-pyrazolo[3,4-b]pyridin-6-yl)amino)nicotinonitrile, I-139

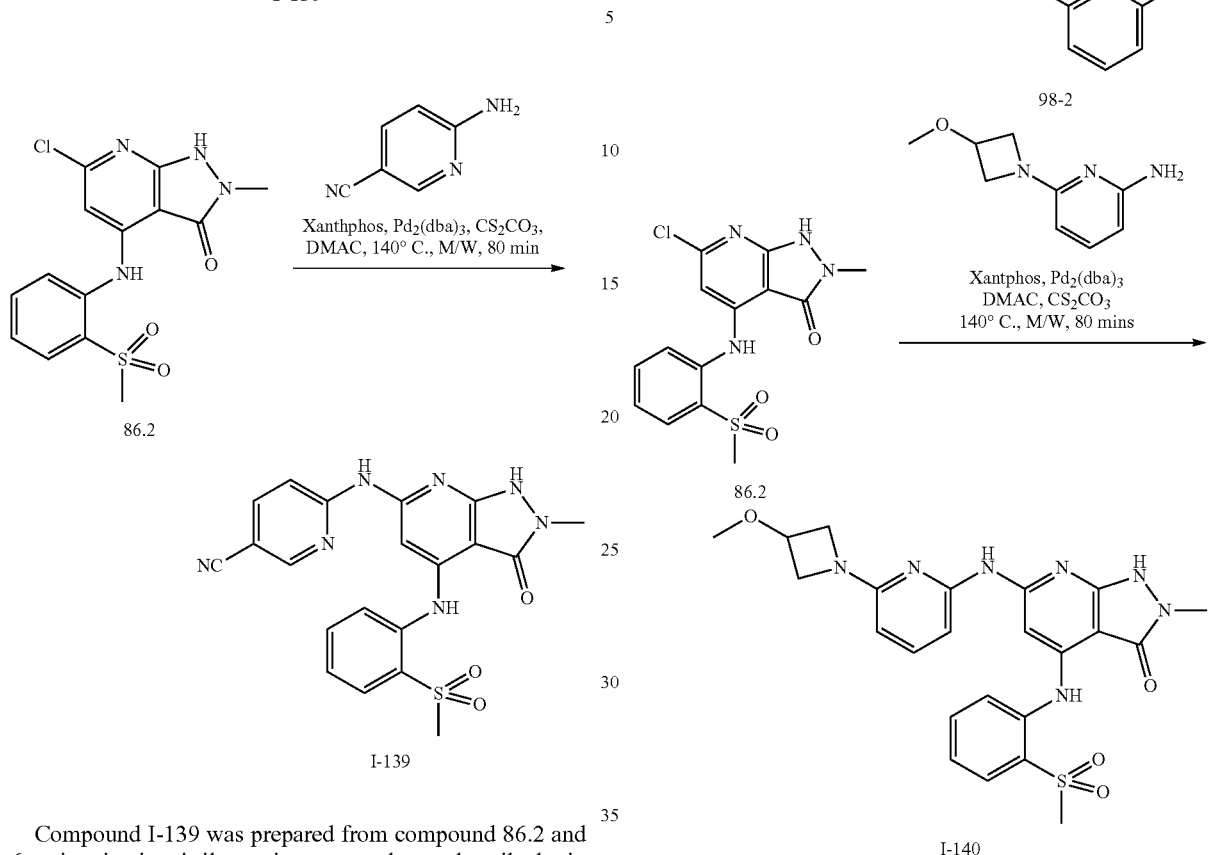

Compound I-139 was prepared from compound 86.2 and 6-aminonicotinonitrile using procedure described in Example 2 (Yield: 16.20%), MS(ES): m/z 436.27 [M+H]$^+$, LCMS purity: 94.62%, HPLC purity: 94.64%, 1H NMR (DMSO-d6, 400 MHz): 10.99 (bs, 1H), 10.43 (s, 1H), 9.18 (s, 1H), 8.66 (s, 1H), 8.14 (s, 2H), 7.97-7.95 (d, J=7.8 Hz, 1H), 7.85 (s, 2H), 7.46-7.42 (m, 1H), 7.09 (s, 1H), 3.31 (s, 3H), 3.19 (s, 3H).

Example 98: Synthesis of 6-((6-(3-methoxyazetidin-1-yl)pyridin-2-yl)amino)-2-methyl-4-((2-(methylsulfonyl)phenyl)amino)-1,2-dihydro-3H-pyrazolo[3,4-b]pyridin-3-one, I-140

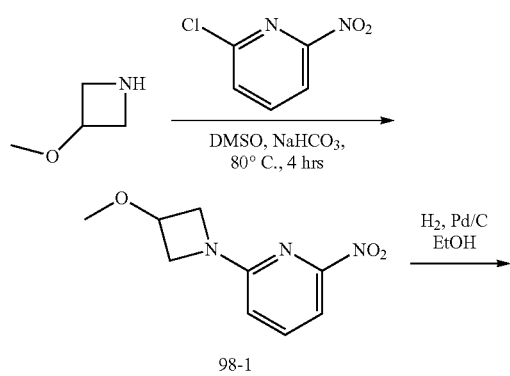

Synthesis of Compound 98.1.

To a solution of 2-chloro-6-nitropyridine (2.0 g, 22.96 mmol, 1.5 eq) and 3-methoxyazetidine (2.43 g, 15.30 mmol, 1.0 eq) in dimethyl sulfoxide (20 mL) was added sodium bicarbonate (2.57 g, 30.60 mmol, 2.0 eq). Reaction mixture was stirred at 80° C. for 4 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane as eluant to obtain pure 98.1 (2.0 g, 62.47%). MS(ES): m/z 210.21 [M+H]$^+$.

Synthesis of Compound 98.2.

To a solution of 1.2 (2.0 g, 9.56 mmol, 1.0 eq) in methanol (20 mL), 10% palladium on charcoal (0.4 g) was added. Hydrogen was purged through reaction mixture for 4 h. After completion of reaction, reaction mixture was filtered through celite-bed and washed with methanol. Filtrate was concentrated under reduced pressure to obtain 98.2. (1.5 g, 87.55%). MS(ES): m/z 180.22 [M+H]$^+$.

Compound I-140 was prepared from compound 86.2 and 98.2 using procedure described in Example 2 (Yield: 12.34%), MS(ES): m/z 496.38 [M+H]$^+$, LCMS purity: 99.42%, HPLC purity: 100.00%, 1H NMR (DMSO-d6, 400 MHz): 10.593 (s, 1H), 9.492 (s, 1H), 8.906 (s, 1H), 7.950-7.932 (d, J=7.2 Hz, 1H), 7.802 (s, 2H), 7.534-7.391 (m, 3H), 6.986 (s, 1H), 5.879-5.860 (d, J=7.6 Hz, 1H), 4.179-4.060

(m, 1H), 3.951-3.722 (m, 2H), 3.590-3.484 (m, 2H), 3.265 (s, 3H), 3.201 (s, 3H), 3.182 (s, 3H).

Example 99: Synthesis of 2-methyl-4-((2-(methylsulfonyl)phenyl)amino)-6-(pyridin-2-ylamino)-1,2-dihydro-3H-pyrazolo[3,4-b]pyridin-3-one, I-142

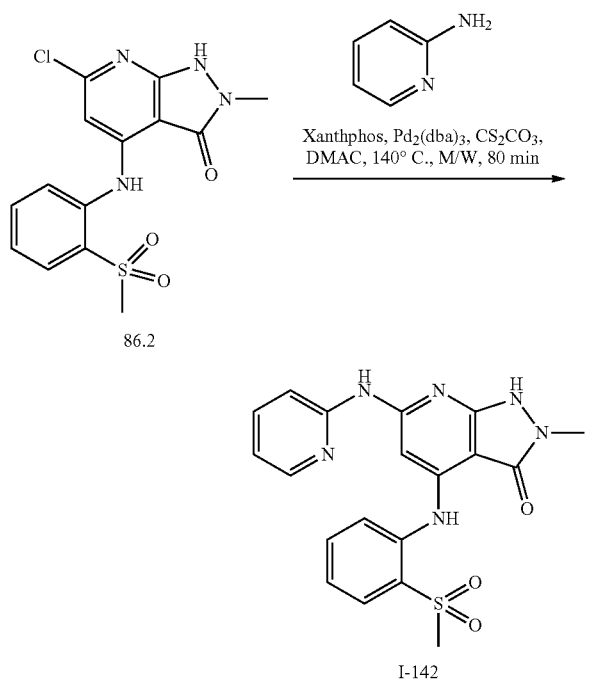

Compound I-142 was prepared from compound 86.2 and pyridin-2-amine using procedure described in Example 2 (Yield: 27.77%), MS(ES): m/z 411.39 [M+H]+, LCMS purity: 93.51%, HPLC purity: 96.50%, 1H NMR (DMSO-d6, 400 MHz): 10.73 (s, 1H), 9.81 (s, 1H), 9.10 (s, 1H), 8.21 (s, 1H), 7.96-7.94 (d, J=7.6 Hz, 2H), 7.88-7.79 (m, 2H), 7.69 (s, 1H), 7.41 (s, 1H), 7.15 (s, 1H), 6.92 (s, 1H), 3.28 (s, 3H), 3.19 (s, 3H).

Example 100: Synthesis of 6-((5-cyclopropylpyridin-2-yl)amino)-2-methyl-4-((2-(methylsulfonyl)phenyl)amino)-1,2-dihydro-3H-pyrazolo[3,4-b]pyridin-3-one, I-143

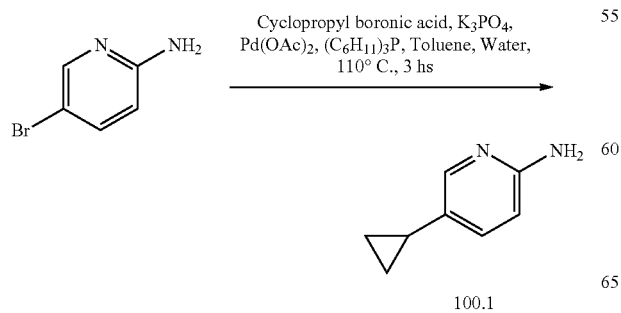

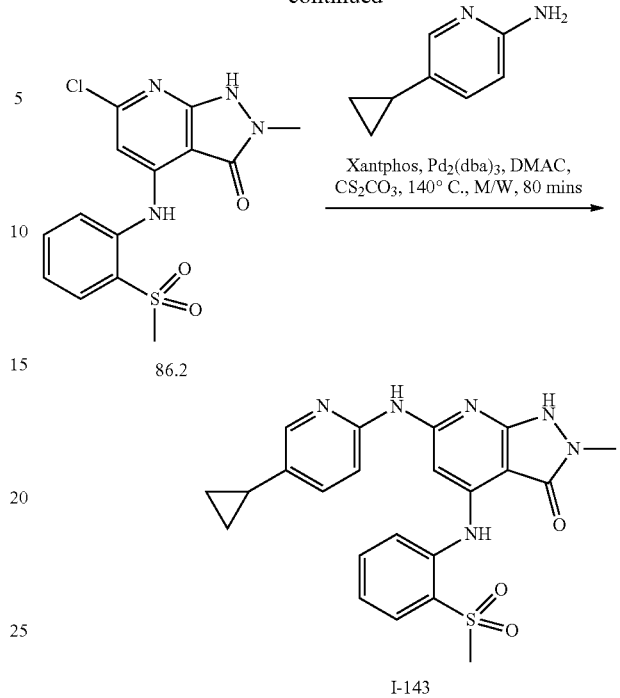

Synthesis of Compound 100.1.

To a solution of 5-bromopyridin-2-amine (1 g, 5.78 mmol, 1.0 eq) in mixture of toluene (12 mL) and water (1 mL) were added cyclopropyl boronic acid (0.65 g, 7.51 mmol, 1.3 eq) and potassium phosphate (2.45 g, 11.56 mmol, 2.0 eq). The reaction mixture was degassed for 10 min under argon atmosphere, and palladium acetate (0.13 g, 0.578 mmol, 0.1 eq) and Tricyclohexylphosphine (0.324 g, 1.15 mmol, 0.2 eq) were added. Reaction mixture was again degassed for 10 min and stirred at 110° C. for 3 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane as eluent to obtain 101.1. (0.5 g, 64.47%). MS(ES): m/z 135.18 [M+H]+.

Compound I-143 was prepared from compound 86.2 and compound 100.1 using procedure described in Example 2 (0.030 g, Yield: 15.66%). MS(ES): m/z 451.32 [M+H]+, LCMS purity: 97.01%, HPLC purity: 98.86%, 1H NMR (DMSO-d6, 400 MHz): 10.67 (s, 1H), 9.71 (s, 1H), 9.07 (s, 1H), 8.04 (s, 1H), 7.95-7.93 (d, J=8.8 Hz, 1H), 7.85-7.81 (m, 3H), 7.40-7.33 (m, 2H), 7.07 (s, 1H), 3.26 (s, 3H), 3.18 (s, 3H), 1.88 (m, 1H), 0.93 (m, 2H), 0.67 (m, 2H).

Example 101: Synthesis of 3-(azetidin-1-yl)-6-((4-((3-chloro-2-methoxyphenyl)amino)-2-methyl-3-oxo-2,3-dihydro-1H-pyrazolo[3,4-b]pyridin-6-yl)amino)picolinonitrile, I-144

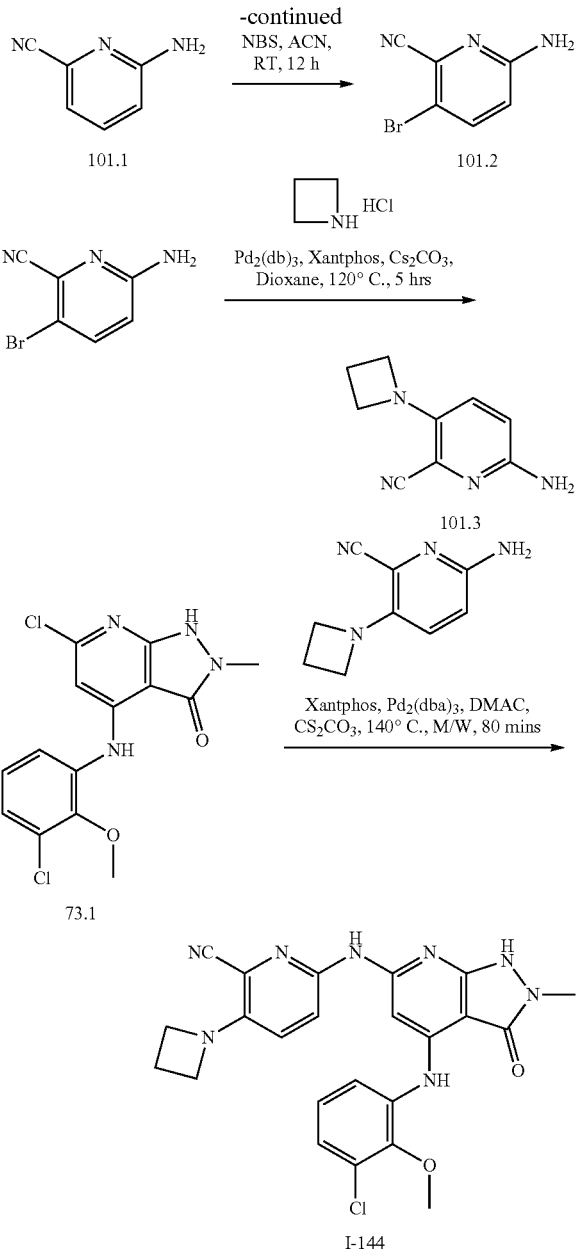

Organic layer was combined, dried over sodium sulphate and concentrated under reduced pressure to obtain crude material. This was further purified by column chromatography and compound was eluted in 25% ethyl acetate in hexane to obtain 101.2. (0.42 g, Yield: 25.27%). MS (ES): m/z 199.02 [M+H]$^+$.

Synthesis of Compound 101.3.

To a solution of 101.2 (2.0 g, 10.10 mmol, 1.0 eq) 1,4-dioxane (20 mL) was added azetidine hydrochloride (1.9 g, 20.20 mmol, 2.0 eq) followed by Tris(dibenzylideneacetone)dipalladium(0) (0.277 g, 0.303 mmol, 0.03 eq), 9,9-Dimethyl-4,5-bis(dl-tert-butylphosphino)xanthene (0.351 g, 0.606 mmol, 0.06 eq) and cesium carbonate (16.4 g, 50.50 mmol, 5.0 eq). The reaction mixture was degassed by argon for 30 min. Further reaction mixture was stirred at 120° C. for 5 h. After completion of reaction, water was added to reaction mixture and extracted with ethyl acetate. Organic layer was combined, dried over sodium sulphate and concentrated under reduced pressure to obtain crude material. This was further purified by column chromatography and compound was eluted in 20% ethyl acetate in hexane to obtain pure 102.3 (0.52 g, 29.95%). MS(ES): m/z 175.21 [M+H]$^+$.

Compound I-144 was prepared from compound 73.1 and compound 101.3 using procedure described in Example 2 (Yield: 14.22%). MS(ES): m/z 477.31 [M+H]$^+$, LCMS purity: 97.17%, HPLC purity: 95.19%, 1H NMR (DMSO-d6, 400 MHz): 10.65 (s, 1H), 9.87 (s, 1H), 8.95 (s, 1H), 7.79-7.77 (d, J=8.4 Hz, 1H), 7.62-7.61 (d, J=8.4 Hz, 1H), 7.45 (s, 1H), 7.27-7.13 (m, 3H), 4.10-4.06 (m, 4H), 3.81 (s, 3H), 3.26 (s, 3H), 2.36-2.29 (m, 2H).

Example 102: Synthesis of (S)-6-((4-((3-chloro-2-methoxyphenyl)amino)-2-methyl-3-oxo-2,3-dihydro-1H-pyrazolo[3,4-b]pyridin-6-yl)amino)-3-(3-methoxypyrrolidin-1-yl)picolinonitrile, I-145

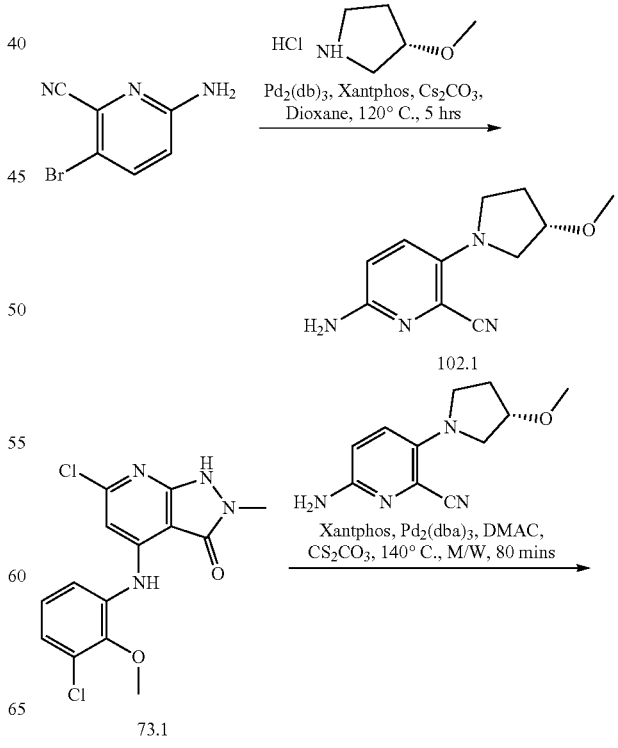

Synthesis of Compound 101.1.

To 6-bromopyridin-2-amine (2.0 g, 11.56 mmol, 1.0 eq) in dimethylformamide (1 ml) was added zinc cyanide (1.35 g, 11.56 mmol, 1.0 eq). The reaction mixture was then heated in microwave at 150° C. for 15 min. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane to obtain 101.1. (1.0 g, Yield: 72.62%). MS (ES): m/z 120.13 [M+H]$^+$.

Synthesis of Compound 101.2.

To compound 101.1 (1.0 g, 8.39 mmol, 1.0 eq) in acetonitrile was added N-Bromosuccinimide (2.24 g, 12.58 mmol, 1.5 eq). The reaction mixture was stirred at room temperature for 12 h. After completion of reaction, reaction mixture was transferred into water and extracted with ethyl acetate.

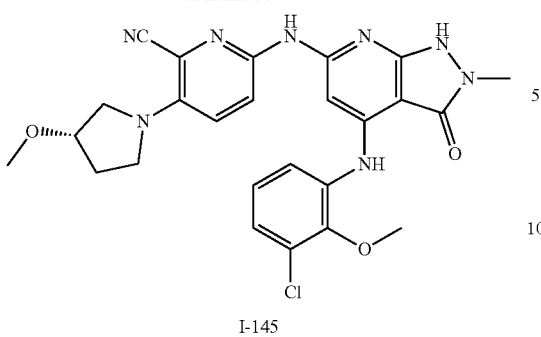

I-145

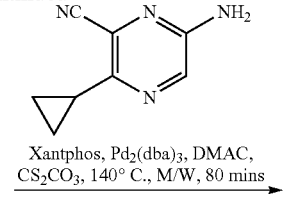

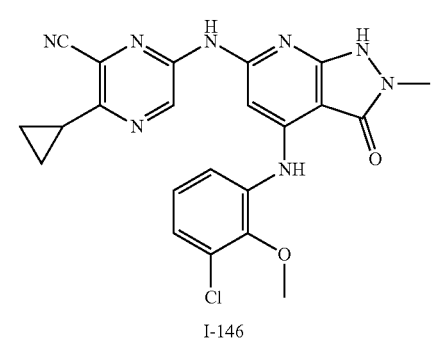

I-146

Synthesis of compound 102.1. To a solution of 6-amino-3-bromopicolinonitrile (0.5 g, 7.57 mmol, 1.0 eq) in 1,4-dioxane (20 mL) was added (S)-3-methoxypyrrolidine hydrochloride (2.1 g, 15.14 mmol, 2.0 eq), Tris(dibenzylideneacetone)dipalladium(0) (0.21 g, 0.227 mmol, 0.03 eq), 9,9-Dimethyl-4,5-bis(dl-tert-butylphosphino)xanthene (0.26 g, 0.454 mmol, 0.06 eq) and potassium carbonate (3.13 g, 22.71 mmol, 3.0 eq). The reaction mixture was degassed by argon for 30 min. Further reaction mixture was stirred at 120° C. for 5 h. After completion of reaction, water was added to reaction mixture and extracted with ethyl acetate. Organic layer was combined, dried over sodium sulphate and concentrated under reduced pressure to obtain crude material. This was further purified by column chromatography and compound was eluted in 20% ethyl acetate in hexane to obtain pure 102.1 (0.055 g, 9.07%). MS(ES): m/z 219.26 [M+H]+.

Compound I-145 was prepared from compound 73.1 and compound 102.1 using procedure described in Example 2 (Yield: 16.28%). MS(ES): m/z 522.31 [M+H]+, LCMS purity: 93.16%, HPLC purity: 91.93%, 1H NMR (DMSO-d6, 400 MHz): 10.66 (s, 1H), 9.86 (s, 1H), 8.99 (s, 1H), 7.82-7.81 (d, J=6.4 Hz, 1H), 7.66-7.64 (d, J=7.8 Hz, 1H), 7.46 (s, 1H), 7.39-7.37 (d, J=9.6 Hz, 1H), 7.31-7.27 (t, J=7.8 Hz, 1H), 7.19-7.18 (d, J=7.8 Hz, 1H), 4.10 (s, 1H), 3.84 (s, 3H), 3.73-3.70 (m, 1H), 3.59-3.49 (m, 3H), 3.28 (s, 6H), 2.09-2.03 (m, 2H).

Example 103: 6-((4-((3-chloro-2-methoxyphenyl)amino)-2-methyl-3-oxo-2,3-dihydro-1H-pyrazolo[3,4-b]pyridin-6-yl)amino)-3-cyclopropylpyrazine-2-carbonitrile, I-146

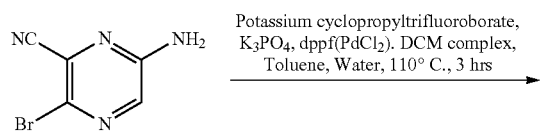

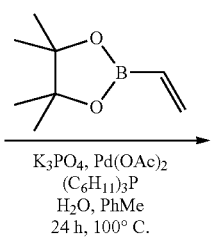

103.1

Synthesis of compound 103.1. To a solution of 6-amino-3-bromopyrazine-2-carbonitrile (1 g, 5.02 mmol, 1.0 eq) in mixture of toluene (12 mL) and water (1 mL) was added Potassium cyclopropyltrifluoroborate (0.965 g, 6.526 mmol, 1.3 eq), potassium phosphate (2.13 g, 10.04 mmol, 2.0 eq). The reaction mixture was degassed for 10 min under argon atmosphere, and then [1,1'-Bis(diphenylphosphino)ferrocene]palladium(II) dichloride complex with dichloromethane (0.205 g, 0.25 mmol, 0.05 eq) was added, again degassed for 10 min. The reaction was then stirred at 110° C. for 3 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane as eluent to obtain 103.1. (0.49 g, 60.88%). MS(ES): m/z 161.18 [M+H]+.

Compound I-146 was prepared from compound 73.1 and compound 103.1 using procedure described in Example 2 (Yield: 15.66%). MS(ES): m/z 463.25 [M+H]+, LCMS purity: 98.63%, HPLC purity: 96.05%, 1H NMR (DMSO-d6, 400 MHz): 10.53 (bs, 2H), 9.21 (s, 1H), 8.98 (s, 1H), 7.64-7.62 (d, J=6.4 Hz, 1H), 7.29-7.23 (m, 3H), 3.84 (s, 3H), 3.32 (s, 3H), 2.34-2.29 (m, 1H), 1.16-1.13 (m, 2H), 1.01 (m, 2H).

Example 104: Synthesis of 6-((4-((3-chloro-2-methoxyphenyl)amino)-2-methyl-3-oxo-2,3-dihydro-1H-pyrazolo[3,4-b]pyridin-6-yl)amino)-3-ethylpyrazine-2-carbonitrile, I-147

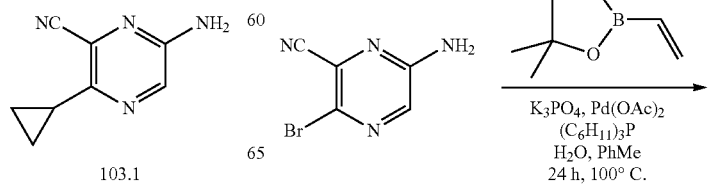

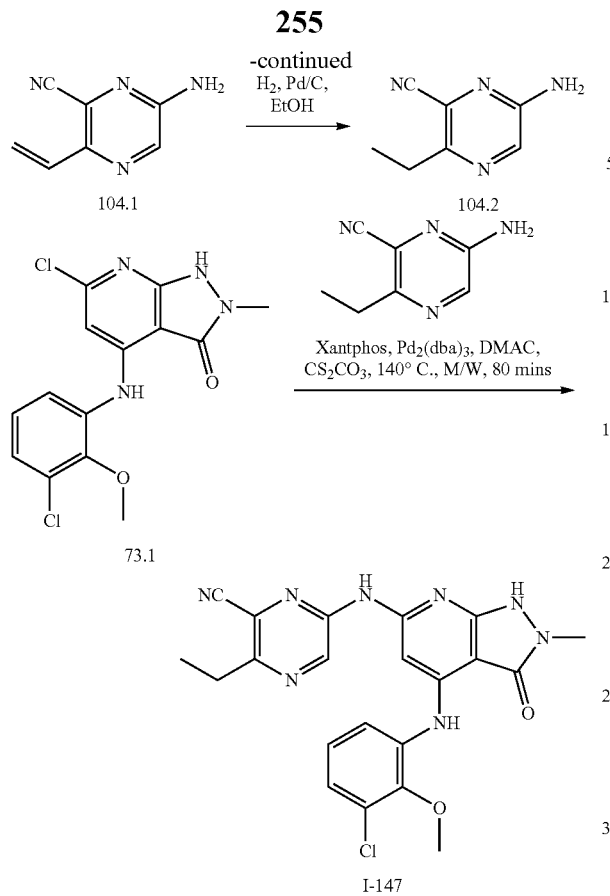

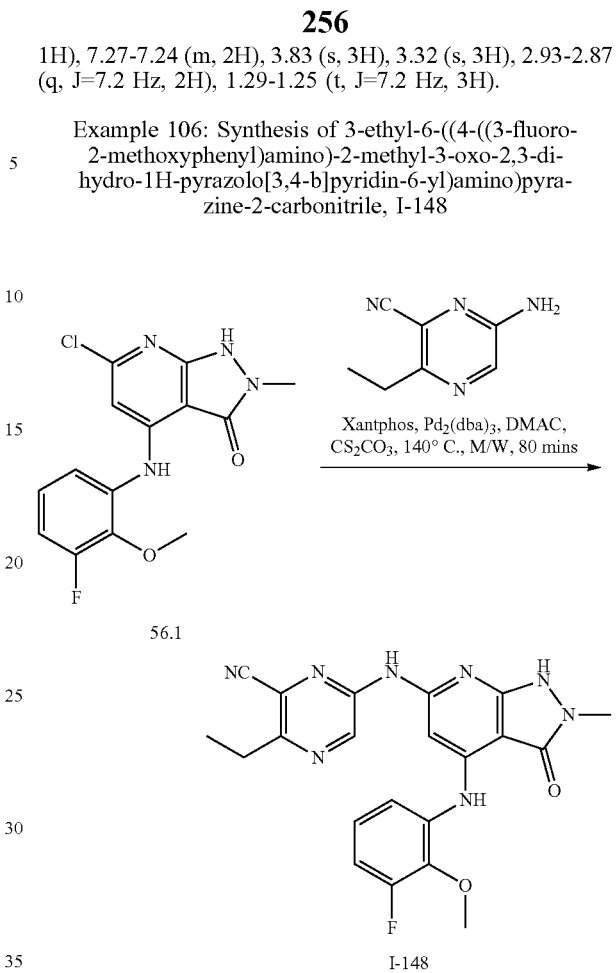

1H), 7.27-7.24 (m, 2H), 3.83 (s, 3H), 3.32 (s, 3H), 2.93-2.87 (q, J=7.2 Hz, 2H), 1.29-1.25 (t, J=7.2 Hz, 3H).

Example 106: Synthesis of 3-ethyl-6-((4-((3-fluoro-2-methoxyphenyl)amino)-2-methyl-3-oxo-2,3-dihydro-1H-pyrazolo[3,4-b]pyridin-6-yl)amino)pyrazine-2-carbonitrile, I-148

Synthesis of Compound 104.1.

To a solution of 6-amino-3-bromopyrazine-2-carbonitrile (0.2 g, 1.0 mmol, 1.0 eq) in mixture of toluene (2.5 mL) and water (0.5 mL) were added 4,4,5,5-tetramethyl-2-vinyl-1,3,2-dioxaborolane (0.201 g, 1.31 mmol, 1.3 eq) and potassium phosphate (0.424 g, 2.0 mmol, 2.0 eq). The reaction mixture was degassed for 10 min under argon atmosphere, and palladium acetate (0.022 g, 0.1 mmol, 0.1 eq) and Tricyclohexylphosphine (0.056 g, 0.2 mmol, 0.2 eq) were added. Reaction mixture was again degassed for 10 min and stirred at 100° C. for 24 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 15% ethyl acetate in hexane as eluent to obtain 104.1. (0.12 g, 81.70%). MS(ES): m/z 147.15 [M+H]⁺.

Synthesis of Compound 104.2.

To a solution of 104.1 (0.12 g, 0.821 mmol, 1.0 eq) in ethanol (5 mL), 10% palladium on charcoal (0.030 g) was added. Hydrogen was purged through reaction mixture for 2-3 h. After completion of reaction, reaction mixture was filter through celite-bed and washed with ethanol. Filtrate was concentrated under reduced pressure to obtain 104.2 (0.09 g, 73.98%). MS(ES): m/z 149.17 [M+H]⁺.

Compound I-147 was prepared from compound 73.1 and compound 104.2 using procedure described in Example (Yield: 20.34%). MS(ES): m/z 451.25 [M+H]⁺, LCMS purity: 98.20%, HPLC purity: 96.27%, 1H NMR (DMSO-d6, 400 MHz): 10.92 (s, 1H), 10.54 (s, 1H), 9.27 (s, 1H), 8.96 (s, 1H), 7.63-7.61 (dd, J=2.0 Hz, 7.2 Hz, 1H), 7.33 (s, 1H), 7.27-7.24 (m, 2H), 3.83 (s, 3H), 3.32 (s, 3H), 2.93-2.87 (q, J=7.2 Hz, 2H), 1.29-1.25 (t, J=7.2 Hz, 3H).

Compound I-148 was prepared from compound 56.1 and 6-amino-3-ethylpyrazine-2-carbonitrile using procedure described in Example 2 (Yield: 18.57%). MS(ES): m/z 435.24 [M+H]⁺, LCMS purity: 96.91%, HPLC purity: 96.60%, 1H NMR (DMSO-d6, 400 MHz): 10.90 (s, 1H), 10.54 (s, 1H), 9.26 (s, 1H), 8.92 (s, 1H), 7.47-7.45 (d, J=8.0 Hz, 1H), 7.35 (s, 1H), 7.25-7.20 (m, 1H), 3.05 (t, 1H), 3.90 (s, 3H), 3.31 (s, 3H), 2.91-2.87 (q, J=7.2 Hz, 2H), 1.29-1.25 (t, J=7.2 Hz, 3H).

Example 106: Synthesis of 4-((4-chloro-2-(methylsulfonyl)phenyl)amino)-6-((2,6-dimethylpyrimidin-4-yl)amino)-2-methyl-1,2-dihydro-3H-pyrazolo[3,4-b]pyridin-3-one, I-199

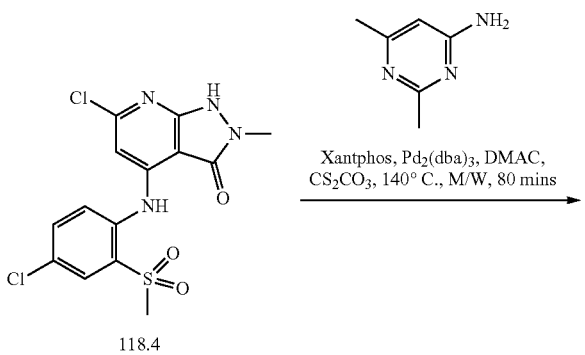

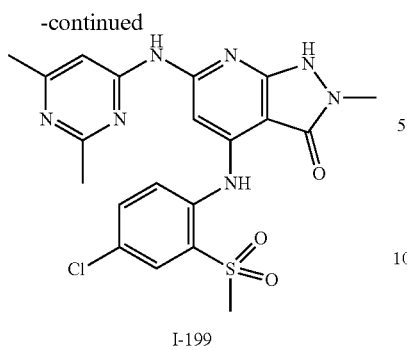

I-199

Compound I-199 was prepared from 2,6-dimethylpyrimidin-4-amine and 118.4 using procedure described in Example 2 (Yield: 14.71%). MS(ES): m/z 474.15 [M+H]$^+$, LCMS purity: 98.47%, HPLC purity: 97.08%, 1H NMR (DMSO-d6, 400 MHz): 11.20 (bs, 2H), 9.23 (s, 1H), 7.93-7.85 (m, 3H), 3.34 (s, 3H), 3.28 (s, 3H), 2.56 (s, 3H), 2.49 (s, 3H).

Example 107: Synthesis of 6-((4-((4-chloro-2-(methylsulfonyl)phenyl)amino)-2-methyl-3-oxo-2,3-dihydro-1H-pyrazolo[3,4-b]pyridin-6-yl)amino)picolinonitrile, I-203

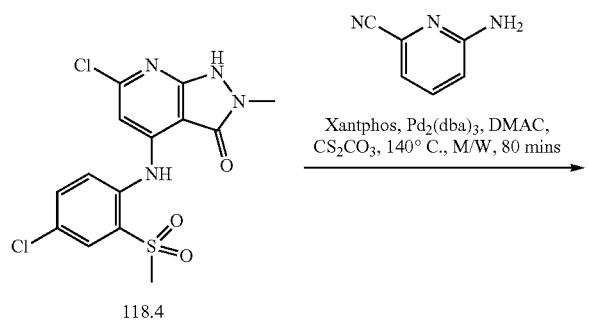

Compound I-203 was prepared from 6-aminopicolinonitrile and 118.4 using procedure described in Example 2 (Yield: 17.58%). MS(ES): m/z 470.27 [M+H]$^+$, LCMS purity: 100.00%, HPLC purity: 98.56%, 1H NMR (DMSO-d6, 400 MHz): 10.71 (bs, 1H), 10.29 (s, 1H), 9.18 (s, 1H), 8.04-8.02 (d, J=8.4 Hz, 1H), 7.94-7.85 (m, 3H), 7.54-7.52 (d, J=7.2 Hz, 1H), 7.27 (s, 1H), 3.29 (s, 3H), 3.26 (s, 3H).

Example 108: Synthesis of 4-((4-chloro-2-(methylsulfonyl)phenyl)amino)-6-((5,6-dimethylpyrazin-2-yl)amino)-2-methyl-1,2-dihydro-3H-pyrazolo[3,4-b]pyridin-3-one, I-207

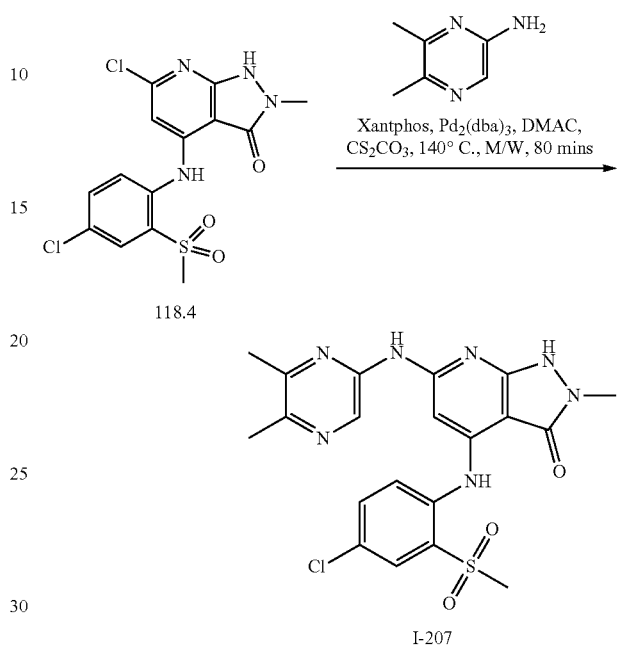

I-207

Compound I-207 was prepared from 5,6-dimethylpyrazin-2-amine and 118.4 using procedure described in Example 2 (Yield: 19.06%). MS(ES): m/z 474.32 [M+H]$^+$, LCMS purity: 100.00%, HPLC purity: 98.78%, 1H NMR (DMSO-d6, 400 MHz): 10.75 (bs, 1H), 9.97 (s, 1H), 9.10 (s, 1H), 8.89 (s, 1H), 7.90-7.86 (m, 3H), 7.09 (s, 1H), 3.29 (s, 3H), 3.26 (s, 3H), 2.40 (s, 3H), 2.38 (s, 3H).

Example I-109: Synthesis of 4-((4-cyclopropyl-2-(methylsulfonyl)phenyl)amino)-6-((2,6-dimethylpyrimidin-4-yl)amino)-2-methyl-1,2-dihydro-3H-pyrazolo[3,4-b]pyridin-3-one, I-206

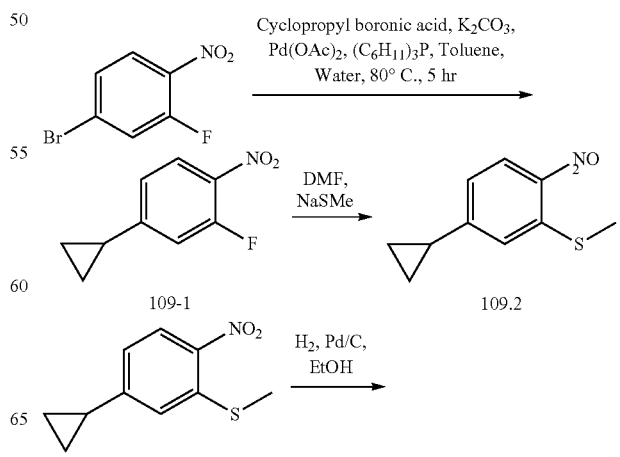

-continued

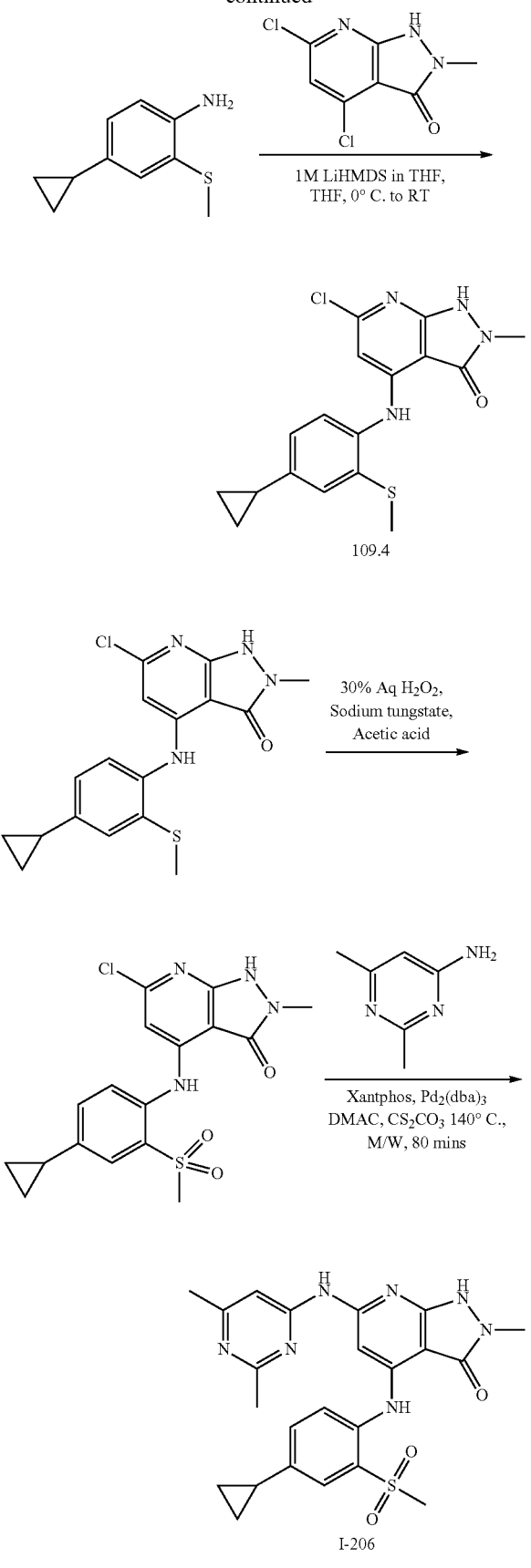

Synthesis of Compound 109.1.

To a solution of 2-fluoro-4-bromonitrobenzene (1.0 g, 4.55 mmol, 1.0 eq) in mixture of toluene (12 mL) and water (5 mL) were added cyclopropyl boronic acid (0.51 g, 5.91 mmol, 1.3 eq) and potassium carbonate (1.25 g, 9.1 mmol, 2.0 eq). The reaction mixture was degassed for 10 min under argon atmosphere, and palladium acetate (0.102 g, 0.455 mmol, 0.1 eq) and Tricyclohexylphosphine (0.255 g, 0.91 mmol, 0.2 eq) were added. Reaction mixture was again degassed for 10 min and stirred at 80° C. for 5 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 10% ethyl acetate in hexane as eluent to obtain 109.1. (0.81 g, 98.36%). MS(ES): m/z 182.17 [M+H]$^+$.

Synthesis of Compound 109.2.

To a solution of 109.1 (0.81 g, 4.47 mmol, 1.0 eq) and sodium thiomethoxide (0.313 g, 4.47 mmol, 1.0 eq) in N,N-Dimethylformamide (10 mL) was added. Reaction mixture was stirred at 150° C. for 5 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 15% ethyl acetate in hexane as eluent to obtain 110.2. (0.78 g, 83.37%). MS(ES): m/z 210.26 [M+H]$^+$.

Synthesis of Compound 109.3.

To a solution of 109.2 (0.78 g, 3.73 mmol, 1.0 eq) in ethanol (10 mL), 10% palladium on charcoal (0.060 g) was added. Hydrogen was purged through reaction mixture for 2-3 h. After completion of reaction, reaction mixture was filtered through celite-bed and washed with ethanol. Filtrate was concentrated under reduced pressure to obtain 109.3 (0.63 g, 94.28%). MS(ES): m/z 180.28 [M+H]$^+$.

Synthesis of Compound 109.4.

Compound was synthesized from 109.3 and 1.9 using general procedure A to obtain 109.4 (Yield: 58.41%). MS (ES): m/z 361.86 [M+H]$^+$.

Synthesis of Compound 109.5. To a solution of 109.4 (0.58 g, 1.61 mmol, 1 eq) in acetic acid (1.0 mL) was added 30% hydrogen peroxide (1.1 g, 32.2 mmol, 20 eq) and sodium tungstate dihydrate (0.53 g, 1.61 mmol, 1 eq). Reaction mixture was stirred at room temperature for 2 h. After completion of reaction, reaction mixture was transferred in ice-water and precipitated product was filtered, washed with 50% ethyl acetate in hexane and dried well to obtain 109.5. (0.36 g, Yield: 57.01%). MS(ES): m/z 393.86 [M+H]$^+$.

Compound I-206 was prepared from 2,6-dimethylpyrimidin-4-amine and compound 109.5 using procedure described in Example 2 (Yield: 5.69%). MS(ES): m/z 480.42 [M+H]$^+$, LCMS purity: 94.51%, HPLC purity: 95.04%, 1H NMR (DMSO-d6, 400 MHz): 10.81 (s, 1H), 10.08 (s, 1H), 9.01 (s, 1H), 7.74-7.72 (d, J=8.4 Hz, 1H), 7.68-7.67 (d, J=2.0 Hz, 1H), 7.49-7.38 (m, 2H), 7.28 (s, 1H), 3.29 (s, 3H), 3.17 (s, 3H), 2.36 (s, 3H), 2.32 (s, 3H), 2.10-2.13 (m, 1H), 1.05-1.10 (m, 2H), 0.76-1.73 (m, 2H).

Example 110: Synthesis of 4-((4-cyclopropyl-2-(methylsulfonyl)phenyl)amino)-6-((5,6-dimethyl-pyrazin-2-yl)amino)-2-methyl-1,2-dihydro-3H-pyrazolo[3,4-b]pyridin-3-one, I-211

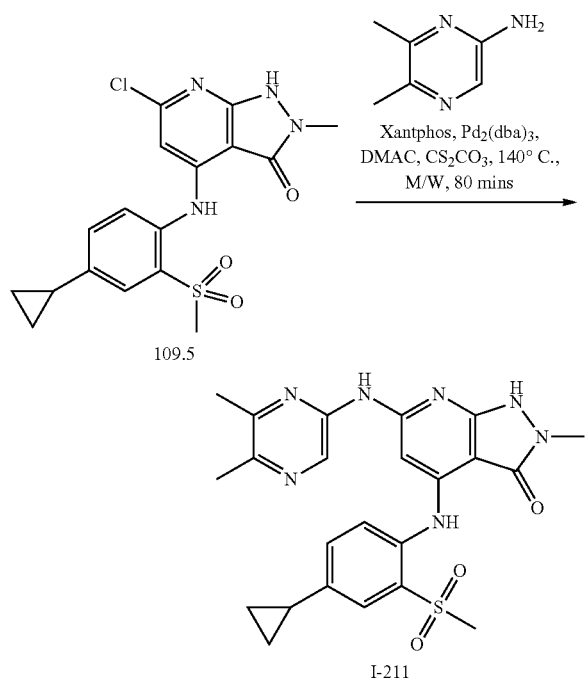

Compound I-211 was prepared from 5,6-dimethyl-pyrazin-2-amine and compound 109.5 using procedure described in Example 2 (Yield: 17.07%). MS(ES): m/z 480.25 [M+H]⁺, LCMS purity: 98.64%, HPLC purity: 96.56%, 1H NMR (DMSO-d6, 400 MHz): 10.75 (bs, 1H), 9.97 (s, 1H), 9.10 (s, 1H), 8.89 (s, 1H), 7.90-7.86 (m, 3H), 7.09 (s, 1H), 3.29 (s, 3H), 3.26 (s, 3H), 2.40 (s, 3H), 2.38 (s, 3H), 2.12-2.07 (m, 1H), 1.16-1.11 (m, 2H), 0.83-0.79 (m, 2H).

Example 111: Synthesis of 6-((4-((4-cyclopropyl-2-(methylsulfonyl)phenyl)amino)-2-methyl-3-oxo-2,3-dihydro-1H-pyrazolo[3,4-b]pyridin-6-yl)amino)pyrazine-2-carbonitrile, I-212

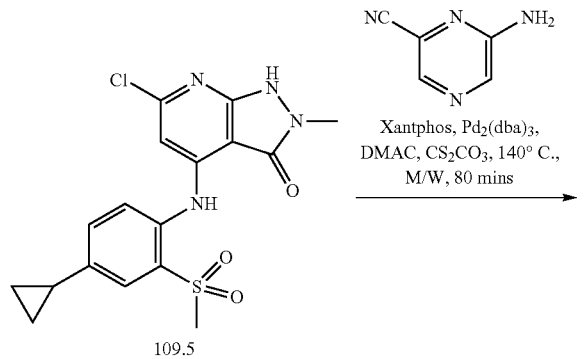

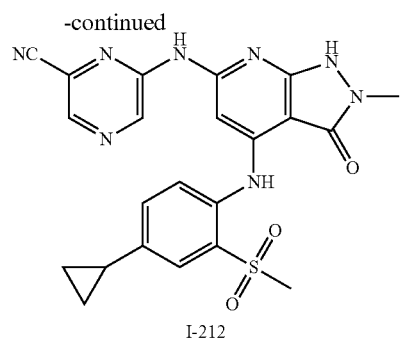

Compound I-212 was prepared from 6-aminopyrazine-2-carbonitrile and compound 109.5 using procedure described in Example 2 (Yield: 13.40%). MS(ES): m/z 477.36 [M+H]⁺, LCMS purity: 97.15%, HPLC purity: 96.84%, 1H NMR (DMSO-d6, 400 MHz): 10.89 (s, 1H), 10.63 (s, 1H), 9.22 (s, 1H), 9.12 (s, 1H), 8.63 (s, 1H), 7.78-7.76 (d, J=8.8 Hz, 1H), 7.71-7.70 (d, J=1.6 Hz, 1H), 7.48-7.46 (d, J=7.2 Hz, 1H), 7.23 (s, 1H), 3.30 (s, 3H), 3.16 (s, 3H), 2.11-2.07 (m, 1H), 1.05-1.02 (m, 2H), 0.79-1.77 (m, 2H).

Example 112: Synthesis of N-(4-((4-cyclopropyl-2-(methylsulfonyl)phenyl)amino)-2-methyl-3-oxo-2,3-dihydro-1H-pyrazolo[3,4-b]pyridin-6-yl)cyclopropanecarboxamide, I-201

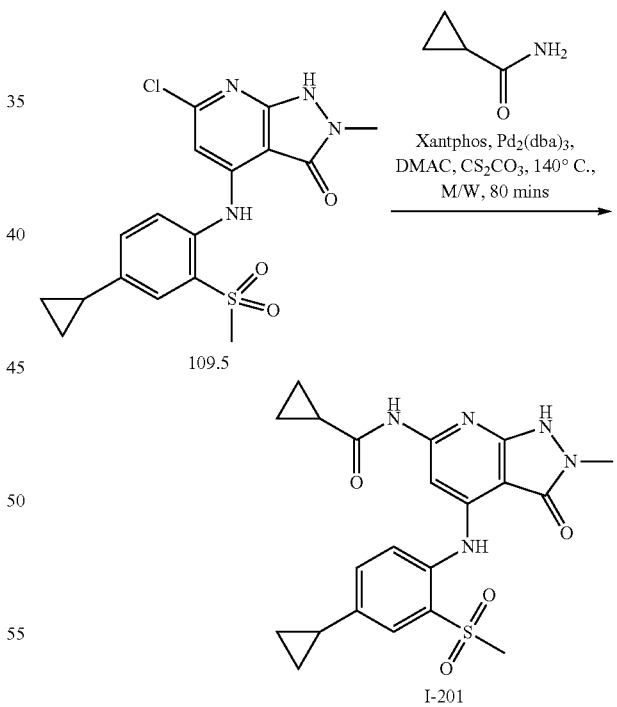

Compound I-112 was prepared from cyclopropanecarboxamide and compound 109.5 using procedure described in Example 2 (Yield: 3.71%). MS(ES): m/z 442.29 [M+H]⁺, LCMS purity: 97.07%, HPLC purity: 95.46%, 1H NMR (MeOD, 400 MHz): 7.77 (s, 1H), 7.72-7.70 (d, J=8.0 Hz, 1H), 7.51-7.49 (d, J=8.0 Hz, 2H), 3.48 (s, 3H), 3.09 (s, 3H), 2.10-2.06 (m, 1H), 1.83 (m, 1H), 1.13-1.09 (m, 2H), 0.99-0.93 (m, 4H), 0.83-0.79 (m, 2H).

Example 113: Synthesis of 6-((4-((4-cyclopropyl-2-(methylsulfonyl)phenyl)amino)-2-methyl-3-oxo-2,3-dihydro-1H-pyrazolo[3,4-b]pyridin-6-yl)amino)nicotinonitrile, I-213

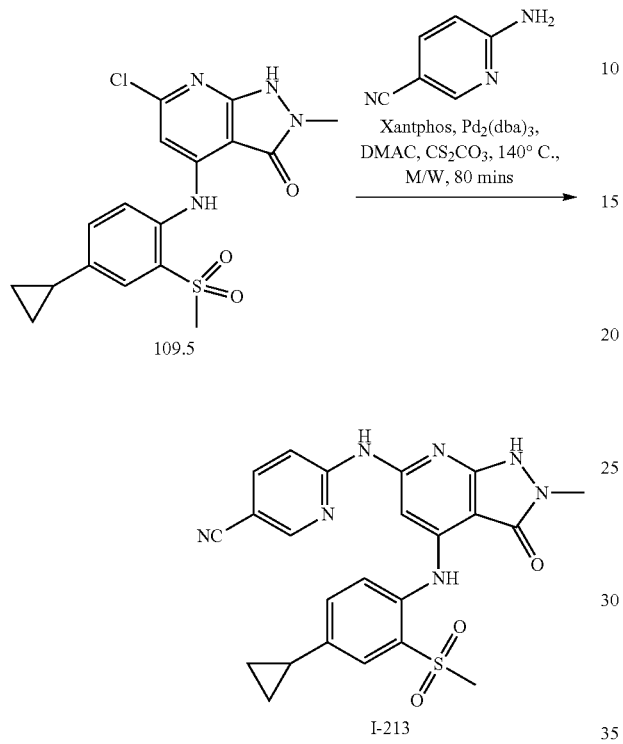

Compound I-213 was prepared from 6-aminonicotinonitrile and compound 109.5 using procedure described in Example 2 (Yield: 15.34%). MS(ES): m/z 476.25 [M+H]+, LCMS purity: 98.48%, HPLC purity: 95.09%, 1H NMR (DMSO-d6, 400 MHz): 10.91 (s, 1H), 10.37 (s, 1H), 9.02 (s, 1H), 8.66 (s, 1H), 8.13 (s, 2H), 7.72-7.70 (d, J=8.0 Hz, 1H), 7.65-7.64 (d, J=2.0 Hz, 1H), 7.53-7.51 (dd, J=2.0 Hz, 8.0 Hz, 1H), 6.98 (s, 1H), 3.29 (s, 3H), 3.16 (s, 3H), 2.13-2.08 (m, 1H), 1.08-1.03 (m, 2H), 0.79-0.75 (m, 2H).

Example 114: Synthesis of 6-((4-((4-cyclopropyl-2-(methylsulfonyl)phenyl)amino)-2-methyl-3-oxo-2,3-dihydro-1H-pyrazolo[3,4-b]pyridin-6-yl)amino)nicotinonitrile, I-33

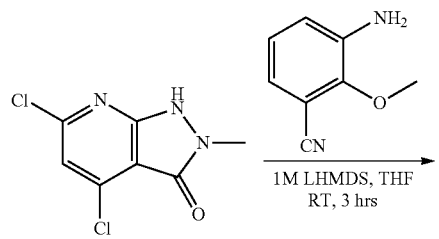

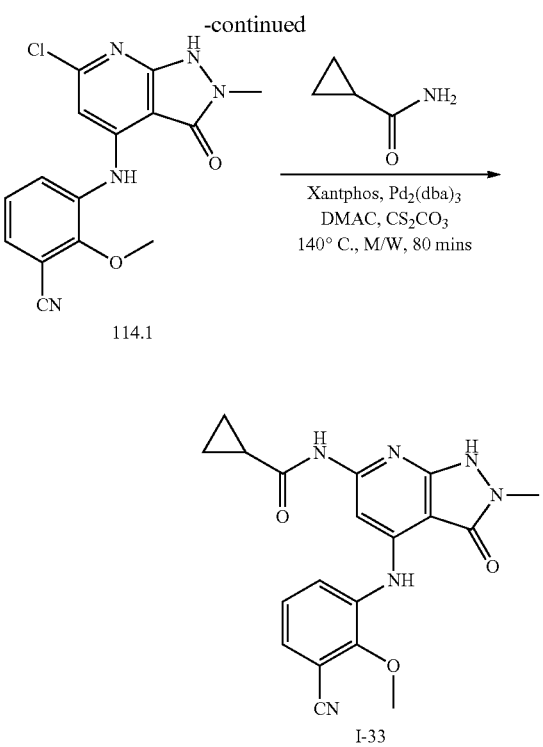

Synthesis of Compound 114.1.

Compound was synthesized from 3-amino-2-methoxybenzonitrile and 1.9 using general procedure A to obtain 114.1 (Yield: 66.12%). MS(ES): m/z 330.74 [M+H]+.

Compound I-33 was prepared from cyclopropanecarboxamide and compound 115.1 using procedure described in Example 2 (Yield: 11.62%). MS(ES): m/z 379.23 [M+H]+, LCMS purity: 99.15%, HPLC purity: 96.87%, 1H NMR (DMSO-d6, 400 MHz): 10.78 (bs, 2H), 8.81 (s, 1H), 7.80-7.78 (d, J=7.2 Hz, 1H), 7.63 (s, 1H), 7.58-7.56 (d, J=6.8 Hz, 1H), 7.39-7.35 (t, J=8.0 Hz, 1H), 3.96 (s, 3H), 3.34 (s, 3H), 2.03-2.00 (m, 1H), 0.81-0.80 (m, 4H).

Example 115: Synthesis of N-(2-methyl-4-((2-(N-methylmethylsulfonamido)phenyl)amino)-3-oxo-2,3-dihydro-1H-pyrazolo[3,4-b]pyridin-6-yl)cyclopropanecarboxamide, I-129

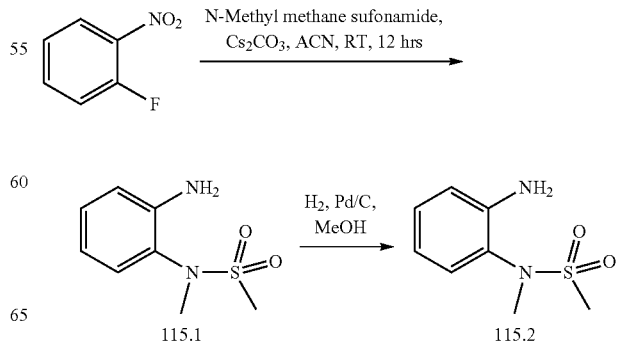

1H), 7.25-7.23 (t, J=6.8 Hz, 1H), 3.34 (s, 6H), 3.16 (s, 3H), 1.24 (m, 1H), 0.87-0.72 (m, 4H).

Example 116: Synthesis of I-133

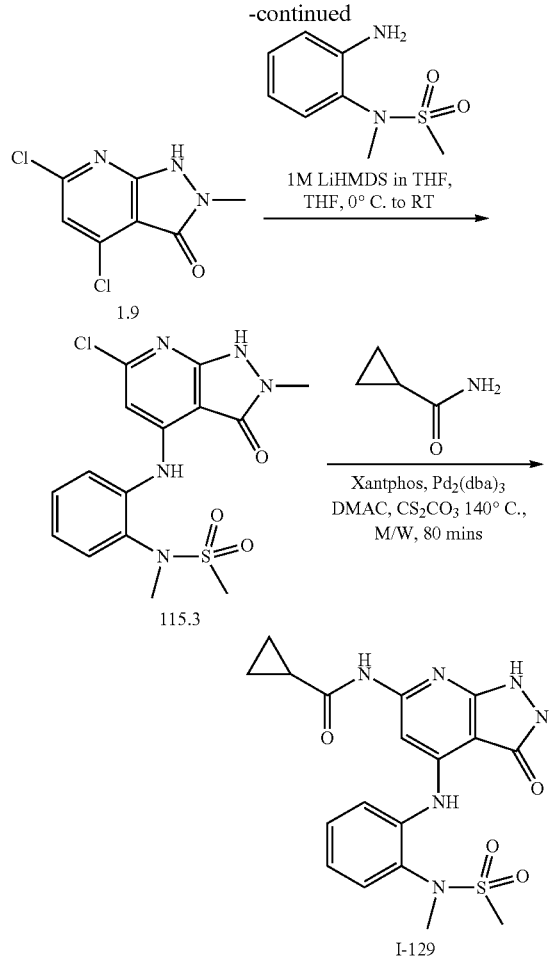

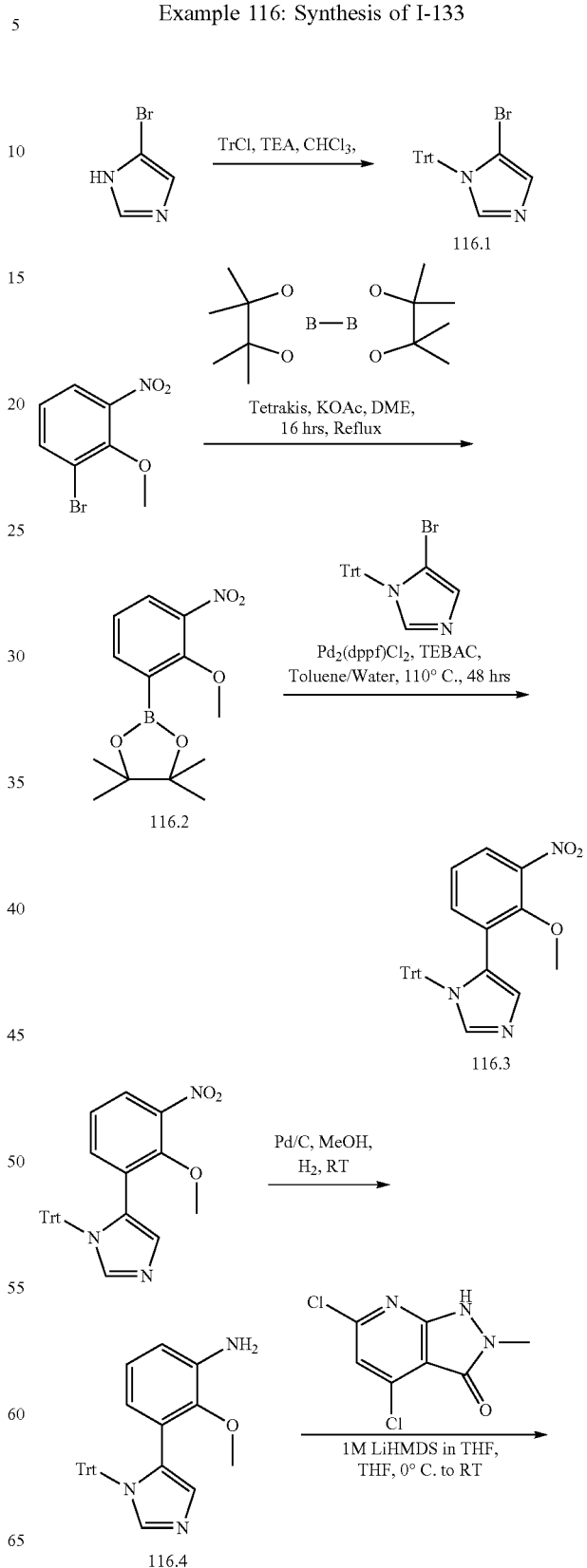

Synthesis of compound 115.1. To a solution of N-Methyl methane sulfonamide (0.85 g, 7.79 mmol, 1.1 eq) in acetonitrile (10 mL) was added cesium carbonate (0.608 g, 14.18 mmol, 2.0 eq). The reaction mixture was stirred at room temperature for 30 min. 1-Fluoro-2-nitrobenzene (1.0 g, 7.09 mmol, 1.0 eq) was added dropwise into reaction mixture and stirred at room temperature for 3 h. After completion of reaction, reaction mixture was filtered. Filtered solid was transferred into water, stirred for 30 min and dried under reduced pressure to obtain pure 115.1. (0.48 g, 29.42%). MS(ES): m/z 231.24 [M+H]$^+$.

Synthesis of compound 115.2. To a solution of 115.1 (0.48 g, 2.08 mmol, 1.0 eq) in methanol (1 mL), 10% palladium on charcoal (0.08 g) was added. Hydrogen was purged through reaction mixture for 2-3 h. After completion of reaction, reaction mixture was filtered through celite-bed and washed with ethanol. Filtrate was concentrated under reduced pressure to obtain 115.2 (0.322 g, 77.13%). MS(ES): m/z 201.26 [M+H]$^+$.

Synthesis of Compound 115.3

Compound 115.3 was synthesized from 1.9 and 115.2 using general procedure A (Yield: 34.26%).

Compound I-129 was prepared from cyclopropanecarboxamide and compound 115.3 using procedure described in Example 2 (Yield: 18.48%). MS(ES): m/z 431.35 [M+H]$^+$, LCMS purity: 100.00%, HPLC purity: 98.23%, 1H NMR (DMSO-d6, 400 MHz): 10.74 (s, 2H), 8.84 (s, 1H), 7.70 (s, 1H), 7.61-7.57 (t, J=7.2 Hz, 2H), 7.47-7.45 (t, J=6.8 Hz,

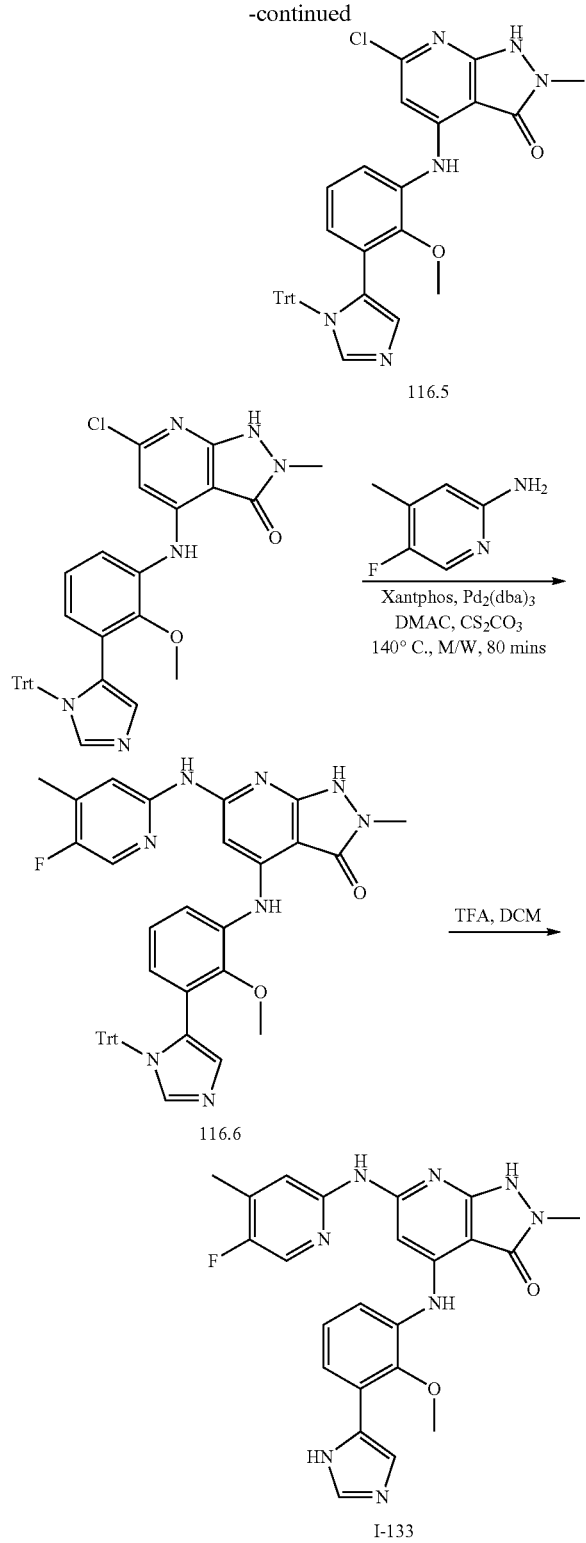

116.5

116.6

I-133

Synthesis of Compound 116.1.

To a solution of 5-bromo-1H-imidazole (3.0 g, 20.41 mmol, 1.0 eq) in dichloromethane (30 mL) were added triethyl amine (5.833 g, 57.76 mmol, 2.83 eq). Trityl chloride (6.15 g, 22.04 mmol, 1.08 eq) was added dropwise into reaction mixture at 0° C. The reaction mixture was stirred at room temperature for 3 h. After completion of reaction, reaction mixture was transferred into water and product was extracted with dichloromethane. Combined organic layer washed with brine solution, dried over sodium sulfate and concentrated under reduced pressure to obtain crude material. This was further triturated with diethyl ether to obtain pure 116.1. (6.0 g, 75.51%). MS(ES): m/z 390.30 [M+H]$^+$.

Synthesis of compound 116.2.

A mixture of 116.1 (3.0 g, 12.93 mmol, 1.0 eq), 1-bromo-2-methoxy-3-nitrobenzene (16.42 g, 64.65 mmol, 5.0 eq), Tetrakis(triphenylphosphine)palladium(0) (0.746 g, 0.646 mmol, 0.05 eq) and potassium acetate (3.80 g, 38.79 mmol, 3.0 eq) in dimethoxyethane (15 mL) was degassed with argon for 30 min. Further reaction mixture was refluxed for 16 h. After completion of reaction, reaction mixture was cooled to room temperature, transferred in water and extracted with ethyl acetate. Combined organic layer dried over sodium sulfate and concentrated under reduced pressure to obtain crude material. This was further purified by column chromatography and compound was eluted in 20% ethyl acetate in hexane to obtain pure 116.2 (3.0 g, 83.14%). MS(ES): m/z 280.10 [M+H]$^+$.

Synthesis of Compound 116.3.

A mixture of 116.2 (3.0 g, 10.75 mmol, 1.0 eq), 116.1 (6.28 g, 16.12 mmol, 1.5 eq), [1,1'-Bis(diphenylphosphino)ferrocene]dichloropalladium(II) (0.393 g, 0.537 mmol, 0.05 eq) and potassium carbonate (4.45 g, 32.25 mmol, 3.0 eq) in mixture of toluene (25 mL) and water (09 mL) was degassed with argon for 30 min. Further reaction mixture was stirred at 110° C. for 48 h. After completion of reaction, reaction mixture was cooled to room temperature, transferred in water and extracted with ethyl acetate. Combined organic layer dried over sodium sulfate and concentrated under reduced pressure to obtain crude material. This was further purified by column chromatography and compound was eluted in 15% ethyl acetate in hexane to obtain pure 116.3 (2.5 g, 50.39%). MS(ES): m/z 462.52 [M+H]$^+$.

Synthesis of Compound 116.4.

To a solution of 116.3 (2.5 g, 5.42 mmol, 1.0 eq) in ethanol (25 mL), 10% palladium on charcoal (0.2 g) was added. Hydrogen was purged through reaction mixture for 2-3 h. After completion of reaction, reaction mixture was filter through celite-bed and washed with ethanol. Filtrate was concentrated under reduced pressure to obtain 117.4 (1.79 g, 76.57%). MS(ES): m/z 432.54 [M+H]$^+$.

Synthesis of Compound 116.5.

Compound 116.5 was synthesized from 1.9 and 116.4 using general procedure A (Yield: 49.79%).

Synthesis of Compound 116.6.

Compound was synthesized from 116.5 and 5-fluoro-4-methylpyridin-2-amine using general procedure B (Yield: 28.66%).

Synthesis of Compound I-133.

To a solution of 116.6 (0.23 g, 0.327 mmol, 1.0 eq) in dichloromethane (3 mL) was added trifluoroacetic acid (0.373 g, 3.27 mmol, 10.0 eq) at 0° C. The reaction mixture was stirred at room temperature for 2 h. After completion of reaction, reaction mixture was transferred into saturated solution of sodium bicarbonate. Reaction mixture was extracted with ethyl acetate. Combined organic layer dried over sodium sulfate and concentrated under reduced pressure to obtain crude material. This was further purified by column chromatography using 5% methanol in dichloromethane as eluant to obtain pure I-133 (0.015 g, 9.95%). MS(ES): m/z 461.40 [M+H]$^+$, LCMS purity: 100.00%, HPLC purity: 99.14%, 1H NMR (DMSO-d6, 400 MHz): 14.62 (bs, 1H), 10.75 (s, 1H), 9.26 (s, 1H), 9.09 (s, 1H), 8.24

(s, 1H), 8.09 (s, 1H), 7.64-7.60 (t, J=8.0 Hz, 2H), 7.44-7.37 (m, 2H), 6.29 (s, 1H), 3.68 (s, 3H), 3.43 (s, 3H), 2.30 (s, 3H).

Example 117: Synthesis of N-(4-((3-fluoro-2-methoxy-4-(pyrrolidine-1-carbonyl)phenyl)amino)-2-methyl-3-oxo-2,3-dihydro-H-pyrazolo[3,4-b]pyridin-6-yl)cyclopropanecarboxamide, I-141

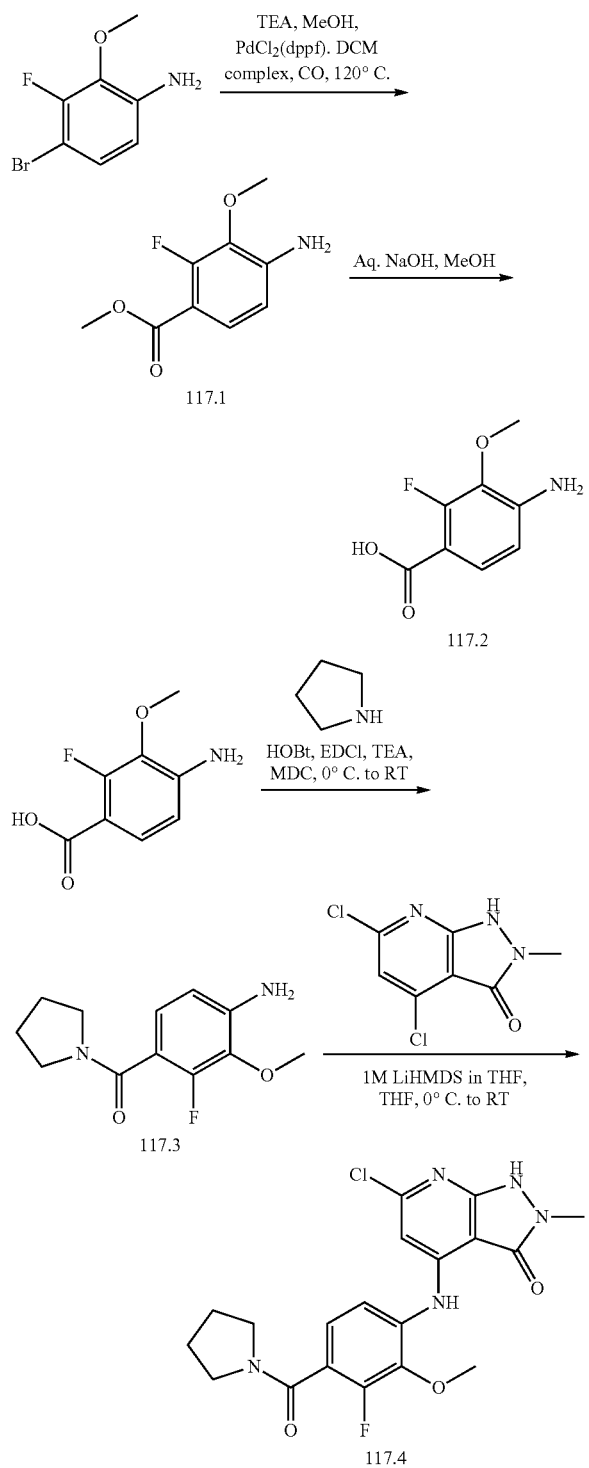

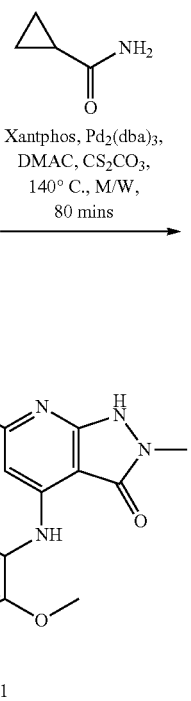

Synthesis of Compound 117.1.

To a solution of 4-bromo-3-fluoro-2-methoxyaniline (2.0 g, 9.09 mmol, 1.0 eq) in methanol (40 mL) was added triethyl amine (7.344 g, 72.72 mmol, 8.0 eq) and degassed with argon for 15 min. [1,1'-Bis(diphenylphosphino)ferrocene]dichloropalladium(II), complex with dichloromethane (0.742 g, 0.909 mmol, 0.1 eq) was added and again degassed for 15 min. The reaction mixture was stirred at 110° C. under carbon monoxide atmosphere for 10 h. After completion of reaction, reaction mixture was filtered through pad of celite. Filtrate was concentrated under reduced pressure to obtain crude material. This was further purified by column chromatography and compound was eluted in 20% ethyl acetate in hexane to obtain pure 117.1 (0.8 g, 44.19%). MS(ES): m/z 200.18 [M+H]$^+$.

Synthesis of Compound 117.2.

To a solution of 1.1 (0.8 g, 4.02 mmol, 1.0 eq) in methanol (40 mL) was added aqueous sodium hydroxide (0.322 g, 8.04 mmol, 2.0 eq). The reaction mixture was stirred at room temperature for 4 h. After completion of reaction, reaction mixture was transferred into water and acidified with citric acid. Obtained solid precipitate was washed with water followed by hexane. The solid was dried under reduced pressure to obtain pure 117.2 (0.8 g, 80.68%). MS(ES): m/z 186.15 [M+H]$^+$.

Synthesis of Compound 113.3.

To a solution of 117.2 (0.6 g, 3.24 mmol, 1.0 eq) and pyrrolidine (0.230 g, 3.24 mmol, 1.0 eq) in dichloromethane (10 mL) was added triethylamine (0.981 g, 9.72 mmol, 3.0 eq). The reaction mixture was cooled to 0° C. and hydroxybenzotriazole (0.991 g, 6.48 mmol, 2.0 eq) was added and stirred for 10 min followed by addition of 1-Ethyl-3-(3-dimethylaminopropyl)carbodiimide (1.0 g, 6.48 mmol, 2.0 eq). Reaction mixture was stirred at room temperature for 4 h. After completion of reaction, reaction mixture was transferred into water and extracted with ethyl acetate. Combined organic layer dried over sodium sulfate and concentrated under reduced pressure to obtain crude material. This was further purified by column chromatography and compound was eluted in 2% methanol in dichloromethane to obtain pure 117.3 (0.485 g, 58.28%). MS(ES): m/z 238.26 [M+H]⁺.

Synthesis of Compound 117.4.

Compound 117.4 was synthesized from 1.9 and 118.3 using general procedure A (Yield: 51.93%).

Synthesis of Compound I-141.

Compound was synthesized from 117.4 and cyclopropanecarboxamide using general procedure B (Yield: 6.73%). MS(ES): m/z 469.42 [M+H]⁺, LCMS purity: 95.09%, HPLC purity: 98.20%, 1H NMR (DMSO-d6, 400 MHz): 10.83 (s, 2H), 8.95 (s, 1H), 7.83 (s, 1H), 7.36-7.34 (d, J=8.4 Hz, 1H), 7.22-7.19 (t, J=8.0 Hz, 1H), 3.91 (s, 3H), 3.48-3.45 (t, J=6.8 Hz, 2H), 3.32 (s, 3H), 3.29-3.26 (t, J=6.8 Hz, 2H), 2.03-1.99 (m, 1H), 1.90-1.82 (m, 4H), 0.88-0.80 (m, 4H).

Example 118: Synthesis of 4-((4-chloro-2-(methylsulfonyl)phenyl)amino)-2-methyl-6-((6-methylpyridazin-3-yl)amino)-1,2-dihydro-3 1-pyrazolo[3,4-b]pyridin-3-one, I-157

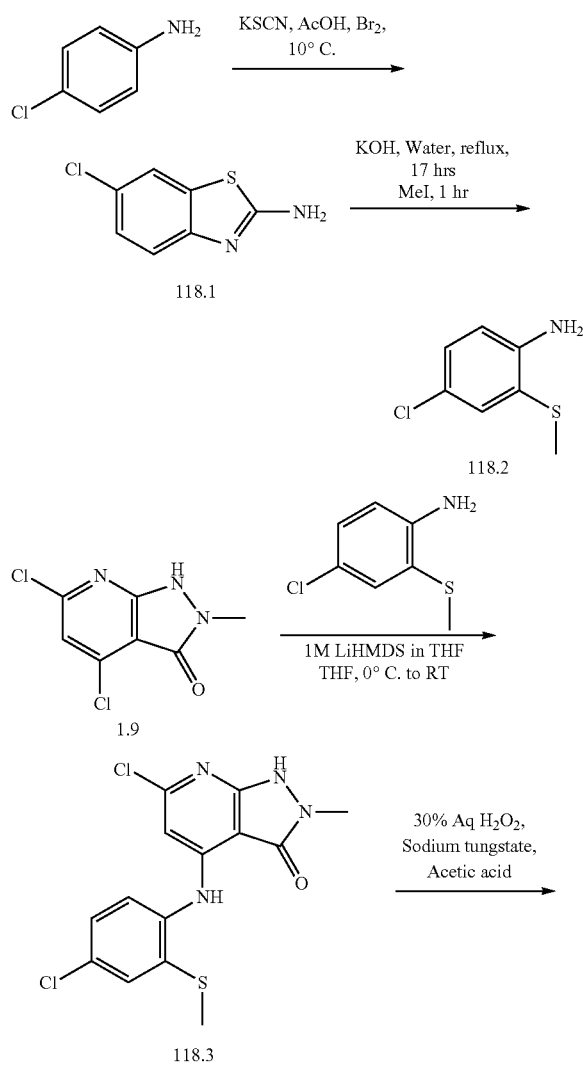

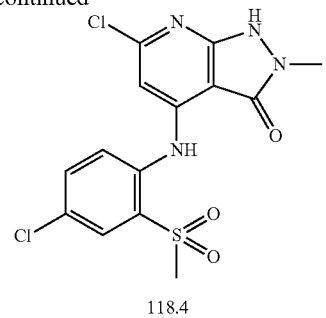

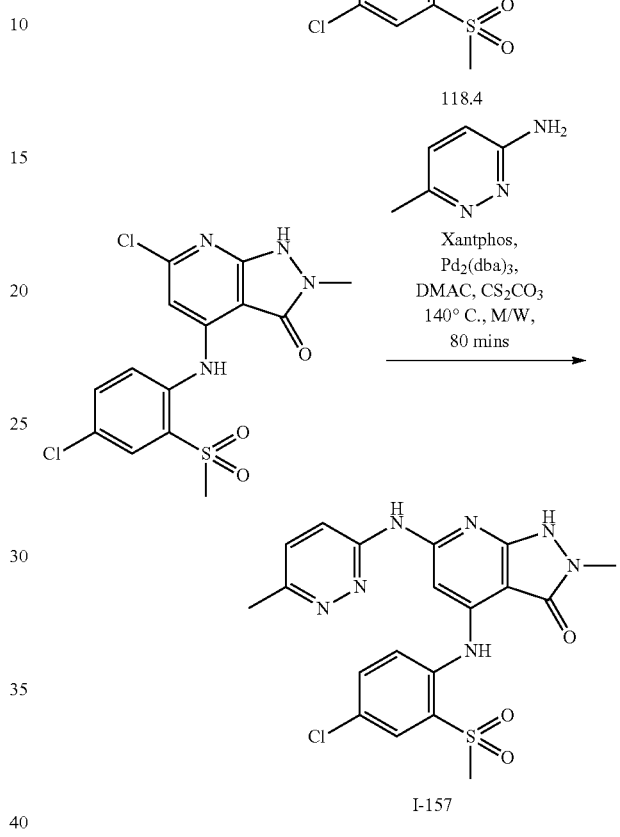

Synthesis of Compound 118.1.

To a solution of 4-chloroaniline (3.0 g, 23.52 mmol, 1.0 eq) in acetic acid (90 mL) were added Potassium thiocyanate (2.28 g, 23.52 mmol, 1.0 eq). The reaction mixture was cooled at 10° C. and bromine solution (3.76 g, 23.52 mmol, 1.0 eq) was added dropwise. Reaction mixture was further stirred at room temperature for 3 h. After completion of reaction, reaction mixture was filtered and washed with acetic acid. Filtered solid was heated in water and then neutralized with aqueous ammonia to obtain solid which was filtered and dried well to obtain pure 118.1. (2.5 g, 57.58%). MS(ES): m/z 185.64 [M+H]⁺.

Synthesis of Compound 118.2.

To 118.1 (2.5 g, 13.54 mmol, 1.0 eq) a solution of potassium hydroxide (9.1 g, 162.48 mmol, 12.0 eq) in water (50 mL) was added. Reaction mixture was refluxed for 17 h. Reaction mixture was cooled to room temperature and methyl iodide was added (2.11 g, 14.89 mmol, 1.1 eq) and stirred for 1 h. After completion of reaction, reaction mixture was extracted with ethyl acetate. Organic layer was combined, dried over sodium sulphate and concentrated under reduced pressure to obtain crude material. This was further purified by column chromatography and compound was eluted in 20% ethyl acetate in hexane as eluent to obtain 118.2. (1.3 g, 55.29%). MS(ES): m/z 174.66 [M+H]⁺.

Synthesis of Compound 118.3.

Compound 118.3 was synthesized from 1.9 and 118.2 using general procedure A. (Yield: 46.03%). MS (ES): m/z 356.24 [M+H]+.

Synthesis of Compound 118.4.

To a solution of 118.3 (0.15 g, 0.422 mmol, 1 eq) in acetic acid (1.0 mL) was added 30% hydrogen peroxide (0.287 g, 8.44 mmol, 20 eq) and sodium tungstate dihydrate (0.14 g, 0.422 mmol, 1 eq). Reaction mixture was stirred at room temperature for 2 h. After completion of reaction, reaction mixture was transferred in ice-water and precipitated product was filtered, washed with 5% ethyl acetate in hexane and dried well to obtain 118.4. (0.11 g, Yield: 67.27%). MS(ES): m/z 388.24 [M+H]+.

Synthesis of compound I-157. Compound was synthesized from 118.4 and 6-methylpyridazin-3-amine using general procedure B to obtain 1-157 (Yield: 27.56%). MS(ES): m/z 460.32 [M+H]+, LCMS purity: 100.00%, HPLC purity: 99.62%, 1H NMR (DMSO-d6, 400 MHz): 10.94 (bs, 1H), 10.21 (s, 1H), 9.09 (s, 1H), 8.23-8.21 (d, J=8.4 Hz, 1H), 7.89-7.84 (m, 3H), 7.50-7.48 (d, J=8.8 Hz, 1H), 6.94 (s, 1H), 3.28 (s, 3H), 3.27 (s, 3H), 2.56 (s, 3H).

Example 119: Synthesis of (1S,2S)—N-(4-((4-cyclopropyl-2-(methylsulfonyl)phenyl)amino)-2-methyl-3-oxo-2,3-dihydro-1H-pyrazolo[3,4-b]pyridin-6-yl)-2-fluorocyclopropane-1-carboxamide, I-210

Synthesis of compound 119.1. To a solution of (1S,2S)-2-fluorocyclopropane-1-carboxylic acid (0.25 g, 2.40 mmol, 1.0 eq) in acetone (4 mL) were added triethyl amine (0.364 g, 3.6 mmol, 1.5 eq) and ethyl chloroformate (0.286 g, 2.64 mmol, 1.1 eq). The reaction mixture was stirred at room temperature for 1 h. Reaction mixture was filtered and added aqueous ammonia (4 mL) to filtrate dropwise. Further, reaction mixture was stirred at room temperature for 16 h. After completion of reaction, reaction mixture was filtered. Filtered solid was dried under reduced pressure to obtain pure 119.1. (0.2 g, 80.76%). MS(ES): m/z 104.10 [M+H]+.

Synthesis of Compound I-210.

Compound was synthesized from 119.1 and 109.5 using general procedure B. (Yield: 11.11%). MS(ES): m/z 460.41 [M+H]+, LCMS purity: 97.95%, HPLC purity: 100.00%, Chiral HPLC purity: 97%, 1H NMR (DMSO-d6, 400 MHz): 10.82 (s, 2H), 9.01 (s, 1H), 7.65-7.60 (m, 3H), 7.51-7.49 (d, J=7.2 Hz, 1H), 4.98-4.81 (m, 1H), 3.29 (s, 3H), 3.14 (s, 3H), 2.33-2.08 (m, 2H), 1.59-1.54 (m, 2H), 1.20-1.00 (m, 2H), 0.75-1.73 (m, 2H).

Example 120: Synthesis of (1S,2S)-2-fluoro-N-(2-methyl-4-((2-(N-methylmethylsulfonamido)phenyl)amino)-3-oxo-2,3-dihydro-1H-pyrazolo[3,4-b]pyridin-6-yl)cyclopropane-1-carboxamide, I-216

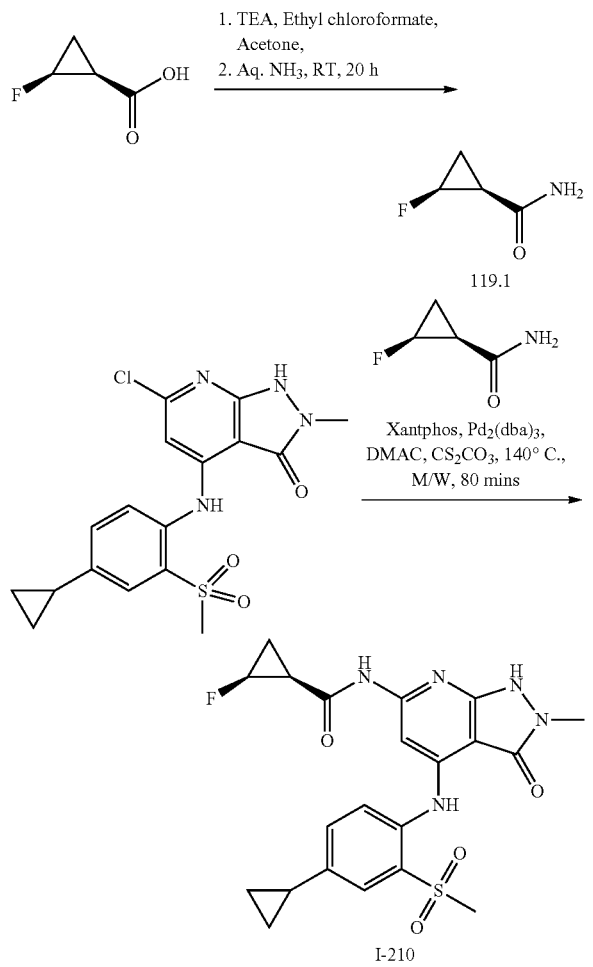

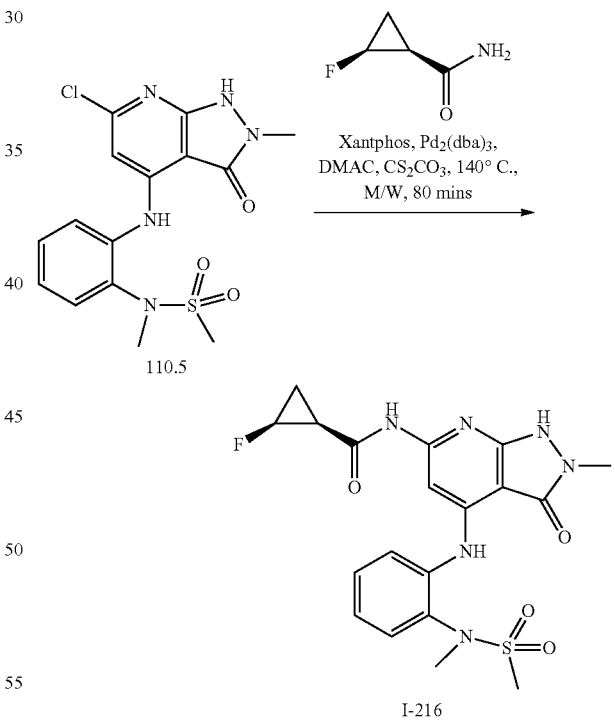

Synthesis of compound I-216. Compound I-216 was synthesized from 109.5 and 119.1 using general procedure B (Yield: 11.07%). MS(ES): m/z 449.30 [M+H]+, LCMS purity: 100.00%, HPLC purity: 98.69%, Chiral HPLC: 100%, 1H NMR (DMSO-d6, 400 MHz): 10.79 (s, 1H), 8.86 (s, 1H), 7.76 (s, 1H), 7.62-7.58 (m, 2H), 7.49-7.45 (t, J=7.2 Hz, 1H), 7.27-7.23 (t, J=8.0 Hz, 1H), 5.01-4.80 (m, 1H), 3.16 (s, 6H), 2.54 (s, 3H), 2.23-2.21 (m, 1H), 1.66-1.55 (m, 1H), 1.19-1.10 (m, 1H).

Example 121: Synthesis of N-(4-((4-chloro-2-(N-methylmethylsulfonamido)phenyl)amino)-2-methyl-3-oxo-2,3-dihydro-1H-pyrazolo[3,4-b]pyridin-6-yl)cyclopropanecarboxamide, I-228

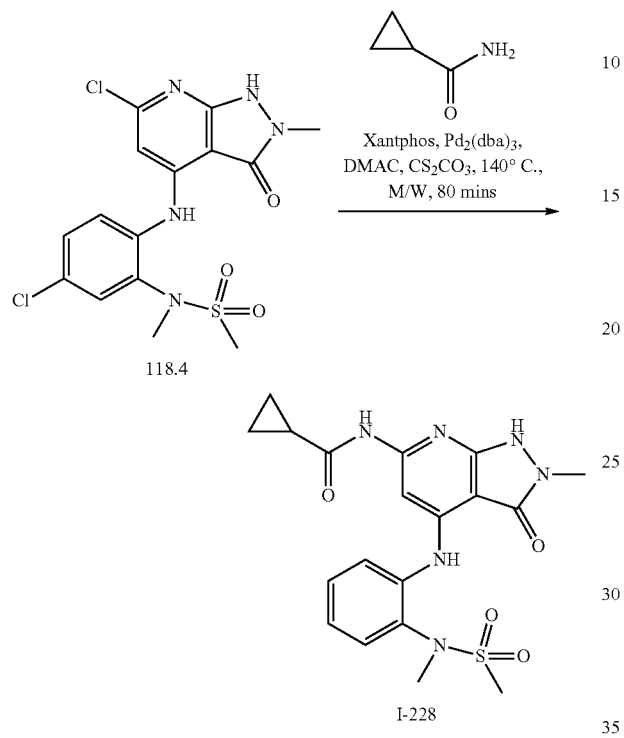

Synthesis of compound I-228. Compound I-228 was synthesized from 118.4 and cyclopropanecarboxamide using general procedure B (Yield: 27.98%). MS(ES): m/z 465.20 [M+H]$^+$, LCMS purity: 100.00%, HPLC purity: 99.36%, 1H NMR (DMSO-d6, 400 MHz): 10.76 (s, 1H), 8.81 (s, 1H), 7.75-7.74 (d, J=2.4 Hz, 1H), 7.63-7.53 (m, 4H), 3.34 (s, 3H), 3.20 (s, 3H), 3.18 (s, 3H), 2.03-2.00 (qui, J=6.0 Hz, 1H), 0.81-0.79 (d, J=6.0 Hz, 4H).

Example 122: Synthesis of N-(2-methyl-4-((4-methyl-2-(N-methylmethylsulfonamido)phenyl)amino)-3-oxo-2,3-dihydro-1H-pyrazolo[3,4-b]pyridin-6-yl)cyclopropanecarboxamide, I-229

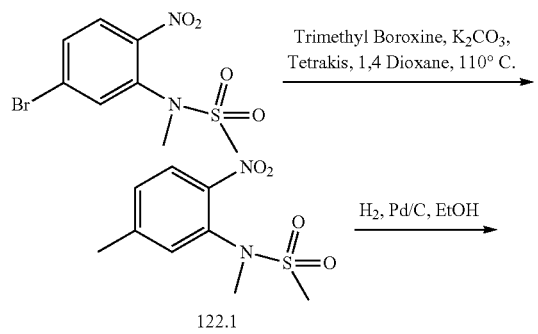

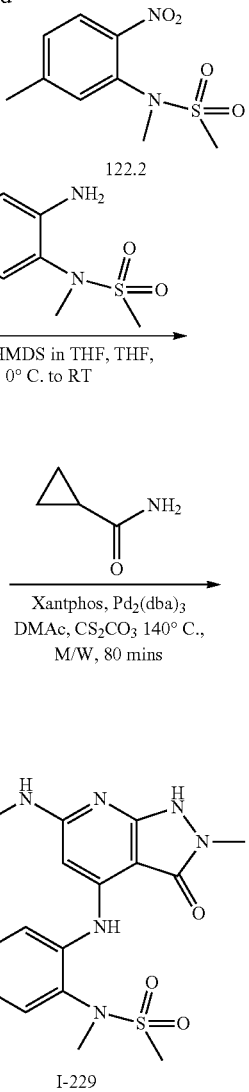

Synthesis of compound 122.1. A mixture of N-(5-bromo-2-nitrophenyl)-N-methylmethanesulfonamide (1.5 g, 4.85 mmol, 1.0 eq), trimethyl boroxine (1.83 g, 14.55 mmol, 3.0 eq), Tetrakis(triphenylphosphine)palladium(0) (0.28 g, 0.242 mmol, 0.05 eq) and potassium carbonate (2.0 g, 14.55 mmol, 3.0 eq) in 1,4-dioxane (15 mL) were degassed with argon for 30 min. Further reaction mixture was stirred at 110° C. for 4 h. After completion of reaction, reaction mixture was cooled to room temperature, transferred in water and extracted with ethyl acetate. Combined organic layer dried over sodium sulfate and concentrated under reduced pressure to obtain crude material. This was further purified by column chromatography and compound was eluted in 20% ethyl acetate in hexane to obtain pure 122.1 (0.9 g, 75.93%). MS(ES): m/z 245.27 [M+H]$^+$.

Synthesis of Compound 122.2.

To a solution of 123.1 (0.9 g, 3.68 mmol, 1.0 eq) in ethanol (5 mL), 10% palladium on charcoal (0.2 g) was added. Hydrogen was purged through reaction mixture for 2-3 h. After completion of reaction, reaction mixture was filter through celite-bed and washed with ethanol. Filtrate was concentrated under reduced pressure to obtain 122.2 (0.7 g, 88.66%). MS(ES): m/z 215.28 [M+H]$^+$.

Synthesis of Compound 122.3.

Compound 122.3 was synthesized from 122.2 and 1.9 using general procedure A (Yield: 41.31%).

Synthesis of Compound I-229.

Compound was synthesized from 122.3 and 1.9 using general procedure B. (Yield: 29.69%). MS(ES): m/z 445.32 [M+H]$^+$, LCMS purity: 99.31%, HPLC purity: 98.78%, 1H NMR (MeOD, 400 MHz): 7.52-7.50 (d, J=8.0 Hz, 1H), 7.45 (s, 2H), 7.33-7.31 (d, J=8.0 Hz, 1H), 3.48 (s, 3H), 3.27 (s, 3H), 3.07 (s, 3H), 2.43 (s, 3H), 1.80 (m, 1H), 1.03-0.94 (m, 4H).

Example 123: Synthesis of 4-((4-chloro-2-(methylsulfonyl)phenyl)amino)-2-methyl-6-((6-(trifluoromethyl)-pyridin-2-yl)amino)-1,2-dihydro-3H-pyrazolo[3,4-b]pyridin-3-one, I-209

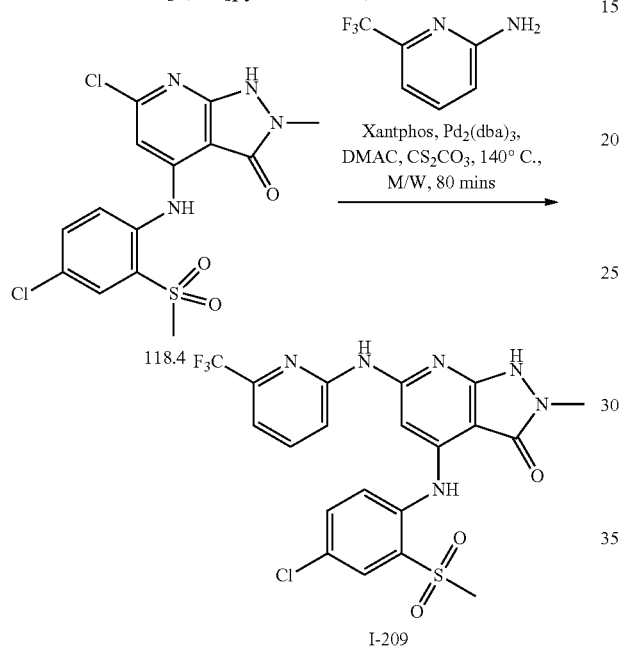

Synthesis of compound I-209. Compound I-209 was synthesized from 118.4 and 6-(trifluoromethyl)pyridin-2-amine using general procedure B (Yield: 12.58%). MS(ES): m/z 513.34 [M+H]$^+$, LCMS purity: 98.38%, HPLC purity: 97.15%, 1H NMR (DMSO-d6, 400 MHz): 10.90 (s, 1H), 10.27 (s, 1H), 9.10 (s, 1H), 8.14-8.12 (d, J=8.0 Hz, 1H), 7.97-7.78 (m, 4H), 7.39-7.37 (d, J=8.0 Hz, 1H), 7.19 (s, 1H), 3.30 (s, 3H), 3.27 (s, 3H).

Example 124: Synthesis of 4-((4-cyclopropyl-2-(methylsulfonyl)phenyl)amino)-2-methyl-6-((6-(trifluoromethyl)-pyridin-2-yl)amino)-1,2-dihydro-3H-pyrazolo[3,4-b]pyridin-3-one, I-215

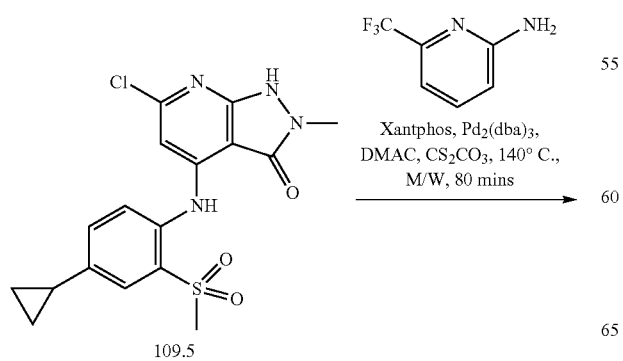

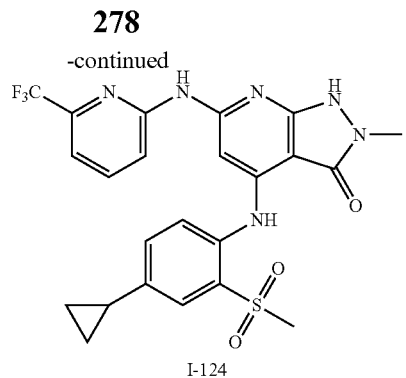

Synthesis of compound I-215. Compound I-215 was synthesized using from 109.5 and 6-(trifluoromethyl)pyridin-2-amine general using procedure B (Yield: 19.70%). MS(ES): m/z 519.39 [M+H]$^+$, LCMS purity: 96.47%, HPLC purity: 97.77%, 1H NMR (DMSO-d6, 400 MHz): 10.77 (s, 1H), 10.21 (s, 1H), 8.96 (s, 1H), 8.10-8.08 (d, J=8.0 Hz, 1H), 7.95-7.91 (t, J=8.0 Hz, 1H), 7.69-7.67 (d, J=8.0 Hz, 2H), 7.42-7.40 (d, J=8.0 Hz, 1H), 7.36-7.34 (d, J=8.0 Hz, 1H), 7.12 (s, 1H), 3.28 (s, 3H), 3.15 (s, 3H), 2.11 (m, 1H), 10.6-1.04 (m, 2H), 0.75-0.74 (m, 2H).

Example 125: Synthesis of N-(4-(4-((4-chloro-2-(N-methylmethylsulfonamido)phenyl)amino)-2-methyl-3-oxo-2,3-dihydro-1H-pyrazolo[3,4-b]pyridin-6-yl) cyclopropanecarboxamide, I-232

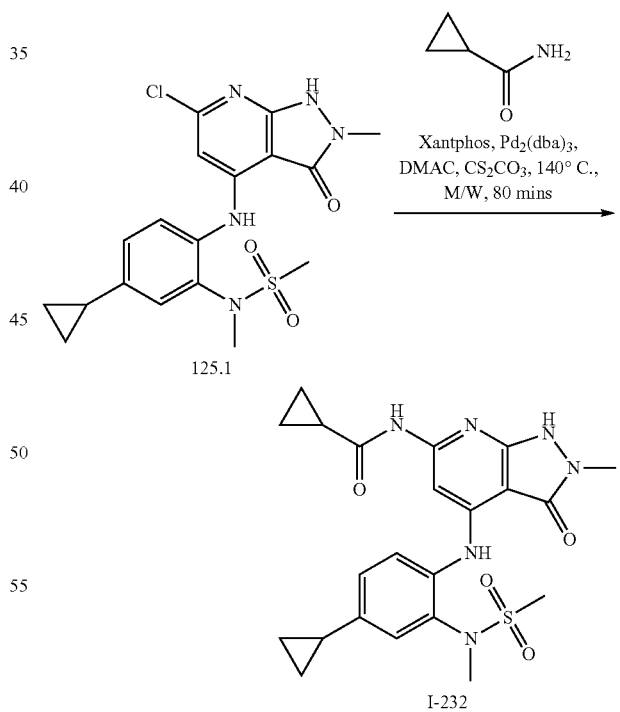

Synthesis of compound I-232. Compound I-232 was synthesized using from 125.1 (prepared in a manner analogous to 109.5) and cyclopropanecarboxamide using procedure B (Yield: 25.62%). MS(ES): m/z 471.37 [M+H]$^+$, LCMS purity: 98.97%, HPLC purity: 94.23%, 1H NMR (DMSO-d6, 400 MHz): 10.71 (s, 2H), 8.68 (s, 1H), 7.57 (s, 1H), 7.47-7.43 (d, J=8.4 Hz, 1H), 7.32-7.31 (d, J=2.4 Hz, 1H), 7.16-7.14 (d, J=8.0 Hz, 1H), 3.29 (s, 3H), 3.14 (s, 6H), 2.02-1.96 (m, 2H), 1.00-0.98 (m, 2H), 0.79-0.73 (m, 6H).

Example I-126: Synthesis of 4-((4-fluoro-2-(methylsulfonyl)phenyl)amino)-2-methyl-6-((6-methylpyridazin-3-yl)amino)-1,2-dihydro-3H-pyrazolo[3,4-b]pyridin-3-one, I-198

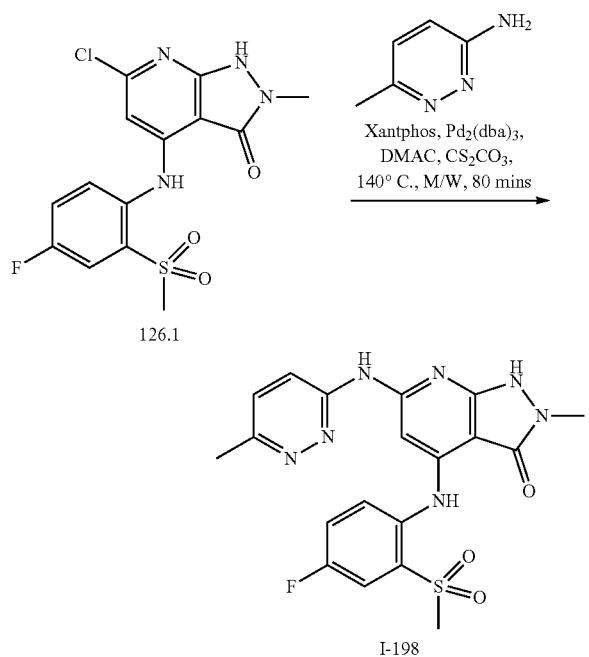

Synthesis of compound I-198. Compound I-198 was synthesized using from 126.1 (prepared in a manner analogous to 118.4) and 6-methylpyridazin-3-amine using procedure B (Yield: 9.48%). MS(ES): m/z 444.32 [M+H]+, LCMS purity: 97.70%, HPLC purity: 97.02%, 1H NMR (DMSO-d6, 400 MHz): 10.19 (s, 1H), 8.92 (s, 1H), 8.23-8.20 (d, J=12 Hz, 1H), 8.17 (s, 1H), 7.90-7.86 (m, 1H), 7.75-7.71 (m, 2H), 7.50-7.48 (d, J=8.0 Hz, 1H), 6.80 (s, 1H), 3.28 (s, 3H), 3.25 (s, 3H), 2.55 (s, 3H).

Example 127: Synthesis of N-(2-methyl-4-((2-(N-methylmethylsulfonamido)-4-(trifluoromethyl)phenyl)amino)-3-oxo-2,3-dihydro-1H-pyrazolo[3,4-b]pyridin-6-yl)cyclopropanecarboxamide, I-235

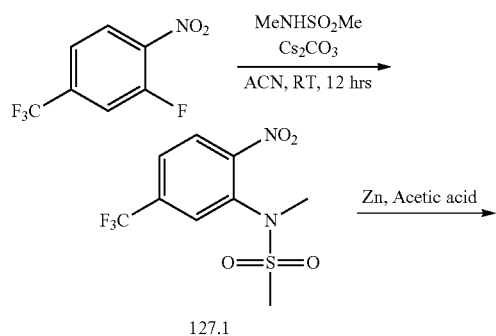

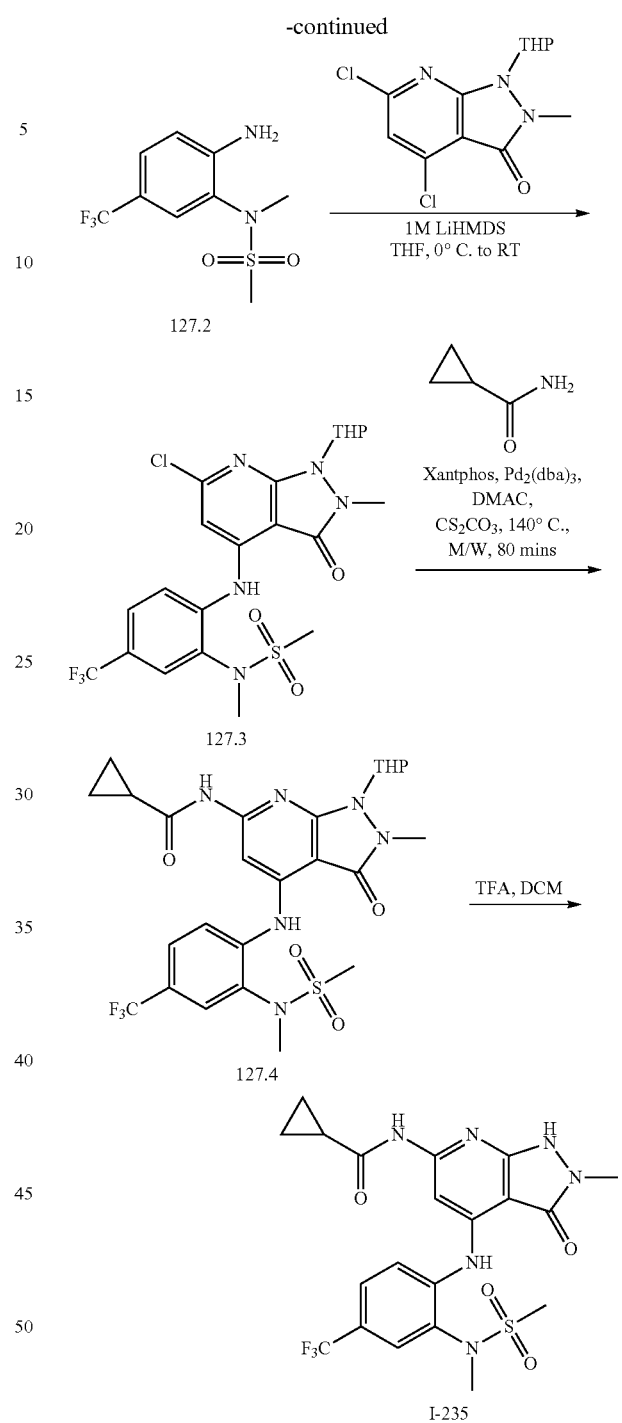

Synthesis of Compound 127.1.

To a solution of N-Methyl methane sulfonamide (5.733 g, 52.60 mmol, 1.1 eq) in acetonitrile (100 mL) were added cesium carbonate (31.18 g, 95.64 mmol, 2.0 eq). The reaction mixture was stirred at room temperature for 30 min. Compound 1 (10.0 g, 47.82 mmol, 1.0 eq) was added dropwise into reaction mixture and stirred at room temperature for 3 h. After completion of reaction, reaction mixture was filtered. Filtered solid was transferred into water, stirred for 30 min and dried under reduced pressure to obtain pure 127.1. (10 g, 70.11%). MS(ES): m/z 299.24 [M+H]+.

Synthesis of Compound 127.2.

To a solution of 128.1 (10.0 g, 33.53 mmol, 1.0 eq) in acetic acid (100 mL) was added zinc powder (10.9 g, 167.65 mmol, 5.0 eq) portion wise. The reaction mixture was stirred at room temperature for 20 h. After completion of reaction, reaction mixture was transferred into saturated solution of sodium bicarbonate. Reaction mixture was extracted with ethyl acetate. Combined organic layer dried over sodium sulfate and concentrated under reduced pressure to obtain crude material. This was further triturated with diethyl ether to obtain pure 127.2. (8.0 g, 88.94%). MS(ES): m/z 269.25 $[M+H]^+$.

Synthesis of Compound 127.3.

Compound 127.3 was synthesized from 127.2 using general procedure A (Yield: 56.59%).

Synthesis of Compound 127.4.

Compound 127.4 was synthesized from 128.3 and cyclopropanecarboxamide using procedure B (Yield: 54.99%).

Synthesis of Compound I-235.

To a solution of 127.4 (0.18 g, 0.31 mmol, 1.0 eq) in dichloromethane (4 mL) was added trifluoroacetic acid (0.353 g, 3.1 mmol, 10.0 eq) at 0° C. The reaction mixture was stirred at room temperature for 2 h. After completion of reaction, reaction mixture was transferred into saturated solution of sodium bicarbonate. Reaction mixture was extracted with ethyl acetate. Combined organic layer dried over sodium sulfate and concentrated under reduced pressure to obtain crude material. This was further purified by column chromatography and compound was eluted in 5% methanol in dichloromethane to obtain pure I-235 (0.12 g, 77.92%). MS(ES): m/z 499.36 $[M+H]^+$, LCMS purity: 95.29%, HPLC purity: 95.29%, 1H NMR (MeOD, 400 MHz): 7.92 (s, 1H), 7.90-7.88 (d, J=8.4 Hz, 1H), 7.80-7.78 (d, J=8.4 Hz, 1H), 7.45 (s, 1H), 3.48 (s, 3H), 3.34 (s, 3H), 3.18 (s, 3H), 1.87-1.84 (m, 1H), 1.03-0.90 (m, 4H).

Example 128: Synthesis of N-(4-((2-(dimethylphosphoryl)phenyl)amino)-2-methyl-3-oxo-2,3-dihydro-1H-pyrazolo[3,4-b]pyridin-6-yl)cyclopropanecarboxamide, I-125

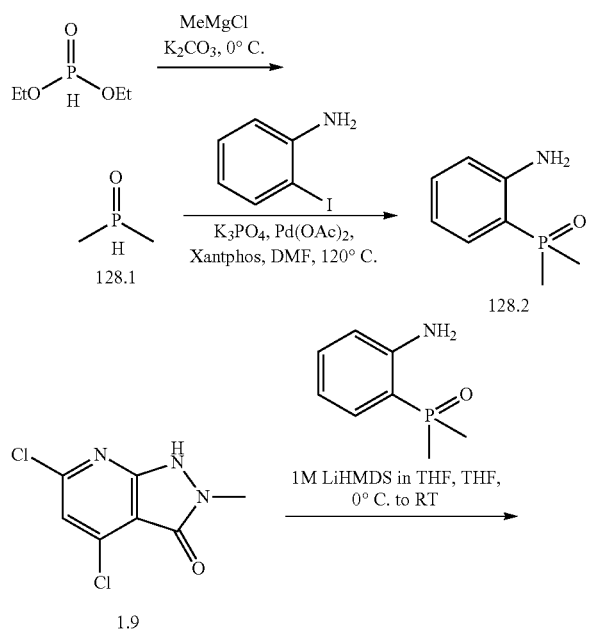

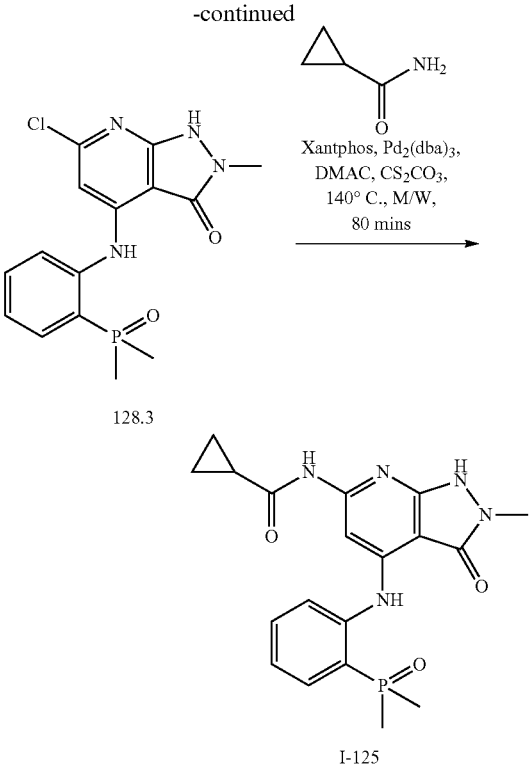

Synthesis of Compound 128.1.

To a solution of diethyl phosphonate (5.0 g, 36.20 mmol, 1 eq) in tetrahydrofuran was added methyl magnesium chloride (5.43 g, 72.4 mmol, 2 eq) and potassium carbonate (14.98 g, 108.6 mmol, 3 eq). The reaction mixture was stirred at 0° C. for 4 h. After completion of reaction, reaction mixture was transferred in water and extracted with ethyl acetate. Organic layer was combined, dried over sodium sulphate and concentrated under reduced pressure to obtain 128.1. (2.3 g, 81.39%). MS(ES): m/z 79.05 $[M+H]^+$.

Synthesis of Compound 128.2.

To a solution of 2-iodoaniline (1.0 g, 4.57 mmol, 1.0 eq) in dimethylformamide (10 mL) were added compound 128.1 (0.463 g, 5.94 mmol, 1.3 eq) and potassium phosphate (1.937 g, 9.14 mmol, 2.0 eq). The reaction mixture was degassed for 10 min under argon atmosphere, and palladium acetate (0.103 g, 0.457 mmol, 0.1 eq) and 4,5-Bis(Diphenylphosphino)-9,9-dimethylxanthene (0.529 g, 0.914 mmol, 0.2 eq) were added. Reaction mixture was again degassed for 10 min and stirred at 120° C. for 6 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 3% methanol in dichloromethane as eluent to obtain 128.2. (0.48 g, 62.15%). MS(ES): m/z 170.16 $[M+H]^+$.

Synthesis of Compound 128.3.

Compound was synthesized from 1.9 and 128.2 using general procedure A to obtain 128.3 (Yield: 5.02%). MS(ES): m/z 351.74 $[M+H]^+$.

Synthesis of Compound I-125.

Compound I-125 was synthesized from 128.3 and cyclopropanecarboxamide using general procedure B (Yield: 19.32%). MS(ES): m/z 400.39 $[M+H]^+$, LCMS purity: 100.00%, HPLC purity: 98.05%, 1H NMR (DMSO-d6, 400

MHz): 10.71 (s, 1H), 9.39 (s, 1H), 7.73-7.68 (dd, J=8.0 Hz, 12.0 Hz, 1H), 7.62-7.53 (m, 2H), 7.49 (s, 1H), 7.33-7.29 (t, J=7.6 Hz, 1H), 3.28 (s, 3H), 1.97-1.96 (m, 1H), 1.70 (s, 3H), 1.67 (s, 3H), 0.77-0.75 (m, 4H).

Example 129: Synthesis of N-(4-((2-methoxy-3-(5-methyl-1H-1,2,4-triazol-3-yl)phenyl)amino)-2-methyl-3-oxo-2,3-dihydro-1H-pyrazolo[3,4-b]pyridin-6-yl)cyclopropanecarboxamide, I-62

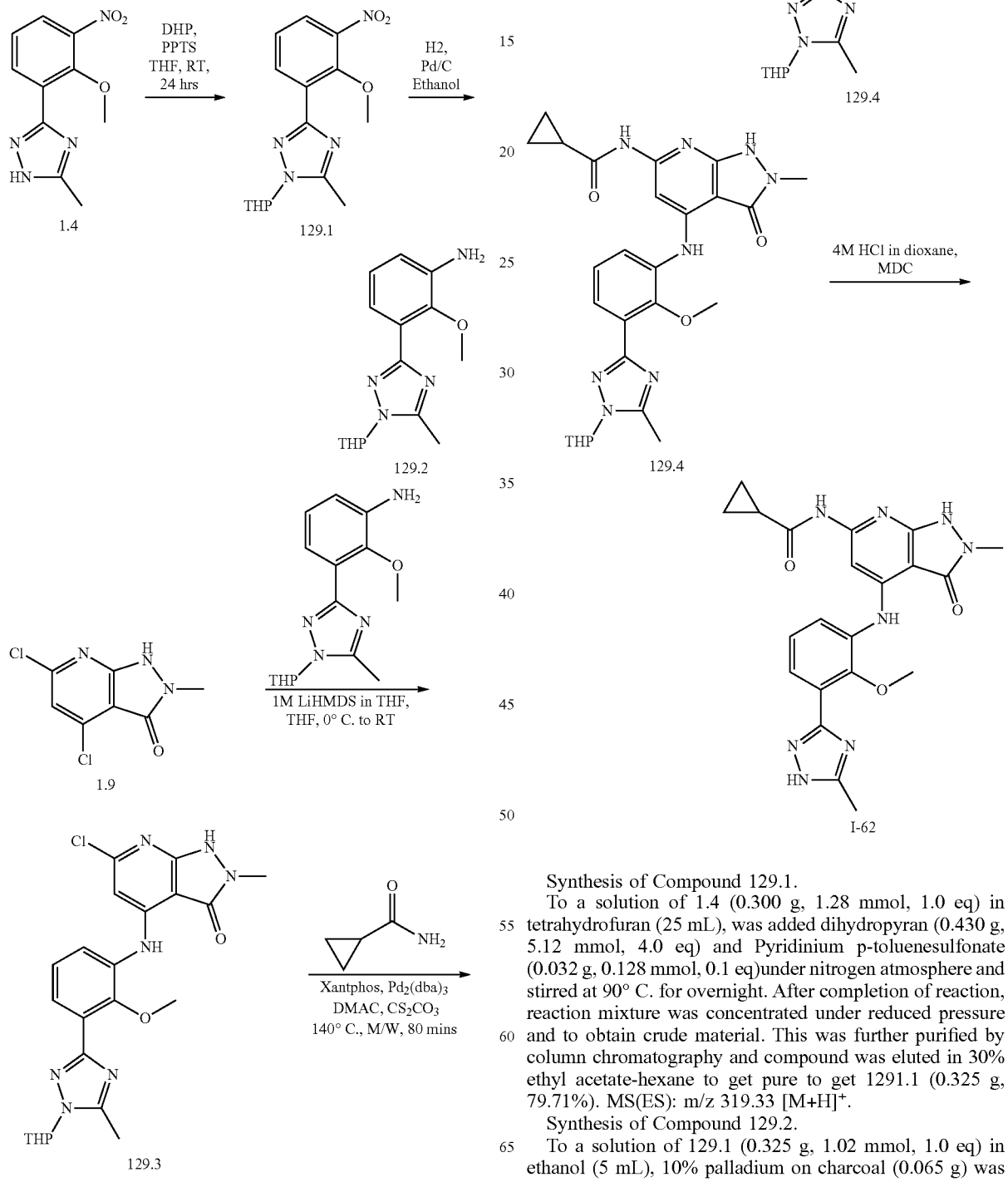

Synthesis of Compound 129.1.

To a solution of 1.4 (0.300 g, 1.28 mmol, 1.0 eq) in tetrahydrofuran (25 mL), was added dihydropyran (0.430 g, 5.12 mmol, 4.0 eq) and Pyridinium p-toluenesulfonate (0.032 g, 0.128 mmol, 0.1 eq)under nitrogen atmosphere and stirred at 90° C. for overnight. After completion of reaction, reaction mixture was concentrated under reduced pressure and to obtain crude material. This was further purified by column chromatography and compound was eluted in 30% ethyl acetate-hexane to get pure to get 1291.1 (0.325 g, 79.71%). MS(ES): m/z 319.33 [M+H]⁺.

Synthesis of Compound 129.2.

To a solution of 129.1 (0.325 g, 1.02 mmol, 1.0 eq) in ethanol (5 mL), 10% palladium on charcoal (0.065 g) was added. Hydrogen was purged through reaction mixture for 2-3 h. After completion of reaction, reaction mixture was filter through celite-bed and washed with ethanol. Filtrate was concentrated under reduced pressure to obtain 129.2 (0.215 g, 73.03%). MS(ES): m/z 289.35 [M+H]$^+$.

Synthesis of Compound 129.3.

To a solution of 1.9 (0.1 g, 0.458 mmol, 1.0 eq) and 129.2 (1.0 g, 1.603 mmol, 3.5 eq) in Tetrahydrofuran (1 mL) at 0° C. was added Lithium bis(trimethylsilyl)amide (1M in THF) (2.0 mL, 1.603 mmol, 3.5 eq). The resulting mixture was stirred at room temperature for 1 h. After completion of reaction, reaction mixture was transferred in water and washed with ethyl acetate. Aqueous layer was acidified with 1N Hydrochloric acid, solid precipitated was filtered and washed with water, dried well to obtain 129.3 (0.162 g, 75.16%). MS (ES): m/z 470.93 [M+H]$^+$.

Synthesis of Compound 129.4.

To 129.3 (0.162 g, 0.344 mmol, 1.0 eq) in dimethylacetamide (2.5 mL) was added cyclopropanecarboxamide (0.117 g, 1.376 mmol, 4.0 eq), cesium carbonate (0.336 g, 1.032 mmol, 3.0 eq). The reaction mixture was degassed for 10 min. under argon atmosphere, then tris(dibenzylideneacetone)dipalladium(0)(0.031 g, 0.034 mmol, 0.1 eq) and 4,5-Bis(diphenylphosphino)-9,9-dimethylxanthene (0.0399 g, 0.069 mmol, 0.2 eq) were added, again degassed for 5 min. The reaction was then heated at 140° C. under microwave irradiation. After completion of reaction, reaction mixture was transferred in water and extracted with ethyl acetate. Combined organic layer was washed with brine, dried over sodium sulphate and concentrated under reduced pressure to obtain crude material. This was further purified by Preparative HPLC using 0.1% Formic acid in water/Acetonitrile in gradient method. The pure fractions were concentrated under reduced pressure to obtain pure 129.4 (0.120 g, 67.13%). MS(ES): m/z 519.58 [M+H]$^+$ Synthesis of Compound I-62.

To a solution of 129.4 (0.120 g, 0.231 mmol, 1.0 eq) in dichloromethane (5 mL) cooled at 0° C. was added dropwise 4M HCl in dioxane and stirred for 1 h. After completion of reaction, reaction mixture was concentrated under reduced pressure and to obtain crude material which was dissolved on methanol (5 mL) and neutralized with Tetraalkyl ammonium carbonate polymer bound. Reaction mixture was filtered and filtrate was concentrated under reduced pressure to obtain residue which was triturated with diethyl ether to obtain pure I-62 (0.075 g, 74.60%). MS(ES): m/z 435.37 [M+H]$^+$, LCMS purity: 99.64%, HPLC purity: 98.47%, 1H NMR (DMSO-d6, 400 MHz): 13.70 (s, 1H), 10.78 (s, 1H), 8.84 (s, 1H), 7.75 (s, 1H), 7.65-7.63 (d, J=7.2 Hz, 1H), 7.57-7.55 (d, J=8.4 Hz, 1H), 7.31-7.27 (d, J=7.2 Hz, 1H), 3.71 (s, 3H), 3.32 (s, 3H), 2.39 (s, 3H), 2.01 (s, 1H), 0.80 (s, 4H).

Example 130: Synthesis of N-(4-((2-methoxy-4-(pyrrolidine-1-carbonyl)phenyl)amino)-2-methyl-3-oxo-2,3-dihydro-H-pyrazolo[3,4-b]pyridin-6-yl)cyclopropanecarboxamide, I-70

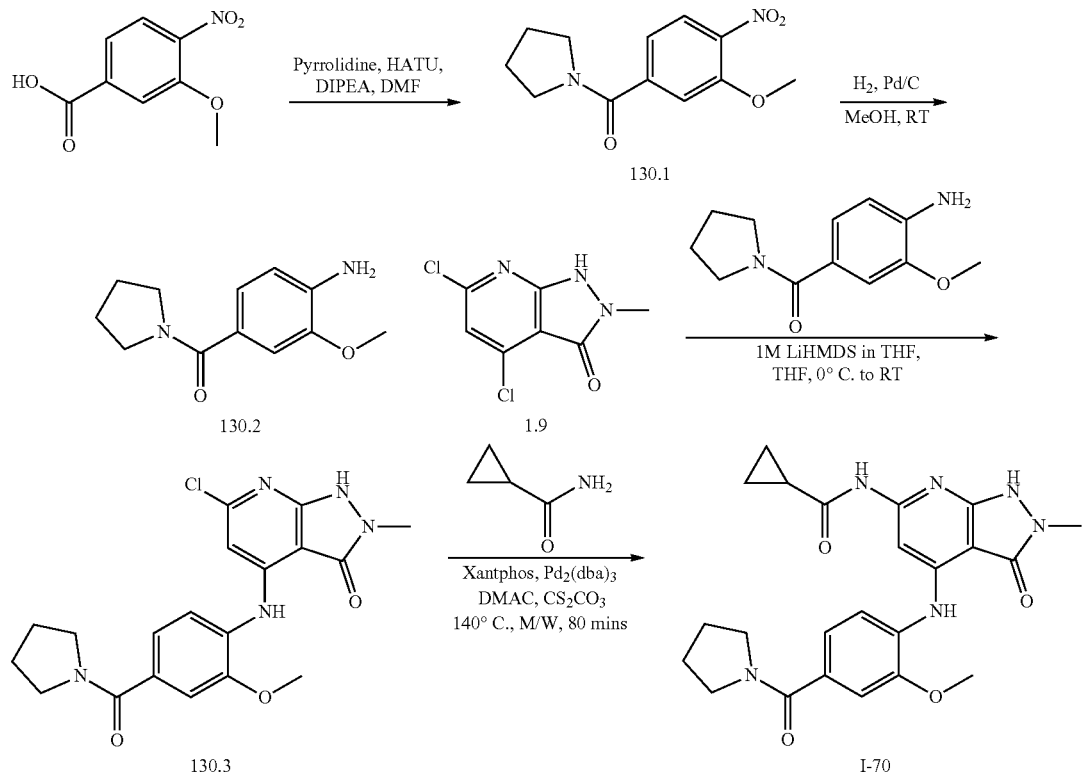

Synthesis of Compound 130.1.

To a cooled solution of 3-methoxy-4-nitrobenzoic acid (1.5 g, 7.61 mmol, 1.0 eq) and pyrrolidine (0.594 g, 8.37 mmol, 1.1 eq) in N,N-dimethylformamide (15 mL) at 0° C. was added (1-[Bis(dimethylamino)methylene]-1H-1,2,3-triazolo[4,5-b]pyridinium3-oxid hexafluoro-phosphate (5.78 g, 15.21 mmol, 2.0 eq) followed by N,N-Diisopropylethylamine (2.95 g, 22.82 mmol, 3.0 eq). Reaction mixture was stirred at room temperature for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 50% ethyl acetate in hexane as eluant to obtain pure 130.1 (1.0 g, 52.52%). MS(ES): m/z 251.25 [M+H]$^+$.

Synthesis of Compound 130.2.

To a solution of 130.1 (1.0 g, 3.99 mmol, 1.0 eq) in methanol (10 mL), 10% palladium on charcoal (0.2 g) was added. Hydrogen was purged through reaction mixture for 4 h. After completion of reaction, reaction mixture was filtered through celite-bed and washed with methanol. Filtrate was concentrated under reduced pressure to obtain 130.2. (0.8 g, 90.89%). MS(ES): m/z 221.27 [M+H]$^+$.

Synthesis of Compound 130.3.

Compound 130.3 was synthesized from 1.9 and 130.2 using general procedure A (Yield: 43.41%). MS (ES): m/z 402.85 [M+H]$^+$.

Synthesis of Compound I-70.

Compound I-70 was synthesized from 130.3 and cyclopropanecarboxamide using general procedure B (Yield: 44.6%), MS(ES): m/z 451.53 [M+H]$^+$, LCMS purity: 97.09%, HPLC purity: 95.0%, 1H NMR (DMSO-d6, 400 MHz): 10.77 (s, 2H), 8.75 (s, 1H), 7.82 (s, 1H), 7.49-7.47 (d, J=8.0 Hz, 1H), 7.25 (s, 1H), 7.20-7.18 (d, J=8.0 Hz, 1H), 3.90 (s, 3H), 3.48 (s, 4H), 3.30 (s, 3H), 2.02 (s, 1H), 1.85 (s, 4H), 0.81 (s, 4H).

Example 131: Synthesis of N-(4-((2-methoxy-4-(morpholine-4-carbonyl)phenyl)amino)-2-methyl-3-oxo-2,3-dihydro-H-pyrazolo[3,4-b]pyridin-6-yl)cyclopropanecarboxamide, I-71

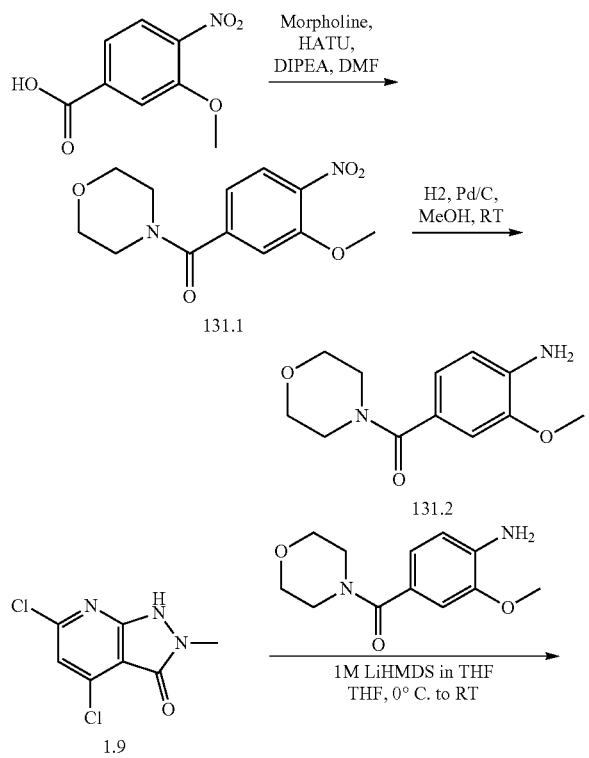

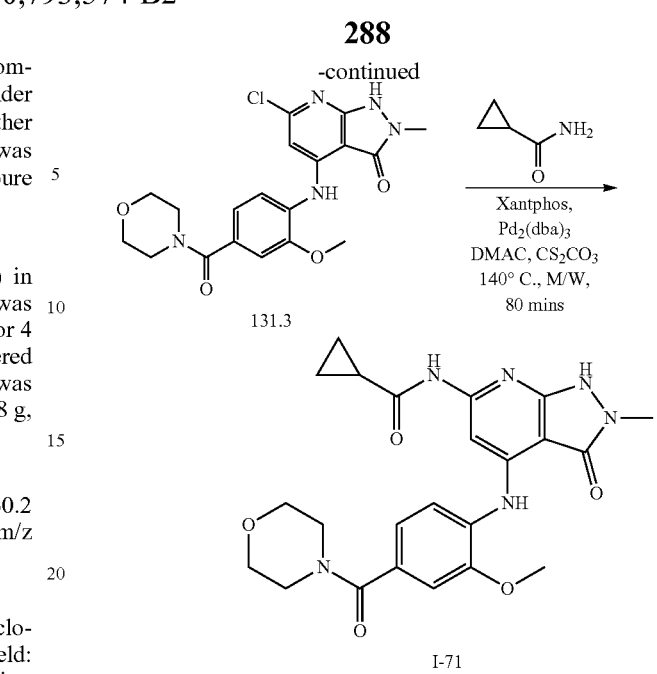

Synthesis of Compound 131.1.

To a cooled solution of 3-methoxy-4-nitrobenzoic acid (1.0 g, 5.07 mmol, 1.0 eq) and morpholine (0.485 g, 5.57 mmol, 1.1 eq) in N,N-dimethylformamide (10 mL) at 0° C. was added (1-[Bis(dimethylamino)methylene]-1H-1,2,3-triazolo[4,5-b]pyridinium-3-oxide hexafluorophosphate) (3.85 g, 10.14 mmol, 2.0 eq) followed by N,N-Diisopropylethylamine (1.96 g, 15.21 mmol, 3.0 eq). Reaction mixture was stirred at room temperature for 16 h. After completion of reaction, reaction mixture was transferred into water and extracted with ethyl acetate. Organic layer was combined, dried over sodium sulphate and concentrated under reduced pressure to pressure to obtain crude material. This was further purified by column chromatography and compound was eluted in 50% ethyl acetate hexane to obtain pure 131.1 (1.2 g, 88.85%). MS(ES): m/z 267.25 [M+H]$^+$.

Synthesis of Compound 131.2.

To a solution of 131.1 (1.2 g, 4.51 mmol, 1.0 eq) in methanol (12 mL), 10% palladium on charcoal (0.25 g) was added. Hydrogen was purged through reaction mixture for 4 h. After completion of reaction, reaction mixture was filtered through celite-bed and washed with methanol. Filtrate was concentrated under reduced pressure to obtain 131.2. (0.9 g, 84.52%). MS(ES): m/z 237.27 [M+H]$^+$.

Synthesis of Compound 131.3.

Compound was synthesized from 1.9 and 131.2 using general procedure A to obtain 131.3 (Yield: 33.92%). MS (ES): m/z 418.85 [M+H]$^+$.

Synthesis of Compound I-71.

Compound I-71 was synthesized from 131.3 and cyclopropanecarboxamide using general procedure B (0.005 g, 1.72%). MS (ES): m/z 467.35 [M+H]$^+$, LCMS purity: 100.00%, HPLC purity: 99.34%, 1H NMR (MeOD, 400 MHz): 7.64-7.62 (d, J=8.4 Hz, 1H), 7.20 (s, 1H), 7.14-7.12 (d, J=8.0 Hz, 2H), 3.99 (s, 3H), 3.73 (bs, 4H), 3.67 (bs, 4H), 3.48 (s, 3H), 1.83 (s, 1H), 1.04-1.02 (m, 2H), 0.98-0.90 (m, 2H).

Example 132: Synthesis of 4-((3-fluoro-2-methoxy-phenyl)amino)-6-((5-fluoro-4-methylpyridin-2-yl)amino)-2-methyl-1,2-dihydro-3H-pyrazolo[3,4-b]pyridin-3-one, I-73

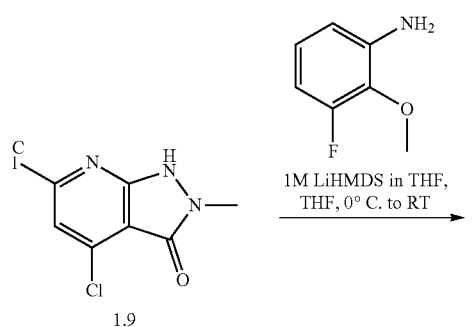

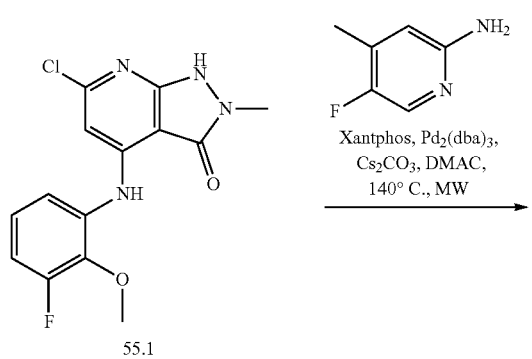

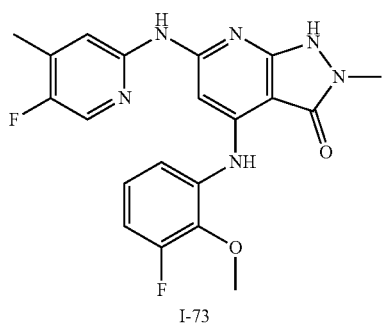

Synthesis of Compound 55.1.

Compound 55.1 was synthesized from 1.9 and 3-fluoro-2-methoxyaniline using general procedure A (Yield: 81.07%). MS (ES): m/z 323.7 [M+H]$^+$.

Synthesis of Compound I-73.

Compound I-73 was synthesized from 55.1 and 5-fluoro-4-methylpyridin-2-amine using general procedure B (Yield: 46.95%), MS(ES): m/z 413.29 [M+H]$^+$, LCMS purity: 98.05%, HPLC purity: 96.79%, 1H NMR (DMSO-d6, 400 MHz): 10.86 (bs, 1H), 9.86 (bs, 1H), 8.85 (s, 1H), 8.15 (s, 1H), 7.95 (bs, 1H), 7.43-7.41 (d, J=8.4 Hz, 1H), 7.22-7.17 (m, 1H), 7.03-6.96 (m, 2H), 3.89 (s, 3H), 3.17 (s, 3H), 2.28 (s, 3H).

Example 133: Synthesis of 6-((2,6-dimethylpyrimidin-4-yl)amino)-4-((3-fluoro-2-methoxyphenyl)amino)-2-methyl-1,2-dihydro-3H-pyrazolo[3,4-b]pyridin-3-one, I-74

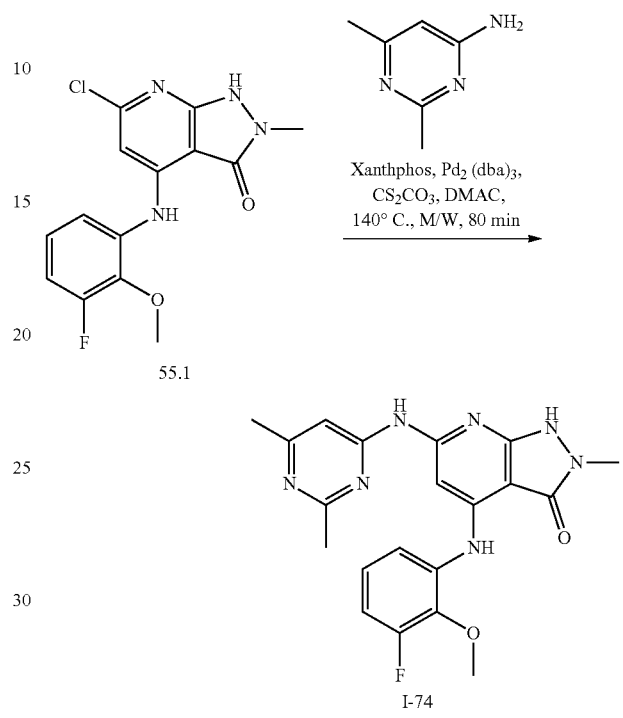

Synthesis of compound I-74.

Compound I-74 was synthesized from 55.1 and 2,6-dimethylpyrimidin-4-amine using general procedure B (Yield: 39.41%), MS(ES): m/z 410.34 [M+H]$^+$, LCMS purity: 95.95%, HPLC purity: 96.80%, 1H NMR (DMSO-d6, 400 MHz): 10.13 (s, 1H), 8.88 (s, 1H), 8.15 (s, 1H), 7.49-7.45 (t, J=8.0 Hz, 3H), 7.21-7.15 (q, J=8.0 Hz, 1H), 7.06-7.01 (t, J=6.4 Hz, 1H), 3.89 (s, 3H), 2.54 (s, 3H), 2.45 (s, 3H), 2.32 (s, 3H).

Example 134: Synthesis of 4-((3-fluoro-2-methoxyphenyl)amino)-2-methyl-6-((6-methylpyridazin-3-yl)amino)-1,2-dihydro-3H-pyrazolo[3,4-b]pyridin-3-one, I-75

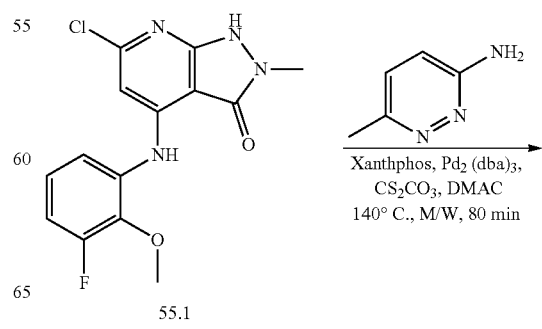

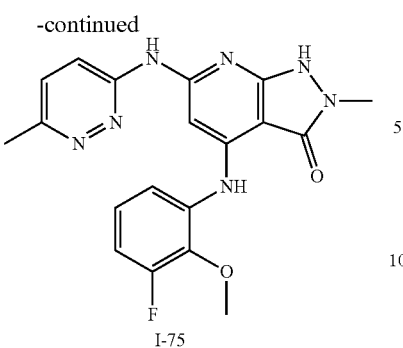

Synthesis of Compound I-75.

Compound I-75 was synthesized from 55.1 and 6-methylpyridazin-3-amine using general procedure B. (Yield: 32.65%), MS(ES): m/z 396.27 [M+H]⁺, LCMS purity: 100.00%, HPLC purity: 97.57%, 1H NMR (DMSO-d6, 400 MHz): 10.85 (s, 1H), 10.22 (s, 1H), 8.85 (s, 1H), 8.32-8.30 (d, J=8.4 Hz, 1H), 7.50-7.47 (d, J=9.2 Hz, 1H), 7.43-7.41 (d, J=8.0 Hz, 1H), 7.20-7.15 (q, J=8.0 Hz, 1H), 7.04-7.01 (d, 2H), 3.90 (s, 3H), 3.28 (s, 3H), 2.67 (s, 3H).

Example 135: Synthesis of 4-((3-fluoro-2-methoxyphenyl)amino)-6-((4-(methoxymethyl)pyridine-2-yl)amino)-2-methyl-1,2-dihydro-3H-pyrazolo[3,4-b]pyridin-3-one, I-76

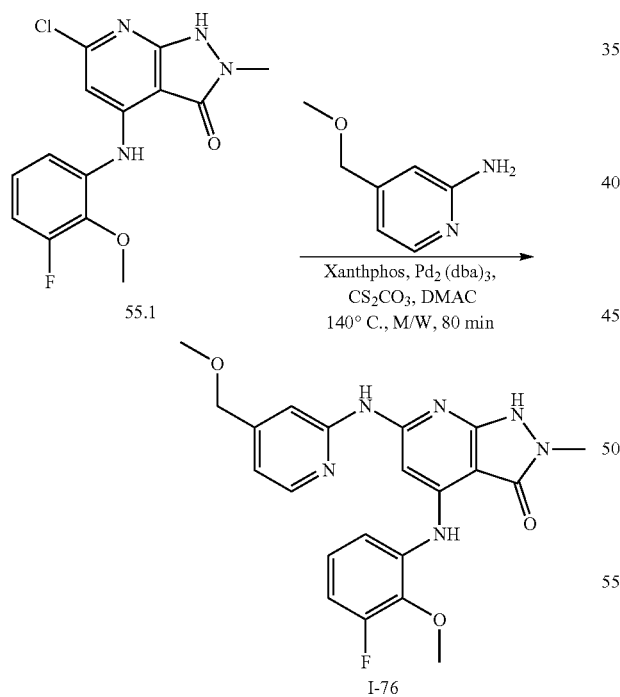

Synthesis of compound I-76.

Compound I-76 was synthesized from 55.1 and 4-(methoxymethyl)pyridin-2-amine using general procedure B. (Yield: 30.41%), MS(ES): m/z 425.43 [M+H]⁺, LCMS purity: 97.57%, HPLC purity: 95.02%, 1H NMR (DMSO-d6, 400 MHz): 10.77 (s, 1H), 9.84 (s, 1H), 8.85 (s, 1H), 8.21 (s, 1H), 7.96 (s, 1H), 7.46-7.37 (m, 2H), 7.23-7.19 (m, 1H), 7.03-7.01 (m, 1H), 6.86 (s, 1H), 4.44 (s, 2H), 3.89 (s, 3H), 3.36 (s, 3H), 3.35 (s, 3H).

Example 136: Synthesis of 4-((3-chloro-2-methoxyphenyl)amino)-6-((4-(hydroxymethyl)pyridin-2-yl)amino)-2-methyl-1,2-dihydro-3H-pyrazolo[3,4-b]pyridin-3-one, I-101

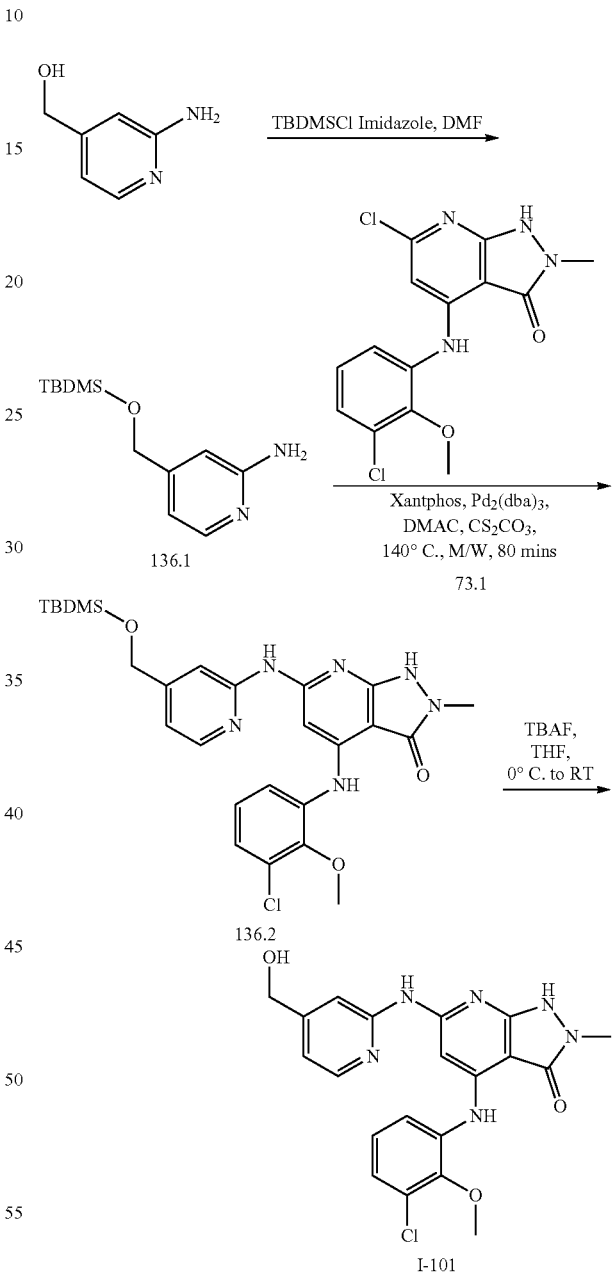

Synthesis of compound 136.1. To a cooled solution of (2-aminopyridin-4-yl)methanol (0.5 g, 4.03 mmol, 1.0 eq) in N,N-dimethylformamide (5 mL) at 0° C., imidazole (0.274 g, 4.03 mmol, 1.0 eq) was added and reaction mixture was stirred for 5 min. To this added tert-Butyldimethylsilyl chloride (0.616 g, 4.03 mmol, 1.0 eq) and stirred at 0° C. for 12 h. After completion of reaction, reaction mixture was transferred into water and extracted with ethyl acetate.

Organic layer was combined, washed with brine, dried over sodium sulphate and concentrated under reduced pressure to obtain crude material. This was further purified by column chromatography and compound was eluted in 2-3% ethyl acetate hexane to obtain pure 55.1 (0.6 g, 62.49%). MS(ES): m/z 239.41 [M+H]+.

Synthesis of Compound 136.2.

Compound 136.2 was synthesized from 73.1 and 136.2 using general procedure B. (Yield: 25.70%). MS (ES): m/z 542.12 [M+H]+.

Synthesis of Compound I-101.

To a solution of 136.2 (0.082 g, 0.151 mmol, 1.0 eq) in tetrahydrofuran (1 mL) at 0° C. was added Tetrabutyl ammonium fluoride (0.081 g, 0.302 mmol, 2.0 eq) dropwise and reaction mixture was stirred at room temperature for 2 h. After completion of reaction, reaction mixture was filtered to obtain crude solid. This crude solid was dissolved in 10% methanol in dichloromethane, washed with brine and concentrated under reduced pressure to obtain pure I-101 (0.032 g, 49.47%), MS(ES): m/z 427.86 [M+H]+, LCMS purity: 100.00%, HPLC purity: 99.07%, 1H NMR (DMSO-d6, 400 MHz): 10.752 (s, 1H), 9.78 (s, 1H), 8.85 (s, 1H), 8.15 (s, 1H), 7.93 (s, 1H), 7.60-7.58 (d, J=8.0 Hz, 1H), 7.25-7.18 (m, 3H), 6.86 (s, 1H), 4.49 (s, 2H), 4.12-4.08 (q, J=5.2 Hz, 1H), 3.80 (s, 3H), 3.27 (s, 3H).

Example 137: Synthesis of 2-methyl-4-((2-(methylsulfonyl)phenyl)amino)-6-((6-(trifluoromethyl)pyridin-2-yl)amino)-1,2-dihydro-3H-pyrazolo[3,4-b]pyridin-3-one, I-113

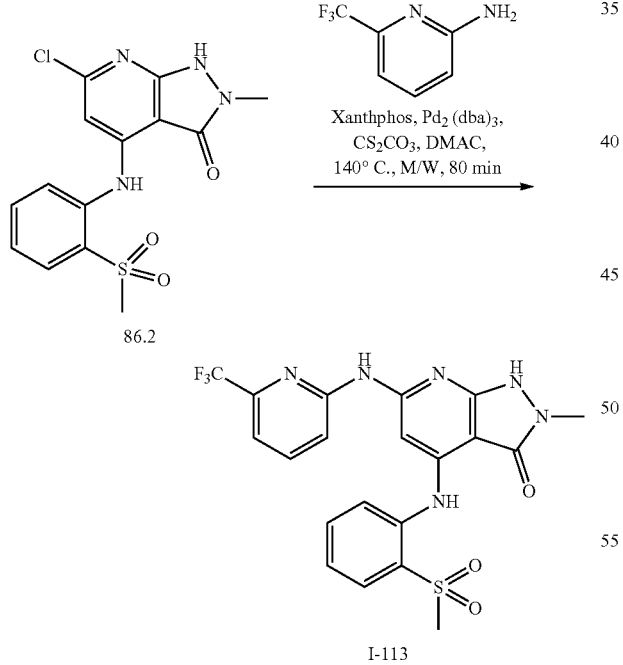

Synthesis of I-113.

Compound I-113 was synthesized from 86.2 and 6-(trifluoromethyl)pyridin-2-amine using general procedure B. (Yield: 21.07%), MS(ES): m/z 479.31 [M+H]+, LCMS purity: 93.97%, HPLC purity: 97.02%, 1H NMR (DMSO-d6, 400 MHz): 10.807 (s, 1H), 10.24 (s, 1H), 9.12 (s, 1H), 8.11-8.09 (d, J=8.4 Hz, 1H), 7.94-7.90 (m, 2H), 7.827-7.737 (m, 2H), 7.21-7.33 (m, 2H), 7.19 (s, 1H), 3.27 (s, 3H), 3.16 (s, 3H).

Example I-138: Synthesis of 4-((6-(cyclopropanecarboxamido)-2-methyl-3-oxo-2,3-dihydro-1H-pyrazolo[3,4-b]pyridin-4-yl)amino)-N-ethyl-3-methoxybenzamide, I-114

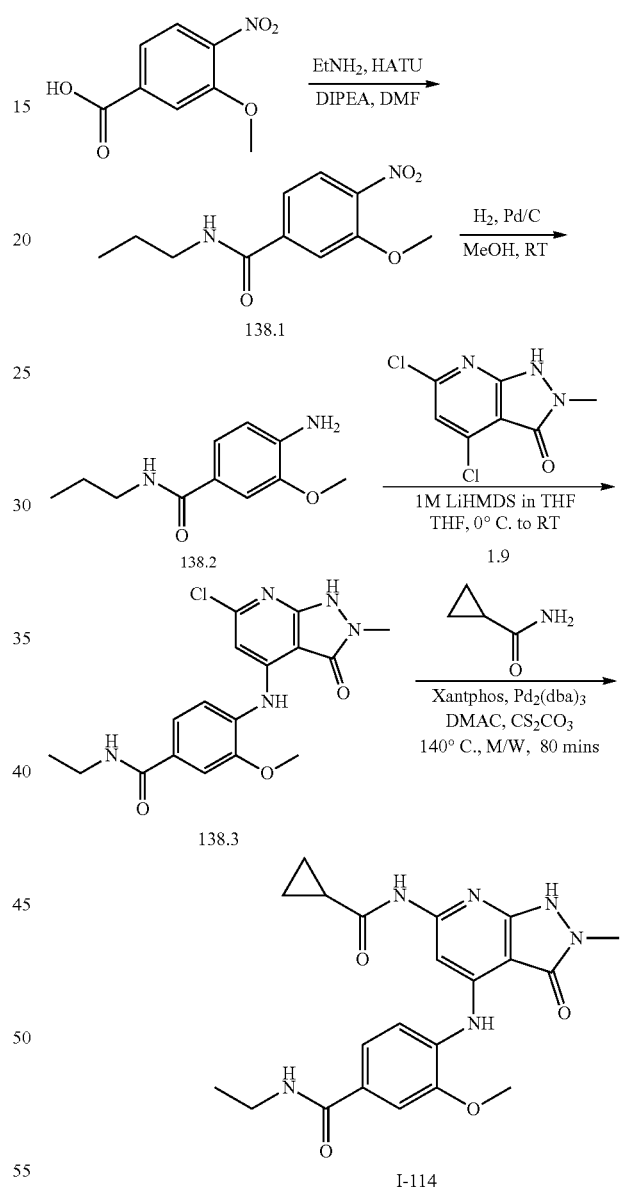

Synthesis of Compound 138.1.

To a cooled solution of 3-methoxy-4-nitrobenzoic acid (1.0 g, 5.07 mmol, 1.0 eq) and ethyl amine (0.296 g, 6.59 mmol, 1.3 eq) in N,N-dimethylformamide (10 mL) at 0° C. was added (1-[Bis(dimethylamino)methylene]-1H-1,2,3-triazolo[4,5-b]pyridinium3-oxid hexafluoro-phosphate)) (2.9 g, 7.60 mmol, 1.5 eq) followed by N,N-Diisopropylethylamine (1.96 g, 15.21 mmol, 3.0 eq). Reaction mixture was stirred at room temperature for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 50% ethyl acetate in hexane as eluant to obtain pure 138.1 (1.0 g, 87.93%). MS(ES): m/z 225.22 [M+H]+.

Synthesis of Compound 138.2.

To a solution of 138.1 (1.0 g, 4.46 mmol, 1.0 eq) in methanol (10 mL), 10% palladium on charcoal (0.2 g) was added. Hydrogen was purged through reaction mixture for 4 h. After completion of reaction, reaction mixture was filtered through celite-bed and washed with methanol. Filtrate was concentrated under reduced pressure to obtain 139.2 (0.85 g, 98.12%). MS(ES): m/z 195.23 [M+H]+.

Synthesis of Compound 138.3.

Compound 138.3 was synthesized from 139.2 and 1.9 using general procedure A. (Yield: 49.31%). MS (ES): m/z 376.81 [M+H]+.

Synthesis of Compound I-114.

Compound I-114 was synthesized from 138.3 and cyclopropanecarboxamide using general procedure B. (Yield: 22.13%), MS(ES): m/z 425.46 [M+H]+, LCMS purity: 96.40%, HPLC purity: 95.03%, 1H NMR (DMSO-d6, 400 MHz): 10.77 (s, 2H), 8.73 (s, 1H), 8.45 (s, 1H), 7.83 (s, 1H), 7.54-7.48 (m, 3H), 3.90 (s, 3H), 3.28-3.26 (m, 5H), 1.99 (m, 1H), 1.13-1.09 (t, J=7.2 Hz, 3H), 0.79 (s, 4H).

Example 139: Synthesis of 4-((3-chloro-2-methoxyphenyl)amino)-2-methyl-6-((5-morpholinopyridin-2-yl)amino)-1,2-dihydro-3H-pyrazolo[3,4-b]pyridin-3-one, I-115

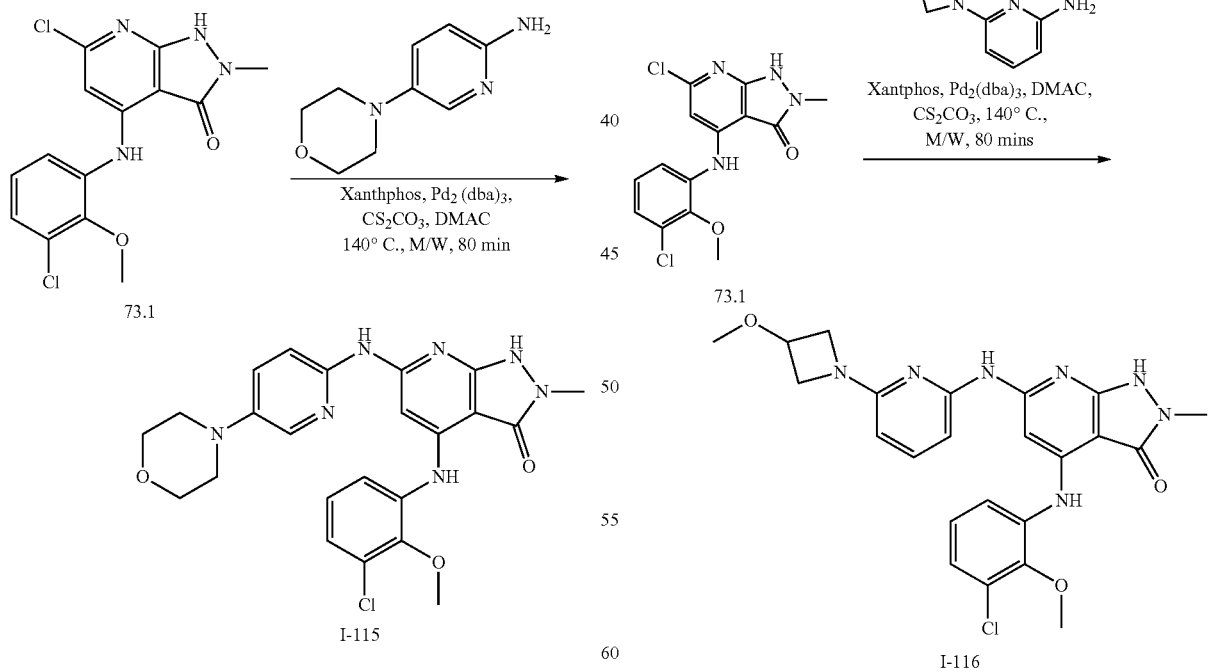

Synthesis of compound I-115.

Compound I-115 was synthesized from 5-morpholinopyridin-2-amine and 73.1 using general procedure B. (Yield: 18.77%), MS(ES): m/z 482.25 [M+H]+, LCMS purity: 96.54%, HPLC purity: 96.43%, 1H NMR (DMSO-d6, 400 MHz): 13.70 (s, 1H), 10.68 (s, 1H), 9.60 (s, 1H), 9.03 (s, 1H), 7.95 (s, 2H), 7.56-7.55 (d, J=6.4 Hz, 1H), 7.42 (s, 1H), 7.32-7.03 (m, 2H), 3.80 (s, 3H), 3.73 (t, 4H), 3.26 (s, 3H), 3.07 (t, 4H).

Example 140: Synthesis of 4-((3-chloro-2-methoxyphenyl)amino)-6-((6-(3-methoxyazetidin-1-yl)pyridin-2-yl)amino)-2-methyl-1,2-dihydro-3H-pyrazolo[3,4-b]pyridin-3-one, I-116

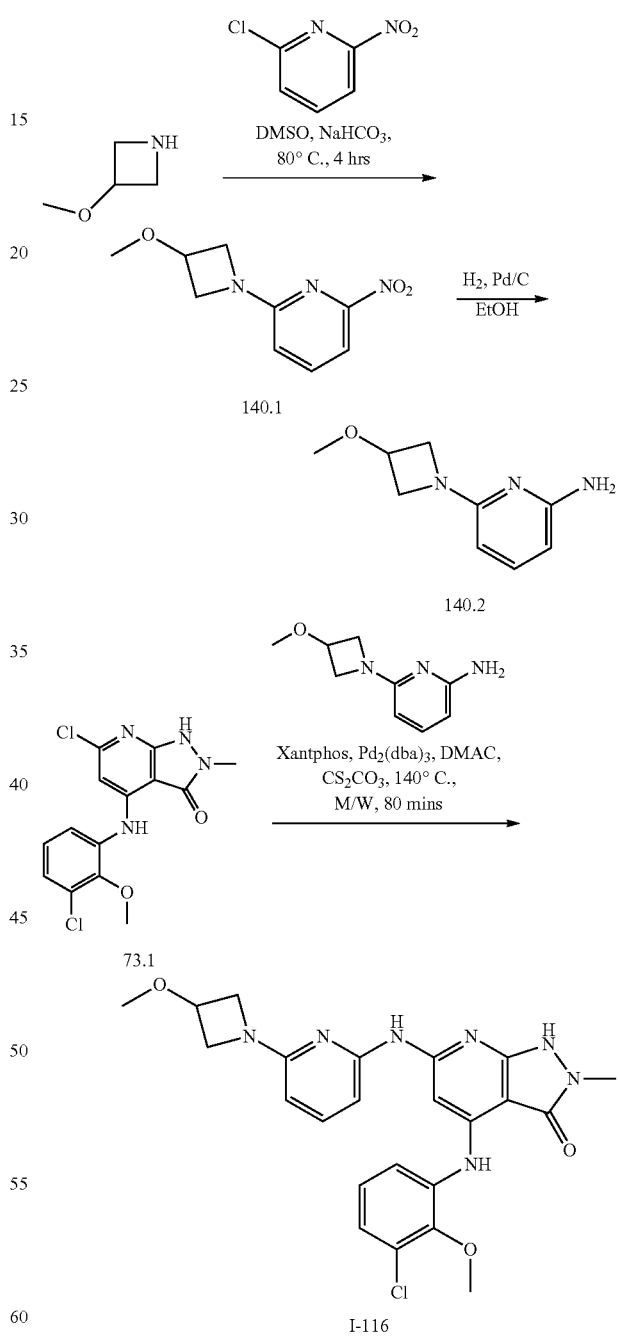

Synthesis of Compound 140.1.

To a solution of 3-methoxyazetidine (2.0 g, 22.96 mmol, 1.5 eq) and 2-chloro-6-nitropyridine (2.43 g, 15.30 mmol, 1.0 eq) in dimethyl sulfoxide (20 mL) was added sodium bicarbonate (2.57 g, 30.60 mmol, 2.0 eq). Reaction mixture was stirred at 80° C. for 4 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane as eluant to obtain pure 141.1 (2.0 g, 62.47%). MS(ES): m/z 210.21 [M+H]$^+$.

Synthesis of Compound 140.2.

To a solution of 140.1 (2.0 g, 9.56 mmol, 1.0 eq) in methanol (20 mL), 10% palladium on charcoal (0.4 g) was added. Hydrogen was purged through reaction mixture for 4 h. After completion of reaction, reaction mixture was filtered through celite-bed and washed with methanol. Filtrate was concentrated under reduced pressure to obtain 141.2. (1.5 g, 87.55%). MS(ES): m/z 180.22 [M+H]$^+$.

Synthesis of Compound I-116.

Compound I-116 was synthesized from 73.1 and 140.2 using general procedure B (Yield: 3.75%), MS(ES): m/z 482.94 [M+H]$^+$, LCMS purity: 96.80%, HPLC purity: 95.08%, 1H NMR (DMSO-d6, 400 MHz): 13.98 (s, 1H), 10.65 (s, 1H), 9.44 (s, 1H), 8.75 (s, 1H), 7.54 (s, 1H), 7.41 (s, 1H), 7.19 (s, 3H), 5.91 (s, 1H), 4.24 (s, 1H), 3.98 (s, 2H), 3.79 (s, 3H), 3.61 (s, 2H), 3.26 (s, 3H), 3.22 (s, 3H).

Example 141: Synthesis of 2-methyl-4-((2-(methyl-sulfonyl)phenyl)amino)-6-((5-(piperidin-1-yl)pyridin-2-yl)amino)-1,2-dihydro-3H-pyrazolo[3,4-b]pyridin-3-one, I-118

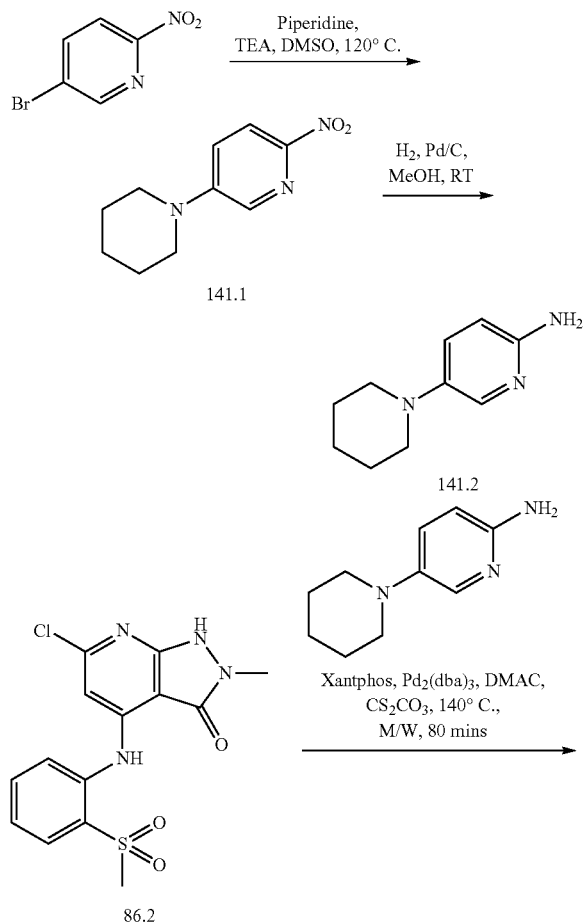

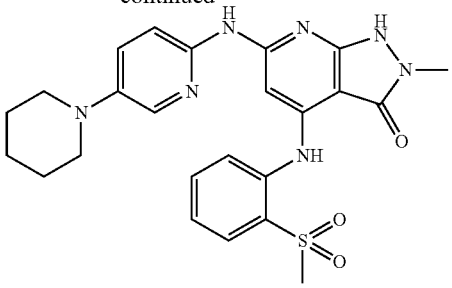

I-118

Synthesis of Compound 141.1.

To a solution of 5-bromo-2-nitropyridine (2.0 g, 9.85 mmol, 1.0 eq), piperidine (1.674 g, 19.7 mmol, 2.0 eq) and triethyl amine (1.09 g, 10.83 mmol, 1.1 eq) in dimethyl sulfoxide (20 mL) was added. Reaction mixture was stirred at 120° C. for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane as eluant to obtain pure 141.1 (1.1 g, 53.88%). MS(ES): m/z 208.23 [M+H]$^+$.

Synthesis of Compound 141.2.

To a solution of 141.1 (1.1 g, 5.31 mmol, 1.0 eq) in methanol (10 mL), 10% palladium on charcoal (0.2 g) was added. Hydrogen was purged through reaction mixture for 4 h. After completion of reaction, reaction mixture was filtered through celite-bed and washed with methanol. Filtrate was concentrated under reduced pressure to obtain 141.2. (0.7 g, 74.40%). MS(ES): m/z 178.25 [M+H]$^+$.

Synthesis of Compound I-118.

Compound I-118 was synthesized from 86.2 and 141.2 using general procedure B. (Yield: 9.29%), MS(ES): m/z 494.59 [M+H]$^+$, LCMS purity: 98.43%, HPLC purity: 98.72%, 1H NMR (CDCl3, 400 MHz): 14.41 (bs, 1H), 11.36 (bs, 1H), 9.41 (s, 1H), 7.77-7.73 (m, 2H), 7.44-7.42 (d, J=7.2 Hz, 1H), 7.29-7.28 (d, J=2.8 Hz, 1H), 7.20-7.15 (m, 2H), 7.01-6.97 (t, J=7.2 Hz, 1H), 5.90 (s, 1H), 3.47 (s, 3H), 3.07 (m, 4H), 2.94 (s, 3H), 1.72 (m, 4H), 1.59-1.57 (m, 2H).

Example 142: Synthesis of 6-((2-methyl-4-((2-(methylsulfonyl)phenyl)amino)-3-oxo-2,3-dihydro-1H-pyrazolo[3,4-b]pyridin-6-yl)amino)pyrazine-2-carbonitrile, I-119

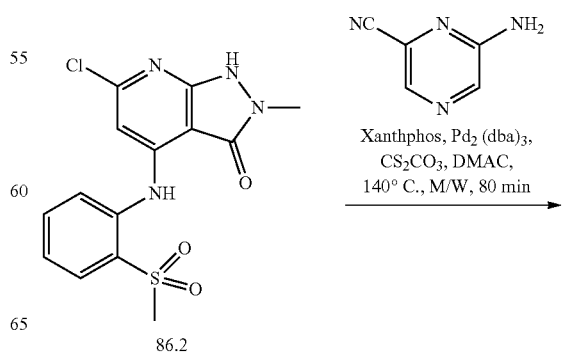

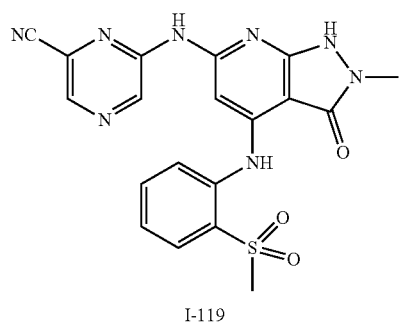

I-119 synthesis of compound i-119.

compound I-119 was synthesized from 6-aminopyrazine-2-carbonitrile and 86.2 using general procedure B. (Yield: 24.25%), MS(ES): m/z 437.19 [M+H]$^+$, LCMS purity: 100.00%, HPLC purity: 98.05%, 1H NMR (DMSO-d6, 400 MHz): 10.94 (s, 1H), 10.64 (bs, 1H), 9.29 (s, 1H), 9.22 (s, 1H), 8.62 (s, 1H), 7.95-7.93 (d, J=8.0 Hz, 1H), 7.88-7.79 (m, 2H), 7.44-7.40 (m, 1H), 7.19 (s, 1H), 3.28 (s, 3H), 3.17 (s, 3H).

Example 143: 6-((5-fluoro-4-methylpyridin-2-yl)amino)-4-((2-methoxy-3-(1-methyl-1H-pyrazol-3-yl)phenyl)amino)-2-methyl-1,2-dihydro-3H-pyrazolo[3,4-b]pyridin-3-one, I-120

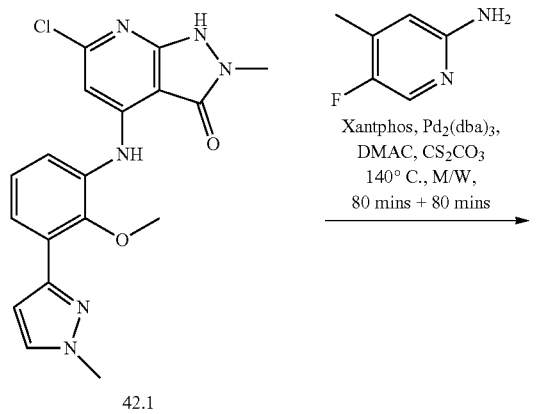

I-120

Synthesis of Compound I-120.

Compound I-120 was synthesized from 5-fluoro-4-methylpyridin-2-amine and 42.1 using general procedure B. (0.040 g, Yield: 27.03%). MS(ES): m/z 475.50 [M+H]$^+$, LCMS purity: 99.34%, HPLC purity: 97.70%, 1H NMR (DMSO-d6, 400 MHz): 10.71 (s, 1H), 9.77 (s, 1H), 8.83 (s, 1H), 8.11 (s, 1H), 8.01 (s, 1H), 7.78 (s, 1H), 7.55-7.51 (m, 2H), 7.24-7.20 (t, J=8.0 Hz, 1H), 7.02 (s, 1H), 6.73 (s, 1H), 3.90 (s, 3H), 3.62 (s, 3H), 3.27 (s, 3H), 2.26 (s, 3H).

Example 144: Synthesis of 4-((2-methoxy-3-(1-methyl-1H-pyrazol-3-yl)phenyl)amino)-2-methyl-6-((6-methylpyridazin-3-yl)amino)-1,2-dihydro-3H-pyrazolo[3,4-b]pyridin-3-one, I-121

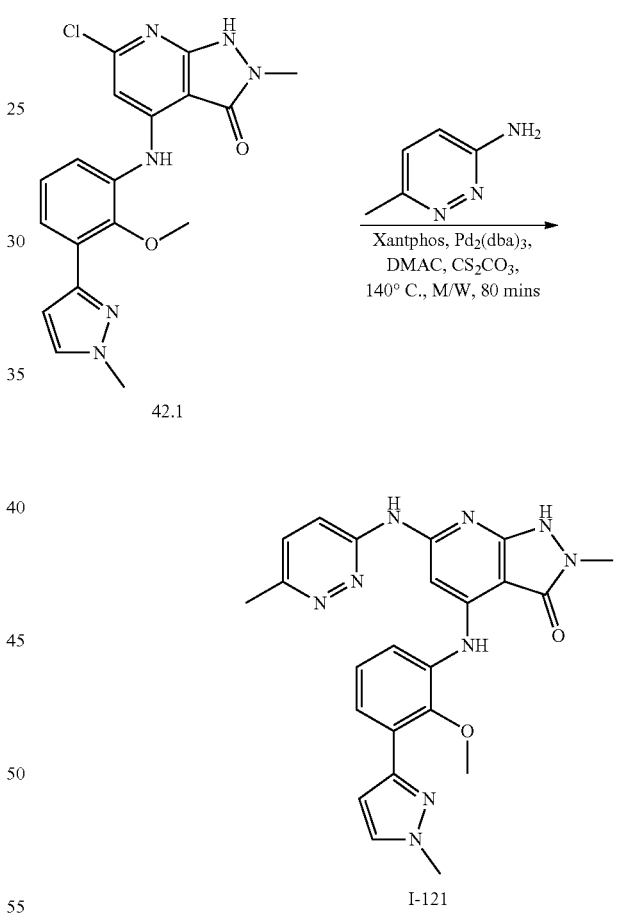

I-121

Synthesis of Compound I-121.

Compound I-121 was synthesized from 6-methylpyridazin-3-amine and 42.1 using general procedure B. (0.040 g, Yield: 28.04%). MS(ES): m/z 458.50 [M+H]$^+$, LCMS purity: 99.36%, HPLC purity: 95.11%, 1H NMR (DMSO-d6, 400 MHz): 10.78 (s, 1H), 10.19 (s, 1H), 8.86 (s, 1H), 8.29 (s, 1H), 7.78 (s, 1H), 7.59-7.46 (m, 3H), 7.23-7.19 (t, J=8.0 Hz, 1H), 7.00 (s, 1H), 6.73 (s, 1H), 3.90 (s, 3H), 3.63 (s, 3H), 3.27 (s, 3H), 2.48 (s, 3H).

Example 145: Synthesis of 6-((4-((2-methoxy-3-(1-methyl-1H-pyrazol-3-yl)phenyl)amino)-2-methyl-3-oxo-2,3-dihydro-1H-pyrazolo[3,4-b]pyridin-6-yl)amino)picolinonitrile, I-122

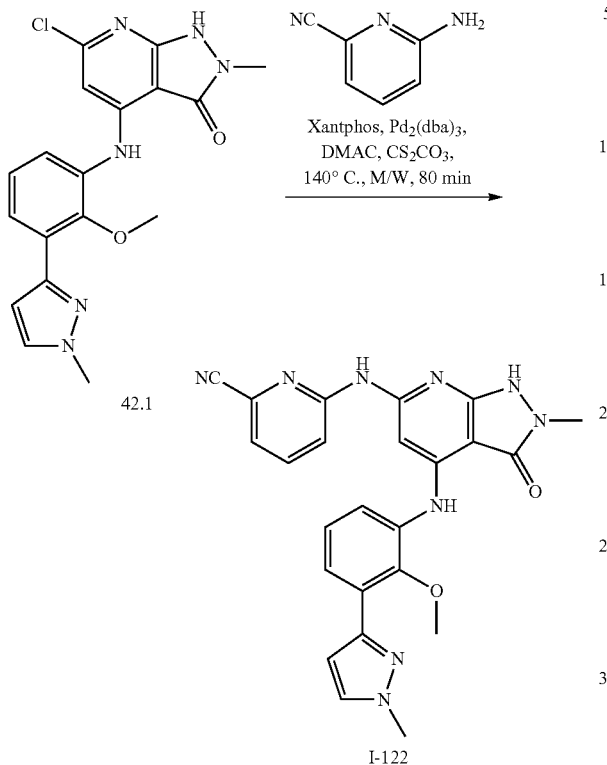

I-122

Synthesis of Compound I-122.

Compound I-122 was synthesized 6-aminopicolinonitrile and 42.1 from using general procedure B. (0.035 g, Yield: 24.01%). MS(ES): m/z 468.37 [M+H]+, LCMS purity: 99.31%, HPLC purity: 99.49%, 1H NMR (DMSO-d6, 400 MHz): 10.79 (bs, 1H), 10.29 (s, 1H), 8.97 (s, 1H), 8.08-8.05 (d, J=8.0 Hz, 1H), 7.91-7.87 (d, J=8.0 Hz, 1H), 7.78-7.78 (d, J=2.0 Hz, 1H), 7.61-7.52 (m, 3H), 7.46 (s, 1H), 7.29-7.25 (t, J=8.0 Hz, 1H), 6.74-6.73 (d, J=2.0 Hz, 1H), 3.90 (s, 3H), 3.62 (s, 3H), 3.29 (s, 3H).

Example 146: Synthesis of 6-((2,6-dimethylpyrimidin-4-yl)amino)-4-((2-methoxy-3-(1-methyl-1H-pyrazol-3-yl)phenyl)amino)-2-methyl-1,2-dihydro-3H-pyrazolo[3,4-b]pyridin-3-one, I-123

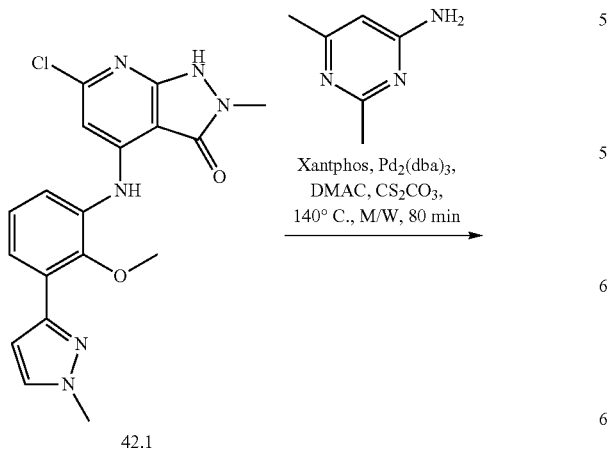

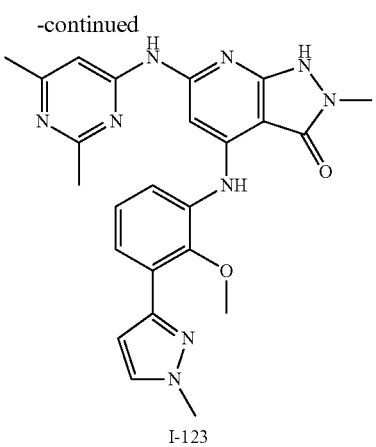

I-123

Synthesis of Compound I-123.

Compound I-146 was synthesized from 2,6-dimethylpyrimidin-4-amine and 42.1 using general procedure B (0.039 g, Yield: 26.52%). MS(ES): m/z 472.35 [M+H]+, LCMS purity: 99.48%, HPLC purity: 95.82%, 1H NMR (DMSO-d6, 400 MHz): 10.83 (bs, 1H), 10.10 (s, 1H), 8.90 (s, 1H), 7.78 (s, 1H), 7.56-7.49 (m, 3H), 7.23 (s, 1H), 6.73 (s, 1H), 3.90 (s, 3H), 3.62 (s, 3H), 3.29 (s, 3H), 2.43 (s, 3H), 2.30 (s, 3H).

Example 147: Synthesis of 4-((2-methoxy-3-(1-methyl-1H-pyrazol-3-yl)phenyl)amino)-2-methyl-6-((5-(piperidin-1-yl)pyridin-2-yl)amino)-1,2-dihydro-3H-pyrazolo[3,4-b]pyridin-3-one, I-124

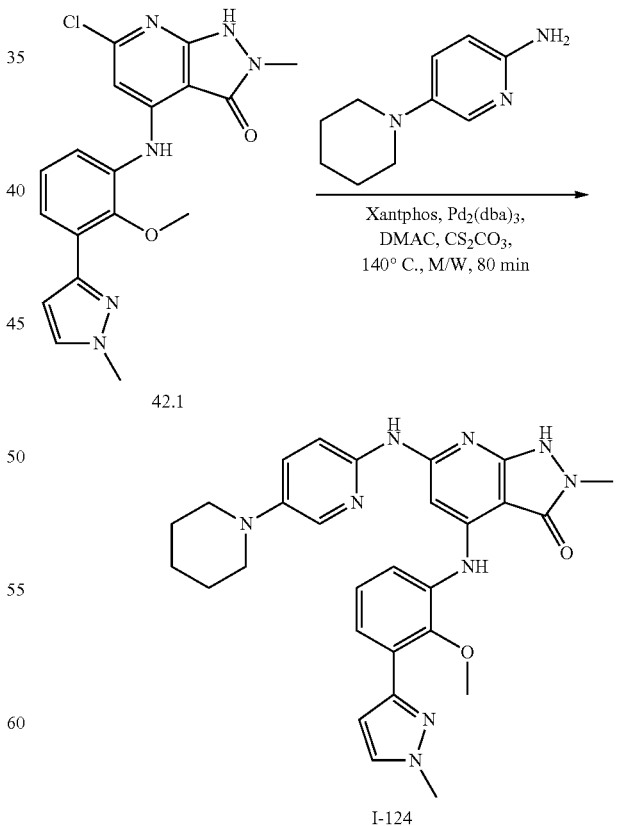

I-124

Synthesis of Compound I-124. Compound I-124 was synthesized from 5-(piperidin-1-yl)pyridin-2-amine and 42.1 using general procedure B. (0.055 g, Yield: 33.56%). MS(ES): m/z 526.54 [M+H]$^+$, LCMS purity: 99.19%, HPLC purity: 97.65%, 1H NMR (DMSO-d6, 400 MHz): 10.60 (bs, 1H), 9.55 (s, 1H), 8.97 (s, 1H), 7.93 (s, 2H), 7.78-7.77 (d, J=4.0 Hz, 1H), 7.58-7.39 (m, 3H), 7.24-7.20 (t, J=8.0 Hz, 1H), 7.04 (s, 1H), 6.73-6.72 (d, J=4.0 Hz, 1H), 3.90 (s, 3H), 3.62 (s, 3H), 3.26 (s, 3H), 3.06 (m, 4H), 1.62 (m, 4H), 1.51 (m, 2H).

Example 148: Synthesis of 3-(difluoromethyl)-6-((4-((3-fluoro-2-methoxyphenyl)amino)-2-methyl-3-oxo-2,3-dihydro-1H-pyrazolo[3,4-b]pyridin-6-yl)amino)picolinonitrile, I-191

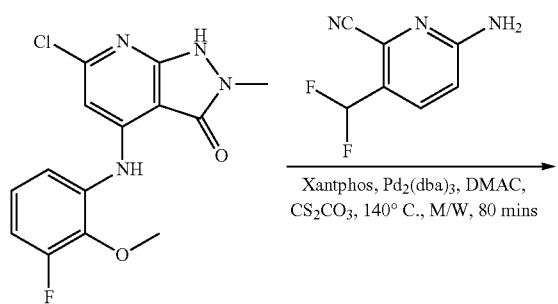

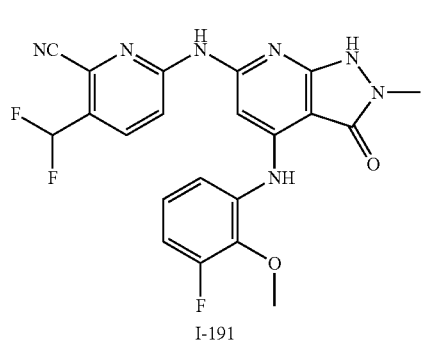

Synthesis of Compound I-191.

Compound I-191 was synthesized from 55.1 and 6-amino-3-(difluoromethyl)picolinonitrile using general procedure B. (Yield: 27.26%). MS(ES): m/z 456.36 [M+H]$^+$, LCMS purity: 99.36%, HPLC purity: 97.87%, 1H NMR (DMSO-d6, 400 MHz): 10.79 (s, 1H), 9.37 (s, 1H), 8.90 (s, 1H), 8.19-8.17 (d, J=7.6 Hz, 1H), 7.79-7.77 (d, J=8.0 Hz, 1H), 7.61-7.62 (t, 1H), 7.50 (s, 2H), 7.26-7.21 (m, 1H), 7.08-7.03 (m, 1H), 3.91 (s, 3H), 3.10 (s, 3H).

Example 149: Synthesis of 4-((3-chloro-2-methoxyphenyl)amino)-6-((6,7-dihydro-4H-pyrazolo[5,1-c][1,4]oxazin-2-yl)amino)-2-methyl-1,2-dihydro-3H-pyrazolo[3,4-b]pyridin-3-one, I-221

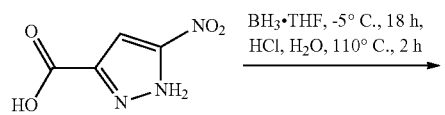

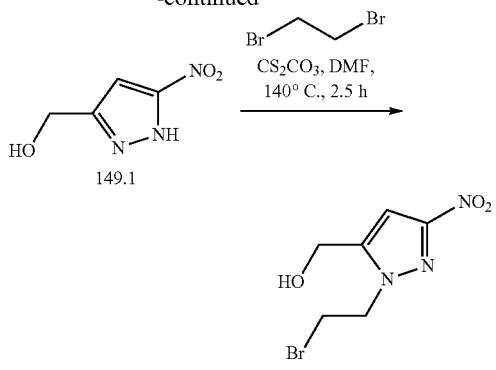

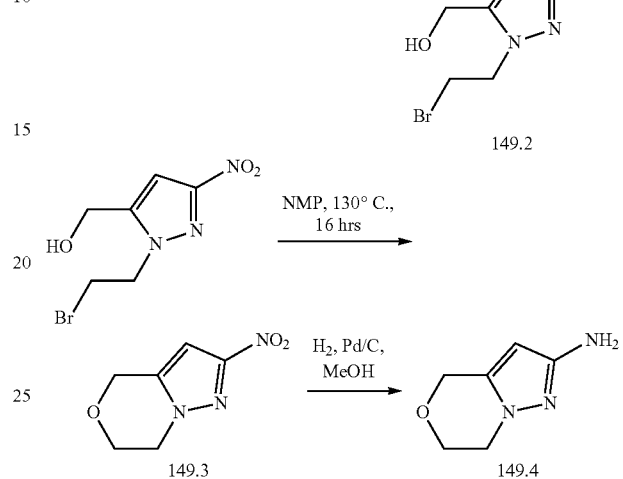

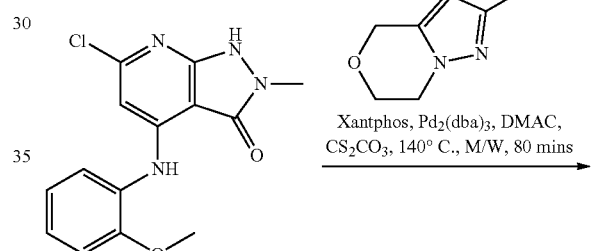

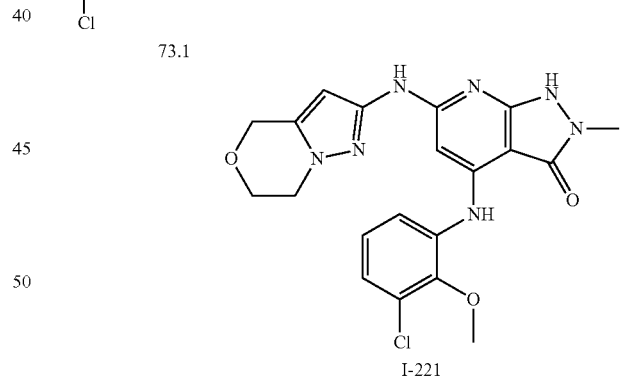

Synthesis of Compound 149.1.

To a solution 5-nitro-1H-pyrazole-3-carboxylic acid (10.0 g, 63.66 mmol, 1.0 eq) in tetrahydrofuran (30 mL) was added dropwise borane tetrahydrofuran complex (194 mL, 190.98 mmol, 3.0 eq) at −0.5° C. The reaction mixture was stirred at room temperature for 18 h. The reaction mixture was cooled to −0.5° C., water (30 mL) was added followed by 4N hydrochloric acid (30 mL). The reaction mixture was stirred at 110° C. for 2 h. After completion of reaction, reaction mixture was filtered, washed with ethyl acetate. Organic layer was dried over sodium sulphate and concentrated under reduced pressure to obtain 149.1 (5.8 g, 63.67%). MS(ES): m/z 144.10 $[M+H]^+$.

Synthesis of Compound 149.2.

To a solution of 149.1 (5.8 g, 40.53 mmol, 1.0 eq) in N,N-dimethylformamide (70 mL) was added cesium carbonate (16.12 g, 49.45 mmol, 1.22 eq). 1,2-dibromoethane (60.91 g, 324.24 mmol, 1.22 eq) was added dropwise to the reaction mixture. The reaction mixture was stirred at room temperature for 2.5 h. After completion of reaction, reaction mixture was transferred in to 10% solution of sodium phosphate (90 mL) and extracted with ethyl acetate. Organic layer was combined, dried over sodium sulphate and concentrated under reduced pressure to obtain crude material. This was further purified by column chromatography and compound was eluted in 35% ethyl acetate in hexane as eluent to obtain 149.2. (4.0 g, 39.47%). MS(ES): m/z 251.05 $[M+H]^+$.

Synthesis of Compound 149.3.

To a solution of 149.2 (3.0 g, 12.00 mmol, 1.0 eq) in N-methyl pyrrolidine (12 mL) was added. The reaction mixture was stirred at 135° C. for 18 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 1% methanol in dichloromethane as eluent to obtain 149.3. (0.30 g, 14.78%). MS(ES): m/z 170.14 $[M+H]^+$.

Synthesis of Compound 149.4.

To a solution of 149.3 (0.3 g, 1.77 mmol, 1.0 eq) in methanol (20 mL), 10% palladium on charcoal (0.05 g) was added. Hydrogen was purged through reaction mixture for 2-3 h. After completion of reaction, reaction mixture was filtered through celite-bed and washed with ethanol. Filtrate was concentrated under reduced pressure to obtain 149.4 (0.22 g, 89.13%). MS(ES): m/z 140.16 $[M+H]^+$.

Synthesis of Compound I-221.

Compound I-221 was synthesized from 149.4 and 73.1 using general procedure B. (Yield: 19.96%). MS(ES): m/z 442.41 $[M+H]^+$, LCMS purity: 96.79%, HPLC purity: 98.27%, 1H NMR (DMSO-d6, 400 MHz): 10.58 (s, 1H), 9.59 (s, 1H), 8.83 (s, 1H), 7.59-7.57 (d, J=8.0 Hz, 1H), 7.33-7.19 (m, 2H), 6.90 (s, 1H), 6.24 (s, 1H), 4.77 (s, 2H), 4.08-4.00 (m, 4H), 3.83 (s, 3H), 3.18 (s, 3H).

Example 150: Synthesis of 6-((4-((3-chloro-2-methoxyphenyl)amino)-2-methyl-3-oxo-2,3-dihydro-1H-pyrazolo[3,4-b]pyridin-6-yl)amino)-3-(2-oxopyrrolidin-1-yl)picolinonitrile, I-134

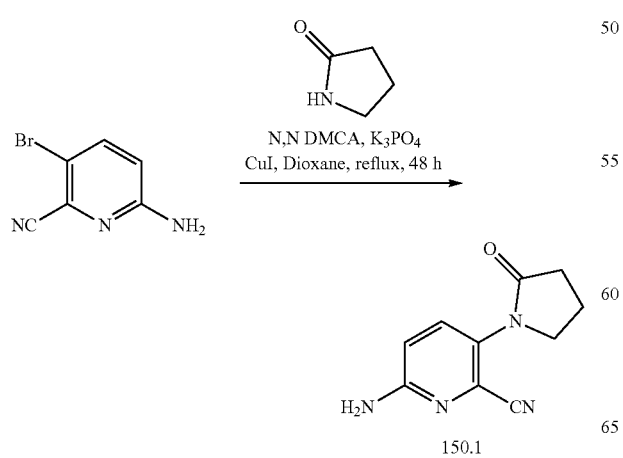

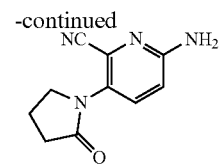

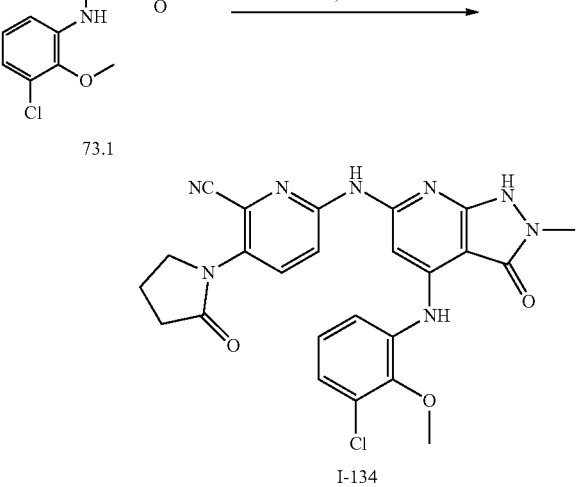

Synthesis of Compound 150.1.

To 6-amino-3-bromopicolinonitrile (0.5 g, 2.52 mmol, 1.0 eq) and pyrrolidin-2-one (0.258 g, 3.03 mmol, 1.2 eq) in 1,4-dioxane (0.5 mL) was added N-Desmethylclozapine (0.079 g, 0.252 mmol, 0.1 eq), potassium phosphate (1.07 g, 5.04 mmol, 2.0 eq) and copper iodide (0.024 g, 0.126 mmol, 0.05 eq). The reaction mixture was degassed for 10 min. under argon atmosphere. The reaction was refluxed for 48 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 40% ethyl acetate in hexane to obtain pure 150.1 (0.125 g, 29.38%). MS(ES): m/z 203.22 $[M+H]^+$ Synthesis of compound I-134.

Compound I-134 was synthesized from 73-1 and 150.1 using general procedure B. (0.028 g, Yield: 37.62%). MS(ES): m/z 505.28 $[M+H]^+$, LCMS purity: 100%, HPLC purity: 98.40%, 1H NMR (DMSO-d6, 400 MHz): 10.86 (bs, 1H), 10.37 (s, 1H), 8.95 (s, 1H), 8.14-8.11 (d, J=9.2 Hz, 1H), 7.92-7.90 (d, J=9.6 Hz, 1H), 7.63-7.61 (d, J=6.8 Hz, 1H), 7.36 (s, 1H), 7.27-7.19 (m, 2H), 3.84-3.81 (m, 5H), 3.29 (s, 3H), 3.15-3.14 (d, J=4.4 Hz, 2H), 2.17-2.10 (m, 2H).

Example 151: Synthesis 6-((4-((3-chloro-2-methoxyphenyl)amino)-2-methyl-3-oxo-2,3-dihydro-1H-pyrazolo[3,4-b]pyridin-6-yl)amino)-3-methylpyrazine-2-carbonitrile, I-135

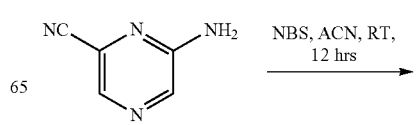

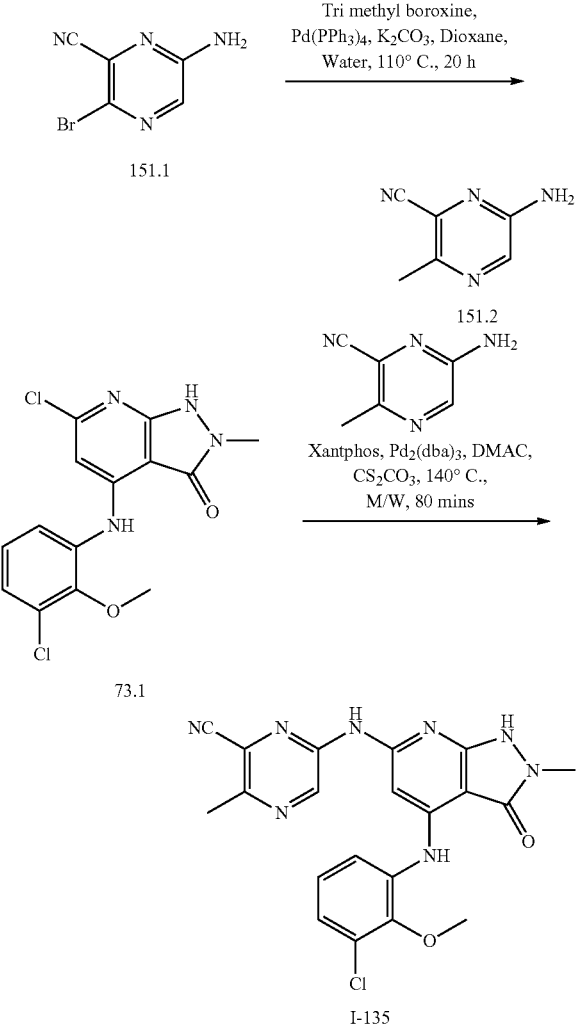

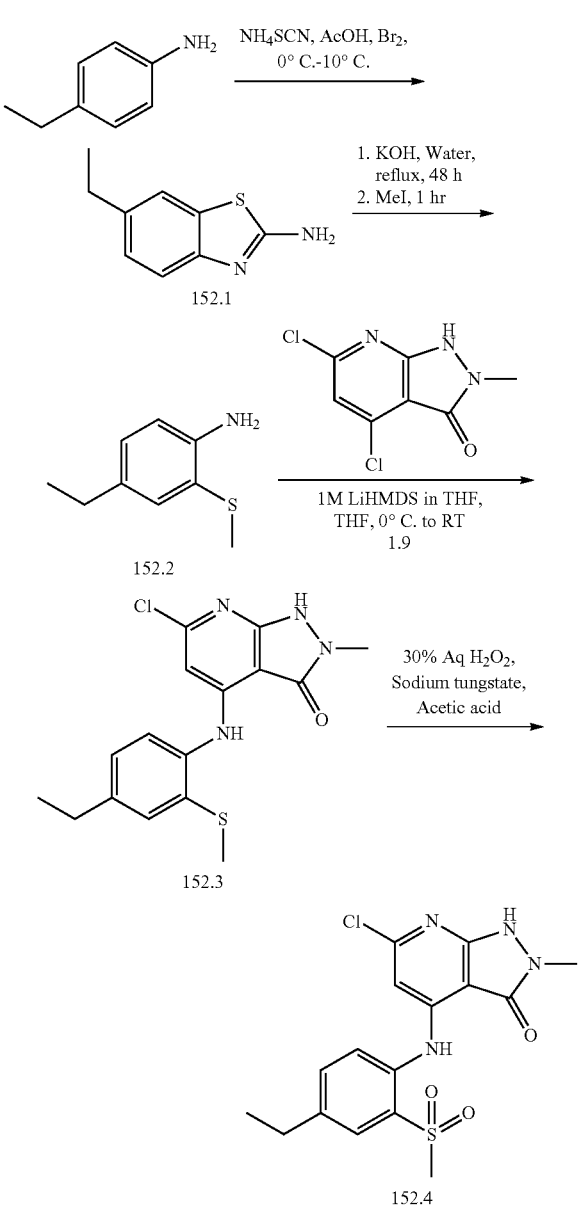

crude material. This was further purified by column chromatography using 15% ethyl acetate in hexane to obtain pure 151.2 (0.15 g, 29.67%). MS(ES): m/z 135.14 [M+H]$^+$ Synthesis of Compound I-135.

Compound was synthesized from 73.1 and 151.2 using general procedure B to obtain I-135 (0.125 g, Yield: 31.06%). MS(ES): m/z 437.24 [M+H]$^+$, LCMS purity: 93.43%, HPLC purity: 94.00%, 1H NMR (DMSO-d6, 400 MHz): 10.91 (s, 1H), 10.50 (s, 1H), 9.22 (s, 1H), 8.93 (s, 1H), 7.59-7.58 (d, J=6.4 Hz, 1H), 7.35 (s, 1H), 7.23 (m, 2H), 3.88 (s, 3H), 3.29 (s, 3H), 2.57 (s, 3H).

Example 152: Synthesis of N-(4-((4-ethyl-2-(methylsulfonyl)phenyl)amino)-2-methyl-3-oxo-2,3-dihydro-1H-pyrazolo[3,4-b]pyridin-6-yl)cyclopropanecarboxamide, I-152

Synthesis of compound 151.1.

To a solution of 6-aminopyrazine-2-carbonitrile (1.0 g, 8.33 mmol, 1.0 eq) in acetonitrile (0.5 mL) was added N-Bromosuccinimide (2.22 g, 12.50 mmol, 1.5 eq). The reaction was stirred at room temperature for 12 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 20% ethyl acetate in hexane to obtain pure 151.1 (0.75 g, 45.27%). MS(ES): m/z 200.01 [M+H]$^+$ Synthesis of Compound 151.2.

To 151.1 (0.75 g, 3.77 mmol, 1.0 eq) in mixture of 1,4-dioxane (0.5 mL) and water (mL) was added Trimethylboroxine (0.40 g, 7.54 mmol, 2.0 eq). The reaction mixture was degassed for 10 min. under argon atmosphere. Potassium carbonate (1.56 g, 11.31 mmol, 3.0 eq) and tetrakis(triphenylphosphine)palladium(0) (0.435 g, 0.377 mmol, 0.1 eq), again reaction mixture was degassed for 10 min. under argon atmosphere. The reaction was stirred at 110° C. for 20 h. After completion of reaction, reaction mixture was transferred in water and extracted with ethyl acetate. Combined organic layer was washed with brine, dried over sodium sulphate and concentrated under reduced pressure to obtain

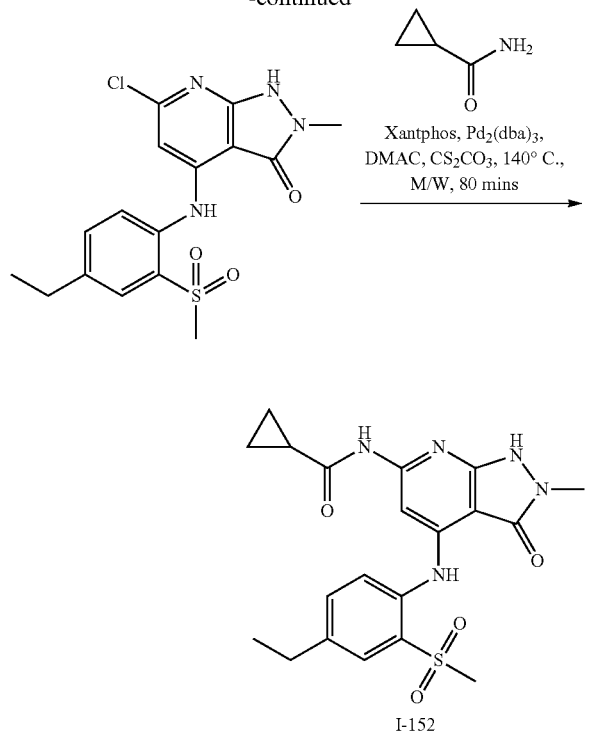

I-152

Synthesis of Compound 152.1

To a solution of 4-ethylaniline (3.0 g, 24.76 mmol, 1.0 eq) in acetic acid (30 mL) were added Ammonium thiocyanate (1.88 g, 24.76 mmol, 1.0 eq). The reaction mixture was cooled to 0° C. and added dropwise bromine solution (3.96 g, 24.76 mmol, 1.0 eq). Reaction mixture was stirred at 10° C. for 3 h. After completion of reaction, reaction mixture was transferred into water and extracted with ethyl acetate. Organic layer was combined, washed by saturated solution of sodium bicarbonate, dried over sodium sulphate and concentrated under reduced pressure to obtain crude material. This was further purified by column chromatography and compound was eluted in 15% ethyl acetate in hexane as eluent to obtain 152.1. (1.10 g, 24.93%). MS(ES): m/z 179.25 [M+H]$^+$.

Synthesis of Compound 152.2.

To a solution of 152.1 (1.1 g, 6.17 mmol, 1.0 eq) in water (10 mL) was added aqueous solution of potassium hydroxide (4.14 g, 74.04 mmol, 12.0 eq). Reaction mixture was refluxed for 48 h. The reaction mixture was maintained at room temperature, methyl iodide (0.963 g, 6.78 mmol, 1.1 eq) was added, and the reaction stirred for 1 h. After completion of reaction, reaction mixture was extracted with ethyl acetate. Organic layer was combined, dried over sodium sulphate and concentrated under reduced pressure to obtain crude material. This was further purified by column chromatography and compound was eluted in 20% ethyl acetate in hexane as eluent to obtain 152.2. (0.5 g, 48.44%). MS(ES): m/z 168.27 [M+H]$^+$.

Synthesis of Compound 152.3.

Compound 152.3 was synthesized from 1.9 and 152.2 using general procedure A. (Yield: 68.75%). MS (ES): m/z 349.85 [M+H]$^+$.

Synthesis of Compound 152.4

To a solution of 152.3 (0.11 g, 0.315 mmol, 1 eq) in acetic acid (0.2 mL) was added 30% hydrogen peroxide (0.214 g, 6.3 mmol, 20.0 eq) and sodium tungstate dihydrate (0.104 g, 0.315 mmol, 1 eq). Reaction mixture was stirred at room temperature for 2 h. After completion of reaction, reaction mixture was transferred in ice-water and precipitated product was filtered, washed with 50% ethyl acetate in hexane and dried well to obtain 152.4 (0.097 g, Yield: 80.77%). MS(ES): m/z 381.85 [M+H]$^+$ Synthesis of Compound I-152.

Compound I-152 was synthesized from 152.4 and cyclopropanecarboxamide using general procedure B (Yield: 23.77%). MS(ES): m/z 430.24 [M+H]$^+$, LCMS purity: 98.41%, HPLC purity: 100%, 1H NMR (DMSO-d6, 400 MHz): 10.75-10.73 (d, J=7.2 Hz, 2H), 9.03 (s, 1H), 7.77 (s, 1H), 8.69-7.63 (m, 3H), 3.29 (s, 3H), 3.15 (s, 3H), 2.75-2.70 (q, J=7.2 Hz, 2H), 1.99 (s, 1H), 1.25-1.22 (t, J=7.2 Hz, 3H), 0.78-0.76 (m, 4H).

Example 153: 6-((4-((3-chloro-2-methoxyphenyl)amino)-2-methyl-3-oxo-2,3-dihydro-1H-pyrazolo[3,4-b]pyridin-6-yl)amino)-3-(difluoromethyl)picolinonitrile, I-156

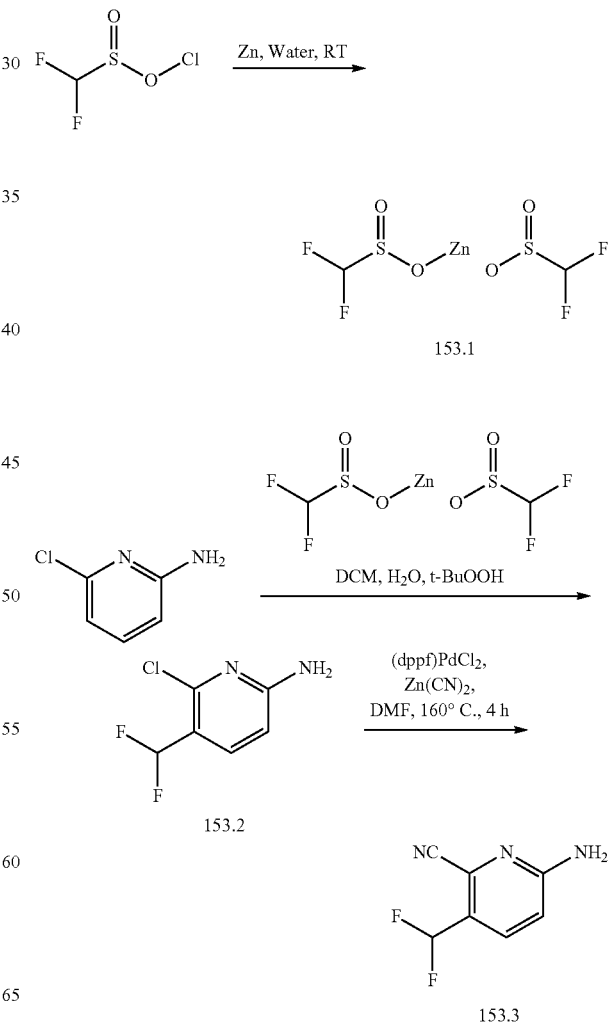

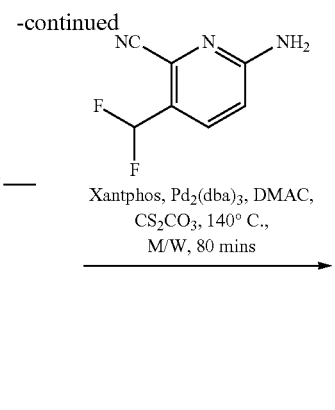

Synthesis of Compound 153.1.

To a cooled suspension of zinc dust (6.08 g, 93.03 mmol, 7.0 eq) in water (7 mL) at 0° C. was added difluoromethanesulfinic hypochlorous anhydride (2.0 g, 13.29 mmol, 1.0 eq) dropwise. The reaction mixture was stirred at room temperature for 2 h. After completion of reaction, reaction mixture was filtered, washed with ethyl acetate. Organic layer was dried over sodium sulphate and concentrated under reduced pressure to obtain 153.1. (2.10 g, 53.48%). MS(ES): m/z 296.53 [M+H]$^+$.

Synthesis of Compound 153.2.

To a solution of 6-chloropyridin-2-amine (0.5 g, 3.89 mmol, 1.0 eq) and 153.1 (3.45 g, 11.67 mmol, 3.0 eq) in mixture of dichloromethane (1 mL) and water (0.4 mL) was added dropwise tert-Butyl hydroperoxide (1.75 g, 19.45 mmol, 5.0 eq). The reaction mixture was stirred at room temperature for 8 h in closed vessel. After completion of reaction, reaction mixture was transferred in to saturated solution of sodium bicarbonate and extracted with dichloromethane. Organic layer was combined, dried over sodium sulphate and concentrated under reduced pressure to obtain crude material. This was further purified by column chromatography and compound was eluted in 15% ethyl acetate in hexane as eluent to obtain 153.2. (0.095 g, 13.68%). MS(ES): m/z 179.57 [M+H]$^+$.

Synthesis of Compound 153.3.

To a solution of 153.2 (0.095 g, 0.532 mmol, 1.0 eq) and zinc cyanide (0.037 g, 0.319 mmol, 0.6 eq) in N,N-dimethylformamide (2.0 mL). The reaction mixture was degassed for 10 min. under argon atmosphere. [1,1'-Bis(diphenylphosphino)ferrocene]palladium(II) dichloride (0.008 g, 0.011 mmol, 0.02 eq) was added and again degassed for 10 min. under argon atmosphere. The reaction mixture was stirred at 160° C. for 4 h. After completion of reaction, reaction mixture was transferred in to saturated solution of sodium bicarbonate and extracted with dichloromethane. Organic layer was combined, dried over sodium sulphate and concentrated under reduced pressure to obtain crude material. This was further purified by column chromatography and compound was eluted in 15% ethyl acetate in hexane as eluent to obtain 153.3. (0.06 g, 66.68%). MS(ES): m/z 170.13 [M+H]$^+$.

Synthesis of Compound I-156.

Compound I-156 was synthesized from 73.1 and 153.3 using general procedure B (Yield: 28.75%). MS(ES): m/z 472.27 [M+H]$^+$, LCMS purity: 98.10%, HPLC purity: 96.85%, 1H NMR (DMSO-d6, 400 MHz): 10.84 (bs, 1H), 9.42 (s, 1H), 8.95 (s, 1H), 8.20-8.18 (d, J=7.2 Hz, 1H), 7.80-7.78 (d, J=7.2 Hz, 1H), 7.67-7.65 (d, J=7.2 Hz, 1H), 7.49 (s, 1H), 7.35-7.25 (m, 2H), 3.84 (s, 3H), 3.32 (s, 3H), 2.10 (s, 1H).

Example 154: Synthesis of 6-((5-fluoro-4-methylpyridin-2-yl)amino)-4-((2-methoxy-3-(1-methyl-1H-1,2,4-triazol-3-yl)phenyl)amino)-2-methyl-1,2-dihydro-3H-pyrazolo[3,4-b]pyridin-3-one, I-21

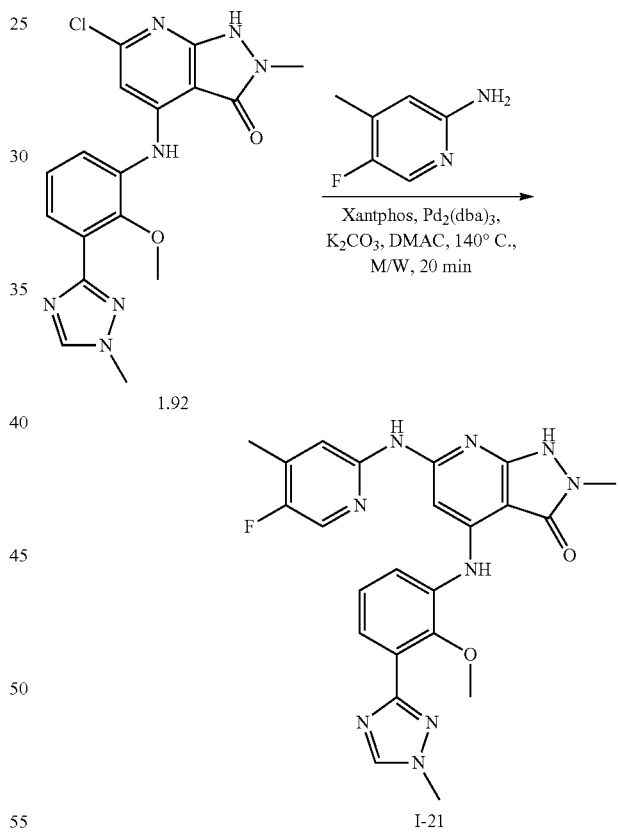

Synthesis of compound I-21.

Compound I-21 was synthesized from 5-fluoro-4-methylpyridin-2-amine and 1.92 using general procedure B. (Yield: 22.72%), MS(ES): m/z 476.48 [M+H]$^+$, LCMS purity: 100.00%, HPLC purity: 99.07%, 1H NMR (DMSO-d6, 400 MHZ): 9.86 (bs, 1H), 8.91 (s, 1H), 8.58 (s, 1H), 8.15 (s, 1H), 7.99 (bs, 1H), 7.67-7.65 (d, J=6.8 Hz, 1H), 7.59-7.57 (d, J=7.6 Hz, 1H), 7.32-7.28 (t, J=8.0 Hz, 1H), 6.98 (bs, 1H), 5.8 (s, 1H), 3.96 (s, 3H), 3.78 (s, 3H), 3.29 (s, 3H), 2.28 (s, 3H).

Example 155: Synthesis of 6-((4-(hydroxymethyl) pyridin-2-yl)amino)-4-((2-methoxy-3-(1-methyl-1H-1,2,4-triazol-3-yl)phenyl)amino)-2-methyl-1,2-dihydro-3H-pyrazolo[3,4-b]pyridin-3-one, I-19

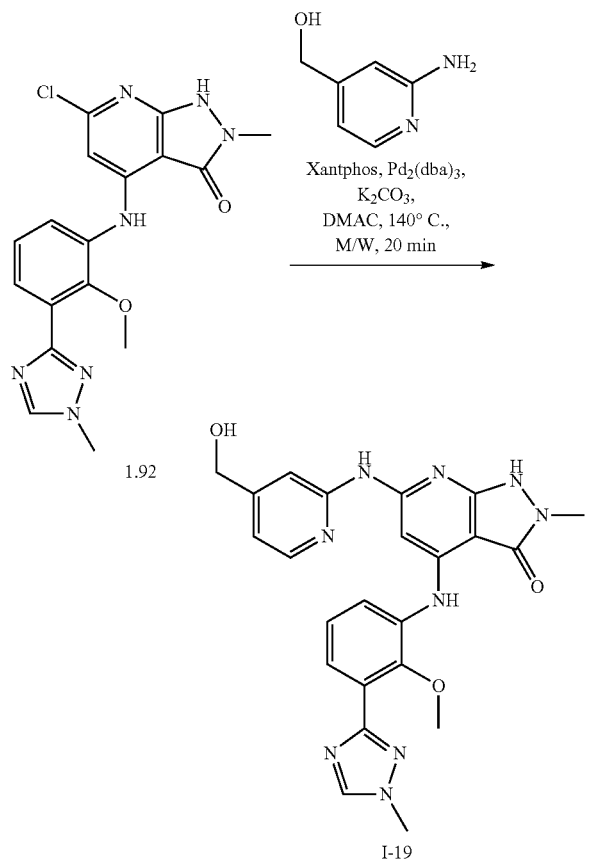

I-19

Synthesis of compound I-19.

Compound I-19 was synthesized from (2-aminopyridin-4-yl)methanol and 1.92 using general procedure B (Yield: 5.43%). MS(ES): m/z 474.58 [M+H]+, LCMS purity: 98.36%, HPLC purity: 96.55%, 1H NMR (DMSO-d6, 400 MHZ): 10.02 (bs, 1H), 8.97 (s, 1H), 8.58 (s, 1H), 8.20 (s, 3H), 7.68-7.59 (m, 3H), 7.30 (s, 1H), 6.92-6.90 (d, J=4.8 Hz, 1H), 4.52 (s, 2H), 3.96 (s, 3H), 3.78 (s, 3H), 3.30 (s, 3H), 2.54 (s, 1H).

Example I-156: Synthesis of 4-((2-methoxy-3-(1-methyl-1H-1,2,4-triazol-3-yl)phenyl)amino)-2-methyl-6-((5-(piperidin-1-yl)pyridin-2-yl)amino)-1,2-dihydro-3H-pyrazolo[3,4-b]pyridin-3-one, I-24

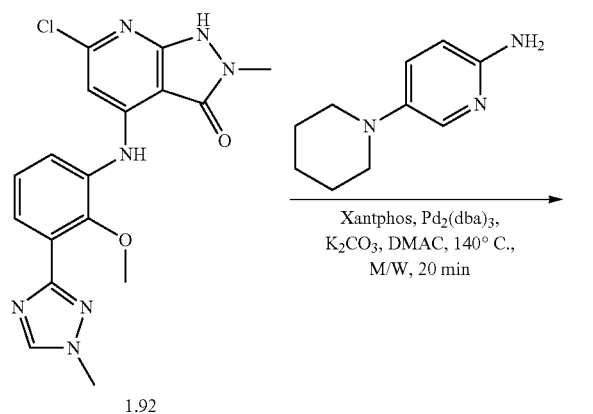

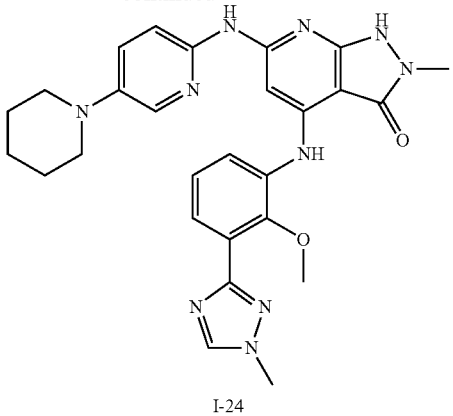

I-24

Synthesis of Compound I-24.

Compound I-24 was synthesized from 5-(piperidin-1-yl)pyridin-2-amine and 1.92 using general procedure B. (Yield: 13.68%), MS(ES): m/z 527.76 [M+H]+, LCMS purity: 99.24%, HPLC purity: 96.02%, 1H NMR (DMSO-d6, 400 MHZ): 9.79 (bs, 2H), 8.94 (s, 1H), 8.58 (s, 1H), 8.16 (s, 1H), 7.96 (s, 1H), 7.66-7.64 (d, J=8.0 Hz, 1H), 7.59-7.58 (d, J=7.6 Hz, 1H), 7.44-7.43 (d, J=7.2 Hz, 1H), 7.32-7.28 (t, J=8.0 Hz, 1H), 6.77-6.44 (m, 1H), 3.96 (s, 3H), 3.78 (s, 3H), 3.28 (s, 3H), 3.09 (s, 4H), 1.64 (s, 4H), 1.52 (s, 2H).

Example 157: Synthesis of 4-((2-methoxy-3-(1-methyl-1H-1,2,4-triazol-3-yl)phenyl)amino)-2-methyl-6-((5-morpholinopyridin-2-yl)amino)-1,2-dihydro-3H-pyrazolo[3,4-b]pyridin-3-one, I-20

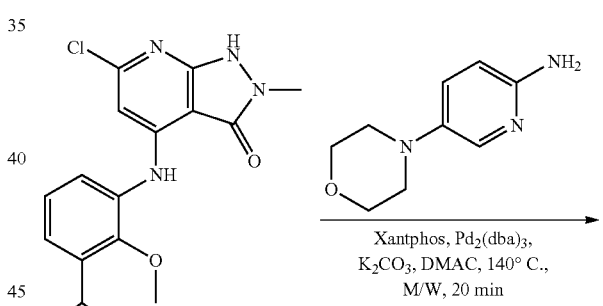

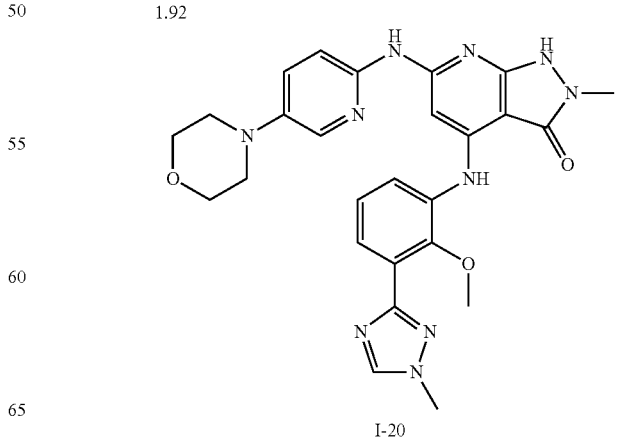

I-20

Synthesis of Compound I-20.

Compound I-20 was synthesized from 5-morpholinopyridin-2-amine and 1.92 using general procedure B. (Yield: 13.68%), MS(ES): m/z 527.76 [M+H]$^+$, LCMS purity: 99.24%, HPLC purity: 96.02%, 1H NMR (DMSO-d6, 400 MHZ): 9.79 (bs, 2H), 8.94 (s, 1H), 8.58 (s, 1H), 8.16 (s, 1H), 7.96 (s, 1H), 7.66-7.64 (d, J=8.0 Hz, 1H), 7.59-7.58 (d, J=7.6 Hz, 1H), 7.44-7.43 (d, J=7.2 Hz, 1H), 7.32-7.28 (t, J=8.0 Hz, 1H), 6.77-6.44 (m, 1H), 3.96 (s, 3H), 3.78 (s, 3H), 3.28 (s, 3H), 3.09 (s, 4H), 1.64 (s, 4H), 1.52 (s, 2H).

Example 158: Synthesis of 6-((4-((2-methoxy-3-(1-methyl-1H-1,2,4-triazol-3-yl)phenyl)amino)-2-methyl-3-oxo-2,3-dihydro-1H-pyrazolo[3,4-b]pyridin-6-yl)amino)pyrimidine-4-carbonitrile, I-31

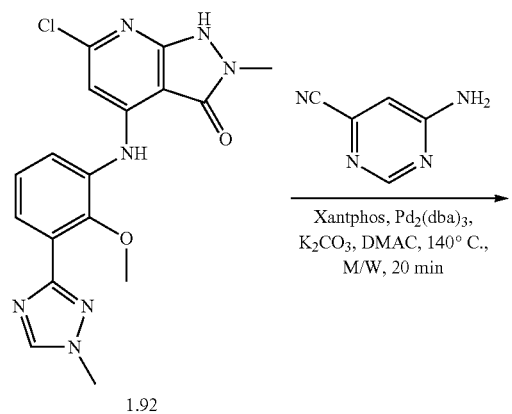

1.92

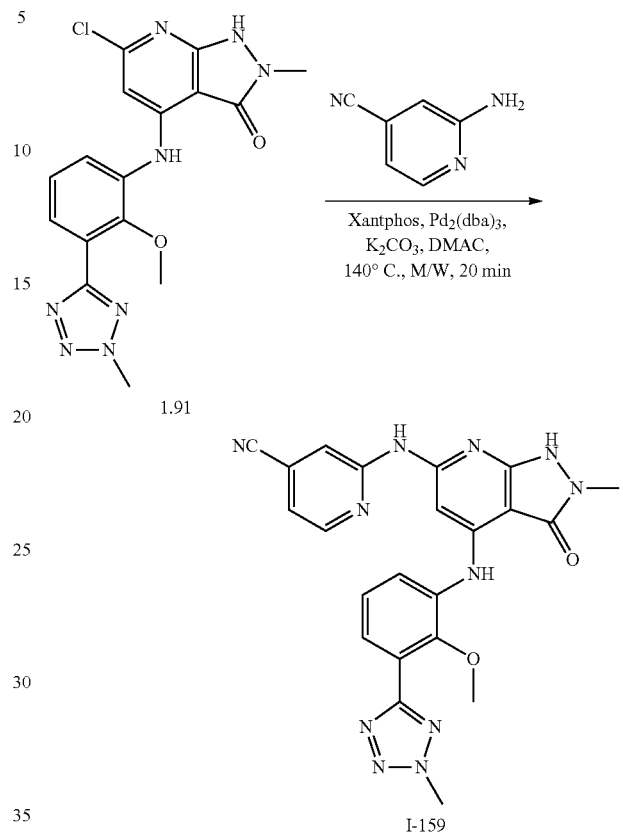

1.91

I-31

Synthesis of Compound I-31.

Compound I-31 was synthesized from 6-aminopyrimidine-4-carbonitrile and 1.92 using general procedure B (Yield: 13.7%) MS(ES): m/z 470.64 [M+H]$^+$, LCMS purity: 94.47%, HPLC purity: 93.57%, 1H NMR (DMSO-d6, 400 MHZ): 11.17 (bs, 1H), 10.85 (bs, 1H), 8.96 (s, 1H), 8.87 (s, 1H), 8.66 (s, 1H), 8.58 (s, 1H), 7.65-7.61 (t, J=7.6 Hz, 2H), 7.31-7.29 (d, J=8.0 Hz, 1H), 7.00 (s, 1H), 3.96 (s, 3H), 3.77 (s, 3H), 3.40 (s, 3H).

Example 159: Synthesis of 2-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)isonicotinonitrile, I-32

I-159

Synthesis of Compound I-159.

Compound I-159 was synthesized from 2-aminoisonicotinonitrile and 1.91 using general procedure B (Yield: 24.72%). MS(ES): m/z 470.43 [M+H]$^+$, LCMS purity: 95.52%, HPLC purity: 96.87%, 1H NMR (DMSO-d6, 400 MHZ): 11.01 (s, 1H), 10.27 (s, 1H), 8.93 (s, 1H), 8.61 (s, 1H), 8.48-8.48 (d, J=4.0 Hz, 1H), 7.78-7.76 (d, J=7.6 Hz, 1H), 7.66-7.64 (d, J=7.2 Hz, 1H), 7.48-7.34 (m, 2H), 6.97 (s, 1H), 4.47 (s, 3H), 3.79 (s, 3H), 3.16 (s, 3H).

Example 160: Synthesis of 6-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)nicotinonitrile, I-12

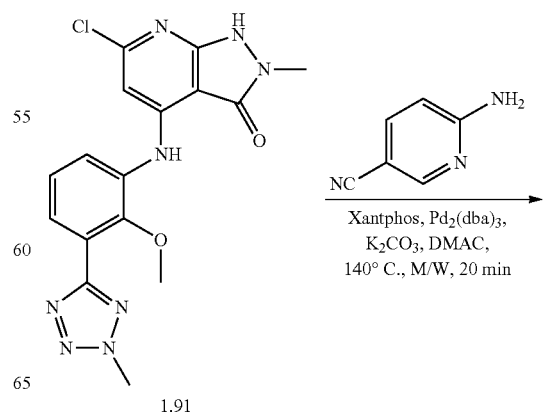

1.91

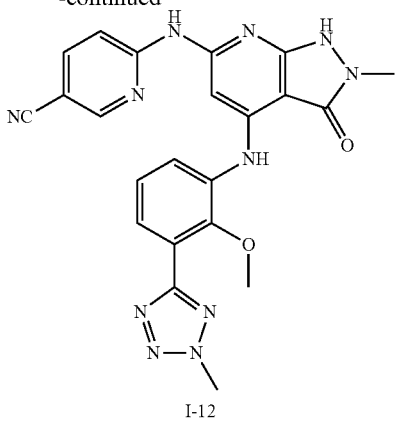

I-12

Synthesis of Compound I-12.

Compound I-12 was synthesized from 1.91 and 6-aminonicotinonitrile using general procedure B. (Yield: 20.60%). MS(ES): m/z 470.68 [M+H]+, LCMS purity: 97.03%, HPLC purity: 99.75%, 1H NMR (DMSO-d6, 400 MHZ): 10.99 (s, 1H), 10.44 (s, 1H), 8.95 (s, 1H), 8.70 (s, 1H), 8.25-8.22 (d, J=8.8 Hz, 1H), 8.15-8.13 (d, J=8.8 Hz, 1H), 7.79-7.78 (d, J=7.6 Hz, 1H), 7.66-7.64 (d, J=7.6 Hz, 1H), 7.44-7.40 (t, J=7.6 Hz, 1H), 7.17 (s, 1H), 4.47 (s, 3H), 3.79 (s, 3H), 3.39 (s, 3H).

Example 161: Synthesis of 4-((2-methoxy-3-(2-methyl-2H-tetrazol-5-yl)phenyl)amino)-2-methyl-6-((1-methyl-1H-pyrazol-3-yl)amino)-1,2-dihydro-3H-pyrazolo[3,4-b]pyridin-3-one, I-13

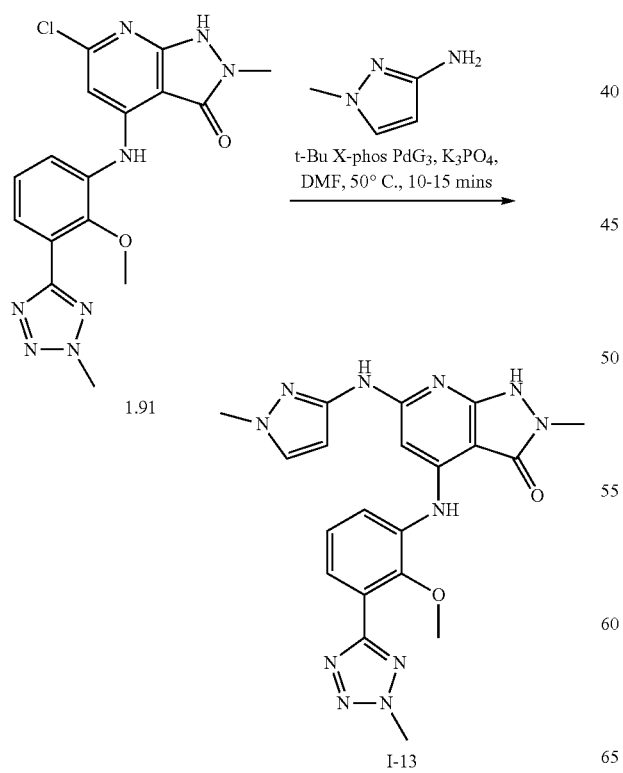

I-13

Synthesis of Compound I-13.

Compound I-13 was synthesized from 1-methyl-1H-pyrazol-3-amine and 1.91 using general procedure C (Yield: 17.29%). MS(ES): m/z 448.43 [M+H]+, LCMS purity: 100.00%, HPLC purity: 99.64%, 1H NMR (DMSO-d6, 400 MHZ): 10.52 (s, 1H), 9.51 (s, 1H), 8.84 (s, 1H), 7.78-7.76 (d, J=7.6 Hz, 1H), 7.62-7.60 (d, J=7.6 Hz, 1H), 7.55 (s, 1H), 7.40-7.36 (t, J=7.6 Hz, 1H), 6.93 (bs, 1H), 6.36 (s, 1H), 4.47 (s, 3H), 3.79 (s, 3H), 3.75 (s, 3H), 3.26 (s, 3H).

Example 162: Synthesis of 6-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)picolinonitrile, I-28 ( )

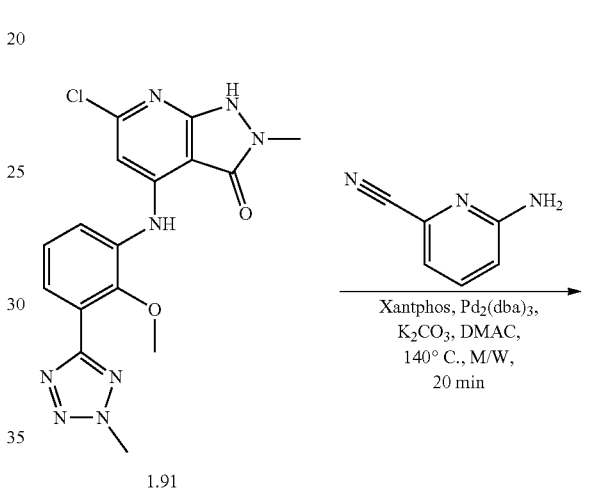

I-28

Synthesis of Compound I-28.

Compound I-28 was synthesized from 6-aminopicolinonitrile and 1.91 using general procedure B. (Yield: 18.13) MS(ES): m/z 470.43 [M+H]+, LCMS purity: 97.40%, HPLC purity: 98.61%, 1H NMR (DMSO-d6, 400 MHZ): 10.32 (s, 1H), 9.03 (s, 1H), 8.10-8.08 (d, J=8.8 Hz, 1H), 7.94-7.89 (t, J=8.8 Hz, 1H), 7.86-7.84 (d, J=7.2 Hz, 1H), 7.65-7.63 (d, J=7.2 Hz, 1H), 7.56-7.54 (d, J=7.2 Hz, 1H), 7.49-7.41 (m, 2H), 4.47 (s, 3H), 3.80 (s, 3H), 3.32 (s, 3H).

Example 163: Synthesis of 6-((4-((2-methoxy-3-(2-methyl-2H-tetrazol-5-yl)phenyl)amino)-2-methyl-3-oxo-2,3-dihydro-1H-pyrazolo[3,4-b]pyridin-6-yl)amino)pyrimidine-4-carbonitrile, I-29

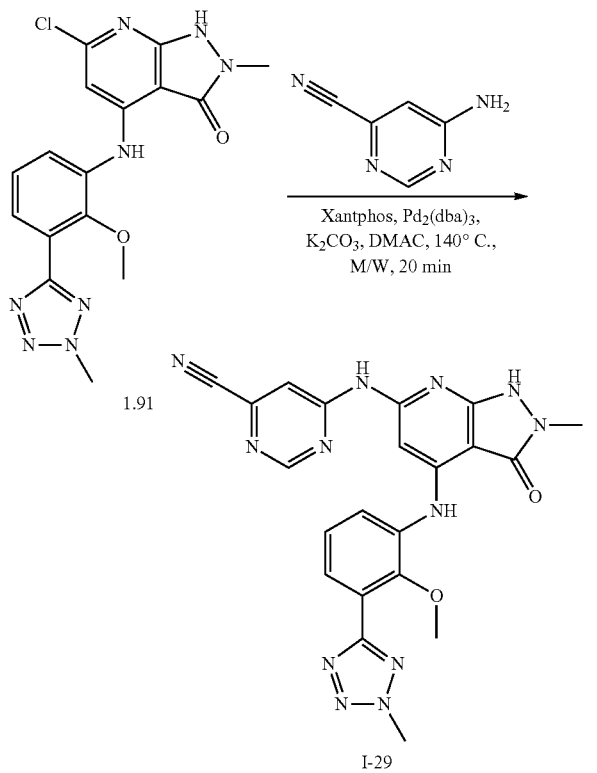

Synthesis of Compound I-29.

Compound I-29 was synthesized from 6-aminopyrimidine-4-carbonitrile and 1.91 using general procedure B. (Yield: 17.27) MS(ES): m/z 471.48 [M+H]$^+$, LCMS purity: 100.00%, HPLC purity: 99.45%, 1H NMR (DMSO-d6, 400 MHZ): 11.20 (bs, 1H), 10.83 (s, 1H), 8.97 (s, 1H), 8.87 (s, 1H), 8.66 (s, 1H), 7.76-7.74 (d, J=8.0 Hz, 1H), 7.69-7.67 (d, J=8.0 Hz, 1H), 7.43-7.39 (t, J=8.0 Hz, 1H), 6.97 (s, 1H), 4.47 (s, 3H), 3.78 (s, 3H), 3.33 (s, 3H).

Example 164: Synthesis of 4-((2-methoxy-3-(1-methyl-1H-1,2,4-triazol-3-yl)phenyl)amino)-2-methyl-6-((4-methylpyridin-2-yl)amino)-1,2-dihydro-3H-pyrazolo[3,4-b]pyridin-3-one, I-18

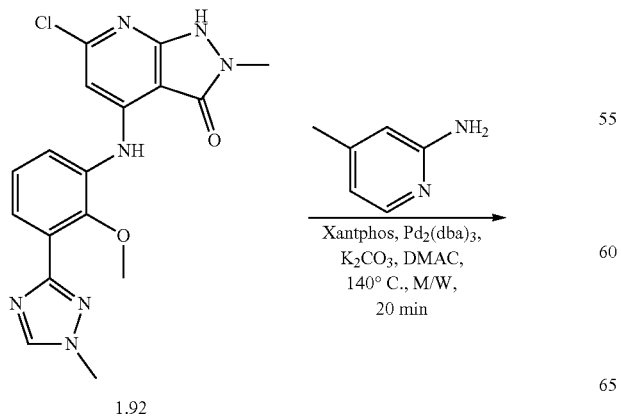

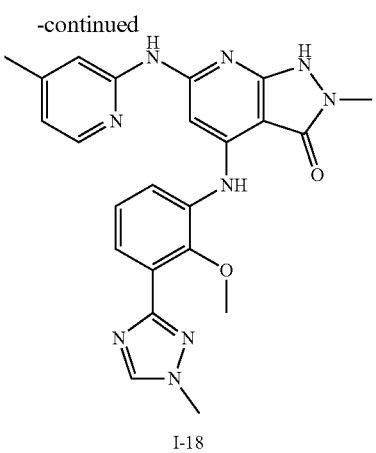

Synthesis of Compound I-18.

Compound I-18 was synthesized from 4-methylpyridin-2-amine and 1.92 using general procedure B (Yield: 11.24%), MS(ES): m/z 458.48 [M+H]$^+$, LCMS purity: 99.71%, HPLC purity: 98.00%, 1H NMR (CDCl3, 400 MHZ): 9.49 (bs, 1H), 8.91 (s, 1H), 8.06 (s, 1H), 8.03-8.01 (d, J=6.4 Hz, 1H), 7.60-7.59 (d, J=7.2 Hz, 1H), 7.02-6.98 (t, J=7.6 Hz, 1H), 6.79 (s, 1H), 6.75-6.74 (d, J=5.2 Hz, 1H), 5.70 (s, 1H), 3.96 (s, 3H), 3.73 (s, 3H), 3.58 (s, 3H), 2.29 (s, 3H).

Example 165: Synthesis of 4-((2-methoxy-3-(1-methyl-1H-1,2,4-triazol-3-yl)phenyl)amino)-6-((4-(methoxymethyl)pyridin-2-yl)amino)-2-methyl-1,2-dihydro-3H-pyrazolo[3,4-b]pyridin-3-one, I-15

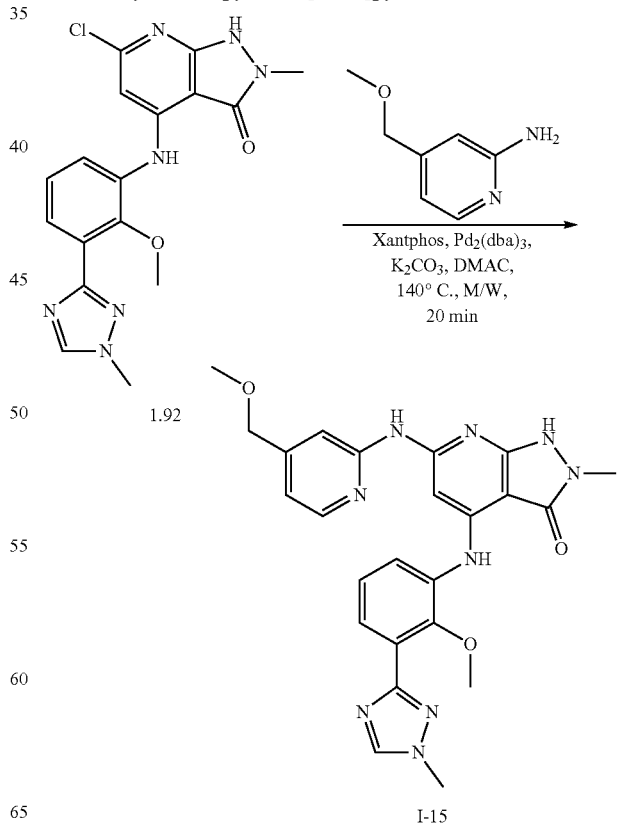

Synthesis of Compound I-15.

Compound I-15 was synthesized from 4-(methoxymethyl)pyridin-2-amine and 1.92 using general procedure B. (Yield: 15.83%), MS(ES): m/z 488.53 [M+H]$^+$, LCMS purity: 98.20%, HPLC purity: 98.44%, 1H NMR (MeOD, 400 MHZ): 8.51 (s, 1H), 8.29-8.28 (d, J=5.2 Hz, 1H), 7.76-7.74 (d, J=7.2 Hz, 1H), 7.65-7.63 (d, J=6.8 Hz, 1H), 7.36-7.32 (t, J=8.0 Hz, 1H), 7.05-7.04 (d, J=5.2 Hz, 1H), 6.96 (s, 1H), 5.78 (s, 1H), 4.51 (s, 2H), 4.04 (s, 3H), 3.79 (s, 3H), 3.56 (s, 3H), 3.46 (s, 3H).

Example 166: Synthesis of 6-((4-((2-methoxy-3-(1-methyl-1H-1,2,4-triazol-3-yl)phenyl)amino)-2-methyl-3-oxo-2,3-dihydro-1H-pyrazolo[3,4-b]pyridin-6-yl)amino)picolinonitrile, I-30

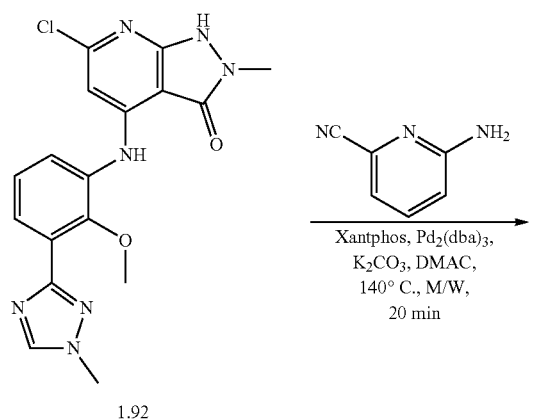

Synthesis of Compound I-30.

Compound I-30 was synthesized from 6-aminopicolinonitrile and 1.92 using general procedure B. (Yield: 13.73%), MS(ES): m/z 469.48 [M+H]$^+$, LCMS purity: 95.85%, HPLC purity: 96.87%, 1H NMR (DMSO-d6, 400 MHZ): 10.81 (bs, 1H), 10.31 (bs, 1H), 9.02 (s, 1H), 8.58 (s, 1H), 8.10-8.08 (d, J=8.8 Hz, 1H), 7.93-7.89 (t, J=8.0 Hz, 1H), 7.76-7.74 (d, J=7.6 Hz, 1H), 7.59-7.50 (m, 3H), 7.36-7.32 (t, J=8.0 Hz, 1H), 3.97 (s, 3H), 3.79 (s, 3H), 3.31 (s, 3H).

Example 167: Synthesis of 6-((2,6-dimethylpyrimidin-4-yl)amino)-4-((2-methoxy-3-(1-methyl-1H-1,2,4-triazol-3-yl)phenyl)amino)-2-methyl-1,2-dihydro-3H-pyrazolo[3,4-b]pyridin-3-one, I-22

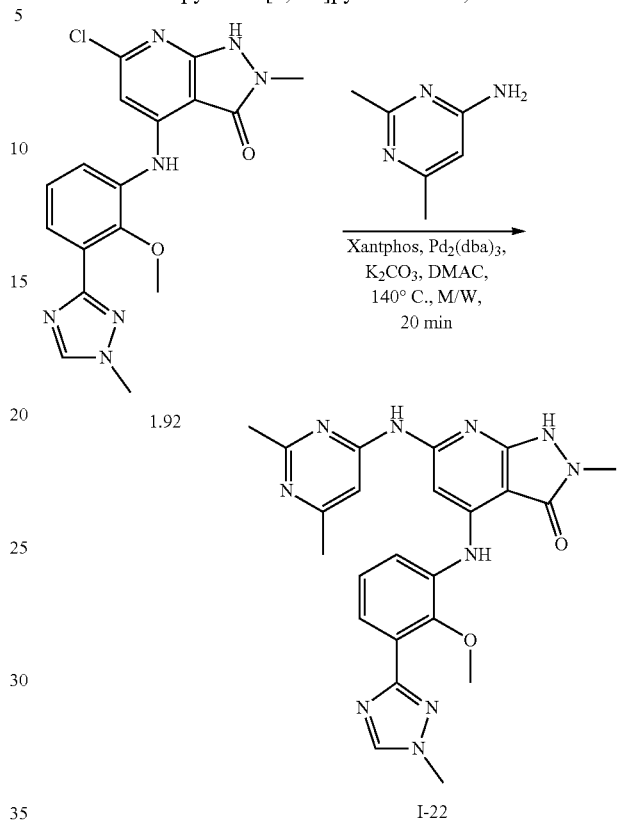

Synthesis of compound I-22.

Compound I-22 was synthesized from 2,6-dimethylpyrimidin-4-amine and 1.92 using general procedure B. (Yield: 9.25%), MS(ES): m/z 473.38 [M+H]$^+$, LCMS purity: 94.70%, HPLC purity: 96.65%, 1H NMR (MeOD, 400 MHZ): 8.52 (s, 1H), 7.74-7.64 (m, 3H), 7.36-7.32 (t, J=8.0 Hz, 2H), 4.04 (s, 3H), 3.78 (s, 3H), 3.54 (s, 3H), 2.68 (s, 3H), 2.43 (s, 3H).

Example 168: Synthesis of 4-((2-methoxy-3-(1-methyl-1H-1,2,4-triazol-3-yl)phenyl)amino)-2-methyl-6-((6-methylpyridazin-3-yl)amino)-1,2-dihydro-3H-pyrazolo[3,4-b]pyridin-3-one, I-23

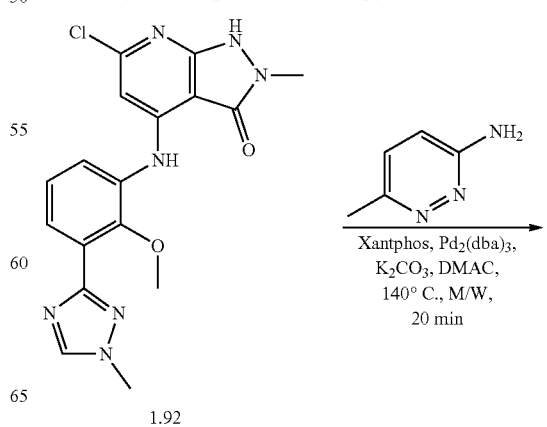

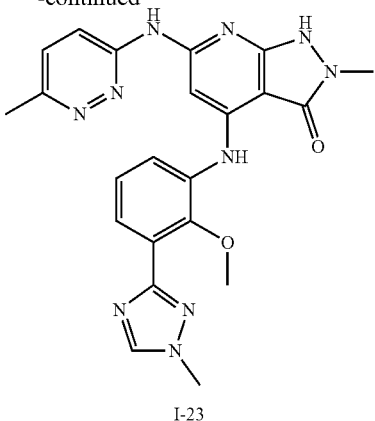

I-23

Synthesis of compound I-23.

Compound I-23 was synthesized from 6-methylpyridazin-3-amine and using general procedure B. (Yield: 7.29%), MS(ES): m/z 459.63 [M+H]⁺, LCMS purity: 99.85%, HPLC purity: 95.09%, 1H NMR (MeOD, 400 MHZ): 8.52 (s, 1H), 7.82-7.55 (m, 3H), 7.36-7.32 (t, J=8.0 Hz, 2H), 5.90 (s, 1H), 4.04 (s, 3H), 3.78 (s, 3H), 3.53 (s, 3H), 2.62 (s, 3H).

Example 169: Synthesis of 4-((2-methoxy-3-(1-methyl-1H-1,2,4-triazol-3-yl)phenyl)amino)-2-methyl-6-(pyridin-2-ylamino)-1,2-dihydro-3H-pyrazolo[3,4-b]pyridin-3-one, I-17

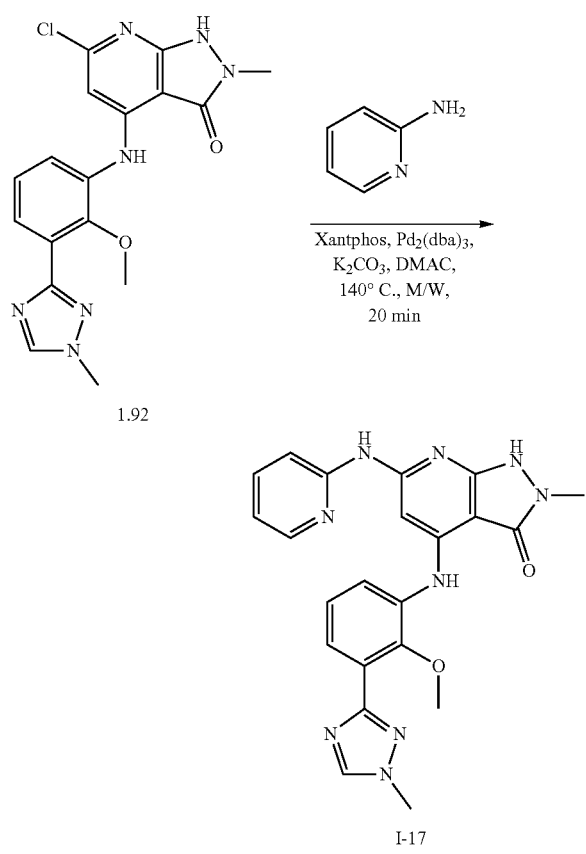

Synthesis of compound I-17.

Compound I-17 was synthesized from pyridin-2-amine and 1.92 using general procedure B. (Yield: 31.9%), MS(ES): m/z 444.43 [M+H]⁺, LCMS purity: 100.00%, HPLC purity: 99.55%, 1H NMR (DMSO-d6, 400 MHZ): 9.96-9.86 (m, 1H), 8.94 (s, 1H), 8.58 (s, 1H), 8.27 (s, 1H), 7.73-7.67 (m, 2H), 7.60-7.58 (d, J=7.6 Hz, 1H), 7.32-7.28 (t, J=8.0 Hz, 1H), 6.96 (s, 1H), 3.96 (s, 3H), 3.78 (s, 3H), 3.30 (s, 3H).

Example 170: Synthesis of 2-methoxy-3-((6-((4-(methoxymethyl)pyridin-2-yl)amino)-2-methyl-3-oxo-2,3-dihydro-1H-pyrazolo[3,4-b]pyridin-4-yl)amino)benzamide, I-126

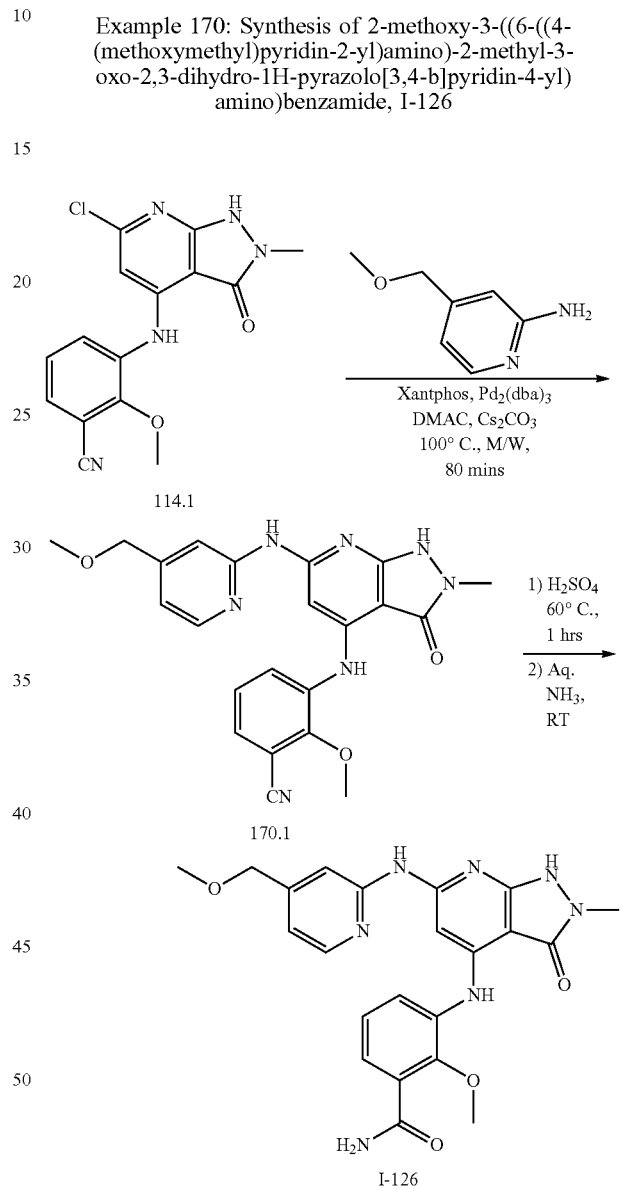

Synthesis of compound 1.2.

Compound 170.1 was synthesized from 114.1 and 4-(methoxymethyl)pyridin-2-amine using general procedure B. (Yield: 48.91%). MS (ES): m/z 432.46 [M+H]⁺.

Synthesis of compound I-126. The solution of compound 170.1 (0.110 g, 0.250 mmol, 1.0 eq) in sulphuric acid (2 mL) is heated at 60° C. for 1 h. After completion of the reaction, the reaction mixture is cooled to room temperature. Reaction mixture is transferred to water and the pH of the solution is adjusted to 7 by using aqueous ammonia to get the solid precipitates which are filtered to get the crude material. These are further purified by trituration using pentane to obtain pure I-126. (Yield: 21.28%). MS(ES): m/z 450.46 [M+H]⁺, LCMS purity: 100%, HPLC purity: 97.39%, 1H NMR (DMSO-d6, 400 MHz): 14.14 (s, 1H), 10.81 (bs, 1H), 8.63 (s, 2H), 8.29-8.28 (d, J=5.6 Hz, 1H), 8.14 (s, 1H), 7.69-7.62 (m, 3H), 7.04-7.02 (d, J=4.8 Hz, 1H), 6.98-6.94 (t, J=8.0 Hz, 1H), 6.59 (bs, 1H), 4.53 (s, 2H), 3.43 (s, 3H), 3.38 (s, 3H), 3.15 (s, 3H).

Example 171: Synthesis of N-(4-((3-methoxypyridin-2-yl)amino)-2-methyl-3-oxo-2,3-dihydro-1H-pyrazolo[3,4-b]pyridin-6-yl)cyclopropanecarboxamide, I-223

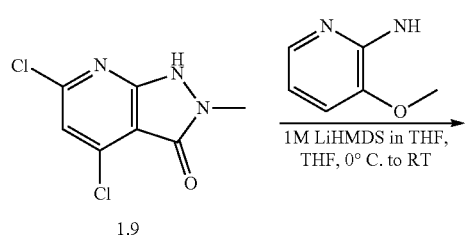

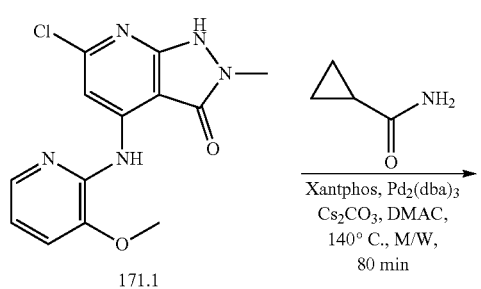

Example 172: Synthesis of N-(4-((2-methoxy-3-(5-methyl-1,2,4-oxadiazol-3-yl)phenyl)amino)-2-methyl-3-oxo-2,3-dihydro-1H-pyrazolo[3,4-b]pyridin-6-yl)cyclopropanecarboxamide, I-131

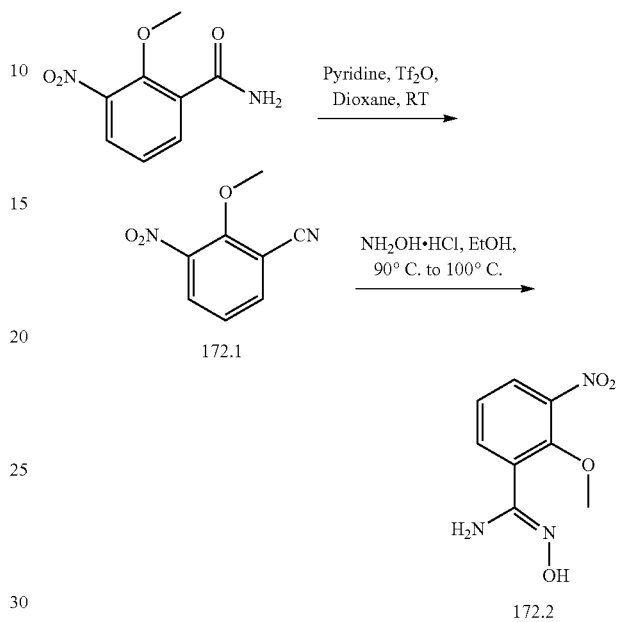

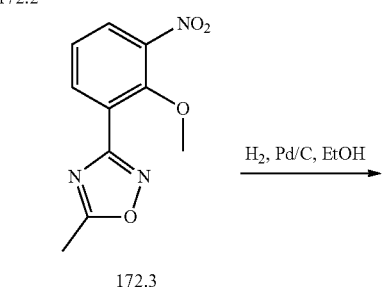

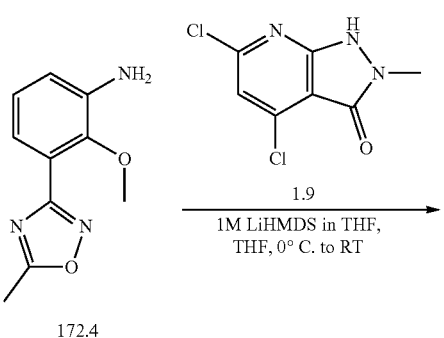

Synthesis of Compound 171.1.

Compound 171.1 was synthesized from 3-methoxypyridin-2-amine and 1.9 using general procedure A. (Yield: 89.15%). MS (ES): m/z 306.7 [M+H]⁺.

Synthesis of Compound I-223.

Compound I-223 was synthesized from 171.1 and cyclopropanecarboxamide using general procedure B (Yield: 17.25%), MS(ES): m/z 355.17 [M+H]⁺, LCMS purity: 99.64%, HPLC purity: 100.00%, 1H NMR (DMSO-d6, 400 MHz): 10.70 (s, 2H), 9.63 (s, 1H), 8.99 (s, 1H), 7.87-7.86 (d, J=4.4 Hz, 1H), 7.38-7.36 (d, J=8.0 Hz, 1H), 6.99-6.96 (m, 1H), 3.91 (s, 3H), 3.29 (s, 3H), 2.02 (m, 1H), 0.83-0.78 (m, 4H).

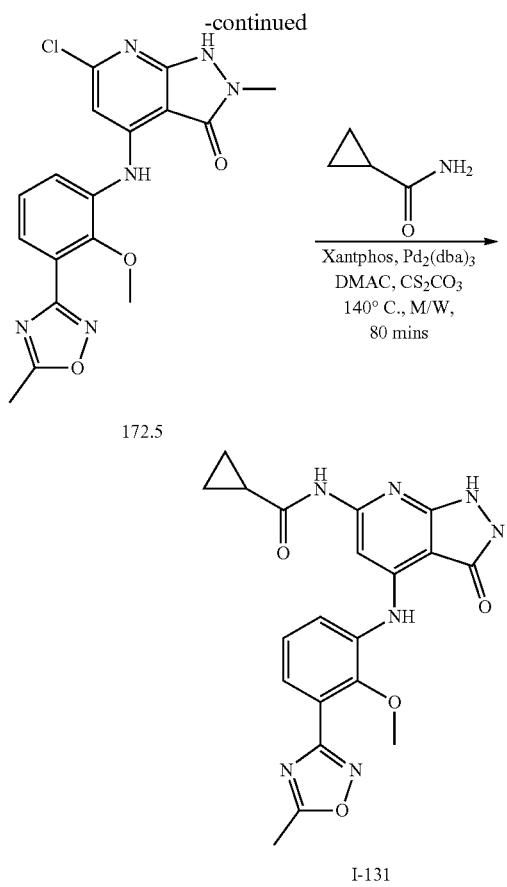

172.5

I-131

Synthesis of compound 172.1. To a cooled solution 2-methoxy-3-nitrobenzamide of (2.0 g, 10.20 mmol, 1.0 eq) in 1,4-dioxane (80 mL) were added dropwise pyridine (2.417 g, 30.6 mmol, 3.0 eq) and Trifluoromethanesulfonic anhydride (5.75 g, 20.40 mmol, 2.0 eq). The reaction mixture was stirred at room temperature for 3 h. After completion of reaction, reaction mixture was transferred into water and extracted with dichloromethane. Combined organic layer dried over sodium sulfate and concentrated under reduced pressure to obtain crude material. This was further triturated in dichloromethane to obtain pure 172.1 (1.0 g, 55.06%). MS(ES): m/z 179.15 [M+H]$^+$.

Synthesis of Compound 172.2.

To a solution of 172.1 (2.5 g, 14.03 mmol, 1.0 eq) in ethanol (40 mL) were added 50% solution of hydroxyl amine (25 mL). The reaction mixture was stirred at 90° C. for 1 h. After completion of reaction, reaction mixture was transferred into water and extracted with ethyl acetate. Combined organic layer dried over sodium sulfate and concentrated under reduced pressure to obtain crude material. This was further purified by column chromatography and compound was eluted in 1% methanol in dichloromethane to obtain pure 172.2 (1.3 g, 43.87%). MS(ES): m/z 212.18 [M+H]$^+$.

Synthesis of Compound 172.3.

To a solution of 172.2 (0.7 g, 3.31 mmol, 1.0 eq) in N,N-dimethylformamide (10 mL) were added potassium phosphate (2.10 g, 9.93 mmol, 3.0 eq). The reaction mixture was cooled at 0° C. and added acetyl chloride (0.516 g, 6.62 mmol, 2.0 eq). The reaction mixture was stirred at 120° C. for 2 h. After completion of reaction, reaction mixture was transferred into water and extracted with ethyl acetate. Combined organic layer dried over sodium sulfate and concentrated under reduced pressure to obtain crude material. This was further purified by column chromatography and compound was eluted in 1% methanol in dichloromethane to obtain pure 172.3 (0.3 g, 38.48%). MS(ES): m/z 236.20 [M+H]$^+$.

Synthesis of Compound 172.4.

To a solution of 172.3 (0.1 g, 0.425 mmol, 1.0 eq) in methanol (1 mL), 10% palladium on charcoal (0.08 g) was added. Hydrogen was purged through reaction mixture for 2-3 h. After completion of reaction, reaction mixture was filtered through celite-bed and washed with ethanol. Filtrate was concentrated under reduced pressure to obtain 172.4 (0.04 g, 45.84%). MS(ES): m/z 206.22 [M+H]$^+$.

Synthesis of Compound 172.5.

Compound 172.5 was synthesized from 1.9 and 172.4 using general procedure A to obtain 1.5 (Yield: 26.31%).

Synthesis of Compound I-131.

Compound I-131 was synthesized from 172.5 and cyclopropanecarboxamide using general procedure B. (Yield: 4.44%).

Example 173: Synthesis of 4-((3-chloro-2-methoxyphenyl)amino)-2-methyl-6-((1-methyl-1H-pyrazol 3-yl)amino)-1,2-dihydro-3H-pyrazolo[3,4-b]pyridin-3-one, I-136

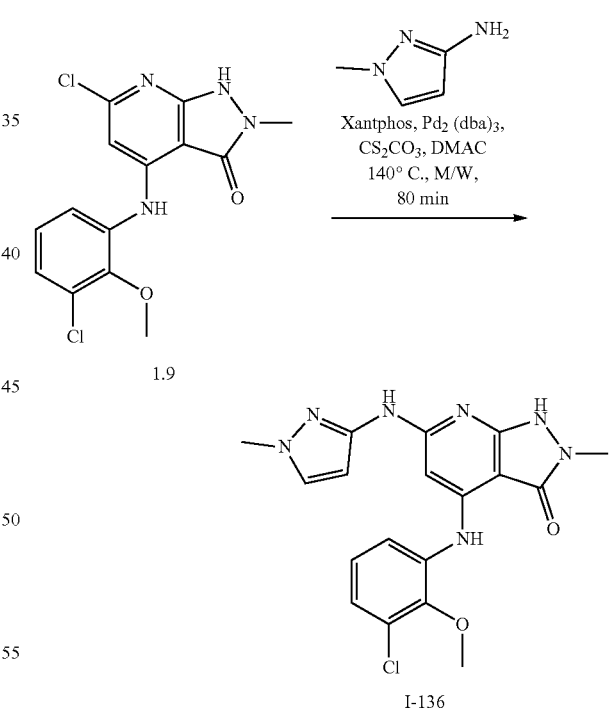

1.9

I-136

Synthesis of Compound I-136.

Compound I-136 was synthesized from 1-methyl-1H-pyrazol-3-amine and 1.9 using general procedure B. (Yield: 14.14%), MS(ES): m/z 400.27 [M+H]$^+$, LCMS purity: 98.81%, HPLC purity: 98.21%, 1H NMR (DMSO-d6, 400 MHz): 9.72 (bs, 1H), 8.84 (s, 1H), 7.55 (s, 2H), 7.21 (s, 2H), 6.67 (bs, 1H), 6.27 (s, 1H), 3.79 (s, 3H), 3.74 (s, 3H), 3.28 (s, 3H).

Example 174: Synthesis of 6-((4-((3-chloro-2-methoxyphenyl)amino)-2-methyl-3-oxo-2,3-dihydro-1H-pyrazolo[3,4-b]pyridin-6-yl)amino)-3-isopropylpyrazine-2-carbonitrile, I-158

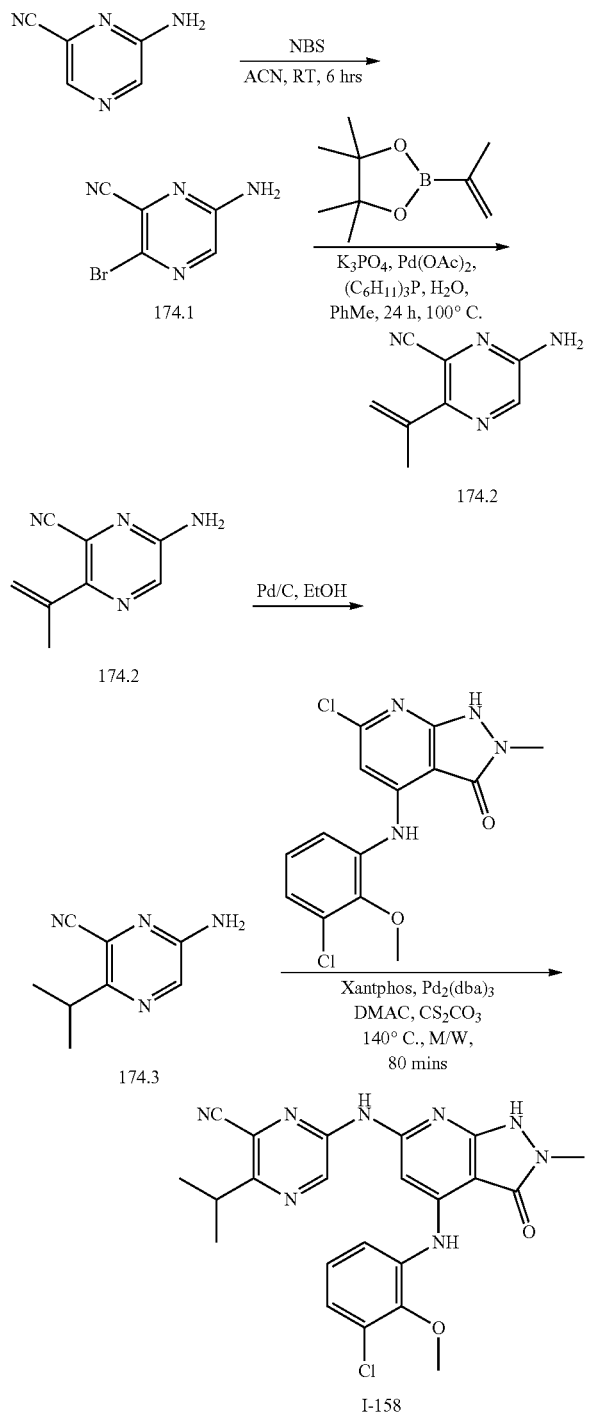

Synthesis of Compound 174.1.

To compound 6-aminopyrazine-2-carbonitrile (5.0 g, 41.63 mmol, 1.0 eq) in acetonitrile was added N-Bromosuccinimide (11.115 g, 62.44 mmol, 1.5 eq). The reaction mixture was stirred at room temperature for 6 h. After completion of reaction, water was added to reaction mixture and extracted with ethyl acetate. Organic layer was combined, dried over sodium sulphate and concentrated under reduced pressure to obtain crude material. This was further purified by column chromatography and compound was eluted in 2% methanol in dichloromethane to obtain 174.1. (5.3 g, Yield: 63.98%). MS (ES): m/z 200.01 [M+H]$^+$.

Synthesis of Compound 174.2.

To a solution of 174.1 (0.5 g, 2.51 mmol, 1.0 eq), 4,4,5,5-tetramethyl-2-(prop-1-en-2-yl)-1,3,2-dioxaborolane (1.10 g, 6.53 mmol, 2.6 eq) in mixture of toluene (13 mL) and water (2 mL). The reaction mixture was degassed by argon for 30 min. Palladium acetate (0.056 g, 0.251 mmol, 0.1 eq), triphenyl phosphine (0.131 g, 0.502 mmol, 0.2 eq) and potassium phosphate (1.59 g, 7.53 mmol, 3.0 eq) was added into reaction mixture and again reaction mixture was degassed by argon for 30 min. Further reaction mixture was stirred at 100° C. for 24 h. After completion of reaction, water was added to reaction mixture and extracted with ethyl acetate. Organic layer was combined, dried over sodium sulphate and concentrated under reduced pressure to obtain crude material. This was further purified by column chromatography and compound was eluted in 2% methanol in dichloromethane to obtain pure 174.2 (0.3 g, 74.55%). MS(ES): m/z 161.18 [M+H]$^+$.

Synthesis of Compound 174.3.

To a solution of 174.2 (0.4 g, 2.50 mmol, 1.0 eq) in methanol (4 mL), 10% palladium on charcoal (0.016 g) was added. Hydrogen was purged through reaction mixture for 2-3 h. After completion of reaction, reaction mixture was filtered through celite-bed and washed with ethanol. Filtrate was concentrated under reduced pressure to obtain 1.3 (0.38 g, 93.82%). MS(ES): m/z 163.20 [M+H]$^+$.

Synthesis of compound I-158.

Compound I-158 was synthesized from 174.3 and 1.91 using general procedure B. (Yield: 16.05%). MS(ES): m/z 465.42 [M+H]$^+$, LCMS purity: 97.37%, HPLC purity: 97.61%, 1H NMR (DMSO-d6, 400 MHz): 10.89 (bs, 1H), 10.55 (s, 1H), 9.28 (s, 1H), 8.96 (s, 1H), 7.64-7.61 (dd, J=2.0 Hz, 7.8 Hz, 1H), 7.34 (s, 1H), 7.29-7.23 (m, 2H), 3.83 (s, 3H), 3.32 (s, 3H), 2.93-2.90 (m, 1H), 1.28 (s, 3H), 1.27 (s, 3H).

Example 175: Synthesis of N-(4-((3-(4,5-dimethyl-2H-1,2,3-triazol-2-yl)-2-methoxyphenyl)amino)-2-methyl-3-oxo-2,3-dihydro-1H-pyrazolo[3,4-b]pyridin-6-yl)cyclopropanecarboxamide, I-149

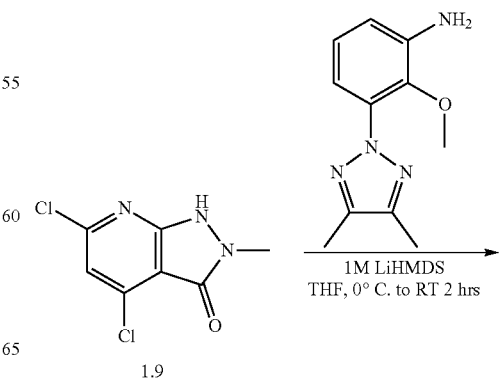

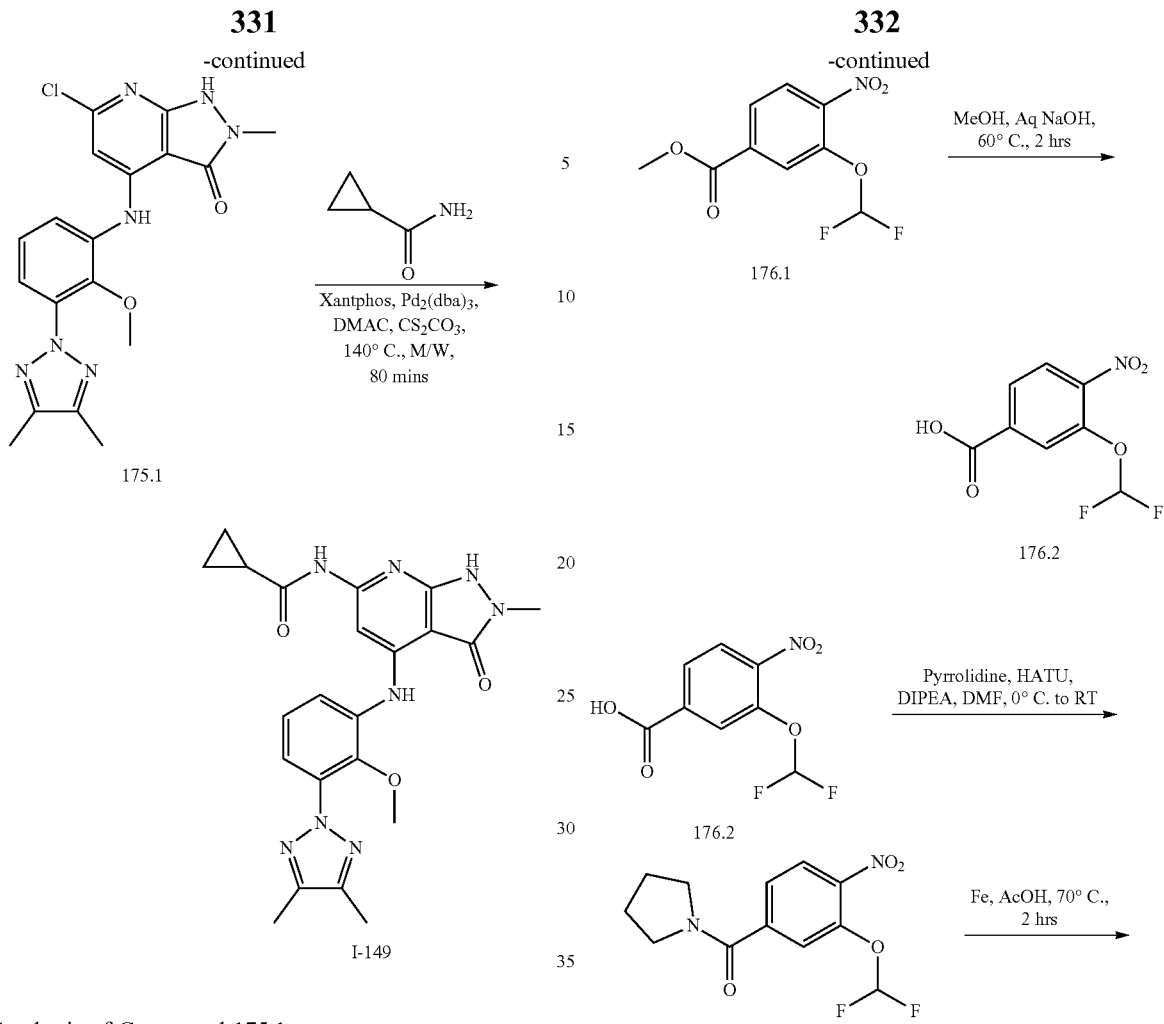

Synthesis of Compound 175.1.

Compound was synthesized from 3-(4,5-dimethyl-2H-1,2,3-triazol-2-yl)-2-methoxyaniline and 1.9 using general procedure B. (Yield: 32.72%). MS(ES): m/z 400.25 [M+H]$^+$.

Synthesis of Compound I-149.

Compound I-149 was synthesized from cyclopropanecarboxamide and 175.1 using general procedure B. (Yield: 52.71%). MS(ES): m/z 449.46 [M+H]$^+$, LCMS purity: 99.65%, HPLC purity: 95.05%, 1H NMR (DMSO-d6, 400 MHz): 10.67 (bs, 1H), 8.90 (s, 1H), 7.67 (s, 1H), 7.59-7.57 (d, J=8.0 Hz, 1H), 7.32-7.24 (m, 2H), 3.62 (s, 3H), 2.32 (s, 3H), 2.30 (s, 6H), 2.02-1.96 (m, 1H), 1.81-0.78 (m, 4H).

Example 176: Synthesis of N-(4-((2-(difluoromethoxy)-4-(pyrrolidine-1-carbonyl)phenyl)amino)-2-methyl-3-oxo-2,3-dihydro-H-pyrazolo[3,4-b]pyridin-6-yl)cyclopropanecarboxamide, I-151

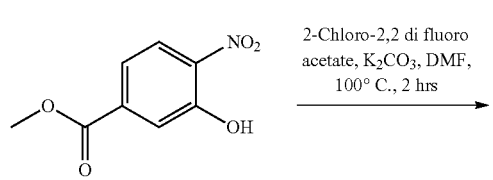

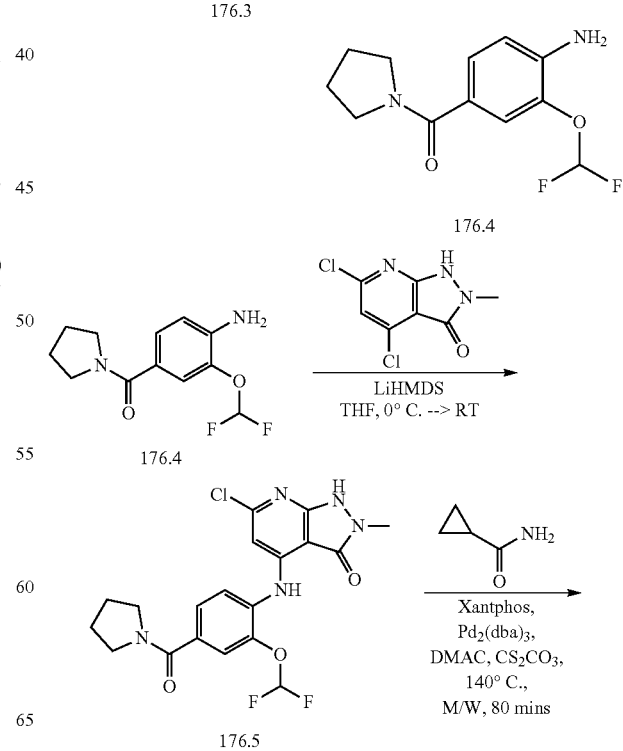

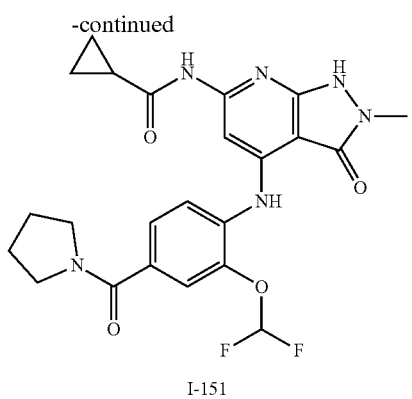

I-151

Synthesis of Compound 176.1.

To a solution of methyl 3-hydroxy-4-nitrobenzoate (3.0 g, 15.2 mmol, 1.0 eq) in dimethylformamide (50 mL), potassium carbonate (3.14 g, 22.82 mmol, 1.5 eq) was added at 0° C. Then 2-chloro-2,2-difluoroacetate (3.29 g, 22.82 mmol, 1.5 eq) was added and the reaction mixture was stirred at 100° C. for 2 h. After completion of the reaction, the reaction mixture transferred into cooled water to get solid precipitation. This was filtered to obtain 176.1. (3.0 g, 79.77%). MS(ES): m/z 248.51 $[M+H]^+$.

Synthesis of Compound 176.2.

To a solution of compound 176.1 (1.5 g, 6.07 mmol, 1.0 eq) in a mixture of methanol (104 mL) and water (26 mL), sodium hydroxide (1.94 g, 48.56 mmol, 8.0 eq) was added. The reaction mixture was stirred at 60° C. for 2 h. After completion of the reaction, the reaction mixture was cooled to 0° C. The pH of the solution was adjusted to 6-7 by using 2N HCl to get solid precipitation which was filtered and dried to obtain 176.2 (1.0 g, 70.68%). MS(ES): m/z 234.76 $[M+H]^+$.

Synthesis of Compound 176.3.

To a solution of 176.2 (0.1 g, 0.42 mmol, 1.0 eq) in dimethylformamide (3 mL), (1-[Bis(dimethylamino)methylene]-1H-1,2,3-triazolo[4,5-b]pyridinium 3-oxid hexafluorophosphate) (0.195 g, 0.51 mmol, 1.2 eq) and diisopropylethylamine (0.083 g, 0.64 mmol, 1.5 eq) were added at 0° C. Reaction mixture was stirred at 0° C. for 30 min. Then pyrrolidine (0.045 g, 0.64 mmol, 1.5 eq) was added and reaction mixture was stirred at room temperature for 24 h. After completion of the reaction, reaction mixture was transferred to water and extracted with ethyl acetate. Organic layer was combined, dried over anhydrous sodium sulfate, filtered and concentrated under reduced pressure to get the crude material. This was further purified by column chromatography using 1% methanol in dichloromethane to obtain 176.3 (0.120 g, 56.12%). MS(ES): m/z 229.48 $[M+H]^+$.

Synthesis of Compound 176.4.

To a solution of 176.3 (0.48 g, 1.68 mmol, 1.0 eq) in acetic acid (6 mL), iron powder (0.275 g, 5 mmolmmol, 3.0 eq) was added. Reaction mixture was stirred at 70° C. for 2 h. After completion of the reaction, reaction mixture was transferred to water and extracted with ethyl acetate. Organic layer was combined, dried over anhydrous sodium sulfate, filtered and concentrated under reduced pressure to obtain 176.4 (0.350 g, 81.11%). MS(ES): m/z 257.29 $[M+H]^+$.

Synthesis of Compound 176.5.

To a solution of 176.4 (0.48 g, 1.68 mmol, 1.0 eq) in tetrahydrofuran (6 mL), lithium bis(trimethylsilyl)amide (0.275 g, 5 mmol, 3.0 eq) was added dropwise at 0° C. Reaction mixture was stirred at room temperature for 3 h. After completion of the reaction, reaction mixture was transferred to water and extracted with ethyl acetate. Organic layer was combined, dried over anhydrous sodium sulfate, filtered and concentrated under reduced pressure to obtain 176.5 (0.055 g, 10.73%). MS(ES): m/z 438.52 $[M+H]^+$.

Synthesis of Compound I-151.

Compound I-151 was synthesized from 176.5 and cyclopropanecarboxamide using general procedure B. (Yield: 23.40%). MS(ES): m/z 487.41 $[M+H]^+$, LCMS purity: 96.51%, HPLC purity: 95.50%, 1H NMR (DMSO-d6, 400 MHz): 10.77 (bs, 2H), 8.81 (s, 1H), 7.71 (s, 1H), 7.64-7.62 (d, J=8.4 Hz, 1H), 7.52-7.49 (m, 2H), 7.49-7.15 (t, 1H), 3.49 (m, 4H), 3.18 (s, 3H), 2.03-2.00 (m, 1H), 1.86 (m, 4H), 0.81-0.79 (m, 4H).

Example 177: Synthesis of N-(4-((4-ethyl-2-(N-methylmethylsulfonamido)phenyl)amino)-2-methyl-3-oxo-2,3-dihydro-1H-pyrazolo[3,4-b]pyridin-6-yl)cyclopropanecarboxamide, I-217

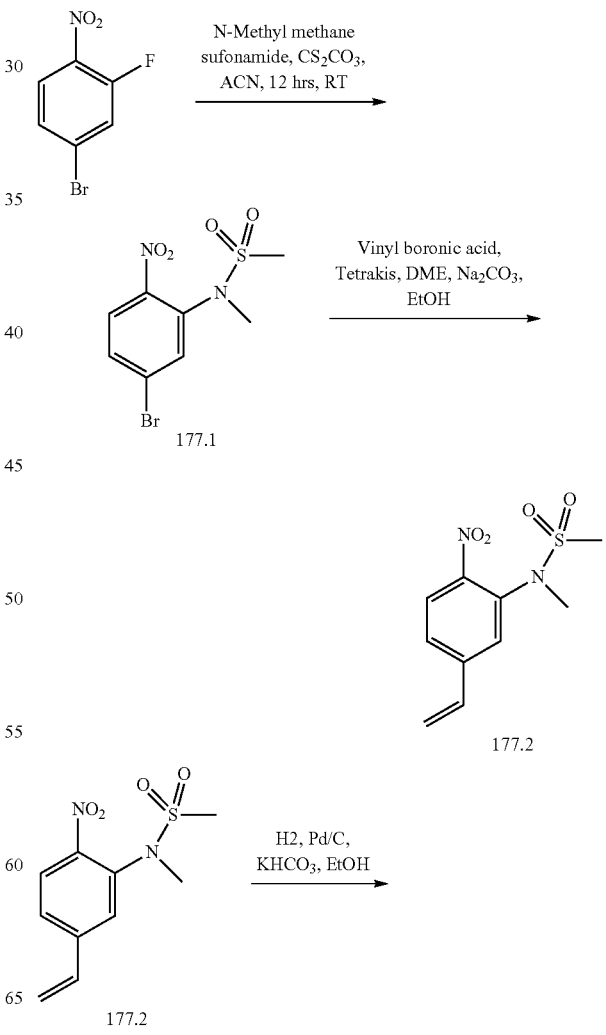

-continued

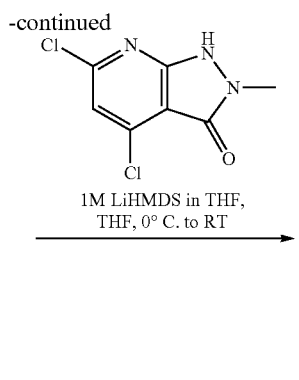

177.3

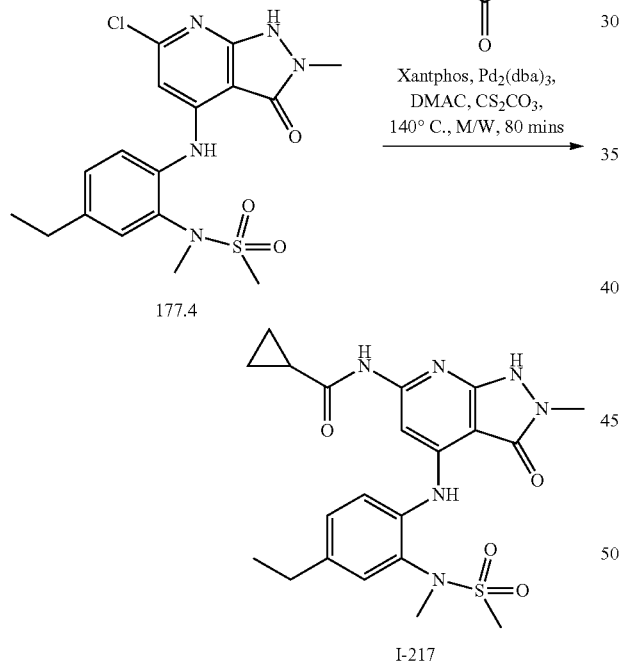

Synthesis of Compound 177.1.

To a suspension of Cesium carbonate (2.8 g, 0.008 mmol, 1.9 eq) in acetonitrile (28 mL), N-methyl methane sulfonamide (0.5 g, 0.004 mmol, 1.1 eq) was added and cooled to 0° C. Then 4-bromo-2-fluoro-1-nitrobenzene (1 g, 0.004 mmol, 1 eq) was added dropwise in the reaction mixture within 15 min. Reaction mixture was stirred at room temperature for 12 hours. After completion of the reaction, the reaction mixture was filtered and the filtrate was concentrated under reduced pressure to obtain 177.1. (0.8 g, 56.93%). MS(ES): m/z 310. 12 [M+H]$^+$.

Synthesis of Compound 177.2.

To a solution of compound 177.1 (0.2 g, 0.64 mmol, 1.0 eq) and vinyl boronic acid (0.24 g, 1.61 mmol, 2.5 eq) in a mixture of toluene (5 mL) and water (0.2 mL), potassium phosphate (0.48 g, 2.26 mmol, 3.5 eq) and tetrakis (0.03 g, 0.12 mmol, 0.2 eq) were added and the reaction mixture was degassed for 10 min. Then palladium acetate (0.014 g, 0.064 mmol, 0.1 eq) was added and the reaction mixture was again degassed for 5 min. Reaction mixture was stirred at 100° C. for 1 h. After completion of the reaction, water was added to the reaction mixture and extracted with ethyl acetate. Organic layer combined, dried over sodium sulphate and concentrated under pressure to obtain 177.2. (0.8 g, 80.14%). MS(ES): m/z 257.86 [M+H]$^+$.

Synthesis of Compound 177.3.

To a solution of 177.2 (0.2 g, 1.77 mmol, 1.0 eq) in methanol (2 mL), 10% palladium on charcoal (0.06 g) was added. Hydrogen was purged through reaction mixture for 12 h. After completion of reaction, reaction mixture was filtered through celite-bed and washed with ethanol. Filtrate was concentrated under reduced pressure to obtain 177.3 (0.1 g, 56.12%). MS(ES): m/z 229.48 [M+H]$^+$.

Synthesis of Compound 177.4.

Compound 177.4 was synthesized from 177.3 and 1.9 using general procedure A. (Yield: 24.88%). MS(ES): m/z 410.16 [M+H]$^+$.

Synthesis of Compound I-217.

Compound I-217 was synthesized from 177.4 and cyclopropanecarboxamide using general procedure B. (Yield: 51.05%). MS(ES): m/z 459.46 [M+H]$^+$, LCMS purity: 96.79%, HPLC purity: 97.19%, 1H NMR (DMSO-d6, 400 MHz): 10.71 (s, 1H), 10.66 (s, 1H), 8.71 (s, 1H), 7.63 (s, 1H), 7.49-7.44 (m, 2H), 7.31-7.29 (d, J=8.0 Hz, 1H), 3.30 (s, 3H), 3.16 (s, 6H), 2.68-2.63 (q, J=7.6 Hz, 2H), 2.02-1.99 (m, 1H), 1.25-1.21 (t, J=7.6 Hz, 3H), 0.79-0.78 (m, 4H).

Example 178: Synthesis of N-(4-((4-(methoxymethyl)-2-(N-methylmethylsulfonamido)phenyl)amino)-2-methyl-3-oxo-2,3-dihydro-1H-pyrazolo[3,4-b]pyridin-6-yl)cyclopropanecarboxamide, I-218

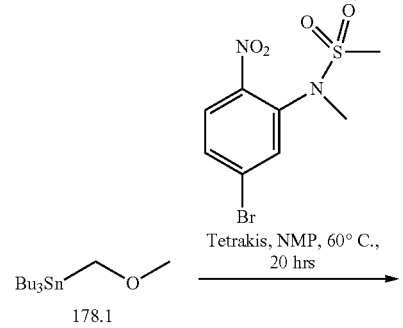

-continued

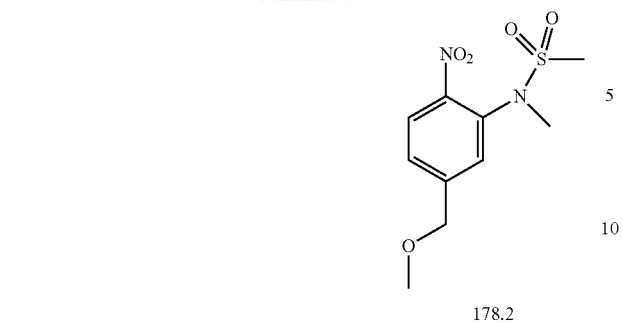

178.2

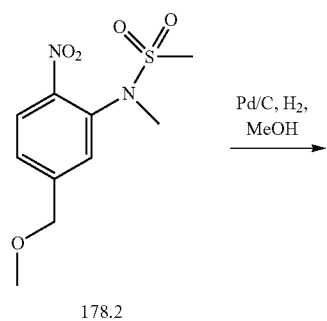

178.2

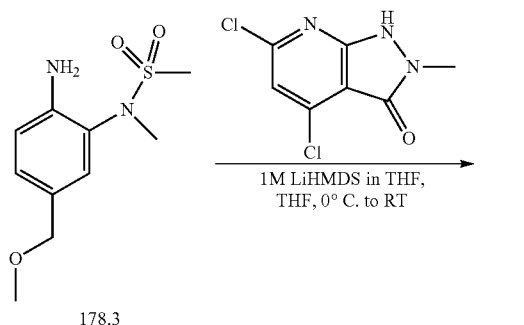

178.3

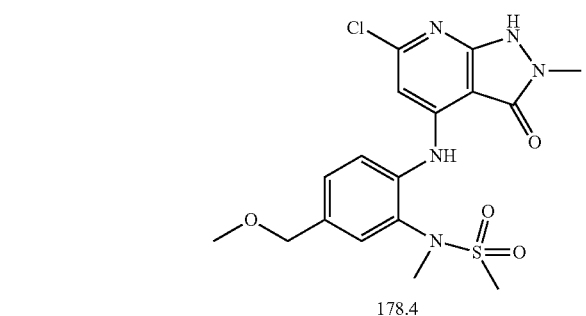

178.4

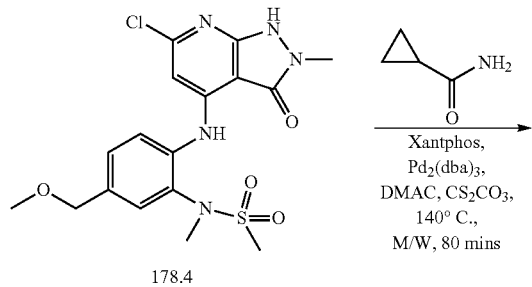

178.4

-continued

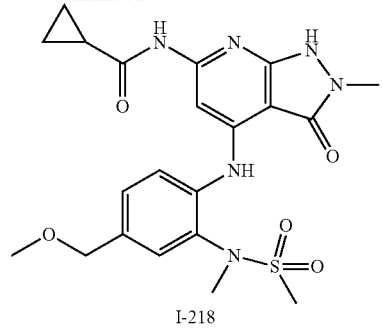

I-218

Synthesis of Compound 178.1.

To a solution of diisopropyl amine (30.11 g, 298.1 mmol, 2.4 eq) in tetrahydrofuran (150 mL) was cooled to −78° C. followed by addition of n-butyl lithium (19.08 g, 298.1 mmol, 2.4 eq) and stirred reaction mixture for 30 min at the same temperature. Tributyltin hydride (86.75 g, 298.1 mmol, 2.4 eq) was added to reaction mixture at same temperature and then maintained 0° C. and stirred for 30 min. The reaction mixture was cooled to −78° C., added compound chloro(methoxy)methane (10 g, 124.21 mmol, 1.0 eq) and reaction mixture was allowed to warm to room temperature. The reaction mixture was stirred at room temperature for 5 h. After completion of reaction, reaction mixture was transferred in to brine solution and extracted with diethyl ether. Organic layer was combined, washed with brine, dried over sodium sulphate and concentrated under reduced pressure to obtain crude material. This was further purified by column chromatography and compound was eluted hexane as eluant to obtain 178.1. (7.0 g, 16.82%). MS(ES): m/z 336.12 [M+H]$^+$.

Synthesis of Compound 178.2.

To a solution of 177.1 (3.0 g, 9.70 mmol, 1.0 eq) in N-methyl pyrrolidine (35 mL) was added 178.1 (7.0 g, 20.89 mmol, 2.15 eq). The reaction mixture was degassed for 10 min. under argon atmosphere. Tetrakis(triphenylphosphine) palladium(0) (1.12 g, 0.97 mmol, 0.1 eq), again reaction mixture was degassed for 10 min. under argon atmosphere. The reaction was stirred at 60° C. for 20 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 15% ethyl acetate in hexane to obtain pure 178.2 (1.2 g, 45.03%). MS(ES): m/z 275.29 [M+H]$^+$ Synthesis of Compound 178.3.

To a solution of 178.2 (1.2 g, 4.37 mmol, 1.0 eq) in methanol (20 mL), 10% palladium on charcoal (0.5 g) was added. Hydrogen was purged through reaction mixture for 4 h. After completion of reaction, reaction mixture was filtered through celite-bed and washed with methanol. Filtrate was concentrated under reduced pressure to obtain 178.3. (0.750 g, 70.17%). MS(ES): m/z 245.31 [M+H]$^+$.

Synthesis of Compound 178.4.

Compound 178.4 was synthesized from 178.3 and 1.9 using general procedure A. (Yield: 13.65%). MS(ES): m/z 426.89 [M+H]$^+$.

Synthesis of Compound I-218.

Compound I-218 was synthesized from 178.4 and cyclopropanecarboxamide using general procedure B (Yield: 13.46%), MS(ES): m/z 475.42 [M+H]$^+$, LCMS purity: 97.30%, HPLC purity: 99.18%, 1H NMR (DMSO-d6, 400

MHz): 8.82 (s, 1H), 8.25 (s, 1H), 7.68 (s, 1H), 7.57 (s, 1H), 7.55-7.53 (d, J=6.4 Hz, 1H), 7.40-7.38 (d, J=8.4 Hz, 1H), 4.44 (s, 2H), 3.34 (s, 3H), 3.28 (s, 3H), 3.18 (s, 3H), 3.16 (s, 3H), 2.02-1.99 (m, 1H), 0.87-0.73 (m, 4H).

Example 179: Synthesis of N-(2-((6-((6,7-dihydro-5H-cyclopenta[b]pyrazin-2-yl)amino)-2-methyl-3-oxo-2,3-dihydro-1H-pyrazolo[3,4-b]pyridin-4-yl)amino)phenyl)-N-methylmethanesulfonamide, I-225

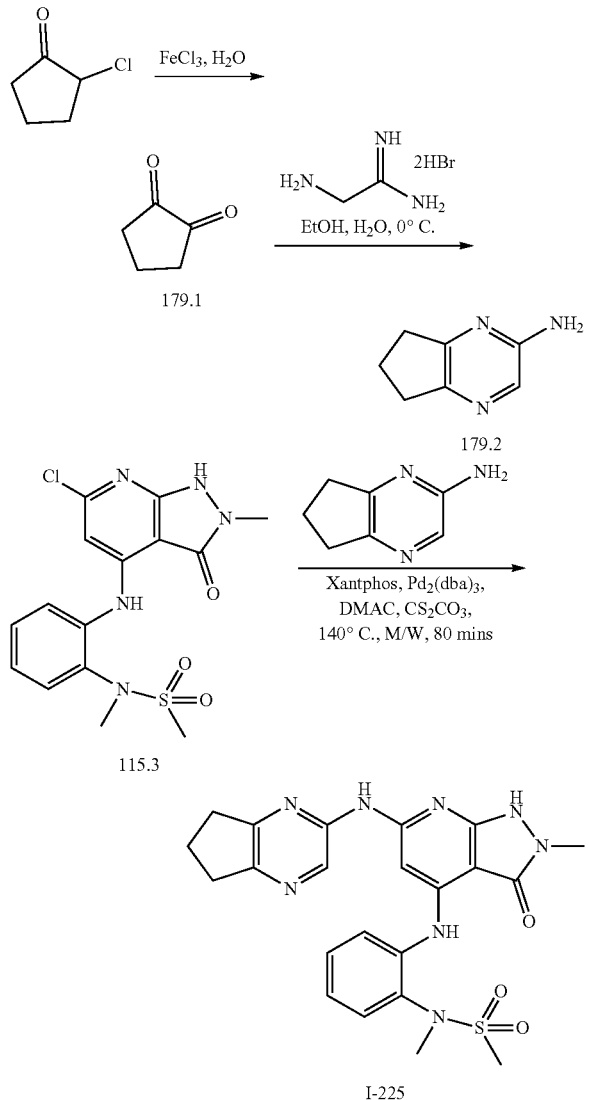

Synthesis of Compound 179.1.

2-chlorocyclopentan-1-one (1.0 g, 4.58 mmol, 1.0 eq) in water (20 mL) was heated to 100° C., to which a preheated solution of ferric chloride (1.48 g, 9.17 mmol, 2 eq) was added. Reaction mixture was stirred at 100° C. for 20 min. After completion of the reaction, the reaction mixture was cooled to room temperature. The pH of the solution was adjusted to 7 by using ammonium sulfate solution and then extracted by ethyl acetate. Organic layers were combined, dried over anhydrous sodium sulfate, filtered and concentrated under reduced pressure to obtain 179.1. (0.55 g, 66.47%). MS(ES): m/z 99.25 [M+H]$^+$.

Synthesis of Compound 179.2.

To a solution of compound 179.1 (0.100 g, 0.10 mmol, 1.0 eq) in ethanol (5 mL) at 0° C., aminoacetamide dihyrobromide (0.23 g, 0.10 mmol, 1.0 eq) was added. Reaction mixture was stirred for 10 min. Then, pH of the reaction mixture was adjusted to 8-9 by using ammonium hydroxide solution. Reaction mixture was stirred at room temperature overnight. After completion of the reaction, pH of the reaction mixture was adjusted to 7 by using 1N HCl and extracted with dichloromethane. Organic layer was combined, dried over sodium sulfate, filtered and concentrated to obtain pure 179.2 (0.021 g, 15.83%). MS(ES): m/z 136.48 [M]+.

Synthesis of Compound I-225.

Compound I-225 was synthesized from 115.3 and 179.2 using general procedure B. (Yield: 35.76%). MS(ES): m/z 481.36 [M+H]$^+$, LCMS purity: 97.58%, HPLC purity: 98.32%, 1H NMR (DMSO-d6, 400 MHz): 10.71 (s, 1H), 9.95 (s, 1H), 8.91 (s, 1H), 8.86 (s, 1H), 7.71-7.69 (d, J=8.0 Hz, 1H), 7.59-7.57 (dd, J=1.2 Hz, 8.0 Hz, 1H), 7.49-7.45 (t, J=8.0 Hz, 1H), 7.25-7.19 (m, 2H), 3.28 (s, 3H), 3.20 (s, 3H), 3.15 (s, 3H), 2.92-2.87 (m, 4H), 2.17-2.09 (qui, J=7.6 Hz, 2H).

Example 180: N-(4-((4-(3-methoxyazetidin-1-yl)-2-(N-methylmethylsulfonamido)phenyl)amino)-2-methyl-3-oxo-2,3-dihydro-1H-pyrazolo[3,4-b]pyridin-6-yl)cyclopropane-carboxamide, I-220

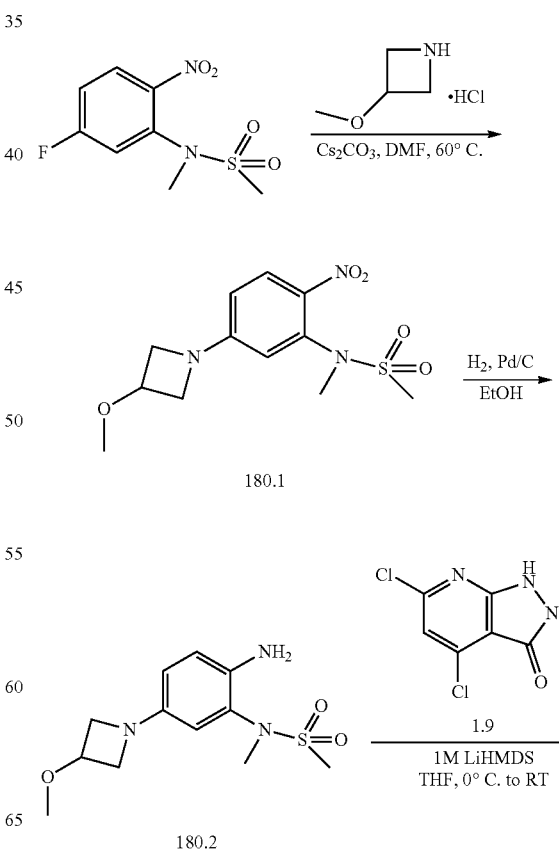

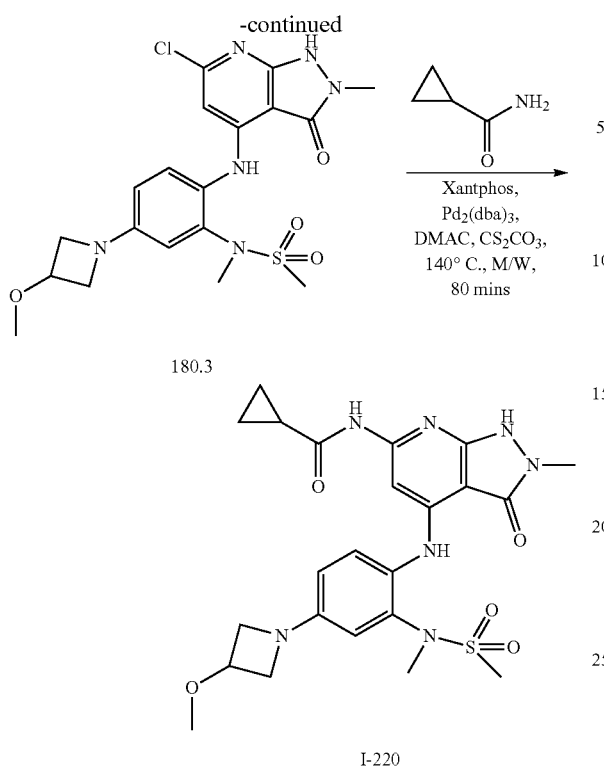

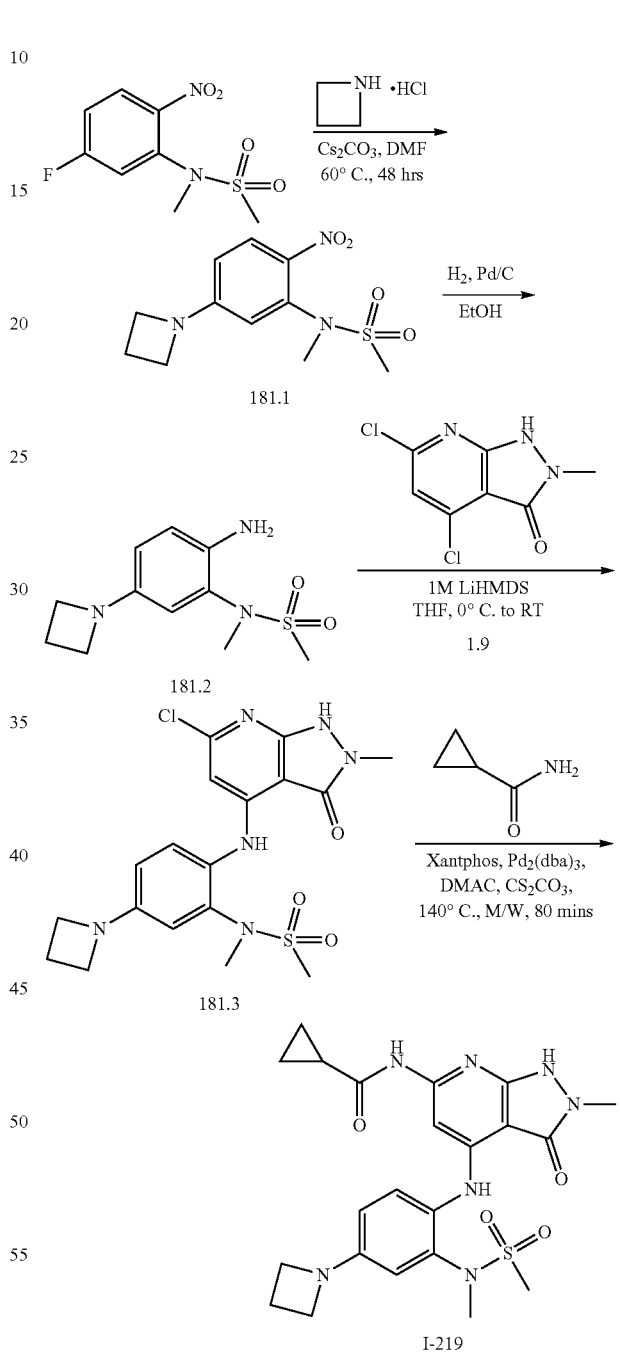

(m, 2H), 3.82-3.79 (m, 2H), 3.51 (s, 3H), 3.37 (s, 3H), 3.23 (s, 3H), 3.03 (s, 3H), 1.76 (m, 1H), 1.01-0.93 (m, 4H).

Example 181: Synthesis of N-(4-((4-(azetidin-1-yl)-2-(N-methylmethylsulfonamido)phenyl)amino)-2-methyl-3-oxo-2,3-dihydro-1H-pyrazolo[3,4-b]pyridin-6-yl)cyclopropanecarboxamide, I-219

Synthesis of Compound 180.1.

To a solution of N-(5-fluoro-2-nitrophenyl)-N-methylmethanesulfonamide (2.0 g, 8.06 mmol, 1.0 eq) in N,N-dimethylformamide (20 mL) was added cesium carbonate (1.35 g, 9.83 mmol, 1.22 eq) followed by addition of 3-methoxyazetidine hydrochloride (1.21 g, 9.83 mmol, 1.22 eq) dropwise. The reaction mixture was stirred at 60° C. for 48 h. After completion of reaction, reaction mixture was transferred into 10% solution of sodium phosphate (90 mL) and extracted with ethyl acetate. Organic layer was combined, dried over sodium sulphate and concentrated under reduced pressure to obtain crude material. This was further purified by column chromatography and compound was eluted in 35% ethyl acetate in hexane as eluent to obtain 180.1. (1.6 g, 62.97%). MS(ES): m/z 316.34 [M+H]$^+$.

Synthesis of compound 180.2. To a solution of 180.1 (1.6 g, 5.07 mmol, 1.0 eq) in ethanol (20 mL), 10% palladium on charcoal (0.6 g) was added. Hydrogen was purged through reaction mixture for 4 h. After completion of reaction, reaction mixture was filtered through celite-bed and washed with methanol. Filtrate was concentrated under reduced pressure to obtain 180.2. (1.2 g, 82.88%). MS(ES): m/z 286.36 [M+H]$^+$.

Synthesis of Compound 180.3

Compound 180.3 was synthesized from 180.2 and 1.9 using general procedure A. (Yield: 32.69%). MS(ES): m/z 467.94 [M+H]$^+$.

Synthesis of Compound I-220.

Compound I-220 was synthesized from 180.3 and cyclopropanecarboxamide using general procedure B (Yield: 12.51%), MS(ES): m/z 516.31 [M+H]$^+$, LCMS purity: 100.00%, HPLC purity: 98.39%, 1H NMR (MeOD, 400 MHz): 8.49 (s, 1H), 7.36-7.33 (d, J=8.4 Hz, 1H), 6.70 (s, 1H), 7.59-7.57 (d, J=8.0 Hz, 1H), 4.39 (m, 1H), 4.18-4.15

Synthesis of Compound 181.1.

To a solution of of N-(5-fluoro-2-nitrophenyl)-N-methylmethanesulfonamide (5.0 g, 20.14 mmol, 1.0 eq) in N,N-dimethylformamide (50 mL) was added cesium carbonate (7.98 g, 24.57 mmol, 1.22 eq) followed by addition of azetidine hydrochloride (1.88 g, 24.57 mmol, 1.22 eq). The reaction mixture was stirred at 60° C. for 48 h. After completion of reaction, reaction mixture was transferred in to 10% solution of sodium phosphate (90 mL) and extracted with ethyl acetate. Organic layer was combined, dried over sodium sulphate and concentrated under reduced pressure to obtain crude material. This was further purified by column chromatography and compound was eluted in 35% ethyl acetate in hexane as eluent to obtain 181.1. (3.4 g, 59.16%). MS(ES): m/z 286.32 [M+H]⁺.

Synthesis of Compound 181.2

To a solution of 181.1 (2.0 g, 7.01 mmol, 1.0 eq) in ethanol (20 mL), 10% palladium on charcoal (0.8 g) was added. Hydrogen was purged through reaction mixture for 4 h. After completion of reaction, reaction mixture was filtered through celite-bed and washed with methanol. Filtrate was concentrated under reduced pressure to obtain 181.2. (1.5 g, 83.84%). MS(ES): m/z 256.34 [M+H]⁺.

Synthesis of Compound 181.3.

Compound 181.3 was synthesized from 181.2 and 1.9 using general procedure A. (Yield: 39.92%). MS(ES): m/z 437.92 [M+H]⁺.

Synthesis of Compound I-219. Compound I-219 was synthesized from 181.3 and cyclopropanecarboxamide using general procedure B. (Yield: 37.12%), MS(ES): m/z 486.30 [M+H]⁺, LCMS purity: 100.00%, HPLC purity: 100.00%, 1H NMR (DMSO-d6, 400 MHz): 10.60 (s, 1H), 8.27 (s, 1H), 8.17 (s, 1H), 7.29-7.18 (m, 2H), 6.82-6.64 (m, 2H), 3.58-3.38 (m, 4H), 3.26 (s, 3H), 3.09 (s, 3H), 3.06 (s, 3H), 3.05-3.00 (m, 2H), 1.92-1.84 (m, 1H), 0.74-0.71 (m, 4H).

Example 182: Synthesis of 4-((4-cyclopropyl-2-(methylsulfonyl)phenyl)amino)-6-((4-(methoxymethyl)pyridin-2-yl)amino)-2-methyl-1,2-dihydro-3H-pyrazolo[3,4-b]pyridin-3-one, I-214

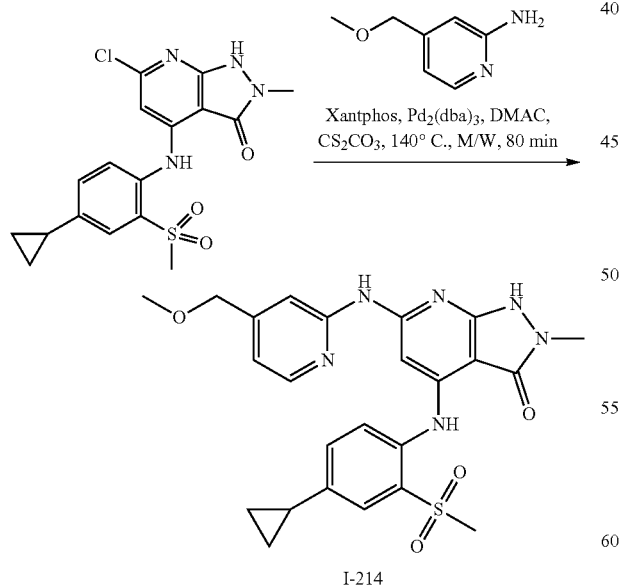

Synthesis of Compound I-214.

Compound I-214 was synthesized from 4-(methoxymethyl)pyridin-2-amine using general procedure B (Yield: 18.91%). MS(ES): m/z 495.26 [M+H]⁺, LCMS purity: 100.00%, HPLC purity: 96.75%, 1H NMR (DMSO-d6, 400 MHz): 10.79 (bs, 1H), 9.04 (s, 1H), 6.25-6.24 (d, J=8.0 Hz, 1H), 7.59-7.57 (d, J=5.6 Hz, 1H), 7.69-7.67 (m, 2H), 7.51-7.49 (m, 1H), 7.24-7.11 (m, 1H), 7.04-6.99 (m, 1H), 6.45 (s, 1H), 4.52 (s, 2H), 3.44 (s, 3H), 3.32 (s, 3H), 3.18 (s, 3H), 2.15-2.09 (m, 1H), 1.09-1.04 (m, 2H), 0.79-0.75 (m, 2H).

Example 183: Synthesis of N-(4-((4,5-difluoro-2-(N-methylmethylsulfonamido)phenyl)amino)-2-methyl-3-oxo-2,3-dihydro-1H-pyrazolo[3,4-b]pyridin-6-yl)cyclopropanecarboxamide, I-230

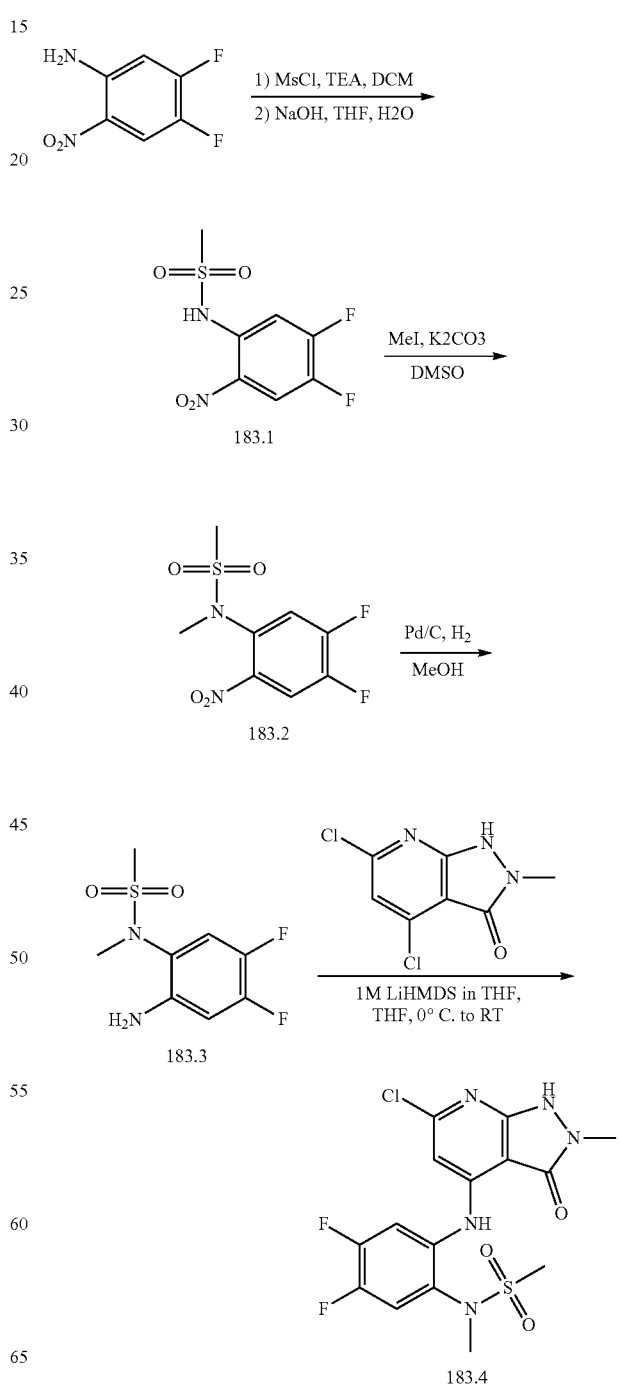

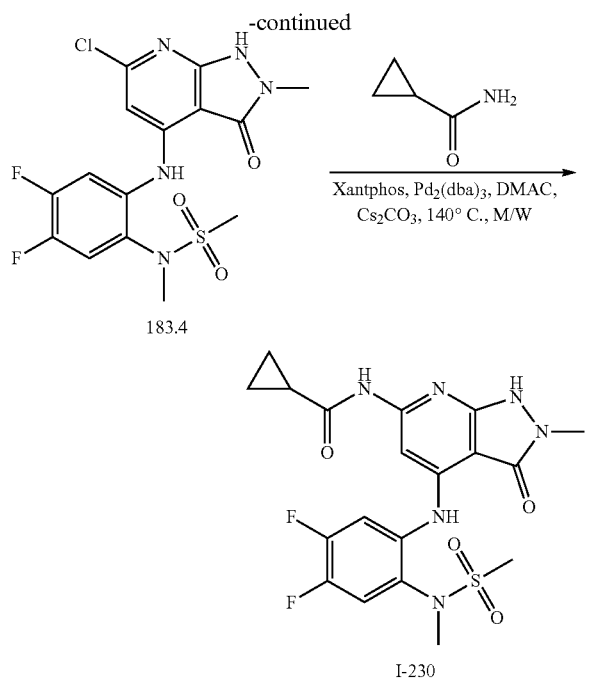

added. Hydrogen was purged through reaction mixture for 2-3 h. After completion of reaction, reaction mixture was filtered through celite-bed and washed with ethanol. Filtrate was concentrated under reduced pressure to obtain 183.3 (0.3 g, 22.54%). MS(ES): m/z 237.24 [M+H]⁺.

Synthesis of Compound 183.4.

Compound 183.4 was synthesized from 183.3 and 1.9 using general procedure A. (Yield: 31.89%). MS (ES): m/z 418.82 [M+H]⁺.

Synthesis of Compound I-230.

Compound I-230 was synthesized from 183.4 and cyclopropanecarboxamide using general procedure B. (Yield: 21.99%). MS(ES): m/z 467.37 [M+H]⁺, LCMS purity: 98.04%, HPLC purity: 97.69%, 1H NMR (DMSO-d6, 400 MHz): 10.78 (s, 1H), 8.76 (s, 1H), 8.17 (s, 1H), 7.90-7.85 (dd, J=2.8 Hz, 8.4 Hz, 1H), 7.67-7.62 (dd, J=4.0 Hz, 8.0 Hz, 1H), 7.60 (s, 1H), 3.29 (s, 3H), 3.16 (s, 3H), 3.15 (s, 3H), 2.04-1.97 (m, 1H), 0.80-0.78 (m, 4H).

Example 184: Synthesis of 3-((6-(cyclopropanecarboxamido)-2-methyl-3-oxo-2,3-dihydro-1H-pyrazolo[3,4-b]pyridin-4-yl)amino)-2-methoxybenzoic acid, I-231

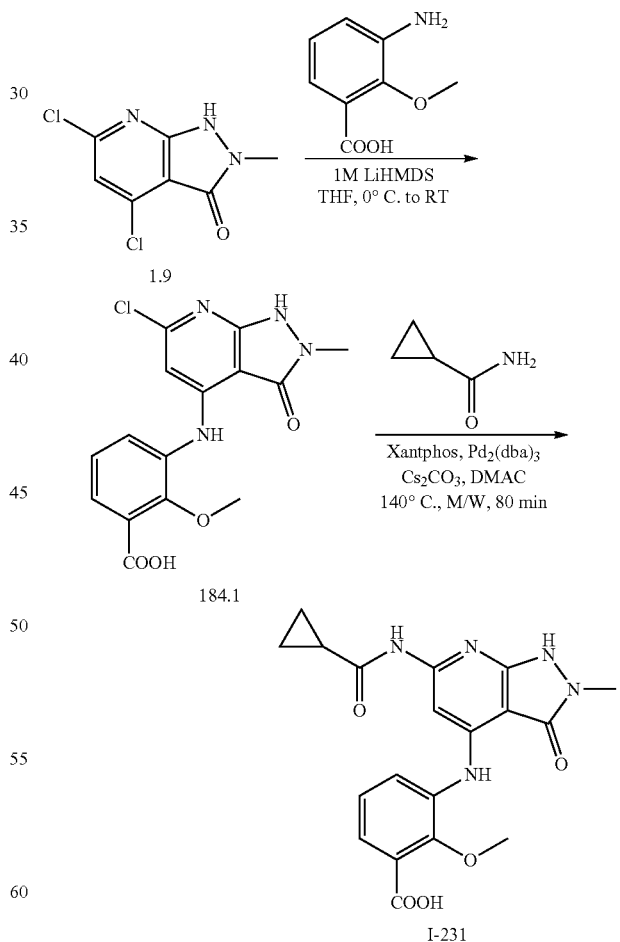

Synthesis of Compound 184.1.

Compound 184.1 was synthesized from 3-amino-2-methoxybenzoic acid and 1.9 using general procedure A. (Yield: 37.51%). MS (ES): m/z 349.7 [M+H]⁺.

Synthesis of Compound 183.1.

To a cooled solution of 4,5-difluoro-2-nitroaniline (5.0 g, 0.287 mmol, 1.0 eq) in dichloromethane (100 mL) was added dropwise triethylamine (9.6 mL, 0.0686 mmol, 2.39 eq) followed by methane sulfonyl chloride (4.8 mL, 0.0619 mmol, 2.16 eq). Reaction mixture was stirred at room temperature for 18 h. After completion of reaction, reaction mixture was transferred into water and extracted with dichloromethane. Organic layer was combined, dried over sodium sulphate and concentrated under reduced pressure to obtain crude material. This was further purified by column chromatography and compound was eluted in 20% ethyl acetate in hexane as eluent to obtain intermediate 5.2 g. To this intermediate was added 1M sodium hydroxide (50 mL) in mixture of water and tetrahydrofuran. Reaction mixture was stirred at room temperature for 18 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 30% ethyl acetate in hexane as eluent to obtain intermediate 183.1. (2.1 g, 29.00%). MS(ES): m/z 253.19 [M+H]⁺.

Synthesis of Compound 183.2.

To a solution of 183.1 (2.1 g, 8.33 mmol, 1.0 eq) in dimethyl sulfoxide (10 mL) was added potassium carbonate (4.6 g, 33.32 mmol, 4.0 eq) and methyl iodide (3.55 g, 24.99 mmol, 3.0 eq). The reaction mixture was stirred at 80° C. for 24 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 30% ethyl acetate in hexane as eluent to obtain 183.2. (1.5 g, 67.67%). MS(ES): m/z 267.22 [M+H]⁺.

Synthesis of Compound 183.3.

To a solution of 183.2 (1.5 g, 5.63 mmol, 1.0 eq) in methanol (20 mL), 10% palladium on charcoal (0.2 g) was Synthesis of Compound I-231.

Compound I-231 was synthesized from 184.1 and cyclopropanecarboxamide using general procedure B. (Yield: 15.80%), MS(ES): m/z 398.43 [M+H]+, LCMS purity: 99.57%, HPLC purity: 94.80%, 1H NMR (DMSO-d6, 400 MHz): 13.08 (bs, 1H), 10.81 (s, 1H), 8.84 (s, 1H), 7.73 (s, 1H), 7.69-7.67 (d, J=8.0 Hz, 1H), 7.48-7.44 (d, J=8.0 Hz, 1H), 7.31-7.27 (t, J=8.0 Hz, 1H), 3.79 (s, 3H), 3.38 (s, 3H), 2.06-1.99 (m, 1H), 0.89-0.80 (m, 4H).

Example 185: Synthesis of 4-((3-chloro-2-methoxyphenyl)amino)-2-methyl-6-((4,5,6,7-tetrahydropyrazolo[1,5-a]pyridin-2-yl)amino)-1,2-dihydro-3H-pyrazolo[3,4-b]pyridin-3-one, I-222

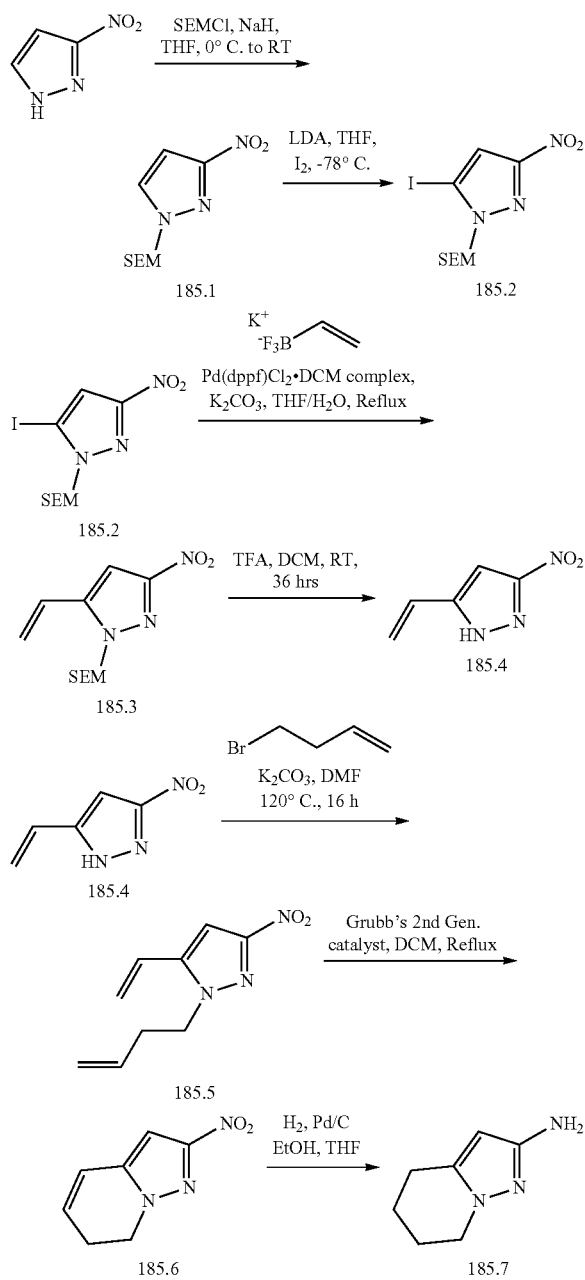

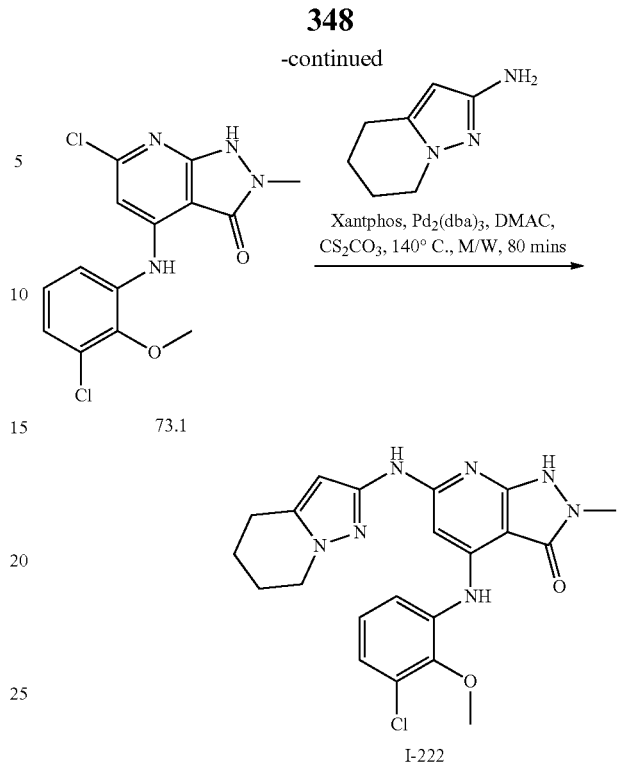

Synthesis of Compound 185.1.

To a solution of 3-nitro-1H-pyrazole (5.0 g, 44.22 mmol, 1.0 eq) in tetrahydrofuran (50 mL) was added sodium hydride (1.6 g, 66.33 mmol, 1.5 eq) at 0° C. and reaction mixture was stirred for 30 min followed by 2-(Trimethylsilyl)ethoxymethyl chloride (8.86 g, 53.06 mmol, 1.2 eq) was added at the same temperature. The reaction mixture was allowed to come at room temperature and stirred for 24 h. After completion of reaction, reaction mixture was transferred in to ice cold water and extracted with ethyl acetate. Organic layer was combined, washed with brine, dried over sodium sulphate and concentrated under reduced pressure to obtain crude material. This was further purified by column chromatography and compound was eluted on 15% ethyl acetate in hexane as eluent to obtain 185.1. (7.9 g, 73.42%). MS(ES): m/z 244.34 [M+H]+.

Synthesis of Compound 185.2.

To a cooled solution of diisopropyl amine (0.622 g, 6.165 mmol, 1.5 eq) in tetrahydrofuran (10 mL) at −78° C. n-butyl lithium (0.394 g, 6.165 mmol, 1.5 eq) was added and stirred reaction mixture for 30 min. at the same temperature. Compound 185.1 (1.0 g, 4.11 mmol, 1.0 eq) was added to reaction mixture and stirred at −78° C. for 1 h. Iodine solution (0.635 g, 2.50 mmol, 0.5 eq) in tetrahydrofuran was added at same temperature. After 1 h reaction mixture was brought to room temperature and stirred for 20 h. After completion of reaction, reaction mixture was transferred in to aqueous sodium thiosulphate solution and extracted with ethyl acetate. Organic layer was combined, washed with brine, dried over sodium sulphate and concentrated under reduced pressure to obtain crude material. This was further purified by column chromatography and compound was eluted in 15% ethyl acetate in hexane as eluent to obtain 185.2. (1.0 g, 65.90%). MS(ES): m/z 370.23 [M+H]+.

Synthesis of Compound 185.3.

To a solution of 185.2 (0.15 g, 0.406 mmol, 1.0 eq) and potassium vinyl trifluoroborate (0.098 g, 0.731 mmol, 1.8 eq) in mixture of tetrahydrofuran (1 mL) and water (0.2 mL)

was added potassium carbonate (0.168 g, 1.22 mmol, 3.0 eq). The reaction mixture was degassed for 10 min. under argon atmosphere. The [1,1'-Bis(diphenylphosphino)ferrocene]palladium(II) dichloride dichloromethane complex (0.017 g, 0.020 mmol, 0.05 eq) was added, again reaction mixture was degassed for 10 min. under argon atmosphere. The reaction was stirred at 100° C. for 24 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 5% ethyl acetate in hexane to obtain pure 185.3 (0.080 g, 73.10%). MS(ES): m/z 270.38 [M+H]$^+$.

Synthesis of Compound 185.4.

To a solution of 185.3 (0.07 g, 0.259 mmol, 1.0 eq) in mixture of dichloromethane (1 mL) was added trifluoroacetic acid (1 mL) at 0° C. The reaction was stirred at room temperature for 6 h. After completion of reaction, reaction mixture was concentrated under vacuum and basified with sodium bicarbonate solution then extracted with ethyl acetate to obtain pure 185.4 (0.025 g, 69.16%). MS(ES): m/z 140.11 [M+H]$^+$.

Synthesis of Compound 185.5.

To a solution of 185.4 (0.5 g, 3.59 mmol, 1.0 eq) in N,N-dimethylformamide (10 mL) was added potassium carbonate (1.486 g, 10.77 mmol, 3.0 eq) at 0° C. and 4-bromobut-1-ene (0.534 g, 3.95 mmol, 1.1 eq). The reaction mixture was stirred at room temperature for 20 h. After completion of reaction, reaction mixture was transferred in water and extracted with ethyl acetate. Organic layer was combined, washed with brine, dried over sodium sulphate and concentrated under reduced pressure to obtain crude material. This was further purified by column chromatography and compound was eluted on 10% ethyl acetate in hexane as eluent to obtain 185.5. (0.34 g, 48.96%). MS(ES): m/z 194.21 [M+H]$^+$.

Synthesis of Compound 185.6.

To a solution of 185.5 (0.34 g, 1.76 mmol, 1.0 eq) in dichloromethane (7 mL) was added Grubb's second generation catalyst (0.110 g, 0.176 mmol, 0.1 eq). The reaction mixture was stirred at 50° C. for 16 h. After completion of reaction, reaction mixture was concentrated under reduced pressure to obtain crude material. This was further purified by column chromatography and compound was eluted on 15% ethyl acetate in hexane as eluent to obtain 185.6. (0.19 g, 65.37%). MS(ES): m/z 166.15 [M+H]$^+$.

Synthesis of Compound 185.7.

To a solution of 185.6 (0.19 g, 1.15 mmol, 1.0 eq) in methanol (2 mL), 10% palladium on charcoal (0.05 g) was added. Hydrogen was purged through reaction mixture for 2-3 h. After completion of reaction, reaction mixture was filtered through celite-bed and washed with ethanol. Filtrate was concentrated under reduced pressure to obtain 185.7 (0.13 g, 82.37%). MS(ES): m/z 138.19 [M+H]$^+$.

Synthesis of Compound I-222.

Compound I-222 was synthesized from 185.7 and 73.1 using general procedure B. (Yield: 11.82%). MS(ES): m/z 440.32 [M+H]$^+$, LCMS purity: 98.23%, HPLC purity: 97.74%, 1H NMR (DMSO-d6, 400 MHz): 10.52 (s, 1H), 9.45 (s, 1H), 8.81 (s, 1H), 7.57-7.55 (d, J=8.0 Hz, 1H), 7.25-7.17 (m, 2H), 6.95 (s, 1H), 6.14 (s, 1H), 3.94 (t, 2H), 3.82 (s, 3H), 3.25 (s, 3H), 2.72-2.67 (m, 2H), 1.96 (m, 2H), 1.77-1.74 (m, 2H).

Example 186: Synthesis of N-(2-((6-((1,3-dihydrofuro[3,4-c]pyridin-6-yl)amino)-2-methyl-3-oxo-2,3-dihydro-1H-pyrazolo[3,4-b]pyridin-4-yl)amino)phenyl)-N-methylmethanesulfonamide, I-227

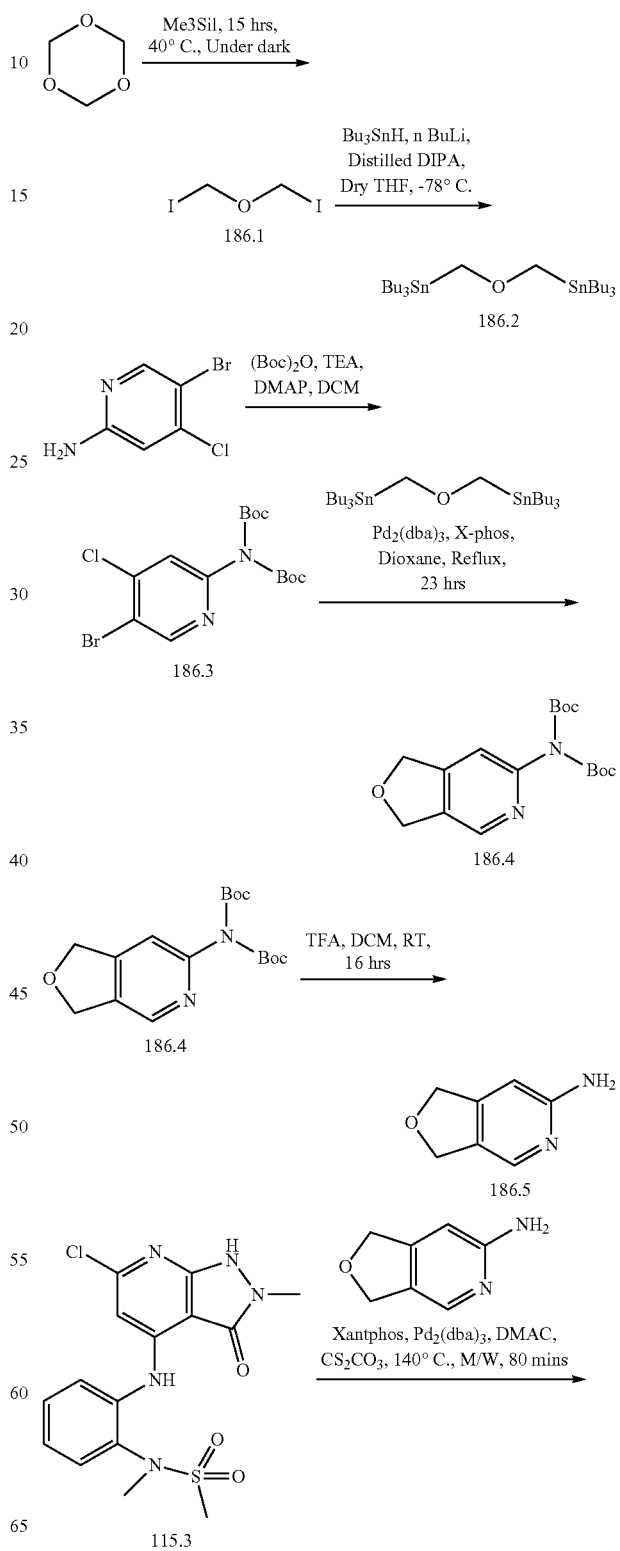

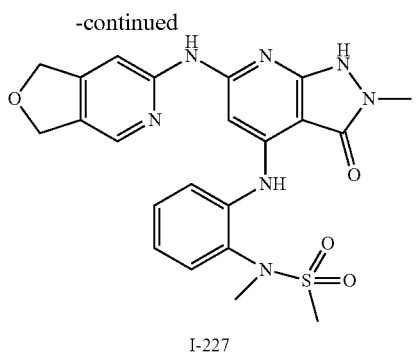

I-227

Synthesis of Compound 181.1.

The reaction mixture of 1,3,5-trioxane (12.0 g, 133.22 mmol, 1.0 eq) and trimethylsilyl iodide (75.9 g, 379.6 mmol, 2.85 eq) was stirred at 40° C. for 48 h. The reaction progress was monitored by NMR analysis. After completion of reaction, reaction mixture was purified by vacuum distillation at 5 mmHg, 105° C. to obtain desired pure product 186.1. (35 g, 88.20%). 1H NMR (CDCl3, 400 MHz): 5.75 (S, 4H).

Synthesis of Compound 186.2.

A solution of diisopropyl amine (16.27 g, 161.16 mmol, 2.4 eq) in tetrahydrofuran (70 mL) was cooled to −78° C. followed by n-butyl lithium (10.31 g, 161.16 mmol, 2.4 eq) was added and stirred reaction mixture for 30 min. at the same temperature. Tributyltin hydride (46.90 g, 161.16 mmol, 2.4 eq) was added to reaction mixture at same temperature and then maintained 0° C. and stirred for 30 min. The reaction mixture was cooled to −78° C., added compound 1 (20 g, 67.15 mmol, 1.0 eq) and reaction mixture was allowed to warm to room temperature. The reaction mixture was stirred at room temperature for 5 h. After completion of reaction, reaction mixture was transferred into brine solution and extracted with diethyl ether. Organic layer was combined, washed with brine, dried over sodium sulphate and concentrated under reduced pressure to obtain crude material. This was further purified by column chromatography and compound was eluted hexane as eluent to obtain 186.2. (0.85 g, 2.03%). MS(ES): m/z 625.17 [M+H]$^+$.

Synthesis of Compound 186.3.

To a solution of 5-bromo-4-chloropyridin-2-amine (2.0 g, 9.64 mmol, 1.0 eq), Di-tert-butyl dicarbonate (5.25 g, 24.1 mmol, 2.5 eq) and triethyl amine (2.423 g, 24.1 mmol, 2.5 eq) in tetrahydrofuran (10 mL) was added. Then 4-Dimethylaminopyridine (0.117 g, 0.964 mmol, 0.1 eq) was added and the reaction mixture was stirred at room temperature for 18 h. After completion of reaction, reaction mixture was concentrated under reduced pressure to obtain crude material. This was further purified by column chromatography and compound was eluted in 10% ethyl acetate in hexane as eluent to obtain 186.3. (2.10 g, 53.43%). MS(ES): m/z 408.69 [M+H]$^+$.

Synthesis of compound 186.4

To a solution of 186.3 (0.650 g, 1.59 mmol, 1.0 eq), oxybis(methylene)bis(tributylstannane) (0.995 g, 1.59 mmol, 1.0 eq), Tris(dibenzylideneacetone)dipalladium(0) (0.146 g, 1.59 mmol, 0.1 eq), 2-Dicyclohexylphosphino-2', 4',6'-triisopropylbiphenyl (0.152 g, 3.19 mmol, 0.2 eq), in Dioxane (20 mL) was added. The reaction mixture was degassed for 15 min. under argon atmosphere. The reaction mixture was stirred at 120° C. for 20 h. After completion of reaction, reaction mixture was transferred in ethyl acetate. Organic layer was filtered through celite-bed and washed with ethyl acetate. Filtrate was concentrated under reduced pressure to obtain crude material. This was further purified by column chromatography using 18% ethyl acetate in hexane to obtain pure 186.4 (0.250 g, 46.61%). MS(ES): m/z 337.39 [M+H]$^+$.

Synthesis of Compound 186.5.

Compound 186.5 was synthesized from 186.4 using general procedure C. (Yield: 79.06%). MS(ES): m/z 137.15 [M+H]$^+$.

Synthesis of Compound I-227.

Compound I-227 was synthesized from 115.3 and 186.5 using general procedure B. (Yield: 24.78%). MS(ES): m/z 482.36 [M+H]$^+$, LCMS purity: 98.38%, HPLC purity: 96.23%, 1H NMR (DMSO-d6, 400 MHz): 10.74 (s, 1H), 9.89 (s, 1H), 8.86 (s, 1H), 8.21 (s, 1H), 8.05 (s, 1H), 7.72-7.70 (d, J=8.0 Hz, 1H), 7.59-7.57 (d, J=8.0 Hz, 1H), 1.50-1.48 (d, J=8.0 Hz, 1H), 7.21 (s, 1H), 7.11 (s, 1H), 5.00 (s, 4H), 3.28 (s, 3H), 3.22 (s, 3H), 3.18 (s, 3H).

Example 187: Synthesis of 3-((6-amino-2-methyl-3-oxo-2,3-dihydro-1H-pyrazolo[3,4-b]pyridin-4-yl)amino)-2-methoxybenzoic Acid, I-241

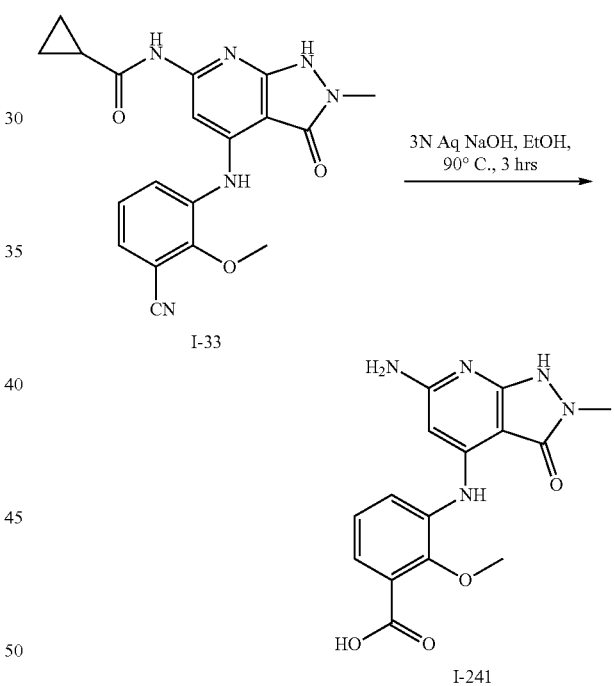

Synthesis of Compound I-241.

To a solution of I-33 (0.070 g, 0.184 mmol, 1.0 eq) in ethanol (1 mL) was added 3N aqueous sodium hydroxide solution (5 mL) dropwise and reaction mixture was stirred at 90° C. for 3 h. After completion of reaction, reaction mixture concentrated under reduced pressure to obtain crude material. This was further purified by Preparative HPLC using 0.1% Formic acid in water/Acetonitrile in gradient method to obtain pure I-241 (0.013 g, 21.34%), MS(ES): m/z 330.25 [M+H]$^+$, LCMS purity: 100.00%, HPLC purity: 98.07%, 1H NMR (DMSO-d6, 400 MHz): 11.89 (s, 1H), 8.77 (s, 1H), 8.19 (s, 1H), 7.64-7.62 (d, J=8.0 Hz, 1H), 7.41-7.39 (d, J=8.0 Hz, 1H), 7.25-7.21 (t, J=8.0 Hz, 1H), 6.53 (s, 2H), 5.78 (s, 1H), 3.80 (s, 3H), 3.18 (s, 3H).

Example 188: Synthesis of N-(4-((4-cyclobutyl-2-(methylsulfonyl)phenyl)amino)-2-methyl-3-oxo-2,3-dihydro-1H-pyrazolo[3,4-b]pyridin-6-yl)cyclopropanecarboxamide, I-182

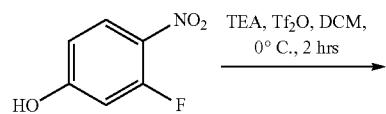

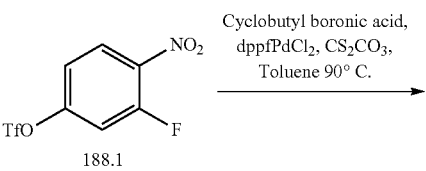

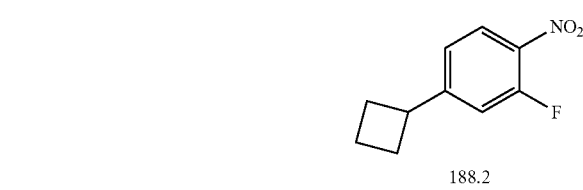

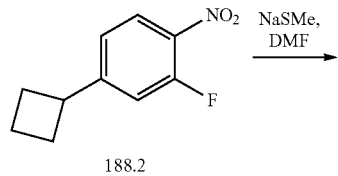

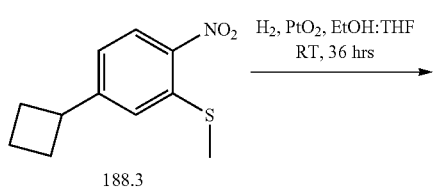

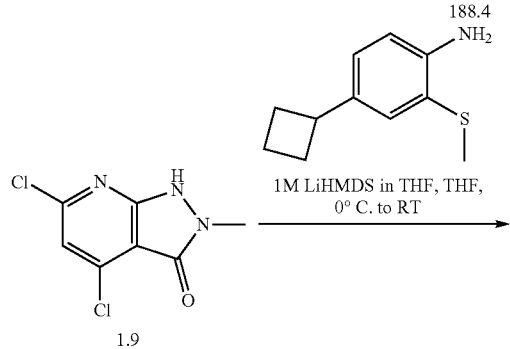

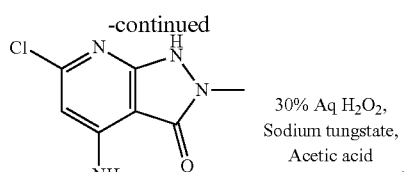

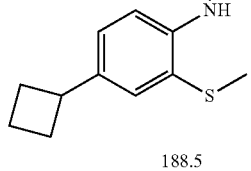

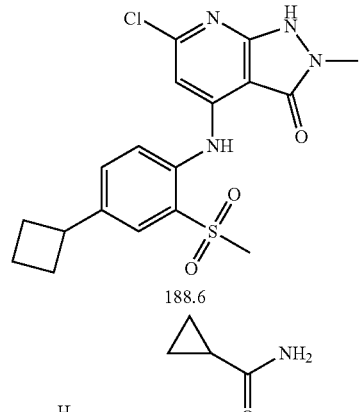

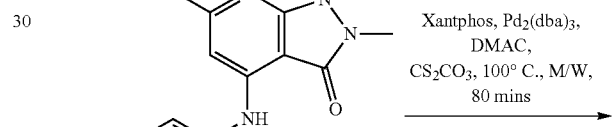

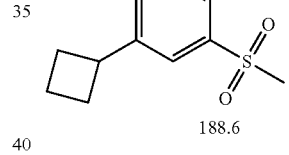

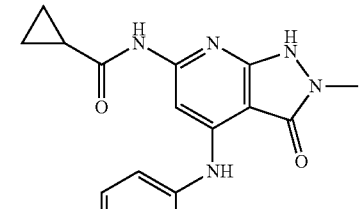

Synthesis of Compound 188.1.

To a cooled solution of 3-fluoro-4-nitrophenol (5.0 g, 31.83 mmol, 1.0 eq) in dichloromethane (50 mL) at 0° C. was added Trifluoromethanesulfonic anhydride (0.520 g, 4.14 mmol, 2.0 eq), stirred for 15 min followed by dropwise addition of triethylamine (0.520 g, 4.14 mmol, 2.0 eq) at the same temperature. The reaction mixture was stirred at room temperature for 2 h. After completion of reaction, reaction mixture was transferred in to water and extracted with dichloromethane. Organic layer was combined, washed with brine, dried over sodium sulphate and concentrated under reduced pressure to obtain crude material. This was further purified by column chromatography in neutral alumina and compound was eluted on 15% ethyl acetate in hexane as eluent to obtain 188.1. (3.0 g, 32.60%). MS(ES): m/z 290.16 [M+H]⁺.

Synthesis of Compound 188.2.

To a solution of 1.1 (3.0 g, 10.38 mmol, 1.0 eq) and cyclobutyl boronic acid (1.3 g, 12.97 mmol, 1.25 eq) in toluene (30 mL) was added cesium carbonate (6.74 g, 20.76 mmol, 2.0 eq). The reaction mixture was degassed for 10 min. under argon atmosphere. The [1,1'-Bis(diphenylphosphino)ferrocene]palladium(II) dichloride (0.607 g, 0.83 mmol, 0.08 eq) was added, again reaction mixture was degassed for 10 min. under argon atmosphere. The reaction was stirred at 90° C. for 4 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 5% ethyl acetate in hexane to obtain pure 188.2 (0.32 g, 15.80%). MS(ES): m/z 196.19 [M+H]⁺.

Synthesis of Compound 188.3.

To a solution of 188.2 (0.34 g, 1.64 mmol, 1.0 eq) in mixture of N—N-dimethylformamide (6 mL) and water (4 mL) was added dropwise sodium thiomethoxide water solution (0.252 g, 3.61 mmol, 2.2 eq) at 0° C. The reaction was stirred at 15-20° C. for 1 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 5% ethyl acetate in hexane to obtain pure 188.3 (0.24 g, 65.56%). MS(ES): m/z 224.29 [M+H]⁺.

Synthesis of Compound 188.4.

To a solution of 188.3 (0.14 g, 0.623 mmol, 1.0 eq) in methanol (5 mL), 10% palladium on charcoal (0.05 g) was added. Hydrogen was purged through reaction mixture for 2-3 h. After completion of reaction, reaction mixture was filtered through celite-bed and washed with ethanol. Filtrate was concentrated under reduced pressure to obtain 188.4 (0.08 g, 66.01%). MS(ES): m/z 194.31 [M+H]⁺.

Synthesis of Compound 188.5.

Compound 188.5 was synthesized from 1.9 and 188.4 using general procedure A. (Yield: 58.16%). MS (ES): m/z 375.89 [M+H]⁺.

Synthesis of compound 188.6. To a solution of 188.5 (0.075 g, 0.200 mmol, 1 eq) in acetic acid (1 mL) was added 30% hydrogen peroxide (0.144 g, 4.0 mmol, 20.0 eq) and sodium tungstate dihydrate (0.066 g, 0.200 mmol, 1 eq). Reaction mixture was stirred at room temperature for 2 h. After completion of reaction, reaction mixture was transferred in ice-water and precipitated product was filtered, washed with 25% ethyl acetate in hexane and dried well to obtain 188.6. (0.070 g, Yield: 85.99%). MS(ES): m/z 407.89 [M+H]⁺.

Synthesis of Compound I-182.

Compound I-182 was synthesized from 188.6 and cyclopropanecarboxamdie using general procedure B. (Yield: 31.90%). MS(ES): m/z 456.37 [M+H]⁺, LCMS purity: 95.00%, HPLC purity: 98.84%, 1H NMR (DMSO-d6, 400 MHz): 10.80 (s, 2H), 9.05 (s, 1H), 7.75-7.68 (m, 4H), 3.65 (m, 1H), 3.30 (s, 3H), 3.16 (s, 3H), 2.34 (m, 2H), 2.14 (m, 2H), 2.00 (m, 2H), 1.86 (m, 1H), 0.77 (m, 4H).

Example 189: Synthesis of 4-((4-chloro-2-(methylsulfonyl)phenyl)amino)-2-methyl-6-((5-methyl-6-(trifluoromethyl)pyridin-2-yl)amino)-1,2-dihydro-3H-pyrazolo[3,4-b]pyridin-3-one, I-208

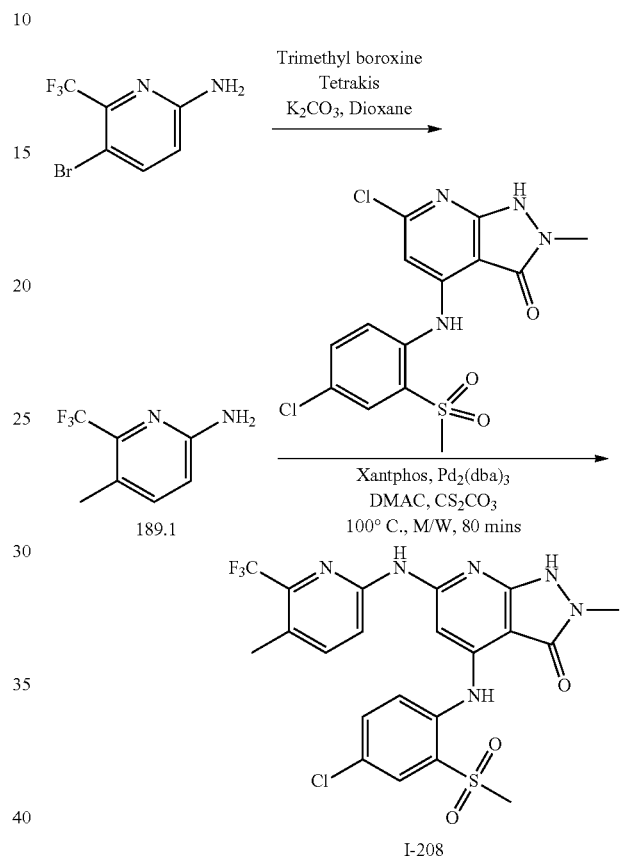

Synthesis of Compound 189.1.

To a solution of 5-bromo-6-(trifluoromethyl)pyridin-2-amine (0.500, 2.07 mmol, 1.0 eq) in 1,4-dioxane (0.5 mL) was added Tri methyl boroxine (0.520 g, 4.14 mmol, 2.0 eq). The reaction mixture was degassed for 10 min. under argon atmosphere. Potassium carbonate (0.858 g, 6.22 mmol, 3.0 eq) and tetrakis(triphenylphosphine)palladium(0) (0.239 g, 0.207 mmol, 0.1 eq), again reaction mixture was degassed for 10 min. under argon atmosphere. The reaction was stirred at 110° C. for 20 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 15% ethyl acetate in hexane to obtain pure 189.1 (0.230 g, 62.94%). MS(ES): m/z 177.14 [M+H]⁺.

Synthesis of compound I-208.

Compound I-208 was synthesized from 189.1 and 118.4 using general procedure B (Yield: 7.10%). MS(ES): m/z 527.34 [M+H]⁺, LCMS purity: 98.28%, HPLC purity: 96.27%, 1H NMR (DMSO-d6, 400 MHz): 10.83 (s, 1H), 10.09 (s, 1H), 9.06 (s, 1H), 8.04-8.02 (d, J=8.0 Hz, 1H), 7.91-7.90 (d, J=1.0 Hz, 1H), 7.86-7.79 (m, 3H), 7.17 (s, 1H), 3.29 (s, 3H), 3.26 (s, 3H), 2.36 (s, 3H).

Example 190: Synthesis of 6-((4-((3-chloro-2-methoxyphenyl)amino)-2-methyl-3-oxo-2,3-dihydro-1H-pyrazolo[3,4-b]pyridin-6-yl)amino)-3-(2-methoxypropan-2-yl)pyrazine-2-carbonitrile, I-155

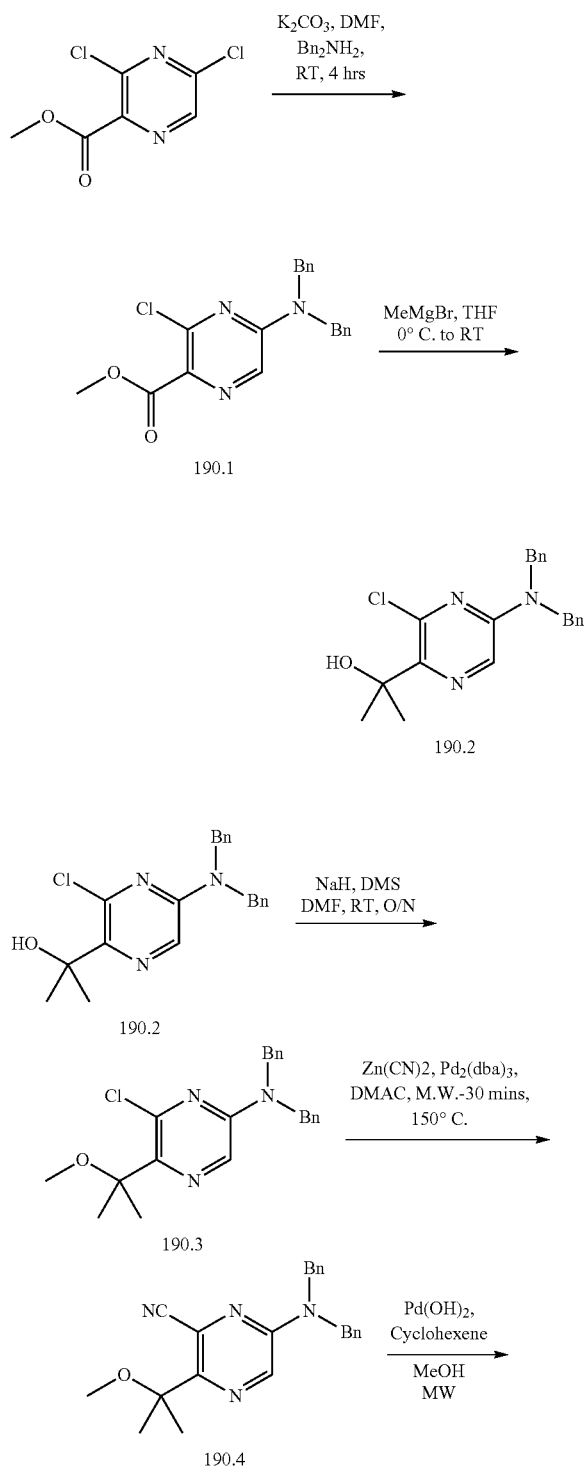

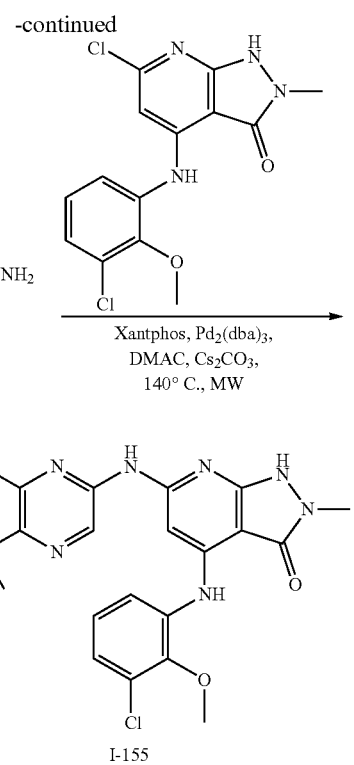

Synthesis of Compound 190.1.

To a solution of compound methyl 3,5-dichloropyrazine-2-carboxylate (0.55 g, 2.6 mmol, 1.0 eq) in dimethylformamide (5 mL), cesium carbonate (0.8 g, 3.1 mmol, 1.2 eq) and dibenzylamine (0.61 g, 3.1 mmol, 1.2 eq) was added. Reaction mixture was stirred at room temperature for 3 hours. After completion of the reaction, reaction mixture transferred into water and extracted with ethyl acetate. Combined organic layer, dried over anhydrous sodium sulfate, filtered and concentrated under reduced pressure to obtain 190.1. (0.5 g, 51.16%). MS(ES): m/z 368.54 [M+H]$^+$.

Synthesis of Compound 190.2.

To a solution of compound 190.1 (0.18 g, 0.4 mmol, 1.0 eq) in tetrahydrofuran (5 mL), methyl magnesium bromide (0.36 g, 1.09 mmol, 2.2 eq) was added at 0° C. Reaction mixture was stirred at room temperature for 1 h. After completion of the reaction, reaction mixture transferred into water and extracted with ethyl acetate. Combined organic layer, dried over anhydrous sodium sulfate, filtered and concentrated under reduced pressure to obtain 190.2. (0.15 g, 83.32%). MS(ES): m/z 368.43 [M+H]$^+$.

Synthesis of Compound 190.3

To a solution of 190.2 (0.15 g, 0.413 mmol, 1.0 eq) in dimethylformamide (1 mL), sodium hydride (0.025 g, 0.490 mmol, 1.2 eq) was added at 0° C. within 5 min. Then methyl iodide (0.07 g, 0.490 mmol, 1.2 eq) was added and the reaction mixture was stirred at room temperature for 4 h. After completion of the reaction, reaction mixture transferred into water and extracted with ethyl acetate. Combined organic layer, dried over anhydrous sodium sulfate, filtered and concentrated under reduced pressure to obtain 190.3. (0.1 g, 64.22%). MS(ES): m/z 382.51 [M+H]$^+$.

Synthesis of Compound 190.4.

To a solution of 190.3 (0.08 g, 0.29 mmol, 1.0 eq) in dimethylacetamide (1 mL), zinc dust (0.003 g, 0.041 mmol, 0.2 eq) and zinc cyanide (0.012 g, 0.10 mmol, 0.5 eq) was added. Reaction mixture was degassed for 15 min and then palladium tris(dibenzylideneacetone)dipalladium(0) (0.02 g, 0.020 mmol, 0.1 eq) was added and the reaction mixture was kept microwave irradiation for 30 min at 120° C. After completion of the reaction, reaction mixture transferred into water and extracted with ethyl acetate. Combined organic layer, dried over anhydrous sodium sulfate, filtered and concentrated under reduced pressure to obtain 190.4. (0.05 g, 64.08%). MS(ES): m/z 373.28 [M+H]$^+$.

Synthesis of Compound 190.5.

To a solution of 190.4 (0.08 g, 0.29 mmol, 1.0 eq) in methanol (1 mL), cyclohexene (0.003 g, 0.041 mmol, 0.2 eq) and palladium hydroxide (0.012 g, 0.10 mmol, 0.5 eq) were added. Reaction mixture was kept in microwave irradiation for 4 h at 100° C. After completion of reaction, reaction mixture was filtered through celite-bed and washed with methanol. Filtrate was concentrated under reduced pressure to 190.5 (0.2 g, 38.75%). MS(ES): m/z 193.53 [M+H]$^+$.

Synthesis of Compound I-155.

Compound I-155 was synthesized from 190.5 and 73.1 using general procedure B. (Yield: 29.13%). MS(ES): m/z 495.58 [M+H]$^+$, LCMS purity: 98.63%, HPLC purity: 98.19%, 1H NMR (DMSO-d6, 400 MHz): 10.95 (s, 1H), 10.65 (s, 1H), 9.28 (s, 1H), 8.99 (s, 1H), 7.64-7.61 (dd, J=1.6 Hz, 8.0 Hz, 1H), 7.32-7.23 (m, 3H), 3.83 (s, 3H), 3.32 (s, 3H), 3.17 (s, 3H), 1.55 (s, 6H).

Example 191: Synthesis of 6-((4-((3-fluoro-2-methoxyphenyl)amino)-2-methyl-3-oxo-2,3-dihydro-1H-pyrazolo[3,4-b]pyridin-6-yl)amino)-3-(2-methoxypropan-2-yl)pyrazine-2-carbonitrile, I-190

Synthesis of Compound I-190.

Compound I-190 was synthesized from 190.5 and 55.1 using general procedure B. (Yield: 14.92%). MS(ES): m/z 479.62 [M+H]$^+$, LCMS purity: 95.39%, HPLC purity: 95.38%, 1H NMR (DMSO-d6, 400 MHz): 10.92 (s, 1H), 10.64 (s, 1H), 9.27 (s, 1H), 8.97 (s, 1H), 7.48-7.46 (d, J=8.4 Hz, 1H), 7.33 (s, 1H), 7.27-7.21 (m, 1H), 7.07-7.02 (m, 1H), 3.91 (s, 3H), 3.32 (s, 3H), 3.17 (s, 3H), 1.54 (s, 6H).

Example 192: Synthesis of N-(4-((4-(3-methoxyazetidin-1-yl)-2-(N-methylmethylsulfonamido)phenyl)amino)-2-methyl-3-oxo-2,3-dihydro-1H-pyrazolo[3,4-b]pyridin-6-yl)cyclopropanecarboxamide, I-240

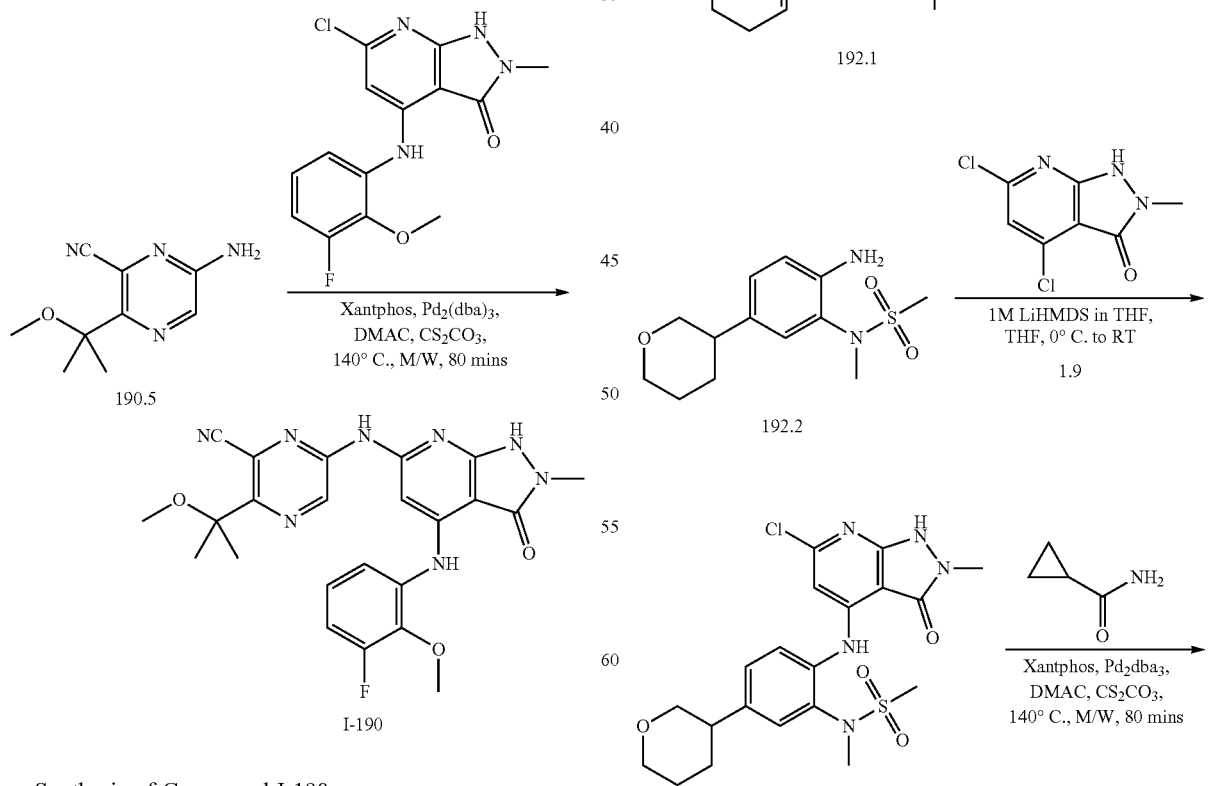

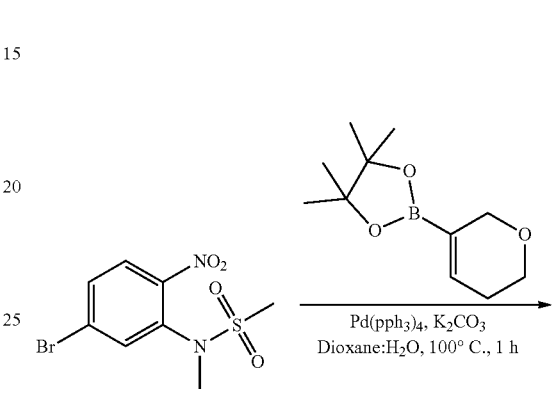

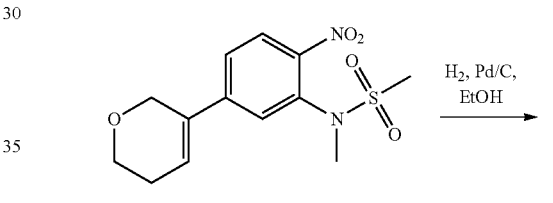

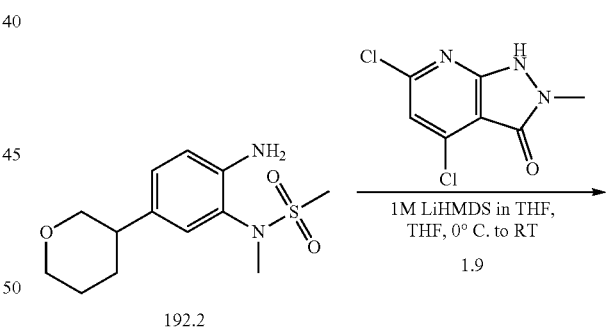

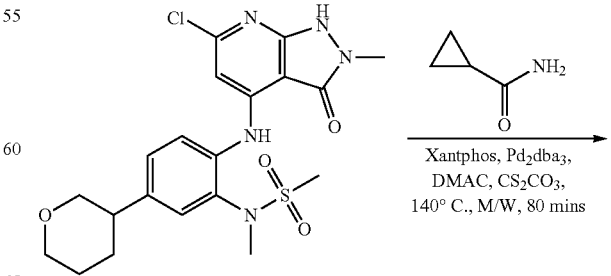

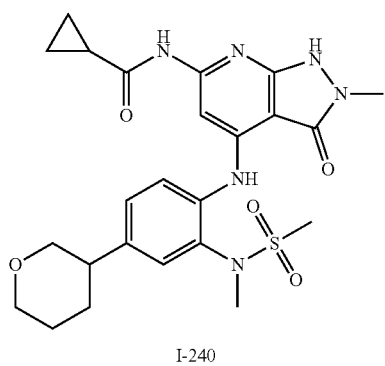

I-240

Synthesis of Compound 192.1.

To a solution of N-(5-bromo-2-nitrophenyl)-N-methyl-methanesulfonamide (0.6 g, 1.94 mmol, 1.0 eq) in mixture of 1,4-dioxane (4 mL) and water (2 mL) was added 2-(5,6-dihydro-2H-pyran-3-yl)-4,4,5,5-tetramethyl-1,3,2-dioxaborolane (0.611 g, 2.91 mmol, 1.5 eq). The reaction mixture was degassed for 10 min. under argon atmosphere. Potassium carbonate (0.803 g, 5.82 mmol, 3.0 eq) and Tetrakis(triphenylphosphine)palladium(0) (0.224 g, 0.194 mmol, 0.1 eq), again reaction mixture was degassed for 10 min. under argon atmosphere. The reaction was stirred at 100° C. for 20 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 15% ethyl acetate in hexane to obtain pure 192.1 (0.5 g, 82.48%). MS(ES): m/z 313.34 [M+H]$^+$ Synthesis of Compound 192.2.

To a solution of 192.1 (0.5 g, 1.6 mmol, 1.0 eq) in ethanol (25 mL), 10% palladium on charcoal (0.3 g) was added. Hydrogen was purged through reaction mixture for 4 h. After completion of reaction, reaction mixture was filtered through celite-bed and washed with methanol. Filtrate was concentrated under reduced pressure to obtain 192.2. (0.4 g, 87.87%). MS(ES): m/z 285.37 [M+H]$_+$.

Synthesis of Compound 192.3.

Compound 192.3 was synthesized from 1.9 and 192.2 using general procedure A. (Yield: 19.56%). MS(ES): m/z 466.94 [M+H]$^+$.

Synthesis of Compound I-240.

Compound I-240 was synthesized from 192.3 and cyclopropanecarboxamide using general procedure B. (Yield: 28.97%), MS(ES): m/z 515.46 [M+H]$^+$, LCMS purity: 97.79%, HPLC purity: 98.19%, Chiral HPLC: (43:57), 1H NMR (DMSO-d6, 400 MHz): 10.73 (s, 1H), 10.68 (s, 1H), 8.79 (s, 1H), 7.69 (s, 1H), 7.51 (s, 2H), 7.37-7.35 (d, J=8.0 Hz, 1H), 3.90-3.87 (m, 2H), 3.40 (m, 2H), 3.30 (s, 3H), 3.17 (s, 3H), 3.15 (s, 3H), 2.84 (m, 1H), 2.00-1.96 (m, 2H), 1.79-1.76 (m, 1H), 1.67 (m, 2H), 0.87-0.80 (m, 4H).

Example 193: Synthesis of 4-((3-chloro-2-methoxyphenyl)amino)-6-((6,7-dihydro-4H-pyrazolo[5,1-c][1,4]oxazin-2-yl)amino)-2-methyl-1,2-dihydro-3H-pyrazolo[3,4-b]pyridin-3-one, I-234

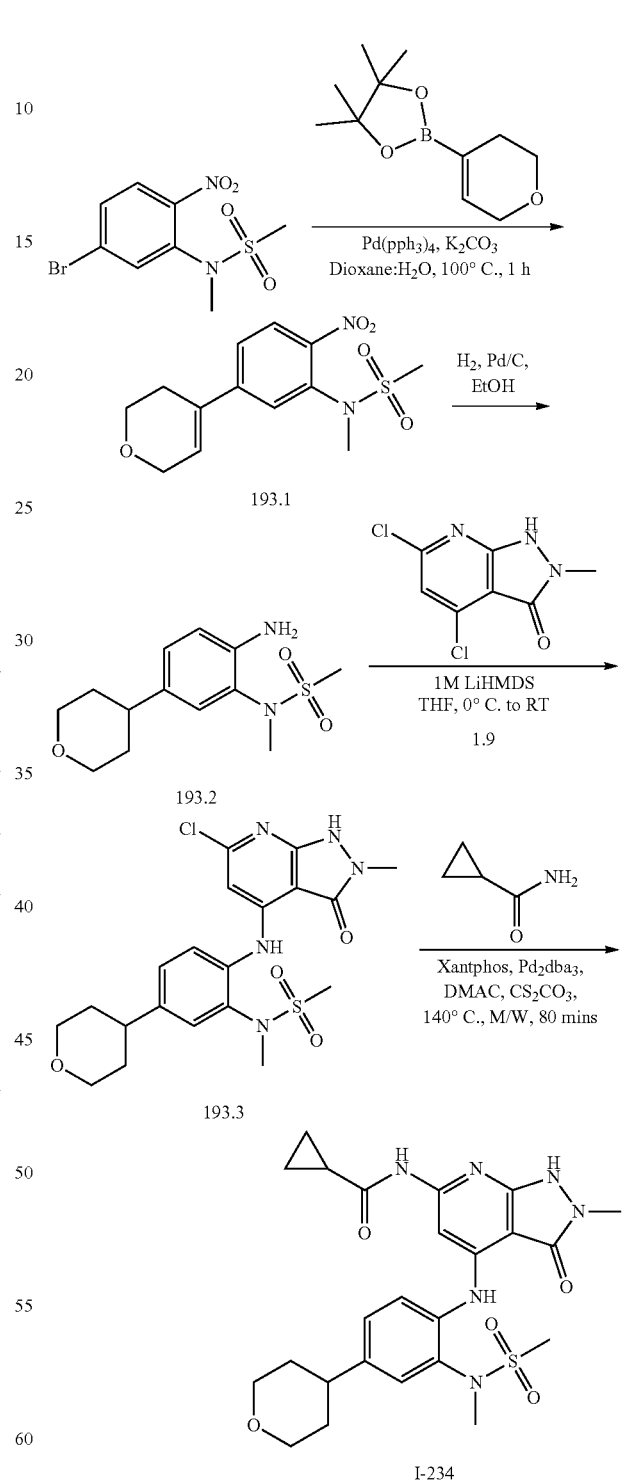

I-234

Synthesis of Compound 193.1.

To a solution of of N-(5-bromo-2-nitrophenyl)-N-methylmethanesulfonamide (1.0 g, 3.58 mmol, 1.0 eq) in mixture of tetrahydrofuran (10 mL) and water (5 mL) was added 2-(cyclohex-1-en-1-yl)-4,4,5,5-tetramethyl-1,3,2-dioxaborolane (1.51 g, 7.16 mmol, 2.0 eq) and potassium carbonate (1.48 g, 10.74 mmol, 3.0 eq). The reaction mixture was degassed for 10 min. under argon atmosphere. [1,1'-Bis (diphenylphosphino)ferrocene]palladium(II) dichloride (0.262 g, 0.358 mmol, 0.1 eq), again reaction mixture was degassed for 10 min. under argon atmosphere. The reaction was stirred at 60° C. for 20 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 15% ethyl acetate in hexane to obtain pure 193.1 (1.0 g, 98.86%). MS(ES): m/z 283.36 [M+H]$^+$.

Synthesis of Compound 193.2.

To a solution of 193.1 (1 g, 3.54 mmol, 1.0 eq) in methanol (20 mL), 10% palladium on charcoal (0.15 g) was added. Hydrogen was purged through reaction mixture for 2-3 h. After completion of reaction, reaction mixture was filtered through celite-bed and washed with ethanol. Filtrate was concentrated under reduced pressure to obtain 193.2 (0.42 g, 41.70%). MS(ES): m/z 285.37 [M+H]$^+$.

Synthesis of Compound 193.3.

Compound 193.3 was synthesized from 1.9 and 193.2 using general procedure A. (Yield: 22.84%). MS(ES): m/z 466.95 [M+H]$^+$.

Synthesis of Compound I-234.

Compound I-234 was synthesized from 193.3 and cyclopropanecarboxamide using general procedure B. (Yield: 51.95%). MS(ES): m/z 515.46 [M+H]$^+$, LCMS purity: 98.21%, HPLC purity: 95.25%, 1H NMR (DMSO-d6, 400 MHz): 10.72 (s, 1H), 10.67 (s, 1H), 8.78 (s, 1H), 7.68 (s, 1H), 7.51 (s, 2H), 7.36-7.34 (d, J=8.0 Hz, 1H), 3.99-3.96 (m, 2H), 3.47-3.43 (m, 2H), 3.30 (s, 3H), 3.18 (s, 3H), 3.15 (s, 3H), 2.83 (m, 1H), 2.01 (m, 1H), 1.74 (m, 4H), 0.87-0.79 (m, 4H).

Example 194: Synthesis of N-(4-((4-cyclopropyl-2-(methylsulfonyl)phenyl)amino)-2-methyl-3-oxo-2,3-dihydro-1H-pyrazolo[3,4-b]pyridin-6-yl)-2,2-difluorocyclopropane-1-carboxamide, I-239

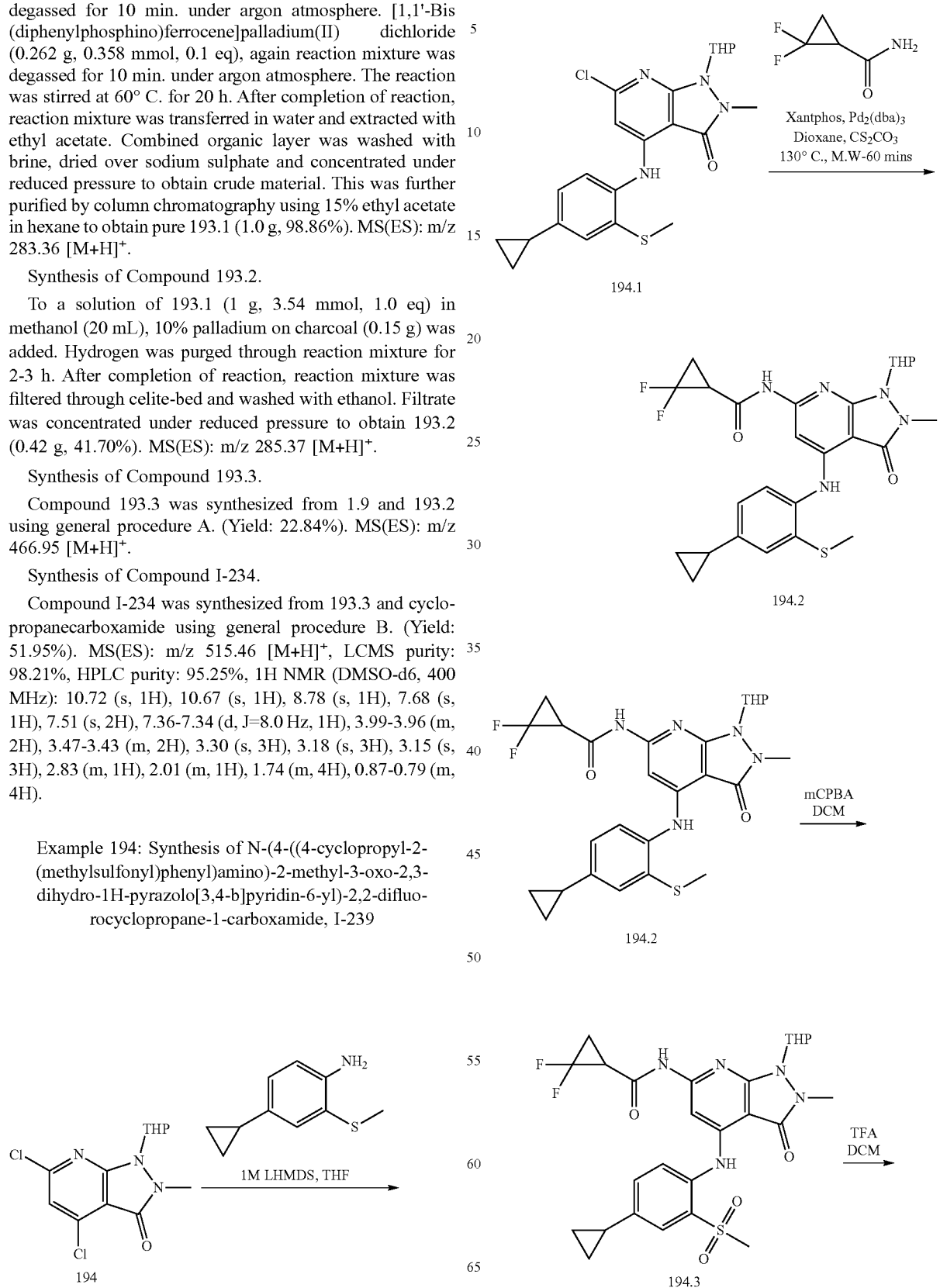

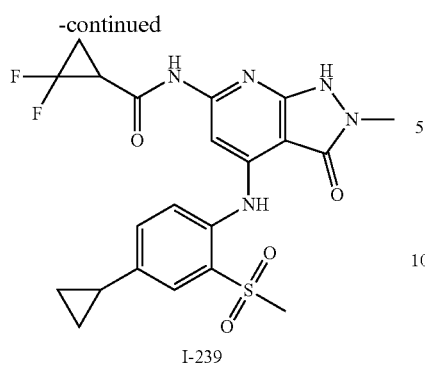

I-239

Synthesis of Compound 194.1.

To a solution of compound 194 (prepared by reaction of 1.9 with dihydropyran, 0.3 g, 0.25 mmol, 1.0 eq) and 109.4 in tetrahydrofuran (3 mL), Lithium bis(trimethylsilyl)amide (0.86 g, 0.75 mmol, 3.0 eq) was added. Reaction mixture was stirred at room temperature to obtain 194.1. (0.28 g, 63.38%). MS(ES): m/z 445.58 [M+H]$^+$.

Synthesis of Compound 194.2.

To a solution of compound 194.1 (0.150 g, 0.33 mmol, 1.0 eq) in 1,4-dioxane (5 mL), 2,2-difluorocyclopropane-1-carboxamide (0.123 g, 1.013 mmol, 3.0 eq) and cesium carbonate (0.44 g, 1.35 mmol, 4.0 eq) was added. The reaction mixture was degassed for 10 min. under argon atmosphere, then tris(dibenzylideneacetone)dipalladium(0) (0.031 g, 0.033 mmol, 0.1 eq) and 4,5-Bis(diphenylphosphino)-9,9-dimethylxanthene (0.040 g, 0.65 mmol, 0.2 eq) were added, again degassed for 5 min. The reaction mixture was then heated in microwave at 130° C. for 60 min. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 13% ethyl acetate in hexane as eluant to obtain pure 194.2 (0.140 g, 78.42%). MS(ES): m/z 530.46 [M]+.

Synthesis of Compound 194.3.

To a solution of 194.2 (0.2 g, 0.04 mmol, 1.0 eq) in ethyl acetate (3 mL), meta-chloroperoxybenzoic acid (0.28 g, 0.12 mmol, 3.0 eq) was added at 0° C. Reaction mixture was stirred at 0° C. for 3 h. After completion of the reaction, water was added to the reaction mixture and extracted with ethyl acetate. Organic layers were combined, dried over anhydrous sodium sulfate, filtered and concentrated under reduced pressure to obtain 194.3. (0.15 g, 70.73%). MS(ES): m/z 562.47 [M+H]$^+$.

Synthesis of Compound I-239.

To a solution of 194.3 (0.150 g, 0.167 mmol, 1.0 eq) in dichloromethane (1.5 mL) was added trifluoroacetic acid (1.0 mL) at 0° C. The reaction mixture was stirred at room temperature for 1 h. After completion of reaction, reaction mixture transferred in saturated sodium bicarbonate solution and product was extracted with dichloromethane. Organic layer was combined, washed with brine solution, dried over sodium sulphate and concentrated under reduced pressure to obtain crude material. This was further purified by trituration with diethyl ether/n-pentane mixture to obtain pure I-239 (0.080 g, 62.73%). MS(ES): m/z 478.42 [M+H]$^+$, LCMS purity: 99.70%, HPLC purity: 98.80%, Chiral HPLC: (51: 49), 1H NMR (DMSO-d6, 400 MHz): 10.98 (s, 1H), 10.87 (s, 1H), 9.03 (s, 1H), 7.65-7.63 (d, J=8.0 Hz, 2H), 7.56-7.50 (m, 2H), 3.31 (s, 3H), 3.15 (s, 3H), 3.02-2.94 (m, 1H), 2.14-2.08 (m, 1H), 2.02-1.95 (m, 2H), 1.07-1.02 (m, 2H), 0.79-0.76 (m, 2H).

Example I-195: Synthesis of (1S,2S)—N-(4-((4-cyclobutyl-2-(N-methylmethylsulfonamido)phenyl)amino)-2-methyl-3-oxo-2,3-dihydro-1H-pyrazolo[3,4-b]pyridin-6-yl)-2-fluorocyclopropane-1-carboxamide, I-236

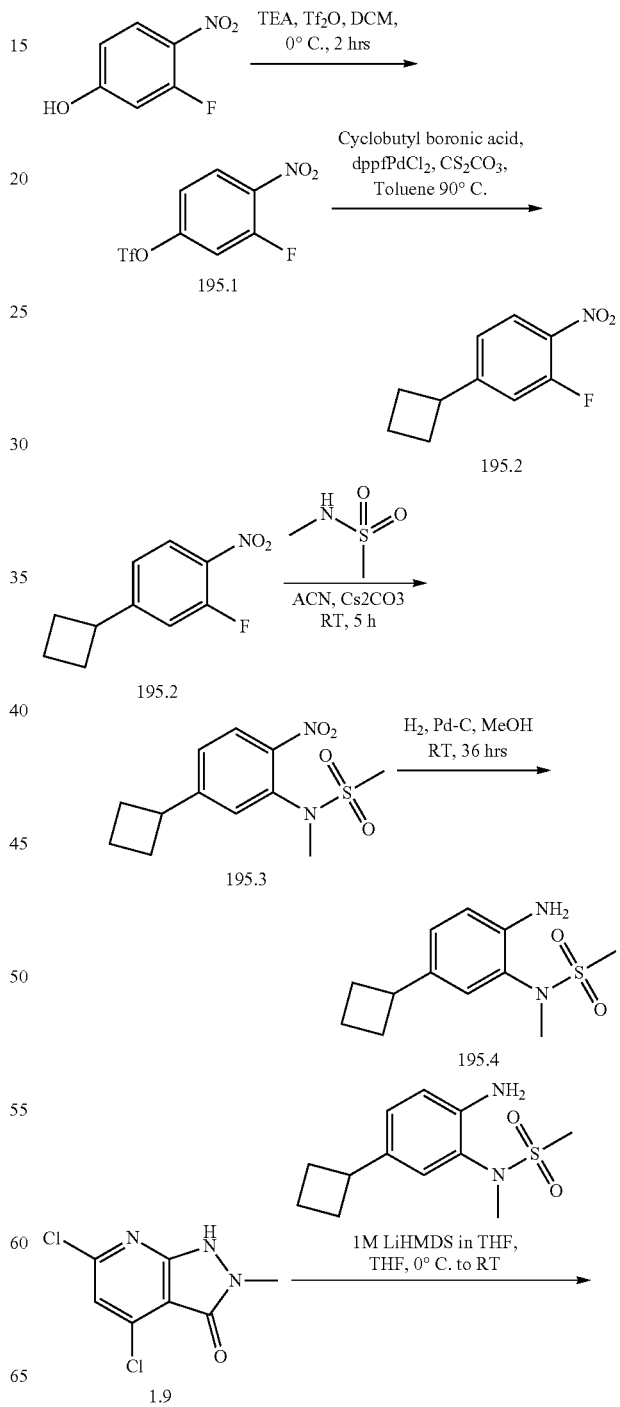

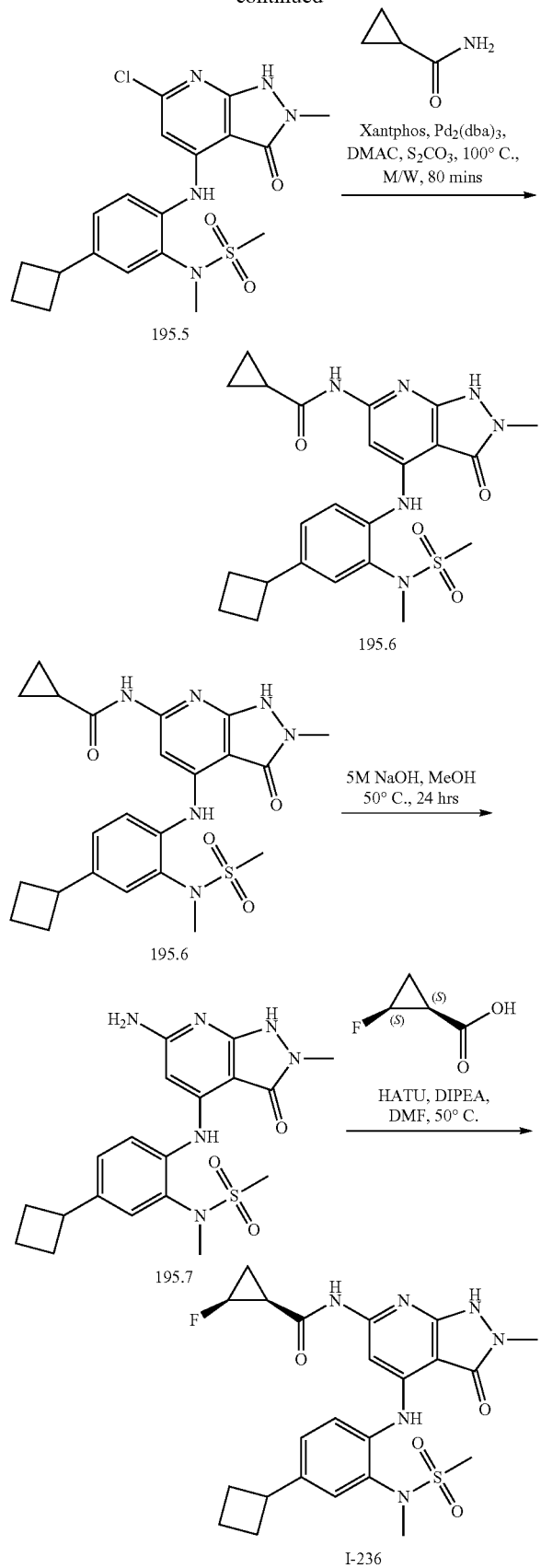

Synthesis of Compound 195.1.

To a cooled solution of 3-fluoro-4-nitrophenol (5.0 g, 31.83 mmol, 1.0 eq) in dichloromethane (50 mL) at 0° C. was added Trifluoromethanesulfonic anhydride (0.520 g, 4.14 mmol, 2.0 eq), stirred for 15 min followed by dropwise addition of triethylamine (0.520 g, 4.14 mmol, 2.0 eq) at the same temperature. The reaction mixture was stirred at room temperature for 2 h. After completion of reaction, reaction mixture was transferred in to water and extracted with dichloromethane. Organic layer was combined, washed with brine, dried over sodium sulphate and concentrated under reduced pressure to obtain crude material. This was further purified by column chromatography in neutral alumina and compound was eluted on 15% ethyl acetate in hexane as eluent to obtain 195.1. (3.0 g, 32.60%). MS(ES): m/z 290.16 [M+H]$^+$.

Synthesis of Compound 195.2.

To a solution of 1.1 (3.0 g, 10.38 mmol, 1.0 eq) and cyclobutyl boronic acid (1.3 g, 12.97 mmol, 1.25 eq) in toluene (30 mL) was added cesium carbonate (6.74 g, 20.76 mmol, 2.0 eq). The reaction mixture was degassed for 10 min. under argon atmosphere. The [1,1'-Bis(diphenylphosphino)ferrocene]palladium(II) dichloride (0.607 g, 0.83 mmol, 0.08 eq) was added, again reaction mixture was degassed for 10 min. under argon atmosphere. The reaction was stirred at 90° C. for 4 h. After completion of reaction, reaction mixture was transferred in water and extracted with ethyl acetate. Combined organic layer was washed with brine, dried over sodium sulphate and concentrated under reduced pressure to obtain crude material. This was further purified by column chromatography using 5% ethyl acetate in hexane to obtain pure 195.2 (0.32 g, 15.80%). MS(ES): m/z 196.19 [M+H]$^+$.

Synthesis of compound 195.3. To a solution of N-Methyl methane sulfonamide (0.615 g, 5.64 mmol, 1.1 eq) in acetonitrile (6 mL) were added cesium carbonate (3.33 g, 10.24 mmol, 2.0 eq). The reaction mixture was stirred at room temperature for 30 min. Compound 195.2 (1.0 g, 5.12 mmol, 1.0 eq) was added dropwise into reaction mixture and stirred at room temperature for 3 h. After completion of reaction, reaction mixture was filtered. Filtered solid was transferred into water, stirred for 30 min and dried under reduced pressure to obtain pure 195.3. (1.0 g, 68.65%). MS(ES): m/z 285.33 [M+H]$^+$.

Synthesis of Compound 195.4.

To a solution of 195.3 (0.14 g, 0.492 mmol, 1.0 eq) in methanol (5 mL), 10% palladium on charcoal (0.05 g) was added. Hydrogen was purged through reaction mixture for 2-3 h. After completion of reaction, reaction mixture was filtered through celite-bed and washed with ethanol. Filtrate was concentrated under reduced pressure to obtain 195.4 (0.08 g, 63.88%). MS(ES): m/z 255.35 [M+H]$^+$.

Synthesis of Compound 195.5.

Compound 195.5 was synthesized from 195.4 and cyclopropanecarboxamide using general procedure A. (Yield: 22.51%). MS (ES): m/z 436.93 [M+H]$^+$.

Synthesis of Compound 195.6.

Compound 195.6 was synthesized from 195.6 and cyclopropanecarboxamide using general procedure B. (Yield: 33.32%). MS(ES): m/z 485.58 [M+H]$^+$.

Synthesis of Compound 195.7.

To a solution of 195.6 (0.1 g, 0.206 mmol, 1 eq), in methanol (4 mL), and 5M sodium hydroxide (1.5 mL) was added. Reaction mixture stirred at room temperature for 36 h. After completion of reaction, reaction mixture transferred in water and extracted with ethyl acetate. Combined organic layer dried over sodium sulfate and concentrated under reduced pressure to obtain crude material. This was further purified by column chromatography and compound was eluted in 5% methanol in Dichloromethane to obtain pure 195.7. (0.070 g, 81.44%). MS(ES): m/z 417.50 [M+H]+.

Synthesis of Compound I-236 To a solution of 195.7 (0.070 g, 0.168 mmol, 1.0 eq) and (1S,2S)-2-fluorocyclopropane-1-carboxylic acid (0.026 g, 0.252 mmol, 1.5 eq) in N,N-dimethylformamide (1 mL) and cooled at 0° C. Added ((1-[Bis(dimethylamino)methylene]-1H-1,2,3-triazolo[4,5-b]pyridinium3-oxid hexafluoro-phosphate)) (0.096 g, 0.252 mmol, 1.5 eq) and N,N-Diisopropylethylamine (0.065 g, 0.504 mmol, 3.0 eq) and stirred the reaction mixture at 50° C. for 2 hr. After completion of reaction, reaction mixture was transferred into water and extracted with ethyl acetate. Organic layer was combined, dried over sodium sulphate and concentrated under reduced pressure to pressure to obtain crude material. This was further purified by column chromatography and compound was eluted in 5% methanol in dichloromethane to obtain pure I-236 (0.024 g, 28.41%). MS(ES): m/z 503.41 [M+H]+, LCMS purity: 94.63%, HPLC purity: 99.76%, $^1$H NMR (DMSO-d$_6$, 400 MHz): 8.52 (s, 1H), 7.51-7.46 (m, 2H), 7.35-7.33 (d, J=8.0 Hz, 1H), 6.77 (s, 2H), 5.90 (s, 1H), 5.23-5.06 (m, 1H), 3.64-3.52 (m, 1H), 3.32 (s, 3H), 3.17 (s, 3H), 3.13 (s, 3H), 2.33-2.29 (m, 2H), 2.19-210 (m, 2H), 2.03-1.96 (m, 1H), 1.88-181 (m, 2H), 1.40-1.36 (m, 1H), 1.28-1.25 (m, 1H).

Examples 196/197: Synthesis of (S)—N-(4-((4-cyclopropyl-2-(methylsulfonyl)phenyl)amino)-2-methyl-3-oxo-2,3-dihydro-1H-pyrazolo[3,4-b]pyridin-6-yl)-2,2-difluorocyclopropane-1-carboxamide, I-237 and (R)—N-(4-((4-cyclopropyl-2-(methylsulfonyl)phenyl)amino)-2-methyl-3-oxo-2,3-dihydro-1H-pyrazolo[3,4-b]pyridin-6-yl)-2,2-difluorocyclopropane-1-carboxamide, I-238

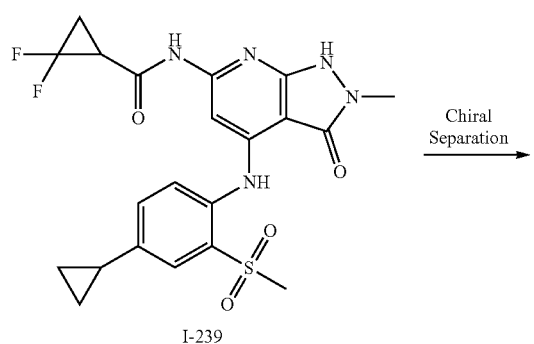

I-239

Chiral Separation →

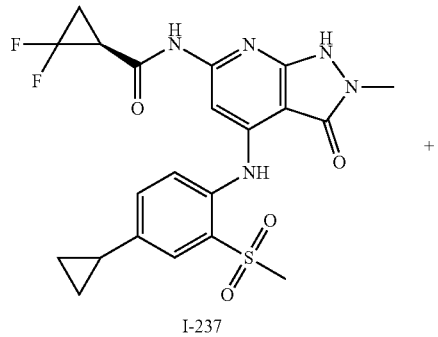

I-237

+

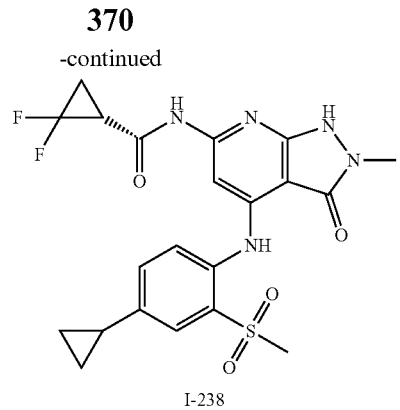

I-238

Synthesis of Compound I-237 & I-238.

Isomers of I-239 (0.090 g) were separated using column (CHIRAL PAK AD-H 250×4.6 mm, 5 u) and 0.1 DEA in Methanol as co-solvent with flow rate of 4 mL/min. to get pure fraction-1 (FR-a) and fraction-2 (FR-b). FR-a was concentrated under reduced pressure at 30° C. to afford pure I-237 (0.021 g). MS(ES): m/z 478.46 [M+H]+, LCMS purity: 96.96%, HPLC purity: 96.45%, Chiral HPLC purity: 97.25%, 1H NMR (DMSO-d6, 400 MHz): 10.80 (s, 1H), 8.99 (s, 1H), 7.64-7.61 (m, 2H), 7.49-7.47 (dd, J=2.0 Hz, 8.4 Hz, 1H), 7.42 (s, 1H), 3.30 (s, 3H), 3.14 (s, 3H), 2.11-2.07 (m, 1H), 1.99-1.92 (m, 2H), 1.12-1.08 (t, J=7.2 Hz, 1H), 1.05-1.00 (m, 2H), 0.77-0.74 (m, 2H). FR-b was concentrated under reduced pressure at 30° C. to afford pure I-238 (0.022 g). MS(ES): m/z 478.51 [M+H]+, LCMS purity: 95.67%, HPLC purity: 96.64%, Chiral HPLC purity: 95%, 1H NMR (DMSO-d6, 400 MHz): 10.79 (s, 1H), 8.98 (s, 1H), 7.64-7.61 (m, 2H), 7.48-7.46 (dd, J=2.0 Hz, 8.4 Hz, 1H), 7.36 (s, 1H), 3.30 (s, 3H), 3.14 (s, 3H), 2.12-2.05 (m, 1H), 1.99-1.92 (m, 2H), 1.11-1.08 (t, J=6.8 Hz, 1H), 1.04-1.00 (m, 2H), 0.77-0.74 (m, 2H).

Example 198: Synthesis of N-(2-((6-((2,3-dihydrofuro[2,3-c]pyridin-5-yl)amino)-2-methyl-3-oxo-2,3-dihydro-1H-pyrazolo[3,4-b]pyridin-4-yl)amino)phenyl)-N-methylmethanesulfonamide, I-226

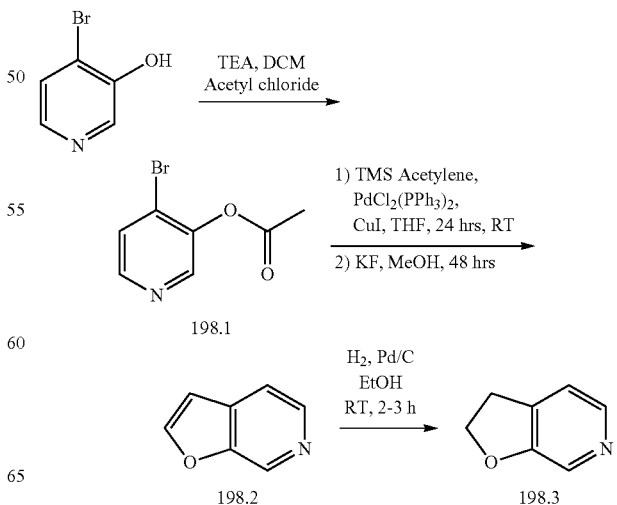

371
-continued
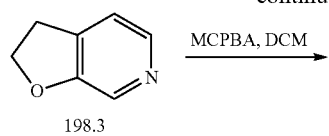
198.3
MCPBA, DCM →
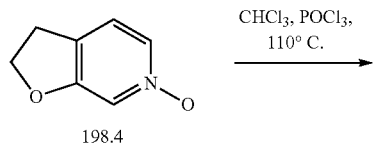
198.4
CHCl₃, POCl₃, 110° C. →
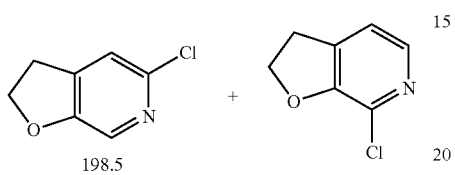
198.5
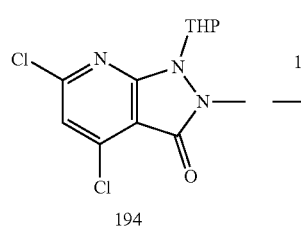
194
1M LiHMDS in THF, THF, 0° C. to RT →
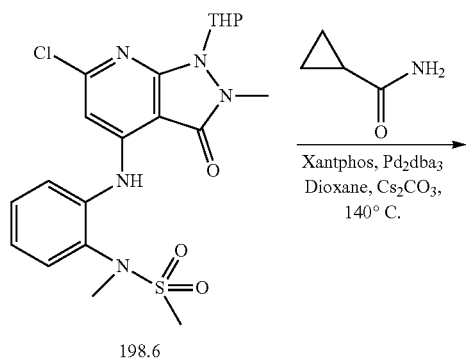
198.6
cyclopropanecarboxamide
Xantphos, Pd₂dba₃
Dioxane, Cs₂CO₃,
140° C. →
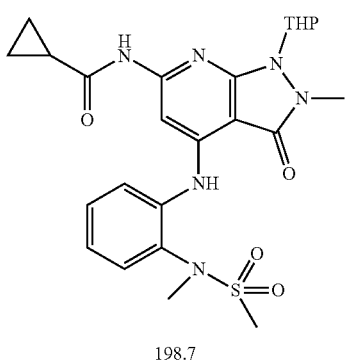
198.7
372
-continued
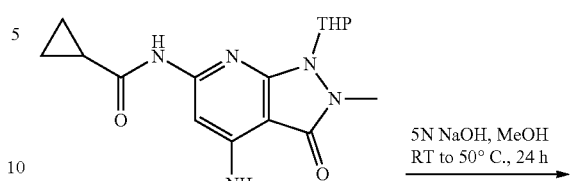
198.7
5N NaOH, MeOH
RT to 50° C., 24 h →
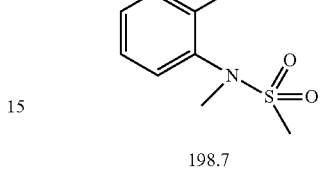
198.8
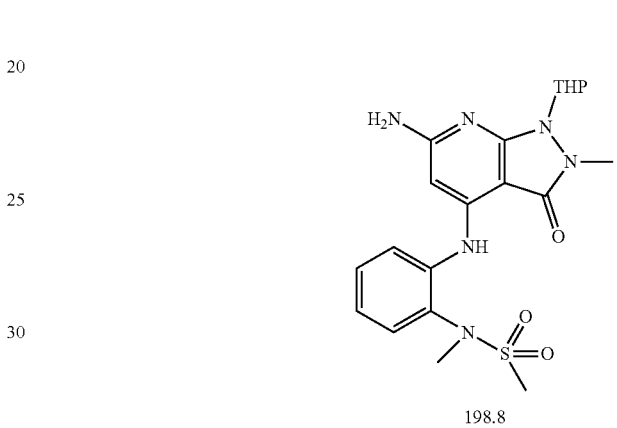
198.8
Xantphos, Pd₂(dba)₃
DMAC, Cs₂CO₃
140° C., M/W, 80 mins →
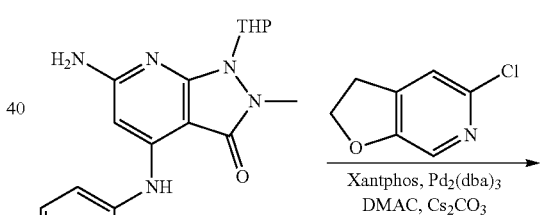
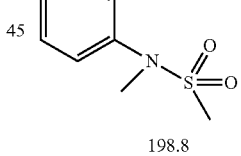
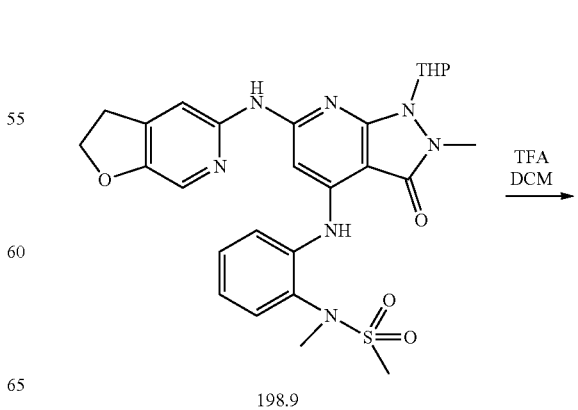
198.9
TFA
DCM →

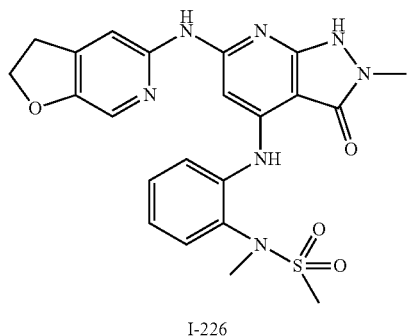

I-226

Synthesis of Compound 198.1.

To a solution of 4-bromopyridin-3-ol (5.0 g, 28.74 mmol, 1.0 eq) in dichloromethane (75 mL) was added dropwise triethylamine (11.61 g, 114.96 mmol, 4.0 eq) followed by acetyl chloride (4.512 g, 57.48 mmol, 2.0 eq) at 0° C. The reaction mixture was stirred at room temperature for 16 h. After completion of reaction, reaction mixture was filtered by bed of celite. The filtrate was transferred into water and extracted with ethyl acetate. Organic layer was combined, washed with brine, dried over sodium sulphate and concentrated under reduced pressure to obtain crude material. This was further purified by column chromatography and compound was eluted on 5% ethyl acetate in hexane as eluent to obtain 198.1. (4.9 g, 78.93%). MS(ES): m/z 217.03 [M+H]$^+$.

Synthesis of Compound 198.2.

To a solution of 198.1 (16.0 g, 74.06 mmol, 1.0 eq), Trimethylsilylacetylene (9.43 g, 96.78 mmol, 1.3 eq) and triethylamine (112.2 g, 1110.9 mmol, 15 eq) in tetrahydrofuran (1.6 L). The reaction mixture was degassed for 10 min. under argon atmosphere. The [1,1'-Bis(diphenylphosphino) ferrocene]palladium(II) dichloride (1.6 g, 2.22 mmol, 0.03 eq) and copper iodide (0.843 g, 4.44 mmol, 0.06 eq) was added, again reaction mixture was degassed for 10 min. under argon atmosphere. The reaction was stirred at room temperature for 24 h. After completion of reaction, reaction mixture was filtered and residue was concentrated under vacuum. The residue was diluted with methanol (2.2 L) and potassium fluoride was added into reaction mixture. The reaction mixture was stirred at room temperature for 48 h. After completion of reaction, reaction mixture was filtered through bed of celite and washed with ethyl acetate. Combined organic layer was washed with brine, dried over sodium sulphate and concentrated under reduced pressure to obtain crude material. This was further purified by column chromatography using 10% ethyl acetate in hexane to obtain pure 1.2 (3.82 g, 43.30%). MS(ES): m/z 120.12 [M+H]$^+$.

Synthesis of Compound 198.3.

To a solution of 198.2 (3.82 g, 32.07 mmol, 1.0 eq) in methanol (300 mL), 10% palladium on charcoal (7.0 g) was added. Hydrogen was purged through reaction mixture for 2-3 h. After completion of reaction, reaction mixture was filtered through celite-bed and washed with ethanol. Filtrate was concentrated under reduced pressure to obtain 198.3 (3.5 g, 90.11%). MS(ES): m/z 122.14 [M+H]$^+$.

Synthesis of Compound 198.4.

To a solution of 198.3 (3.5 g, 28.89 mmol, 1.0 eq) in dichloromethane (140 mL) was added meta-chloroperbenzoic acid (5.96 g, 34.66 mmol, 1.2 eq). The reaction was stirred at room temperature for 18 h. After completion of reaction, reaction mixture was concentrated under reduced pressure to obtain crude material. This was further purified by column chromatography in basic alumina using 0.1% methanol in dichloromethane to obtain pure 198.4 (3.4 g, 85.81%). MS(ES): m/z 138.14 [M+H]$^+$.

Synthesis of Compound 198.5.

To a solution of 198.4 (1.1 g, 8.02 mmol, 1.0 eq) in chloroform (33 mL) was added phosphoryl chloride (4.91 g, 32.08 mmol, 4.0 eq). The reaction was stirred at 70° C. for 7 h. After completion of reaction, reaction mixture was transferred in ice and basified with sodium bicarbonate solution then extracted with ethyl acetate. Organic layer was combined, washed with brine, dried over sodium sulphate and concentrated under reduced pressure to obtain crude material. This was further purified by column chromatography and compound was eluted on 15% ethyl acetate in hexane as eluent to obtain 198.5. (0.3 g, 24.04%). MS(ES): m/z 156.58 [M+H]$^+$.

Synthesis of Compound 198.6.

Compound 198.6 was synthesized from 194 and 115.2 using general procedure A. (Yield: 38.91%). MS(ES): m/z 466.95 [M+H]$^+$.

Synthesis of Compound 198.7.

Compound 198.7 was synthesized from 198.6 and cyclopropanecarboxamide using general procedure B. (Yield: 72.44%). MS(ES): m/z 515.60 [M+H]$^+$.

Synthesis of Compound 198.8.

To a solution of 198.7 (0.16 g, 0.311 mmol, 1 eq), in methanol (6 mL) and 5N sodium hydroxide (1 mL) was added. Reaction mixture stirred at 50° C. for 24 h. After completion of reaction, reaction mixture transferred in water and extracted with ethyl acetate. Combined organic layer dried over sodium sulfate and concentrated under reduced pressure to obtain crude material. This was further triturated in 30% diethyl ether in hexane to obtain pure 198.8. (0.12 g, 86.43%). MS(ES): m/z 447.53 [M+H]$^+$.

Synthesis of Compound 198.9.

Compound 198.9 was synthesized from 198.8 and 198.5 using general procedure B. (Yield: 46.05%). MS(ES): m/z 566.65 [M+H]$^+$.

Synthesis of Compound I-226.

To a solution of 198.9 (0.070 g, 0.123 mmol, 1 eq), in dichloromethane (2 mL) was added trifluoroacetic acid (0.21 g, 1.845 mmol, 15 eq) at 0° C. Reaction mixture stirred at room temperature for 30 min. After completion of reaction, reaction mixture was concentrated under reduced pressure, transferred into aqueous sodium bicarbonate solution and extracted with ethyl acetate. Combined organic layer dried over sodium sulfate and concentrated under reduced pressure to obtain crude material. This was further triturated in diethyl ether to obtain pure I-226 (0.05 g, 83.91%). MS(ES): m/z 482.53 [M+H]$^+$. LCMS purity: 100%, HPLC purity: 100%, 1H NMR (DMSO-d6, 400 MHz): 9.05 (s, 1H), 8.91 (s, 1H), 8.40 (s, 1H), 7.70-7.67 (m, 2H), 7.42-7.35 (m, 2H), 7.03-6.99 (t, J=7.6 Hz, 1H), 6.28 (s, 1H), 4.56-4.52 (t, J=8.4 Hz, 2H), 3.33 (s, 3H), 3.29 (s, 3H), 3.26-3.22 (t, J=8.4 Hz, 2H), 3.17 (s, 3H).

Example 199. Synthesis of N-(5-(5-chlorothiazol-2-yl)-4-((2-methoxy-3-(2-methyl-2H-tetrazol-5-yl)phenyl)amino)pyridin-2-yl)cyclopropanecarboxamide, VIII-1

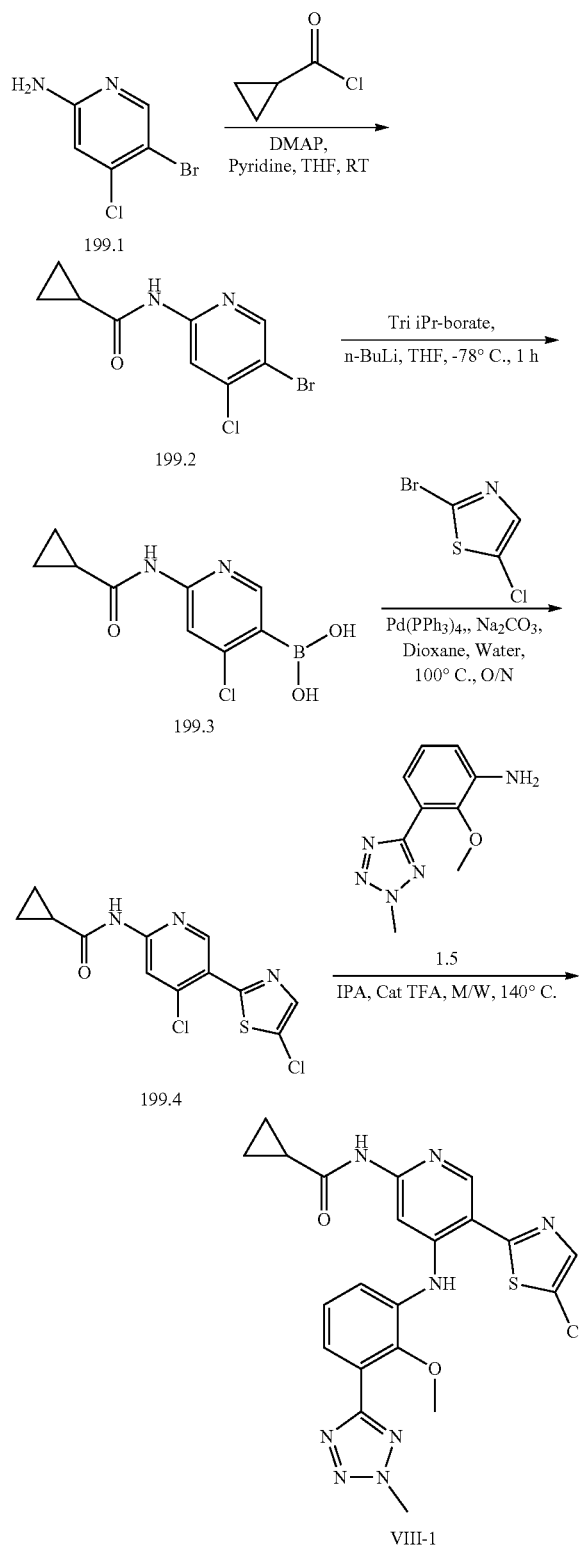

Synthesis of Compound 199.2.

To a solution of 199.1 (20.0 g, 96.4 mmol, 1.0 eq) in THF (200 mL) was added Pyridine (15.7 mL, 193.2 mmol, 2.0 eq). Reaction mixture was cooled to 0° C. To this added DMAP (1.18 g, 9.64 mmol, 0.1 eq) followed by cyclopropanecarbonyl chloride (15.12 g, 144.6 mmol, 1.5 eq). Reaction mixture was stirred at room temperature for 3 h. After completion of the reaction, reaction mixture was was quenched with ice-water. Precipitate was filtered and dried to provide 199.2 (16.5 g, 62.1%). MS(ES): m/z 275.3 [M]$^+$.

Synthesis of Compound 199.3.

To a solution of 199.2 (1.0 g, 3.63 mmol, 1.0 eq) in THF (20 mL) was added n-BuLi (7.5 mL, 18.18 mmol, 5.0 eq) at −78° C. and stirred for 30 min. To the solution was added triisopropyl-borate (3.4 mL, 14.53 mmol, 4.0 eq) and reaction was stirred at −78° C. for 1 h. After completion reaction was quenched slowly and solvents were removed under reduced pressure. Residue was acidified with 1.0 N HCl. Obtained precipitate was filtered off, washed with ice cold water to provide 199.3 (0.35 g, 40.1%). MS(ES): m/z 241.5 [M+H]$^+$.

Synthesis of Compound 199.4.

To a solution of 2-bromo-5-chlorothiazole (0.068 g, 0.34 mmol, 1.0 eq) in 1,4-dioxane (2.0 mL) was added compound 199.3 (0.10 g, 0.41 mmol, 1.2 eq) followed by addition of 1M aq. Na$_2$CO$_3$ (0.68 mL, 0.68 mmol, 2.0 eq). Reaction mixture was degassed with argon for 10 min and Pd(PPh$_3$)$_4$(0.037 g, 0.034 mmol, 0.1 eq) was added. Reaction mixture was stirred at 100° C. for 16 h. After completion of reaction was quenched with water and extracted with EtOAc. Organic layers were combined, washed with brine, dried over Na$_2$SO$_4$ and concentrated under reduced pressure to obtain crude material. The crude was purified by column chromatography to furnish 1.4. (0.025 g, 23.0%). MS(ES): m/z 314.4 [M]$^+$.

Synthesis of Compound VIII-1.

To a solution of 199.4 (0.025 g, 0.079 mmol, 1.2 eq) in i-PrOH (2.5 mL) was added 1.5 (0.014 g, 0.066 mmol, 1.0 eq) followed by addition of TFA (catalytic). The reaction mixture was heated in microwave at 140° C. for 4 hours. After completion of reaction, mixture concentrated under reduced pressure to obtain crude material. The crude was purified by preparative HPLC to furnish VIII-1 (0.0035 g, 10.9%). MS(ES): m/z 483.7 [M+H]$^+$; $^1$H NMR (CDCl$_3$, 400 MHz): 10.99 (s, 1H), 8.35 (s, 1H), 8.27 (s, 1H), 8.18 (s, 1H), 7.81-7.79 (d, 1H), 7.74-7.72 (d, 1H), 7.37-7.31 (m, 2H), 4.44 (s, 3H), 3.80 (s, 3H), 1.59-1.52 (m, 1H), 1.10-1.08 (m, 2H), 0.90-0.87 (m, 2H).

Example 200. Synthesis of N-(5-(5-fluorothiazol-2-yl)-4-((2-methoxy-3-(2-methyl-2H-tetrazol-5-yl)phenyl)amino)pyridin-2-yl)cyclopropanecarboxamide, VIII-2

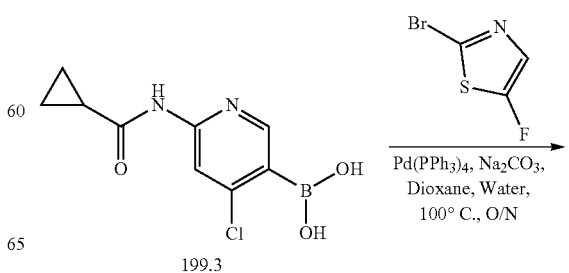

Example 201. Synthesis of N-(4-((2-methoxy-3-(1-methyl-1H-1,2,4-triazol-3-yl)phenyl)amino)-5-(5-(trifluoromethyl)-1,3,4-oxadiazol-2-yl)pyridin-2-yl) cyclopropanecarboxamide, VIII-3

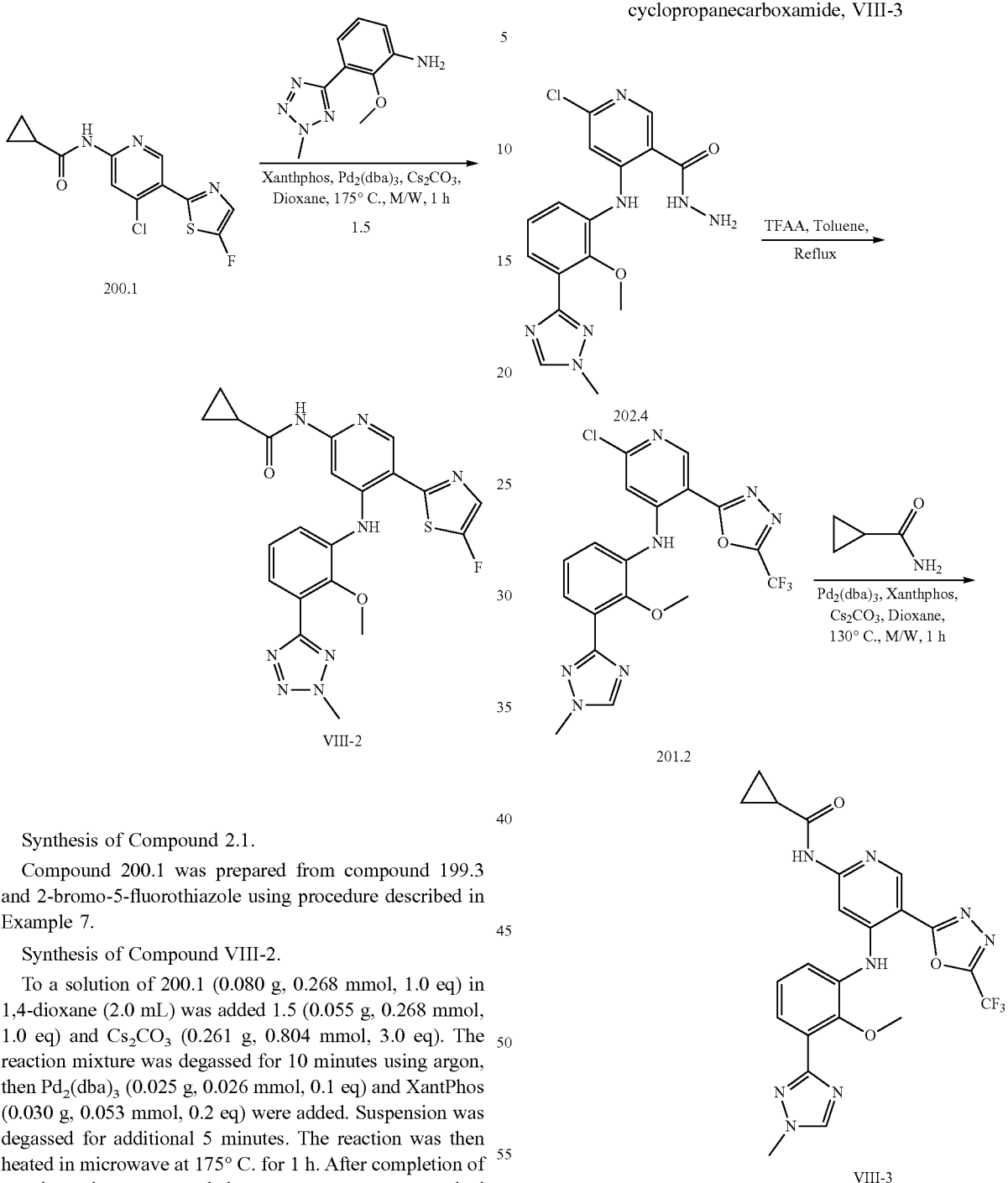

Synthesis of Compound 2.1.

Compound 200.1 was prepared from compound 199.3 and 2-bromo-5-fluorothiazole using procedure described in Example 7.

Synthesis of Compound VIII-2.

To a solution of 200.1 (0.080 g, 0.268 mmol, 1.0 eq) in 1,4-dioxane (2.0 mL) was added 1.5 (0.055 g, 0.268 mmol, 1.0 eq) and $Cs_2CO_3$ (0.261 g, 0.804 mmol, 3.0 eq). The reaction mixture was degassed for 10 minutes using argon, then $Pd_2(dba)_3$ (0.025 g, 0.026 mmol, 0.1 eq) and XantPhos (0.030 g, 0.053 mmol, 0.2 eq) were added. Suspension was degassed for additional 5 minutes. The reaction was then heated in microwave at 175° C. for 1 h. After completion of reaction, mixture was cooled to room temperature, quenched with water and extracted with EtOAc. Organic layers were combined, washed with brine, dried over $Na_2SO_4$ and concentrated under reduced pressure to obtain crude which was purified by column chromatography to provide VIII-2 (0.025 g, 19.94%). MS(ES): m/z 467.48 $[M+H]^+$; $^1H$ NMR ($CDCl_3$, 400 MHz): 11.02 (s, 1H), 8.37 (s, 1H), 8.29 (s, 1H), 8.23 (s, 1H), 7.84-7.81 (dd, 1H), 7.77-7.75 (m, 1H), 7.44-7.34 (m, 2H), 4.47 (s, 3H), 3.82 (s, 3H), 1.58-1.55 (m, 1H), 1.13-1.10 (m, 2H), 0.90-0.87 (m, 2H).

Synthesis of Compound 201.2.

To compound 202.4 (0.3 g, 0.802 mmol, 1.0 eq) in toluene (3.0 mL) was added TFAA (1.5 mL) and reaction mixture was refluxed for 1 h. After completion of the reaction, mixture was concentrated under reduced pressure to obtain crude which was purified by column chromatography to provide 201.2. (0.070 g, 19.31%). MS(ES): m/z 452.7 $[M]^+$.

Synthesis of Compound VIII-3.

To 201.2 (0.050 g, 0.110 mmol, 1.0 eq) in 1,4-dioxane (2.0 mL) was added cyclopropanecarboxamide (0.011 g, 0.132 mmol, 1.0 eq) and Cs$_2$CO$_3$ (0.080 g, 0.27 mmol, 2.5 eq). The reaction mixture was degassed for 10 minutes using argon then Pd$_2$(dba)$_3$ (0.010 g, 0.011 mmol, 0.1 eq) and XantPhos (0.012 g, 0.022 mmol, 0.2 eq) were added. Suspension was degassed for additional five minutes. The reaction was then heated in microwave at 130° C. for 1 h. After completion of the reaction, mixture was cooled to room temperature, quenched with water and extracted with EtOAc. Organic layers were combined, washed with brine, dried over Na$_2$SO$_4$ and concentrated under reduced pressure to obtain the crude product. Crude was purified by column chromatography to provide VIII-3 (0.019 g, 34.3%). MS(ES): m/z 501.53 [M+H]$^+$; $^1$H NMR (CDCl$_3$, 400 MHz): 9.86 (s, 1H), 8.72 (s, 1H), 8.26 (s, 1H), 8.20 (s, 1H), 8.13 (s, 1H), 7.86-7.84 (d, 1H), 7.65-7.63 (d, 1H), 7.33-7.28 (m, 1H), 4.03 (s, 3H), 3.81 (s, 3H), 1.48-1.42 (m, 1H), 1.12-1.11 (m, 2H), 0.93-0.91 (m, 2H).

Example 202. Synthesis of methyl 5-(6-(cyclopropanecarboxamido)-4-((2-methoxy-3-(1-methyl-1H-1,2,4-triazol-3-yl)phenyl)amino)pyridin-3-yl)-1,3,4-oxadiazole-2-carboxylate, VIII-4

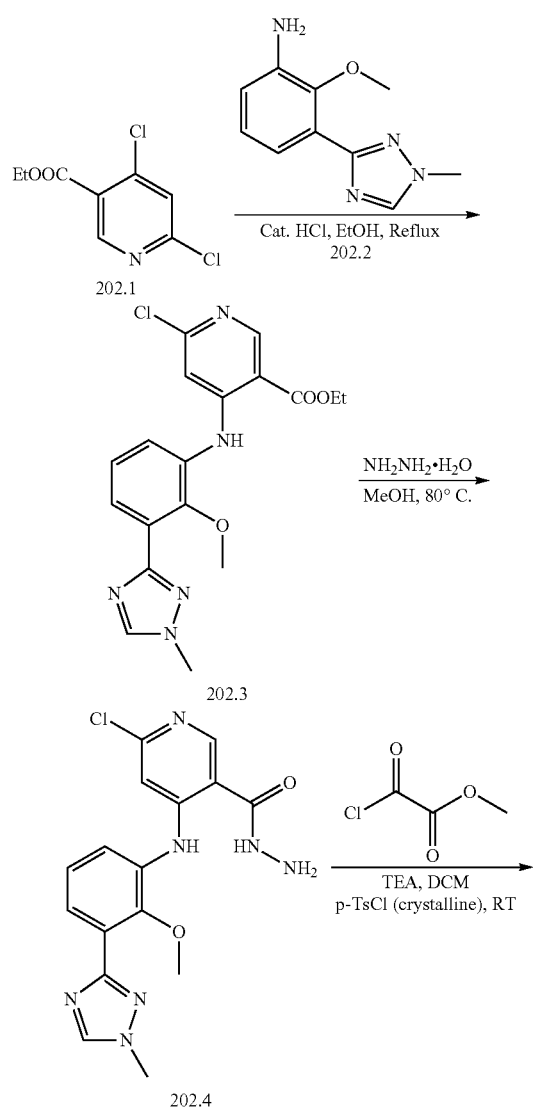

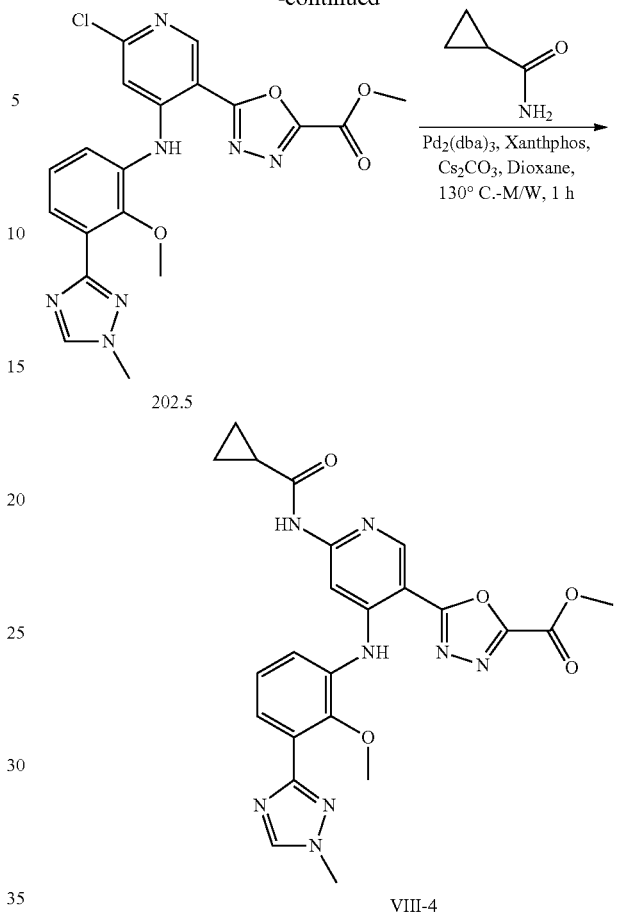

Synthesis of Compound 202.3.

To solution of compound 202.1 (2.0 g, 9.09 mmol, 1.0 eq) in EtOH (20.0 mL) was added compound 202.2 (1.86 g, 9.09 mmol, 1.0 eq) followed by the addition of conc. HCl (catalytic). Reaction mixture was refluxed for 4 h. After completion of the reaction, mixture was concentrated under reduced pressure. Residue was dissolved in CH$_2$Cl$_2$ washed with satd. NaHCO$_3$, brine, then dried over Na$_2$SO$_4$ and concentrated under reduced pressure to pressure to obtain crude material. The crude was purified by column chromatography to provide 202.3. (1.4 g, 39.7%). MS(ES): m/z 388.7 [M]$^+$.

Synthesis of Compound 202.4.

To a solution of 202.3 (1.4 g, 3.61 mmol, 1.0 eq) in MeOH (20.0 mL) was added hydrazine hydrate (g, 2.08 mmol, 3.0 eq). Reaction mixture was stirred at 80° C. for 3 h. After completion of the reaction, mixture was concentrated under reduced pressure. Residue obtained was triturated with diethyl ether to provide 202.4. (0.83 g, 61.51%). MS(ES): m/z 374.5 [M]$^+$.

Synthesis of Compound 202.5.

To solution of 202.4 (0.7 g, 1.87 mmol, 1.0 eq) in CH$_2$Cl$_2$ (7.0 mL) was added Et$_3$N (0.56 g, 5.63 mmol, 3.0 eq). Solution was cooled to 0° C., then methyl oxalyl chloride (0.275 g, 2.25 mmol, 1.2 eq) was added. Mixture was stirred for 4 h at room temperature. To this was added p-TsCl (0.73 g, 3.75 mmol, 2.0 eq). Reaction was stirred at room temperature for 16 h. After completion, of the reaction was quenched with water and extracted with CH$_2$Cl$_2$. Organic layer were combined, washed with brine, dried over Na$_2$SO$_4$ and concentrated under reduced pressure to obtain crude which was purified by column chromatography to provide 202.5. (0.3 g, 36.3%). MS(ES): m/z 442.6 [M]+.

Synthesis of Compound VIII-4.

To 202.5 (0.10 g, 0.226 mmol, 1.0 eq) in 1,4-dioxane (2.0 mL) was added cyclopropanecarboxamide (0.021 g, 0.248 mmol, 1.0 eq), $Cs_2CO_3$ (0.060 g, 0.44 mmol, 2.0 eq). The reaction mixture was degassed for 10 minutes using argon, then $Pd_2(dba)_3$ (0.022 g, 0.026 mmol, 0.1 eq) and XantPhos (0.025 g, 0.044 mmol, 0.2 eq) were added, again degassed for 5 min. The reaction was heated in microwave at 130° C. for 1 h. After completion of the reaction, mixture was cooled to room temperature, quenched with water and extracted with EtOAc. Organic layers were combined, washed with brine, dried over $Na_2SO_4$ and concentrated under reduced pressure to obtain crude material. The crude was purified by column chromatography to furnish VIII-4 (0.04 g, 36.0%). MS(ES): m/z 491.7 [M+H]+; $^1$H NMR (CDCl$_3$, 400 MHz): 9.98 (s, 1H), 8.80 (s, 1H), 8.25 (s, 1H), 8.18 (s, 1H), 8.12 (s, 1H), 7.84-7.83 (d, 1H), 7.66-7.64 (d, 1H), 7.34-7.30 (m, 1H), 4.12 (s, 3H), 4.03 (s, 3H), 3.82 (s, 3H), 1.58-1.55 (m, 1H), 1.12-1.10 (m, 2H), 0.92-0.90 (m, 2H).

Example 203. Synthesis of N-(5-(5-(hydroxymethyl)-1,3,4-oxadiazol-2-yl)-4-((2-methoxy-3-(1-methyl-1H-1,2,4-triazol-3-yl)phenyl)amino)pyridin-2-yl)cyclopropanecarboxamide, VIII-5

To a solution of VIII-4 (0.030 g, 0.061 mmol, 1.0 eq) in MeOH (1.0 mL) and THF (1.0 mL) was added LiBH$_4$ (0.004 g, 0.183 mmol, 3.0 eq) at 0° C. Reaction mixture was stirred at room temperature for 1 hour. After completion of the reaction was quenched with water and extracted with EtOAc. Organic layers was combined, washed with brine, dried over $Na_2SO_4$ and concentrated under reduced pressure to obtain crude material. The crude was purified by column chromatography to provide VIII-5 (0.008 g, 28.2%). MS(ES): m/z 463.53 [M+H]+; $^1$H NMR (CDCl$_3$, 400 MHz): 10.02 (s, 1H), 8.70 (s, 1H), 8.23 (s, 1H), 8.18 (s, 1H), 8.13 (s, 1H), 7.82-7.81 (d, 1H), 7.65-7.63 (d, 1H), 7.33-7.28 (m, 1H), 4.99 (s, 2H), 4.03 (s, 3H), 3.81 (s, 3H), 1.58-1.55 (m, 1H), 1.12-1.11 (m, 2H), 0.92-0.88 (m, 2H).

Example 204. Synthesis of N-(5-(5-(hydroxymethyl)thiazol-2-yl)-4-((2-methoxy-3-(1-methyl-1H-1,2,4-triazol-3-yl)phenyl)amino)pyridin-2-yl)cyclopropanecarboxamide, VIII-6

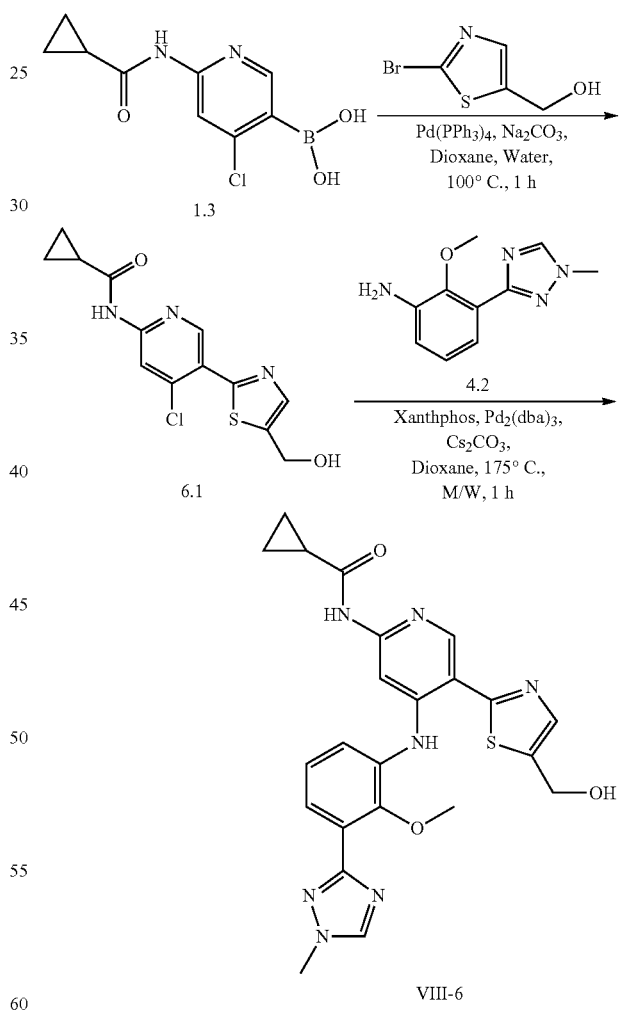

VIII-6

Synthesis of Compound 6.1.

Compound 6.1 was prepared from 1.3 and (2-bromothiazol-5-yl)methanol using procedure described in Example 7.

Synthesis of Compound VIII-6.

Compound VIII-6 was prepared from 6.1 and 4.2 using procedure described in Example 8. (0.008 g, 3.71%).

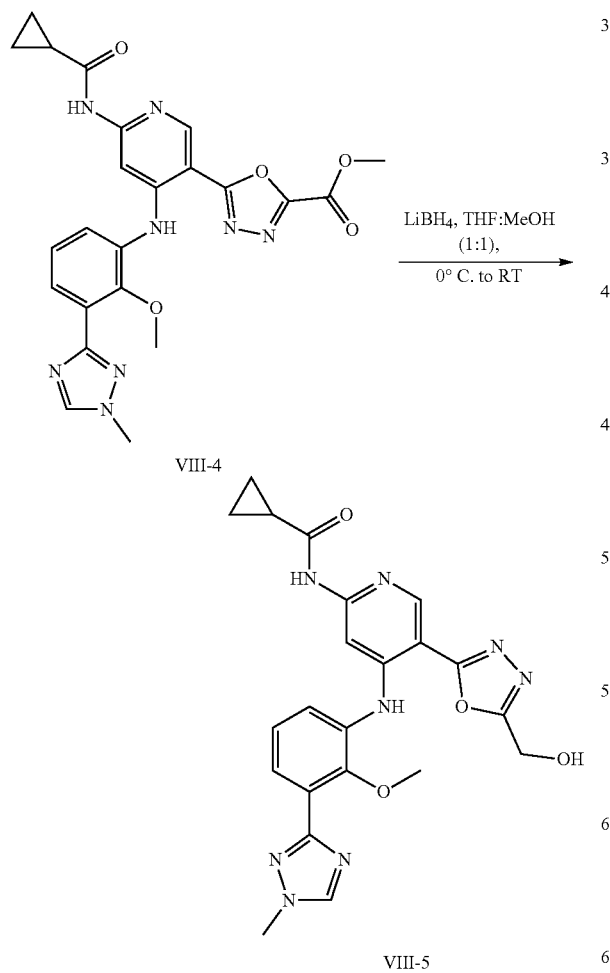

VIII-5

MS(ES): m/z 478.69 [M+H]+; 1H NMR (MeOD, 400 MHz): 8.58 (s, 1H), 8.49 (s, 1H), 8.38 (s, 1H), 8.18 (s, 1H), 7.77 (s, 1H), 7.70-7.68 (d, 1H), 7.65-7.63 (d, 1H), 7.32-7.28 (t, 1H), 4.88 (s, 2H), 4.04 (s, 3H), 3.74 (s, 3H), 1.89 (bs, 1H), 1.31 (bs, 1H), 0.98-0.90 (m, 4H).

Example 205. Synthesis of N-(4-((2-methoxy-3-(1-methyl-1H-1,2,4-triazol-3-yl)phenyl)amino)-5-(5-methyl-1,3,4-thiadiazol-2-yl)pyridin-2-yl)cyclopropanecarboxamide, VIII-7

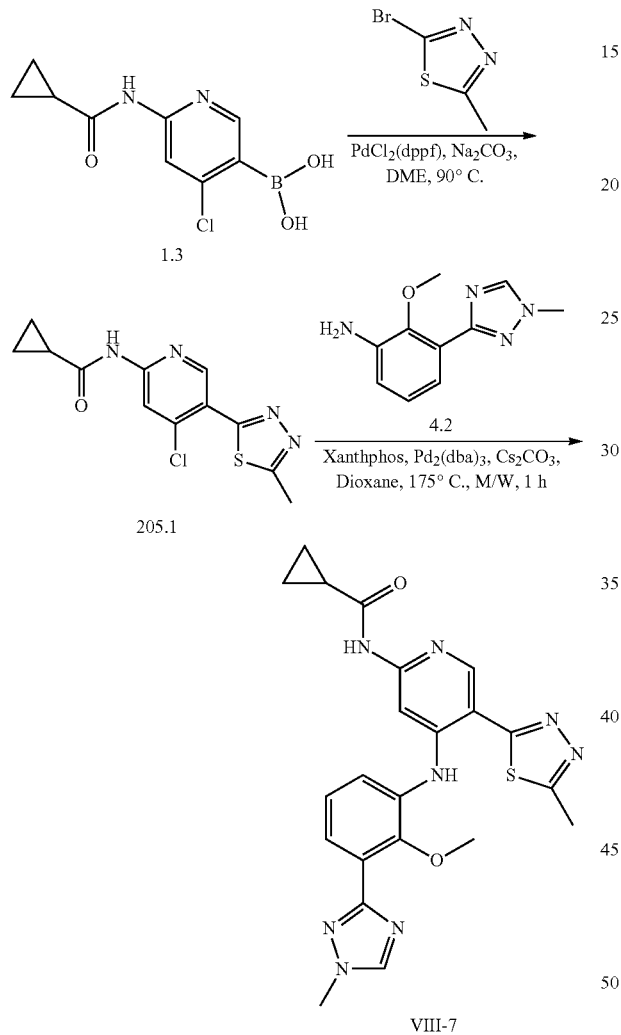

Synthesis of Compound 205.1.

To a solution of 2-bromo-5-methyl-1,3,4-thiadiazole (0.62 g, 3.47 mmol, 1.0 eq) in DME (10 mL) was added compound 1.3 (1.0 g, 4016 mmol, 1.2 eq) followed by addition of Na$_2$CO$_3$ (0.735 g, 6.94 mmol, 2.0 eq). Reaction mixture was degassed with argon for 10 min and (dppf)PdCl$_2$ (0.253 g, 0.347 mmol, 0.1 eq) was added. Reaction mixture was stirred at 90° C. for 16 hours. After completion of the reaction, mixture was transferred into water and extracted with EtOAc. Organic layers were combined, washed with brine, dried over Na$_2$SO$_4$ and concentrated under reduced pressure to obtain crude which was purified by preparative HPLC to furnish 7.1. (0.08 g, 7.83%). MS(ES): m/z 295.7 [M]+.

Synthesis of Compound VIII-7.

Compound VIII-7 was prepared from 7.1 and 4.2 using procedure described in Example 8. (0.019 g, 15.1%). MS(ES): m/z 463.48 [M+H]+; 1H NMR (CDCl$_3$, 400 MHz): 10.80 (s, 1H), 8.39 (s, 1H), 8.20 (s, 1H), 8.18 (s, 1H), 8.12 (s, 1H), 7.80-7.78 (d, 1H), 7.66-7.64 (d, 1H), 7.32-7.28 (m, 1H), 4.06 (s, 3H), 3.85 (s, 3H), 2.83 (s, 3H), 1.56-1.54 (m, 1H), 1.12-1.10 (m, 2H), 0.91-0.88 (m, 2H).

Example 206: N-(5-(isoxazol-3-yl)-4-((2-methoxy-3-(2-methyl-2H-tetrazol-5-yl)phenyl)amino)pyridin-2-yl)cyclopropanecarboxamide, VIII-8

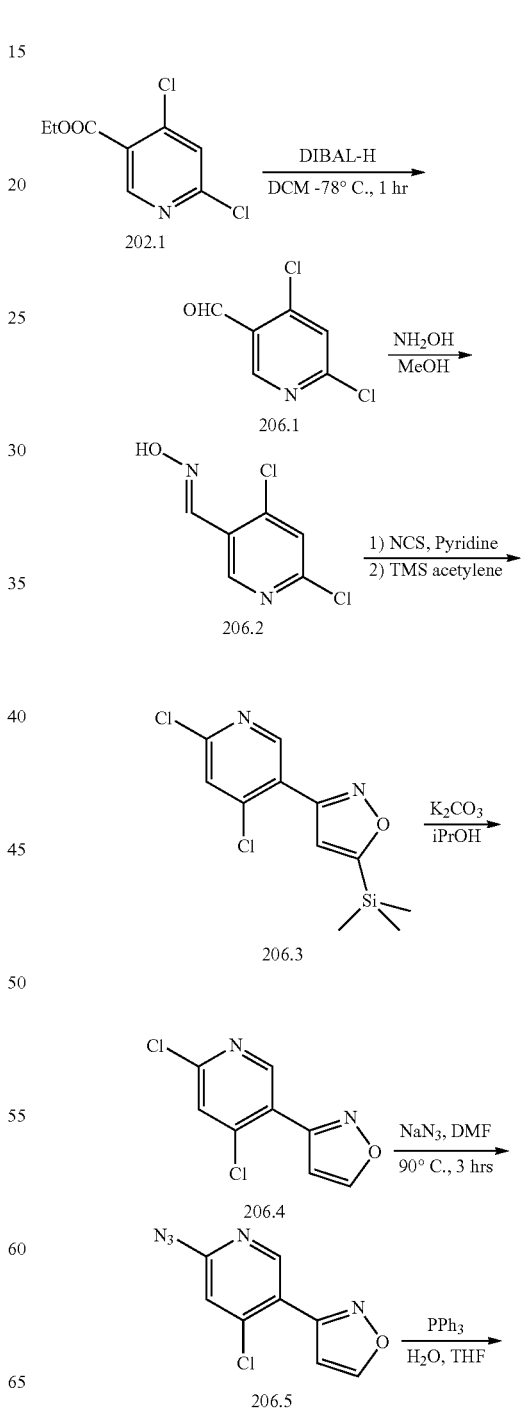

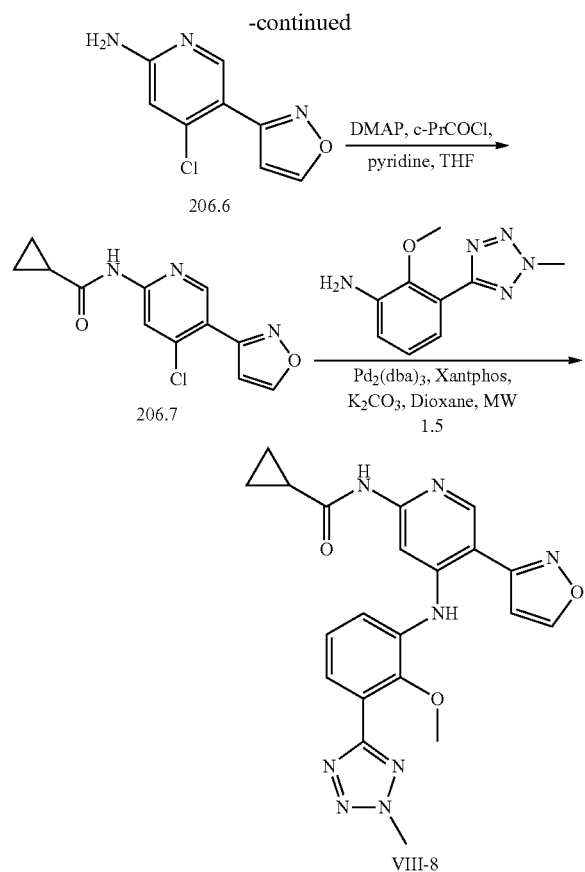

Synthesis of compound 206.1. To a solution of 202.1 (10 g, 0.045 mmol, 1.0 eq) in dichloromethane (100 mL) at −78° C., diisobutyl aluminium hydride (54 mL, 0.054 mmol, 1.2 eq) was added. Reaction mixture was stirred at −78° C. for 1 h. After completion of reaction, methanol was slowly added to the reaction mixture at −78° C. followed by addition of 1N HCl and extracted with dichloromethane. Organic layer was combined, washed with brine solution, dried over sodium sulphate and concentrated under reduced pressure to obtain 206.1. (7.0 g, 87.52%). MS(ES): m/z 175.48 [M]+.

Synthesis of Compound 206.2.

To a solution of 206.1 (8.0 g, 0.045 mmol, 1.0 eq) in methanol (150 mL) was added hydroxylamine (70 mL, 0.045 mmol, 1.0 eq) at 0° C. Reaction mixture was stirred at 40° C. for 24 h. After completion of reaction, reaction mixture was transferred into water slowly and extracted with dichloromethane. Organic layer was combined, washed with brine solution, dried over sodium sulphate and concentrated under reduced pressure to obtain 206.2. (2.0 g, 23.03%). MS(ES): m/z 192.38 [M]+.

Synthesis of Compound 206.3.

To a solution of compound 206.2 (2.0 g, 10.4 mmol, 1.0 eq) in dichloromethane (20 mL) at 0° C., pyridine (4.2 mL, 41.88 mmol, 5.0 eq), N-chloro succinimide (7.0 g, 52.35 mmol, 5.0 eq) was added. Reaction mixture was stirred at room temperature for 3 h. Then, trimethylsilane acetylene (4.11 g, 41.8 mmol, 4.0 eq) and triethylamine (5.9 mL, 41.8 mmol, 4.0 eq) was added. Reaction mixture was stirred at room temperature for 16 h. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 3% ethyl acetate in hexane to obtain 206.3. (1.0 g, 33.25%). MS(ES): m/z 288.41 [M]+.

Synthesis of Compound 206.4.

To a solution of compound 206.3 (0.4 g, 1.3 mmol, 1.0 eq) in isopropyl alcohol (4 mL), potassium carbonate (0.192 mL, 1.3 mmol, 1.0 eq) was added. Reaction mixture was stirred at room temperature for 24 h. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 5% ethyl acetate in hexane to obtain 206.4. (0.150 g, 50.09%). MS(ES): m/z 216.53 [M]+.

Synthesis of Compound 206.5.

To a solution of compound 206.4 (0.150 g, 0.69 mmol, 1.0 eq) in dimethylformamide (1 mL), sodium azide (0.045 g, 0.69 mmol, 1.0 eq) was added. Reaction mixture was stirred at 90° C. for 3 h. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 10% ethyl acetate in hexane to obtain 206.5. (0.060 g, 38.81%). MS(ES): m/z 222.53 [M]+.

Synthesis of Compound 206.6.

To a solution of compound 206.5 (0.060 g, 0.26 mmol, 1.0 eq) in a mixture of tetrahydrofuran (2.4 mL) and water (0.4 mL), triphenylphosphine (0.14 g, 0.54 mmol, 2.0 eq) was added. Reaction mixture was stirred at 75° C. for 3 h. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 10% ethyl acetate in hexane to get 1.6. (0.050 g, 68.41%). MS(ES): m/z 196.35 [M]+.

Synthesis of Compound 206.7.

To a solution of compound 206.6 (0.050 g, 0.2 mmol, 1.0 eq) in pyridine (0.5 mL), 4-dimethylaminopyridine (0.071 mL, 0.27 mmol, 2.0 eq) and cyclopropyl carbonyl chloride (0.1 mL, 1.22 mmol, 5 eq) was added. Reaction mixture was heated in microwave at 90° C. for 1 h. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 10% ethyl acetate in hexane to obtain 206.7. (0.050 g, 74.15%). MS(ES): m/z 264.53 [M]+.

Synthesis of VIII-8.

To a solution of compound 206.7 (0.05 g, 0.11 mmol, 1.0 eq) in 1,4-dioxane (2 mL) was added 1.5 (0.058 g, 0.22 mmol, 1.5 eq), potassium carbonate (0.065 g, 0.47 mmol, 2.5 eq). The reaction mixture was degassed for 10 min. under argon atmosphere, then tris(dibenzylideneacetone) dipalladium(0) (0.017 g, 0.019 mmol, 0.1 eq) and 4,5-Bis (diphenylphosphino)-9,9-dimethylxanthene (0.021 g, 0.037 mmol, 0.2 eq) were added, again degassed for 5 min. The reaction was stirred at 100° C. for 30 min. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 5% methanol in dichloromethane as eluant to obtain pure VIII-8 (0.023 g, 28.05%). MS(ES): m/z 433.25 [M+H]⁺, LCMS purity: 97.99%, HPLC purity: 96.22%, ¹H NMR (CDCl₃, 400 MHZ): 10.59 (s, 1H), 8.58 (s, 1H), 8.52 (s, 1H), 8.46-8.40 (d, J=10.2 Hz, 1H), 8.34 (s, 1H), 7.71-7.69 (d, J=3.2 Hz, 1H), 7.36 (s, 1H), 7.33 (s, 1H), 6.84 (s, 1H), 4.49 (s, 3H), 3.87 (s, 3H), 1.19-1.16 (m, 2H), 1.00-0.98 (m, 2H), 0.90 (s, 1H).

Example 207: N-(5-(5-(hydroxymethyl)-1,2,4-oxadiazol-3-yl)-4-((2-methoxy-3-(1-methyl-1H-1,2,4-triazol-3-yl)phenyl)amino)pyridin-2-yl)cyclopropanecarboxamide, VIII-9

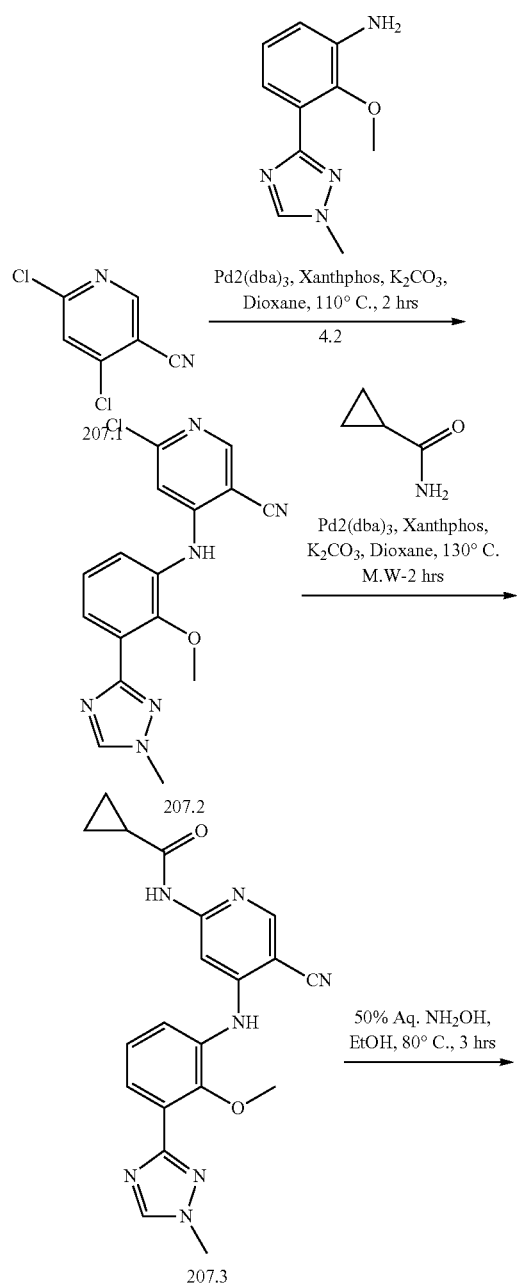

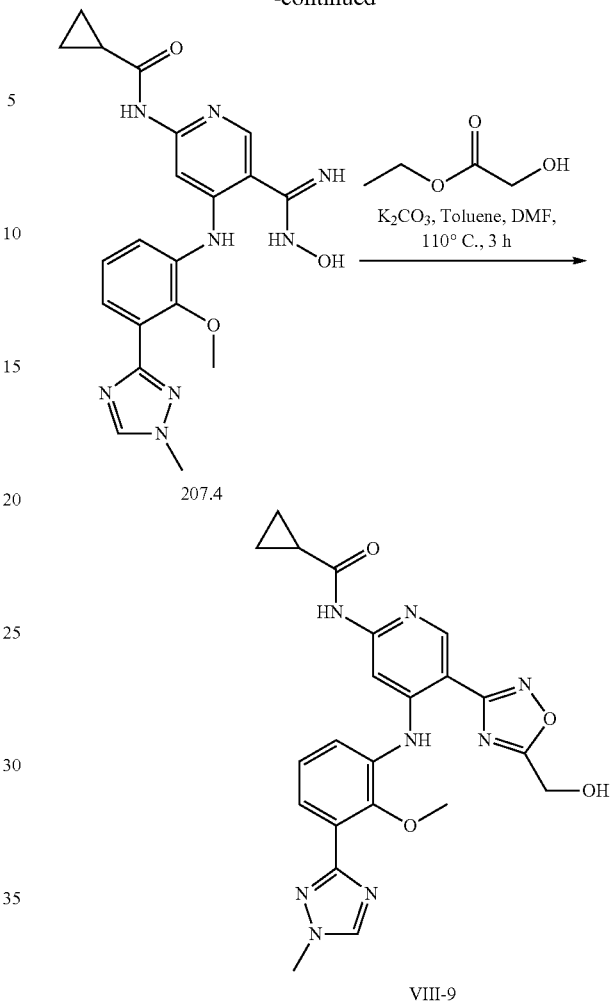

Synthesis of Compound 207.2.

To a solution of compound 4.2 (2 g, 9.8 mmol, 1.0 eq) in 1,4-dioxane (20 mL) was added 207.1 (1.7 g, 9.8 mmol, 1.0 eq), potassium carbonate (3.38 g, 24.5 mmol, 2.5 eq). The reaction mixture was degassed for 10 min. under argon atmosphere, then tris(dibenzylideneacetone)dipalladium(0) (0.89 g, 0.098 mmol, 0.1 eq) and 4,5-Bis(diphenylphosphino)-9,9-dimethylxanthene (1.13 g, 1.9 mmol, 0.2 eq) were added, again degassed for 5 min. The reaction was stirred at 110° C. for 2 h. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 1% methanol in dichloromethane as eluant to obtain pure 207.2 (0.9 g, 22.84%). MS(ES): m/z 341.45 [M+H]⁺.

Synthesis of Compound 207.3.

To a solution of 207.2 (0.270 g, 0.79 mmol, 1.0 eq) in 1,4-dioxane (3 mL) was added cyclopropane carboxamide (0.101 g, 1.19 mmol, 1.5 eq), potassium carbonate (0.27 g, 1.98 mmol, 2.5 eq). The reaction mixture was degassed for 10 min. under argon atmosphere, then tris(dibenzylideneacetone)dipalladium(0) (0.072 g, 0.079 mmol, 0.1 eq) and 4,5-Bis(diphenylphosphino)-9,9-dimethylxanthene (0.091 g, 0.158 mmol, 0.2 eq) were added, again degassed for 5 min. The reaction was stirred at 130° C. for 2 h under microwave irradiation. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 2% methanol in dichloromethane as eluant to obtain pure 207.3 (0.250 g, 81.03%). MS(ES): m/z 390.25 [M+H]$^+$.

Synthesis of Compound 207.4.

To a solution of 207.3 (0.250 g, 0.64 mmol, 1.0 eq) in ethanol (2 mL) was added hydroxylamine (2 mL). Reaction mixture was stirred at 80° C. for 3 h. After completion of the reaction, the reaction mixture was cooled to room temperature and solvent was evaporated to get the crude material. This was further transferred into ice water to get the solid precipitate which was filtered, dried well to obtain pure 207.4 (0.220 g, 81.81%). MS(ES): m/z 423.58 [M+H]$^+$.

Synthesis of VIII-9.

To a solution of 207.4 (0.150 g, 0.35 mmol, 1.0 eq) in a mixture of toluene (0.9 mL) and dimethylformamide (0.1 mL), potassium carbonate (0.058 g, 0.42 mmol, 1.2 eq) and ethyl-2-hydroxy acetate (0.055 g, 0.53 mmol, 1.5 eq) was added. Reaction mixture was stirred at 110° C. for 3 h. After completion of reaction, reaction mixture concentrated under reduced pressure to obtain crude material. This was further purified by Preparative HPLC to obtain VIII-9 (0.028 g, 17.05%). MS(ES): m/z 463.59 [M+H]$^+$, LCMS purity: 98.10%, HPLC purity: 98.82%, $^1$H NMR (DMSO-d$_6$, 400 MHZ): 10.33 (s, 1H), 8.93 (s, 1H), 8.72 (s, 1H), 8.55 (s, 1H), 8.04-7.99 (m, 2H), 7.52-7.50 (d, J=7.6 Hz, 1H), 7.19-7.15 (t, J=16.0 Hz, 1H), 6.15 (s, 1H), 4.85 (s, 2H), 3.94 (s, 3H), 3.67 (s, 3H), 1.84-1.79 (m, 1H), 0.93-0.91 (m, 4H).

Example 208: N-(5-(4-(hydroxymethyl)-1H-pyrazol-1-yl)-4-((2-methoxy-3-(1-methyl-1H-1,2,4-triazol-3-yl)phenyl)amino)pyridin-2-yl)cyclopropanecarboxamide, VIII-10

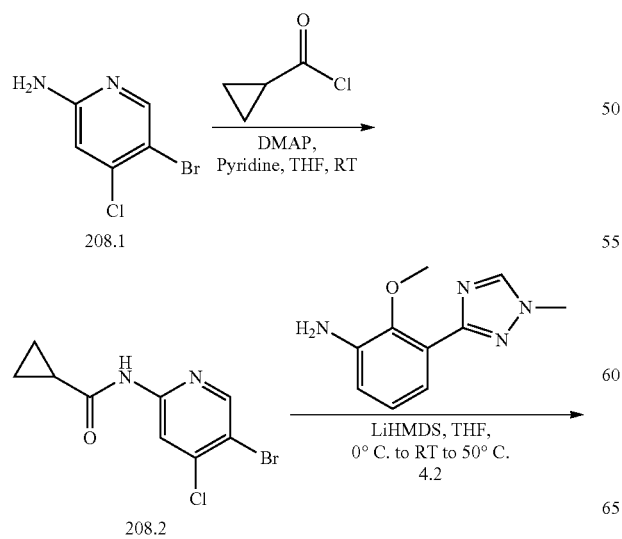

Synthesis of Compound 208.2.

To a solution of 208.1 (20 g, 96.4 mmol, 1.0 eq) in Tetrahydrofuran (200 mL) was added Pyridine (15.7 mL, 193.2 mmol, 2.0 eq) and reaction mixture was cooled to 0° C. To this added dimethylaminopyridine (1.18 g, 9.64 mmol, 0.1 eq) followed by cyclopropanecarbonyl chloride (15.12 g, 144.6 mmol, 1.5 eq) and reaction mixture was stirred at room temperature for 3 h. After completion of reaction, reaction mixture was transferred in ice-water and precipitated product was filtered, dried well to obtain 208.2 (16.5 g, 62.1%). MS(ES): m/z 275.3 [M]$^+$.

Synthesis of Compound 208.3.

To a solution of compound 208.2 (4.5 g, 16.36 mmol, 1.0 eq) in tetrahydrofuran (60 mL) at 0° C., compound 4.2 (4.0 g, 19.63 mmol, 1.2 eq) was added. Then, lithium-bis(trimethylsilyl)amide (49 mL, 49.09 mmol, 3 eq) was added dropwise at 0° C. Reaction mixture was stirred at 50° C. for 24 h. After completion of the reaction, the reaction mixture was cooled to room temperature, transferred to water and extracted with ethyl acetate. Organic layer combined, dried over anhydrous sodium sulfate, filtered and concentrated under reduced pressure to get the crude material. This was further purified by column chromatography using 30% ethyl acetate in hexane to obtain pure 208.3. (3.5 g, 48.34%). MS(ES): m/z 444.25 [M]$^+$.

Synthesis of Compound 208.4.

To a solution of compound 208.3 (0.5 g, 1.12 mmol, 1.0 eq) in dimethylformamide (5 mL), pyrazole ethyl ester (0.48 g, 3.35 mmol, 3 eq) was added. Reaction mixture was degassed with argon for 15 min. Then, copper iodide (0.010 g, 0.05 mmol, 0.05 eq) and potassium carbonate (0.4 g, 2.84 mmol, 2.5 eq) was added. Reaction mixture was stirred in microwave at 180° C. for 40 min. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 0.5% methanol in dichloromethane to obtain 208.4. (0.045 g, 7.94%). MS(ES): m/z 502.64 [M]$^+$.

Synthesis of VIII-10.

To a solution of 208.4 (0.040 g, 0.07 mmol, 1.0 eq) in a mixture of methanol (1 mL) and tetrahydrofuran (1 mL) at 0° C., lithium borohydride (0.008 g, 0.39 mmol, 5.0 eq) was added. The reaction mixture was stirred at 40° C. for 24 h. After completion of reaction, reaction mixture was transferred into water and extracted with ethyl acetate. Organic layer was combined, washed with brine solution, dried over sodium sulphate and concentrated under reduced pressure to obtain crude material. This was further purified by preparative thin layer chromatography using 5% methanol in dichloromethane as mobile phase to obtain pure VIII-10 (0.014 g, 33.95%). MS(ES): m/z 461.53 [M+H]$^+$, LCMS purity: 100%, HPLC purity: 99.77%, $^1$H NMR (MeOD, 400 MHZ): 8.49 (s, 1H), 8.26-8.21 (d, J=8.0 Hz, 2H), 8.06 (s, 1H), 7.88 (s, 1H), 7.62-7.57 (t, J=11.2 Hz, 2H), 7.28-7.24 (t, J=1.6 Hz, 1H), 4.64 (s, 2H), 4.03 (s, 3H), 3.72 (s, 3H), 1.88 (s, 1H), 0.98-0.90 (bs, 4H).

Example 209: N-(4-((2-methoxy-3-(1-methyl-1H-1,2,4-triazol-3-yl)phenyl)amino)-5-(pyridazin-3-yl)pyridin-2-yl)cyclopropanecarboxamide, VIII-11

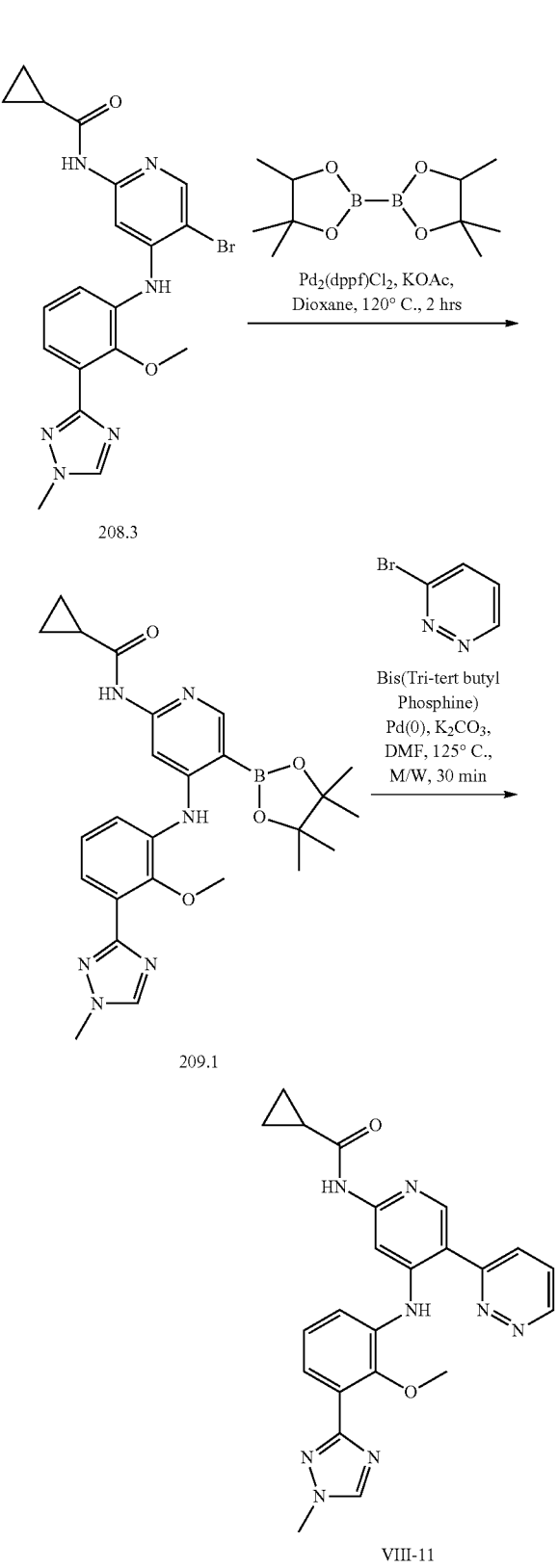

Synthesis of Compound 209.1

To a solution of compound 208.3 (2.0 g, 4.50 mmol, 1.0 eq) in 1,4-dioxane (40 mL) was added bis-pinacolato-diboron (4.59 g, 18.02 mmol, 4.0 eq). Reaction mixture was degassed with argon for 15 min. Then, potassium acetate (0.88 g, 9.05 mmol, 2.0 eq) was added and again degassed with argon for 10 min. Then, 1,1'-Bis(diphenylphosphino)ferrocene-palladium(II)dichloride complex with dichloromethane (0.36 g, 0.45 mmol, 0.1 eq) was added and the reaction mixture was heated at 120° C. for 2 h. After completion of reaction, reaction mixture was transferred into water and extracted with ethyl acetate. Organic layer was combined, washed with brine solution, dried over sodium sulphate and concentrated under reduced pressure to obtain crude material. This was further purified by trituration using diethyl ether and hexane to obtain 209.1 (1.7 g, 76.84%). MS(ES): m/z 491.26 [M]⁻.

Synthesis of VIII-11.

To a solution of compound 209.1 (1.0 g, 0.204 mmol, 1.0 eq) in a mixture of water (0.5 mL) and dimethylformamide (1.5 mL) was added bromopyridazine (0.48 g, 0.306 mmol, 1.5 eq) and potassium carbonate (0.098 g, 0.714 mmol, 3.5 eq). Reaction mixture was degassed with argon for 15 min. Then, bis(Tri-tert butyl Phosphine) palladium (0) (0.028 g, 0.040 mmol, 0.2 eq) was added. Reaction mixture was stirred at 125° C. for 30 min under microwave irradiation. After completion of reaction, reaction mixture was transferred into water and extracted with ethyl acetate. Organic layer was combined, washed with brine solution, dried over sodium sulphate and concentrated under reduced pressure to obtain crude material. This was further purified by column chromatography and the product was eluted in 3% methanol in dichloromethane to obtain VIII-11 (0.020 g, 22.16%). MS(ES): m/z 443.43 [M+H]⁺, LCMS purity: 98.78%, HPLC purity: 99.38%, ¹H NMR (CDCl₃, 400 MHZ): 11.48 (s, 1H), 9.14 (s, 1H), 8.75 (s, 1H), 8.43 (s, 1H), 8.31 (s, 1H), 8.12 (s, 1H), 7.97-7.95 (d, J=8.8 Hz, 1H), 7.66-7.64 (d, J=8 Hz, 1H), 7.63-7.59 (m, 2H), 4.02 (s, 3H), 3.90 (s, 3H), 1.61 (s, 1H), 1.12-1.11 (m, 2H), 0.91-0.89 (m, 2H).

Example 210: (5-(4-((2-methoxy-3-(1-methyl-1H-1,2,4-triazol-3-yl)phenyl)amino)-6-((6-methyl-pyridazin-3-yl)amino)pyridin-3-yl)-1,3,4-oxadiazol-2-yl)methanol, VIII-12

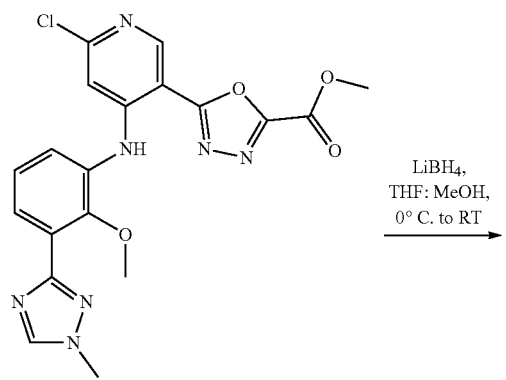

202.5

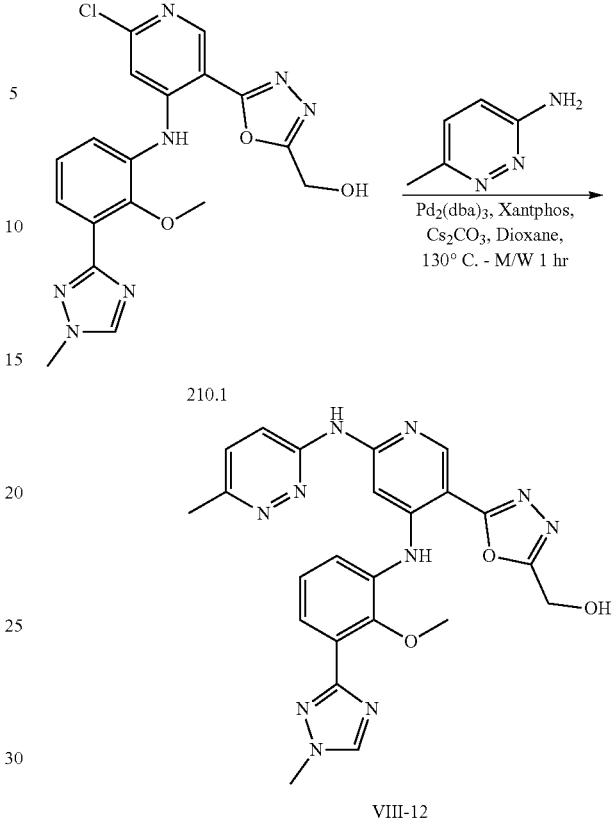

210.1

VIII-12

Synthesis of Compound 210.1.

To a solution of compound 202.5 (0.15 g, 1.13 mmol, 1.0 eq) in a mixture of water (5 mL) and tetrahydrofuran (5 mL) at 0° C., lithium borohydride (2.93 mL, 20.9 mmol, 3 eq) was added. Reaction mixture was stirred at room temperature for 3 h. After completion of the reaction, the reaction mixture was concentrated, transferred to water and extracted with ethyl acetate. Organic layer combined, dried over anhydrous sodium sulfate, filtered and concentrated under reduced pressure to get the crude material. This was further purified by column chromatography using 10% ethyl acetate in hexane to obtain pure 210.1. (0.1 g, 71.18%). MS(ES): m/z 414.57 [M]⁺.

Synthesis of VIII-12.

To a solution of compound 210.1 (0.150 g, 0.12 mmol, 1.0 eq) in 1,4-dioxane (2 mL) was added methylpyridazinamine (0.015 g, 0.14 mmol, 1.2 eq), cesium carbonate (0.05 g, 0.36 mmol, 3.0 eq). The reaction mixture was degassed for 10 min. under argon atmosphere, then tris(dibenzylideneacetone)dipalladium(0) (0.011 g, 0.012 mmol, 0.1 eq) and 4,5-Bis(diphenylphosphino)-9,9-dimethylxanthene (0.013 g, 0.024 mmol, 0.2 eq) were added, again degassed for 5 min. The reaction mixture was stirred at 130° C. for 1 h under microwave irradiation. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure VIII-12 (0.037 g, 20.98%). MS(ES): m/z 487.43 [M+H]⁺, LCMS purity: 100%, HPLC purity: 99.01%, ¹H NMR (DMSO-d₆, 400

MHZ): 10.24 (s, 1H), 9.84 (s, 1H), 8.65 (s, 1H), 8.58 (s, 2H), 7.96-7.93 (d, J=8.8 Hz, 1H), 7.87 (s, 1H), 7.72-7.68 (t, J=11.5 Hz, 2H), 7.47-7.44 (d, J=6.8 Hz, 1H), 7.33-7.29 (t, J=15.6 Hz, 1H), 4.77 (s, 2H), 3.96 (s, 3H), 3.76 (s, 3H), 2.50 (s, 3H).

Example 211: 6-((5-(5-(hydroxymethyl)-1,3,4-oxadiazol-2-yl)-4-((2-methoxy-3-(1-methyl-1H-1,2,4-triazol-3-yl)phenyl)amino)pyridin-2-yl)amino)picolinonitrile, VIII-13

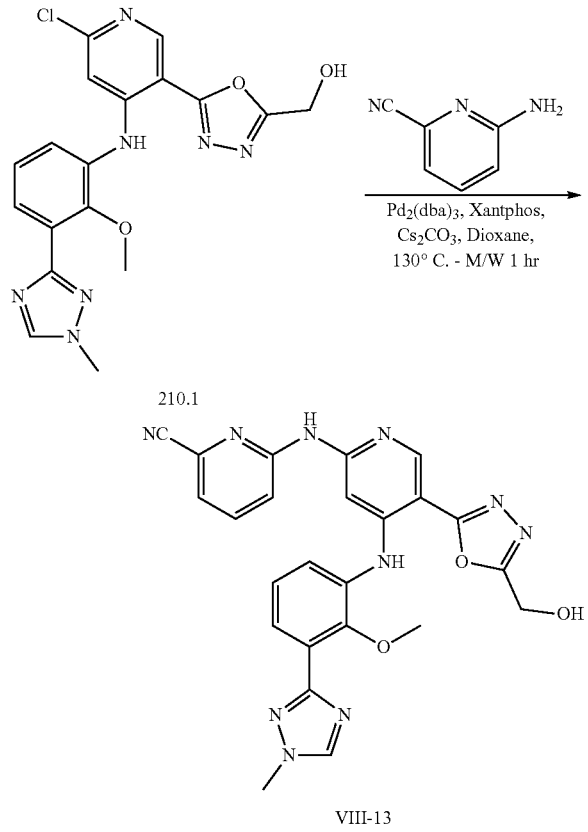

VIII-13

Synthesis of VIII-13.

To a solution of compound 210.1 (0.150 g, 0.36 mmol, 1.0 eq) in 1,4-dioxane (5 mL) was added 6-aminopicolinonitrile (0.051 g, 0.43 mmol, 1.2 eq), potassium carbonate (0.15 g, 1.08 mmol, 3.0 eq). The reaction mixture was degassed for 10 min. under argon atmosphere, then tris(dibenzylideneacetone)dipalladium(0) (0.032 g, 0.036 mmol, 0.1 eq) and 4,5-Bis(diphenylphosphino)-9,9-dimethylxanthene (0.041 g, 0.072 mmol, 0.2 eq) were added, again degassed for 5 min. The reaction was stirred at 130° C. for 1 h under microwave irradiation. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure VIII-13 (0.027 g, 15.00%). MS(ES): m/z 497.65 [M+H]$^+$, LCMS purity: 97.91%, HPLC purity: 97.55%, $^1$H NMR (DMSO-d$_6$, 400 MHZ): 10.47 (s, 1H), 10.04 (s, 1H), 8.69 (s, 1H), 8.54 (s, 1H), 8.16 (s, 1H), 7.91-7.89 (d, J=8.0 Hz, 1H), 7.87-7.80 (m, 2H), 7.77-7.47 (m, 1H), 7.67-7.65 (m, 1H), 7.53-7.4 (m, 1H), 6.03-6.00 (t, J=12.4 Hz, 1H), 4.77 (s, 2H), 3.96 (s, 3H), 3.76 (s, 3H).

Example 212: (5-(6-((2,6-dimethylpyrimidin-4-yl)amino)-4-((2-methoxy-3-(1-methyl-1H-1,2,4-triazol-3-yl)phenyl)amino)pyridin-3-yl)-1,3,4-oxadiazol-2-yl)methanol, VIII-14

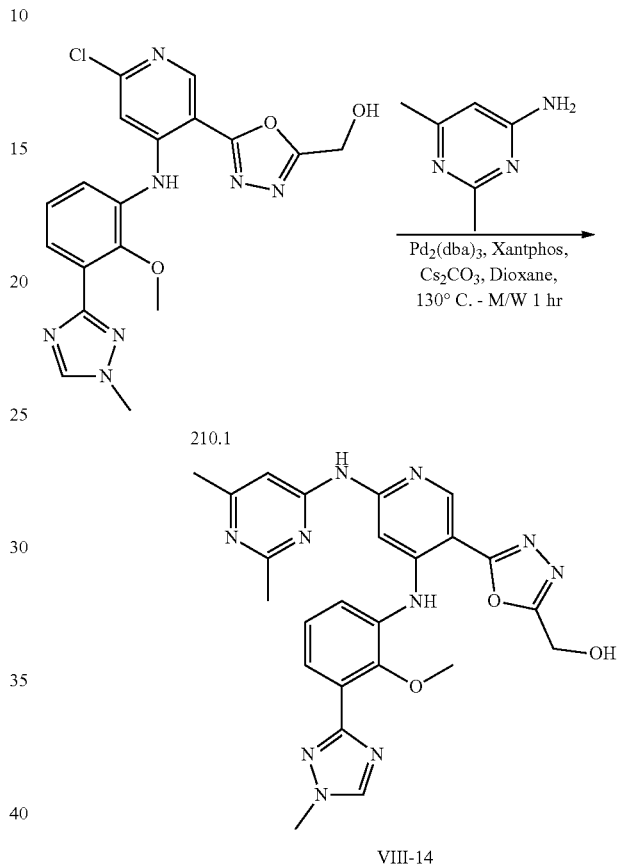

VIII-14

Synthesis of VIII-14.

To a solution of compound 210.1 (0.150 g, 0.36 mmol, 1.0 eq) in 1,4-dioxane (5 mL) was added dimethylpyrimidinamine (0.059 g, 0.43 mmol, 1.2 eq), potassium carbonate (0.15 g, 1.08 mmol, 3.0 eq). The reaction mixture was degassed for 10 min. under argon atmosphere, then tris (dibenzylideneacetone)dipalladium(0) (0.032 g, 0.036 mmol, 0.1 eq) and 4,5-Bis(diphenylphosphino)-9,9-dimethylxanthene (0.041 g, 0.072 mmol, 0.2 eq) were added, again degassed for 5 min. The reaction was stirred at 130° C. for 1 h under microwave irradiation. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure VIII-14 (0.021 g, 11.57%). MS(ES): m/z 501.58 [M+H]$^+$, LCMS purity: 98.90%, HPLC purity: 98.6%, $^1$H NMR (DMSO-d$_6$, 400 MHZ): 10.27 (s, 1H), 9.87 (s, 1H), 8.68 (s, 1H), 8.58 (s, 1H), 8.36 (s, 1H), 7.76-7.69 (m, 2H), 7.36-7.33 (m, 1H), 7.03 (s, 1H), 6.03-6.00 (t, J=8.0 Hz, 1H), 4.77 (s, 2H), 3.96 (s, 3H), 3.74 (s, 3H), 2.37 (s, 3H), 2.96 (s, 3H).

Example 213: 6-((5-(5-chlorothiazol-2-yl)-4-((2-methoxy-3-(2-methyl-2H-tetrazol-5-yl)phenyl)amino)pyridin-2-yl)amino)picolinonitrile, VIII-15

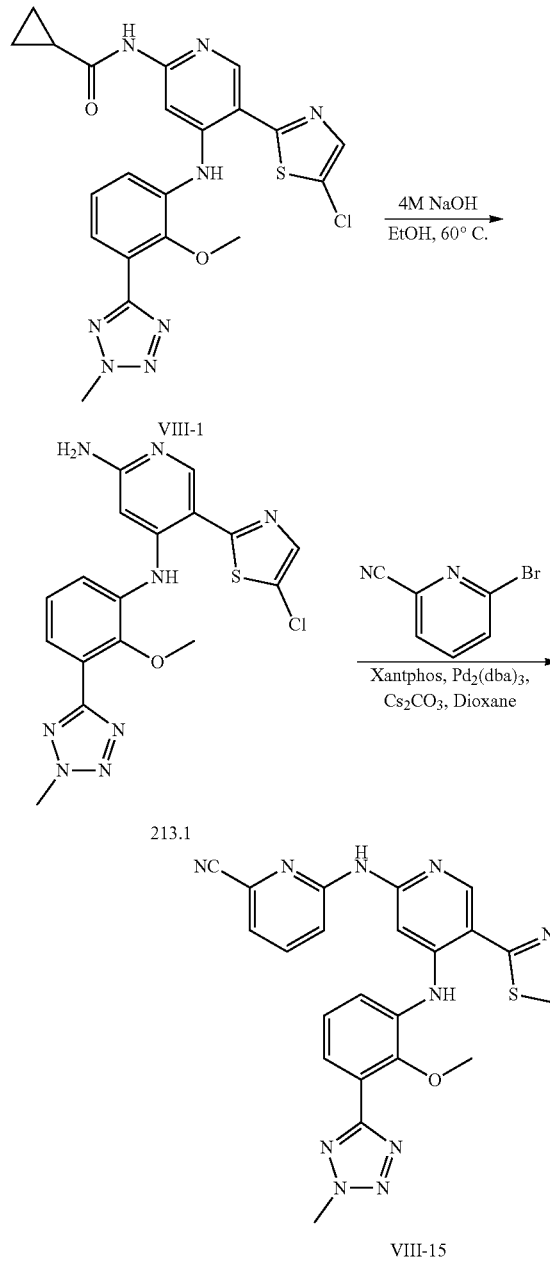

Synthesis of Compound 213.1.

To a solution of compound VIII-1 (0.3 g, 0.62 mmol, 1.0 eq) in ethanol (5 mL) was added 4M sodium hydroxide solution (4.1 mLg, 3.11 mmol, 5.0 eq). Reaction mixture was stirred at 60° C. for 3 h. After completion of reaction, reaction mixture concentrated under reduced pressure to obtain residue which was transferred into water and extracted with dichloromethane. Organic layer was combined, washed with brine solution, dried over sodium sulphate and concentrated under reduced pressure to obtain 213.1 (0.25 g, 83.15%). MS(ES): m/z 416.57 [M]+.

Synthesis of VIII-15.

To a solution of compound 213.1 (0.08 g, 0.19 mmol, 1.0 eq) in 1,4-dioxane (1 mL) was added 6-bromopicolinonitrile (0.04 g, 0.231 mmol, 1.2 eq), cesium carbonate (0.187 g, 0.57 mmol, 3.0 eq). The reaction mixture was degassed for 10 min. under argon atmosphere, then tris(dibenzylideneacetone)dipalladium(0) (0.017 g, 0.019 mmol, 0.1 eq) and 4,5-Bis(diphenylphosphino)-9,9-dimethylxanthene (0.027 g, 0.037 mmol, 0.2 eq) were added, again degassed for 5 min. The reaction was stirred at 100° C. for 30 min. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 2% methanol in dichloromethane as eluant to obtain pure VIII-15 (0.018 g, 18.06%). MS(ES): m/z 517.43 [M+H]+, LCMS purity: 91.32%, HPLC purity: 95.86%, $^1$H NMR (DMSO-$d_6$, 400 MHZ): 11.05 (s, 1H), 10.39 (s, 1H), 8.59 (s, 1H), 8.14 (s, 1H), 8.06 (s, 1H), 7.92-7.86 (m, 2H), 7.78-7.76 (d, J=8.8 Hz, 1H), 7.67-7.65 (d, J=7.2 Hz, 1H), 7.54-7.48 (m, 2H), 4.45 (s, 3H), 3.76 (s, 3H).

Example 214: 5-(5-chlorothiazol-2-yl)-N4-(2-methoxy-3-(2-methyl-2H-tetrazol-5-yl)phenyl)-N2-(6-methylpyridazin-3-yl)pyridine-2,4-diamine, VIII-16

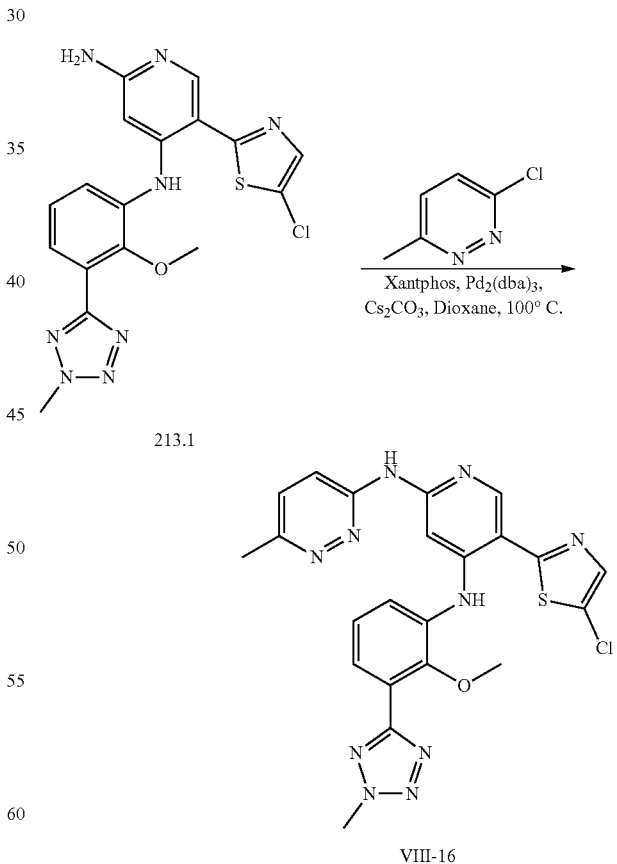

Synthesis of VIII-16.

To a solution of compound 213.1. (0.08 g, 0.19 mmol, 1.0 eq) in 1,4-dioxane (1 mL) was added methylchloropyridazine (0.04 g, 0.231 mmol, 1.2 eq), cesium carbonate (0.187 g, 0.57 mmol, 3.0 eq). The reaction mixture was degassed for 10 min. under argon atmosphere, then tris (dibenzylideneacetone)dipalladium(0) (0.017 g, 0.019 mmol, 0.1 eq) and 4,5-Bis(diphenylphosphino)-9,9-dimethylxanthene (0.027 g, 0.037 mmol, 0.2 eq) were added, again degassed for 5 min. The reaction was stirred at 100° C. for 30 min. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 2% methanol in dichloromethane as eluant to obtain pure VIII-16 (0.020 g, 20.46%). MS(ES): m/z 507.31 [M+H]$^+$, LCMS purity: 97.53%, HPLC purity: 97.31%, $^1$H NMR (DMSO-d$_6$, 400 MHZ): 10.84 (s, 1H), 10.18 (s, 1H), 8.56 (s, 1H), 8.03-7.98 (m, 2H), 7.83-7.81 (d, J=7.6 Hz, 2H), 7.69-7.67 (d, J=6.8 Hz, 1H), 7.46-7.43 (d, J=9.2 Hz, 1H), 7.40-7.36 (t, J=13.2 Hz, 1H), 4.47 (s, 3H), 3.77 (s, 3H), 2.49 (s, 3H).

Example 215: 5-(5-chlorothiazol-2-yl)-N4-(2-methoxy-3-(2-methyl-2H-tetrazol-5-yl)phenyl)-N2-(4-(methoxymethyl)pyridin-2-yl)pyridine-2,4-diamine, VIII-17

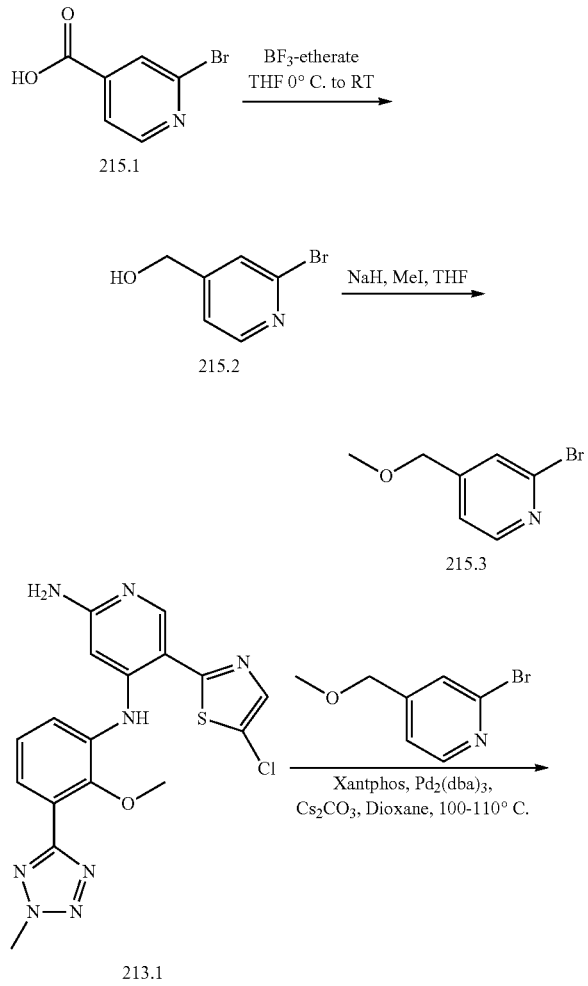

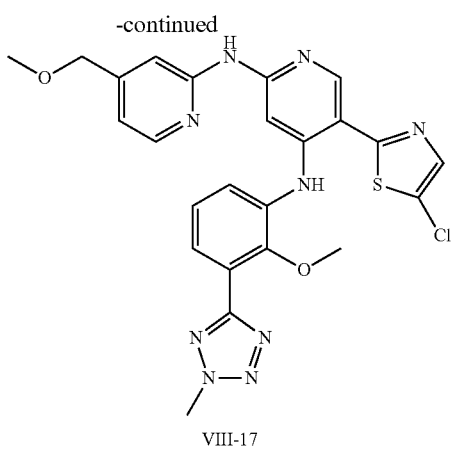

VIII-17

Synthesis of Compound 215.2.

To a solution of 215.1 (2 g, 9.9 mmol, 1.0 eq) in tetrahydrofuran (30 mL) at 0° C., boron trifluoride etherate (4.18 g, 29.7 mmol, 3.0 eq) was added dropwise. Reaction mixture was stirred at room temperature for 3 h. After completion of reaction, reaction mixture was transferred in ice-water and product was extracted with ethyl acetate. Organic layer was combined, washed with brine solution, dried over sodium sulphate and concentrated under reduced pressure to obtain 1.1 (1.4 g, 75.21%). MS(ES): m/z 189.65 [M]$^+$.

Synthesis of Compound 215.3.

To a solution of 215.2 (1.4 g, 7.4 mmol, 1.0 eq) in tetrahydrofuran (15 mL) at 0° C., sodium hydride (0.35 g, 14.8 mmol, 2.0 eq) was added. Reaction mixture was stirred at 0° C. for 20 min. Then, methyl iodide (1.57 g, 11.2 mmol, 1.5 eq) was added. Reaction mixture was stirred at room temperature for 3 h. After completion of reaction, reaction mixture was transferred in ice-water and product was extracted with ethyl acetate. Organic layer was combined, washed with brine solution, dried over sodium sulphate and concentrated under reduced pressure to obtain 215.3 (0.7 g, 46.53%). MS(ES): m/z 203.58 [M]$^+$.

Synthesis of VIII-17.

To a solution of compound 215.3 (0.046 g, 0.23 mmol, 1.2 eq) in 1,4-dioxane (1 mL) was added 213.1 (0.080 g, 0.19 mmol, 1.0 eq), cesium carbonate (0.187 g, 0.57 mmol, 3.0 eq). The reaction mixture was degassed for 10 min. under argon atmosphere, then tris(dibenzylideneacetone)dipalladium(0) (0.017 g, 0.019 mmol, 0.1 eq) and 4,5-Bis(diphenylphosphino)-9,9-dimethylxanthene (0.027 g, 0.037 mmol, 0.2 eq) were added, again degassed for 5 min. The reaction was stirred at 110° C. for 30 min. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 2% methanol in dichloromethane as eluant to obtain pure VIII-17 (0.016 g, 15.48%). MS(ES): m/z 536.35 [M+H]$^+$, LCMS purity: 96.59%, HPLC purity: 98.40%, $^1$H NMR (CDCl$_3$, 400 MHZ): 10.84 (s, 1H), 9.91 (s, 1H), 8.55 (s, 1H), 8.16-8.15 (d, J=5.60 Hz, 2H), 8.12 (s, 1H), 7.88-7.86 (d, J=7.6 Hz, 1H), 7.67-7.65 (d, J=8.8 Hz, 1H), 7.44 (s, 1H), 7.55 (s, 1H), 6.82 (s, 1H), 4.47 (s, 3H), 4.42 (s, 2H), 3.71 (s, 3H), 3.34 (s, 3H).

401

Example 216: N-(1-(2-methoxy-3-(1-methyl-1H-1,2,4-triazol-3-yl)phenyl)-3-(methylamino)-1H-pyrazolo[4,3-c]pyridin-6-yl)cyclopropanecarboxamide, XVI-1

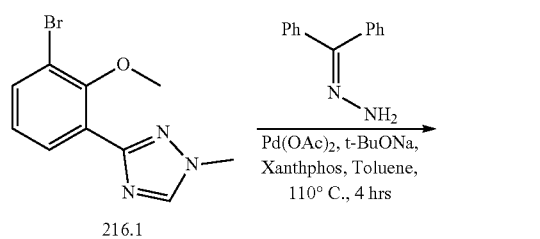

216.1

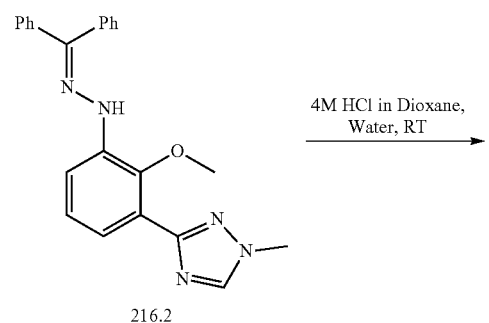

216.2

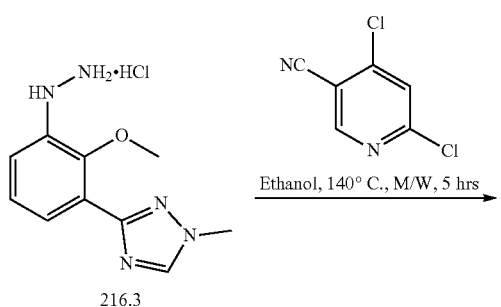

216.3

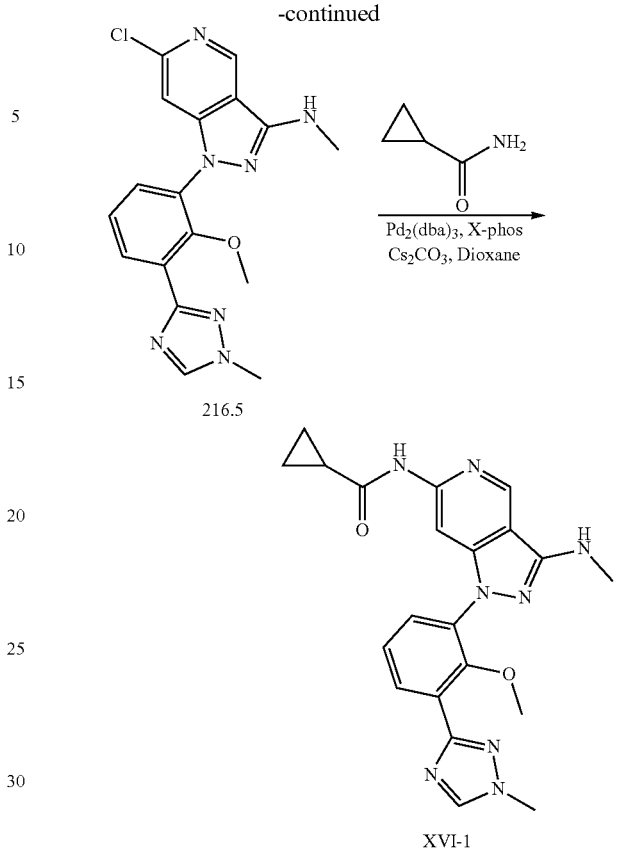

216.5

XVI-1

Synthesis of Compound 216.2.

To a solution of compound 216.1 (2.0 g, 7.4 mmol, 1.0 eq) in toluene (10 mL), compound benzophenone hydrazone (1.5 g, 7.4 mmol, 1.0 eq) and sodium-tert-butoxide (1.8 g, 18.50 mmol, 2.5 eq) were added. Reaction mixture was degassed with argon for 15 min. Then, tris(dibenzylideneacetone)dipalladium(0) (0.68 g, 0.74 mmol, 0.1 eq) and 4,5-Bis(diphenylphosphino)-9,9-dimethylxanthene (0.86 g, 1.49 mmol, 0.2 eq) were added. Reaction mixture was stirred at 110° C. for 4 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography using 11% methanol in dichloromethane as eluant to obtain 216.2 (1.5 g, 52.44%). MS(ES): m/z 384.15 [M+H]⁺.

Synthesis of Compound 216.3.

To a suspension of 216.2 (1.5 g, 3.91 mmol, 1.0 eq) in water (3 mL) was added 4M hydrogen chloride in dioxane (15 mL) and stirred at room temperature for 24 h. After completion of the reaction, the reaction mixture was concentrated under reduced pressure to obtain the crude material. This was further purified by trituration with dichloromethane and diethyl ether to obtain 216.3 (0.7 g, 69.98%). MS(ES): m/z 256.46 [M+H]⁺.

Synthesis of Compound 216.4.

To a solution of compound 216.3 (0.4 g, 1.8 mmol, 1.0 eq) in ethanol (5 mL), dichloropyridine carbonitrile (0.35 g, 1.8 mmol, 1.0 eq) was added. Reaction mixture was heated in microwave at 140° C. for 5 h. After completion of the reaction, the reaction mixture was concentrated under reduced pressure to obtain the crude product. This was further purified by column chromatography using 5% methanol in dichloromethane to obtain pure 216.4. (0.09 g, 16.17%). MS(ES): m/z 356.48 [M]+.

Synthesis of Compound 216.5.

To a solution of compound 216.4 (0.050 g, 0.14 mmol, 1.0 eq) in methanol (5 mL), paraformaldehyde (0.025 g, 0.84 mmol, 6.0 eq) and sodium methoxide (0.023 g, 0.43 mmol, 3.0 eq) were added. Reaction mixture was stirred at 60-65° C. for 3 h. Reaction mixture was cooled to room temperature and sodium borohydride (0.005 g, 0.35 mmol, 2.5 eq) was added in portions. Reaction mixture was again stirred at 60-65° C. for 24 h. After completion of the reaction, the reaction mixture was transferred into water and extracted with dichloromethane. Organic layer combined, dried over anhydrous sodium sulfate, filtered and concentrated under reduced pressure to get 216.5. (0.04 g, 76.97%). MS(ES): m/z 370.28 [M]+.

Synthesis of XVI-1.

To a solution of compound 216.5 (0.040 g, 0.10 mmol, 1.0 eq) in 1,4-dioxane (3 mL) was added cyclopropanecarboxamide (0.010 g, 0.10 mmol, 1.0 eq), cesium carbonate (0.08 g, 0.25 mmol, 2.5 eq). The reaction mixture was degassed for 10 min. under argon atmosphere, then tris(dibenzylideneacetone)dipalladium(0) (0.016 g, 0.010 mmol, 0.1 eq) and 4,5-Bis(diphenylphosphino)-9,9-dimethylxanthene (0.013 g, 0.020 mmol, 0.2 eq) were added, again degassed for 5 min. The reaction was stirred at 130° C. for 1 h under microwave irradiation. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure XVI-1 (0.010 g, 22.09%). MS(ES): m/z 419.48 [M+H]+, LCMS purity: 99.86%, HPLC purity: 99.81%, $^1$H NMR (MeOD, 400 MHZ): 8.99 (s, 1H), 8.53 (s, 1H), 8.04-8.02 (d, J=6.8 Hz, 1H), 7.77 (s, 1H), 7.61-7.59 (d, J=8.8 Hz, 1H), 7.46-7.42 (t, J=11.5 Hz, 1H), 4.04 (s, 3H), 3.47 (s, 3H), 3.28 (s, 3H), 1.90 (s, 1H), 1.02 (s, 2H), 0.92 (s, 2H).

Example 217: tert-butyl (6-chloro-3-(2-methoxy-3-(2-methyl-2H-tetrazol-5-yl)phenyl)imidazo[1,5-a]pyrazin-1-yl)carbamate XVI-2

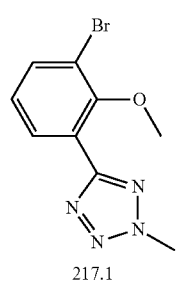

217.1

BuLi, Et₂O
−78° C., CO₂
→

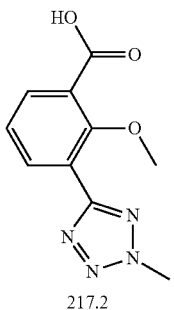

217.2

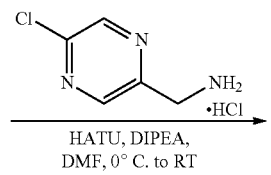

HATU, DIPEA,
DMF, 0° C. to RT
→

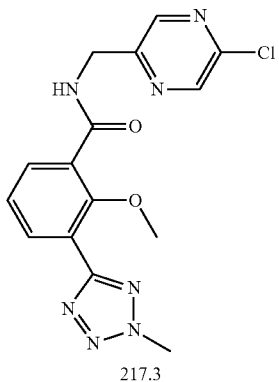

217.3

POCl₃, DMF
→

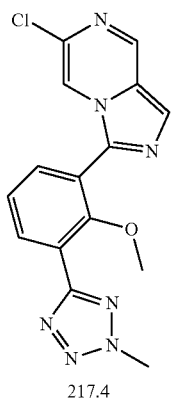

217.4

NIS, DMF
→

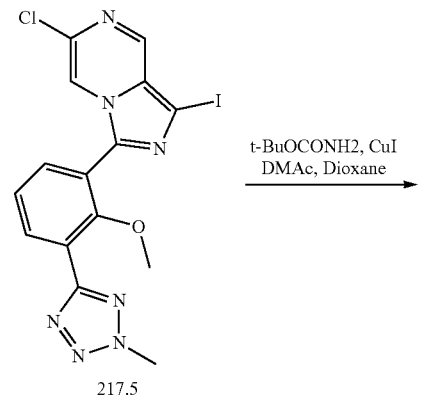

217.5 t-BuOCONH2, CuI
DMAc, Dioxane
→

-continued

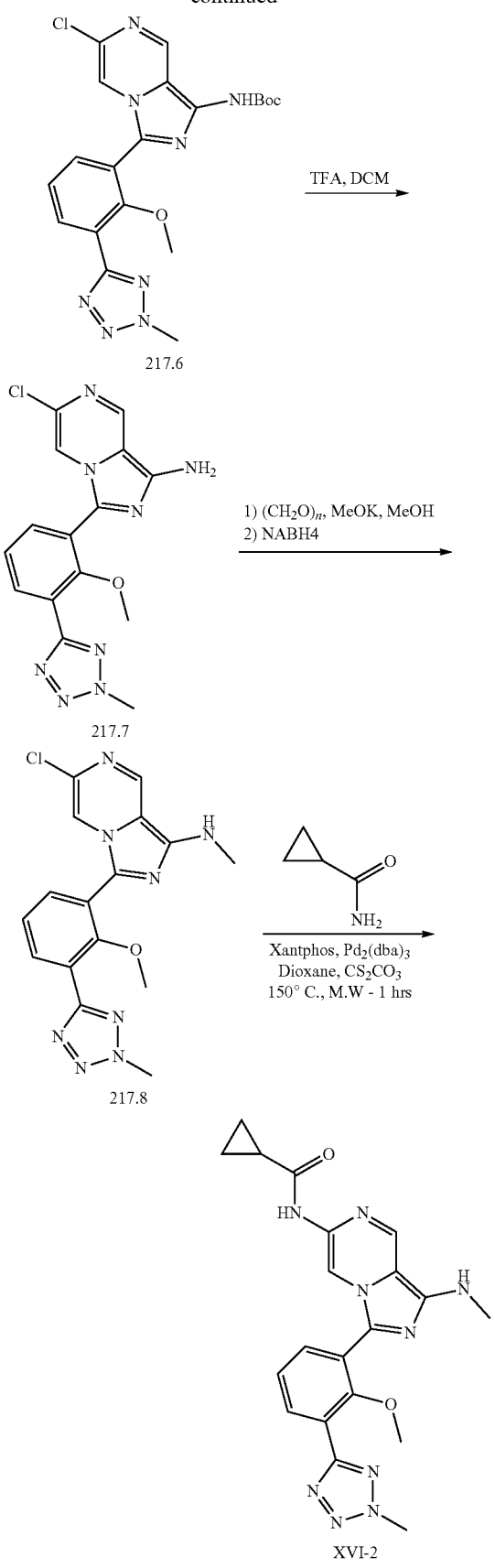

Synthesis of Compound 217.2

To a solution of compound 217.1 (0.1 g, 0.37 mmol, 1.0 eq) in diethyl ether (1 mL), n-butyl lithium (0.7 mL, 0.74 mmol, 2.0 eq) was added dropwise under argon atmosphere at −78° C. Reaction mixture was stirred at −78° C. for 40 min and carbon dioxide was bubbled through the reaction mixture for 45 min. After completion of the reaction, the reaction mixture was transferred in 1N hydrochloric acid, neutralized using 1N sodium hydroxide solution and extracted with dichloromethane. Organic layer combined, dried over anhydrous sodium sulfate, filtered and concentrated under reduced pressure to obtain 217.2 (0.070 g, 80.43%). MS(ES): m/z 235.48 [M+H]$^+$.

Synthesis of Compound 217.3.

To a solution of 217.2 (0.083 g, 0.35 mmol, 1.0 eq) in N,N-dimethylformamide (1.5 mL) was added 1-[Bis(dimethylamino)methylene]-1H-1,2,3-triazolo[4,5-b]pyridinium 3-oxid hexafluorophosphate (0.1 g, 24.6 mmol, 1.0 eq) at 0° C. Reaction mixture was stirred at 0° C. for 40 min. Then, compound 1.2 and di-isopropylethylamine was added at 0° C. Reaction mixture was stirred at room temperature for 4 h. After completion of reaction, reaction mixture was transferred into water and extracted with ethyl acetate. Organic layer combined, washed with brine solution, dried over sodium sulphate and concentrated under reduced pressure to obtain crude material. This was further purified by column chromatography and the product was eluted in 10% ethyl acetate in hexane to obtain 217.3 (0.080 g, 38.46%). MS(ES): m/z 360.54 [M+H]$^+$.

Synthesis of Compound 217.4.

To a solution of compound 217.3 (0.1 g, 0.27 mmol, 1.0 eq) in N,N-dimethylformamide (0.7 mL), phosphorous oxychloride (0.7 mL) was added. Reaction mixture was stirred at 55° C. for 3 h. After completion of the reaction, the reaction mixture was quenched using aqueous ammonia solution and extracted with dichloromethane. Organic layer combined, dried over anhydrous sodium sulphate, filtered and concentrated under reduced pressure to get the crude material. This was further purified by column chromatography using 1% methanol in dichloromethane to obtain pure 217.4. (0.070 g, 73.69%). MS(ES): m/z 342.52 [M]$^+$.

Synthesis of Compound 217.5.

To a solution of compound 217.4 (0.050 g, 0.14 mmol, 1.0 eq) in N,N-dimethylformamide (1 mL), N-iodo succinimide (0.035 mL, 0.15 mmol, 1.05 eq) was added. Reaction mixture was stirred at 60° C. for 3 h. After completion of the reaction, the reaction mixture was transferred into water and extracted with ethyl acetate. Organic layer combined, dried over anhydrous sodium sulfate, filtered and concentrated under reduced pressure to obtain crude material. This was further purified by column chromatography using 0.2% methanol in dichloromethane to obtain pure 217.5. (0.045 g, 65.77%). MS(ES): m/z 468.51 [M]$^+$.

Synthesis of Compound 217.6.

To a solution of compound 217.5 (0.16 g, 0.34 mmol, 1.0 eq) in 1,4-dioxane (10 mL), tert-butyl carbamate (0.4 g, 3.42 mmol, 10.0 eq) was added. Reaction mixture was degassed with argon for 15 min followed by addition of N,N-dimethylcyclohexylamine (0.097 g, 0.68 mmol, 2.0 eq) and again degassed with argon for 5 min. Then, copper iodide (0.067 g, 0.34 mmol, 2.0 eq) was added. Reaction mixture was stirred 75° C. for 6 h. After completion of the reaction, the reaction mixture was concentrated, transferred into water and extracted with ethyl acetate. Organic layer combined, dried over anhydrous sodium sulfate, filtered and concentrated under reduced pressure to obtain the crude material.

This was further purified by column chromatography using 40% ethyl acetate in hexane to obtain pure 217.6. (0.055 g, 35.18%). MS(ES): m/z 457.82 [M]+.

Synthesis of Compound 217.7.

To a solution of compound 217.6 (0.055 g, 0.12 mmol, 1.0 eq) in dichloromethane (1 mL), trifluoroacetic acid (0.2 mL) was added. Reaction mixture was stirred at room temperature under nitrogen atmosphere for 30 min. After completion of the reaction, reaction mixture was transferred into water, neutralized using sodium bicarbonate solution and then extracted with ethyl acetate. Organic layer combined, dried over anhydrous sodium sulfate, filtered and concentrated under reduced pressure to obtain 217.7. (0.037 g, 86.15%). MS(ES): m/z 357.28 [M]+.

Synthesis of Compound 217.8.

To a solution of compound 217.7 (0.037 g, 0.10 mmol, 1.0 eq) in methanol (2.3 mL), paraformaldehyde (0.020 g, 0.62 mmol, 6.0 eq) and sodium methoxide (0.017 g, 0.312 mmol, 3.0 eq) was added. Reaction mixture was stirred at 65° C. for 2 h. Then, reaction mixture was cooled to room temperature and sodium borohydride (0.011 g, 0.270 mmol, 2.6 eq) was added. Reaction mixture was stirred at 65° C. for 45 min. After completion of the reaction, reaction mixture was concentrated, transferred into water and extracted with dichloromethane. Organic layer combined, dried over anhydrous sodium sulfate, filtered and concentrated under reduced pressure to obtain 217.8. (0.025 g, 65.01%). MS(ES): m/z 371.47 [M]+.

Synthesis of XVI-2.

To a solution of compound 217.8 (0.025 g, 0.067 mmol, 1.0 eq) in 1,4-dioxane (2 mL) was added cyclopropanecarboxamide (0.040 g, 0.47 mmol, 7.0 eq), cesium carbonate (0.087 g, 0.26 mmol, 4.0 eq). The reaction mixture was degassed for 10 min. under argon atmosphere, then tris(dibenzylideneacetone)dipalladium(0) (0.006 g, 0.006 mmol, 0.1 eq) and 4,5-Bis(diphenylphosphino)-9,9-dimethylxanthene (0.008 g, 0.013 mmol, 0.2 eq) were added, again degassed for 5 min. The reaction was stirred at 150° C. for 1 h under microwave irradiation. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure XVI-2 (0.006 g, 21.22%). MS(ES): m/z 420.53 [M+H]+, LCMS purity: 99.42%, HPLC purity: 96.00%, $^1$H NMR (DMSO-d$_6$, 400 MHZ): 8.65 (s, 1H), 8.13 (s, 2H), 7.74-7.73 (d, J=4.0 Hz, 1H), 7.45 (s, 1H), 4.48 (s, 3H), 3.41 (s, 3H), 3.09 (s, 3H), 1.81 (s, 1H), 1.30 (s, 2H), 0.92-0.82 (m, 4H).

Example 218: N-(1-(2-methoxy-3-(2-methyl-2H-tetrazol-5-yl)phenyl)-3-(methylamino)-1H-pyrazolo[4,3-c]pyridin-6-yl)cyclopropanecarboxamide, XVI-3

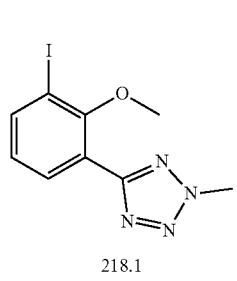

218.1

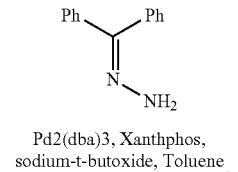

Pd2(dba)3, Xanthphos, sodium-t-butoxide, Toluene

-continued

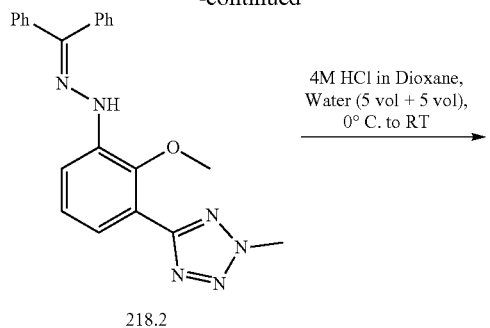

218.2

4M HCl in Dioxane, Water (5 vol + 5 vol), 0° C. to RT

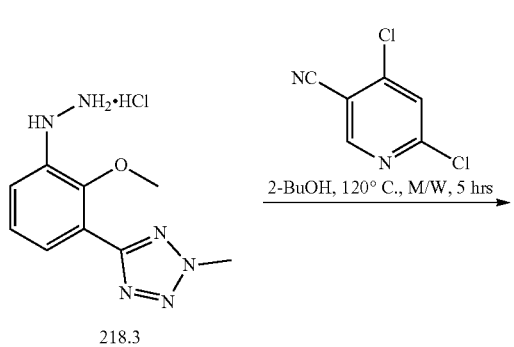

218.3

2-BuOH, 120° C., M/W, 5 hrs

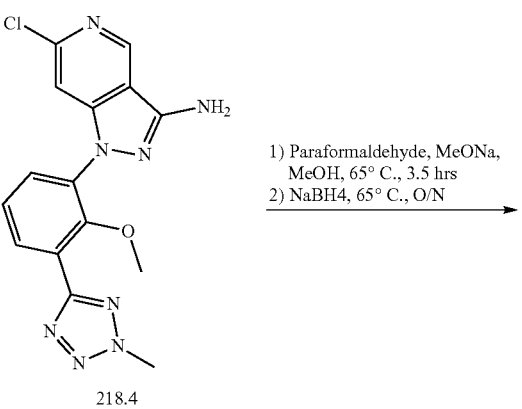

218.4

1) Paraformaldehyde, MeONa, MeOH, 65° C., 3.5 hrs
2) NaBH4, 65° C., O/N

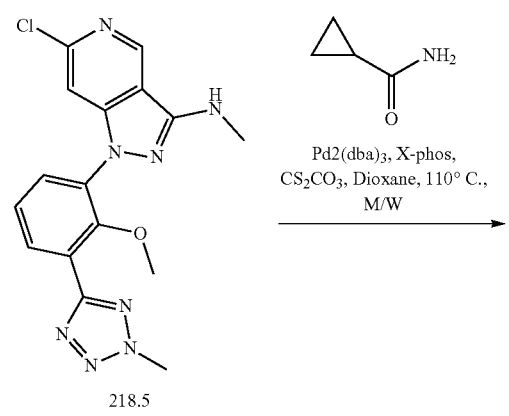

218.5

Pd2(dba)3, X-phos, CS2CO3, Dioxane, 110° C., M/W

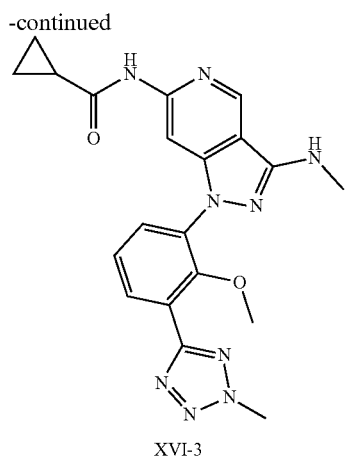

XVI-3

Synthesis of Compound 218.2.

To a solution of compound 218.1 (2.0 g, 7.4 mmol, 1.0 eq) in toluene (15 mL), compound benzophenonehydrazone (1.8 g, 8.9 mmol, 1.2 eq) and sodium-tert-butoxide (1.8 g, 18.5 mmol, 2.5 eq) were added. Reaction mixture was purged with argon for 15 min. Then, tris(dibenzylideneacetone)dipalladium(0) (0.68 g, 0.74 mmol, 0.1 eq) and 4,5-Bis(diphenylphosphino)-9,9-dimethylxanthene (0.86 g, 1.49 mmol, 0.2 eq) were added. Reaction mixture was stirred at 110° C. for 4 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography using 20% ethyl acetate in hexane as eluant to obtain 218.2 (1.6 g, 65.78%). MS(ES): m/z 384.15 [M+H]$^+$.

Synthesis of Compound 218.3.

To a suspension of 218.2 (1.7 g, 4.4 mmol, 1.0 eq) in water (2 mL) was added 4M hydrogen chloride in dioxane (17 mL) dropwise. Reaction mixture was stirred at room temperature for 24 h. After completion of the reaction, the reaction mixture was concentrated under reduced pressure to obtain crude material. This was further purified by trituration with dichloromethane and ether to obtain 218.3 (0.8 g, 70.48%). MS(ES): m/z 256.46 [M+H]$^+$.

Synthesis of Compound 218.4.

To a solution of dichloropyridinecarbonitrile (0.3 g, 1.3 mmol, 1.0 eq) in butanol (2 mL), compound 218.3 (0.23 g, 1.3 mmol, 1.0 eq) was added. Reaction mixture was heated in microwave at 120° C. for 5 h. After completion of the reaction, the reaction mixture was concentrated to get the crude product. This was further purified by column chromatography using 5% methanol in dichloromethane to obtain pure 218.4. (0.17 g, 40.77%). MS(ES): m/z 357.48 [M]$^+$.

Synthesis of Compound 218.5.

To a solution of compound 218.4 (0.2 g, 0.56 mmol, 1.0 eq) in methanol (2 mL), paraformaldehyde (0.1 g, 3.3 mmol, 6.0 eq) and sodium methoxide (0.09 g, 1.6 mmol, 3.0 eq) were added. Reaction mixture was stirred at 60-65° C. for 3 h, cooled to room temperature and sodium borohydride (0.005 g, 0.14 mmol, 2.5 eq) was added in portions. Reaction mixture was again stirred at 60-65° C. for 24 h. After completion of the reaction, the reaction mixture was transferred into water, and extracted with dichloromethane. Organic layer combined, dried over anhydrous sodium sulfate, filtered and concentrated under reduced pressure to obtain 218.5. (0.12 g, 57.73%). MS(ES): m/z 371.48 [M]$^+$.

Synthesis of XVI-3.

To a solution of compound 218.5 (0.050 g, 0.13 mmol, 1.0 eq) in 1,4-dioxane (2 mL) was added cyclopropanecarboxamide (0.057 g, 0.67 mmol, 5.0 eq), cesium carbonate (0.1 g, 3.3 mmol, 2.5 eq). The reaction mixture was degassed for 10 min. under argon atmosphere, then tris(dibenzylideneacetone)dipalladium(0) (0.012 g, 0.013 mmol, 0.1 eq) and 4,5-Bis(diphenylphosphino)-9,9-dimethylxanthene (0.015 g, 0.021 mmol, 0.2 eq) were added, again degassed for 5 min. The reaction was stirred at 110° C. for 1 h under microwave irradiation. After completion of reaction, reaction mixture was cooled to room temperature, transferred in water and product was extracted with ethyl acetate. Organic layer combined, washed with brine solution, dried over sodium sulphate and concentrated under reduced pressure to obtain crude material. This was further purified by column chromatography using 1.5% methanol in dichloromethane as eluant to obtain pure XVI-3 (0.015 g, 26.52%). MS(ES): m/z 420.38 [M+H]$^+$, LCMS purity: 100%, HPLC purity: 100%, $^1$H NMR (MeOD, 400 MHZ): 8.99 (s, 1H), 8.18-8.17 (m, 2H), 7.67-7.65 (m, 2H), 7.53-7.49 (m, 1H), 4.48 (s, 3H), 3.54 (s, 3H), 3.27 (s, 3H), 1.92-1.87 (m, 1H), 1.04-1.01 (m, 2H), 0.99-0.90 (m, 2H).

Example 219: N-(3-ethyl-1-(2-methoxy-3-(2-methyl-2H-tetrazol-5-yl)phenyl)-1H-pyrazolo[4,3-c]pyridin-6-yl)cyclopropanecarboxamide, XVI-4

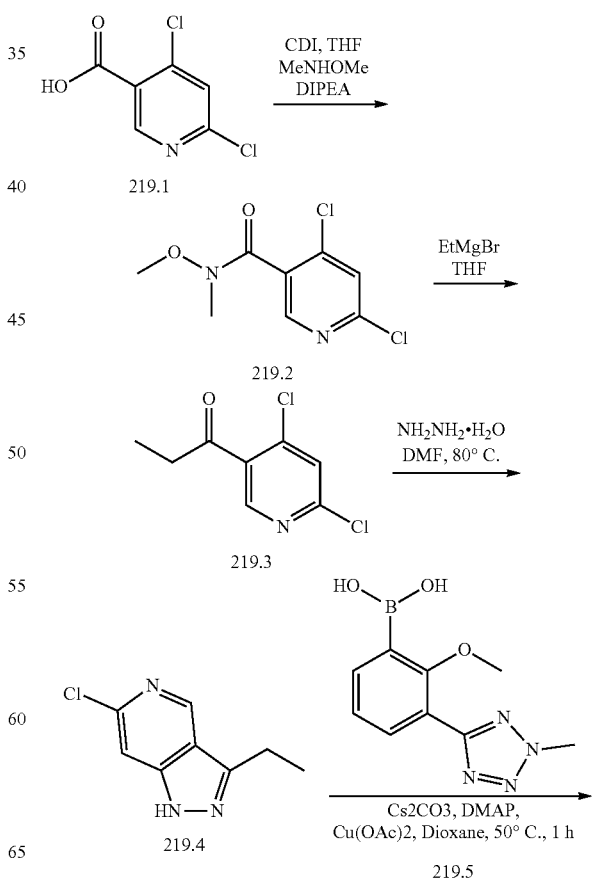

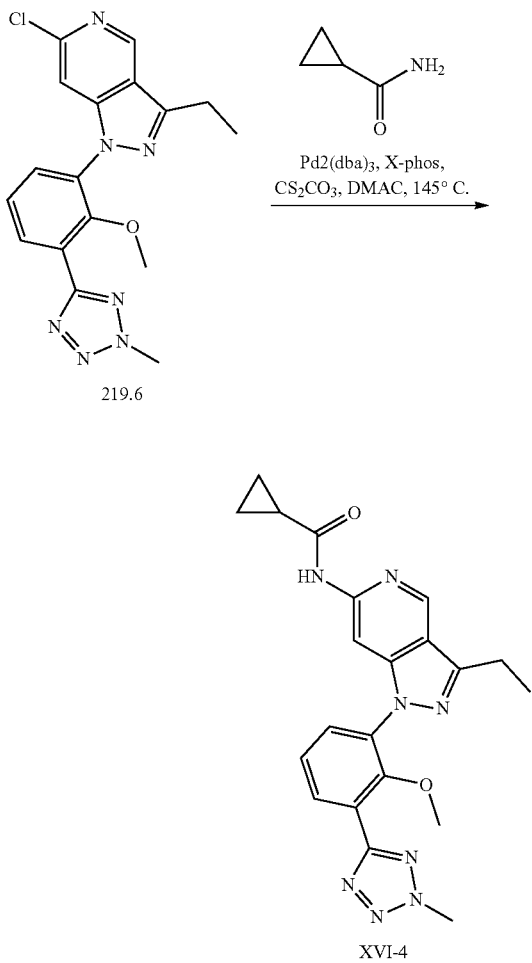

Synthesis of Compound 219.2.

To a solution of compound 219.1 (0.5 g, 2.61 mmol, 1.0 eq) in tetrahydrofuran (10 mL), 1,1'-carbonyldiimidazole (0.63 g, 3.91 mmol, 1.5 eq) was added. Reaction mixture was stirred for 30 min at room temperature. Then, di-isopropylethylamine (0.67 g, 5.22 mmol, 2.0 eq) and N,O-dimethylhydroxyamine hydrochloride (0.30 g, 3.13 mmol, 1.2 eq) was added and the reaction mixture was stirred for 18 h. After completion of the reaction, the reaction mixture was transferred into water and extracted with ethyl acetate. Organic layer combined, dried over anhydrous sodium sulfate, filtered and concentrated under reduced pressure to obtain the crude material. This was further purified by column chromatography using 20% ethyl acetate in hexane to obtain pure 219.2 (0.3 g, 49.01%). MS(ES): m/z 236.06 [M+H]$^+$.

Synthesis of Compound 219.3.

To a solution of 219.2 (0.1 g, 0.42 mmol, 1.0 eq) in tetrahydrofuran (0.5 mL) was added ethyl magnesium bromide (1M in THF) (0.84 mL, 0.84 mmol, 2.0 eq) at 0° C. Reaction mixture was stirred at room temperature for 18 h. After completion of reaction, the reaction mixture was transferred to ammonium chloride and product was extracted with ethyl acetate. Organic layer was combined, washed with brine solution, dried over sodium sulphate and concentrated under reduced pressure to obtain crude material. This was further purified by column chromatography and the product was eluted in 10% ethyl acetate in hexane to get 219.3 (0.8 g, 92.16%). MS(ES): m/z 205.48 [M+H]$^+$.

Synthesis of Compound 219.4.

To a solution of compound 219.3 (0.028 g, 0.13 mmol, 1.0 eq) in dimethylformamide (0.5 mL), di-isopropylethylamine (0.084 g, 0.65 mmol, 5 eq) and hydrazine hydrate (0.022 g, 0.45 mmol, 3.5 eq) were added. Reaction mixture was stirred at 80° C. for 18 h. After completion of the reaction, the reaction mixture was transferred into water and extracted with ethyl acetate. Organic layer combined, dried over anhydrous sodium sulfate, filtered and concentrated under reduced pressure to obtain 1.3 (0.023 g, 99.99%). MS(ES): m/z 182.37 [M+H]$^+$.

Synthesis of Compound 219.6.

To a solution of compound 219.4 (0.07 g, 0.38 mmol, 1.0 eq) in dioxane (5 mL), compound 219.5 (0.18 mL, 0.77 mmol, 2.0 eq) was added. Reaction mixture was degassed for 5 min. Then, 4-dimethylaminopyridine (0.188 g, 1.54 mmol, 4.0 eq) and cesium carbonate (0.32 g, 0.98 mmol, 2.5 eq) was added and again degassed for 15 min. Then, copper acetate (0.07 g, 0.42 mmol, 1.1 eq) was added. Reaction mixture was stirred at 50° C. for 1 hour. After completion of the reaction, the reaction mixture was concentrated, transferred to water and extracted with ethyl acetate. Organic layers were combined, dried over anhydrous sodium sulfate, filtered and concentrated under reduced pressure to get the crude material. This was further purified by column chromatography using 12% ethyl acetate in hexane to obtain pure 219.6. (0.05 g, 41.45%). MS(ES): m/z 370.48 [M]$^+$.

Synthesis of XVI-4.

To a solution of compound 219.6 (0.05 g, 0.14 mmol, 1.0 eq) in N—N'-dimethylacetamide (1 mL) was added cyclopropane carboxamide (0.038 g, 0.44 mmol, 3.0 eq), cesium carbonate (0.14 g, 0.44 mmol, 3.0 eq). The reaction mixture was degassed for 10 min. under argon atmosphere, then tris(dibenzylideneacetone)dipalladium(0) (0.013 g, 0.013 mmol, 0.1 eq) and 4,5-Bis(diphenylphosphino)-9,9-dimethylxanthene (0.017 g, 0.029 mmol, 0.2 eq) were added, again degassed for 5 min. Reaction mixture was stirred at 130° C. for 1 h under microwave irradiation. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure XVI-4 (0.020 g, 32.14%). MS(ES): m/z 419.63 [M+H]$^+$, LCMS purity: 100%, HPLC purity: 100%, $^1$H NMR (DMSO-d$_6$, 400 MHZ): 10.99 (s, 1H), 8.99 (s, 1H), 8.06-8.04 (d, J=6.8 Hz, 1H), 7.92 (s, 1H), 7.71-7.69 (d, J=8.8 Hz, 1H), 7.53-7.49 (t, J=11.5 Hz, 1H), 4.47 (s, 3H), 3.29 (s, 3H), 3.10-3.05 (m, 2H), 2.01 (s, 1H), 1.42-1.39 (t, J=11.5 Hz, 3H), 0.77-0.74 (m, 4H).

Example 220: N-(1-ethyl-3-(2-methoxy-3-(2-methyl-2H-tetrazol-5-yl)phenyl)-1H-pyrazolo[3,4-c]pyridin-5-yl)cyclopropanecarboxamide, XVI-5

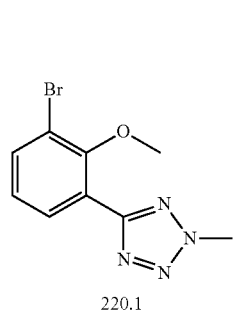
220.1

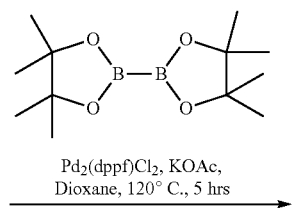
Pd₂(dppf)Cl₂, KOAc, Dioxane, 120° C., 5 hrs

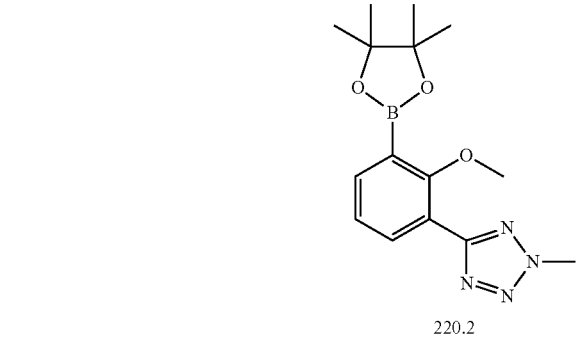
220.2

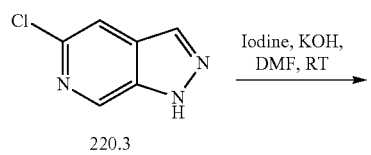
220.3
Iodine, KOH, DMF, RT

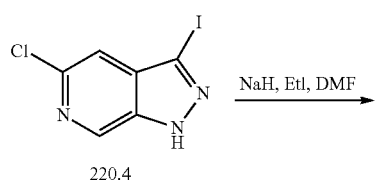
220.4
NaH, EtI, DMF

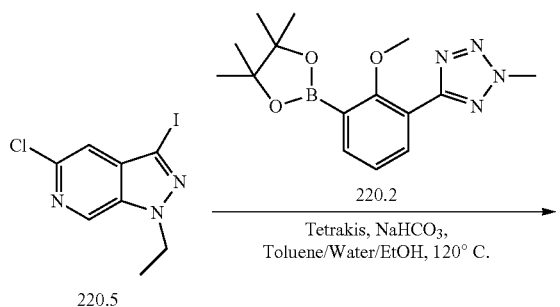
220.5
Tetrakis, NaHCO₃, Toluene/Water/EtOH, 120° C.

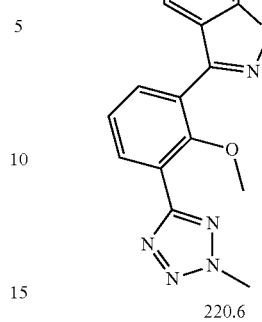
220.6

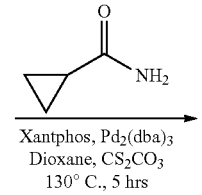
Xantphos, Pd₂(dba)₃
Dioxane, CS₂CO₃
130° C., 5 hrs

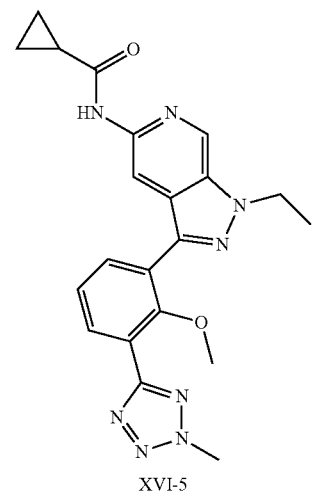
XVI-5

Synthesis of Compound 220.2.

To a solution of compound 220.1 (0.5 g, 1.85 mmol, 1.0 eq) in 1,4-dioxane (1 mL), compound bispinacolato diboron (0.70 g, 2.2 mmol, 1.2 eq), (1,1'-Bis(diphenylphosphino)ferrocene)palladium(II) dichloride (0.04 g, 0.05 mmol, 0.03 eq) and potassium acetate (0.54 g, 5.52 mmol, 3 eq) was added. Reaction mixture was degassed with argon for 15 min and then stirred at 120° C. for 5 h. After completion of the reaction, the reaction mixture was transferred into water and extracted with ethyl acetate. Organic layer combined, dried over anhydrous sodium sulfate, filtered and concentrated under reduced pressure to obtain crude material. This was further purified by column chromatography using 20% ethyl acetate in hexane as eluent to obtain pure 220.2 (0.4 g, 68.09%). MS(ES): m/z 317.58 [M+H]⁺.

Synthesis of Compound 220.4.

To a solution of 220.3 (1.0 g, 0.50 mmol, 1.0 eq) in dimethylformamide (10 mL) was added potassium hydroxide (0.54 g, 0.75 mmol, 1.5 eq) and iodine (2.2 g, 0.75 mmol, 1.5 eq) at room temperature. Reaction mixture was stirred at room temperature for 2 h. After completion of reaction, to the reaction mixture was added solution of sodium carbonate slowly and extracted with ethyl acetate. Organic layer was combined, washed with brine solution, dried over sodium sulphate and concentrated under reduced pressure to obtain 220.4 (1.3 g, 71.44%). MS(ES): m/z 280.53 [M+H]⁺.

Synthesis of Compound 220.5.

To a solution of compound 220.5 (1.5 g, 5.30 mmol, 1.0 eq) in dimethylformamide (15 mL) at 0° C., ethyl iodide (0.32 g, 6.3 mmol, 1.2 eq) was added. Then, sodium hydride (1.0 g, 7.9 mmol, 1.5 eq) was added in portions at 0° C.

Reaction mixture was stirred at room temperature for 2 h. After completion of the reaction, the reaction mixture was transferred to water and extracted with ethyl acetate. Organic layer combined, dried over anhydrous sodium sulfate, filtered and concentrated under reduced pressure to obtain crude material. This was further purified by column chromatography using 10% ethyl acetate in hexane to obtain pure 220.5. (1.0 g, 60.58%). MS(ES): m/z 308.56 [M]⁺.

Synthesis of Compound 220.6.

To a solution of compound 220.5 (0.1 g, 0.32 mmol, 1.0 eq) in a mixture of toluene (1.0 mL), ethanol (0.5 mL) and water (0.5 mL), compound 220.2 (0.12 g, 0.39 mmol, 1.2 eq) was added. Then, sodium bicarbonate (0.08 g, 0.9 mmol, 3.0 eq) and Tetrakis(triphenylphosphine)palladium(0) (0.030 g, 0.032 mmol, 0.1 eq) was added. Reaction mixture was stirred at room temperature for 2 h. After completion of the reaction, the reaction mixture was transferred into water and extracted with dichloromethane. Organic layer combined, dried over anhydrous sodium sulfate, filtered and concentrated under reduced pressure to obtain crude material. This was further purified by column chromatography using 60% ethyl acetate in hexane to obtain pure 220.6 (0.033 g, 27.44%). MS(ES): m/z 370.43 [M]⁺.

Synthesis of XVI-5.

To a solution of compound 220.6 (0.150 g, 0.40 mmol, 1.0 eq) in 1,4-dioxane (1.5 mL) was added cyclopropane carboxamide (0.052 g, 0.60 mmol, 1.5 eq), cesium carbonate (0.26 g, 0.81 mmol, 2.0 eq). The reaction mixture was degassed for 10 min. under argon atmosphere, then tris (dibenzylideneacetone)dipalladium(0) (0.037 g, 0.040 mmol, 0.1 eq) and 4,5-Bis(diphenylphosphino)-9,9-dimethylxanthene (0.047 g, 0.081 mmol, 0.2 eq) were added, again degassed for 5 min. The reaction was stirred at 130° C. for 5 h under microwave irradiation. After completion of reaction, reaction mixture was cooled to room temperature, transferred in water and product was extracted with ethyl acetate. Organic layer was combined, washed with brine solution, dried over sodium sulphate and concentrated under reduced pressure to obtain crude material. This was further purified by column chromatography using 1.5% methanol in dichloromethane as eluant to obtain pure XVI-5 (0.030 g, 17.67%). MS(ES): m/z 419.48 [M+H]⁺, LCMS purity: 98.63%, HPLC purity: 96.58%, ¹H NMR (DMSO-d₆, 400 MHZ): 10.77 (s, 1H), 9.04 (s, 1H), 8.34 (s, 1H), 7.95-7.93 (d, J=8.8 Hz, 1H), 7.78-7.76 (d, J=11.5 Hz, 1H), 7.44-7.42 (m, 1H), 7.42-7.40 (m, 1H), 4.64-4.59 (m, 2H), 4.45 (s, 3H), 3.39 (s, 3H), 1.99-1.96 (d, J=13.2 Hz, 1H), 1.52-1.48 (m, 2H), 0.74 (s, 4H).

Example 221: N-(1-ethyl-3-(2-methoxy-3-(2-methyl-2H-tetrazol-5-yl)phenyl)-1H-pyrrolo[2,3-c]pyridin-5-yl)cyclopropanecarboxamide, XVI-6

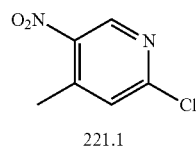

221.1

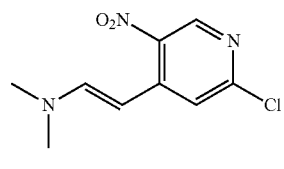

221.2

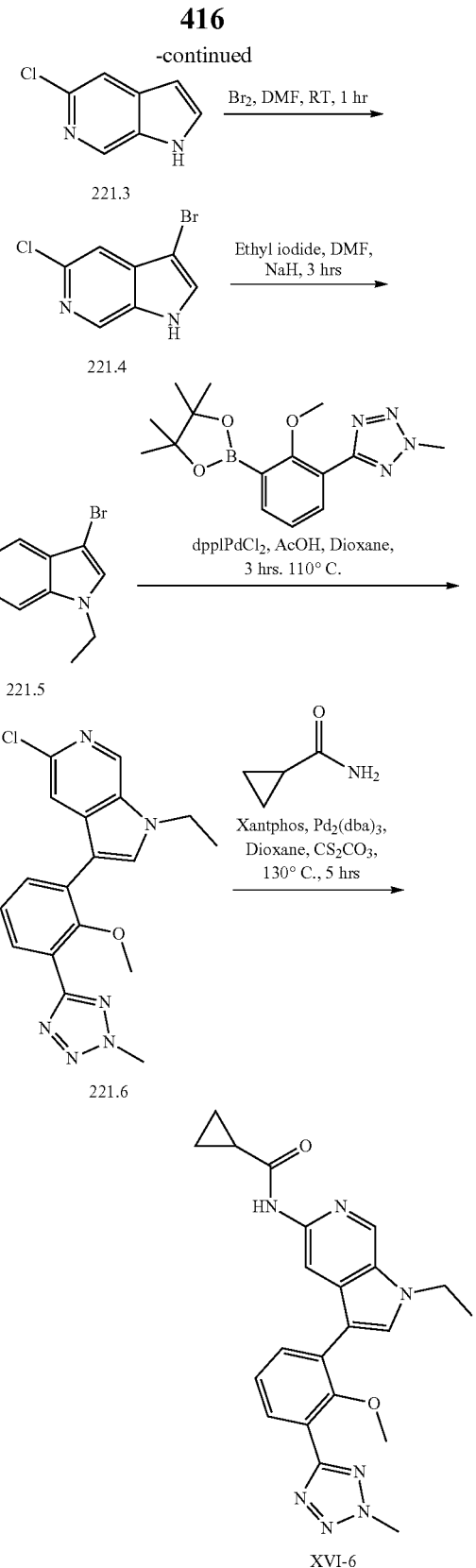

Synthesis of Compound 221.2.

To a solution of compound 221.1 (2 g, 11.62 mmol, 1.0 eq) in dimethylformamide (10 mL), dimethylformamide dimethyl acetal (2 mL) was added. Reaction mixture was stirred at 90° C. for 2 h. After completion of the reaction, the reaction mixture was transferred into water and extracted with ethyl acetate. Organic layer combined, dried over anhydrous sodium sulfate, filtered and concentrated under reduced pressure to obtain 221.2 (1.2 g, 45.48%). MS(ES): m/z 228.15 [M+H]$^+$.

Synthesis of Compound 221.3.

To a solution of 221.2 (1.0 g, 4.4 mmol, 1.0 eq) in acetic acid (10 mL) was added iron powder (1.2 g, 22.0 mmol, 5.0 eq) at room temperature. Reaction mixture was stirred at 90° C. for 2 h. After completion of reaction, to the reaction mixture was added solution of sodium carbonate slowly and extracted with ethyl acetate. Organic layer was combined, washed with brine solution, dried over sodium sulphate and concentrated under reduced pressure to obtain crude material. This was further purified by column chromatography and the product was eluted in 30% ethyl acetate in hexane to obtain 221.3 (0.65 g, 96.98%). MS(ES): m/z 153.47 [M+H]$^+$.

Synthesis of Compound 221.4.

To a solution of compound 221.3 (1.2 g, 7.7 mmol, 1.0 eq) in dimethylformamide (5 mL), bromine solution (1.2 g, 7.7 mmol, 1.0 eq) was added. Reaction mixture was stirred at room temperature for 1 h. After completion of the reaction, the reaction mixture was transferred into water to obtain the precipitate which was filtered, washed with water and dried well under vacuum to obtain 221.4. (1.1 g, 60.42%). MS(ES): m/z 232.53 [M]$^+$.

Synthesis of Compound 221.5.

To a solution of compound 221.4 (1.1 g, 7.2 mmol, 1.0 eq) in dimethylformamide (20 mL) at 0° C., sodium hydride (0.5 mL, 10.8 mmol, 1.5 eq) was added. Reaction mixture was stirred at 0° C. for 20 min. Then, ethyl iodide (1.6 mL, 10.8 mmol, 1.5 eq) was added. Reaction mixture was stirred at room temperature for 3 h. After completion of the reaction, the reaction mixture was transferred into water to obtain the precipitate which was filtered, washed with water and dried well under vacuum to obtain 221.5. (0.9 g, 72.97%). MS(ES): m/z 260.37 [M]$^+$.

Synthesis of Compound 221.6.

To a solution of compound 221.5 (0.4 g, 1.5 mmol, 1.0 eq) in a mixture of water (2 mL), ethanol (4 mL) and toluene (4 mL), compound 220.2 (0.63 mL, 2.0 mmol, 1.3 eq) and sodium bicarbonate (0.3 g, 3.6 mmol, 3.0 eq) was added. Reaction mixture was degassed with argon for 15 min. Then, tetrakis(triphenylphosphine)palladium(0) (0.17 g, 0.15 mmol, 0.1 eq) was added and again degassed for 5 min. Reaction mixture was stirred at 110° C. for 24 h. After completion of the reaction, the reaction mixture was concentrated, transferred to water and extracted with ethyl acetate. Organic layer combined, dried over anhydrous sodium sulfate, filtered and concentrated under reduced pressure to obtain crude material. This was further purified by column chromatography using 55% ethyl acetate in hexane to obtain pure 221.6. (0.15 g, 26.39%). MS(ES): m/z 369.43 [M]$^+$.

Synthesis of XVI-6.

To a solution of compound 221.6 (0.150 g, 0.40 mmol, 1.0 eq) in 1,4-dioxane (5 mL) was added cyclopropane carboxamide (0.052 g, 0.61 mmol, 1.5 eq), potassium carbonate (0.1 g, 1.92 mmol, 3.0 eq). The reaction mixture was degassed for 10 min. under argon atmosphere, then tris (dibenzylideneacetone)dipalladium(0) (0.058 g, 0.040 mmol, 0.1 eq) and 4,5-Bis(diphenylphosphino)-9,9-dimethylxanthene (0.036 g, 0.080 mmol, 0.2 eq) were added, again degassed for 5 min. The reaction was stirred at 130° C. for 5 h. After completion of reaction, reaction mixture was cooled to room temperature, transferred in water and product was extracted with ethyl acetate. Organic layer combined, washed with brine solution, dried over sodium sulphate and concentrated under reduced pressure to obtain crude material. This was further purified by column chromatography using 2% methanol in dichloromethane as eluant to obtain pure XVI-6 (0.050 g, 29.45%). MS(ES): m/z 418.48 [M+H]$^+$, LCMS purity: 99.91%, HPLC purity: 100%, $^1$H NMR (DMSO-d$_6$, 400 MHZ): 10.58 (s, 1H), 8.72 (s, 1H), 8.38 (s, 1H), 7.98 (s, 1H), 7.79-7.76 (d, J=8.8 Hz, 1H), 7.69-7.67 (d, J=7.6 Hz, 1H), 7.41-7.37 (t, J=15.6 Hz, 1H), 4.46 (s, 3H), 4.41-4.35 (m, 2H), 3.40 (s, 3H), 1.99 (s, 1H), 1.48-1.44 (t, J=14.4, 3H), 0.77-0.74 (m, 4H).

Example 222. TYK2 JH2 Domain Binding Assay

Binding constants for compounds of the present invention against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP_003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2(JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a ≥10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. K$_d$s were determined using an 11-point 3-fold compound dilution series with three DMSO control points. All compounds for K$_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound.

The washed based were re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. qPCR reactions were assembled by adding 2.5 μL of kinase eluate to 7.5 μL of qPCR master mix containing 0.15 μM amplicon primers and 0.15 μM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{HillSlope}}{Dose^{HillSlope}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)). In some cases Results of the JH2 binding assay are reported in Table 4. Compounds described as "A" have a $K_d$ less than 100 pM. Compounds described as "B" have a $K_d$ equal to or greater than 100 pM and less than 500 pM. Compounds described as "C" have a $K_d$ equal to or greater than 500 pM and less than 1 nM. Compounds described as "D" have a $K_d$ equal to or greater than 1 nM and less than 10 nM. Compounds described as "E" have a $K_d$ equal to or greater than 10 nM.

TABLE 4

JH2 binding assay.

| Compound | JH2 $K_d$ |
|---|---|
| I-1 | A |
| I-2 | B |
| I-3 | B |
| I-4 | B |
| I-5 | E |
| I-6 | E |
| I-7 | D |
| I-8 | A |
| I-9 | A |
| I-10 | A |
| I-11 | E |
| I-12 | A |
| I-13 | A |
| I-14 | B |
| I-15 | B |
| I-16 | B |
| I-17 | A |
| I-18 | B |
| I-19 | D |
| I-20 | B |
| I-21 | B |
| I-22 | C |
| I-23 | E |
| I-24 | B |
| I-25 | B |
| I-27 | E |
| I-28 | D |
| I-29 | B |
| I-30 | E |
| I-31 | A |
| I-32 | E |
| I-33 | E |
| I-34 | E |
| I-35 | E |
| I-36 | E |
| I-37 | E |
| I-38 | E |
| I-39 | E |
| I-40 | E |
| I-41 | E |
| I-42 | E |
| I-43 | E |
| I-44 | D |
| I-45 | D |
| I-46 | C |
| I-47 | E |
| I-48 | C |
| I-49 | C |
| I-50 | D |
| I-51 | E |
| I-52 | D |
| I-53 | B |
| I-54 | C |
| I-55 | C |
| I-56 | C |
| I-57 | A |
| I-58 | E |
| I-59 | B |
| I-60 | B |
| I-61 | D |
| I-62 | A |
| I-63 | B |
| I-64 | A |
| I-65 | B |
| I-66 | C |
| I-67 | D |
| I-68 | B |
| I-69 | D |
| I-70 | B |
| I-71 | C |
| I-72 | D |
| I-73 | D |
| I-74 | B |
| I-75 | B |
| I-76 | D |
| I-77 | D |
| I-78 | D |
| I-79 | D |
| I-80 | D |
| I-81 | B |
| I-82 | B |
| I-83 | D |
| I-84 | D |
| I-85 | C |
| I-86 | D |
| I-87 | D |
| I-88 | D |
| I-89 | D |
| I-90 | E |
| I-91 | D |
| I-92 | B |
| I-93 | D |
| I-94 | D |
| I-95 | D |
| I-96 | B |
| I-97 | C |
| I-98 | C |
| I-99 | C |
| I-100 | A |
| I-101 | D |

TABLE 4-continued

JH2 binding assay.

| Compound | JH2 $K_d$ |
|---|---|
| I-102 | E |
| I-103 | E |
| I-104 | E |
| I-105 | D |
| I-106 | D |
| I-107 | B |
| I-108 | B |
| I-109 | B |
| I-110 | D |
| I-111 | B |
| I-112 | A |
| I-113 | B |
| I-114 | D |
| I-115 | D |
| I-116 | E |
| I-117 | E |
| I-118 | E |
| I-119 | D |
| I-120 | D |
| I-121 | C |
| I-122 | B |
| I-123 | B |
| I-124 | D |
| I-125 | E |
| I-126 | E |
| I-127 | E |
| I-128 | B |
| I-129 | B |
| I-130 | B |
| I-131 | B |
| I-132 | B |
| I-133 | B |
| I-134 | B |
| I-135 | D |
| I-136 | D |
| I-137 | C |
| I-138 | C |
| I-139 | B |
| I-140 | D |
| I-141 | D |
| I-142 | B |
| I-143 | B |
| I-144 | B |
| I-145 | B |
| I-146 | E |
| I-147 | E |
| I-148 | E |
| I-149 | E |
| I-151 | E |
| I-152 | C |
| I-155 | C |
| I-156 | E |
| I-157 | C |
| I-158 | E |
| I-182 | B |
| I-190 | C |
| I-191 | E |
| I-198 | B |
| I-199 | B |
| I-201 | A |
| I-203 | C |
| I-206 | C |
| I-207 | D |
| I-208 | C |
| I-209 | C |
| I-210 | B |
| I-211 | C |
| I-212 | E |
| I-213 | B |
| I-214 | B |
| I-215 | B |
| I-216 | B |
| I-217 | A |
| I-218 | A |
| I-219 | B |
| I-220 | B |

TABLE 4-continued

JH2 binding assay.

| Compound | JH2 $K_d$ |
|---|---|
| I-221 | B |
| I-222 | D |
| I-223 | D |
| I-225 | A |
| I-226 | B |
| I-227 | A |
| I-228 | B |
| I-229 | A |
| I-230 | C |
| I-231 | D |
| I-232 | A |
| I-234 | B |
| I-235 | B |
| I-236 | E |
| I-237 | D |
| I-238 | B |
| I-239 | B |
| I-240 | B |
| I-241 | E |

Results of the JH2 binding assay are listed in Table 5, below. Compounds designated as "A" had a $K_d$ between 100 pM and 1 nM. Compounds designated as "B" had a $K_d$ between 1 nM and 10 nM. Compounds designated as "C" had a $K_d$ between 10 nM and 100 nM. Compounds designated as "D" had a $K_d$ greater than 100 nM.

TABLE 5

Results of Tyk2 JH2 Domain Binding Assay

| Compound | JH2 $K_d$ |
|---|---|
| VIII-1 | B |
| VIII-2 | C |
| VIII-3 | D |
| VIII-4 | B |
| VIII-5 | B |
| VIII-6 | C |
| VIII-7 | B |
| VIII-8 | D |
| VIII-9 | D |
| VIII-10 | D |
| VIII-11 | C |
| VIII-12 | A |
| VIII-13 | A |
| VIII-14 | A |
| VIII-15 | B |
| VIII-16 | A |
| VIII-17 | A |
| XVI-1 | C |
| XVI-2 | D |
| XVI-3 | D |
| XVI-4 | A |
| XVI-5 | C |
| XVI-6 | C |

Results of the Tyk2 JH2 Domain Binding Assay indicate that compounds XVI-1 and XVI-3 have a $K_d$ between 7-10 uM, and compounds XVI-2 and XVI-4 through XVI-6 have a Kd between 10-185 nM.

Example 223. Tyk2 & JAK2 Radioactive Kinase Assay

Peptide substrate, [KKSRGDYMTMQIG], (20 µM) is prepared in reaction buffer (20 mM Hepes pH 7.5, 10 mM MgCl$_2$, 1 mM EGTA, 0.02% Brij35, 0.02 mg/mL BSA, 0.1 mM Na$_3$PO$_4$, 2 mM DTT, 1% DMSO. TYK2 (Invitrogen)

kinase is added, followed by compounds in DMSO. 33PATP is added to initiate the reaction in ATP at 10 μM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr](4:1), 0.2 mg/ml is used, in the reaction carried out the same as for TYK2.

Results of the active kinase assay indicate that compounds I-1 and I-2 have no detectable inhibitory activity against TYK2 JH1 kinase function.

Results of the active kinase assay indicate that compounds VIII-1, VIII-2, VIII-3, and VIII-4 have no detectable inhibitory activity against TYK2 or JAK2 JH1 kinase function.

Example 224. Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Example 225. IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 μl per well is 200,000 cells. 15 μl of compound or DMSO is added to the well at the desired concentrations and incubated at 1 hr at 37 C. 15 μl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

Results of the IL-12 induced pSTAT4 assay in human PBMC indicate that each of compounds VIII-1 through VIII-17 inhibited pSTAT4 production with an $IC_{50}$ of between 100 nM and 10 uM.

Example 226. GM-CSF Induced pSTAT5 in Human PBMC

Cells are prepared for analysis as in the above procedure and 15 μl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Results of the GM-CSF Induced pSTAT5 assay in human PBMC indicate that compound VIII-1 inhibits pSTAT5 production with an $IC_{50}$ of greater than 50 uM.

Example 227. Ex Vivo Mouse IL-12 Induced IFNγ Studies

C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 228. T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1 \times 10^4$ cells per well in 96-well plates. T-ALL cell lines DU.528, LOUCY, and SUP-T13 are cultured in the same medium and plated at a density of $1.5 \times 10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. $IC_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula VIII:

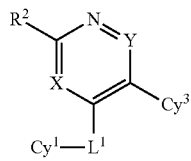

or a pharmaceutically acceptable salt thereof, wherein:

X is $C(R^3)$;

Y is $C(R^1)$;

$R^1$ is H, D, or halogen;

$R^2$ is —N(R)C(O)Cy$^2$, —N(R)S(O)$_2$Cy$^2$, or —N(R)Cy$^2$;

$R^3$ is H or halogen;

Cy$^1$ is phenyl or a 5-6 membered monocyclic heteroaryl ring having 1-4 heteroatoms independently selected from nitrogen, oxygen, and sulfur; wherein Cy$^1$ is substituted with n instances of $R^5$;

Cy$^2$ is phenyl; a 5-6 membered monocyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; wherein Cy$^2$ is substituted with p instances of $R^6$;

Cy$^3$ is a 5-6 membered monocyclic heteroaromatic ring having 1-4 heteroatoms independently selected from nitrogen, oxygen, and sulfur; wherein Cy$^3$ is substituted with r instances of $R^8$;

$L^1$ is —N(R)—;

each instance of $R^4$, $R^5$, $R^6$, $R^7$ and $R^8$ is independently $R^A$ or $R^B$, and is substituted by q instances of $R^C$;

each instance of $R^A$ is independently oxo, halogen, —CN, —NO$_2$, —OR, —OR$^D$, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^D$ is a C$_1$-4 aliphatic group wherein one or more hydrogens are replaced by deuterium;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, q, and r is independently 0, 1, 2, 3, or 4.

2. The compound of claim 1 of formula XI-b:

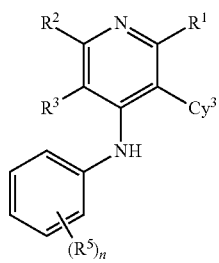

XI-b or a pharmaceutically acceptable salt thereof.

3. The compound of claim 1 of formula XII-b:

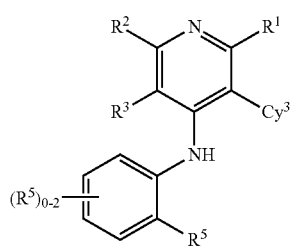

XII-b or a pharmaceutically acceptable salt thereof.

4. The compound of claim 1, wherein $R^1$ is H.
5. The compound of claim 4, wherein $R^3$ is H.
6. The compound of claim 5, wherein $Cy^3$ is a 5-membered ring.
7. The compound of claim 6, wherein $Cy^1(R^5)_n$ taken together is one of the following:

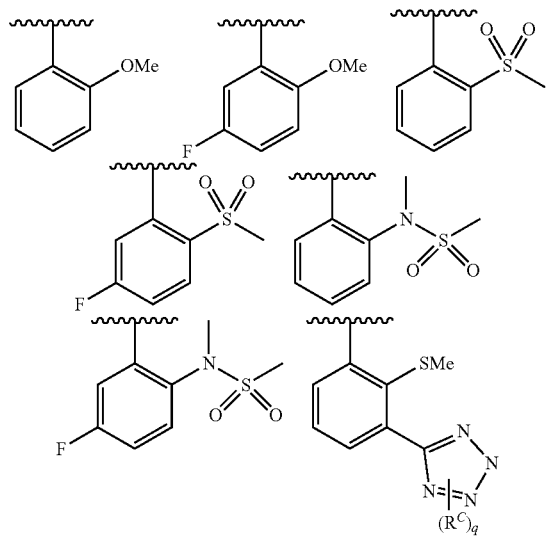

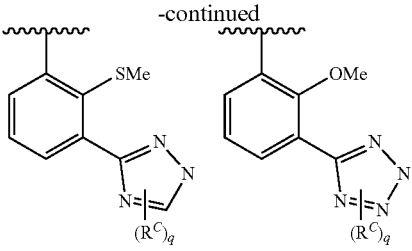

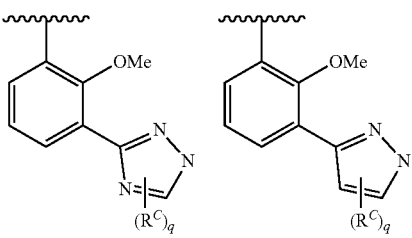

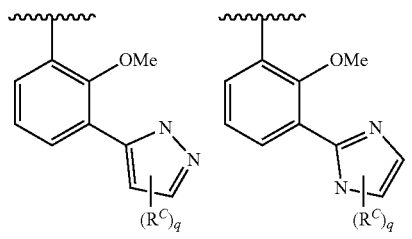

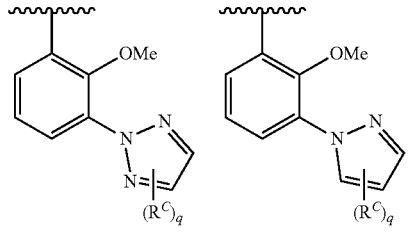

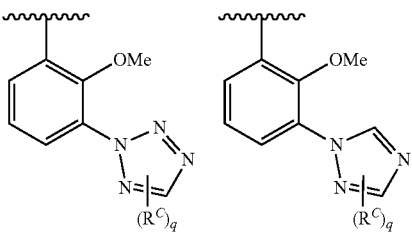

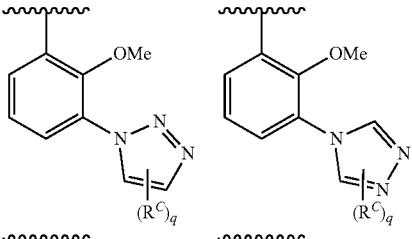

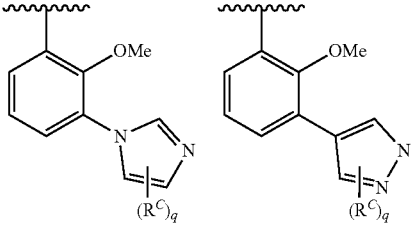

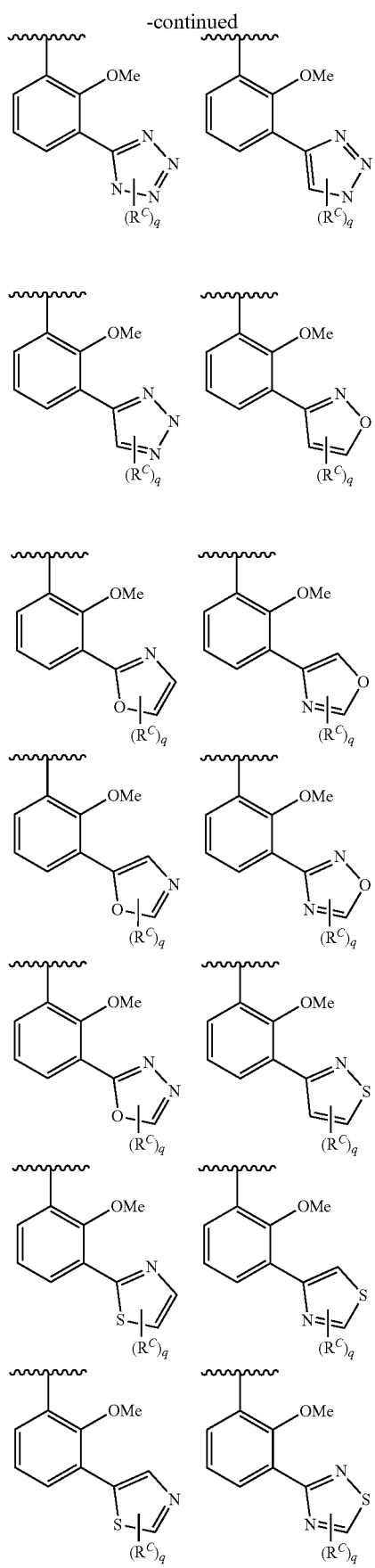
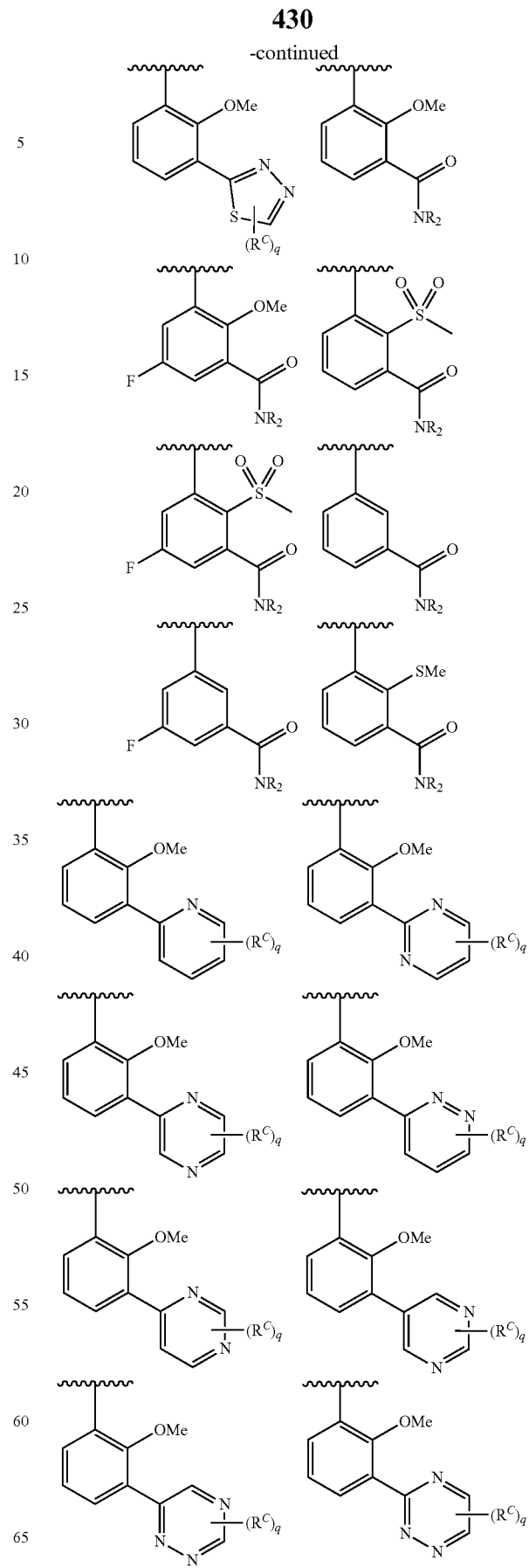

431
-continued
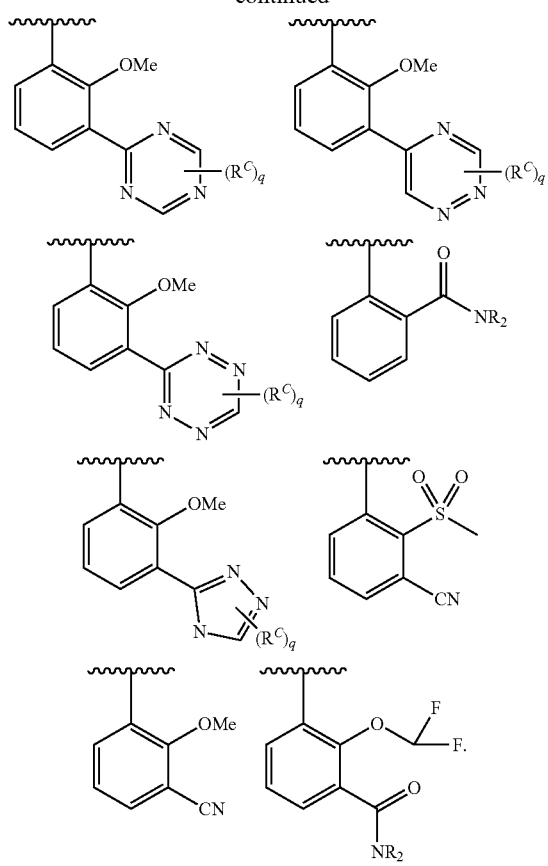
8. The compound of claim 7, wherein $R^2$ is —N(H)Cy$^2$ or —N(H)C(O)Cy$^2$.
9. The compound of claim 8, wherein Cy$^2$ is selected from the following:
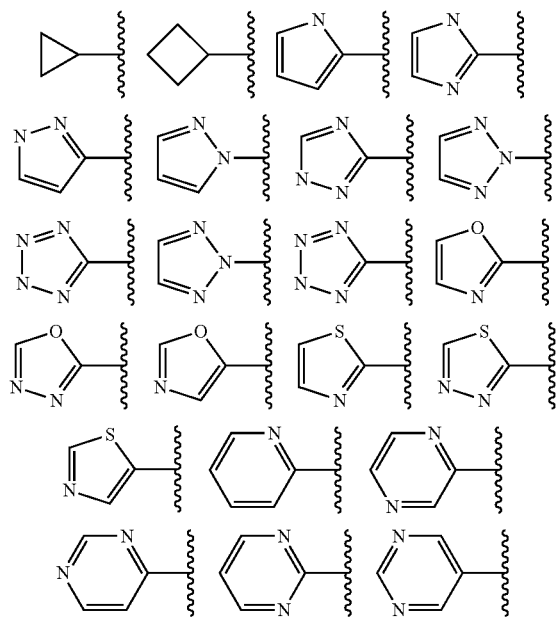
432
-continued
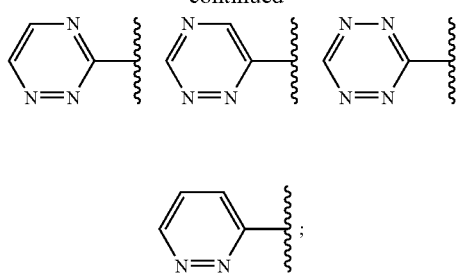
each of which is substituted by p instances of $R^6$.
10. The compound of claim 9, wherein $R^2$ is
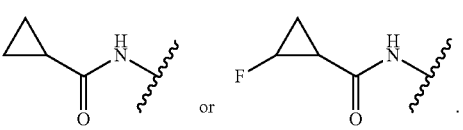 [SMILES: *NC(=O)C1CC1 ; *NC(=O)C1CC1F]
11. A compound selected from
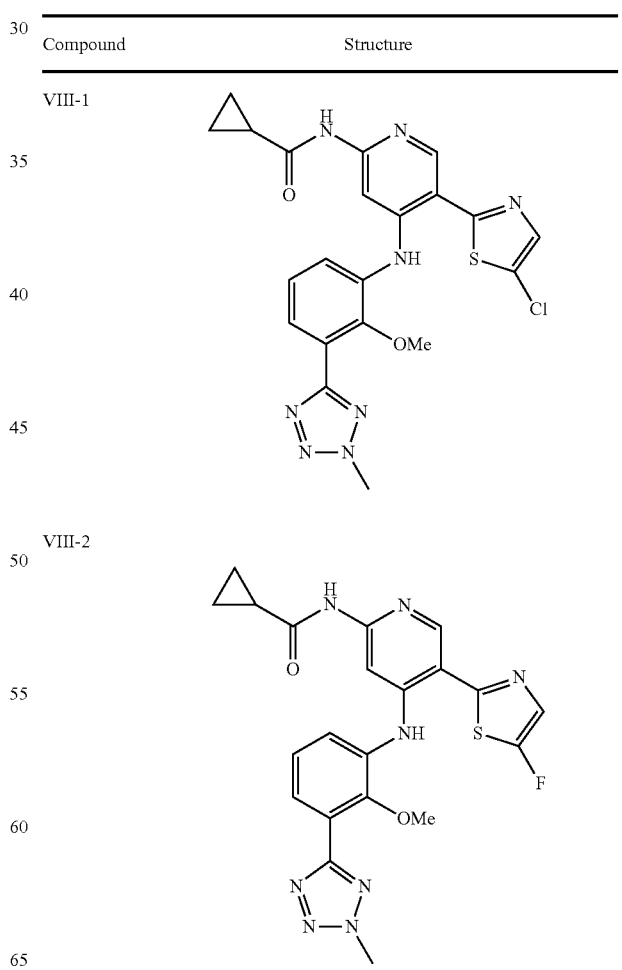

-continued
| Compound | Structure |
|---|---|
| VIII-3 | 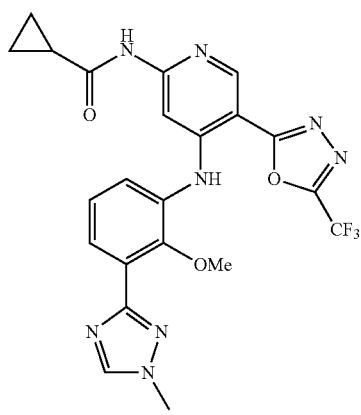 [SMILES: COc1c(Nc2cc(NC(=O)C3CC3)ncc2-c2nnc(C(F)(F)F)o2)cccc1-c1ncn(C)n1] |
| VIII-4 | 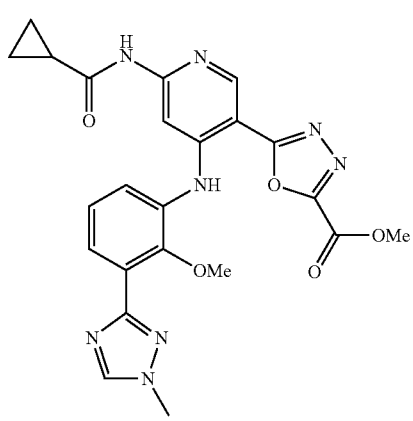 [SMILES: COC(=O)c1nnc(-c2cnc(NC(=O)C3CC3)cc2Nc2cccc(-c3ncn(C)n3)c2OC)o1] |
| VIII-5 | 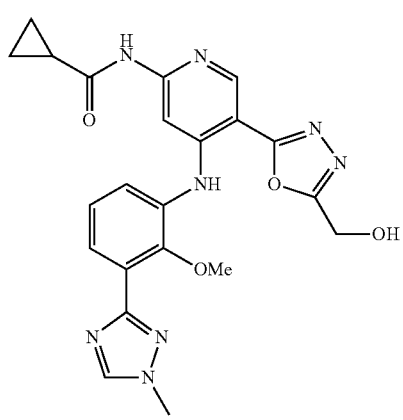 [SMILES: COc1c(Nc2cc(NC(=O)C3CC3)ncc2-c2nnc(CO)o2)cccc1-c1ncn(C)n1] |
-continued
| Compound | Structure |
|---|---|
| VIII-6 | 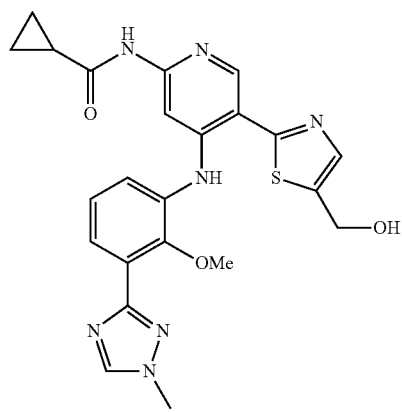 [SMILES: COc1c(Nc2cc(NC(=O)C3CC3)ncc2-c2ncc(CO)s2)cccc1-c1ncn(C)n1] |
| VIII-7 | 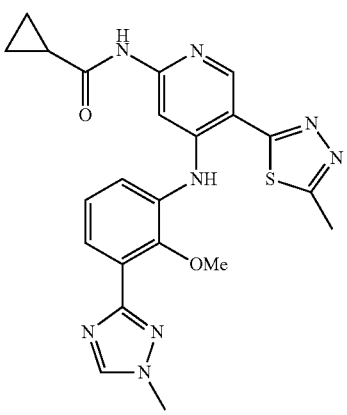 [SMILES: COc1c(Nc2cc(NC(=O)C3CC3)ncc2-c2nnc(C)s2)cccc1-c1ncn(C)n1] |
| VIII-8 | 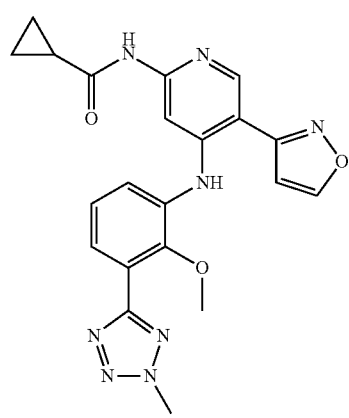 [SMILES: COc1c(Nc2cc(NC(=O)C3CC3)ncc2-c2ccon2)cccc1-c1nnn(C)n1] |

-continued
| Compound | Structure |
|---|---|
| VIII-9 | 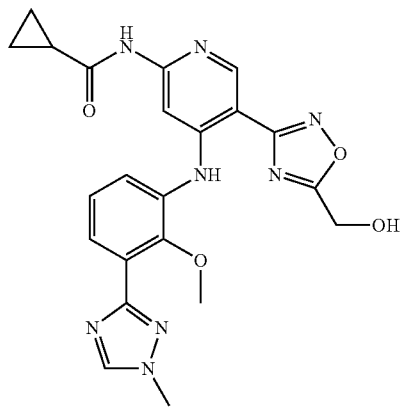 [SMILES: COc1c(Nc2cc(NC(=O)C3CC3)ncc2-c2noc(CO)n2)cccc1-c1ncn(C)n1] |
| VIII-10 | 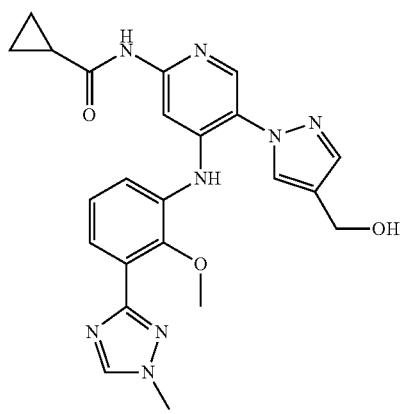 [SMILES: COc1c(Nc2cc(NC(=O)C3CC3)ncc2-n2cc(CO)cn2)cccc1-c1ncn(C)n1] |
| VIII-11 | 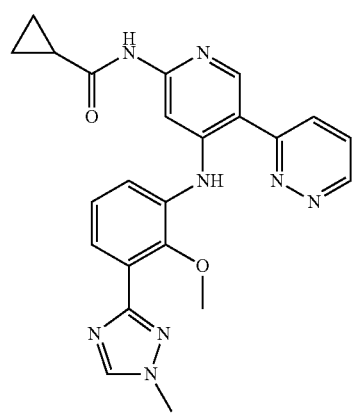 [SMILES: COc1c(Nc2cc(NC(=O)C3CC3)ncc2-c2cccnn2)cccc1-c1ncn(C)n1] |
-continued
| Compound | Structure |
|---|---|
| VIII-12 | 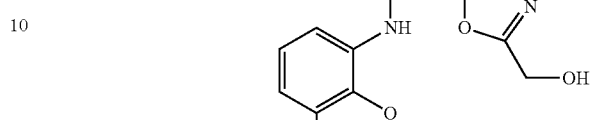 |
| VIII-13 | 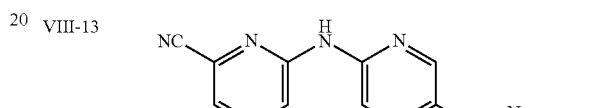 |
| VIII-14 | 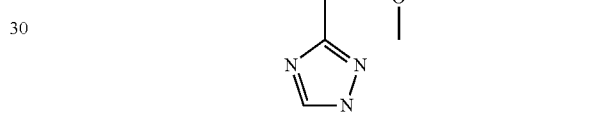 |
| VIII-15 | 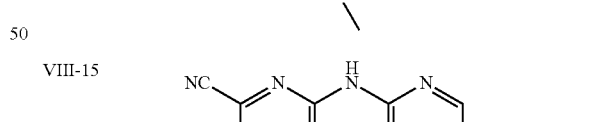 |

| Compound | Structure |
|---|---|
| VIII-16 | 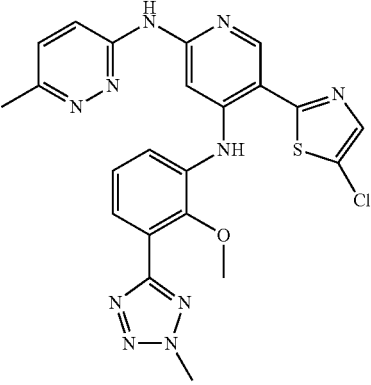 [SMILES: COc1c(Nc2cc(Nc3ccc(C)nn3)ncc2-c2ncc(Cl)s2)cccc1-c1nnn(C)n1] |
| Compound | Structure |
|---|---|
| VIII-17 | 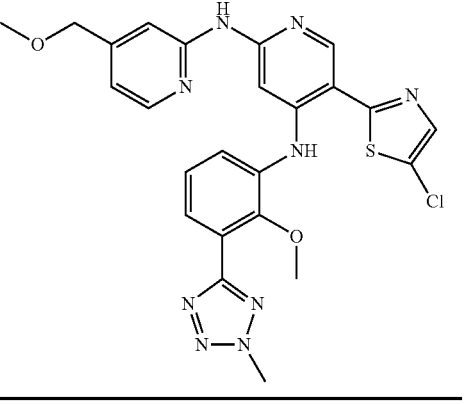 |
or a pharmaceutically acceptable salt thereof.
12. A pharmaceutical composition comprising a compound according to claim 1, or a pharmaceutically acceptable salt thereof, and a pharmaceutically acceptable carrier, adjuvant, or vehicle.
* * * * *